(12) United States Patent
Fang et al.

(10) Patent No.: US 11,643,418 B2
(45) Date of Patent: May 9, 2023

(54) MACROCYCLIZATION REACTIONS AND INTERMEDIATES AND OTHER FRAGMENTS USEFUL IN THE SYNTHESIS OF ANALOGS OF HALICHONDRIN B

(71) Applicant: EISAI R&D MANAGEMENT CO., LTD., Tokyo (JP)

(72) Inventors: Francis G. Fang, Andover, MA (US); Dae-Shik Kim, Andover, MA (US); Hyeong-Wook Choi, Andover, MA (US); Charles E. Chase, Londonderry, NH (US); Jaemoon Lee, Andover, MA (US)

(73) Assignee: EISAI R&D MANAGEMENT CO., LTD., Tokyo (JP)

( * ) Notice: Subject to any disclaimer, the term of this patent is extended or adjusted under 35 U.S.C. 154(b) by 226 days.

(21) Appl. No.: 17/188,819

(22) Filed: Mar. 1, 2021

(65) Prior Publication Data
US 2021/0188867 A1    Jun. 24, 2021

Related U.S. Application Data

(62) Division of application No. 16/833,923, filed on Mar. 30, 2020, now Pat. No. 10,934,307, which is a division of application No. 16/246,999, filed on Jan. 14, 2019, now Pat. No. 10,611,773, which is a division of application No. 15/707,412, filed on Sep. 18, 2017, now Pat. No. 10,221,189, which is a division of application No. 15/033,970, filed as application No. PCT/US2014/063960 on Nov. 4, 2014, now Pat. No. 9,783,549.

(60) Provisional application No. 61/899,697, filed on Nov. 4, 2013.

(51) Int. Cl.
| | |
|---|---|
| *C07D 493/22* | (2006.01) |
| *C07F 7/18* | (2006.01) |
| *C07D 407/14* | (2006.01) |
| *C07D 307/28* | (2006.01) |
| *C07D 407/06* | (2006.01) |
| *C07D 493/14* | (2006.01) |

(52) U.S. Cl.
CPC ......... *C07D 493/22* (2013.01); *C07D 307/28* (2013.01); *C07D 407/06* (2013.01); *C07D 407/14* (2013.01); *C07D 493/14* (2013.01); *C07F 7/1804* (2013.01)

(58) Field of Classification Search
CPC .. C07D 493/22; C07D 307/28; C07D 407/06; C07D 407/14; C07D 493/14; C07F 7/1804
See application file for complete search history.

(56) References Cited

U.S. PATENT DOCUMENTS

| | | |
|---|---|---|
| 4,107,206 A | 8/1978 | Hewett et al. |
| 5,338,865 A | 8/1994 | Kishi et al. |
| 5,436,238 A | 7/1995 | Kishi et al. |
| 5,451,573 A | 9/1995 | Hemmerle et al. |
| 6,194,586 B1 | 2/2001 | Martinelli et al. |
| 6,214,865 B1 | 4/2001 | Littlefield et al. |
| 6,365,759 B1 | 4/2002 | Littlefield et al. |
| 6,469,182 B1 | 10/2002 | Littlefield et al. |
| 6,653,341 B1 | 11/2003 | Littlefield et al. |
| 7,470,720 B2 | 12/2008 | Littlefield et al. |
| 7,982,060 B2 | 7/2011 | Austad et al. |
| 8,093,410 B2 | 1/2012 | Chase et al. |
| 8,097,648 B2 | 1/2012 | Littlefield et al. |
| 8,148,554 B2 | 4/2012 | Seletsky et al. |
| 8,203,010 B2 | 6/2012 | Endo et al. |
| 8,350,067 B2 | 1/2013 | Endo et al. |
| 8,445,701 B2 | 5/2013 | Austad et al. |
| 8,598,373 B2 | 12/2013 | Hu |
| 8,618,313 B2 | 12/2013 | Benayoud et al. |
| 8,884,031 B2 | 11/2014 | Chase et al. |
| RE45,324 E | 1/2015 | Austad et al. |
| 8,927,597 B2 | 1/2015 | Endo et al. |
| 8,975,422 B2 | 3/2015 | Fang et al. |
| 8,987,479 B2 | 3/2015 | Chase et al. |
| 9,206,194 B2 | 12/2015 | Hu |
| 9,303,039 B2 | 4/2016 | Zhang et al. |
| 9,303,050 B2 | 4/2016 | Benayoud et al. |

(Continued)

FOREIGN PATENT DOCUMENTS

| | | |
|---|---|---|
| CN | 1993342 A | 7/2007 |
| EP | 0572109 A1 | 12/1993 |

(Continued)

OTHER PUBLICATIONS

U.S. Appl. No. 16/684,332, Benayoud et al.

(Continued)

*Primary Examiner* — Daniel R Carcanague
(74) *Attorney, Agent, or Firm* — Clark & Elbing LLP

(57) ABSTRACT

The invention provides methods for the synthesis of eribulin or a pharmaceutically acceptable salt thereof (e.g., eribulin mesylate) through a macrocyclization strategy. The macrocyclization strategy of the present invention involves subjecting a non-macrocyclic intermediate to a carbon-carbon bond-forming reaction (e.g., an olefination reaction (e.g., Horner-Wadsworth-Emmons olefination), Dieckmann reaction, catalytic Ring-Closing Olefin Metathesis, or Nozaki-Hiyama-Kishi reaction) to afford a macrocyclic intermediate. The invention also provides compounds useful as intermediates in the synthesis of eribulin or a pharmaceutically acceptable salt thereof and methods for preparing the same.

5 Claims, 7 Drawing Sheets

(56) References Cited

U.S. PATENT DOCUMENTS

| | | |
|---|---|---|
| 9,382,262 B2 | 7/2016 | Endo et al. |
| 9,469,651 B2 | 10/2016 | Hu |
| 9,604,993 B2 | 3/2017 | Chase et al. |
| 9,695,188 B2 | 7/2017 | Hu et al. |
| 9,783,549 B2 | 10/2017 | Fang et al. |
| 9,802,953 B2 | 10/2017 | Chase et al. |
| 9,856,276 B2 | 1/2018 | Endo et al. |
| RE46,965 E | 7/2018 | Austad et al. |
| 10,030,032 B2 | 7/2018 | Hu et al. |
| 10,214,539 B2 | 2/2019 | Chase et al. |
| 10,221,189 B2 | 3/2019 | Fang et al. |
| 10,308,661 B2 | 6/2019 | Fang et al. |
| 10,344,038 B2 | 7/2019 | Kishi et al. |
| 10,450,324 B2 | 10/2019 | Hu et al. |
| 10,494,388 B2 | 12/2019 | Endo et al. |
| RE47,797 E | 1/2020 | Benayoud et al. |
| 10,611,773 B2 | 4/2020 | Fang et al. |
| 10,633,392 B2 | 4/2020 | Kishi et al. |
| 10,676,481 B2 | 6/2020 | Baran et al. |
| 10,717,743 B2 | 7/2020 | Chase et al. |
| 10,934,307 B2 | 3/2021 | Fang et al. |
| 2002/0103387 A1 | 8/2002 | Smith et al. |
| 2004/0092581 A1 | 5/2004 | Burzlaff et al. |
| 2006/0045846 A1 | 3/2006 | Horstmann et al. |
| 2009/0093649 A1 | 4/2009 | Nobis |
| 2009/0203771 A1 | 8/2009 | Inanaga et al. |
| 2010/0184860 A1 | 7/2010 | Yoshimura et al. |
| 2011/0184190 A1 | 7/2011 | Endo et al. |
| 2012/0029213 A1 | 2/2012 | Austad et al. |
| 2012/0309988 A1 | 12/2012 | Austad et al. |
| 2015/0065733 A1 | 3/2015 | Souza et al. |
| 2015/0225415 A1 | 8/2015 | Chase et al. |
| 2016/0152631 A1 | 6/2016 | Souza et al. |
| 2016/0176895 A1 | 6/2016 | Hu et al. |
| 2016/0214992 A1 | 7/2016 | Chase et al. |
| 2016/0376294 A1 | 12/2016 | Endo et al. |
| 2018/0009825 A1 | 1/2018 | Kovi et al. |
| 2018/0037588 A1 | 2/2018 | Chase et al. |
| 2018/0118755 A1 | 5/2018 | Fang et al. |
| 2018/0162885 A1 | 6/2018 | Endo et al. |
| 2018/0230164 A1 | 8/2018 | Kishi et al. |
| 2019/0144463 A1 | 5/2019 | Fang et al. |
| 2019/0161495 A1 | 5/2019 | Chase et al. |
| 2019/0263826 A1 | 8/2019 | Chase et al. |
| 2019/0300542 A1 | 10/2019 | Baran et al. |
| 2019/0308992 A1 | 10/2019 | Fang et al. |
| 2020/0331928 A1* | 10/2020 | Choi .................. C07F 9/6561 |

FOREIGN PATENT DOCUMENTS

| | | |
|---|---|---|
| EP | 0642345 B1 | 9/2000 |
| JP | 2010-168320 A | 8/2010 |
| JP | 2016-536316 A | 11/2016 |
| RU | 2489437 C2 | 8/2013 |
| SU | 652180 A1 | 3/1979 |
| WO | WO-93/17690 A1 | 9/1993 |
| WO | WO-98/09942 A1 | 3/1998 |
| WO | WO-2006/076100 A2 | 7/2006 |
| WO | WO-2008/010776 A1 | 1/2008 |
| WO | WO-2009/014105 A1 | 1/2009 |
| WO | WO-2009/064029 A1 | 5/2009 |
| WO | WO-2012/147900 A1 | 11/2012 |
| WO | WO-2013/078559 A1 | 6/2013 |
| WO | WO-2013/142999 A1 | 10/2013 |
| WO | WO-2015/000070 A1 | 1/2015 |
| WO | WO-2016/038624 A1 | 3/2016 |
| WO | WO-2016/179607 A1 | 11/2016 |
| WO | WO-2017/139664 A1 | 8/2017 |
| WO | WO-2018/006031 A1 | 1/2018 |
| WO | WO-2018/217894 A1 | 11/2018 |
| WO | WO-2019/136145 A1 | 7/2019 |

OTHER PUBLICATIONS

Aicher et al., "Synthetic studies towards halichondrins: synthesis of the C.27-C.38 segment," Tetrahedron Lett. 33(12):1549-52 (1992).
Aicher et al., "Total synthesis of halichondrin B and norhalichondrin B," J Am Chem Soc. 114(8):3162-4 (1992).
Aicher, Thesis, Chapter 4, "Synthetic studies towards halichondrin B," Doctor of Philosophy in Chemistry, Harvard University, 35-54, 1989 (26 pages).
AkzoNobel Polymer Chemicals, "Diisobutylaluminum hydride (DIBAL-H) and other isobutyl aluminum Alkyls (DIBAL-BOT, TIBAL) as specialty organic synthesis reagents," The AkzoNobel Technical Bulletin, 1-14 (2006).
Alley et al. "Comparison of the relative efficacies and toxicities of Halichondrin B analogues," Proceedings of the AACR-NCI-EORTC Conference on Molecular Targets and Cancer Therapeutics. C230:257 (2005).
Anderson, "Developing processes for crystallization-induced asymmetric transformation," Org Process Res Dev. 9:800-13 (2005).
Ando et al., "Z-selective intramolecular Horner-Wadsworth-Emmons reaction for the synthesis of macrocyclic lactones," Org Lett. 12(7):1460-3 (2010).
Astles et al., "Cembranoid Synthesis Using Ketophosphonate—Aldehyde Cyclization: Syntheses of Thunbergols and alpha- and beta-cembra-2,7,11-triene-4,6-diols," Synlett. 1:42-5 (1989).
Austad et al. (2005): STN International HCAPLUS database, Columbus (OH), accession No. 2005:1313925.
Austad et al., "Commercial manufacture of Halaven®: chemoselective transformations en route to structurally complex macrocyclic ketones," Synlett. 24 (2013). Supporting Information, (13 pages.).
Austad et al., "Commercial manufacture of Halaven®: chemoselective transformations en route to structurally complex macrocyclic ketones," Synlett. 24(3):333-7 (2013).
Austad et al., "Process development of Halaven®: synthesis of the C14-C35 fragment via iterative Nozaki-Hiyama-Kishi reaction—Williamson ether cyclization," Synlett. 24(3):327-32 (2013).
Bai et al., "Halichondrin B and Homohalichondrin B, marine natural products binding in the vinca domain of tubulin. Discovery of tubulin-based mechanism of action by analysis of differential cytotoxicity data," J Biol Chem. 266(24):15882-9 (1991).
Bernet et al., "Carbocyclische verbindungen aus monosacchariden. Umsetzungen in der glucosereihe," Helv Chim Acta. 62(6):1990-2016 (1979).
Blanchette et al., "Horner-Wadsworth-Emmons reaction: use of lithium chloride and an amine for base-sensitive compounds," Tetrahedron Lett. 25(21):2183-6 (1984).
Burke et al., "Enantioselective synthesis of a Halichondrin B C(20) → C(36) precursor," Tetrahedron Lett. 36(39):7023-6 (1995).
Burke et al., "Synthesis of a C(22)-C(34) Halichondrin B precursor via ring opening—double ring closing metathesis," J Org Chem. 63:8626-7 (1998).
Burke et al., "Synthesis of a C(22) → C(34) Halichondrin precursor via a double dioxanone-to-dihydropyran rearrangement," Tetrahedron Lett. 32(32):3961-4 (1991).
Burke et al., "Synthetic studies toward complex polyether macrolides of marine origin," Spec Publ R Soc Chem. 198:(Anti-Infectives) 73-85 (1997).
Carruthers et al., Main-group chemistry. *Modern Methods of Organic Synthesis, Fourth Edition*. Cambridge University Press, 65 (2004).
Chase et al., "Process development of Halaven®: Synthesis of the C1-C13 fragment from D-(–)-Gulono-1, 4-lactone," Synlett. 24(3):323-6 (2013).
Chen et al., "Ni(II)/Cr(II)-mediated coupling reaction: An asymmetric process," J Org Chem. 60(17):5386-7 (1995).
Choi et al., "Asymmetric Ni(II)/Cr(II)-mediated coupling reaction: catalytic process," Org Lett. 4(25):4435-8 (2002).
Choi et al., "Prins reaction of homoallenyl alcohols: Access to substituted pyrans in the halichondrin series," Org Lett. 19(22): 6092-5 (2017).
Choi et al., "Supporting information for asymmetric Ni(II)/Cr(II)-mediated coupling reaction: catalytic process," Org Lett. 4(25) (2002) (8 pages).
Choi et al., "Synthetic studies on the marine natural product Halichondrins," Pure Appl Chem. 75(1):1-17 (2003).

(56) References Cited

OTHER PUBLICATIONS

Cooper et al., "Total Synthesis of Halichondrin B from common sugars: an F-ring intermediate from D-glucose and efficient construction of the C1 to C21 segment," Tetrahedron Lett. 34(51):8193-6 (1993).
Cunningham et al., "The influence of pH on the kinetic constants of alpha-chymotrypsin-catalyzed esterolysis," J Biol Chem. 221(1):287-99 (1956).
Dabydeen et al., "Comparison of the activities of the truncated Halichondrin B analog NSC 707389 (E7389) with those of the parent compound and a proposed binding site on tubulin," Mol Pharmacol. 70(6):1866-75 (2006).
Del Valle et al., "Total synthesis of (+)-trienomycins A and F via C-C bond-forming hydrogenation and transfer hydrogenation," J Am Chem Soc. 135(30):10986-89 (2013).
Dong et al., "New syntheses of E7389 C14-C35 and halichondrin C14-C38 building blocks: reductive cyclization and oxy-michael cyclization approaches," J Am Chem Soc. 131(43):15642-6 (2009).
Duan et al., "Synthetic studies on halichondrins: a new practical synthesis of the C.1-C.12 segment," Tetrahedron Lett. 34(47):7541-4 (1993).
Extended European Search Report for European Application No. 20156829.2, dated Apr. 22, 2020 (6 pages).
Extended European Search Report for European Patent Application No. 14858240.6, dated Mar. 28, 2017 (7 pages).
Favretto et al., "Highly regioselective microwave-assisted synthesis of enantiopure $C_3$-symmetric trialkanolamines," Tetrahedron Letters. 43(14): 2581-2584 (2002).
Fleming et al., "Nitrile anion cyclizations," Tetrahedron. 58(1):1-23 (2002).
Gesinski et al., "Symmetric macrocycles by a Prins dimerization and macrocyclization strategy," available in PMC Nov. 1, 2010, published in final edited form as: Org Lett. 11(22):5342-5 (2009) (13 pages).
Gradillas et al., "Macrocyclization by ring-closing metathesis in the total synthesis of natural products: reaction conditions and limitations," Angew Chem Int Ed Engl. 45(37): 6086-6101 (2006).
Guo et al., "Toolbox approach to the search for effective ligands for catalytic asymmetric Cr-mediated coupling reactions," J Am Chem Soc. 131(42):15387-93 (2009).
Hatakeyama et al., "Preparation of racemic and chiral alkyl(1,3-butadien-2-yl)methanol derivatives utilizing 1-trimethylsilyl-2,3-butadiene as a diene source," Tetrahedron Letters. 32(35):4509-12 (1991).
Hirata et al., "Halichondrins—antitumor polyether macrolides from a marine sponge," Pure Appl Chem. 58(5):701-10 (1986).
Hori et al., "Efficient synthesis of 2,3-trans-tetrahydropyrans and oxepanes: rearrangement-ring expansion of cyclic ethers having a chloromethanesulfonate," Tetrahedron Lett. 40(11):2145-8 (1999).
Horita et al., "Research on anti-tumor active site of marine source natural product, Halichondrin B," International Congress Series, 1157 (Towards Natural Medicine Research in the 21st Century), 327-336 (1998).
Horita et al., "Synthetic studies of halichondrin B, an antitumor polyether macrolide isolated from a marine sponge. 2. Efficient synthesis of C16-C26 fragments via construction of the D ring by a highly stereocontrolled iodoetherification," Synlett. 40-43 (1994).
Horita et al., "Synthetic studies of Halichondrin B, an antitumor polyether macrolide isolated from a marine sponge. 3. Synthesis of C27-C36 subunit via completely stereoselective C-glycosylation to the F ring," Synlett. 43-45 (1994).
Horita et al., "Synthetic studies of Halichondrin B, an antitumor polyether macrolide isolated from a marine sponge. 7. Synthesis of two C27-C36 units via construction of the F ring and completely stereoselective C-glycosylation using mixed Lewis acids," Chem Pharm Bull. 45(10):1558-72 (1997).
Horita et al., "Synthetic studies of Halichondrin B, an antitumor polyether macrolide isolated from a marine sponge. 8. Synthesis of the lactone part (C1-C36) via Horner-Emmons coupling between C1-C15 and C16-C36 fragments and yamaguchi lactonization," Tetrahedron Lett. 38(52):8965-8 (1997).
Horita et al., "Synthetic studies on Halichondrin B, an antitumor polyether macrolide isolated from a marine sponge. 9. Synthesis of the C16-C36 unit via stereoselective construction of the D and E rings," Chem Pharm Bull. 46(8):1199-216 (1998).
Horita et al., Synthetic study of a highly antitumorigenic marine phytochemical, Halichondrin B. *Phytochemicals and Phytopharmaceuticals*. Fereidoon Shahidi and Chi-Tang Ho, 386-397 (2000).
International Search Report and Written Opinion for International Application No. PCT/US2014/063960, dated Jan. 21, 2015 (13 pages).
Isagulyants et al., "Condensation of unsaturated compounds with formaldehyde (Prince reaction)." Advances in Chemistry. 37(1): 61-77 (1968).
Jackson et al., "A total synthesis of norhalichondrin B," Angew Chem Int Ed. 48(13):2346-50 (2009).
Jackson et al., "The halichondrins and E7389," Chem Rev. 109(7):3044-79 (2009).
Jiang et al., "A novel route to the F-ring of Halichondrin B. Diastereoselection in Pd(0)-mediated meso and C2 diol desymmetrization," Org Lett. 4(20):3411-4 (2002).
Jiang et al., "A practical synthesis of the F-ring of halichondrin B via ozonolytic desymmetrization of a C(2)-symmetric dihydroxycyclohexene," J Org Chem. 68(3):1150-3 (2003).
Kawaguchi et al., "Drug and crystal polymorphism," Journal of Human Environmental Engineering. 4(2):310-7 (2002) (10 pages).
Kim et al., "New syntheses of E7389 C14-C35 and Halichondrin C14-C38 building blocks: double-inversion approach," J Am Chem Soc. 131 (43):15636-41 (2009).
Ko, "Prins reactions and applications," http://gbdong.cm.utexas.edu/seminar/old/Prins%20reactions%20and%20Applications_Haye%20Min%20Ko.pdf, retrieved Jan. 21, 2020, dated Nov. 28, 2012 (30 pages).
Kong et al., "Total synthesis of the spirocyclic imine marine toxin (−)-gymnodimine and an unnatural C4-epimer," J Am Chem Soc. 133(49): 19844-56 (2011).
Kurosu et al., "Fe/Cr- and Co/Cr-mediated catalytic asymmetric 2-Haloallylations of aldehydes," J Am Chem Soc. 126(39):12248-9 (2004).
Kurosu et al., "Supporting information for Fe/Cr- and Co/Cr-mediated catalytic asymmetric 2-haloallylations of aldehydes," J Am Chem Soc. 126(39) (2004) (31 pages).
Lee et al., "Extension of Pd-Mediated One-Pot Ketone Synthesis to Macrocyclization: Application to a New Convergent Synthesis of Eribulin," J Am Chem Soc. 138(50):16248-51 (2016).
Li et al., "Unified Synthesis of C1-C19 Building Blocks of Halichondrins via Selective Activation/Coupling of Polyhalogenated Nucleophiles in (Ni)/Cr-Mediated Reactions," J Am Chem Soc. 137(19):6226-31 (2015).
Mattocks, "371. Novel reactions of some alpha-acyloxy acid chlorides," J Chem Soc. Resumed. 1918-30 (1964).
Mattocks, "932. Novel reactions of some alpha-acyloxy-acid halides," J Chem Soc. 4840-5 (1964).
Mitsunobu, "The use of diethyl azodicarboxylate and triphenylphosphine in synthesis and transformation of natural products," Synthesis. 1-28 (1981).
Namba et al., "A simple but remarkably effective device for forming the C8-C14 polycyclic ring system of halichondrin B," J Am Chem Soc. 126(25): 7770-1 (2004) (10 pages).
Namba et al., "New catalytic cycle for couplings of aldehydes with organochromium reagents," Org Lett. 6(26):5031-3 (2004).
Narayan et al., "Novel second generation analogs of eribulin. Part II: Orally available and active against resistant tumors in vivo," Bioorg Med Chem Lett. 21(6):1634-8 (2011).
Newman, "Drug evaluation: eribulin, a simplified ketone analog of the tubulin inhibitor Halichondrin B, for the potential treatment of cancer," Curr Opin Invest Drugs. 8(12):1057-66 (2007).
Nicolaou et al., "Total synthesis of brevetoxin A: Part 3: construction of GHIJ and BCDE ring systems," Chem Eur J. 5(2):628-45 (1999).

(56) References Cited

OTHER PUBLICATIONS

Nicolaou et al., "Total synthesis of the CP molecules CP-263, 114 and CP-225,917—Part 1: synthesis of key intermediates and intelligence gathering," Angew Chem Int Ed. 38(11):1669-75 (1999).
PubChem Compound Summary for CID 10501910, <https://pubchem.ncbi.nlm.nih.gov/compound/10501910>, created Oct. 25, 2006, retrieved Aug. 30, 2017 (8 pages).
PubChem Compound Summary for Methyl 2-[(1S,3R,4S,5R,7R,8S,9S,11R)-4,8-diacetyloxy-5-(2-oxoethyl)-2,6,10-trioxatricyclo[7.4.0.03,7]tridecan-11-yl]acetate, <https://pubchem.ncbi.nlm.nih.gov/compound/10501910>, retrieved Jul. 1, 2020 (6 pages).
Ritter, "Synthetic transformations of vinyl and aryl triflates," Synthesis: Reviews. 8:735-62 (1993).
Sakamoto et al., "Stereoselective ring expansion via bicyclooxonium ion. A novel approach to oxocanes," Org Lett. 4(5):675-8 (2002).
Schreiber, "Hydrogen transfer from tertiary amines to trifluoroacetic anhydride," Tetrahedron Lett. 21(11):1027-30 (1980).
Search Report from Russian Application No. 2016121648 dated Aug. 6, 2018 (5 pages).
Search Report issued in Russian Patent Application No. 2019102375, date of completion Jul. 1, 2021 (4 pages).
Seletsky et al., "Structurally simplified macrolactone analogues of halichondrin B," Bioorg Med Chem Lett. 14(22):5547-50 (2004).
Stamos et al., "A mild preparation of vinyliodides from vinylsilanes," Tetrahedron Lett. 37(48):8647-50 (1996).
Stamos et al., "New synthetic route to the C.14-C.38 segment of Halichondrins," J Org Chem. 62(22):7552-3 (1997).
Stamos et al., "Ni(II)/Cr(II)-mediated coupling reaction: beneficial effects of 4-tert-butylpyridine as an additive and development of new and improved workup procedures," Tetrahedron Lett. 38(36):6355-8 (1997).
Stamos et al., "Synthetic studies on Halichondrins: a practical synthesis of the C.1-C.13 segment," Tetrahedron Lett. 37(48):8643-6 (1996).
Sutherland et al., "The synthesis of 6alpha- and 6beta-fluoroshikimic acids," J Chem Soc Chem Commun. 18:1386-7 (1989).
Takai et al., "Reactions of alkenylchromium reagents prepared from alkenyl trifluoromethanesulfonates (triflates) with chromium(II) chloride under nickel catalysis" J Am Chem Soc. 108(19):6048-50 (1986).
Tokunaga et al., "Asymmetric catalysis with water: efficient kinetic resolution of terminal epoxides by means of catalytic hydrolysis," Science. 277(5328):936-8 (1997).
Towle et al., "Halichondrin B macrocyclic ketone analog E7389: medicinal chemistry repair of lactone ester instability generated during structural simplification to clinical Candidate," Annual Meeting of the American Association for Cancer Research, Apr. 6-10, 2002, 5721 (3 pages).
Towle et al., "In vitro and in vivo anticancer activities of synthetic macrocyclic ketone analogues of Halichondrin B," Cancer Res. 61(3):1013-21 (2001).
Ueda et al., "Total synthesis of halichondrin A, the missing member in the halichondrin class of natural products," J Am Chem Soc. 136(13):5171-6 (2014).
Uemura et al., "Norhalichondrin A: an antitumor polyether macrolide from a marine sponge," J Am Chem Soc. 107(16):4796-8 (1985).
Vahdat et al., "Phase II study of eribulin mesylate, a Halichondrin B analog, in patients with metastatic breast cancer previously treated with an anthracycline and a taxane," J Clin Oncol. 27(18):2954-61 (2009).
Varseev et al., "Enantioselective total synthesis of (+)-neosymbioimine," Org Lett. 9(8):1461-4 (2007).
Wan et al., "Asymmetric Ni(II)/Cr(II)-mediated coupling reaction: Stoichiometric process," Org Lett. 4(25):4431-4 (2002) (includes supporting information) (12 pages).
Wan et al., "Asymmetric Ni(II)/Cr(II)-mediated coupling reaction: Stoichiometric process," Org Lett. 4(25):4431-4 (2002).
Wang et al., "Facile preparation of peracetates and per-3-bromobenzoates of alpha-mono- and disaccharides," Molecules. 10(10):1325-34 (2005).
Wang et al., "Structure-activity relationships of halichondrin B analogues: modifications at C.30-C.38" Bioorg Med Chem Lett. 10(10):1029-32 (2000).
Wang et al., "The syntheses of pharmaceutical intermediates in supercritical fluids," Ind Eng Chem Res. 39(12):4487-90 (2000).
Ward et al., "Catalytic enantioselective diels-alder reaction by self-assembly of the components on a Lewis acid template," Org Lett. 7(16):3533-6 (2005) (Abstract only) (2 pages).
Xie et al., "Synthesis of the C20-C26 building block of Halichondrins via a regiospecific and stereoselective SN2' reaction," Org Lett. 4(25): 4427-9 (2002).
Yahata et al., "Unified Synthesis of Right Halves of Halichondrins A-C," J Org Chem. 82(17):8792-8807 (2017).
Yamamoto et al., "Total synthesis of halichondrin C," J Am Chem Soc. 134(2):893-6 (2012).
Yan et al., "Selective activation/coupling of polyhalogenated nucleophiles in ni/cr-mediated reactions: synthesis of c1-c19 building block of halichondrin bs," J Am Chem Soc. 137(19):6219-25 (2015).
Yang et al., "Second generation synthesis of C27-C35 building block of E7389, a synthetic Halichondrin analogue," Org Lett. 11(20): 4516-9 (2009).
Youssefyeh, "Acylations of ketals and enol ethers," J Am Chem Soc. 85(23):3901-2 (1963).
Yu et al., "Atom-based enumeration: new eribulin analogues with low susceptibility to P-glycoprotein-mediated drug efflux," Bioorg Med Chem Lett. 22(24):7363-6 (2012).
Yu et al., "From micrograms to grams: scale-up synthesis of eribulin mesylate," Nat Prod Rep. 30(9):1158-64 (2013).
Yu et al., "Macrocyclic drugs and synthetic methodologies toward macrocycles," Molecules 18(6):6230-68 (2013).
Yu et al., "New synthetic route to the C.14-C.21 fragment of Halichondrin B," Book of Abstracts. 219th ACS National Meeting, San Francisco, CA, Mar. 26-30, 2000 (1 page).
Yu et al., Discovery of E7389 a fully synthetic macrocyclic ketone analog of Halichondrin B. *Anticancer Agents from Natural Products*. CRC Press, 241-265 (2005) (27 pages).
Zheng et al., "Macrocyclic ketone analogues of halichondrin B," Bioorg Med Chem Lett. 14(22):5551-4 (2004).
Zheng et al., "Synthetic macrocyclic ketone analogs of halichondrin B: structure-activity relationships" Proceedings of the American Association for Cancer Research, 41:301, Abstract #1915 (2000).

* cited by examiner

MACROCYCLIZATION REACTIONS AND INTERMEDIATES AND OTHER FRAGMENTS USEFUL IN THE SYNTHESIS OF ANALOGS OF HALICHONDRIN B

BACKGROUND

The invention relates to intermediates useful in the synthesis of pharmaceutically active macrolide compounds and methods of synthesizing macrolide compounds. Halichondrin B is a potent anticancer agent originally isolated from the marine sponge *Hachondria okadai*, and subsequently found in *Axinella* sp., *Phakellia carter*, and *Lissodendaryx* sp. A total synthesis of halichondrin B was published in 1992 (Aicher, T. D. et al., J. Am. Chem. Soc. 114:3162-3164). Eribulin mesylate (also called Halaven®, E7389, and the mesylate salt of B1939), a nontaxane microtubule dynamics inhibitor, is a structurally simplified, synthetic analogue of halichondrin B. Methods and intermediates for the synthesis of eribulin mesylate and other halichondrin B analogues are described in International Publication Nos. WO 2005/118565, WO 2009/046308, WO 2009/064029, and WO 2009/124237; U.S. Pat. No. 6,214,865; Austad et al., Synlett 24(3):333-337, 2013; Austad et al., Synlett. 24(3):327-332, 2013; and Chase et al., Synlett 24(3):323-326, 2013; each of which is hereby incorporated by reference in its entirety. New methods for the synthesis of halichondrin B analogs, in particular eribulin, are desirable.

SUMMARY OF THE INVENTION

In general, the present invention provides methods for macrocyclization of intermediates in the synthesis of eribulin or a pharmaceutically acceptable salt thereof (e.g., eribulin mesylate). The invention also provides intermediates that can be employed in the macrocyclization reactions described herein.

In a first aspect, the invention provides a method of preparing an intermediate in the synthesis of eribulin, the method including performing a macrocyclization reaction on a non-macrocyclic intermediate, the macrocyclization reaction producing the intermediate in the synthesis of eribulin by forming a C.15-C.16, C.2-C.3, C.3-C.4, C.19-C.20, C.0-C.1, or C.26-C.27 bond in the structure of eribulin.

In some embodiments of the first aspect, performing the macrocyclization reaction can involve contacting the non-macrocyclic intermediate (e.g., a compound of formula (IA)) with an olefin metathesis catalyst (e.g., a ruthenium-carbene complex). The non-macrocyclic intermediate can be a compound of formula (IA) or a salt thereof:

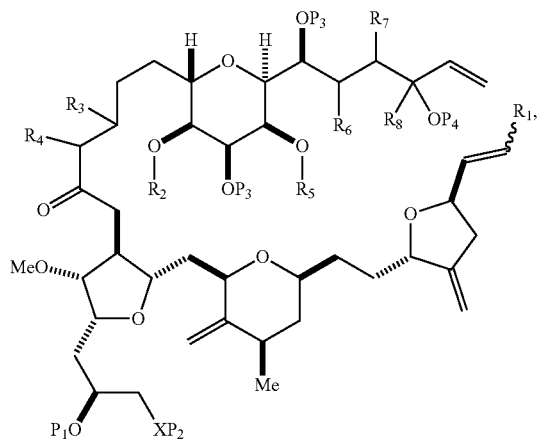

where $R_1$ is H or $-CH_2X_1CH_2CH=CH_2$, where $X_1$ is O, $-C(R_9)_2-$, or $NP_5$, and where each $R_9$ is independently H or $-COOR_{10}$, $P_5$ is an N-protecting group, and $R_{10}$ is $C_{1-6}$ alkyl;

(a1) $R_2$ is H or a hydroxyl protecting group, $R_3$ is $C_{1-6}$ alkyl ether, and $R_4$ is H;

(a2) $R_2$ is H or a hydroxyl protecting group, and $R_3$ and $R_4$ combine to form a double bond;

or (a3) $R_2$ and $R_3$ combine to form a bond, and $R_4$ is H;

(b1) $R_5$ is H or a hydroxyl protecting group, and $R_6$ and $R_7$ combine to form a double bond;

or (b2) $R_5$ and $R_6$ combine to form a bond, and $R_7$ is H;

(c1) $R_8$ is H, and $P_4$ is H or a hydroxyl protecting group;

or (c2) $R_8$ and $P_4$ combine to form a double bond;

each $P_3$ is independently H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl; and where the intermediate in the synthesis of eribulin can be a compound of formula (IB) or a salt thereof:

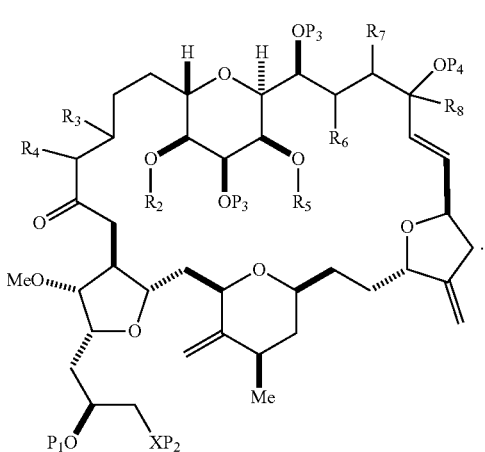

(IB)

In formula (IA) or (IB), each $P_3$ and $P_4$ can be independently a hydroxyl protecting group (e.g., a silyl). In formula (IA) or (IB), $P_1$ can be a hydroxyl protecting group (e.g., a silyl). In formula (IA) or (IB), X can be O. In formula (IA) or (IB), $P_2$ is a hydroxyl protecting group (e.g., a silyl). In formula (IA) or (IB), X can be N, and $P_1$ and $P_2$, together with the atoms to which each is attached, can combine to form an aminal. In formula (IA) or (IB), $R_2$ and $R_3$ can combine to form a bond, and $R_4$ can be H. In formula (IA) or (IB), $R_5$ and $R_6$ can combine to form a bond, and $R_7$ can be H. In formula (IA) or (IB), $R_8$ can be H, and $P_4$ can be a hydroxyl protecting group (e.g., a silyl).

In particular embodiments of the first aspect, performing the macrocyclization reaction involves reacting the non-macrocyclic intermediate (e.g., a compound of formula (IIA)) with an organic base (e.g., an organic base having a pKa of 11±2 (e.g., DBU or trialkylamine (e.g., triethylamine))) and a Lewis acid (e.g., a salt of Li, Mg, or Zn (e.g., lithium chloride or zinc trifluoromethanesulfonate)). In particular, the method can involve performing a Horner-Wadsworth-Emmons reaction on the compound of formula (IIA) to afford the compound of formula (IIB). The non-macrocyclic intermediate can be a compound of formula (IIA) or a salt thereof:

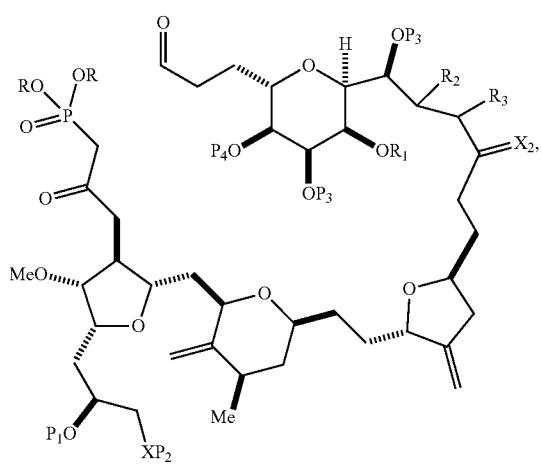

(IIA)

where
  each R is independently optionally substituted alkyl or optionally substituted aryl;
  (i) $R_1$ is H or a hydroxyl protecting group, and $R_2$ and $R_3$ combine to form a double bond;
  or
  (ii) $R_1$ and $R_2$ combine to form a bond, and $R_3$ is H;
  each $P_3$ is independently H or a hydroxyl protecting group, and $X_2$ is oxo; or both $P_3$ groups and $X_2$, together with the atoms to which each is attached, combine to form ketal;
  $P_4$ is H or a hydroxyl protecting group; and
    X is O, and
      each of $P_1$ and $P_2$ is independently H or a hydroxyl protecting group,
    or
      $P_1$ and $P_2$, together with the atoms to which each is attached, combine to form a cyclic protected diol;
  or
    X is N, and
      $P_1$ is H or a hydroxyl protecting group, and X and $P_2$ combine to form optionally masked amino;
    or
      $P_1$ and $P_2$, together with the atoms to which each is attached, combine to form an aminal or 1,3-oxazolidin-2-one-5-yl; and
where the intermediate in the synthesis of eribulin can be a compound of formula (IIB) or a salt thereof:

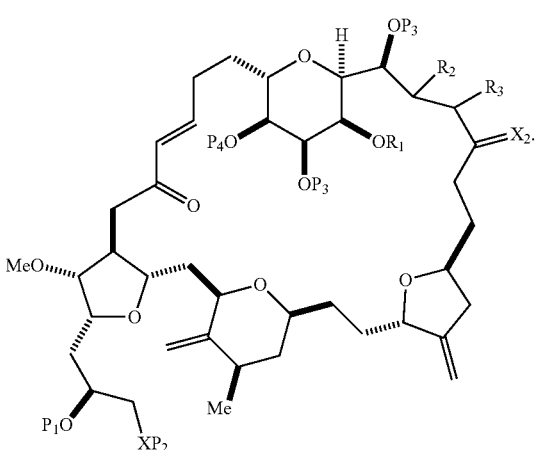

(IIB)

In formula (IIA), each R can be optionally substituted alkyl. In formula (IIA) or (IIB), $P_1$ can be a hydroxyl protecting group (e.g., a silyl). In formula (IIA) or (IIB), $P_2$ can be a hydroxyl protecting group (e.g., a silyl). In formula (IIA) or (IIB), both $P_3$ groups and $X_2$, together with the atoms to which each is attached, can combine to form ketal. In formula (IIA) or (IIB), $R_1$ and $R_2$ can forma bond, and $R_3$ can be H. In formula (IIA) or (IIB), $P_4$ can be a hydroxyl protecting group (e.g., a silyl).

In some embodiments of the first aspect, performing the macrocyclization reaction involves contacting the non-macrocyclic intermediate (e.g., a compound of formula (IIA)) with an olefin metathesis catalyst (e.g., a ruthenium-carbene complex). The non-macrocyclic Intermediate can be a compound of formula (IIA) or a salt thereof:

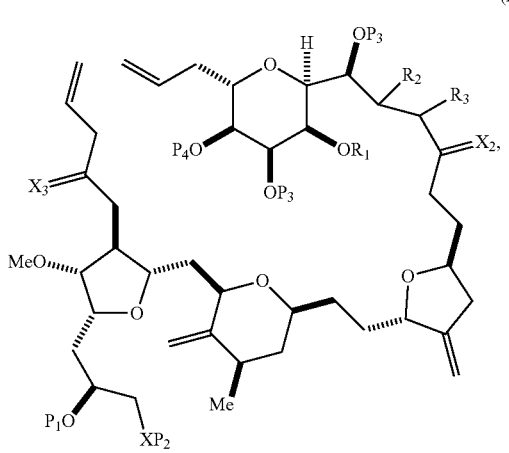

(IIIA)

where
(i) $R_1$ is H or a hydroxyl protecting group, and $R_2$ and $R_3$ combine to form a double bond;
or
(ii) $R_1$ and $R_2$ combine to form a bond, and $R_3$ is H;
$X_3$ is oxo, or $X_3$ combine with the carbon atom to which it is attached to form a ketal, a thioketal, or —(CH($OP_5$))—, where $P_5$ is H or a hydroxyl protecting group;
each $P_3$ is independently H or a hydroxyl protecting group, and $X_2$ is oxo; or both $P_3$ groups and $X_2$, together with the atoms to which each is attached, combine to form ketal;
$P_4$ is H or a hydroxyl protecting group; and
  X is O, and
    each of $P_1$ and $P_2$ is independently H or a hydroxyl protecting group,
    or
    $P_1$ and $P_2$, together with the atoms to which each is attached, combine to form a cyclic protected diol;
  or
  X is N, and
    $P_1$ is H or a hydroxyl protecting group, and X and $P_2$ combine to form optionally masked amino;
    or
    $P_1$ and $P_2$, together with the atoms to which each is attached, combine to form an aminal or 1,3-oxazolidin-2-one-5-yl; and
where the intermediate in the synthesis of eribulin can be a compound of formula (IIIB) or a salt thereof:

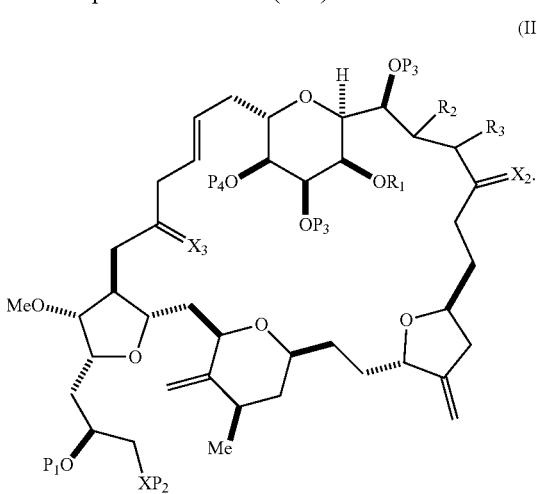

(IIIB)

In formula (IIIA) or (IIIB), $P_4$ can be a hydroxyl protecting group (e.g., a silyl). In formula (IIIA) or (IIIB), both $P_3$ groups and $X_2$, together with the atoms to which each is attached, can combine to form ketal. In formula (IIIA) or (IIIB), $R_1$ and $R_2$ can form a bond, and $R_3$ can be H. In formula (IIIA) or (IIIB), $X_3$ can combine with the carbon atom to which it is attached to form —(CH($OP_5$))—. In particular, in formula (IIIA) or (IIIB), $P_5$ can be H. In formula (IIIA) or (IIIB), $P_1$ can be a hydroxyl protecting group (e.g., silyl). In formula (IIIA) or (IIIB), $P_2$ can be a hydroxyl protecting group.

In certain embodiments of the first aspect, performing the macrocyclization reaction includes contacting the non-macrocyclic intermediate (e.g., a compound of formula (IVA)) with a Cr(II) salt and a Ni(II) salt. In particular, the method can involve subjecting a compound of formula (IVA) to Nozaki-Hiyama-Kishi reaction conditions. The non-macrocyclic intermediate can be a compound of formula (IVA) or a salt thereof:

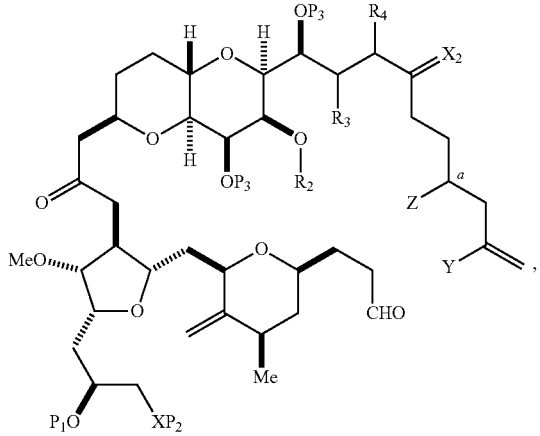

(IVA)

where
Y is iodide, bromide, or trifluoromethanesulfonate;
a can designate R stereogenic center, and Z is a sulfonate, chloride, bromide, or iodide; or a can designate S stereogenic center, and Z is $OR_1$, where $R_1$ is a hydroxyl protecting group;
(i) $R_2$ is H or a hydroxyl protecting group, and $R_3$ and $R_4$ combine to form a double bond;
or
(ii) $R_2$ and $R_3$ combine to form a bond, and $R_4$ is H;
each $P_3$ is independently H or a hydroxyl protecting group, and $X_2$ is oxo; or both $P_3$ groups and $X_2$, together with the atoms to which each is attached, combine to form ketal; and
  X is O, and
    each of $P_1$ and $P_2$ is independently H or a hydroxyl protecting group,
    or
    $P_1$ and $P_2$, together with the atoms to which each is attached, combine to form a cyclic protected diol;
  or
  X is N, and
    $P_1$ is H or a hydroxyl protecting group, and X and $P_2$ combine to form optionally masked amino;

or

P₁ and P₂, together with the atoms to which each is attached, combine to form an aminal or 1,3-oxazolidin-2-one-5-yl; and where the intermediate in the synthesis of eribulin can be a compound of formula (IVB) or a salt thereof:

(IVB)

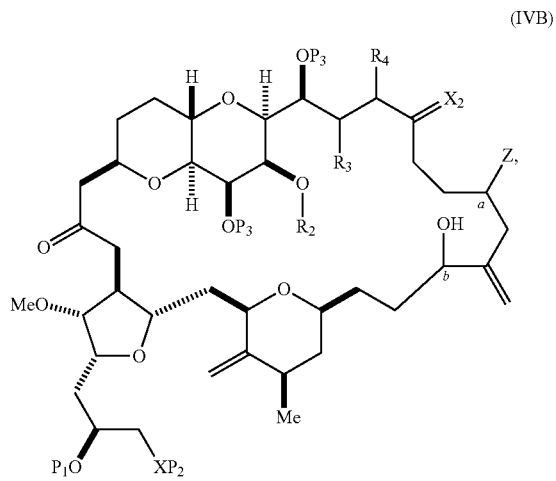

where
- a designates R stereogenic center, b designates S stereogenic center, and Z is a sulfonate, chloride, bromide, or iodide;

or
- a designates S stereogenic center, b designates R stereogenic center, and Z is OR₁, where R₁ is a hydroxyl protecting group.

In formula (IVA) or (IVB), Y can be bromide. In formula (IVA) or (IVB), R₂ and R₃ can combine to form a bond, and R₄ can be H. In formula (IVA) or (IVB), both P₃ groups and X₂, together with the atoms to which each is attached, can combine to form ketal. In formula (IVA) or (IVB), P₁ can be a hydroxyl protecting group (e.g., a silyl). In formula (IVA) or (IVB), P₂ can be a hydroxyl protecting group (e.g., a silyl). In formula (IVA) or (IVB), Z can be a sulfonate. In formula (IVA) or (IVB), Z can be OR₁, where R₁ can be a hydroxyl protecting group (e.g., Z can be an ester, carbonate, or carbamate (e.g., Z can be an ester)).

In some embodiments of the first aspect, performing the macrocyclization reaction involves contacting the non-macrocyclic intermediate (e.g., a compound of formula (VA)) with a base (e.g., a tertiary $C_{4-6}$ alkoxide (e.g., an alkali tertiary $C_{4-6}$ alkoxide)). In particular, the method can involve subjecting a compound of formula (VA) to the Dieckmann reaction conditions. The non-macrocyclic intermediate can be a compound of formula (VA) or a salt thereof:

(VA)

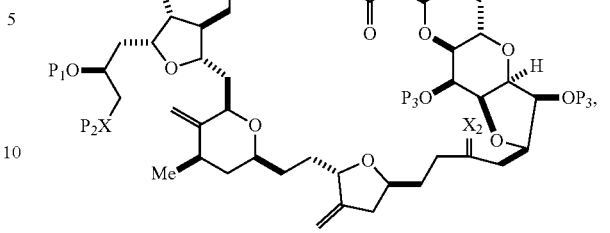

where

Y is $SO_2R_1$ or $COOR_1$, where, when Y is $SO_2R_1$, $R_1$ is optionally substituted aryl or optionally substituted non-enolizable alkyl, and when Y is $COOR_1$, $R_1$ is optionally substituted alkyl, optionally substituted aryl, or optionally substituted arylalkyl;

each $P_3$ is independently H or a hydroxyl protecting group, and $X_2$ is oxo, or both $P_3$ groups and $X_2$, together with the atoms to which each is attached, combine to form ketal;

$R_2$ is optionally substituted alkyl, optionally substituted arylalkyl, or optionally substituted aryl; and X is O, and
each of $P_1$ and $P_2$ is independently a hydroxyl protecting group, or $P_1$ and $P_2$, together with the atoms to which each is attached, combine to form a cyclic protected diol;

or

X is N, and
$P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl; and where the intermediate in the synthesis of eribulin can be a compound of formula (VB) or a salt thereof:

(VB)

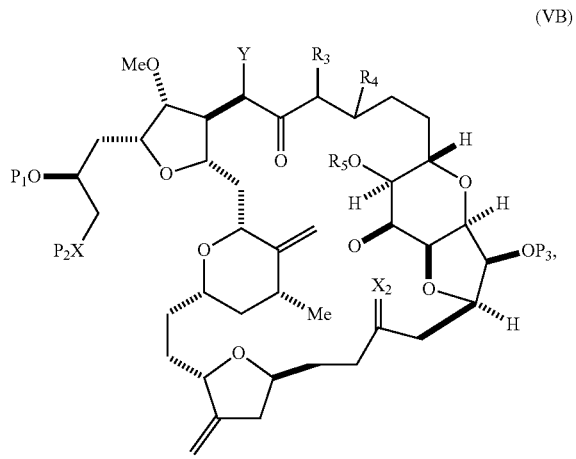

where
(i) $R_3$ is H, $R_4$ is optionally substituted $C_{1-6}$ alkyl ether, and $R_5$ is H;
(ii) $R_5$ is H, and $R_3$ and $R_4$ combine to form a double bond; or
(iii) $R_3$ is H, and $R_4$ and $R_5$ combine to form a bond.

In formula (VA) or (VB), Y can be $SO_2R_1$ (e.g., $R_1$ can be optionally substituted aryl). In formula (VA) or (VB), both $P_3$ groups and $X_2$, together with the atoms to which each is attached, can combine to form ketal. In formula (VA) or (VB), $R_2$ can be optionally substituted alkyl (e.g., unsubstituted $C_{1-6}$ alkyl). In formula (VA) or (VB), $R_3$ can be H, and $R_4$ and $R_5$ can combine to form a bond.

In other embodiments of the first aspect, performing the macrocyclization reaction includes contacting the non-macrocyclic intermediate (e.g., a compound of formula (VIA)) with a Cr(II) salt and a Ni(II) salt. In particular, the method can involve subjecting a compound of formula (VIA) to Nozaki-Hiyama-Kishi reaction conditions. The non-macrocyclic intermediate can be a compound of formula (VIA) or a salt thereof:

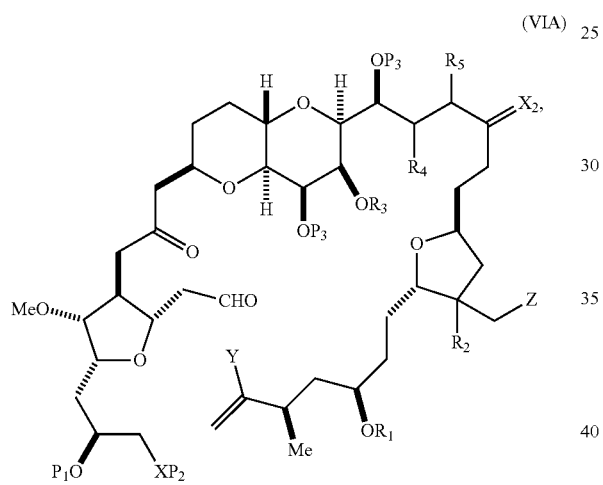

(VIA)

where
Y is iodide, bromide, or trifluoromethanesulfonate;
(a1) $R_3$ is H or a hydroxyl protecting group, $R_4$ and $R_5$ combine to form a double bond, each $P_3$ is independently H or a hydroxyl protecting group, and $X_2$, together with the carbon to which it is attached, form a carbonyl or —(CH($OR_6$))—, where $R_6$ is H or a hydroxyl protecting group;
or
(a2) $R_3$ and $R_4$ combine to form a bond, $R_5$ is H, and each $P_3$ is independently H or a hydroxyl protecting group, and $X_2$, together with the carbon to which it is attached, form a carbonyl or —(CH($OR_6$))—;
or
both $P_3$ groups and $X_2$, together with the atoms to which each is attached, combine to form ketal;
(b1) Z is chloride, bromide, or iodide, and $R_1$ and $R_2$ combine to form a bond;
or
(b2) Z and $R_2$ combine to form a double bond, and $R_1$ is a hydroxyl protecting group; and
X is O, and
each of $P_1$ and $P_2$ is independently H or a hydroxyl protecting group, or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl; and
where the intermediate in the synthesis of eribulin is a compound of formula (VIB) or a salt thereof:

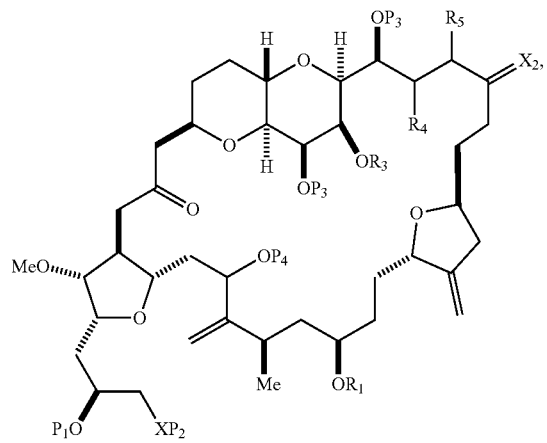

(VIB)

where $P_4$ is H or a hydroxyl protecting group.

In formula (VIA), Z can be iodide, and $R_1$ and $R_2$ can combine to form a bond. In formula (VIA), Y can be trifluoromethanesulfonate. In formula (VIA) or (VIB), $R_1$ can be H, or O and $R_1$ can combine to form a sulfonate. In formula (VIA) or (VIB), $P_1$ can be a hydroxyl protecting group (e.g., a silyl). In formula (VIA) or (VIB), $P_2$ can be a hydroxyl protecting group (e.g., a silyl). In formula (VIA) or (VIB), $R_3$ can be H or a hydroxyl protecting group, $R_4$ and $R_5$ can combine to form a double bond, each $P_3$ can be independently H or a hydroxyl protecting group, and $X_2$, together with the carbon to which it is attached, can form a carbonyl or —(CH($OR_6$))—, where $R_6$ can be H or a hydroxyl protecting group. In formula (VIA) or (VIB), $R_3$ can be a hydroxyl protecting group (e.g., a silyl), $R_4$ and $R_5$ can combine to form a double bond, each $P_3$ can be independently a hydroxyl protecting group, and $X_2$, together with the carbon to which it is attached, can form a carbonyl or —(CH($OR_6$))—, where $R_6$ can be H or a hydroxyl protecting group (e.g., O can combine with $R_6$ to form an ester). In formula (VIB), $P_4$ can be a hydroxyl protecting group (e.g., O and $P_4$ can combine to form an ester).

Preparation of the compound of formula (VIB) from the compound of formula (VIA) can further involve In a second aspect, the invention provides a method of preparing:

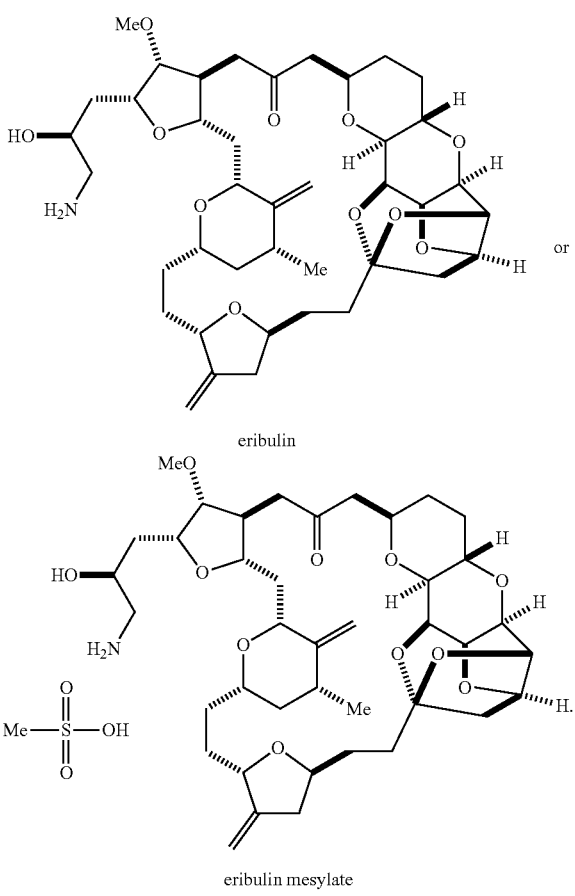

eribulin eribulin mesylate

In some embodiments of the second aspect, the method involves:

(A) producing a compound of formula (IB) from a compound of formula (IA), the compound of formula (IA) having the following structure:

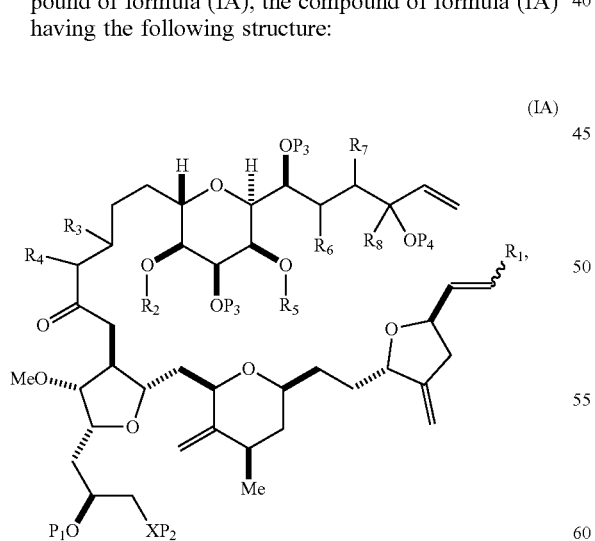

(IA)

where
$R_1$ is H or —$CH_2X_1CH_2CH$=$CH_2$, where $X_1$ is O, —$C(R_9)_2$—, or $NP_5$, and where each $R_9$ is independently H or —$COOR_{10}$, $P_5$ is an N-protecting group, and $R_{10}$ is $C_{1-6}$ alkyl;

(a1) $R_2$ is H or a hydroxyl protecting group, $R_3$ is $C_{1-6}$ alkyl ether, and $R_4$ is H;

(a2) $R_2$ is H or a hydroxyl protecting group, and $R_3$ and $R_4$ combine to form a double bond;

or (a3) $R_2$ and $R_3$ combine to form a bond, and $R_4$ is H;

(b1) $R_5$ is H or a hydroxyl protecting group, and $R_6$ and $R_7$ combine to form a double bond;

or (b2) $R_5$ and $R_6$ combine to form a bond, and $R_7$ is H;

(c1) $R_8$ is H, and $P_4$ is H or a hydroxyl protecting group;

or (c2) $R_8$ and $P_4$ combine to form a double bond;

each $P_3$ is independently H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl;

the compound of formula (IB) having the following structure:

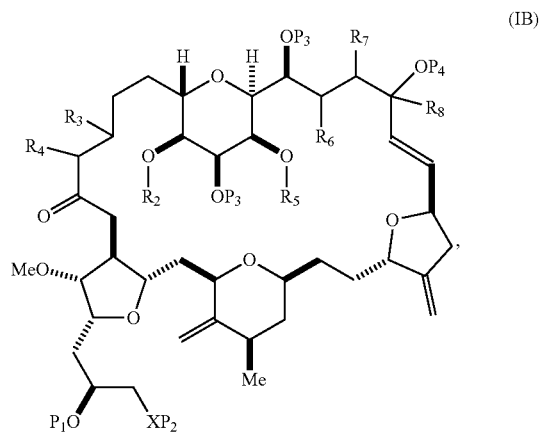

(IB)

where each variable is as defined for formula (IA).

The method can involve (B) producing a compound of formula (IC) from the compound of formula (IB), the compound of formula (IC) having the following structure:

(IC)

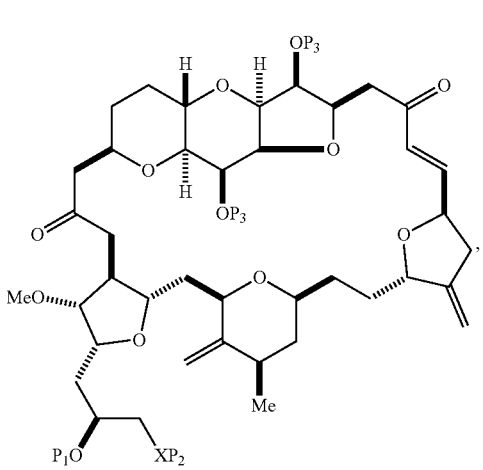

where each variable can be as defined for formula (IB).

The method can involve (C) producing a compound of formula (ID) from the compound of formula (IC), the compound of formula (ID) having the following structure:

(ID)

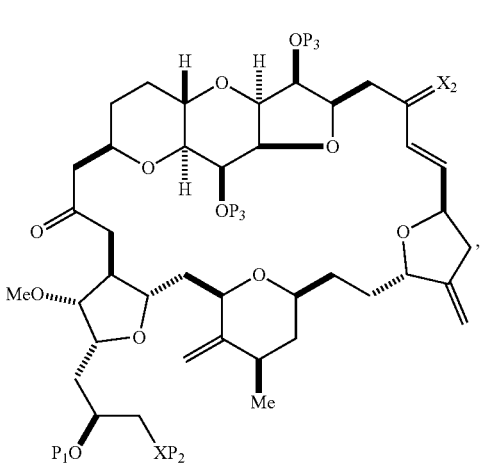

where each $P_3$ is independently H or a hydroxyl protecting group, and $X_2$ is oxo; or both $P_3$ groups and $X_2$, together with the atoms to which each is attached, combine to form ketal; and each of the remaining variables is ne as defined for formula (IC).

The method can further involve (D) producing eribulin or eribulin mesylate from the compound of formula (ID).

In formula (IA) or (IB), $P_4$ can be a hydroxyl protecting group (e.g., a silyl). In formula (IA) or (IB), $R_2$ and $R_3$ can combine to form a bond, and $R_4$ can be H. In formula (IA) or (IB), $R_5$ and $R_6$ can combine to form a bond, and $R_7$ can be H. In formula (IA) or (IB), $R_8$ can be H, and $P_4$ can be a hydroxyl protecting group (e.g., a silyl).

In formula (IA) or (IB), each $P_3$ can be independently a hydroxyl protecting group (e.g., a silyl). In formula (IC), $P_3$ can be H or a hydroxyl protecting group (e.g., a silyl).

In formula (IA), (IB), (IC), or (ID), $P_1$ can be a hydroxyl protecting group (e.g., a silyl). In formula (IA) or (IB), X can be O. In formula (IA), (IB), (IC), or (ID), $P_2$ is a hydroxyl protecting group (e.g., a silyl). In formula (IA), (IB), (IC), or (ID), X can be N, and $P_1$ and $P_2$, together with the atoms to which each is attached, can combine to form an aminal.

The method can further involve oxidizing the compound of formula (IB) (e.g., when $R_8$ is H) with an olefin metathesis catalyst, e.g., by reacting with an oxidizing agent capable of oxidizing an alcohol to a carbonyl group (e.g., Dess-Martin periodinane). If, $P_4$ is a hydroxyl protecting group (e.g., a silyl) in the compound of formula (IB), this compound can be reacted with a hydroxyl protecting group removing agent prior to oxidizing the compound of formula (IB).

Producing the compound of formula (IB) from the compound of formula (IA) can involve reacting the compound of formula (IA) with an olefin metathesis catalyst.

Producing the compound of formula (IC) can include oxidizing the compound of formula (IB), where, in the compound of formula (IB), $R_8$ is H, and $P_4$ is H, e.g., by reacting the compound of formula (IB) with an oxidizing agent capable of oxidizing an alcohol to a carbonyl group (e.g., Dess-Martin periodinane).

Producing the compound of formula (ID) can include reacting the compound of formula (IC) with a 1,4-reducing agent. The compound of formula (ID), in which each $P_3$ is independently a hydroxyl protecting group, can be reacted with a hydroxyl protecting group removing agent to afford the compound of formula (ID), in which each $P_3$ is H or both $P_3$ groups and $X_2$, together with the atoms to which each is attached, combine to form ketal.

In formula (ID), both $P_3$ groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In certain embodiments of the second aspect, the method involves:

(A) producing a compound of formula (IIB) from a compound of formula (IIA) or a salt thereof:

(IIA)

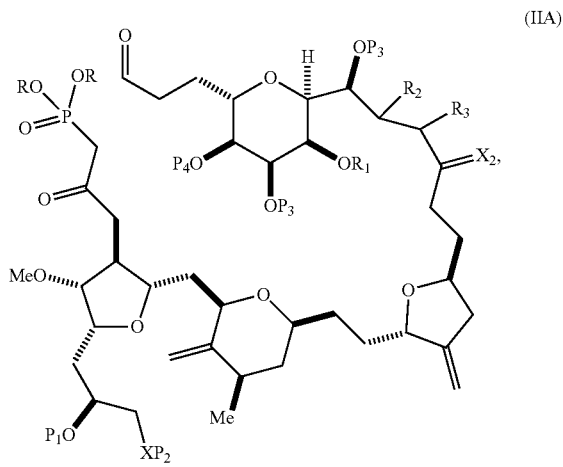

where
each R is independently optionally substituted alkyl or optionally substituted aryl;

(i) $R_1$ is H or a hydroxyl protecting group, and $R_2$ and $R_3$ combine to form a double bond;

or (ii) $R_1$ and $R_2$ combine to form a bond, and $R_3$ is H;

each $P_3$ is independently H or a hydroxyl protecting group, and $X_2$ is oxo; or both $P_3$ groups and $X_2$, together with the atoms to which each is attached, combine to form ketal;

$P_4$ is H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl; and the compound of formula (IIB) having the following structure:

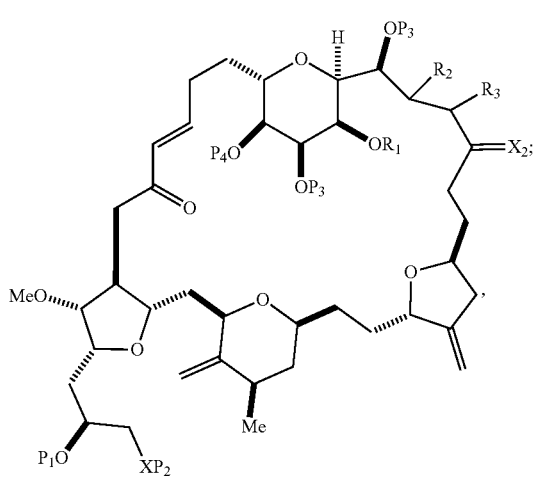

(IIB)

(B) producing a compound of formula (ID) form the compound of formula (IIB), the compound of formula (ID) having the following structure:

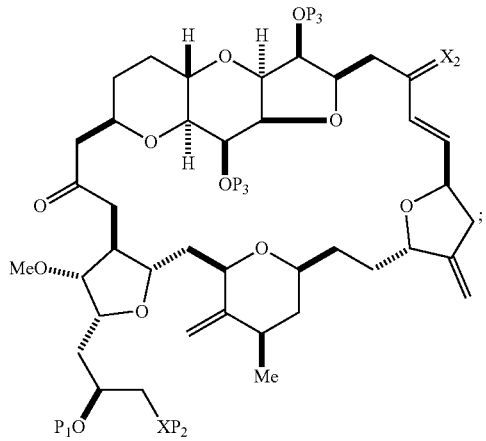

(ID)

and (C) producing eribulin or eribulin mesylate from the compound of formula (ID).

In formula (IIA), each R can be optionally substituted alkyl. In formula (IIA) or (IIB), $P_1$ can be a hydroxyl protecting group (e.g., a silyl). In formula (IIA) or (IIB), $P_2$ can be a hydroxyl protecting group (e.g., a silyl). In formula (IIA) or (IIB), $R_1$ and $R_2$ can form a bond, and $R_3$ can be H. In formula (IIA) or (IIB), $P_4$ can be a hydroxyl protecting group (e.g., a silyl). In formula (IIA), (IIB), or (ID), both $P_3$ groups and $X_2$, together with the atoms to which each is attached, can combine to form ketal.

Producing the compound of formula (IIB) can involve reacting the compound of formula (IIA) with an organic base (e.g., an organic base having a pKa of 11±2 (e.g., DBU or trialkylamine (e.g., triethylamine))) and a Lewis acid (e.g., a salt of Li, Mg, or Zn (e.g., lithium chloride or zinc trifluoromethanesulfonate)).

Producing the compound of formula (ID) can involve reacting the compound of formula (IIB) with a hydroxyl protecting group removing agent.

In formula (ID), both $P_3$ groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In certain embodiments of the second aspect, the method involves:

(A) producing a compound of formula (IIIB) from the compound of formula (IIA), the compound of formula (IIIA) having the following structure:

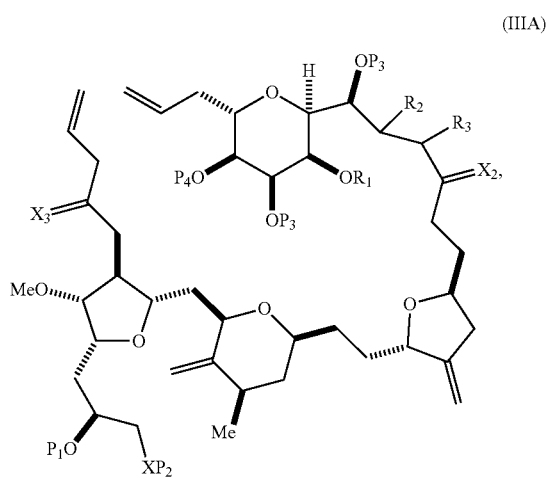

(IIIA)

where (i) $R_1$ is H or a hydroxyl protecting group, and $R_2$ and $R_3$ combine to form a double bond;
or
(ii) $R_1$ and $R_2$ combine to form a bond, and $R_3$ is H;

$X_3$ is oxo, or $X_3$ combines with the carbon atom to which it is attached to form a ketal, a thioketal, or —(CH($OP_5$))—, where $P_5$ is H or a hydroxyl protecting group;

each $P_3$ is independently H or a hydroxyl protecting group, and $X_2$ is oxo; or both $P_3$ groups and $X_2$, together with the atoms to which each is attached, combine to form ketal;

$P_4$ is H or a hydroxyl protecting group; and

X is O, and
each of $P_1$ and $P_2$ is independently H or a hydroxyl protecting group,
or
$P_1$ and $P_2$, together with the atoms to which each is attached, combine to form a cyclic protected diol;
or X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl;

the compound of formula (IIIB) having the following structure:

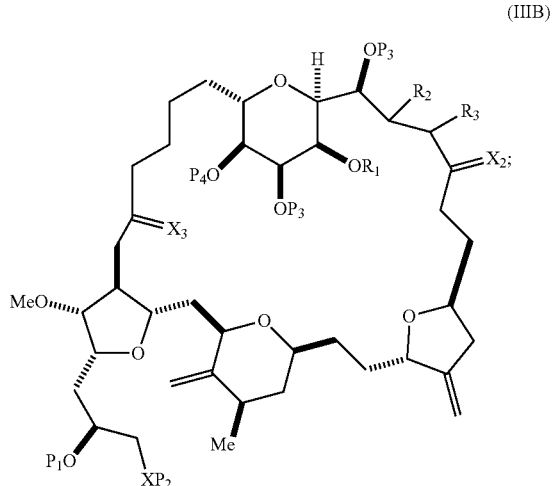

(IIIB)

(B) producing a compound of formula (ID) from the compound of formula (IIIB), the compound of formula (ID) having the following structure:

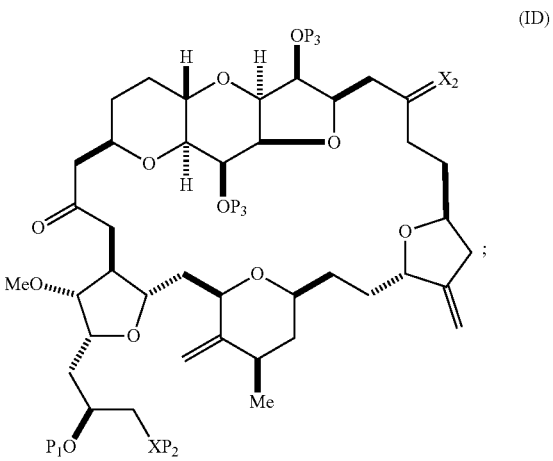

(ID)

and (C) producing eribulin or eribulin mesylate from the compound of formula (ID).

In formula (IIIA) or (IIIB), $P_4$ can be a hydroxyl protecting group (e.g., a silyl). In formula (IIIA) or (IIIB), $R_1$ and $R_2$ can form a bond, and $R_3$ can be H. In formula (IIIA) or (IIIB), $X_3$ can combine with the carbon atom to which it is attached to form —(CH($OP_5$))—. In particular, in formula (IIIA) or (IIIB), $P_5$ can be H. In formula (IIIA) or (IIIB), $P_1$ can be a hydroxyl protecting group (e.g., silyl). In formula (IIIA) or (IIIB), $P_2$ can be a hydroxyl protecting group. In formula (IIIA), (IIIB), or (ID), both $P_3$ groups and $X_2$, together with the atoms to which each is attached, can combine to form ketal.

Producing the compound of formula (IIIB) can involve reacting the compound of formula (IIIA) with an olefin metathesis catalyst.

Producing the compound of formula (ID) can involve oxidizing (e.g., by reacting with an oxidizing agent capable of oxidizing an alcohol to a carbonyl group) the compound of formula (IIIB), where, in the compound of formula (IIIB), $X_3$, together with the carbon to which it is attached, forms —(CH($OP_5$))—, where $P_5$ is H.

Producing the compound of formula (ID) can also involve reacting the compound of formula (IIIB), where, in the compound of formula (IIIB), $P_4$ is a hydroxyl protecting group, and $R_4$ and $R_5$ combine to form a double bond, with a hydroxyl protecting group removing agent.

In formula (ID), both $P_5$ groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In certain embodiments of the second aspect, the method includes:

(A) producing a compound of formula (IVB) from a compound of formula (IVA), the compound of formula (IVA) having the following structure:

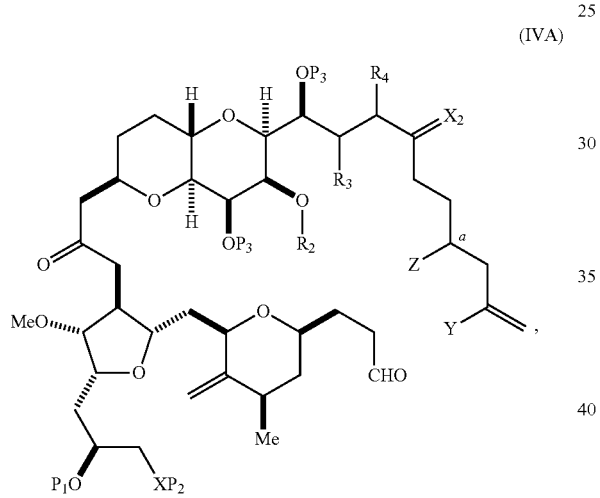

(IVA)

where

Y is iodide, bromide, or trifluoromethanesulfonate;

a designates R stereogenic center, and Z is a sulfonate, chloride, bromide, or iodide; or a designates S stereogenic center, and Z is $OR_1$, where $R_1$ is a hydroxyl protecting group;

(i) $R_2$ is H or a hydroxyl protecting group, and $R_3$ and $R_4$ combine to form a double bond;

or (ii) $R_2$ and $R_3$ combine to form a bond, and $R_4$ is H;

each $P_3$ is independently H or a hydroxyl protecting group, and $X_2$ is oxo; or both $P_5$ groups and $X_2$, together with the atoms to which each is attached, combine to form ketal; and X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl;

the compound of formula (IVB) having the following structure:

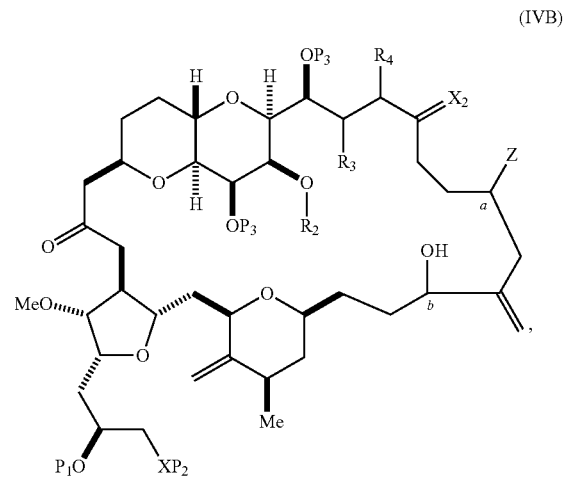

(IVB)

where a designates R stereogenic center, b designates S stereogenic center, and Z is a sulfonate, chloride, bromide, or iodide;

or a designates S stereogenic center, b designates R stereogenic center, and Z is $OR_1$, where $R_1$ is a hydroxyl protecting group;

(B) producing a compound of formula (ID) from the compound of formula (IVB), the compound of formula (ID) having the following structure:

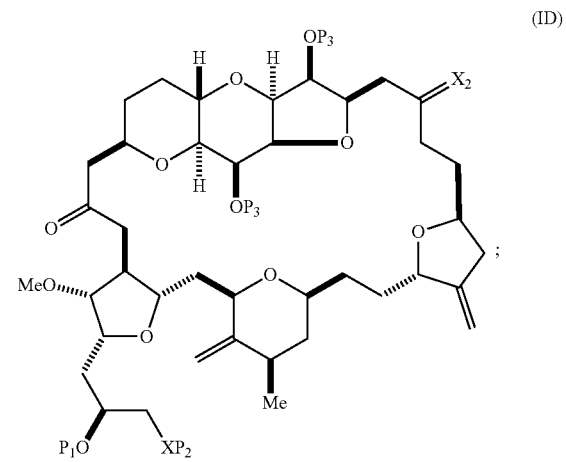

(ID)

and (C) producing eribulin or eribulin mesylate from the compound of formula (ID).

In formula (IVA) or (IVB), Y can be bromide. In formula (IVA) or (IVB), $R_2$ and $R_3$ can combine to form a bond, and $R_4$ can be H. In formula (IVA) or (IVB), $P_1$ can be a hydroxyl protecting group (e.g., a silyl). In formula (IVA) or (IVB), $P_2$ can be a hydroxyl protecting group (e.g., a silyl). In formula (IVA) or (IVB), Z can be a sulfonate. In formula (IVA) or (IVB), Z can be $OR_1$, where $R_1$ can be a hydroxyl protecting group (e.g., Z can be an ester, carbonate, or carbamate (e.g., Z can be an ester)). In formula (IVA), (IVB), or (ID), both $P_3$ groups and $X_2$, together with the atoms to which each is attached, can combine to form ketal.

Producing the compound of formula (IVB) can involve reacting the compound of formula (IVA) with a Cr(II) salt and a Ni(II) salt. Producing the compound of formula (IVB) can involve subjecting the compound of formula (IVA) to Nozaki-Hiyama-Kishi reaction conditions.

Producing the compound of formula (ID) can involve the step of nucleophilic ring-closing of the compound of formula (IVB).

In formula (ID), both $P_5$ groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In particular embodiments of the second aspect, the method includes:

(A) producing a compound of formula (VB) from a compound of formula (VA):

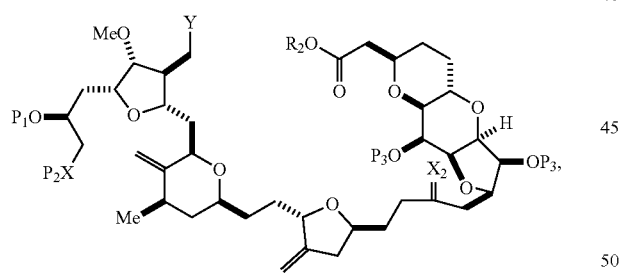

(VA)

where

Y is $SO_2R_1$ or $COOR_1$, where, when Y is $SO_2R_1$, $R_1$ is optionally substituted aryl or optionally substituted non-enolizable alkyl, and when Y is $COOR_1$, $R_1$ is optionally substituted alkyl, optionally substituted aryl, or optionally substituted arylalkyl;

each $P_3$ is independently H or a hydroxyl protecting group, and $X_2$ is oxo, or both $P_3$ groups and $X_2$, together with the atoms to which each is attached, combine to form ketal;

$R_2$ is optionally substituted alkyl, optionally substituted arylalkyl, or optionally substituted aryl; and X is O, and each of $P_1$ and $P_2$ is independently a hydroxyl protecting group, or $P_1$ and $P_2$, together with the atoms to which is each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl;

the compound of formula (VB) having the following structure:

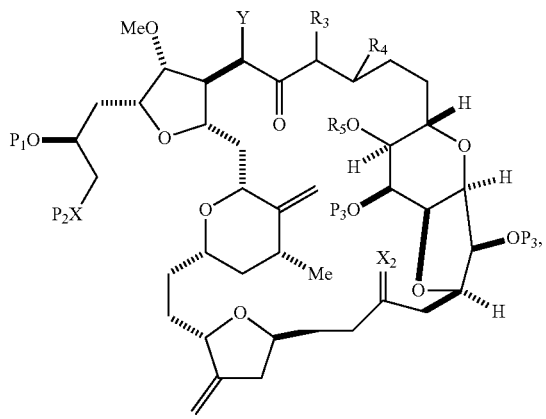

(VB)

where (i) $R_3$ is H, $R_4$ is ether, and $R_5$ is H;

(ii) $R_5$ is H, and $R_3$ and $R_4$, together with the bond connecting the atoms to which each is attached, combine to form a double bond;

or (iii) $R_3$ is H, and $R_4$ and $R_5$ combine to form a bond;

(B) producing a compound of formula (ID) from the compound of formula (VB), the compound of formula (ID) having the following structure:

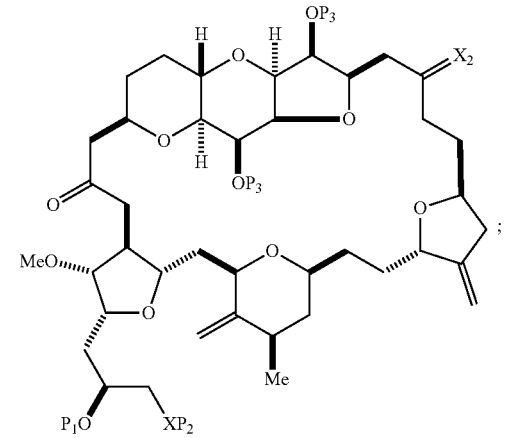

(ID)

and (C) producing eribulin or eribulin mesylate from the compound of formula (ID).

In formula (VA) or (VB), Y can be $SO_2R_1$ (e.g., $R_1$ can be optionally substituted aryl). In formula (VA) or (VB), $R_2$ can be optionally substituted alkyl (e.g., unsubstituted $C_{1-6}$ alkyl). In formula (VB), $R_3$ can be H, and $R_4$ and $R_5$ can combine to form a bond. In formula (VA), (VB), or (ID), both P groups and $X_2$, together with the atoms to which each is attached, can combine to form ketal.

Producing the compound of formula (VB) can involve reacting the compound of formula (VA) with a strong base (e.g., a tertiary $C_{4-6}$ alkoxide).

Producing the compound of formula (ID) can involve reacting the compound of formula (VB), in which Y is $SO_2R_1$, and $R_1$ is optionally substituted aryl, with an electron-transferring reducing agent (e.g., $SmI_2$, Mg(0), or Cr(III) with Mn(0)).

In formula (ID), both $P_5$ groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In other embodiments of the second aspect, the method includes:

(A) producing a compound of formula (VIB) from a compound of formula (VIA), the compound of formula (VIA) having the following structure:

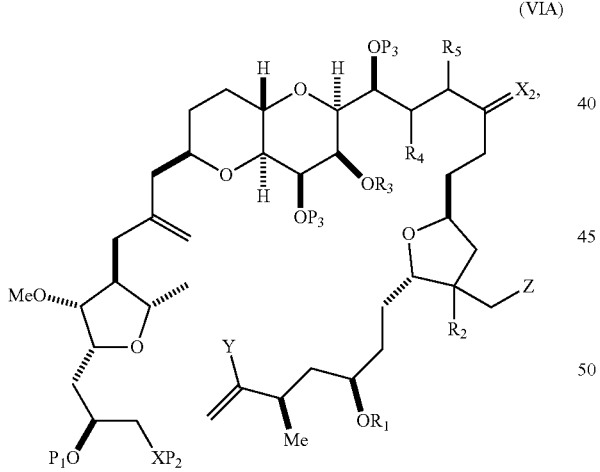

where
Y is iodide, bromide, or trifluoromethanesulfonate;
(a1) $R_3$ is H or a hydroxyl protecting group, $R_4$ and $R_5$ combine to form a double bond, each $P_3$ is independently H or a hydroxyl protecting group, and $X_2$, together with the carbon to which it is attached, forms a carbonyl or —(CH($OR_6$))—, where $R_6$ is H or a hydroxyl protecting group;

or
(a2) $R_3$ and $R_4$ combine to form a bond, $R_5$ is H, and
each $P_3$ is independently H or a hydroxyl protecting group, and $X_2$, together with the carbon to which it is attached, forms a carbonyl or —(CH($OR_6$))—;

or
both $P_3$ groups and $X_2$, together with the atoms to which each is attached, combine to form ketal;

(b1) Z is chloride, bromide, or iodide, and $R_1$ and $R_2$ combine to form a bond;

or
(b2) Z and $R_2$ combine to form a double bond, and $R_1$ is a hydroxyl protecting group; and X is O, and
each of $P_1$ and $P_2$ is independently H or a hydroxyl protecting group, or
$P_1$ and $P_2$, together with the atoms to which each is attached, combine to form a cyclic protected diol;

or
X is N, and
$P_1$ is H or a hydroxyl protecting group, and X and $P_2$ combine to form optionally masked amino;

or
$P_1$ and $P_2$, together with the atoms to which each is attached, combine to form an aminal or 1,3-oxazolidin-2-one-5-yl; and the compound of formula (VIB) having the following structure:

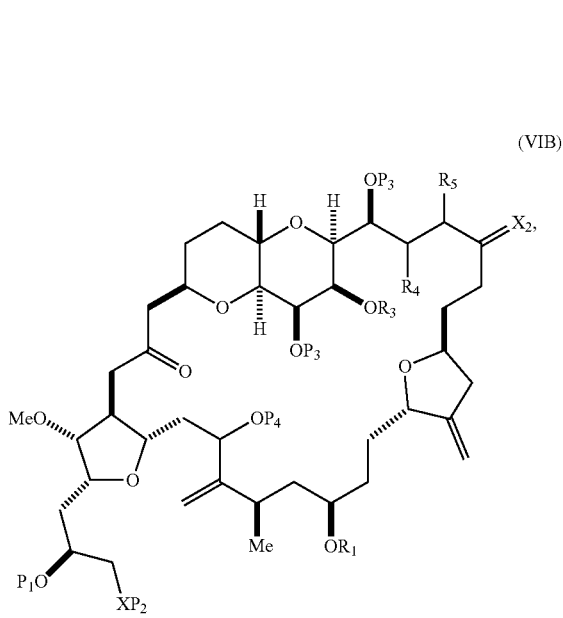

where $P_4$ is H or a hydroxyl protecting group;

(B) producing a compound of formula (VIC) from the compound of formula (VIB), the compound of formula (VIC) having the following structure:

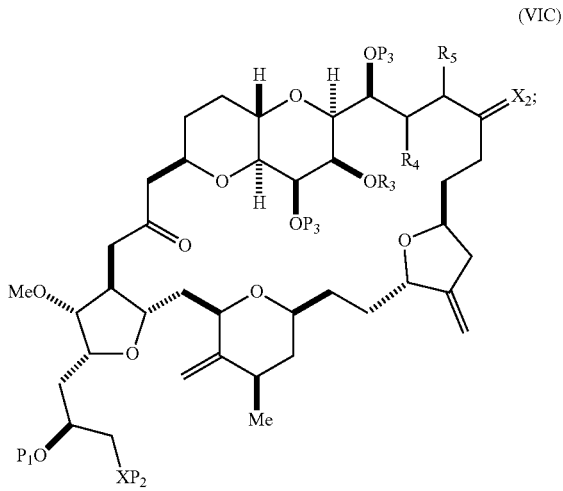

(C) producing a compound of formula (ID) from the compound of formula (VIC), the compound of formula (ID) having the following structure:

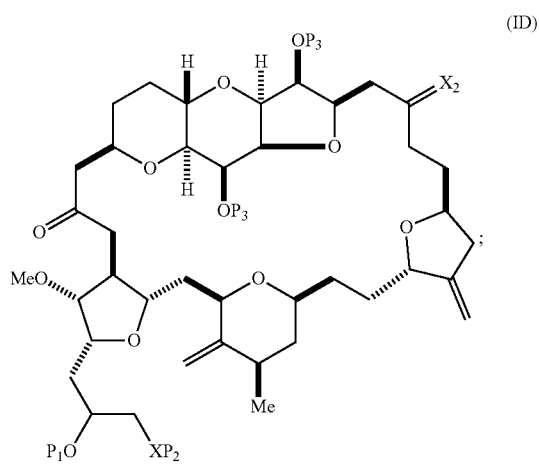

and (D) producing eribulin or eribulin mesylate from the compound of formula (ID).

Producing the compound of formula (VIB) can include reacting the compound of formula (VIA) with a Cr(II) salt and a Ni(II) salt.

Producing the compound of formula (ID) can include reacting the compound of formula (VIB) with a hydroxyl protecting group removing agent.

In formula (ID), both Pa groups and $X_2$, together with the atoms to which each is attached, can combine to form ketal. In formula (ID), $P_1$ can be H. In formula (ID), X can be O, and $P_2$ can be H. Producing eribulin or eribulin mesylate from the compound of formula (ID) can include aminating the compound of formula (ID).

In formula (ID), X and $P_2$ can combine to form a masked amino. Producing eribulin or eribulin mesylate from the compound of formula (ID) can involve reacting the compound of formula (ID) with an amino unmasking agent.

Eribulin mesylate can be produced by salifying eribulin with methanesulfonic acid.

In a third aspect, the invention provides a method of preparing an intermediate in the synthesis of eribulin, the method including performing a Prins reaction by contacting a compound of formula (VIIA) with a compound of formula (VIIB) and $R_3OH$, where $R_3$ can be an optionally substituted acyl;

where the compound of formula (VIIA) can have the following structure:

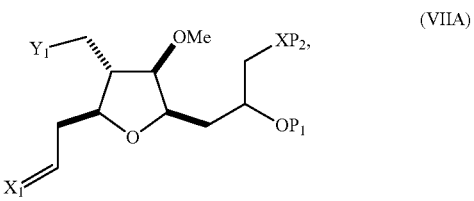

where $Y_1$ is $SO_2R_1$ or $COOR_1$, and $R_1$ is optionally substituted alkyl, optionally substituted aryl, or optionally substituted arylalkyl;

$X_1$ is O, or $X_1$, together with the carbon to which it is attached, forms a cyclic acetal; and X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl;

where the compound of formula (VIIB) can have the following structure:

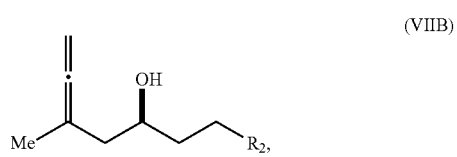

where $R_2$ is —$CH_2$—$OP_3$,

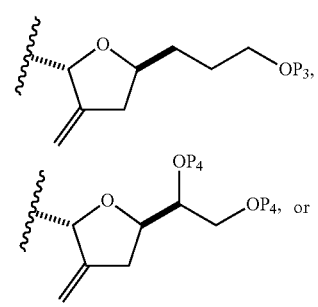

-continued

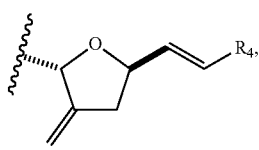

where P$_3$ is H or a hydroxyl protecting group; each P$_4$ is independently a hydroxyl protecting group, or both P$_4$ groups, together with the atoms to which each is attached, combine to form a cyclic protected diol; and R$_4$ is H or —CH$_2$X$_2$CH$_2$CH═CH$_2$, where X$_2$ is O, —CH$_2$—, or NP$_5$, where P$_5$ is sulfonyl;

and where the intermediate is a compound of formula (VIIC):

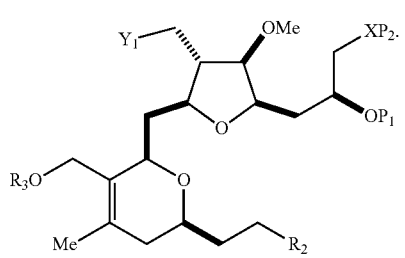
(VIIC)

Performing a Prins reaction can involve reacting the compound of formula (VIIA) with a Lewis acid (e.g., boron trifluoride or a solvate thereof).

In a fourth aspect, the invention provides a method of preparing an intermediate in the synthesis of eribulin, the method can involve:

(A) cleaving the double bond in a compound of formula (VIIIA) to afford a compound of formula (VIIIB), the compound of formula (VIIIA) having the structure:

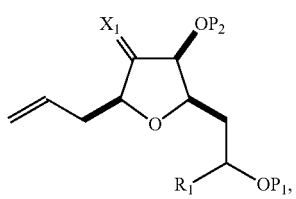
(VIIA)

where
X$_1$ can be oxo, or X$_1$, together with the carbon atom to which it can be attached, forms a ketal or
—(CH(OP$_3$))—, where P$_5$ can be H or a hydroxyl protecting group;
R$_1$ can be H or —CH$_2$OP$_4$;
each of P$_1$, P$_2$, and P$_4$ can be independently a hydroxyl protecting group, or
P$_1$ and P$_4$, together with the atoms to which each can be attached, can combine to form a cyclic protected diol; and the compound of formula (VIIIB) having the structure:

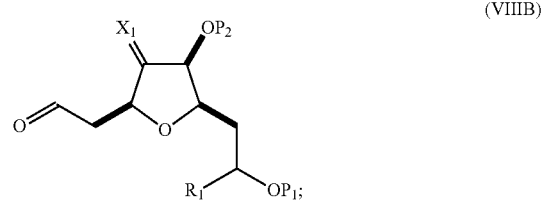
(VIIIB)

(B) reacting the compound of formula (VIIIB) with a compound of formula (VIIB-a) to afford a compound of formula (VIIIC):

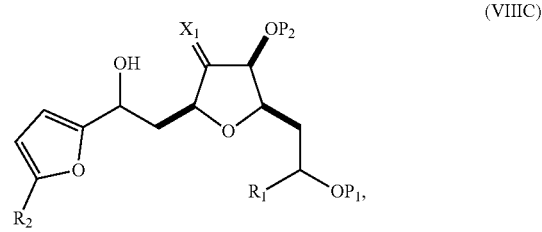
(VIIIC)

where R$_2$ can be H or —CH$_2$CH$_2$OP$_5$, and P$_5$ can be a hydroxyl protecting group;

and the compound of formula (VIIIB-a) has the following structure:

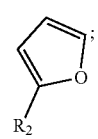
(VIIB-a)

(C) reacting the compound of formula (VIIIC) with a dehydrating agent to afford a compound of formula (VIIID):

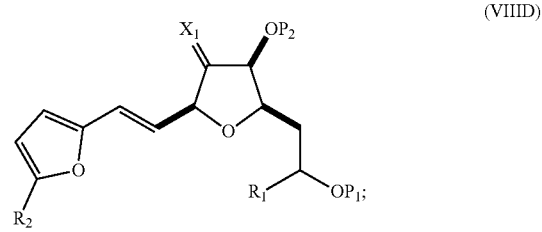
(VIIID)

(D) reacting the compound of formula (VIIID) with a dihydroxylating agent to afford a compound of formula (VIIIE):

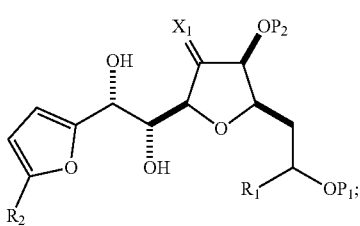
(VIIIE)

(E) preparing a compound of formula (VIIIF) through a reaction sequence including reacting the compound of formula (VIIIE) with N-bromosuccinimide to afford a first intermediate, reacting the first intermediate with an acylating agent (e.g., a carboxylic acid anhydride) to afford a second intermediate, and (a), when R$_2$ can be —CH$_2$CH$_2$OP$_5$, contacting the second intermediate with a reducing agent, or (b), when R$_2$ can be H, alylating the second intermediate compound of formula (VIIIF):

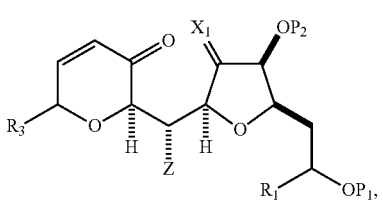
(VIIIF)

where Z can be an ester or —OP$_7$ where P$_7$ can be H or a hydroxyl protecting group, and R can be —CH$_2$CH$_2$OP$_5$ or —CH$_2$CH=CH$_2$;

(F) reacting the compound of formula (VIIIF) with a 1,4-reducing agent to afford a compound of formula (VIIIG):

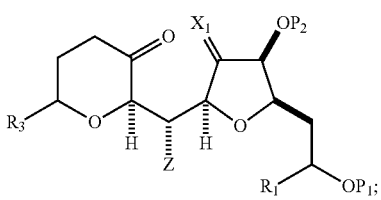
(VIIIG)

and (G) forming a compound of formula (VIIIH) through a reaction sequence including reacting the compound of formula (VIIIG) with a Brønsted acid and Y—H, where Y can be optionally substituted C$_{1-6}$ alkyl, the compound of formula (VIIIH) having the following structure:

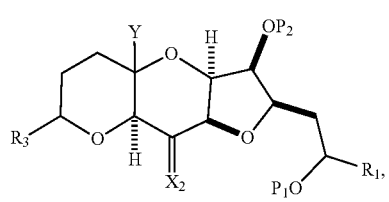
(VIIIH)

where Y can be optionally substituted C$_{1-6}$ alkyl ether; R$_2$ can be —CH$_2$CH$_2$OP$_5$; X$_2$ can be oxo, or X$_2$, together with the carbon to which it can be attached, forms a ketal or —(CH(OP$_6$))—, where P$_6$ can be a hydroxyl protecting group.

In some embodiments of the fourth aspect, the method further includes:

(H) replacing P$_2$ in the compound of formula (VIIIH) with —S(R$_4$)$_2$H to afford a compound of formula (VIIIJ):

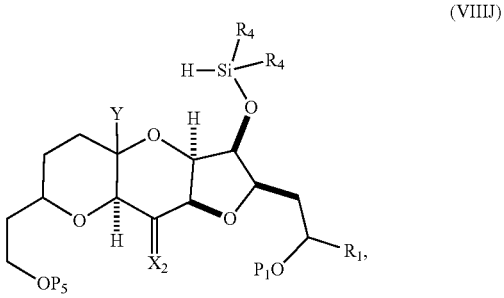
(VIIIJ)

where each R$_4$ is independently optionally substituted alkyl, optionally substituted aryl, or optionally substituted arylalkyl;

(I) reacting the compound of formula (VIIIJ) with a Lewis acid to afford a compound of formula (VIIIK):

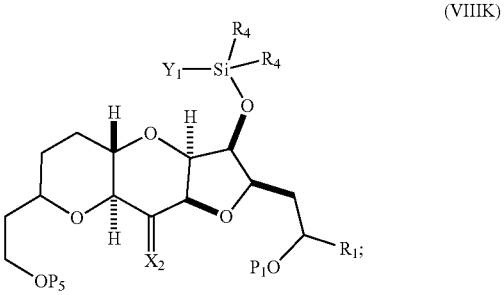
(VIIIK)

where Y$_1$ is fluoro, chloro, or bromo; and (J) reacting the compound of formula (VIIIK) with a hydroxyl protecting group removing agent and then reacting with a hydroxyl protecting agent to afford a compound of formula (VIIIL):

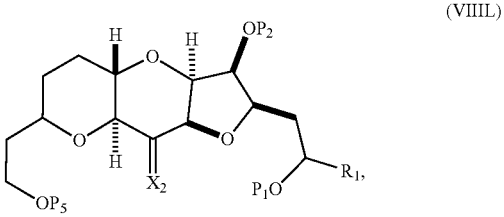
(VIIIL)

where P$_2$ is a hydroxyl protecting group.

In a fifth aspect, the invention provides compounds of formulas (IA), (IB), (IC), (IIA), (IIB), (IIIA), (IIIB), (IVA), (IVB), (IVE), (VA), (VB), (VIA), (VIB), (VIIB), and (VIIC). The invention also provides compounds of formulas (VIIIC), (VIIID), (VIIIE), (VIIIF), (VIIIG), (VIIIH), (VIIIJ), (VIIIK), and (VIIIL).

A compound of the fifth aspect can be a compound of formula (IA) or (IB):

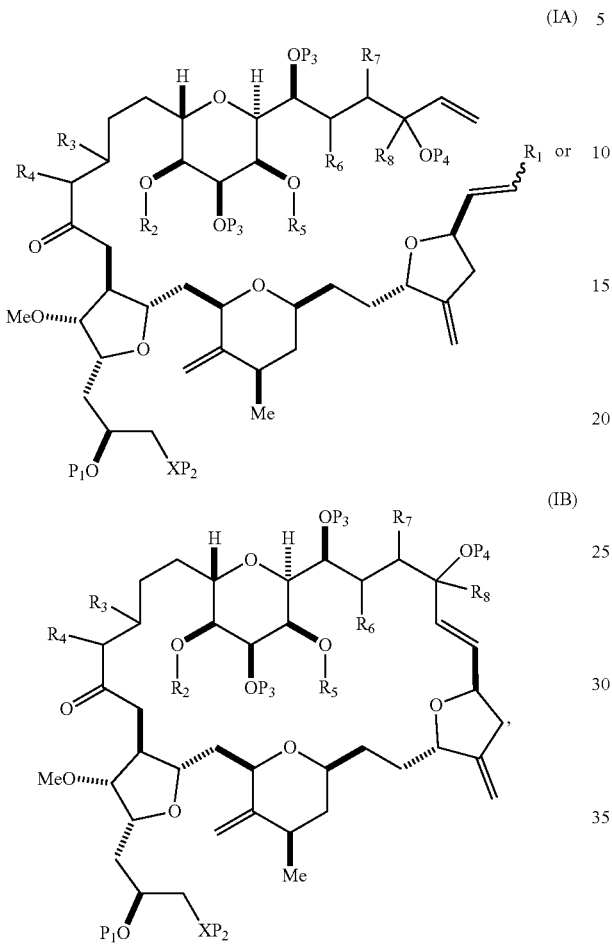

(IA)

(IB)

or a salt thereof,
where
R$_1$ is H or —CH$_2$X$_1$CH$_2$CH=CH$_2$, where X$_1$ is O, —C(R$_9$)$_2$—, or NP$_5$, and where each R$_9$ is independently H or —COOR$_{10}$, P$_5$ is an N-protecting group, and R$_{10}$ is C$_{1-6}$ alkyl;
(a1) R$_2$ is H or a hydroxyl protecting group, R$_3$ is C$_{1-6}$ alkyl ether, and R$_4$ is H;
(a2) R$_2$ is H or a hydroxyl protecting group, and R$_3$ and R$_4$ combine to form a double bond;
or
(a3) R$_2$ and R$_3$ combine to form a bond, and R$_4$ is H;
(b1) R$_5$ is H or a hydroxyl protecting group, and R$_6$ and R$_7$ combine to form a double bond;
or
(b2) R$_5$ and R$_6$ combine to form a bond, and R$_7$ is H;
(c1) R$_8$ is H, and P$_4$ is H or a hydroxyl protecting group;
or
(c2) R$_8$ and P$_4$ combine to form a double bond;
each P$_3$ is independently H or a hydroxyl protecting group; and
X is O, and
each of P$_1$ and P$_2$ is independently H or a hydroxyl protecting group, or
P$_1$ and P$_2$, together with the atoms to which each is attached, combine to form a cyclic protected diol;
or
X is N, and
P$_1$ is H or a hydroxyl protecting group, and X and P$_2$ combine to form optionally masked amino;
or
P$_1$ and P$_2$, together with the atoms to which each is attached, combine to form an aminal or 1,3-oxazolidin-2-one-5-yl.

A compound of the fifth aspect can be a compound of formula (IC):

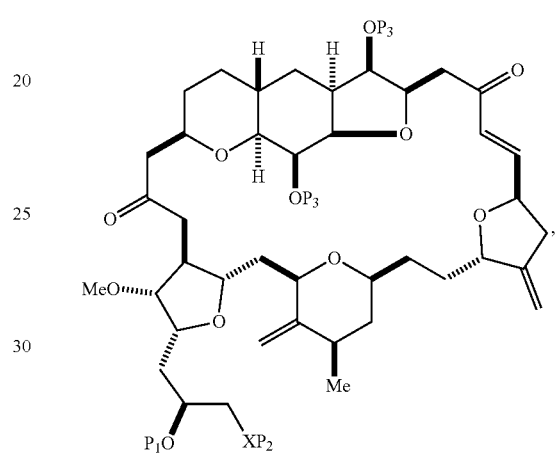

(IC)

or a salt thereof,
where
each P$_3$ is independently a hydroxyl protecting group; and
X is O, P$_1$ is a hydroxyl protecting group, and P$_2$ is H or a hydroxyl protecting group;
or
P$_1$ is a hydroxyl protecting group, and X and P$_2$ combine to form optionally masked amino.

A compound of fifth aspect can be a compound of formula (IIA) or (IIB):

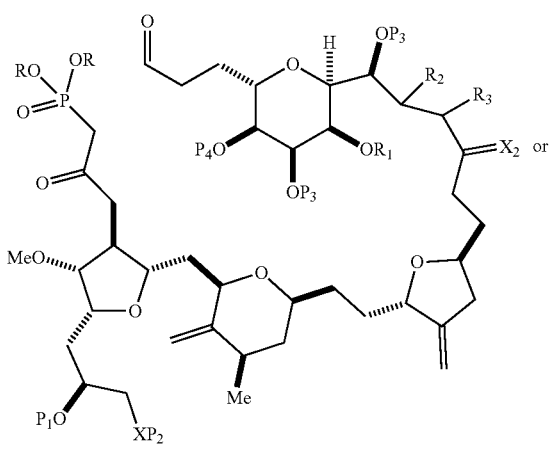

(IIA)

-continued

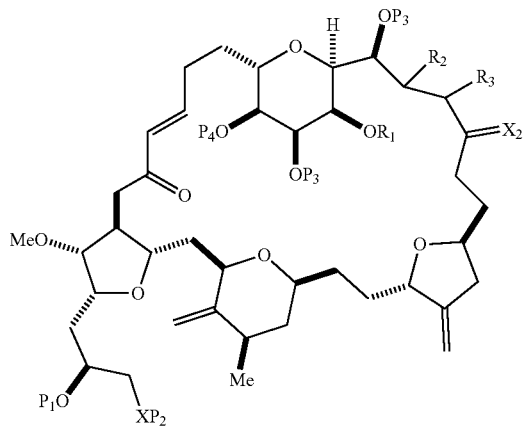

(IIB)

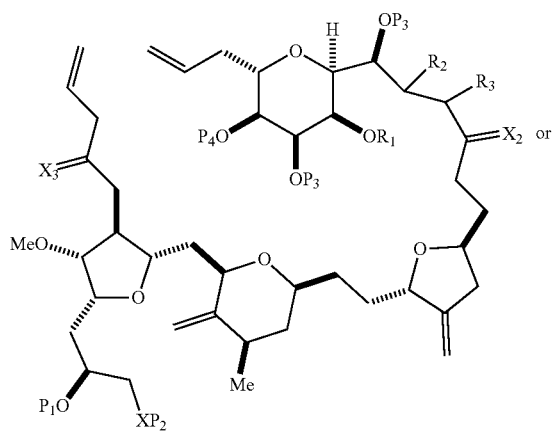

(IIIA)

or a salt thereof, where each R is independently optionally substituted alkyl or optionally substituted aryl;

(i) $R_1$ is H or a hydroxyl protecting group, and $R_2$ and $R_3$ combine to form a double bond;

or (ii) $R_1$ and $R_2$ combine to form a bond, and $R_3$ is H;

each $P_3$ is independently H or a hydroxyl protecting group, and $X_2$ is oxo; or both $P_3$ groups and $X_2$, together with the atoms to which each is attached, combine to form ketal;

$P_4$ is H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

A compound of the fifth aspect can be a compound of formula (IIIA) or (IIIB):

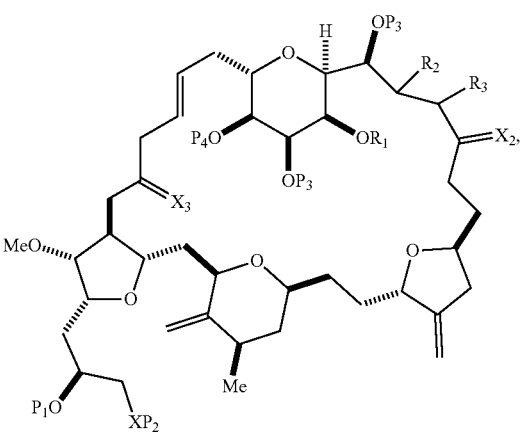

(IIIB)

or a salt thereof, where (i) $R_1$ is H or a hydroxyl protecting group, and $R_2$ and $R_3$ combine to form a double bond;

or (ii) $R_1$ and $R_2$ combine to form a bond, and $R_3$ is H;

$X_3$ is oxo, or $X_3$ combines with the carbon atom to which it is attached to form a ketal, a thioketal, or —(CH(OP$_5$))—, where $P_5$ is H or a hydroxyl protecting group;

each $P_3$ is independently H or a hydroxyl protecting group, and $X_2$ is oxo; or both P groups and $X_2$, together with the atoms to which each is attached, combine to form ketal;

$P_4$ is H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

A compound of the fifth aspect can be a compound of formula (IVA) or (IVB):

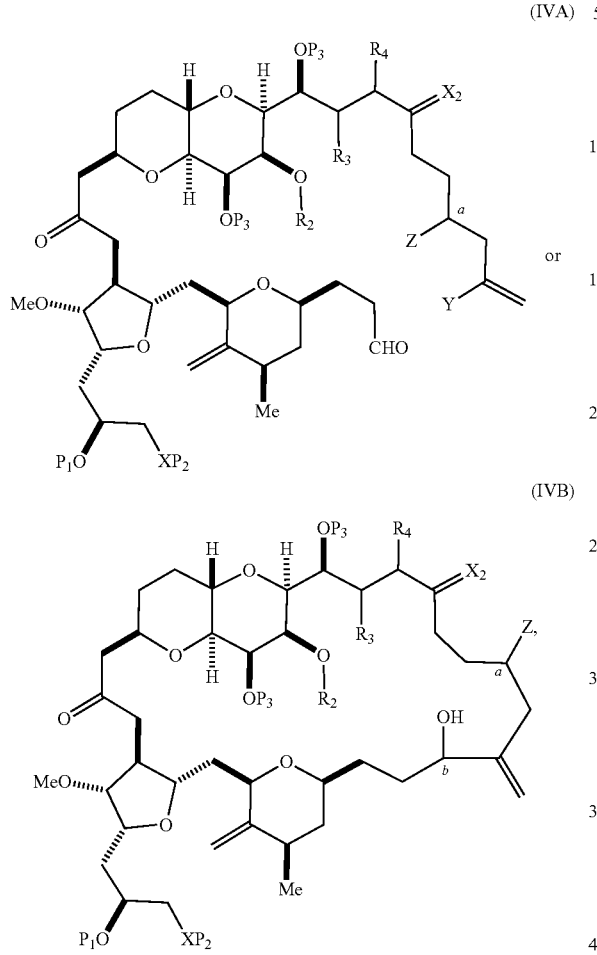

or a salt thereof,
where
Y is iodide, bromide, or trifluoromethanesulfonate;
(a1) a designates R stereogenic center, b designates S stereogenic center, and Z is a sulfonate, chloride, bromide, or iodide;
or
(a2) a designates S stereogenic center, b designates R stereogenic center, and Z is $OR_1$, where $R_1$ is a hydroxyl protecting group;
(b1) $R_2$ is H or a hydroxyl protecting group, and $R_3$ and $R_4$ combine to form a double bond;
or
(b2) $R_2$ and $R_3$ combine to form a bond, and $R_4$ is H;
each $P_3$ is independently H or a hydroxyl protecting group, and $X_2$ is oxo; or both P groups and $X_2$, together with the atoms to which each is attached, combine to form ketal; and
X is O, and
  each of $P_1$ and $P_2$ is independently H or a hydroxyl protecting group,
  or
  $P_1$ and $P_2$, together with the atoms to which each is attached, combine to form a cyclic protected diol;
or
X is N, and
  $P_1$ is H or a hydroxyl protecting group, and X and $P_2$ combine to form optionally masked amino;
  or
  $P_1$ and $P_2$, together with the atoms to which each is attached, combine to form an aminal or 1,3-oxazolidin-2-one-5-yl A compound of the fifth aspect can be a compound of formula (VA) or (VB):

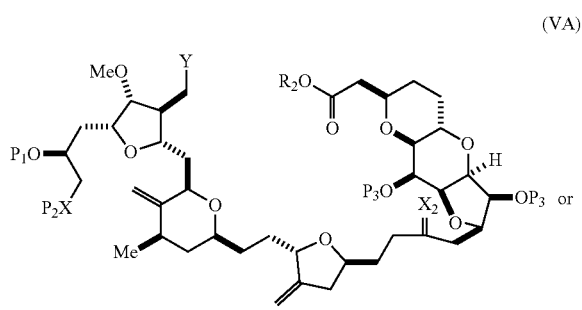

or a salt thereof,
where
Y is $SO_2R_1$ or $COOR_1$, where, when Y is $SO_2R_1$, $R_1$ is optionally substituted aryl or optionally substituted non-enolizable alkyl, and when Y is $COOR_1$, $R_1$ is optionally substituted alkyl, optionally substituted aryl, or optionally substituted arylalkyl;
each $P_3$ is independently H or a hydroxyl protecting group, and $X_2$ is oxo, or both P groups and $X_2$, together with the atoms to which each is attached, combine to form ketal;
$R_2$ is optionally substituted alkyl, optionally substituted arylalkyl, or optionally substituted aryl; and
X is O, and
  each of $P_1$ and $P_2$ is independently a hydroxyl protecting group,
  or
  $P_1$ and $P_2$, together with the atoms to which is each is attached, combine to form a cyclic protected diol;
or
X is N, and
  $P_1$ is H or a hydroxyl protecting group, and X and $P_2$ combine to form optionally masked amino;
  or
  $P_1$ and $P_2$, together with the atoms to which each is attached, combine to form an aminal or 1,3-oxazolidin-2-one-5-yl.

A compound of formula (VIA) or (VIB):

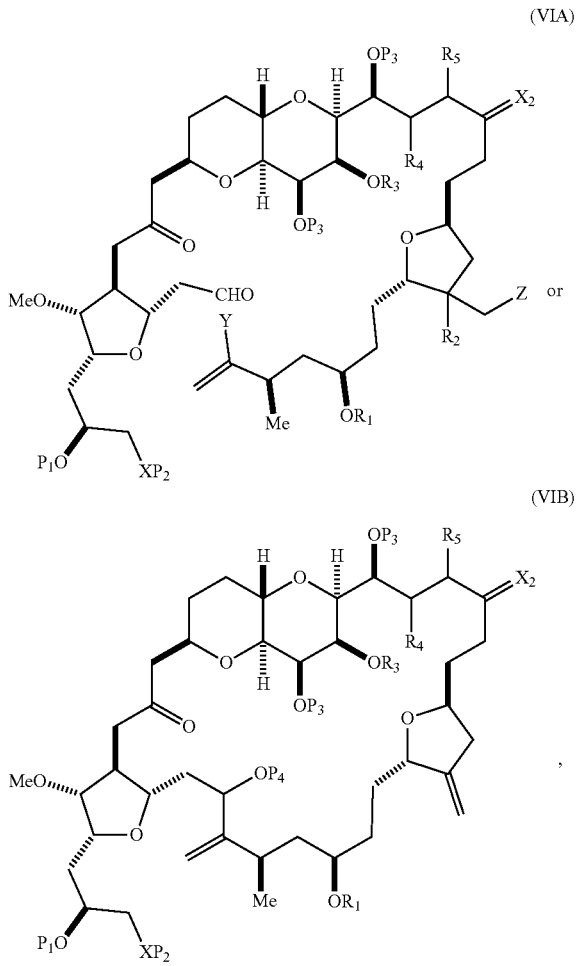

or a salt thereof,
where
Y is iodide, bromide, or trifluoromethanesulfonate;
$P_4$ is H or a hydroxyl protecting group;
(a1) $R_3$ is H or a hydroxyl protecting group, $R_4$ and $R_5$ combine to form a double bond, each $P_3$ is independently H or a hydroxyl protecting group, and $X_2$, together with the carbon to which it is attached, forms a carbonyl or —(CH($OR_6$))—, where $R_6$ is H or a hydroxyl protecting group;
or
(a2) $R_3$ and $R_4$ combine to form a bond, $R_5$ is H, and each $P_3$ is independently H or a hydroxyl protecting group, and $X_2$, together with the carbon to which it is attached, forms a carbonyl or —(CH($OR_6$))—;
or
both $P_3$ groups and $X_2$, together with the atoms to which each is attached, combine to form ketal;
(b1) Z is chloride, bromide, or iodide, and $R_1$ and $R_2$ combine to form a bond;
or
(b2) Z and $R_2$ combine to form a double bond, and $R_1$ is a hydroxyl protecting group;
and
X is O, and
each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

A compound of the fifth aspect can be a compound of formula (VIIC):

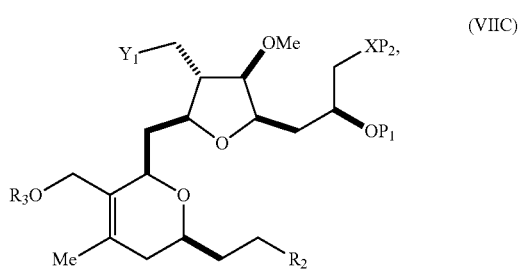

or a salt thereof,
where
$Y_1$ is $SO_2R_1$ or $COOR_1$, and $R_1$ is optionally substituted alkyl, optionally substituted aryl, or optionally substituted arylalkyl;
$R_2$ is —$CH_2$—$OP_3$, —CH=$CH_2$,

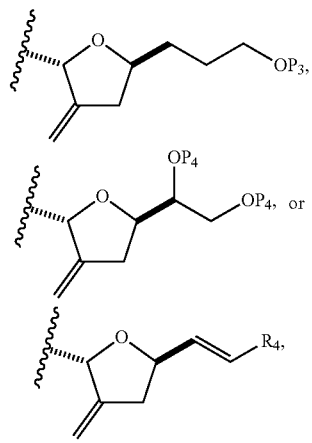

where $P_3$ is H or a hydroxyl protecting group; each $P_4$ is independently a hydroxyl protecting group, or both $P_4$ groups, together with the atoms to which each is attached, combine to form a cyclic protected diol; and $R_4$ is H or —$CH_2X_2CH_2$CH=$CH_2$, where $X_2$ is O, —$CH_2$—, or $NP_5$,
where $P_5$ is sulfonyl;
$R_3$ is an optionally substituted acyl; and
X is O, and
each of $P_1$ and $P_2$ is independently H or a hydroxyl protecting group,
or
$P_1$ and $P_2$, together with the atoms to which each is attached, combine to form a cyclic protected diol;

or

X is N, and

P$_1$ is H or a hydroxyl protecting group, and X and P$_2$ combine to form optionally masked amino;

or

P$_1$ and P$_2$, together with the atoms to which each is attached, combine to form an aminal or 1,3-oxazolidin-2-one-5-yl.

A compound of the fifth aspect can be a compound of formula (VIIB):

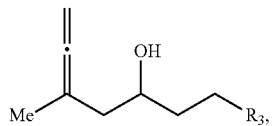
(VIIB)

where

R$_3$ is —CH$_2$—OP$_3$,

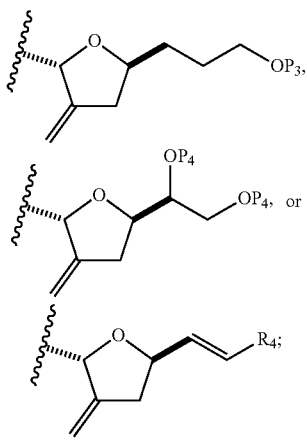

where

P$_3$ is a hydroxyl protecting group; each P$_4$ is independently a hydroxyl protecting group, or both P$_4$ groups, together with the atoms to which each is attached, combine to form a cyclic protected diol; and R$_4$ is H or —CH$_2$X$_2$CH$_2$CH═CH$_2$, where X$_2$ is O, —CH$_2$—, or NP$_5$, where P$_5$ is sulfonyl.

A compound of the fifth aspect can be a compound of formula (IVE):

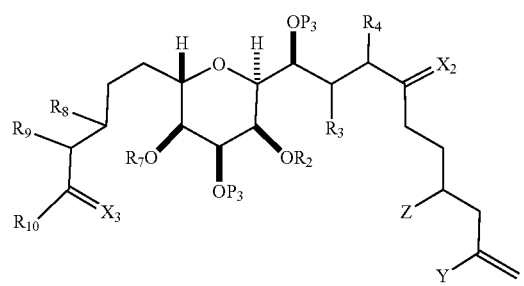
(IVE)

where

Y is iodide, bromide, or trifluoromethanesulfonate;

Z is an ester, a sulfonate, chloride, bromide, or iodide;

each P$_3$ is independently H or a hydroxyl protecting group, and X$_2$ is oxo; or both P$_3$ groups and X$_2$, together with the atoms to which each is attached, combine to form ketal; and (a1) R$_2$ is H or a hydroxyl protecting group, R$_3$ and R$_4$ combine to form a double bond;

or (a2) R$_2$ and R$_3$ combine to form a bond, and R$_4$ is H;

(b1) R$_7$ and R$_8$ combine to form a bond, and R$_9$ is H;

or (b2) R$_7$ is H or a hydroxyl protecting group, and R$_8$ and R$_9$ combine to form a double bond;

(c1) X$_3$ is oxo and R$_{10}$ is H or —OP$_5$, where P$_5$ is H or an ether hydroxyl protecting group;

or (c2) X$_3$ and R$_{10}$ together with the carbon atom to which they are attached form —CH$_2$OP$_6$, wherein P$_6$ is H or a hydroxyl protecting group, and R$_{10}$ is H.

Definitions

Compounds useful in the invention may be isotopically labeled compounds. Useful isotopes include hydrogen, carbon, nitrogen, and oxygen (e.g., $^2$H, $^3$H, 13C, $^{14}$C, $^{15}$N, $^{18}$O, and $^{17}$O). Isotopically-labeled compounds can be prepared by synthesizing a compound using a readily available isotopicaly-labeled reagent in place of a non-isotopically-labeled reagent.

For any of the following chemical definitions, a number following an atomic symbol indicates that total number of atoms of that element that are present in a particular chemical moiety. As will be understood, other atoms, such as hydrogen atoms, or substituent groups, as described herein, may be present, as necessary, to satisfy the valences of the atoms. For example, an unsubstituted C$_2$ alkyl group has the formula —CH$_2$CH$_3$. When used with the groups defined herein, a reference to the number of carbon atoms includes the divalent carbon in acetal and ketal groups but does not include the carbonyl carbon in acyl, ester, carbonate, or carbamate groups. A reference to the number of oxygen, nitrogen, or sulfur atoms in a heteroaryl group only includes those atoms that form a part of a heterocyclic ring.

By "acetal" is meant —O—(CHR)—O—, where R is H, optionally substituted alkyl, optionally substituted alkenyl, optionally substituted aryl, or optionally substituted arylalkyl.

By "acyl" is meant —C(O)R, where R is H, alkyl, alkenyl, aryl, or arylalkyl. In exemplary acyl groups, R is H, C$_{1-12}$ alkyl (e.g., C$_{1-8}$, C$_{1-6}$, C$_{1-4}$, C$_{2-7}$, C$_{3-12}$, or C$_{3-6}$ alkyl), C$_{2-12}$ alkenyl (e.g., C$_{2-8}$, C$_{2-6}$, C$_{2-4}$, C$_{3-12}$, or C$_{3-6}$ alkenyl), C$_{6-20}$ aryl (e.g., C$_{6-15}$, C$_{6-10}$, C$_{8-20}$, or C$_{8-15}$ aryl), monocyclic C$_{1-6}$ heteroaryl (e.g., monocyclic C$_{1-4}$ or C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{1-6}$)heteroaryl(C$_{1-6}$)alkyl, or (C$_{4-19}$)heteroaryl(C$_{1-6}$)alkyl. As defined herein, any heteroaryl group present in an acyl group has from 1 to 4 heteroatoms selected independently from O, N, and S. An acyl group can be unsubstituted or substituted (e.g., optionally substituted acyl). In the optionally substituted acyl group, the substituent R is H, optionally substituted alkyl, optionally substituted alkenyl, optionally substituted aryl, or optionally substituted arylalkyl.

By "acylating agent" is meant a compound that reacts with an amine or a hydroxyl group to produce an amide or an ester, respectively. An acylating agent has a formula R-LG, where R is acyl, and LG is halogen, carbonate, or —OR', where R' is acyl.

By "alkoxide" is meant an anionic compound RO⁻, where R is alkyl. A counterion for alkoxide can be an alkali metal cation, an alkali earth metal cation, or a tetraalkylammonium cation. Alkoxide can be optionally substituted in the same manner as alkyl.

By "alkoxy" is meant —OR, where R is alkyl. Alkoxy can be optionally substituted in the same manner as alkyl.

By "alkoxyalkyl" is meant —OR, where R is alkyl substituted by alkoxy. Each portion of the alkoxyalkyl can be optionally substituted in the same manner as alkyl.

By "alkyl" is meant a straight or branched chain saturated cyclic (i.e., cycloalkyl) or acyclic hydrocarbon group of from 1 to 12 carbons, unless otherwise specified. Exemplary alkyl groups include $C_{1-8}$, $C_{1-6}$, $C_{1-4}$, $C_{2-7}$, $C_{3-12}$, and $C_{3-6}$ alkyl. Specific examples include methyl, ethyl, 1-propyl, 2-propyl, 2-methyl-1-propyl, 1-butyl, 2-butyl, and the like. Alkyl group can be optionally substituted with 1, 2, 3, or 4 substituents selected from the group consisting of halogen, alkoxy, aryloxy, arylalkyloxy, oxo, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "alkylamino" is meant —NHR, where R is alkyl. By "[alkenyl]alkylamino" is meant —NRR', where R is alkyl, and R' is alkenyl. By "[aryl]alkylamino" is meant —NRR', where R is alkyl, and R' is aryl. By "[arylalkyl]alkylamino" is meant —NRR', where R is alkyl, and R' is arylalkyl. By "dialkylamino" is meant —NR₂, where each R is alkyl, selected independently.

By "alkylene" is meant a divalent alkyl group. Alkylene groups can be optionally substituted in the same manner as alkyl groups. For example, a $C_1$ akylene group is —CH₂—.

By "alkylenedithio" is meant —S-alkylene-S—. Alkylenedithio can be optionally substituted in the same manner as an alkylene group.

By "alkylthio" is meant —SR, where R is alkyl. Akylthio can be optionally substituted in the same manner as an alkyl group.

By "alkenyl" is meant a straight or branched chain cyclic or acyclic hydrocarbon group of, unless otherwise specified, from 2 to 12 carbons and containing one or more carbon-carbon double bonds. Exemplary alkenyl groups include $C_{2-8}$, $C_{2-7}$, $C_{2-8}$, $C_{2-4}$, $C_{3-12}$, and $C_{3-6}$ alkenyl. Specific examples include ethenyl (i.e., vinyl), 1-propenyl, 2-propenyl (i.e., allyl), 2-methyl-1-propenyl, 1-butenyl, 2-butenyl (i.e., crotyl), and the like. Alkenyl group can be optionally substituted in the same manner as alkyl groups. Alkenyl groups, used in any context herein, may also be substituted with an aryl group.

By "amido" is meant —NHR, where R is acyl. Amido can be optionally substituted in the same manner as acyl.

By "aminal" is meant —O—CR₂—NR'—, where each R is independently H, optionally substituted alkyl, optionally substituted alkenyl, optionally substituted aryl, or optionally substituted arylalkyl, or both R groups are together optionally substituted alkylene, and R' is H or an N-protecting group. In particular, R' can be an N-protecting group (e.g., Boc).

By "amino" is meant —NR₂, where N and R₂ combine to form azido, or each R is independently H or an N-protecting group, or both R combine to form an N-protecting group. Amino can be unmasked, when each R is H, or masked, when at least one R is not H. Thus, optionally masked amino can be masked or unmasked amino.

By "aryl" is meant a monocyclic or multicyclic ring system having one or more aromatic rings, where the ring system is carbocyclic or heterocyclic. Heterocyclic aryl groups are also referred to as heteroaryl groups. A heteroaryl group includes 1 to 4 atoms selected independently from O, N, and S. Exemplary carbocyclic aryl groups include $C_{6-20}$, $C_{6-15}$, $C_{6-10}$, $C_{8-20}$, and $C_{8-15}$ aryl. A preferred aryl group is a C6-10 aryl group. Specific examples of carbocyclic aryl groups include phenyl, indanyl, indenyl, naphthyl, phenanthryl, anthracyl, and fluorenyl. Exemplary heteroaryl groups include monocylic rings having from 1 to 4 heteroatoms selected independently from O, N, and S and from 1 to 6 carbons (e.g., $C_{1-6}$, $C_{1-4}$, and $C_{2-6}$). Monocyclic heteroaryl groups preferably include from 5 to 9 ring members. Other heteroaryl groups preferably include from 4 to 19 carbon atoms (e.g., $C_{4-10}$). Specific examples of heteroaryl groups include pyridinyl, quinolinyl, dihydroquinolinyl, isoquinolinyl, quinazolinyl, dihydroquinazolyl, and tetrahydroquinazolyl. Aryl group can be optionally substituted with 1, 2, 3, 4, or 5 substituents selected from the group consisting of alkyl, alkenyl, aryl, arylalkyl, halogen, alkoxy, aryloxy, arylalkyloxy, alkylthio, alkylenedithio, alkylamino, [alkenyl]alkylamino, [aryl]alkylamino, [arylalkyl]alkylamino, dialkylamino, silyl, sulfonyl, cyano, nitro, carboxyl, and azido.

By "arylalkyl" is meant —R'R", where R' is alkylene, and R" is aryl. Arylalkyl can be optionally substituted in the same manner as defined for each R' and R" group.

By "arylalkyloxy" is meant —OR, where R is arylalkyl. Arylalkyloxy can be optionally substituted in the same manner as defined for arylalkyl.

By "aryloxy" is meant —OR, where R is aryl. Aryloxy can be optionally substituted in the same manner as aryl.

By "azido" is meant —N₃.

By "boronate" is meant —OBRO—, where R is alkyl, alkenyl, aryl, arylalkyl, alkoxy, or 2,6-diacetamidophenyl. Boronate can be substituted, when R is a substituted alkyl, substituted alkenyl, substituted aryl, substituted arylalkyl, or substituted alkoxy. Alternatively, boronate can be unsubstituted, when R is unsubstituted alkyl, unsubstituted alkenyl, aryl, unsubstituted arylalkyl, unsubstituted alkoxy, or 2,6-diacetamidophenyl.

By "carbamate" is meant a group, when a hydroxyl protecting group, having the formula —OC(O)NR₂, or, when an amine protecting group, having the formula —NR'—C(O)OR, where each R and R' is independently H, optionally substituted alkyl, optionally substituted alkenyl, optionally substituted aryl, or optionally substituted arylalkyl.

By "carbonate" is meant —OC(O)OR, where R is optionally substituted alkyl, optionally substituted alkenyl, optionally substituted aryl, or optionally substituted arylalkyl.

By "carbonyl" is meant —C(O)—.

By "carboxyl" is meant —C(O)OH, in free acid, ionized, or salt form.

By "carboxylic acid" is meant R—OH, where R is optionally substituted acyl.

By "carboxylic acid anhydride" is meant R—O—R, where each R is independently optionally substituted acyl.

By "dicarbonyl" is meant —C(O)—C(O)—.

By "ester" is meant —OC(O)R, where —C(O)R is an optionally substituted acyl group.

By "ether" is meant —OR, where R is alkyl, alkenyl, arylalkyl, silyl, or 2-tetrahydropyranyl. Ether can be optionally substituted as defined for each R group.

By "halogen" is meant fluoro, chloro, bromo, or iodo.

By "hydroxyl protecting group" is meant any group capable of protecting the oxygen atom to which it is attached from reacting or bonding. Hydroxyl protecting groups are known in the art, e.g., as described in Wuts, Greene's Protective Groups in Organic Synthesis, Wiley-Interscience, 4th Edition, 2006. Exemplary protecting groups (with the oxygen atom to which they are attached) are independently selected from the group consisting of esters, carbonates, carbamates, sulfonates, and ethers. In exemplary ester hydroxyl protecting groups, R of the acyl group is $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$alkyl, or $(C_{1-6})$heteroaryl$(C_{1-6})$alkyl. Specific examples of acyl groups for use in esters include formyl, benzoyformyl, acetyl (e.g., unsubstituted or chloroacetyl, trifluoroacetyl, methoxyacetyl, triphenylmethoxyacetyl, and p-chlorophenoxyacetyl), 3-phenylpropionyl, 4-oxopentanoyl, 4,4-(ethylenedithio)pentanoyl, pivaloyl (Piv), vinylpivaloyl, crotonoyl, 4-methoxy-crotonoyl, naphthoyl (e.g., 1- or 2-naphthoyl, and benzoyl (e.g., unsubstituted or substituted, e.g., p-methoxybenzoyl, phthaloyl (including salts, such a triethylamine and potassium), p-bromobenzoyl, and 2,4,6-trimethylbenzoyl. As defined herein, any heteroaryl group present in an ester group has from 1 to 4 heteroatoms selected independently from O, N, and S. In exemplary carbonate hydroxyl protecting groups, R is $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$alkyl, or $(C_{1-6})$heteroaryl$(C_{1-6})$alkyl. Specific examples include methyl, 9-fluorenylmethyl, ethyl, 2,2,2-trichloroethyl, 2-(trimethylsilyl)ethyl, 2-(phenylsulfonyl)ethyl, vinyl, allyl, t-butyl, p-nitrobenzyl, and benzyl carbonates. As defined herein, any heteroaryl group present in a carbonate group has from 1 to 4 heteroatoms selected independently from O, N, and S. In exemplary carbamate hydroxyl protecting groups, each R is independently H, $C_{1-12}$ alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), carbocyclic $C_{6-20}$ aryl (e.g., $C_{6-15}$, $C_{6-10}$, $C_{8-20}$, and $C_{8-15}$ aryl), monocyclic $C_{1-6}$ heteroaryl (e.g., $C_{1-4}$ and $C_{2-6}$ heteroaryl), $C_{4-19}$ heteroaryl (e.g., $C_{4-10}$ heteroaryl), $(C_{6-15})$aryl$(C_{1-6})$alkyl, $(C_{4-19})$heteroaryl$(C_{1-6})$ alkyl, or $(C_{1-6})$heteroaryl$(C_{1-6})$alkyl. Specific examples include N-phenyl and N-methyl-N-(o-nitrophenyl) carbamates. As defined herein, any heteroaryl group present in a carbamate group has from 1 to 4 heteroatoms selected independently from O, N, and S. Exemplary ether hydroxyl protecting groups include C1-12 alkyl (e.g., $C_{1-8}$, $C_{1-6}$, $C_{1-4}$, $C_{2-7}$, $C_{3-12}$, and $C_{3-6}$ alkyl), $C_{2-12}$ alkenyl (e.g., $C_{2-8}$, $C_{2-6}$, $C_{2-4}$, $C_{3-12}$, and $C_{3-6}$ alkenyl), $(C_{6-15})$aryl$(C_{1-6})$alkyl, $(C_{4-19})$heteroaryl$(C_{1-6})$alkyl, $(C_{1-6})$heteroaryl$(C_{1-6})$alkyl, $(C_{1-6})$alkoxy$(C_{1-6})$alkyl, $(C_{1-6})$alkylthio$(C_{1-6}a)$alkyl, $(C_{6-10})$aryl$(C_{1-6})$alkoxy$(C_{1-6})$alkyl, and silyl (e.g., tri$(C_{1-6}$ alkyl)silyl, tri$(C_{6-10}$ aryl or $C_{1-6}$ heteroaryl)silyl, di$(C_{6-10}$ aryl or $C_{1-6}$ heteroaryl)$(C_{1-6}$ alkyl)silyl, and $(C_{6-10}$ aryl or $C_{1-6}$ heteroaryl)di$(C_{1-6}$ alkyl)silyl). Specific examples of alkylethers include methyl and t-butyl, and an example of an alkenyl ether is allyl. Ether hydroxyl protecting groups can be used to protect a carboxyl group (e.g., with a $C_{1-12}$ alkyl (e.g., $C_{1-8}$, $C_{1-6}$, $C_{1-4}$, $C_{2-7}$, $C_{3-12}$, and $C_{3-6}$ alkyl), $(C_{6-15})$aryl$(C_{1-6})$alkyl, $(C_{1-6})$alkoxy$(C_{1-6})$alkyl, $(C_{1-6})$alkylthio$(C_{1-6})$alkyl, or $(C_{6-10})$aryl$(C_{1-6})$alkoxy$(C_{1-6})$alkyl). Examples of alkoxyalkyls and alkylthioalkyls that can be used as ether hydroxyl protecting groups include methoxymethyl, methylthiomethyl, (2-methoxyethoxy)methyl, and β-(trimethylsilyl)ethoxymethyl. Examples of arylalkyl groups that can be used as ether hydroxyl protecting groups include benzyl, p-methoxybenzyl (MPM), 3,4-dimethoxybenzyl, triphenylmethyl (trityl), o-nitrobenzyl, p-nitrobenzyl, p-halobenzyl, 2,6-dichlorobenzyl, p-cyanobenzyl, naphthylmethyl, and 2- and 4-picolyl ethers. Specific examples of silylethers include trimethylsilyl (TMS), triethylsilyl (TES), t-butyldimethylsilyl (TBS), t-butyldiphenylsilyl (TBDPS), triisopropylsilyl (TIPS), and triphenylsilyl (TPS) ethers. An example of an arylalkyloxyalkylether is benzyloxymethyl ether. As defined herein, any heteroaryl group present in an ether group has from 1 to 4 heteroatoms selected independently from O, N, and S. Vicinal or 1,3-diols may be protected with a diol protecting group (e.g., to produce a "cyclic protected diol"), such as acetal (e.g., containing $C_{1-6}$ alkylene), ketal (e.g., containing $C_{3-6}$ alkylene or $C_{3-6}$ cycloalkyl), cyclic silylene, cyclic carbonate, and cyclic boronate. Examples of acetal and ketal groups include methylene-dioxo, ethylidene-dioxo, benzylidene-dioxo, isopropylidene-dioxo, cyclohexylidene-dioxo, and cyclopentylidene-dioxo. An example of a cyclic silylene is di-t-butylsilylene. Another diol protecting group is 1,1,3,3-tetraisopropylsiloxanediyl. Examples of cyclic boronates include methyl, ethyl, phenyl, and 2,6-diacetamidophenyl boronates. Protecting groups may be substituted as is known in the art; for example, aryl and arylalkyl groups, such as phenyl, benzyl, naphthyl, or pyridinyl, can be substituted with $C_{1-6}$ alkyl, $C_{1-6}$ alkoxy, nitro, cyano, carboxyl, or halogen. Alkyl groups, such as methyl, ethyl, isopropyl, n-propyl, t-butyl, n-butyl, and sec-butyl, and alkenyl groups, such as vinyl and allyl, can also be substituted with oxo, arylsulfonyl, halogen, and trialkylsilyl groups. Preferred protecting groups are TBS and Piv. Protecting groups that are orthogonal are removed under different conditions, as in known in the art.

By "imido" is meant —NR$_2$, where each R is independently optionally substituted acyl.

By "ketal" is meant —O—CR$_2$—O—, where each R is independently optionally substituted alkyl, optionally substituted alkenyl, optionally substituted aryl, or optionally substituted arylalkyl, or both R groups are together optionally substituted alkylene.

By "macrocyclization" is meant a reaction converting a non-macrocyclic compound into a compound containing at least one n-membered ring, where n is equal to or greater than 16.

By "non-enolizable" is meant a group that, either alone or in combination with a group to which it is attached, cannot form an enol through a deprotonation/reprotonation sequence. For example, a "non-enolizable alkyl" can be bonded to a sulfone group or to a carbonyl group through a quaternary carbon atom (i.e., the carbon atom that is not bonded to a hydrogen atom).

By "non-macrocyclic" is meant a compound not containing rings or containing one or more m-membered rings, where m is less than or equal to 15.

By "N-protecting group" is meant a group protecting a nitrogen atom in a molecule from participating in one or more undesirable reactions during chemical synthesis (e.g., oxidation reactions, or certain nucleophilic and electrophilic substitutions). Commonly used N-protecting groups are disclosed in Wuts, Greene's Protective Groups in Organic Synthesis, Wiley-Interscience, 4th Edition, 2006. Exemplary N-protecting groups include acyl (e.g., formyl, acetyl, trifluoroacetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, and 4-bromobenzoyl; sulfonyl-containing groups (e.g., benzenesulfonyl, p-toluenesulfonyl, o-nitrobenzenesulfonyl, and p-nitrobenzenesulfonyl); carbamate forming groups (e.g., benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2,-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, and phenylthiocarbonyl), arylalkyl (e.g., triphenylmethyl); silyl groups (e.g., trimethylsilyl); and imine-forming groups (e.g., diphenylmethylene). Preferred N-protecting groups are acetyl, benzoyl, phenylsulfonyl, p-toluenesulfonyl, p-nitrobenzenesulfonyl, o-nitrobenzenesulfonyl, t-butyloxycarbonyl (Boc), and benzyloxycarbonyl (Cbz).

By "1,3-oxazolidin-2-one-5-yl" is meant 1,3-oxazolidin-2-one-5-yl, in which the nitrogen atom is substituted with H or an N-protecting group (e.g., Boc).

By "oxo" or (O) is meant =O.

By "pharmaceutically acceptable salt" is meant a salt within the scope of sound medical judgment, suitable for use in contact with the tissues of humans and animals without undue toxicity, irritation, allergic response and the like and commensurate with a reasonable benefit/risk ratio. Pharmaceutically acceptable salts are well known in the art. For example, pharmaceutically acceptable salts are described in: Berge et al., J. Pharmaceutical Sciences 66:1-19, 1977 and in Pharmaceutical Salts: Properties, Selection, and Use, (Eds. P. H. Stahl and C. G. Wermuth), Wiley-VCH, 2008. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxyethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. A preferred salt is the mesylate salt.

By "silyl" is meant —SiR$_3$, where each R is independently alkyl, alkenyl, aryl, or arylalkyl. Examples of silyl groups include tri(C$_{1-6}$ alkyl)silyl, tri(C$_{6-10}$ aryl or C$_{1-6}$ heteroaryl)silyl, di(C$_{6-10}$ aryl or C$_{1-6}$ heteroaryl)(C$_{1-6}$ alkyl)silyl, and (C$_{6-10}$ aryl or C$_{1-6}$ heteroaryl)di(C$_{1-6}$ alkyl)silyl. It will be understood that, when a silyl group includes two or more alkyl, alkenyl, aryl, heteroaryl, or arylalkyl groups, these groups are independently selected. As defined herein, any heteroaryl group present in a silyl group has from 1 to 4 heteroatoms selected independently from O, N, and S. Silyl can be optionally substituted in the same manner as defined for each R group.

By "silylene" is meant —SiR$_2$—, where each R is independently alkyl, alkenyl, aryl, arylalkyl, or alkoxy. By "dialkylsilylene" is meant a silylene, where each R is alkyl. Silylene can be optionally substituted in the same manner as defined for each R group.

By "strong base" is meant a Brønsted base, the conjugate acid of which has pKa that is greater than or equal to 13. Non-limiting examples of strong bases include alkyl alkali metals (e.g., butyl lithium or Schlosser's base), Grignard reagents (e.g., alkyl magnesium halide), alkoxides (e.g., tertiary alkoxides, such as t-butoxide), amides (e.g., diisopropylamide, tetramethylpiperidide, or bis(trimethylsilyl) amide), and phosphazene bases (e.g., Schwesinger base).

By "sulfonamide" is meant —NR, where R is sulfonyl.

By "sulfonate" is meant —OS(O)$_2$R, where R is optionally substituted alkyl, optionally substituted alkenyl, optionally substituted aryl, or optionally substituted arylalkyl. In exemplary sulfonates, R is C$_{1-12}$ alkyl (e.g., C$_{1-8}$, C$_{1-6}$, C$_{1-4}$, C$_{2-7}$, C$_{3-12}$, or C$_{3-6}$ alkyl), C$_{2-12}$ alkenyl (e.g., C$_{2-8}$, C$_{2-6}$, C$_{2-4}$, C$_{3-12}$, or C$_{3-6}$ alkenyl), carbocyclic C$_{6-20}$ aryl (e.g., C$_{6-15}$, C$_{6-10}$, C$_{6-20}$, or C$_{8-15}$ aryl), monocyclic C$_{1-6}$ heteroaryl (e.g., C$_{1-4}$ and C$_{2-6}$ heteroaryl), C$_{4-19}$ heteroaryl (e.g., C$_{4-10}$ heteroaryl), (C$_{6-15}$)aryl(C$_{1-6}$)alkyl, (C$_{4-19}$)heteroaryl (C$_{1-6}$)alkyl, or (C$_{1-6}$)heteroaryl(C$_{1-6}$)alkyl. As defined herein, any heteroaryl group present in a sulfonate group has from 1 to 4 heteroatoms selected independently from O, N, and S.

By "sulfonyl" is meant —S(O)$_2$R, where R is optionally substituted alkyl, optionally substituted alkenyl, optionally substituted aryl, optionally substituted arylalkyl, or silyl. Preferred R groups for sulfonyl are the same as those described above for sulfonates.

By "thioacetal" is meant —S—(CHR)—S—, where R is H, optionally substituted alkyl, optionally substituted alkenyl, optionally substituted aryl, or optionally substituted arylalkyl.

By "thioketal" is meant —S—(CR$_2$)—S—, where each R is independently optionally substituted alkyl, optionally substituted alkenyl, optionally substituted aryl, or optionally substituted arylalkyl.

By "triflate" is meant trifluoromethanesulfonate.

The pKa values recited herein refer to the pKa values of a conjugate Brønsted acid in water at room temperature, unless stated otherwise.

DETAILED DESCRIPTION

The present invention provides methods for the synthesis of eribulin or a pharmaceutically acceptable salt thereof (e.g., eribulin mesylate) through a macrocyclizations. The macrocyclizations of the present invention involve subjecting a non-macrocyclic intermediate to a carbon-carbon bond-forming reaction (e.g., catalytic Ring-Closing Olefin Metathesis, an olefination reaction (e.g., Homer-Wadsworth-Emmons olefination), Nozaki-Hiyama-Kishi reaction, or Dieckmann reaction) to afford a macrocyclic intermediate (e.g., a compound of formula (IB), (IIB), (IIIB), (IVB), (VB), or (VIB)). The carbon-carbon bond forming reaction provides a C.0-C.1, C.2-C.3, C.3-C.4, C.15-C.16, C.19-C.20, or C.26-C.27 bond in the structure of eribulin or a pharmaceutically acceptable salt thereof. The carbon-atom numbering scheme for eribulin and pharmaceutically acceptable salts thereof is shown in Chart 1.

Chart 1

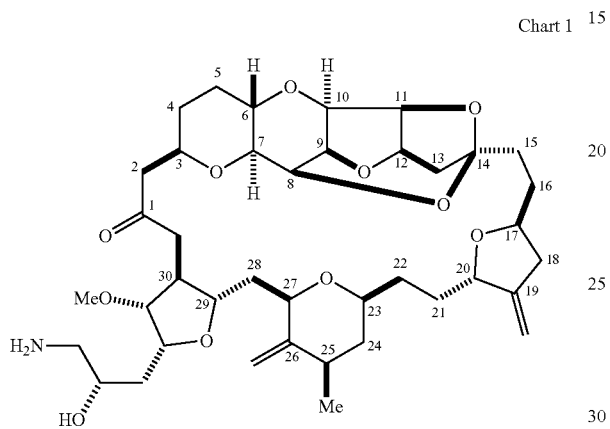

The invention also provides intermediates in the synthesis of eribulin and methods of preparing the same, as described herein.

C.15-C.16 Bond-Forming Macrocyclization

Figure 1:
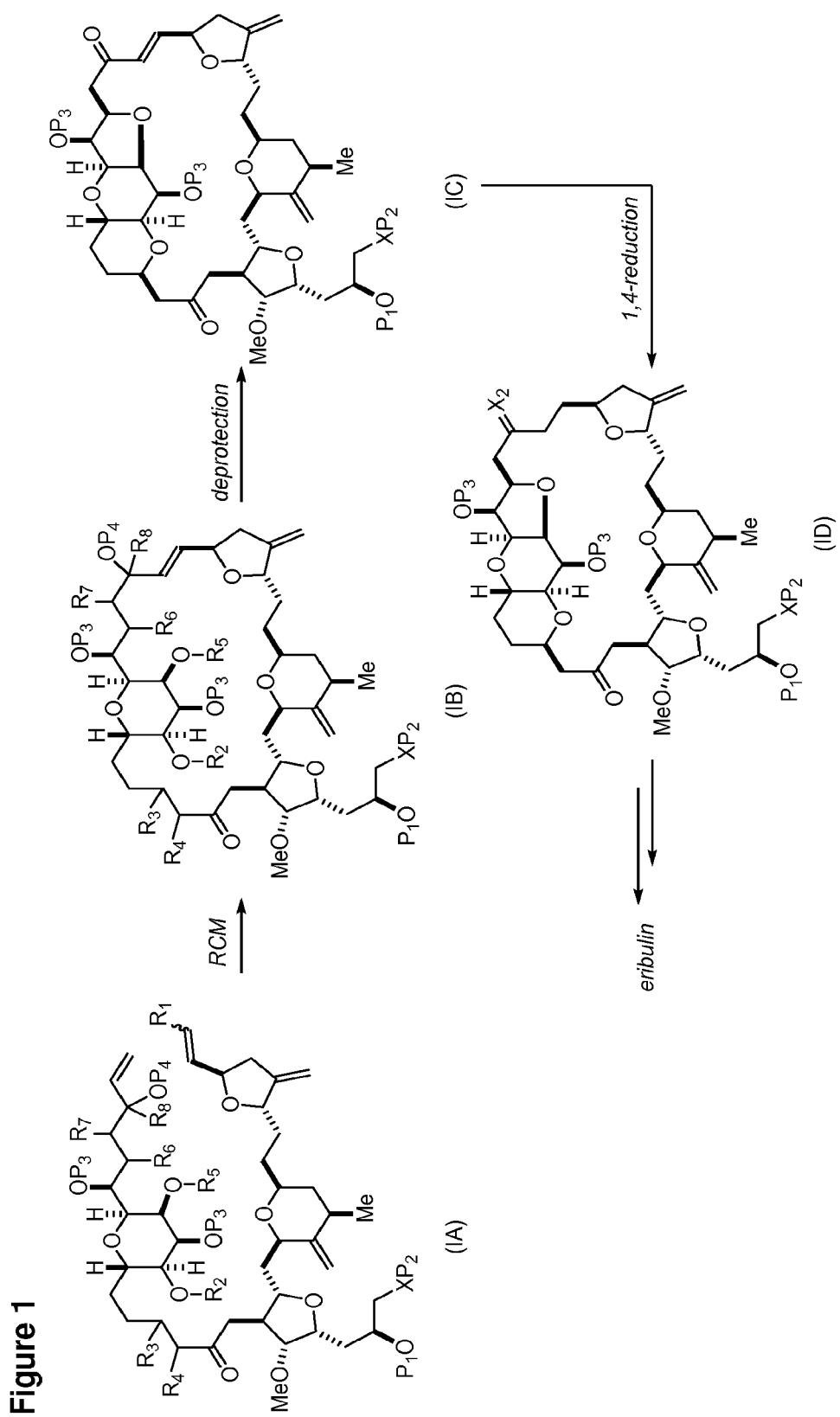
FIG. 1 is a scheme showing preparation of eribulin through a C.15-C.16 bond-forming macrocyclization.

The macrocyclization reaction of the invention can be a carbon-carbon bond-forming reaction (e.g., catalytic Ring-Closing olefin Metathesis (RCM)) that provides a C.15-C.16 bond in eribulin or a pharmaceutically acceptable salt thereof (e.g., eribulin mesylate). The general synthetic sequence including RCM that can be used to prepare eribulin or a pharmaceutically acceptable salt thereof (e.g., a mesylate salt) is shown in FIG. 1. As shown in FIG. 1, the non-macrocyclic intermediate in the synthesis of eribulin can be a compound of formula (IA):

(IA)

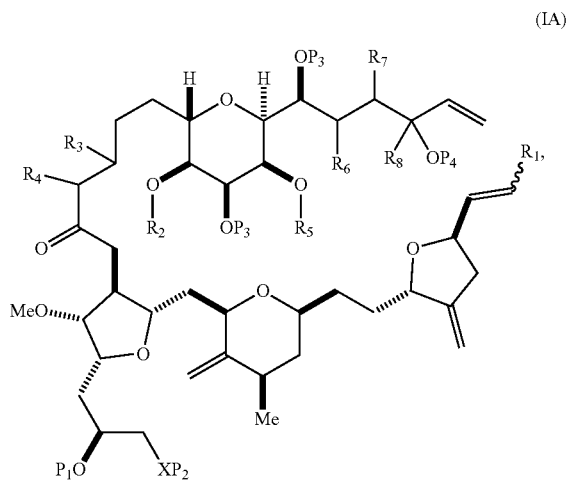

where $R_1$ is H or —$CH_2X_1CH_2CH=CH_2$, wherein $X_1$ is O, —$C(R_9)_2$—, or $NP_5$, and where each $R_9$ is independently H or —$COOR_{10}$, $P_5$ is an N-protecting group, and $R_{10}$ is $C_{1-6}$ alkyl;

(a1) $R_2$ is H or a hydroxyl protecting group, $R_3$ is $C_{1-6}$ alkyl ether, and $R_4$ is H;

(a2) $R_2$ is H or a hydroxyl protecting group, and $R_3$ and $R_4$ combine to form a double bond;

or (a3) $R_2$ and $R_3$ combine to form a bond, and $R_4$ is H;

(b1) $R_5$ is H or a hydroxyl protecting group, and $R_6$ and $R_7$ combine to form a double bond;

or (b2) $R_5$ and $R_6$ combine to form a bond, and $R_7$ is H;

(c1) $R_8$ is H, and $P_4$ is H or a hydroxyl protecting group;

or (c2) $R_8$ and $P_4$ combine to form a double bond;

each $P_3$ is independently H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

An intermediate in the synthesis of eribulin can be a compound of formula (IB), which can be produced by reacting the compound of formula (IA) with an olefin metathesis catalyst (e.g., a ruthenium-carbene complex). The compound of formula (IB) has the following structure:

(IB)

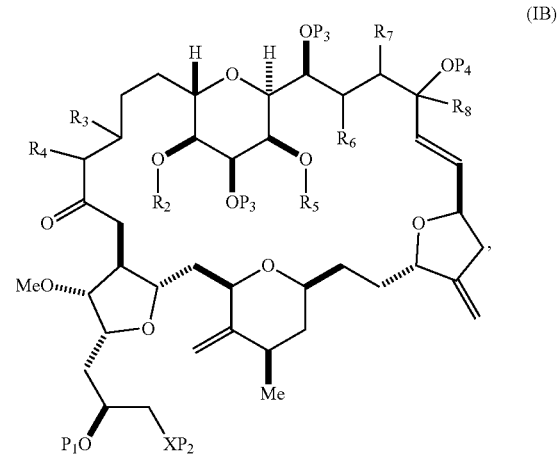

where all variables are as defined for compound of formula (IA).

The catalysts that can be used to convert the compound of formula (IA) to the compound of formula (IB) can be those known in the art. Olefin metathesis catalysts include Ru-carbene complexes (e.g., Grubbs and Hoveyda-Grubbs catalysts).

The compound of formula (IB) can be reacted with a hydroxyl protecting group removing agent and, optionally, an oxidizing agent (e.g., when $R_8$ is H in the compound of formula (IB)) capable of converting an alcohol to a carbonyl group (e.g., capable of converting an allylic alcohol to an enone) to afford the compound of formula (IC):

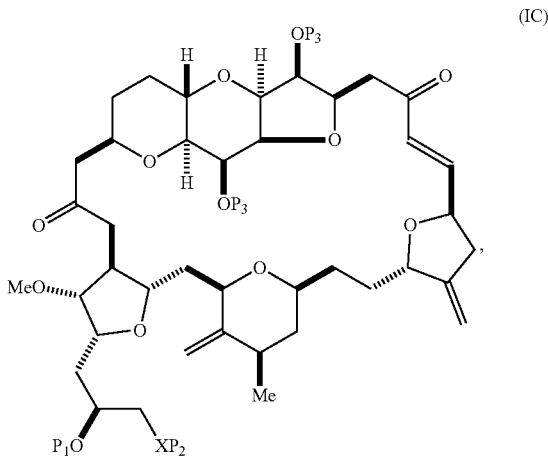

(IC)

where $P_1$, $P_2$, $P_3$, and X are as defined for compound of formula (IB).

The hydroxyl protecting group removing agent used in the step forming the compound of formula (IC) can be a Brønsted acid (e.g., a carboxylic acid, such as a carboxylic acid having a pKa of 4±1).

The compound of formula (ID) can be prepared from the compound of formula (IC) by a synthesis involving reacting the compound of formula (IC) with a 1,4-reducing agent to afford a compound of formula (ID):

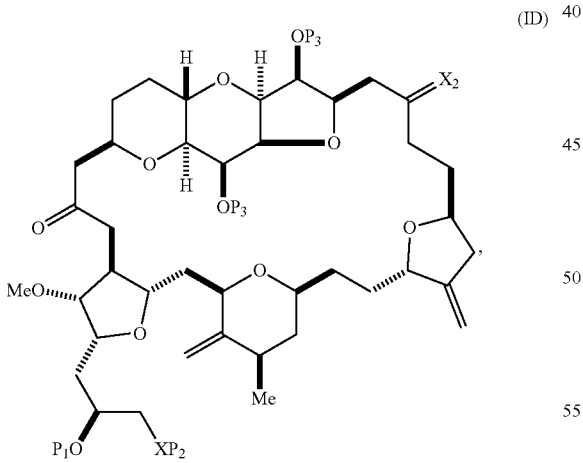

(ID)

where $P_1$, $P_2$, and X are as defined for compound of formula (IC); and each $P_3$ is independently H or a hydroxyl protecting group, and $X_2$ is oxo; or both P groups and $X_2$, together with the atoms to which each is attached, combine to form ketal.

The 1,4-reducing agents include copper (I) hydrides, which can be isolated (e.g., Stryker's reagent) or prepared in situ (e.g., from a copper (I) or copper (II) salt and a hydride source). Catalytic quantities of a copper salt (either copper (I) or copper (II) salt) in combination with stoichiometric or superstoichiometric quantities of a hydride source (e.g., a borohydride salt, borane, PMHS, or a hydrosilane (e.g., $Ph_2SiH_2$)). A non-limiting example of the reaction conditions that can be used for conversion of the compound of formula (IC) to the compound of formula (ID) are described, e.g., in Baker et al., Org. Lett., 10:289-292, 2008, the disclosure of which is incorporated herein by reference. Other metals can be used to catalyze 1,4-reduction of the compound of formula (IC) to afford the compound of formula (ID), e.g., Ru, Pd, and Ir compounds.

If $P_1$ is a hydroxyl protecting group in the compound of formula (ID), the compound of formula (ID) can be reacted with a hydroxyl protecting group removing agent to afford:

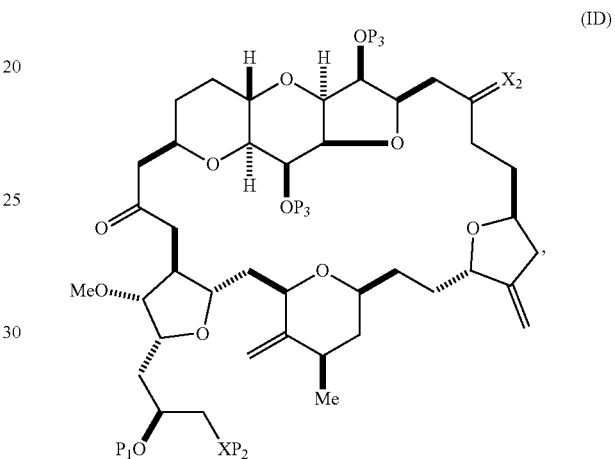

(ID)

where both $P_3$ groups and $X_2$, together with the atoms to which each is attached, combine to form ketal; and X is O, and each of $P_1$ and $P_2$ is H, or $P_1$ is H, and X and $P_2$ combine to form optionally masked amino.

The compound of formula (ID) (e.g., the compound of formula (ID), in which X is O, $P_2$ is H, and both $P_3$ groups and $X_2$, together with the atoms to which each is attached, combine to form ketal) can be aminated to afford eribulin, e.g., using sulfonylation followed by the treatment with a nitrogen source (e.g., ammonia (e.g., aqueous ammonia) or sulfamic acid). When the nitrogen source is not ammonia or sulfamic acid, further contacting with an amino unmasking agent may be used to afford eribulin. The compound of formula (ID), in which $P_1$ is a hydroxyl protecting group, can be reacted with a hydroxyl protecting group removing agent prior to the amination reaction. Alternatively, the compound of formula (ID) (in which $P_1$ is H, X and $P_2$ combine to form a masked amino, and both $P_5$ groups and $X_2$, together with the atoms to which each is attached, combine to form ketal) can be reacted with an amino unmasking agent to afford eribulin, as described herein. Eribulin mesylate can then be produced by salification of eribulin with methanesulfonic acid. The details of the amination and salification reactions are described below.

The compound of formula (IA) can be prepared from a compound of formula (IE):

(IE)

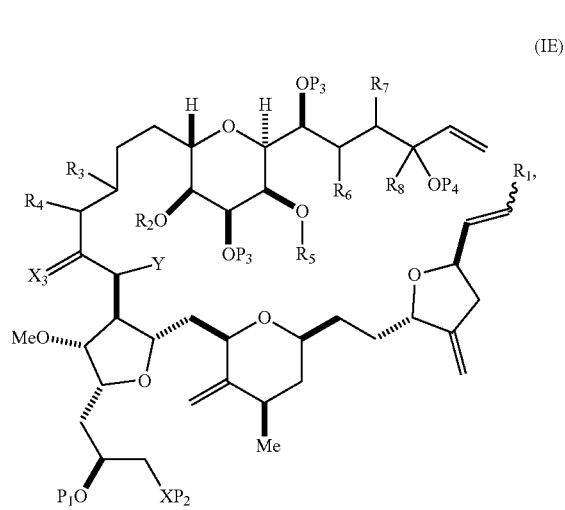

where
R₁ is H or —CH₂X₁CH₂CHCH₂, wherein X₁ is O, —C(R₉)₂—, or NP₅, and where each R₉ is independently H or —COOR₁₀, P₅ is an N-protecting group, and R₁₀ is C₁₋₆ alkyl;
(a1) $R_2$ is H or a hydroxyl protecting group, $R_3$ is $C_{1-6}$ alkyl ether, and $R_4$ is H;
(a2) $R_2$ is H or a hydroxyl protecting group, and $R_3$ and $R_4$ combine to form a double bond;
or
(a3) $R_2$ and $R_3$ combine to form a bond, and $R_4$ is H;
(b1) $R_5$ is H or a hydroxyl protecting group, and $R_6$ and $R_7$ combine to form a double bond;
or
(b2) $R_5$ and $R_6$ combine to form a bond, and $R_7$ is H;
(c1) $R_8$ is H, and $P_4$ is H or a hydroxyl protecting group;
or
(c2) $R_8$ and $P_4$ combine to form a double bond;
each Pa is independently H or a hydroxyl protecting group;
Y is $SO_2R_1$ and $R_1$ is optionally substituted aryl or optionally substituted non-enolizable alkyl; or Y is $COOR_{11}$, and $R_1$ is optionally substituted alkyl, optionally substituted aryl, or optionally substituted arylalkyl;
$X_3$ is oxo, or $X_3$, together with the carbon atom to which it is attached, forms —(CH(OH))—; and
X is O, and
  each of $P_1$ and $P_2$ is independently H or a hydroxyl protecting group,
  or
  $P_1$ and $P_2$, together with the atoms to which each is attached, combine to form a cyclic protected diol;
or
X is N, and
  $P_1$ is H or a hydroxyl protecting group, and X and $P_2$ combine to form optionally masked amino;
  or
  $P_1$ and $P_2$, together with the atoms to which each is attached, combine to form an aminal or 1,3-oxazolidin-2-one-5-yl.

In some embodiments, the preparation of the compound of formula (IA) from the compound of formula (IE) involves a decarboxylation reaction (when $X_3$ is oxo, and Y is $COOR_{11}$) or a desulfonylation (when $X_3$ is oxo, and Y is $SO_2R_{11}$) reaction. The conditions for the decarboxylation or desulfonylation reaction can be those described herein. The preparation of the compound of formula (IA) from the compound of formula (IE) can further involve oxidizing the compound of formula (IE) (e.g., the compound of formula (IE), in which $X_3$, together with the carbon atom to which it is attached, forms —(CH(OH))—), e.g., by contacting with an oxidizing agent capable of oxidizing an alcohol to a carbonyl group.

C.2-C.3 Bond-Forming Macrocyclization

Figure 2:
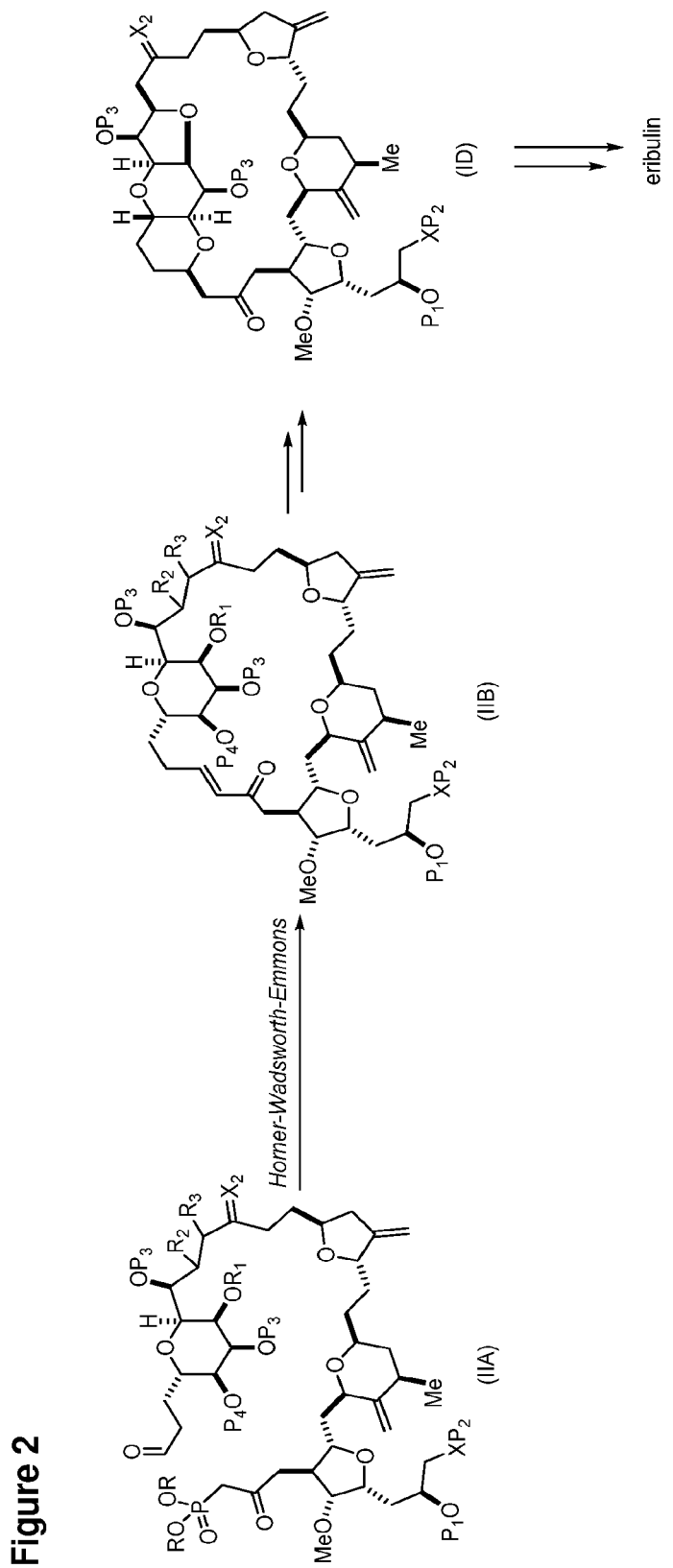
FIG. 2 is a scheme showing preparation of eribulin through a C.2-C.3 bond-forming macrocyclization.

The macrocyclization reaction of the invention can be a carbon-carbon bond-forming reaction (e.g., Homer-Wadsworth-Emmons reaction) that provides a C.2-C.3 bond in eribulin or a pharmaceutically acceptable salt thereof (e.g., eribulin mesylate). The general synthetic sequence including the Homer-Wadsworth-Emmons reaction that can be used to prepare eribulin or a pharmaceutically acceptable salt thereof (e.g., a mesylate salt) is shown in FIG. 2. As shown in FIG. 2, the non-macrocyclic intermediate can be a compound of formula (IIA):

(IIA)

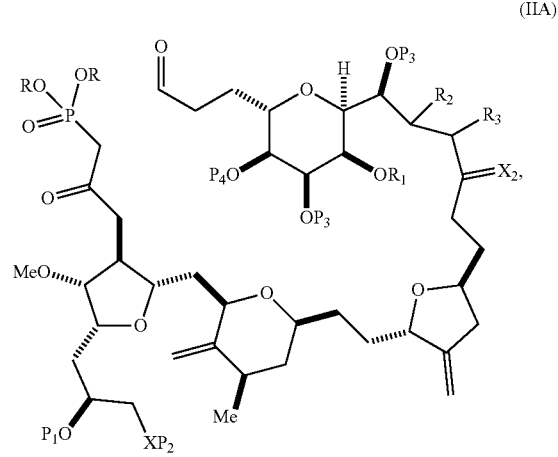

where
each R is independently optionally substituted alkyl or optionally substituted aryl;
(i) $R_1$ is H or a hydroxyl protecting group, and $R_2$ and $R_3$ combine to form a double bond;
or
(ii) $R_1$ and $R_2$ combine to form a bond, and $R_3$ is H;
each $P_3$ is independently H or a hydroxyl protecting group, and $X_2$ is oxo; or both $P_3$ groups and $X_2$, together with the atoms to which each is attached, combine to form ketal;
$P_4$ is H or a hydroxyl protecting group; and
X is O, and
  each of $P_1$ and $P_2$ is independently H or a hydroxyl protecting group,
  or
  $P_1$ and $P_2$, together with the atoms to which each is attached, combine to form a cyclic protected diol;
or
X is N, and
  $P_1$ is H or a hydroxyl protecting group, and X and $P_2$ combine to form optionally masked amino;
  or
  $P_1$ and $P_2$, together with the atoms to which each is attached, combine to form an aminal or 1,3-oxazolidin-2-one-5-yl.

The intermediate in the synthesis of eribulin can be a compound of formula (IIB), which can be produced from the compound of formula (IIA) using Homer-Wadsworth-Emmons reaction. The compound of formula (IIB) has the following structure:

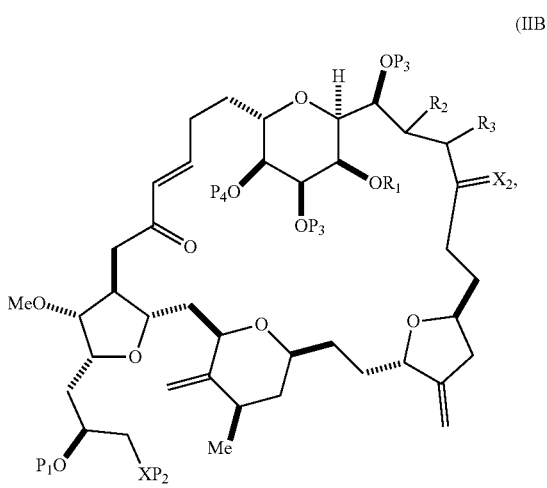
(IIB)

where all variables are as defined for the compound of formula (IIA).

The reaction conditions that can be used to convert the compound of formula (IIA) into the compound of formula (IIB) include those known in the art for Homer-Wadsworth-Emmons reaction, e.g., Masamune-Roush conditions or Helquist protocol. In particular, the compound of formula (IIA) can be reacted with an organic base (e.g., an organic base, the conjugate acid of which has a pKa of from 11±2) and a Lewis acid (e.g., a salt of Li, Mg, or Zn). Non-limiting examples of an organic base that can be used in the Homer-Wadsworth-Emmons reaction include trialkylamines (e.g., triethylamine or Hünig's base), DBU, and DBN. Non-limiting examples of Lewis acids that can be used in the Homer-Wadsworth-Emmons reaction include LiCl, $Zn(OTf)_2$, and $MgCl_2$.

The compound of formula (IIB) can be converted to a compound of formula (ID):

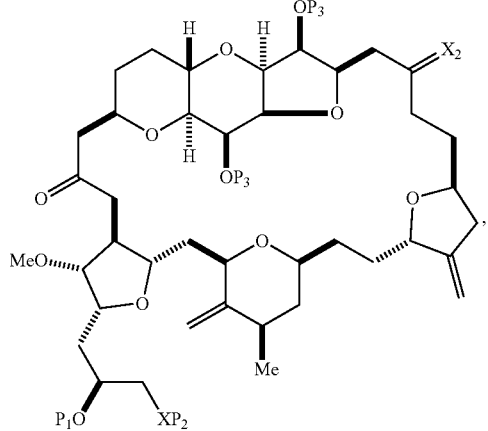
(ID)

where
each $P_3$ is independently H or a hydroxyl protecting group, and $X_2$ is oxo; or both $P_3$ groups and $X_2$, together with the atoms to which each is attached, combine to form ketal; and
X is O, and
each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

In a non-limiting example, the synthesis of the compound of formula (ID) from the compound of formula (IIB) can involve reacting the compound of formula (IIB) (e.g., the compound of formula (IIB), in which $P_4$ is a protecting group, $R_1$ and $R_2$ form a bond, and $R_3$ is H) with a hydroxyl protecting group removing agent.

The compound of formula (ID) (in which X is O, $P_1$ and $P_2$ are H, and both $P_3$ groups and $X_2$, together with the atoms to which each is attached, combine to form ketal) can be aminated to afford eribulin, as described herein. Alternatively, the compound of formula (ID) (in which $P_1$ is H, X and $P_2$ combine to form a masked amino, and both $P_3$ groups and $X_2$, together with the atoms to which each is attached, combine to form ketal) can be reacted with an amino unmasking agent to afford eribulin, as described herein. Eribulin mesylate can be produced by salification of eribulin, as described herein.

The compound of formula (IIA) can be prepared from a compound of formula (IIC):

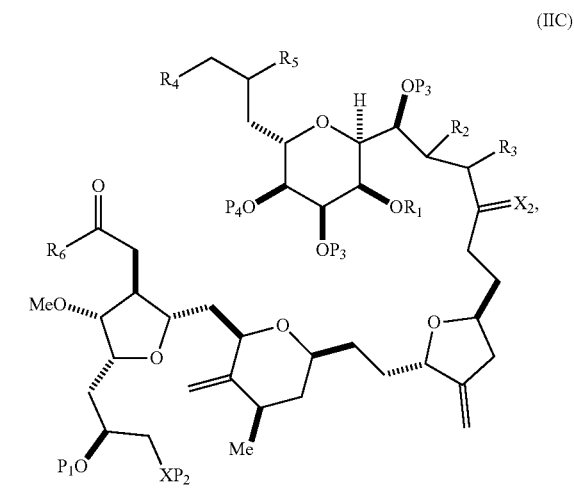
(IIC)

where
(i) $R_1$ is H or a hydroxyl protecting group, and $R_2$ and $R_3$ combine to form a double bond;
or
(ii) $R_1$ and $R_2$ combine to form a bond, and $R_3$ is H;
$R_4$ is OH, and $R_5$ is H, or $R_4$ and $R_5$ combine to form a double bond;
$R_6$ is $-OP_5$ or $CH_2P(O)(OR)_2$, where $P_5$ is an ether hydroxyl protecting group, and each $R_6$ is independently optionally substituted alkyl or optionally substituted aryl;

each $P_3$ is independently H or a hydroxyl protecting group, and $X_2$ is oxo; or both $P_3$ groups and $X_2$, together with the atoms to which each is attached, combine to form ketal;

$P_4$ is H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

In some embodiments, the preparation of the compound of formula (IIA) from the compound of formula (IIC) can involve performing hydroboration/oxidation reaction on the compound of formula (IIC) (e.g., the compound of formula (IIC), in which $R_4$ and $R_5$ combine to form a double bond; $R_1$ and $R_2$ combine to form a bond; and $R_3$ is H). The preparation may involve subjecting the compound of formula (IIC) (e.g., the compound of formula (IIC), in which $R_6$ is $-OP_5$) to a phospha-Claisen reaction with $CHP(O)(OR_6)_2$. Phospha-Claisen reaction conditions can be those known in the art. In a non-limiting example, $CH_3P(O)(OR)_2$ can be deprotonated (e.g., by a contact with a strong base) and subsequently contacted with the compound of formula (IIC). The preparation may also involve oxidizing the compound of formula (IIC) (e.g., the compound of formula (IIC), in which $R_4$ is OH, $R_5$ is H, and $R_6$ is $CH_2P(O)(OR_6)_2$), e.g., by contacting this product with an oxidizing agent capable of oxidizing an alcohol to a carbonyl group.

The compound of formula (IIC) can be prepared from a compound of formula (VIIE), the compound of formula (VIIE) having the following structure:

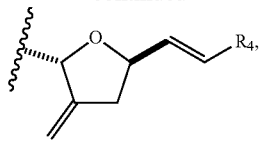

(VIIE)

where $Y_1$ is $SO_2R_1$ and $R_1$ is optionally substituted non-enolizable alkyl or optionally substituted aryl, or $Y_1$ is $COOR_1$, and $R_1$ is optionally substituted alkyl, optionally substituted aryl, or optionally substituted arylalkyl;

$R_2$ is

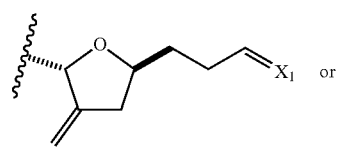 or

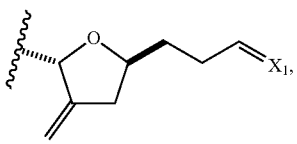

where $X_1$ is oxo, and $R_4$ is CHO; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

In a non-limiting example, the compound of formula (IIC) is prepared by reacting the compound of formula (VIIE) (e.g., the compound of formula (VIIE), in which $R_2$ is

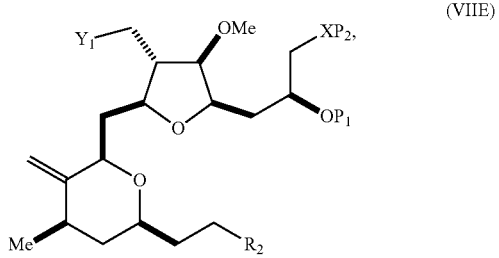

and $X_1$ is oxo) with a compound of formula (IID), the compound of formula (IID) having the following structure:

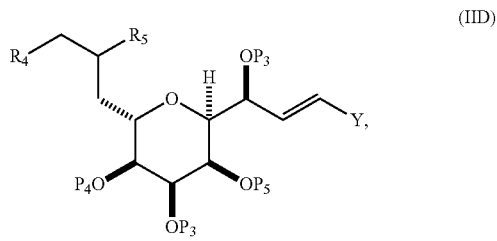

(IID)

where $R_4$ is OH or $OP_5$, and $R_5$ is H, or $R_4$ and $R_5$ combine to form a double bond;

each $P_3$, $P_4$, and $P_5$ is independently a hydroxyl protecting group; and

Y is chloro, bromo, iodo, or trifluoromethanesulfonate.

The compound of formula (VIIE), in which $X_1$ is oxo, can be reacted with the compound of formula (IID) under the Nozaki-Hiyama-Kishi reaction conditions, as described herein.

C.3-C.4 Bond-Forming Macrocyclization

Figure 3:
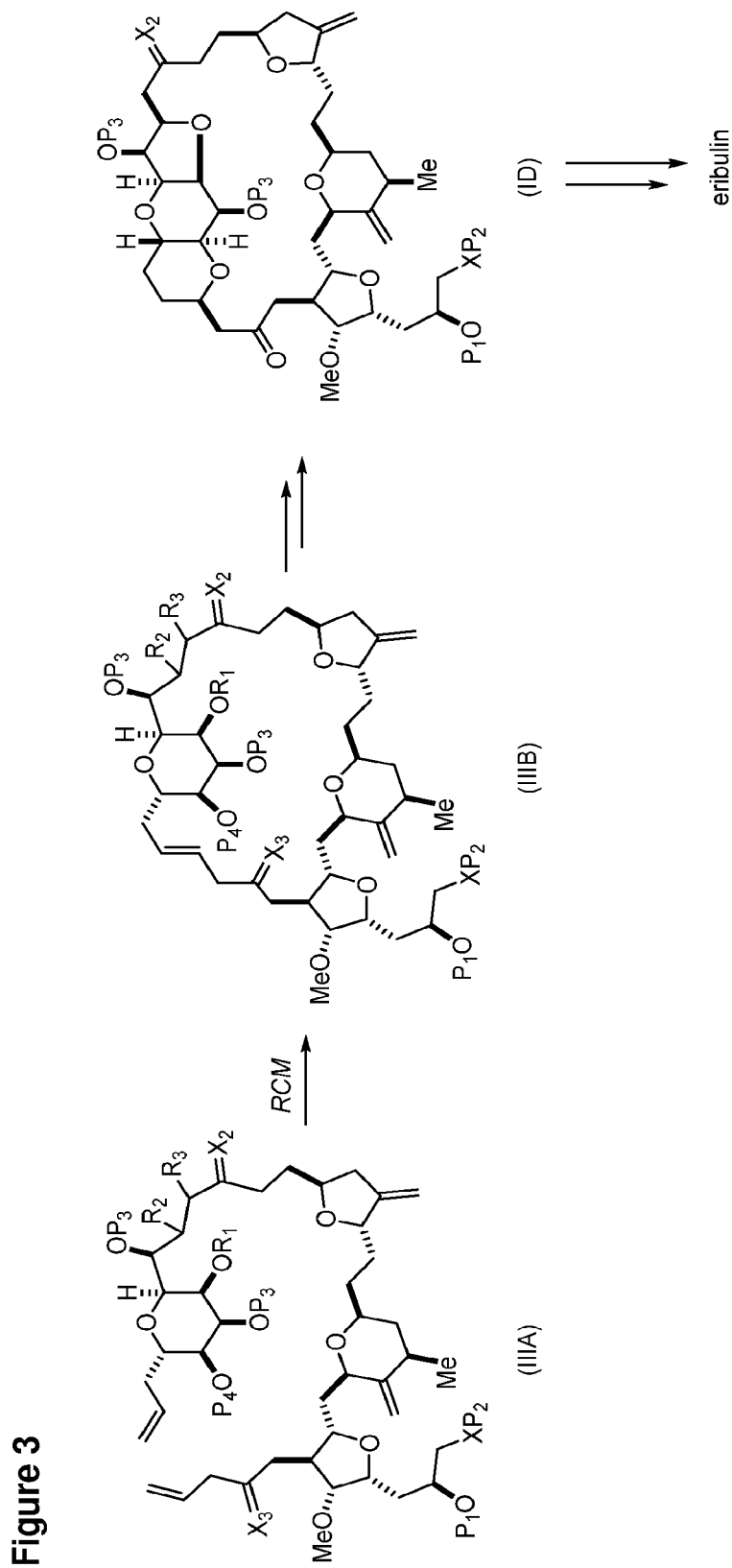
FIG. 3 is a scheme showing preparation of eribulin through a C.3-C.4 bond-forming macrocyclization.

The macrocyclization reaction of the invention can be a carbon-carbon bond-forming reaction (e.g., catalytic Ring-Closing olefin Metathesis (RCM)) that provides a C.3-C.4 bond in eribulin or a pharmaceutically acceptable salt thereof (e.g., eribulin mesylate). The general synthetic sequence including RCM that can be used to prepare eribulin or a pharmaceutically acceptable salt thereof (e.g., a mesylate salt) is shown in FIG. 3. As shown in FIG. 3, the non-macrocyclic intermediate in the synthesis of eribulin can be a compound of formula (IIIA):

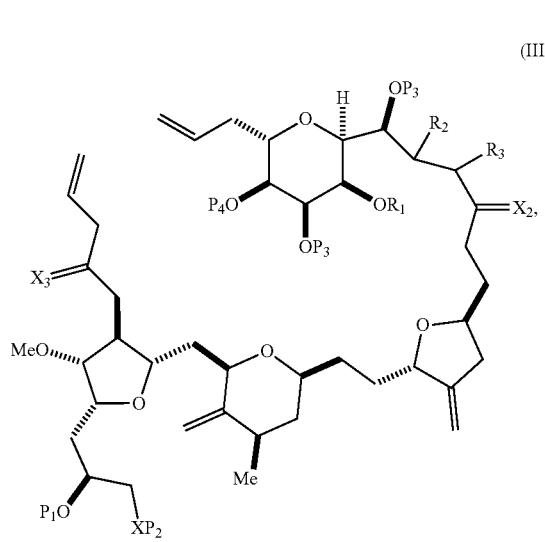
(IIIA)

where (i) $R_1$ is H or a hydroxyl protecting group, and $R_2$ and $R_3$ combine to form a double bond; or (ii) $R_1$ and $R_2$ combine to form a bond, and $R_3$ is H;

$X_3$ is oxo, or $X_3$ combines with the carbon atom to which it is attached to form a ketal, a thioketal, or —(CH(OP$_5$))—, wherein $P_5$ is H or a hydroxyl protecting group;

each $P_3$ is independently H or a hydroxyl protecting group, and $X_2$ is oxo; or both $P_3$ groups and $X_2$, together with the atoms to which each is attached, combine to form ketal;

$P_4$ is H or a hydroxyl protecting group; and

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

An intermediate in the synthesis of eribulin can be a compound of formula (IIIB), which can be produced by reacting the compound of formula (IIIA) with an olefin metathesis catalyst (e.g., a ruthenium-carbene complex). The compound of formula (IIIB) has the following structure:

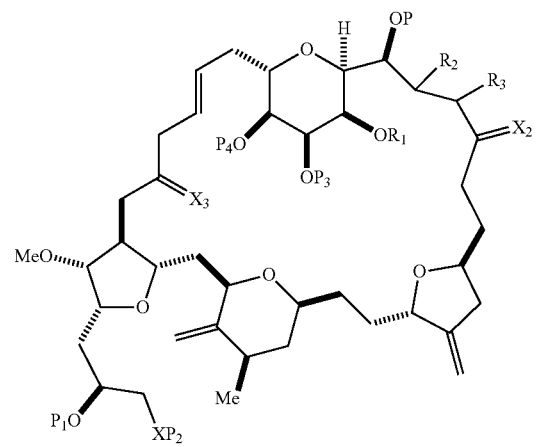
(IIIB)

where all variables are as defined for formula (IIIA).

The catalysts that can be used to convert the compound of formula (IIIA) to the compound of formula (IIIB) can be those known in the art. Olefin metathesis catalysts include Ru-carbene complexes (e.g., Grubbs and Hoveyda-Grubbs catalysts).

The compound of formula (IIIB) can be converted to a compound of formula (ID), from which eribulin or eribulin mesylate can be prepared as described herein. A non-limiting example of the preparation of the compound of formula (ID) from the compound of formula (IIIB) is provided below.

The compound of formula (IIIB), in which $X_3$, together with the carbon to which it is attached, forms —(CH(OP$_5$))—, where $P_5$ is H, can be oxidized to afford the compound of formula (IIIB), in which $X_3$ is oxo.

Oxidation of the —(CH(OH))— in the compound of formula (IIIB) to give the compound of formula (IIIB), in which $X_3$ is oxo, can be performed using methods known in the art for oxidation of alcohols to carbonyl groups, e.g., by contacting the compound of formula (IIIB) with an oxidizing agent capable of converting an alcohol to a carbonyl group.

The compound of formula (IIIB) (e.g., the compound of formula (IIIB), in which $X_3$ is oxo, and $P_1$ is a hydroxyl protecting group) can be reacted with a hydroxyl protecting group removing agent to afford a compound of formula (ID):

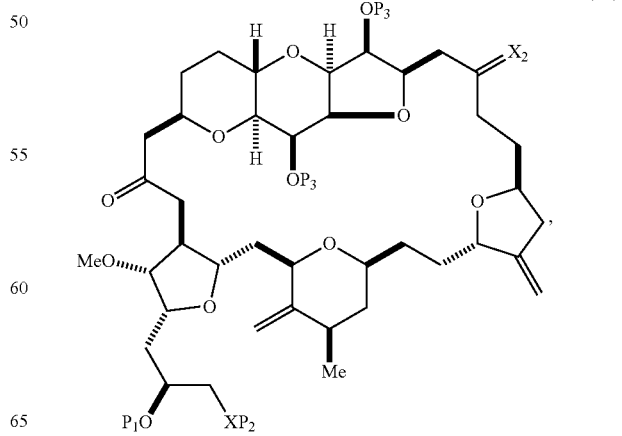
(ID)

where
each $P_3$ is H, and $X_2$ is oxo; or both $P_3$ groups and $X_2$, together with the atoms to which each is attached, combine to form ketal; and
X is O, and $P_1$ and $P_2$ are H;
or
$P_1$ is H, and X and $P_2$ combine to form optionally masked amino.

The conditions for the reaction used in preparing the compound of formula (ID) from the compound of formula (IIIB) can be those allowing for isomerization of a β,γ-enone to an α,β-enone (e.g., including basic or acidic compounds). For example, a hydroxyl protecting group removing agent, such as a fluoride source (e.g., TBAF), can mediate the isomerization of a β,γ-enone to an α,β-enone, while unmasking hydroxyl groups protected with optionally substituted silyl groups.

The compound of formula (ID) (in which X is O, $P_1$ and $P_2$ are H, and both $P_3$ groups and $X_2$, together with the atoms to which each is attached, combine to form ketal) can be aminated to afford eribulin, as described herein. Alternatively, the compound of formula (ID) (in which $P_1$ is H, X and $P_2$ combine to form a masked amino, and both $P_3$ groups and $X_2$, together with the atoms to which each is attached, combine to form ketal) can be reacted with an amino unmasking agent to afford eribulin, as described herein. Eribulin mesylate can be produced by salification of eribulin, as described herein.

The compound of formula (IIIA) can be prepared from a compound of formula (IIIC):

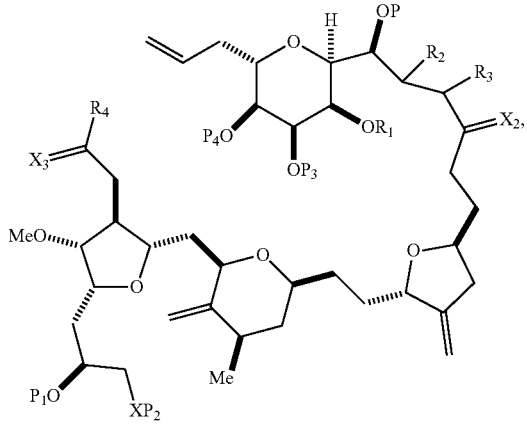

(IIIC)

where
(i) $R_1$ is H or a hydroxyl protecting group, and $R_2$ and $R_3$ combine to form a double bond; or
(ii) $R_1$ and $R_2$ combine to form a bond, and $R_3$ is H;
$X_3$ is oxo and $R_4$ is H or $OP_6$, or $X_3$ and $R_4$ combine with the carbon atom to which they are attached to form an acetal, a thioacetal, or —$CH_2OP_5$; where $P_5$ is H or a hydroxyl protecting group, and $P_6$ is an ether hydroxyl protecting group;
each $P_3$ is independently H or a hydroxyl protecting group, and $X_2$ is oxo; or both $P_3$ groups and $X_2$, together with the atoms to which each is attached, combine to form ketal;
$P_4$ is H or a hydroxyl protecting group; and
X is O, and each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

In some embodiments, the preparation of the compound of formula (IIIA) from the compound of formula (IIIC) involves allylating the compound of formula (IIIC) (e.g., the compound of formula (IIIC), in which $R_4$ is H, and $X_3$ is oxo, or $X_3$ and $R_4$ combine with the carbon atom to which they are attached to form a thioacetal). Allylation of the compound of formula (IIIC) can be performed using conditions known in the art. In a non-limiting example, when $X_3$ is oxo, and $R_4$ is H, allylation of the compound of formula (IIIC) can be a nucleophilic allylation (e.g., by contacting the compound of formula (IIIC) with a nucleophilic allylating agent (e.g., allylboron reagent (e.g., allyl boronate or allyl borane), allylstannane, allyl Grignard reagent, allylsilane, or allyl indium). Alternatively, allylation of the compound of formula (IIIC) can be performed using electrophilic allylation (e.g., when $X_3$ and $R_4$ combine with the carbon to which they are attached to form a thioacetal). In a non-limiting examples of electrophilic allylation, the compound of formula (IIIC), in which $X_3$ and $R_4$ combine with the carbon to which they are attached to form a thioacetal, can be contacted with a strong base followed by an allylic electrophile (e.g., allyl halide or allyl sulfonate).

The preparation of the compound of formula (IIIA) from the compound of formula (IIIC) can also involve reducing the compound of formula (IIIC), in which $X_3$ is oxo and $R_4$ is $OP_6$, with a 1,2-reducing agent to afford a compound of formula (IIIC), in which $X_3$ is oxo or —(CH(OH))—, and $R_4$ is H. Formation of the compound of formula (IIIC), in which $X_3$ is oxo, and $R_4$ is H, can be direct (e.g., by treating with DIBAL at a temperature between about −70° C. and about −80° C.) or indirect via the compound of formula (IIIC), in which $X_3$ combines with the carbon atom to which it is attached to form —(CH(OH))—, and $R_4$ is H. The indirect route to the compound of formula (IIIC), in which $X_b$ is oxo, and $R_4$ is H, thus involves first reducing the compound of formula (IIIC), in which $X_3$ is oxo, and $R_4$ is $OP_6$, with a 1,2-reducing agent to give the compound of formula (IIIC), in which $X_3$ combines with the carbon atom to which it is attached to form —(CH(OH))—, and $R_4$ is H. The latter compound can be reacted with an oxidizing agent capable of oxidizing an alcohol to a carbonyl group to furnish the compound of formula (IIIC), in which $X_3$ is oxo, and $R_4$ is H.

Throughout the oxidation, reduction, and allylation reactions described above, the sensitive functional groups present in the compound of formula (IIIC) can be protected (e.g., $R_1$ and each $P_3$ is independently a hydroxyl protecting group) or can be present in an unreactive form (e.g., both $P_3$ groups and $X_2$, together with the atoms to which each is attached, combine to form ketal).

C.19-C.20 Bond-Forming Macrocyclization

Figure 4:
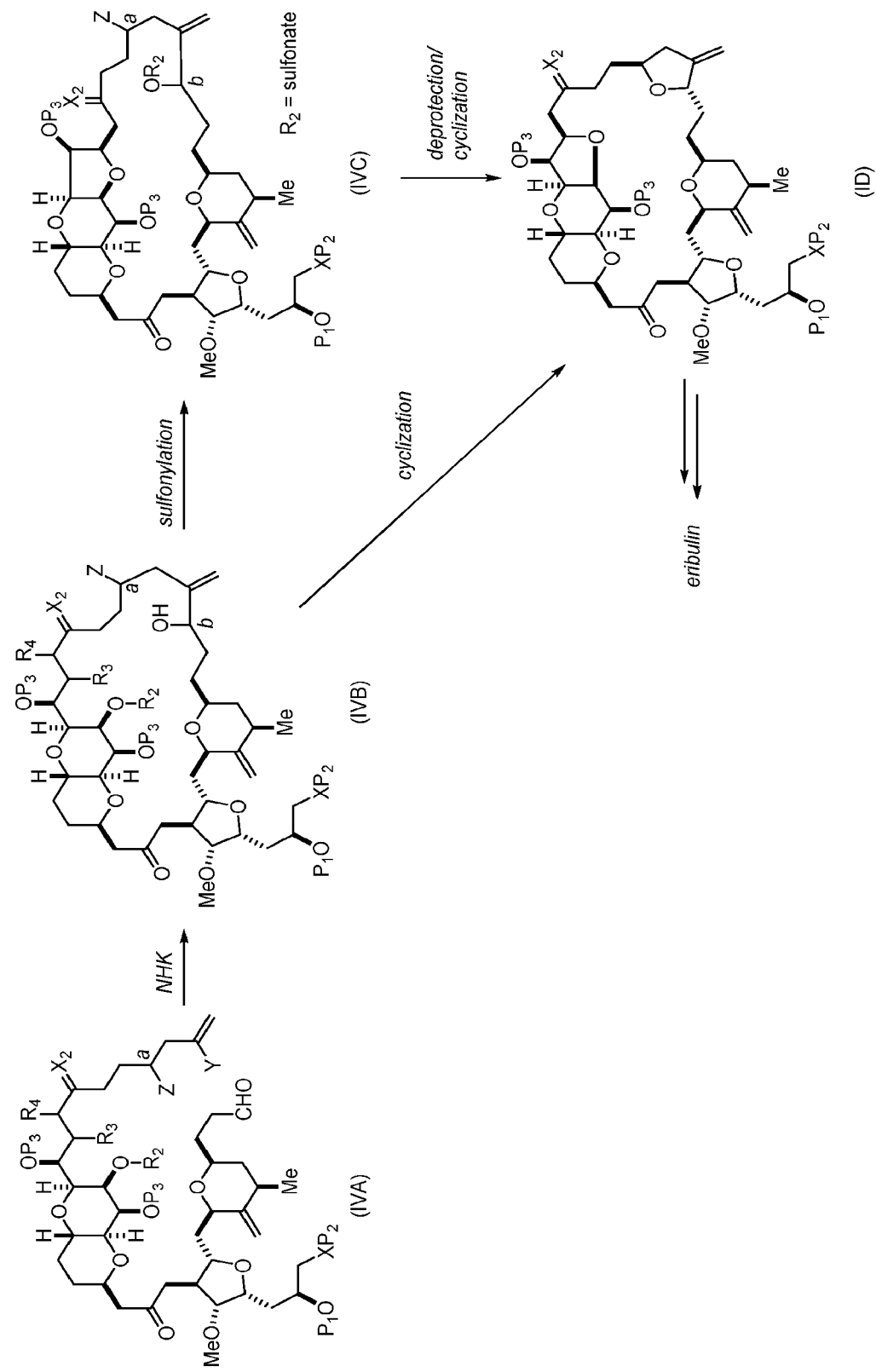
FIG. 4 is a scheme showing preparation of eribulin through a C.19-C.20 bond-forming macrocyclization.

The macrocyclization reaction of the invention can be a carbon-carbon bond-forming reaction (e.g., Nozaki-Hiyama-Kishi reaction (NHK)) that provides a C.19-C.20 bond in eribulin or a pharmaceutically acceptable salt thereof (e.g., eribulin mesylate). The general synthesis sequence including NHK that can be used to prepare eribulin or a pharmaceutically acceptable salt thereof (e.g., a mesylate salt) is shown in FIG. 4. As shown in FIG. 4, the non-macrocyclic intermediate in the synthesis of eribulin can be a compound of formula (IVA):

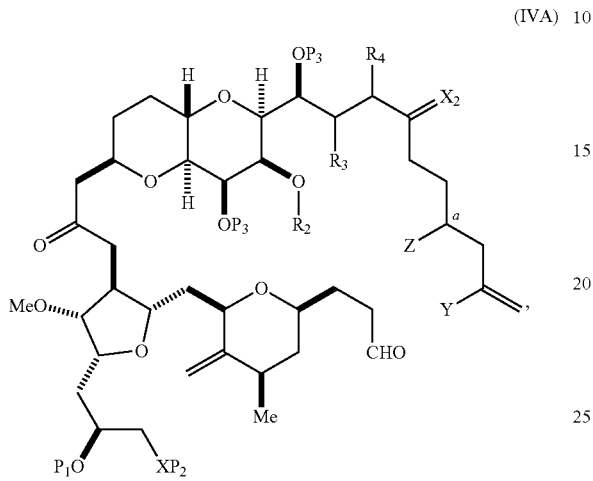

(IVA)

where

Y is iodide, bromide, or trifluoromethanesulfonate;

a designates R stereogenic center, and Z is a sulfonate, chloride, bromide, or iodide; or a designates S stereogenic center, and Z is $OR_1$, wherein $R_1$ is a hydroxyl protecting group;

(i) $R_2$ is H or a hydroxyl protecting group, $R_3$ and $R_4$ combine to form a double bond;

or (ii) $R_2$ and $R_3$ combine to form a bond, and $R_4$ is H;

each $P_3$ is independently H or a hydroxyl protecting group, and $X_2$ is oxo; or both $P_3$ groups and $X_2$, together with the atoms to which each is attached, combine to form ketal; and X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl.

An intermediate in the synthesis of eribulin can be a compound of formula (IVB), which can be produced by subjecting the compound of formula (IVA) to Nozaki-Hiyama-Kishi reaction conditions (e.g., by reacting with a Cr(II) salt and a Ni(II) salt). The compound of formula (IVB) has the following structure:

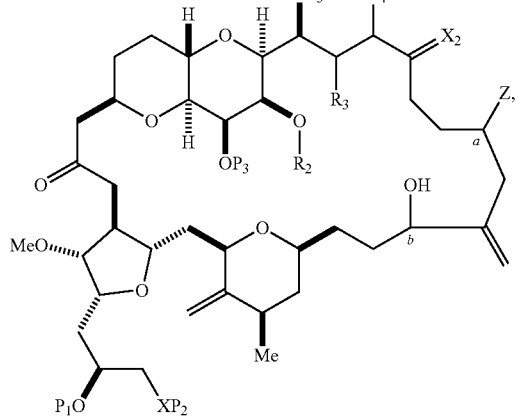

(IVB)

where $P_1$, $P_2$, $P_3$, X, and $X_2$ are as defined for compound of formula (IVB);

a designates R stereogenic center, b designates S stereogenic center, Z is a sulfonate, chloride, bromide, or iodide;

or a designates S stereogenic center, b designates R stereogenic center, and Z is $OR_1$, wherein $R_1$ is a hydroxyl protecting group.

Nozaki-Hiyama-Kishi reaction conditions that may be used to prepare the compound of formula (IVB) from the compound of formula (IVA) can be those known in the art. Nozaki-Hiyama-Kishi reaction on the compound of formula (IVA) can include reacting the compound of formula (IVA) with a Cr(II) salt and a Ni(II) salt. Ancillary ligands can be used in combination with the metal salts. In a non-limiting example, a substituted 1,10-phenanthroline can be used in combination with a Ni(II) salt. Chiral ancillary ligands can be used to render the reaction stereoselective. In a non-limiting example, chiral N-(dihydrooxazoyl-phenyl)-sulfonamides can be used with a Cr(II) salt to control the stereochemistry of the carbonyl carbon, to which a vinyl nucleophile is added in the course of Nozaki-Hiyama-Kishi reaction.

The compound of formula (IVB) can be converted to a compound of formula (ID), from which eribulin or erinulin mesylate can be prepared, as described herein. A non-limiting exemplary reaction sequence from the compound of formula (IVB) to the compound of formula (ID) is provided below.

The compound of formula (IVB) can be converted to a compound of formula (ID) directly or via an intermediate of formula (IVC). Thus, the compound of formula (IVB), in which Z is an ester, a designates S stereogenic center, b designates R stereogenic center, can be converted to the compound of formula (IVC), e.g., by reacting with a sulfonyl electrophile, such as a sulfonyl chloride or a sulfonyl anhydride.

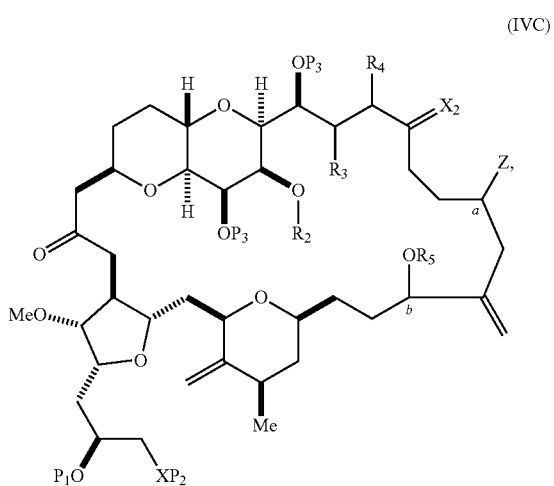

(IVC)

where
a designates S stereogenic center;
b designates R stereogenic center;
Z is an ester;
(i) $R_2$ is H or a hydroxyl protecting group, $R_3$ and $R_4$ combine to form a double bond;
or
(ii) $R_2$ and $R_3$ combine to form a bond, and $R_4$ is H;
$R_5$ is sulfonyl;
each $P_3$ is independently a hydroxyl protecting group, and $X_2$ is oxo; or both P groups and $X_2$, together with the atoms to which each is attached, combine to form ketal; and
X is O, and
each of $P_1$ and $P_2$ is independently a hydroxyl protecting group,
or
$P_1$ and $P_2$, together with the atoms to which each is attached, combine to form a cyclic protected diol;
or
$P_1$ is a hydroxyl protecting group, and X and $P_2$ combine to form optionally masked amino.

The preparation of the compound of formula (ID) from the compound of formula (IVC) can involve reacting the compound of formula (IVC) with a $C_{1-6}$ alkoxide. The compound of formula (ID) has the following structure:

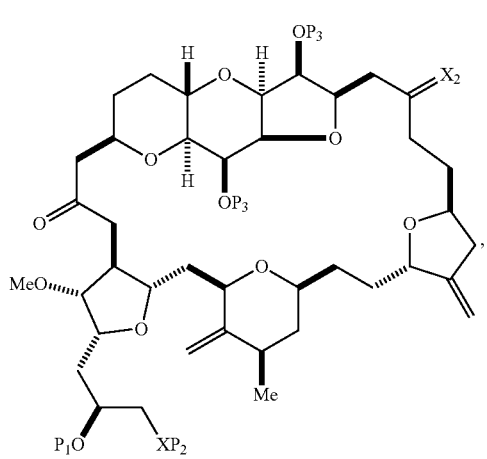

(ID)

where
each $P_3$ is independently H or a hydroxyl protecting group, and $X_2$ is oxo; or both $P_3$ groups and $X_2$, together with the atoms to which each is attached, combine to form ketal; and
X is O, and
each of $P_1$ and $P_2$ is independently a hydroxyl protecting group,
or
$P_1$ and $P_2$, together with the atoms to which each is attached, combine to form a cyclic protected diol;
or
$P_1$ is a hydroxyl protecting group, and X and $P_2$ combine to form optionally masked amino.

The compound of formula (IVB) (in which Z is a sulfonate, chloride, bromide, or iodide, a designates R stereogenic center, b designates S stereogenic center, $R_2$ and $R_3$ combine to form a bond, and $R_4$ is H) can be converted to the compound of formula (ID) directly, e.g., upon isolation from the Nozaki-Hiyama-Kishi reaction mixture (e.g., by treatment with a base) or by contacting a mixture containing the product of the Nozaki-Hiyama-Kishi reaction with silica gel.

The compound of formula (ID) (e.g., the compound of formula (ID) in which $P_1$ is a hydroxyl protecting group) can be reacted with a hydroxyl protecting group removing agent to afford:

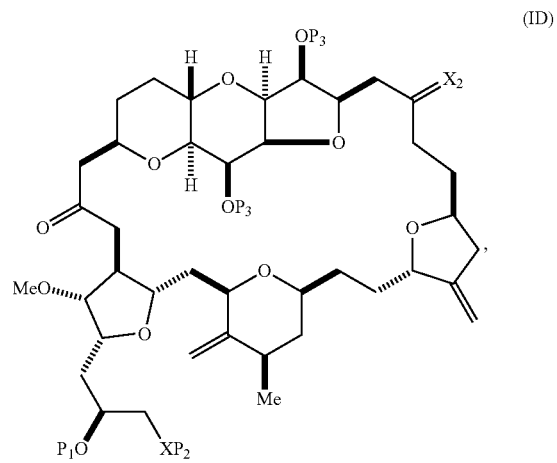

(ID)

where
each $P_3$ is independently H or a hydroxyl protecting group, and $X_2$ is oxo; or both $P_3$ groups and $X_2$, together with the atoms to which each is attached, combine to form ketal; and
X is O, and
each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

The compound of formula (ID) (in which X is O, $P_1$ and $P_2$ are H, and both $P_3$ groups and $X_2$, together with the atoms to which each is attached, combine to form ketal) can be aminated to afford eribulin, as described herein. Alternatively, the compound of formula (ID) (in which $P_1$ is H, X and $P_2$ combine to form a masked amino, and both $P_3$ groups and $X_2$, together with the atoms to which each is attached, combine to form ketal) can be reacted with an amino unmasking agent to afford eribulin, as described herein. Eribulin mesylate can be produced by salification of eribulin, as described herein.

The compound of formula (IVA) can be prepared from the compound of formula (IVD):

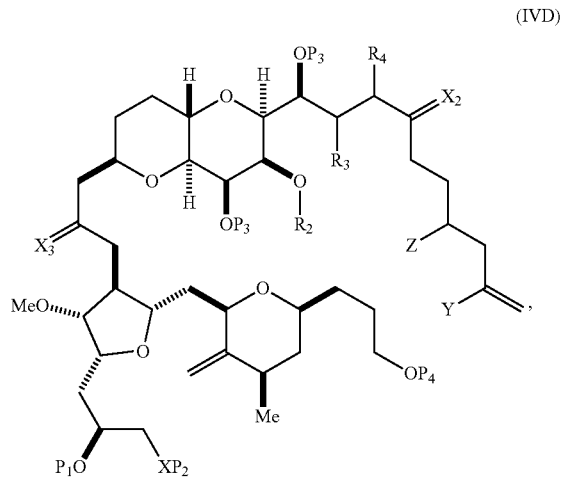

(IVD)

where
Y is iodide, bromide, or trifluoromethanesulfonate;
$Y_1$ is H, $COOR_6$, or $SO_2R_6$, where, when $Y_1$ is $COOR_6$, $R_6$ is optionally substituted alkyl, optionally substituted aryl, or optionally substituted arylalkyl, and, when $Y_1$ is $SO_2R_6$, $R_6$ is optionally substituted aryl or optionally substituted non-enolizable alkyl;
Z is an ester, a sulfonate, chloride, bromide, or iodide;
(i) $R_2$ is H or a hydroxyl protecting group, $R_3$ and $R_4$ combine to form a double bond;
or
(ii) $R_2$ and $R_3$ combine to form a bond, and $R_4$ is H;
each $P_3$ is independently H or a hydroxyl protecting group, and $X_2$ is oxo; or both $P_3$ groups and $X_2$, together with the atoms to which each is attached, combine to form ketal;
$X_3$ is oxo, or $X_3$ combines with the carbon atom to which it is attached to form —(CH(OH))—; and
X is O, and
each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

In some embodiments, the preparation of the compound of formula (IVA) involves oxidizing the compound of formula (IVD), in which $X_3$ is —(CH(OH))—, and/or $P_4$ is H, e.g., by reacting with an oxidizing agent capable of oxidizing an alcohol to a carbonyl group. The preparation of the compound of formula (IVA) can also involve performing a decarboxylation or desulfonylation reaction on the compound of formula (IVA), in which $Y_1$ is $COOR_6$ (decarboxylation) or $SO_2R$ (desulfonylation).

In certain embodiments, the compound of formula (IVD) can be prepared from a compound of formula (IVE) and the compound of formula (VIIE):

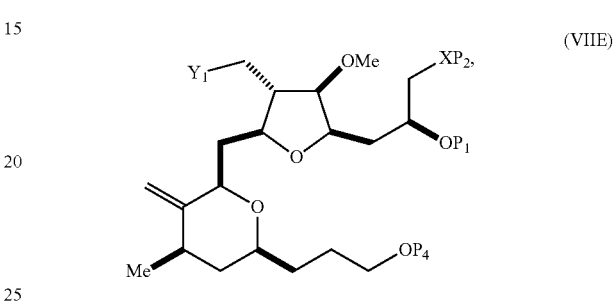

(VIIE)

or a salt thereof,
where all variables are as defined in formula (IVD).
The compound of formula (IVE) can have the following structure:

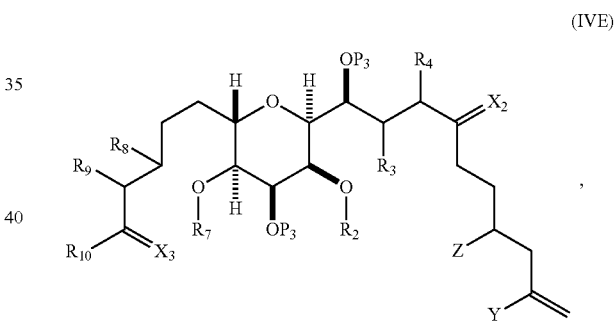

(IVE)

where
(a1) $R_7$ and $R_8$ combine to form a bond, and $R_9$ is H;
or
(a2) $R_7$ is H or a hydroxyl protecting group, and $R_8$ and $R_9$ combine to form a double bond; $X_3$ is oxo, and $R_{10}$ is H or —$OP_5$, where $P_5$ is H or an ether hydroxyl protecting group; and the remaining variables are as defined in formula (IVD).

In particular embodiments, the compound of formula (IVD) is prepared by reacting the compound of formula (IVE) (e.g., the compound of formula (IVE), in which X is oxo) with the compound of formula (VIIE) which was pretreated with a strong base.

C.0-C.1 Bond-Forming Macrocyclization

Figure 5:
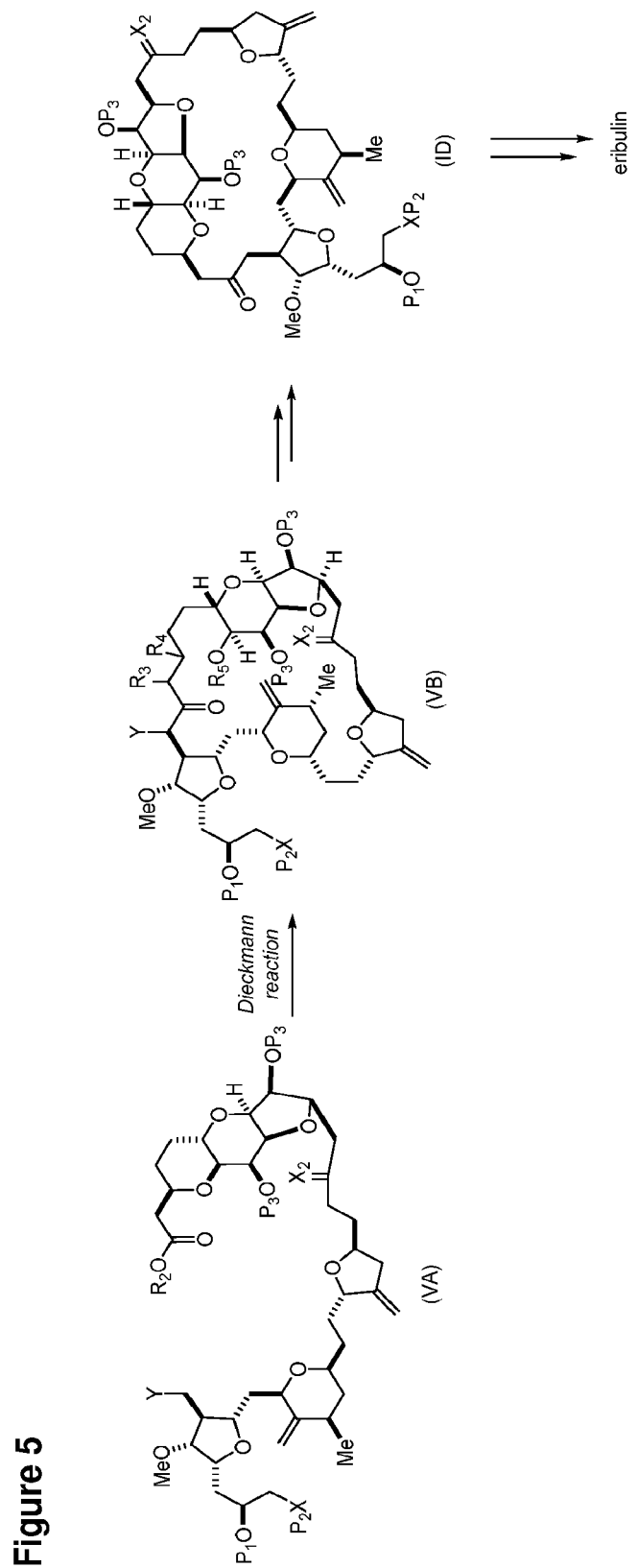
FIG. 5 is a scheme showing preparation of eribulin through a C.0-C.1 bond-forming macrocyclization.

The macrocyclization reaction of the invention can be a carbon-carbon bond-forming reaction (e.g., Dieckmann reaction) that provides a C.0-C.1 bond in eribulin or a pharmaceutically acceptable salt thereof (e.g., eribulin mesylate). The general synthetic sequence including the Dieckmann reaction that can be used to prepare eribulin or a pharmaceutically acceptable salt thereof (e.g., a mesylate salt) is shown in FIG. 5. As shown in FIG. 5, the non-macrocyclic intermediate in the synthesis of eribulin can be:

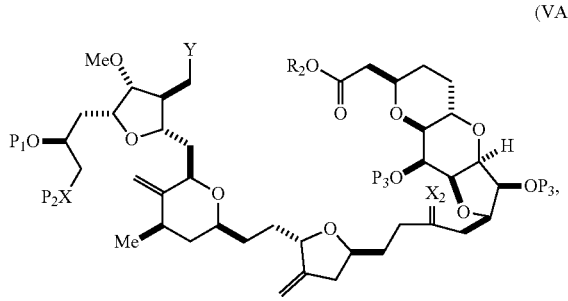

(VA)

where
Y is $SO_2R_1$ or $COOR_1$, where, when Y is $SO_2R_1$, $R_1$ is optionally substituted aryl or optionally substituted non-enolizable alkyl, and when Y is $COOR_1$, $R_1$ is optionally substituted alkyl, optionally substituted aryl, or optionally substituted arylalkyl;
each $P_3$ is independently H or a hydroxyl protecting group, and $X_2$ is oxo, or both $P_5$ groups and $X_2$, together with the atoms to which each is attached, combine to form ketal;
$R_2$ is optionally substituted alkyl, optionally substituted arylalkyl, or optionally substituted aryl; and
X is O, and
  each of $P_1$ and $P_2$ is independently a hydroxyl protecting group,
  or
  $P_1$ and $P_2$, together with the atoms to which each is attached, combine to form a cyclic protected diol;
or
X is N, and
  $P_1$ is H or a hydroxyl protecting group, and X and $P_2$ combine to form optionally masked amino;
  or
  $P_1$ and $P_2$, together with the atoms to which each is attached, combine to form an aminal or 1,3-oxazolidin-2-one-5-yl.

An intermediate in the synthesis of eribulin can be a compound of formula (VB), which can be produced from the compound of formula (VA) using Dieckmann reaction. The compound of formula (VB) has the following structure:

where $P_1$, $P_2$, $P_3$, X, $X_2$, and Y are as defined for compound of formula (VA); and (i) $R_3$ is H, $R_4$ is optionally substituted $C_{1-6}$ alkyl ether, and $R_5$ is H;

(ii) $R_5$ is H, and $R_3$ and $R_4$ combine to form a double bond; or (iii) $R_3$ is H, and $R_4$ and $R_5$ combine to form a bond.

The reaction conditions that can be used to convert the compound of formula (VA) into the compound of formula (VB) include those known in the art for the Dieckmann reaction or Claisen condensation. In particular, the compound of formula (VA) can be contacted with a strong base (e.g., a $C_{4-6}$ alkoxide) to afford the compound of formula (VB). The compound of formula (VB)(i) or (VB)(ii) can be converted to the compound of formula (VB)(iii) prior to the next step by contacting the compound of formula (IIB)(i) or (VB)(ii) with aqueous bicarbonate (e.g., during a work up of the Dieckmann reaction mixture) or with silica gel (e.g., by purification of the compound of formula (VB) by silica gel chromatography).

The compound of formula (VB) can be converted to the compound of formula (ID), from which eribulin or eribulin mesylate can be produced as described herein. For example, the reaction sequence from the compound of formula (VB) to the compound of formula (ID) can include (i) a desulfonylation or a decarboxylation reaction and (ii) reactions with hydroxyl protecting group removing agent or an amino unmasking agent. The conditions for the decarboxylation reaction can be those known in the art, e.g., Krapcho decarboxylation or a sequence including deprotection (converting $R_1$ to H) and protodecarboxylation. The conditions for the desulfonylation reaction can be those known in the art. For example, the desulfonylation reaction can include contacting the compound of formula (IIB), in which Y is $SO_2R_1$, with an electron-transferring reducing agent (e.g., $SmI_2$; Cr(III) salt and Mn(0); or Mg(0)). For exemplary desulfonylation conditions, see WO 2009/064029.

The compound of formula (ID) (e.g., the compound of formula (ID) in which $P_1$ is a hydroxyl protecting group) can be reacted with a hydroxyl protecting group removing agent to afford:

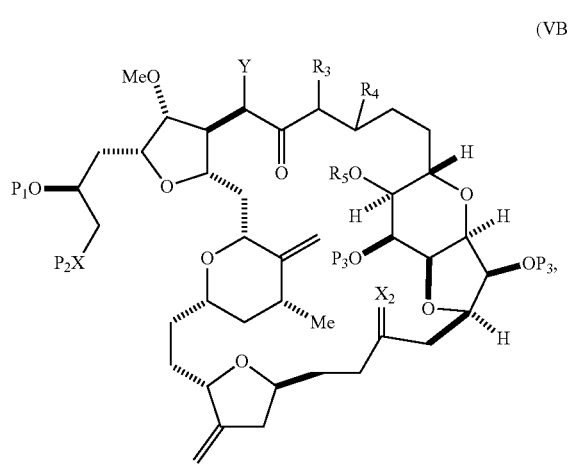

(VB)

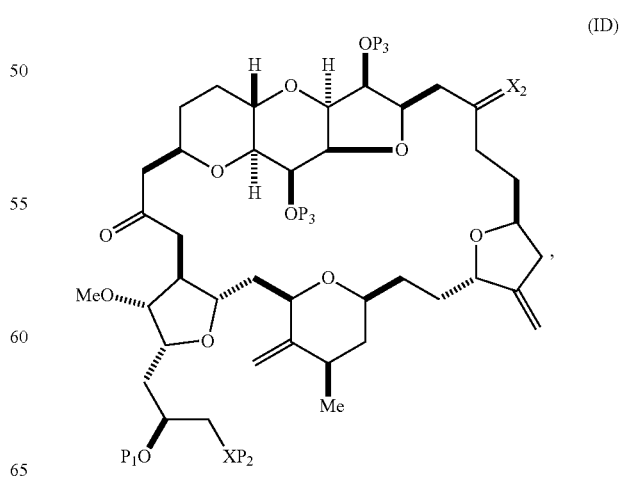

(ID)

where
both P$_3$ groups and X$_2$, together with the atoms to which each is attached, combine to form ketal; and
X is O, and each of P$_1$ and P$_2$ is H, or P$_1$ is H, and X and P$_2$ combine to form optionally masked amino.

The compound of formula (ID) (in which X is O, P$_1$ and P$_2$ are H, and both P$_3$ groups and X$_2$, together with the atoms to which each is attached, combine to form ketal) can be aminated to afford eribulin, as described herein. Alternatively, the compound of formula (ID) (in which P$_1$ is H, X and P$_2$ combine to form a masked amino, and both P$_3$ groups and X$_2$, together with the atoms to which each is attached, combine to form ketal) can be reacted with an amino unmasking agent to afford eribulin, as described herein. Eribulin mesylate can be produced by salification of eribulin, as described herein.

The compound of formula (VA) can be prepared from the compound of formula (VIIE):

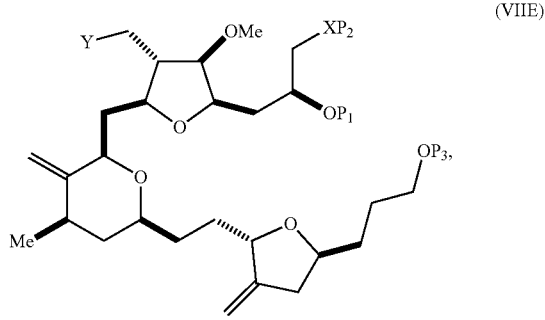

(VIIE)

where

Y is SO$_2$R$_1$ or COOR$_1$, where, when Y is SO$_2$R$_1$, R$_1$ is optionally substituted aryl or optionally substituted non-enolizable alkyl, and when Y is COOR$_1$, R$_1$ is optionally substituted alkyl, optionally substituted aryl, or optionally substituted arylalkyl;

P$_3$ is H or a hydroxyl protecting group; and
X is O, and
each of P$_1$ and P$_2$ is independently H or a hydroxyl protecting group, or P$_1$ and P$_2$, together with the atoms to which each is attached, combine to form a cyclic protected diol;

or

X is N, and
P$_1$ is H or a hydroxyl protecting group, and X and P$_2$ combine to form optionally masked amino;

or

P$_1$ and P$_2$, together with the atoms to which each is attached, combine to form an aminal or 1,3-oxazolidin-2-one-5-yl.

The preparation of the compound of formula (VA) from the compound of formula (VIIE) can involve oxidizing the compound of formula (VIIE), in which P$_3$ is H, and subjecting the product to the Nozaki-Hiyama-Kishi reaction with a compound of formula (VC):

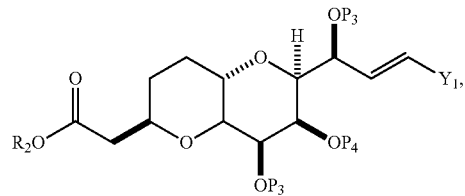

(VC)

where

R$_2$ is optionally substituted alkyl, optionally substituted arylalkyl, or optionally substituted aryl;

Y$_1$ is chloro, bromo, iodo, or trifluoromethanesulfonate; and each P$_3$ and P$_4$ is independently a hydroxyl protecting group.

Further reaction with a hydroxyl protecting group removing agent and a reaction with a Brønsted acid can provide the compound of formula (VA).

C.26-C.27 Bond-Forming Macrocyclization

Figure 6:
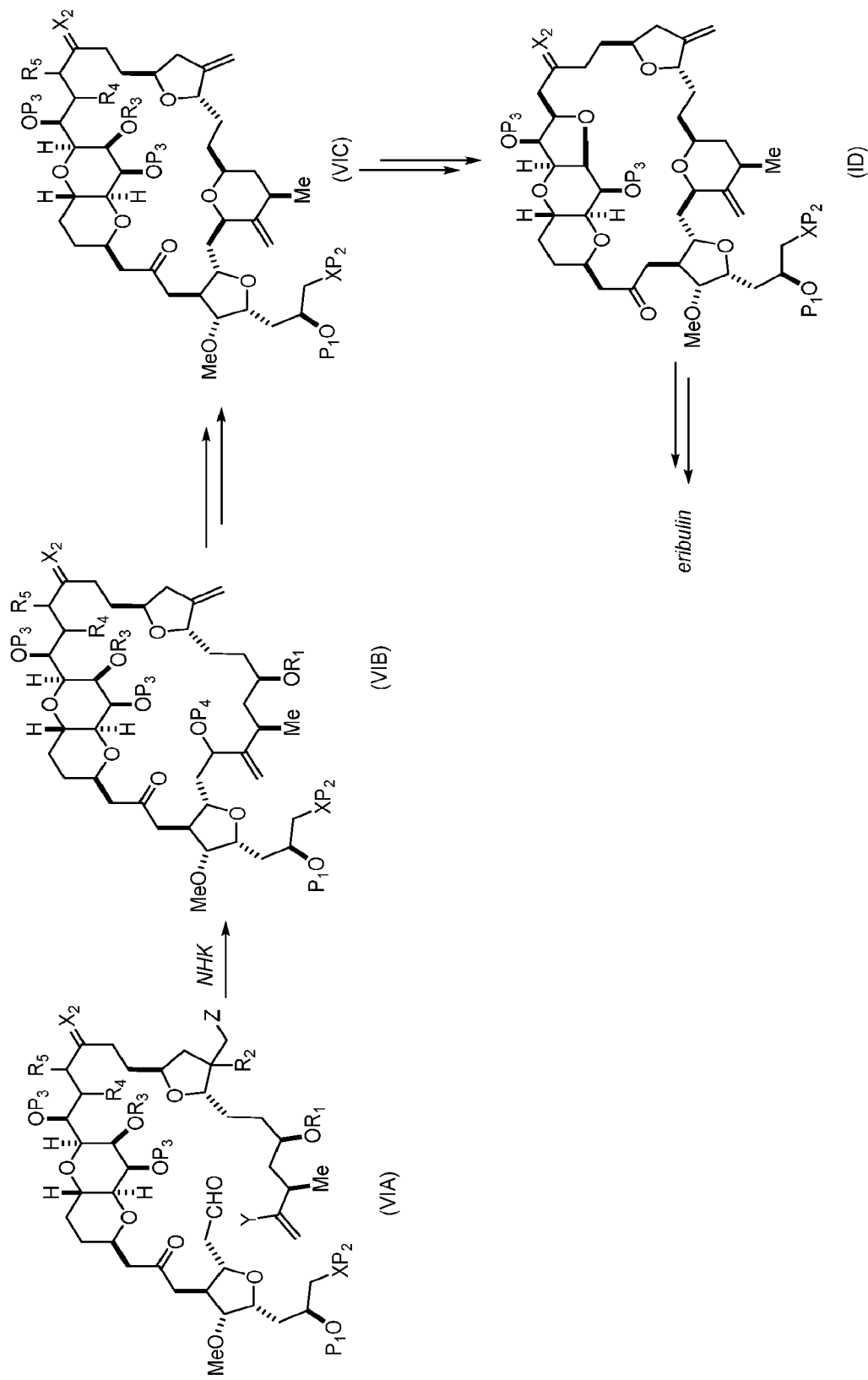
FIG. 6 is a scheme showing preparation of eribulin through a C.26-C.27 bond-forming macrocyclization.

The macrocyclization reaction of the invention can be a carbon-carbon bond-forming reaction (e.g., Nozaki-Hiyama-Kishi reaction (NHK)) that provides a C.26-C.27 bond in eribulin or a pharmaceutically acceptable salt thereof (e.g., eribulin mesylate). The general synthesis sequence including NHK that can be used to prepare eribulin or a pharmaceutically acceptable salt thereof (e.g., a mesylate salt) is shown in FIG. 6. As shown in FIG. 6, the non-macrocyclic intermediate in the synthesis of eribulin can be a compound of formula (VIA):

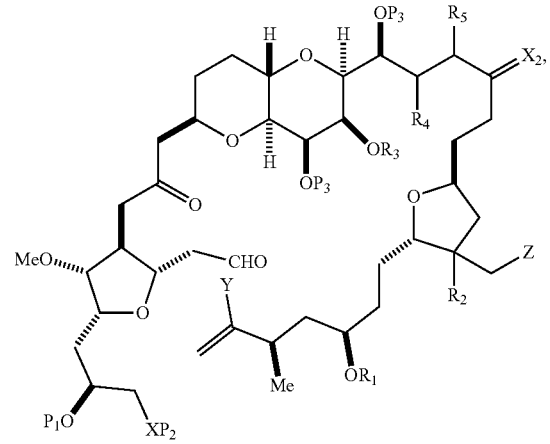

(VIA)

where

Y is iodide, bromide, or trifluoromethanesulfonate;

(a1) R$_3$ is H or a hydroxyl protecting group, R$_4$ and R$_5$ combine to form a double bond, each P$_3$ is independently H or a hydroxyl protecting group, and X$_2$, together with the carbon to which it is attached, forms a carbonyl or —(CH(OR$_6$))—, where R$_6$ is H or a hydroxyl protecting group;

or (a2) R$_3$ and R$_4$ combine to form a bond, R$_5$ is H, and each P$_3$ is independently H or a hydroxyl protecting group, and X$_2$, together with the carbon to which it is attached, forms a carbonyl or —(CH(OR$_6$))—;

or
 both P₃ groups and X₂, together with the atoms to which each is attached, combine to form ketal;

(b1) Z is chloride, bromide, or iodide, and R₁ and R₂ combine to form a bond;

or (b2) Z and R₂ combine to form a double bond, and R₁ is H or a hydroxyl protecting group;

and

X is O, and
  each of P₁ and P₂ is independently H or a hydroxyl protecting group,
  or
  P₁ and P₂, together with the atoms to which each is attached, combine to form a cyclic protected diol;
 or
 X is N, and
  P₁ is H or a hydroxyl protecting group, and X and P₂ combine to form optionally masked amino;
  or
  P₁ and P₂, together with the atoms to which each is attached, combine to form an aminal or 1,3-oxazolidin-2-one-5-yl.

An intermediate in the synthesis of eribulin can be a compound of formula (VIB), which can be produced by subjecting the compound of formula (VIA) to Nozaki-Hiyama-Kishi reaction conditions (e.g., by reacting with a Cr(II) salt and a Ni(II) salt). The compound of formula (VIB) has the following structure:

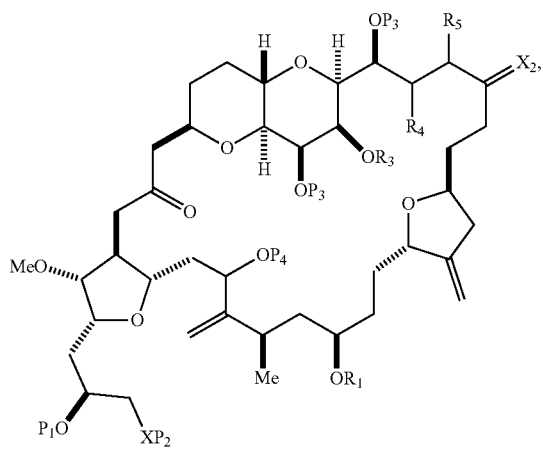

(VIB)

where all variables are as defined for compound of formula (VIA); and

P₄ is H or a hydroxyl protecting group.

Nozaki-Hiyama-Kishi reaction conditions are as described above.

The compound of formula (VIC) can be prepared from the compound of formula (VIB):

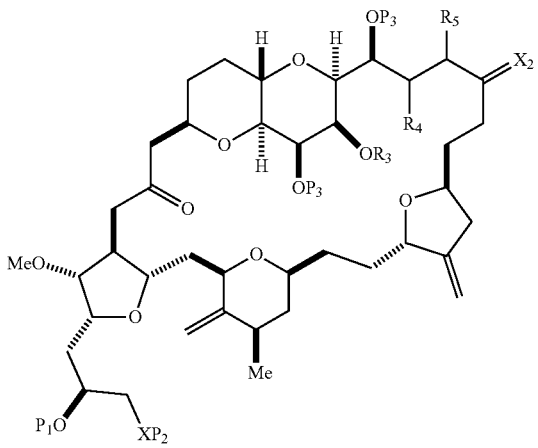

(VIC)

where all variables are as defined for compound of formula (VIB).

The synthesis of the compound of formula (VIC) can involve Vasella fragmentation, reaction(s) with one or more hydroxyl protecting agents, a nucleophilic cyclization reaction, and oxidation reactions, e.g., before or after the NHK step (i.e., the reaction affording the compound of formula (VIB)).

The compound of formula (VIC) can be converted to the compound of formula (ID), from which eribulin or eribulin mesylate can be prepared as described herein. In a non-limiting example, the compound of formula (VIC) (e.g., the compound of formula (VIC) in which each of P₁, P₂, P₃, and R₃ is a hydroxyl protecting group, X₂ is oxo, and R₄ and R₅ combine to form a double bond) can be converted to a compound of formula (ID) through a synthesis involving reacting the compound of formula (VIC) with a hydroxyl protecting group removing agent. The synthesis may further involve a reaction with a Brønsted acid (e.g., a Brønsted acid having a pKa of 5±3) after the reaction of the compound of formula (VIC) with a hydroxyl protecting group removing agent.

The compound of formula (ID) (e.g., the compound of formula (ID) in which P₁ is a hydroxyl protecting group) can be reacted with a hydroxyl protecting group removing agent:

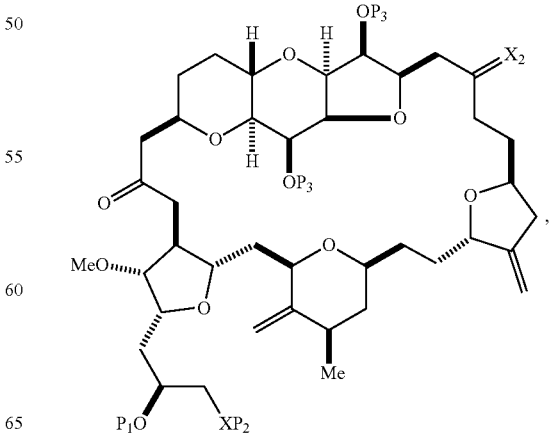

(ID)

where
- both $P_3$ groups and $X_2$, together with the atoms to which each is attached, combine to form ketal; and
- X is O, and each of $P_1$ and $P_2$ is H, or

- $P_1$ is H, and X and $P_2$ combine to form optionally masked amino.

The compound of formula (ID) (in which X is O and $P_1$ and $P_2$ are H) can be aminated to afford eribulin, as described herein. Alternatively, the compound of formula (ID) (in which $P_1$ is H and X and $P_2$ combine to form a masked amino) can be reacted with an amino unmasking agent to afford eribulin, as described herein. Eribulin mesylate can be produced by salification of eribulin, as described herein.

The compound of formula (VIA) can be prepared from the compound of formula (VID):

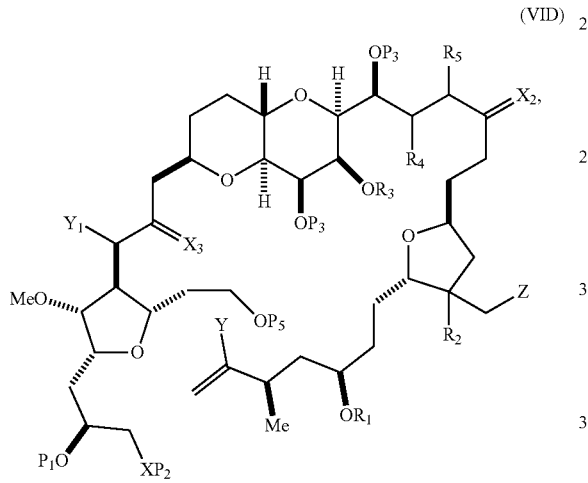

(VID)

where
- Y is iodide, bromide, or trifluoromethanesulfonate;
- $Y_1$ is H, $SO_2R_7$, or $COOR_7$, where, when $Y_1$ is $COOR_7$, $R_7$ is optionally substituted alkyl, optionally substituted aryl, or optionally substituted arylalkyl, and, when $Y_1$ is $S_2R_7$, $R_7$ is optionally substituted aryl or optionally substituted non-enolizable alkyl;
- $X_3$ is oxo, or $X_3$ combines with the carbon to which it is attached to form —(CH(OR$_6$))—;
- $P_5$ is H or a hydroxyl protecting group;
- (a1) $R_3$ is H or a hydroxyl protecting group, $R_4$ and $R_5$ combine to form a double bond, each $P_3$ is independently H or a hydroxyl protecting group, and $X_2$, together with the carbon to which it is attached, forms a carbonyl or —(CH(OR$_6$))—;

or

- (a2) $R_3$ and $R_4$ combine to form a bond, $R_5$ is H, and each P is independently H or a hydroxyl protecting group, and $X_2$, together with the carbon to which it is attached, forms a carbonyl or —(CH(OR$_6$))—;

or

- both $P_3$ groups and $X_2$, together with the atoms to which each is attached, combine to form ketal;
- (b1) Z is chloride, bromide, or iodide, and $R_1$ and $R_2$ combine to form a bond;

or

- (b2) Z and $R_2$ combine to form a double bond, and $R_1$ is a hydroxyl protecting group;

and

- X is O, and
  - each of $P_1$ and $P_2$ is independently H or a hydroxyl protecting group, or

- $P_1$ and $P_2$, together with the atoms to which each is attached, combine to form a cyclic protected diol;

or

- X is N, and
  - $P_1$ is H or a hydroxyl protecting group, and X and $P_2$ combine to form optionally masked amino;

or

- $P_1$ and $P_2$, together with the atoms to which each is attached, combine to form an aminal or 1,3-oxazolidin-2-one-5-yl;

where each $R_6$ is independently H or a hydroxyl protecting group.

The preparation of the compound of formula (VIA) can involve oxidizing the compound of formula (VID) (e.g., the compound of formula (VID), in which $P_5$ is H or a hydroxyl protecting group, and/or $X_3$ combines with the carbon to which it is attached to form —(CH(OR$_6$))—), e.g., by reacting with an oxidizing agent capable of oxidizing hydroxyl to a carbonyl group. The mixture containing the oxidizing agent can also act as a hydroxyl protecting removing agent. The preparation may further involve a desulfonylation reaction (when $Y_1$ is $COOR_7$) or a desulfonylation (when $Y_1$ is $SO_2R_7$), as described herein.

The compound of formula (VID) can be formed by reacting the compound of formula (VIE) with the compound of formula (VIF). The compound of formula (VIE) can have the following structure:

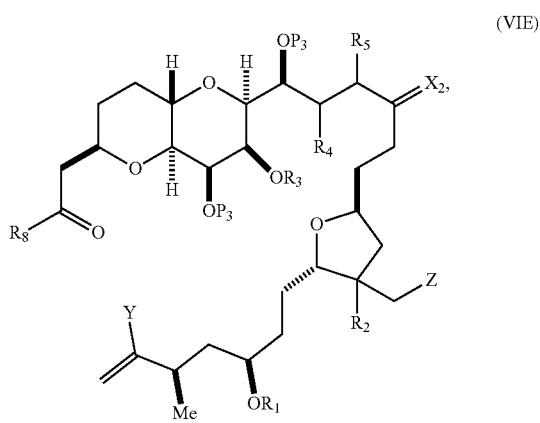

(VIE)

where
- $R_8$ is H or —OR$_9$, where $R_9$ is H or an ether hydroxyl protecting group; and
- the remaining variables are as defined in formula (VID).

The compound of formula (VIF) can have the following structure

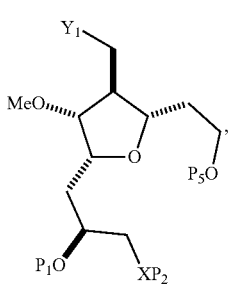

(VIF)

where all variables are as defined in formula (VID).

Allene-Prins Reaction in the Preparation of C.20-C.35, C.16-C.35, and C.14-C35 Fragments of Eribulin The invention further features a method of preparing a fragment of eribulin (e.g., C.20-C.35, C.16-C.35, and C.14-C35 fragments), which can be an intermediate in the synthesis of eribulin or a pharmaceutically acceptable salt thereof (e.g., eribulin mesylate). The advantages of the process relative to the current synthesis of C.14-C.35, C.16-C.35, and C.20-C.35 fragments of eribulin include non-metal mediated assembly that does not employ a C.23 leaving group. Additionally, the process obviates the need for a chiral ligand. The method involves performing an allene-Prins reaction on a compound of formula (VIIA), a compound of formula (VIIB), and $R_3OH$ to afford the intermediate in the synthesis of eribulin, where $R_3$ is an optionally substituted acyl;

where the compound of formula (VIIA) has the following structure:

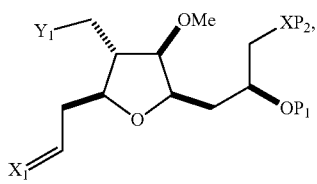

(VIIA)

where $Y_1$ is $SO_2R_1$ or $COOR_1$, and $R_1$ is optionally substituted alkyl, optionally substituted aryl, or optionally substituted arylalkyl;

$X_1$ is O, or $X_1$, together with the carbon to which the $X_1$ groups are attached, forms a cyclic acetal;

X is O, and each of $P_1$ and $P_2$ is independently H or a hydroxyl protecting group, or $P_1$ and $P_2$, together with the atoms to which each is attached, combine to form a cyclic protected diol;

or

X is N, and $P_1$ is H or a hydroxyl protecting group, and X and $P_2$ combine to form optionally masked amino;

or $P_1$ and $P_2$, together with the atoms to which each is attached, combine to form an aminal or 1,3-oxazolidin-2-one-5-yl; and where the compound of formula (VIIB) has the following structure:

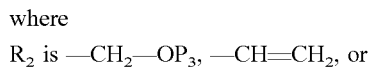

(VIIB)

where $R_2$ is $—CH_2—OP_3$, $—CH=CH_2$, or

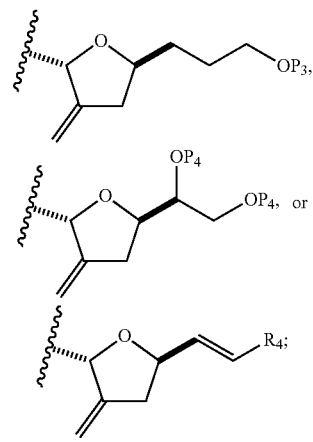

where $P_3$ is H or a hydroxyl protecting group; each $P_4$ is independently a hydroxyl protecting group, or both $P_4$ groups, together with the atoms to which each is attached, combine to form a cyclic protected diol; and $R_4$ is H or $—CH_2X_2CH_2CH=CH_2$, where $X_2$ is O, $—CH_2—$, or $NP_5$, where $P_5$ is sulfonyl;

and where the intermediate in the synthesis of eribulin is a compound of formula (VIIC):

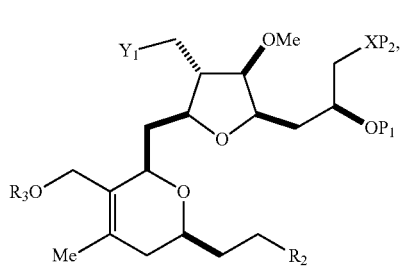

(VIIC)

The reaction conditions that can be used to prepare the compound of formula (VIIC) using allene-Prins reaction are those known in the art for Prins reaction and can include reacting the compound of formula (VIIA), the compound of formula (VIB), and $R_3OH$ with a Lewis acid (e.g., boron trifluoride or a solvate thereof).

The compound of formula (VIIC) can be subjected to allylic reducing conditions to afford a compound of formula (VIID):

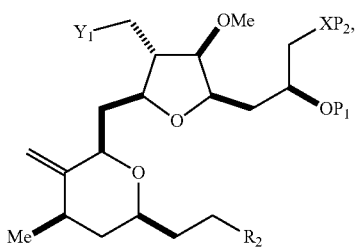

(VIID)

$Y_1$ is $SO_2R_1$ or $COOR_1$, and $R_1$ is optionally substituted alkyl, optionally substituted aryl, or optionally substituted arylalkyl;

$R_2$ is —$CH_2$—$OP_3$, —$CH$=$CH_2$,

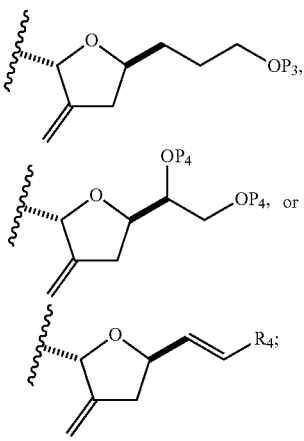

where $P_3$ is H or a hydroxyl protecting group; each $P_4$ is independently a hydroxyl protecting group, or both $P_4$ groups, together with the atoms to which each is attached, combine to form a cyclic protected diol; and $R_4$ is H or —$CH_2X_2CH_2CH$=$CH_2$, where $X_2$ is O, —$CH_2$—, or $NP_5$, where $P_5$ is sulfonyl;

X is O, and
each of $P_1$ and $P_2$ is independently H or a hydroxyl protecting group,
or
$P_1$ and $P_2$, together with the atoms to which each is attached, combine to form a cyclic protected diol;
or
X is N, and
$P_1$ is H or a hydroxyl protecting group, and X and $P_2$ combine to form optionally masked amino;
or
$P_1$ and $P_2$, together with the atoms to which each is attached, combine to form an aminal or 1,3-oxazolidin-2-one-5-yl.

The compound of formula (VIIB) can be prepared from the compound of formula (VIIF):

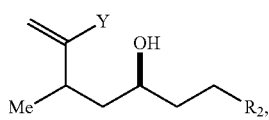

(VIIF)

where

Y is chloro, bromo, iodo, or sulfonate; and $R_2$ is —$CH_2$—$OP_3$, —$CH$=$CH_2$,

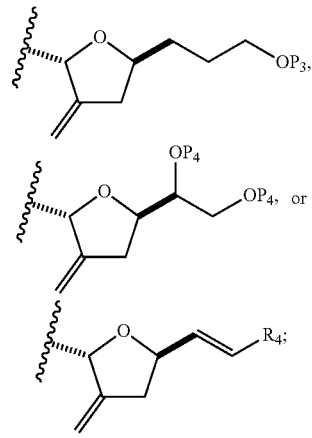

where $P_3$ is a hydroxyl protecting group; each $P_4$ is independently a hydroxyl protecting group, or both $P_4$ groups, together with the atoms to which each is attached, combine to form a cyclic protected diol; and $R_4$ is H or —$CH_2X_2CH_2CH$=$CH_2$, where $X_2$ is O, —$CH_2$—, or $NP_5$, where $P_5$ is sulfonyl.

The compound of formula (VIIF) can be reacted with a Pd(0) complex, which can be prepared in situ, and a base to afford the compound of formula (VIIB). Alternatively, the compound of formula (VIIB) can be reacted with a base directly (e.g., N-methylimidazole) to afford the compound of formula (VIIB).

The compound of formula (VIIB) can be prepared from a compound of formula (VIIG):

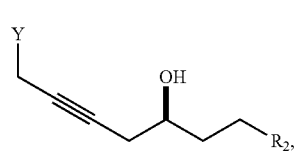

(VIIG)

where

Y is chloro, bromo, iodo, or sulfonate; and $R_2$ is —$CH_2$—$OP_3$, —$CH$=$CH_2$, -continued

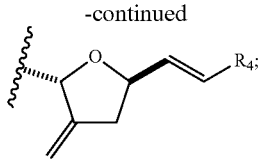

where
P$_3$ is a hydroxyl protecting group; each P$_4$ is independently a hydroxyl protecting group, or both P$_4$ groups, together with the atoms to which each is attached, combine to form a cyclic protected diol; and R$_4$ is H or —CH$_2$X$_2$CH$_2$CH═CH$_2$, where X$_2$ is O, —CH$_2$—, or NP$_5$, where P$_5$ is sulfonyl.

The compound of formula (VIIG) can be reacted with a methylcuprate (I) salt (e.g., lithium methyl-cyanocuprate) to form the compound of formula (VIIB).

The compound of formula (VIIB) can be prepared from a compound of formula (VIIH):

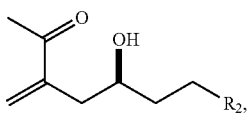
(VIIH)

where
R$_2$ is —CH$_2$—OP$_3$, —CH═CH$_2$,

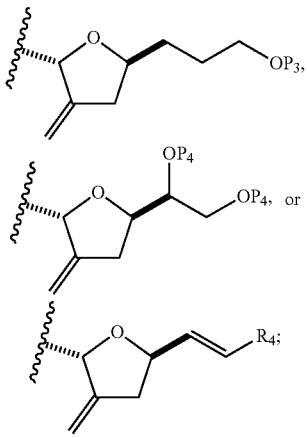

where
P$_3$ is a hydroxyl protecting group; each P$_4$ is independently a hydroxyl protecting group, or both P$_4$ groups, together with the atoms to which each is attached, combine to form a cyclic protected diol; and R$_4$ is H or —CH$_2$X$_2$CH$_2$CH═CH$_2$, where X$_2$ is O, —CH$_2$—, or NP$_5$, where P$_5$ is sulfonyl.

The compound of formula (VIIH) can be reacted with a sulfonyl hydrazide (e.g., mesitylsulfonyl hydrazide) and a base (e.g., an organic base having a pKa from 10 to 14).

C.1-C.15 Fragment

The invention also features a C.1-C.15 fragment of eribulin, which can be used in the synthesis of eribulin. The C.1-C.15 fragment can be prepared from the waste stream in the synthesis or eribulin disclosed in WO 2005/118565 (see preparation of the intermediate ER-806055). The C.1-C.15 fragment can be a compound of formula (VIIIL):

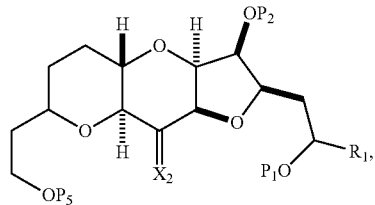
(VIIIL)

where
R$_1$ is H or —CH$_2$OP$_4$;
X$_2$ is oxo, or X$_2$, together with the carbon to which it is attached, forms a ketal or —(CH(OP$_6$))—;
each of P$_1$ and P$_4$, when present, is independently H or a hydroxyl protecting group, or P$_1$ and P$_4$, when present, together with the atoms to which each is attached, combine to form a cyclic protected diol; and
each of P$_2$, P$_5$, and P$_6$ is independently H or a hydroxyl protecting group.

The method of preparing the C.1-C.15 fragment can involve:
(A) cleaving the double bond in a compound of formula (VIIIA) to afford a compound of formula (VIIIB), the compound of formula (VIIIA) having the structure:

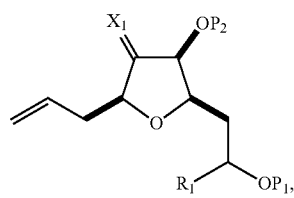
(VIIIA)

where
X$_1$ is oxo, or X$_1$, together with the carbon atom to which it is attached, forms a ketal or —(CH(OP$_3$))—, wherein P$_5$ is H or a hydroxyl protecting group;
R$_1$ is H or —CH$_2$OP$_4$;
each of P$_1$, P$_2$, and P$_4$ is independently a hydroxyl protecting group, or
P$_1$ and P$_4$, together with the atoms to which each is attached, combine to form a cyclic protected diol; and
the compound of formula (VIIIB) having the structure:

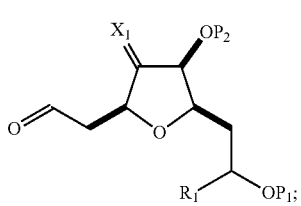
(VIIIB)

(B) reacting the compound of formula (VIIIB) with a compound of formula (VIIB-a) to afford a compound of formula (VIIC):

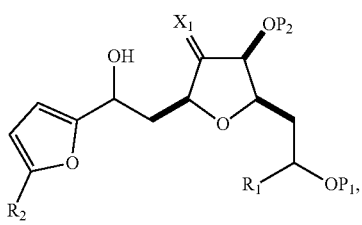

(VIIIC)

where $R_2$ is H or —$CH_2CH_2OP_5$, and $P_5$ is a hydroxyl protecting group;

and the compound of formula (VIIIB-a) has the following structure:

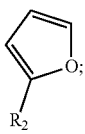

(VIIIB-a)

(C) reacting the compound of formula (VIIIC) with a dehydrating agent to afford a compound of formula (VIIID):

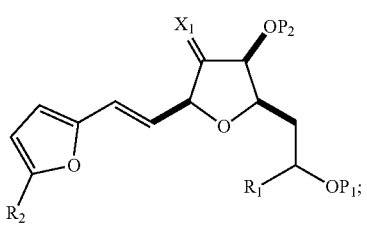

(VIIID)

(D) reacting the compound of formula (VIIID) with a dihydroxylating agent to afford a compound of formula (VIIIE):

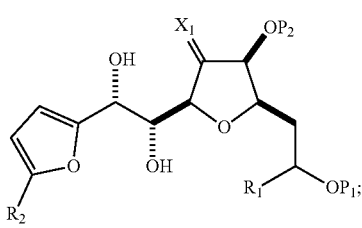

(VIIIE)

(E) preparing a compound of formula (VIIIF) through a reaction sequence comprising reacting the compound of formula (VIIIE) with N-bromosuccinimide to afford a first intermediate, and (a), when $R_2$ is —$CH_2CH_2OP_5$, contacting said first intermediate with a reducing agent (e.g., a hydrosilane and a Brønsted or Lewis acid), or (b), when $R_2$ is H, reacting said first intermediate with an acylating agent (e.g., carboxylic acid anhydride) to afford a second intermediate, and allylating said second intermediate to afford a compound of formula (VIIIF):

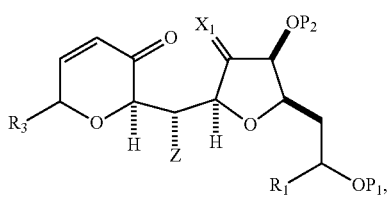

(VIIIF)

where Z is an ester or —OP, where P is H or a hydroxyl protecting group, and $R_3$ is —$CH_2CH_2OP_5$ or —$CH_2CH$=$CH_2$;

(F) reacting the compound of formula (VIIIF) with a 1,4-reducing agent to afford a compound of formula (VIIIG):

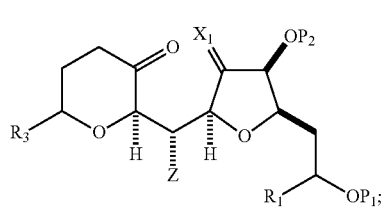

(VIIIG)

(G) forming a compound of formula (VIIIH) through a reaction sequence comprising reacting the compound of formula (VIIIG) with a Brønsted acid and Y—H, wherein Y is optionally substituted $C_{1-6}$ alkyl, the compound of formula (VIIIH) having the following structure:

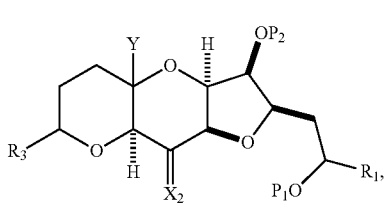

(VIIIH)

where Y is optionally substituted $C_{1-6}$ alkyl ether; $R_3$ is —$CH_2CH_2OP_5$; $X_2$ is oxo, or $X_2$, together with the carbon to which it is attached, forms a ketal or —(CH($OP_5$))—, where $P_6$ is a hydroxyl protecting group;

(H) replacing $P_2$ in the compound of formula (VIIIH) with —$Si(R_4)_2H$ to afford a compound of formula (VIIIJ):

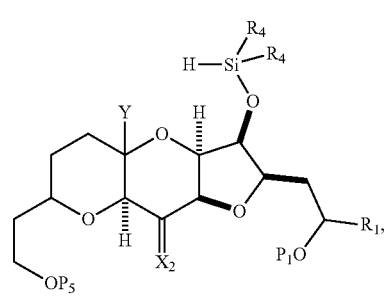

(VIIIJ)

where each R$_4$ is independently optionally substituted alkyl, optionally substituted aryl, or optionally substituted arylalkyl;

(I) reacting the compound of formula (VIIIJ) with a Lewis acid to afford a compound of formula (VIIIK):

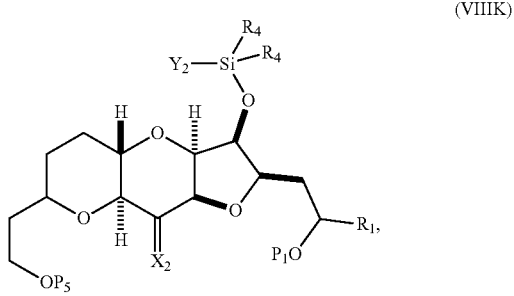

(VIIIK)

where Y$_2$ is fluoro, chloro, or bromo; and (J) reacting the compound of formula (VIIK) with a hydroxyl protecting group removing agent and then reacting with a hydroxyl protecting agent to afford a compound of formula (VIIL):

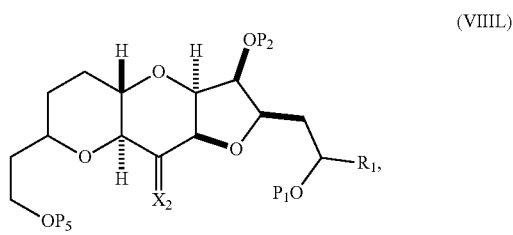

(VIIIL)

where P$_2$ is a hydroxyl protecting group.

Compounds

The present invention also provides compounds that can be used in the synthesis of eribulin or a pharmaceutically acceptable salt thereof (e.g., eribulin mesylate), e.g., the compounds of formula (IA), (IB), (IC), (ID), (IE), (IIA), (IIB), (IIC), (IIIA), (IIIB), (IIIC), (IVA), (IVB), (IVC), (IVD), (VA), (VB), (VIA), (VIB), (VIC), (VID), (VIIB), (VIIC), (VIIF), (VIIG), (VIIH), or (VIIIL), or a salt thereof. The present invention also includes a compound of formula (VIIE):

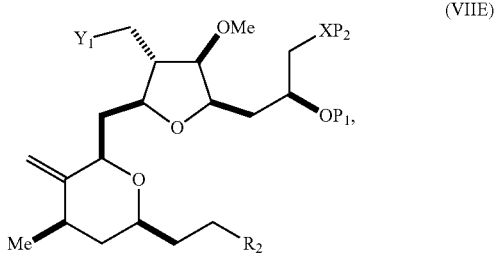

(VIIE)

or a salt thereof, where

Y$_1$ is SO$_2$R$_1$ or COOR$_1$, and R$_1$ is optionally substituted alkyl, optionally substituted aryl, or optionally substituted arylalkyl;

R$_2$ is —CH$_2$—OP$_3$, —CH=CH$_2$,

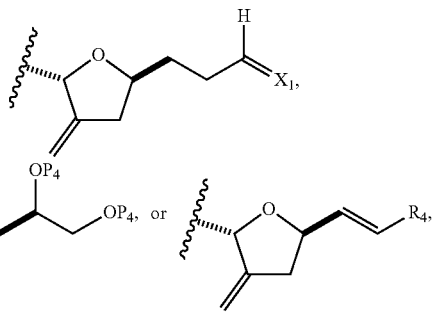

where X$_1$ is oxo, or X$_1$ combines with the carbon atom to which it is attached to form —(CH(OP$_5$))—; each P$_3$ is independently H or a hydroxyl protecting group; each P$_4$ is independently H or a hydroxyl protecting group, or both P$_4$ groups, together with the atoms to which each is attached, combine to form a cyclic protected diol; R$_4$ is H, CHO, or —CH$_2$X$_2$CH$_2$CH=CH$_2$, where X$_2$ is O, —CH$_2$—, or NP$_5$, where P$_5$ is sulfonyl; and X is N, and P$_1$ is H or a hydroxyl protecting group, and X and P$_2$ combine to form optionally masked amino; or P$_1$ and P$_2$, together with the atoms to which each is attached, combine to form an aminal or 1,3-oxazolidin-2-one-5-yl.

The present invention includes a compound of formula (IVE):

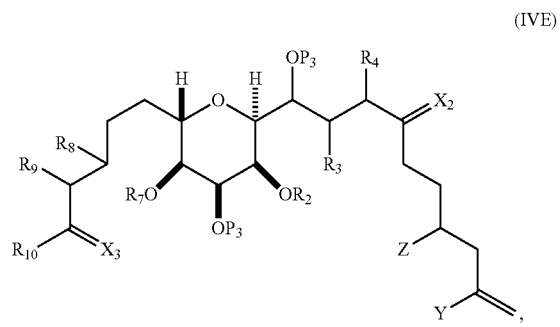

(IVE)

where

Y is iodide, bromide, or trifluoromethanesulfonate;

Z is an ester, a sulfonate, chloride, bromide, or iodide;

each P$_3$ is independently H or a hydroxyl protecting group, and X$_2$ is oxo; or both P$_3$ groups and X$_2$, together with the atoms to which each is attached, combine to form ketal;

(a1) R$_2$ is H or a hydroxyl protecting group, R$_3$ and R$_4$ combine to form a double bond;

or (a2) R$_2$ and R$_3$ combine to form a bond, and R$_4$ is H;

(b1) R$_7$ and R$_8$ combine to form a bond, and R$_9$ is H;

or (b2) R$_7$ is H or a hydroxyl protecting group, and R$_8$ and R$_9$ combine to form a double bond; and (c1) X$_3$ is oxo, and R$_{10}$ is H or —OP$_5$, where P$_5$ is H or an ether hydroxyl protecting group;

or (c2) $X_3$ and $R_{10}$ combine with the carbon atom to which they are attached to form an acetal or —CH$_2$OP, where P$_5$ is H or a hydroxyl protecting group.

The present invention includes a compound of formula (VIE):

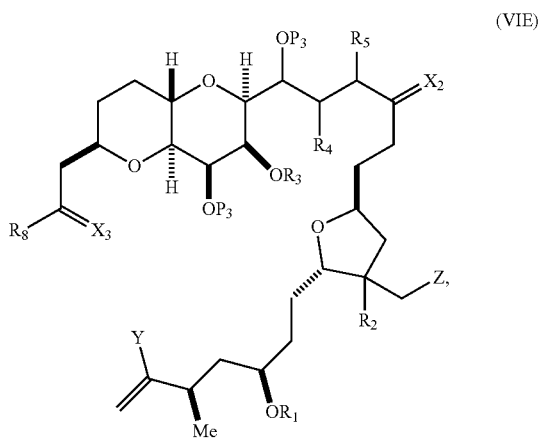

(VIE)

where
Y is iodide, bromide, or trifluoromethanesulfonate;
(a1) $R_3$ is H or a hydroxyl protecting group, $R_4$ and $R_5$ combine to form a double bond, each $P_3$ is independently H or a hydroxyl protecting group, and $X_2$, together with the carbon to which it is attached, forms a carbonyl or —(CH(OR$_6$))—;
or
(a2) $R_3$ and $R_4$ combine to form a bond, $R_5$ is H, and each $P_3$ is independently H or a hydroxyl protecting group, and $X_2$, together with the carbon to which it is attached, forms a carbonyl or —(CH(OR$_6$))—;
or
both $P_3$ groups and $X_2$, together with the atoms to which each is attached, combine to form ketal;
(b1) Z is chloride, bromide, or iodide, and $R_1$ and $R_2$ combine to form a bond;
or
(b2) Z and $R_2$ combine to form a double bond, and $R_1$ is H or a hydroxyl protecting group;
(c1) $X_3$ is oxo, and $R_8$ is H or —OR$_9$, where $R_9$ is H or a hydroxyl protecting group;
(c2) $X_3$ and $R_8$ combine with the carbon atom to which they are attached to form an acetal;
(c3) $X_3$ and $R_8$ combine with the carbon atom to which they are attached to form —CH$_2$OR$_6$;
or
(c4) $X_3$ and $R_8$ combine with the carbon atom to which they are attached to form —CN;
and
X is O, and
each of P$_1$ and P$_2$ is independently H or a hydroxyl protecting group,
or
P$_1$ and P$_2$, together with the atoms to which each is attached, combine to form a cyclic protected diol;
or
X is N, and
P$_1$ is H or a hydroxyl protecting group, and X and P$_2$ combine to form optionally masked amino;

or
P$_1$ and P$_2$, together with the atoms to which each is attached, combine to form an aminal or 1,3-oxazolidin-2-one-5-yl;
where each $R_6$ is independently H or a hydroxyl protecting group.

Amination

Amination conditions can be those known in the art. In a non-limiting example, C.35 hydroxyl in the compound of formula (IC) (e.g., a compound of formula (IC) in which each of P$_1$ and P$_2$ is H and X is O) can be sulfonylated (e.g., by a reaction with a sulfonyl anhydride or a sulfonyl chloride) and reacted with a nitrogen source (e.g., ammonia, azide, sulfamic acid, urea (H$_2$NCONH$_2$), or thiourea (H$_2$NCSNH$_2$)) to afford eribulin or a pharmaceutically acceptable salt thereof upon optional unmasking of the amino group (if the nitrogen source was azide, urea, or thiourea). In another non-limiting example, C.35 hydroxyl in the compound of formula (IC) (e.g., a compound of formula (IC) in which P$_1$ is a hydroxyl protecting group, and P$_2$ is H and X is O) can be halogenated (e.g., by Appel reaction or a reaction with thionyl chloride, sulfuryl chloride, phosphorus(III) chloride, or phosphorus(V) oxychloride) and reacted with a nitrogen source (e.g., ammonia, azide, sulfamic acid, a phthalimide salt, urea (H$_2$NCONH$_2$), or thiourea (H$_2$NCSNH$_2$)) to afford eribulin or a pharmaceutically acceptable salt thereof upon optional unmasking of the amino group (if the nitrogen source was azide, a phthalimide salt, urea, or thiourea). In yet another non-limiting example, C.35 hydroxyl in the compound of formula (IC) (e.g., a compound of formula (IC) in which P$_1$ is a hydroxyl protecting group, and X and P$_2$ combine to form optionally masked amino) can be reacted with a hydroxyl protecting group removing agent to afford eribulin (when X and P$_2$ combine to form unmasked amino) or, when X and P$_2$ combine to form a masked amino, either before or after the treatment with the hydroxyl protecting group removing agent, the compound of formula (IC) can be reacted with an amino unmasking agent to afford eribulin. Amino unmasking agents are further described herein. The amination reaction can provide a pharmaceutically acceptable salt of eribulin directly. Alternatively, the amination reaction can provide eribulin in a free base form. A pharmaceutically acceptable salt of eribulin can be prepared from eribulin through a salification reaction as described herein.

Salification

Salification reaction conditions are known in the art. Salification of eribulin can afford a pharmaceutically acceptable salt of eribulin (e.g., eribulin mesylate). In particular, salification reaction can involve contacting eribulin with a Brønsted acid (e.g., a pharmaceutically acceptable Brønsted acid (e.g., methanesulfonic acid)) to afford a pharmaceutically acceptable salt of eribulin (e.g., *Handbook of Pharmaceutical Salts: Properties, Selection and Use*, ed.: Stahl and Wermuth, Wiley-VCH/VHCA, Weinheim/Zurich, 2002). Pharmaceutically acceptable salts of eribulin, e.g., eribulin mesylate, can be formed by methods known in the art, e.g., in situ during the final isolation and purification of the compound or separately by reacting the free base group with a suitable organic acid. In one example, eribulin is treated with a solution of MsOH and NH$_4$OH in water and acetonitrile. The mixture is concentrated. The residue is dissolved in DCM-pentane, and the solution is added to anhydrous pentane. The resulting precipitate is filtered and dried under high vacuum to provide eribulin mesylate Oxidizing Agents Capable of Converting an Alcohol to a Carbonyl Group Oxidizing agents capable of converting an alcohol to a carbonyl group are known in the art. Non-limiting examples of these oxidizing agents include Dess-Martin periodinane, a TEMPO (in the presence of bleach or BAIB), a dimethylsulfonium compound (e.g., dimethylchlorosulfonium chloride), aluminum trialkoxide with an excess of a ketone (e.g., acetone), and catalytic tetrapropylammonium perruthenate (TPAP) (in the presence of N-methylmorpholine oxide). The dimethylsulfonium compound can be prepared in situ under the conditions known for Parikh-Doering oxidation, Swern oxidation, Corey-Kim oxidation, or Pfitzner-Moffatt oxidation. An oxidation reaction of an alcohol to a carbonyl group (e.g., a ketone) can be performed using aluminum trialkoxide and an excess of a ketone (e.g., acetone) under the conditions known in the art for Oppenauer oxidation. Allylic and benzylic alcohols can also be oxidized with $MnO_2$.

Reducing Agents

Reducing agents that can be used in the methods of the invention are those known in the art. A reducing agent can be an electron-transfer reducing agent, a metal hydride, or a metalloid hydride. Non-limiting examples of electron-transfer reducing agent include alkali metals in oxidation state (0), alkali earth metals in oxidation state (0), alkali arenides, lanthanide (II) salts (e.g., $SmI_2$), $Zn(0)$, $Fe(0)$, and $Mn(0)$.

Non-limiting examples of metal hydrides and metalloid hydrides include boron hydride compounds (e.g., $NaBH_4$, $LiBH_4$, $LiB(Et)_3H$, selectrides (e.g., L-selectride), and boranes (e.g., 9-BBN and alpine borane)), aluminum hydride compounds (e.g., LAlH4, Red-Al®, and alanes (e.g., DIBAL)), hydrosilanes (e.g., PMHS and $Ph_2SiH_2$), hydrostannanes (e.g., $Bu_3SnH$), copper hydride complexes (e.g., Stryker's reagent), palladium hydride complexes, platinum hydride complexes, iridium hydride complexes, rhodium hydride complexes, and ruthenium hydride complexes. Reducing agents can be formed in situ, e.g., a copper hydride complex can be formed by a reaction of a copper salt with, e.g., a boron hydride compound or a hydrosilane. Thus, some reducing reagents (e.g., boron hydride compounds, hydrosilanes, and hydrostannanes) can be used in combination with a catalytic quantity of a metal salt (e.g., Cu, Pd, Pt, Ir, Rh, or Ru salt). Alternatively, catalytic reducing agents can be metal salts (e.g., aluminum isopropoxide or a ruthenium complex) in combination with an alcohol, which undergo transfer hydrogenation of carbonyl-containing compounds without intermediacy of a metal hydride. Non-limiting examples of transfer hydrogenation reactions include Meerwein-Ponndorf-Verley reduction (e.g., using aluminum isopropoxide/isopropanol) and Ru-catalyzed transfer hydrogenation (e.g., Hashiguchi et al., *J. Am. Chem. Soc.*, 117:7562-7563, 1995).

When a substrate is an α,β-unsaturated carbonyl compound (e.g., an α,β-enone), a reducing agent can be a 1,2-reducing agent or a 1,4-reducing agent. For example, a reaction between an α,β-unsaturated carbonyl compound and a 1,2-reducing agent can afford, e.g., an allylic alcohol (or an allylic amine, if the starting compound is an enamide), whereas a reaction between an α,β-unsaturated carbonyl compound and a 1,4-reducing agent can afford an α,β-saturated compound and can leave the carbonyl group intact after work up of the reaction mixture. Non-limiting examples of 1,2-reducing agents include metal hydrides and metalloid hydrides, e.g., aluminum hydride compounds, boron hydride compounds (e.g., $CeCl_3$ with $NaBH_4$), and ruthenium hydride complexes. Non-limiting examples of 1,4-reducing agents include boron hydride compounds, hydrostannanes, copper hydride complexes (e.g., Stryker's reagent), palladium hydride complexes, platinum hydride complexes, iridium hydride complexes, rhodium hydride complexes, and ruthenium hydride complexes.

A compound having an allylic leaving group (e.g., a carboxylate, a halide, or a sulfonate) can be treated with an allylic reducing agent to replace the leaving group with a hydrogen atom. A non-limiting example of allylic reducing agent is a palladium salt in combination with a formic acid salt (e.g., trialkylammonium formate).

Masked Amines and Amine Unmasking Agents

The compounds used in the methods of the invention can contain a masked or unmasked amine (e.g., at C.35 carbon of the structure of eribulin). An unmasked amine is $—NH_2$. Amine can be masked using methods known in the art, e.g., by protecting amine with an N-protecting group. Alternatively, amine can be masked as a nitrogen-containing moiety, which can be reacted with an amine unmasking agent to afford an amine. Non-limiting examples of the nitrogen-containing moieties include azide, an imide (e.g., phathalimide), Amine unmasking agents can be those known in the art for removing N-protecting groups from amines. In a non-limiting example, a Boc group can be removed using amine unmasking agents known in the art, e.g., a Brønsted acid (e.g., HCl in 1,4-dioxane trifluoroacetic acid). When amine is masked as azide, the amine can be unmasked by subjecting the compound containing the masked amine to Staudinger reaction conditions (e.g., by contacting with a phosphine, such as trialkylphosphine, dialkylarylphosphine, alkykdiarylphosphine, or triarylphosphine) or by reacting the compound containing the masked amine with a reducing agent (e.g., $LiAlH_4$). When amine is masked as an imide (e.g., phthalimide), the amine can be unmasked by reacting with an amine unmasking agent known in the art, e.g., hydrazine.

Hydroxyl Protecting Groups and Hydroxyl Protecting Group Removing Agents

Hydroxyl protecting groups can be as defined herein. In particular, a hydroxyl protecting group can be an acyl, a sulfonyl, an arylalkyl (e.g., benzyl or p-methoxybenzyl), an aryl (e.g., p-methoxyphenyl), or an optionally substituted silyl (e.g., TMS, TES, TBS, TIPS, TBDPS, or TPS). Hydroxyl protecting groups, hydroxyl protecting agents, and hydroxyl protecting reaction conditions can be selected to protect selectively certain hydroxyl groups in a compound, while leaving other hydroxyl groups unprotected. The choice of hydroxyl protecting groups for a compound can facilitate subsequent deprotection strategies, as some hydroxyl protecting groups can be removed in the presence of others using appropriate hydroxyl protecting group removing agents. Some of these strategies involving the choice of silyl hydroxyl protecting groups are discussed in, e.g., *Silicon-Based Blocking Agents*, Gelest, Inc., 2011.

Hydroxyl protecting group removing agents are those agents that can react with a compound having a protected hydroxyl group to afford the compound with a deprotected hydroxyl group. Hydroxyl protecting group removing agents and deprotection reaction conditions can be those known in the art. In a non-limiting example, hydroxyl masked as silyl ether can be unmasked by a reaction with a fluoride source (e.g., a fluoride salt, such as KF or TBAF). Alternatively, hydroxyl protected as TMS or TES ether can be deprotected by a reaction with a Brønsted acid (e.g., a carboxylic acid). In another non-limiting example, hydroxyl protected as an ester can be deprotected by a reaction with a $C_{1-6}$ alkoxide (e.g., alkali $C_{1-6}$ alkoxide or alkali earth $C_{1-6}$ alkoxide). In yet another non-limiting example, hydroxyl protected as an arylalkyl ether (e.g., 1-arylalk-1-yl ether) can be deprotected using a reduction reaction, e.g., with Pd/C and H$_2$ or with Na/NH$_3$. Alternatively, hydroxyl protected as an alkoxyarylalkyl ether (e.g., MPM ether) can be deprotected by a reaction with 2,3-dichloro-5,6-dicyano-1,4-benzoquinone (DDQ). In still another non-limiting example, hydroxyl protected as alkoxyalkyl ether (e.g., 1-alkoxyalk-1-yl) or THP ether can be deprotected by a reaction with a Brønsted acid. Cyclic protected diols, such as acetals or ketals (e.g., as 2-alkyl-1,3-dioxolane, 2,2-dialkyl-1,3-dioxolane, 2-alkyl-1,3-dioxane, or 2,2-dialkyl-1,3-dioxane), can be deprotected by a reaction with a Brønsted acid (e.g., a carboxylic acid).

Dihydroxylation and Oxidative Carbon-Carbon Bond Cleavage

Dihydroxylation reaction produces diols from olefins. The reaction conditions can be those known in the art. Dihydroxylation reaction may be direct (e.g., Sharpless dihydroxylation, Upjohn dihydroxylation, or Milas dihydroxylation) or indirect (e.g., through epoxidation/hydrolysis, diborylation/oxidation, or carboxylation/hydrolysis (e.g., Woodward reaction or Prevost reaction)). A direct dihydroxylation reaction can be performed using an osmium complex (e.g., OsO$_4$ or osmate salt). A catalytic quantity of the osmium complex can be used in the dihydroxylation reactions in combination with an additional oxidizing agent (e.g., N-methylmorpholine N-oxide or hydrogen peroxide). The dihydroxylation reaction can be rendered stereoselective by including a chiral ligand (e.g., in AD-mix, which is a mixture of osmate and a chiral ligand).

When a dihydroxylation reaction is performed with an osmium complex and a periodate sat as oxidizing agent, the carbon-carbon double bond of an olefin can be cleaved to afford two carbonyl groups. The transformation of an olefin to two carbonyl groups is referred to herein as a cleavage reaction. Cleavage reaction conditions can be those known in the art. Non-limiting examples of cleavage reaction conditions can be ozonolysis reaction conditions or a reaction with an osmium complex (e.g., OsO$_4$ or osmate salt) and a periodate salt. A vicinal diol can be cleaved by sodium periodate or potassium permanganate.

Epimerizations

Epimerization reactions can be used to invert a stereogenic center having an undesired stereochemical identity. For example, through epimerization, R stereogenic center can be converted to S stereogenic center and vice versa. Epimerization of a stereogenic sp$^3$-carbon bonded to one hydrogen atom and to one hydroxyl group can be achieved through a reaction sequence involving oxidation of the hydroxyl group to a carbonyl group followed by a 1,2-reduction reaction. The 1,2-reduction reaction can provide the desired stereochemical identity diastereoselectively, or the reaction can be carried out using a chiral catalyst, chiral auxiliary, or a chiral reducing agent. Non-limiting examples of chiral reducing agents include alpine borane and prapine borane. Non-limiting examples of 1,2-reduction reactions involving chiral catalysts are Corey-Bakshi-Shibata reduction, Noyori hydrogenation, and Noyori transfer hydrogenation. The oxidation/reduction reaction sequence can be carried out in situ using dynamic kinetic resolution. A dynamic kinetic resolution can further involve a reaction with a hydroxyl protecting agent, which removes the desired stereoisomer from the reduction/oxidation equilibrium. In a non-limiting example, a dynamic kinetic resolution of chiral secondary alcohols can involve reduction/oxidation equilibration using η$^5$-Ph$_5$CpRu(CO)$_2$H in combination with enantioselective esterification using isopropenyl acetate catalyzed by a lipase enzyme (e.g., lipase B from *Candida Antarctica*, see, e.g., Martin-Matute et al., *J. Am. Chem. Soc.*, 127:8817-8825, 2005).

Epimerization can also be carried out on a compound containing a tetrahydropyran-2-yl-acetaldehyde moiety, in which carbon 2 of the pyran ring exhibits an undesired stereochemical identity. Contacting this compound with L-proline can provide equilibrium between two stereoisomers. If other, non-equilibrating stereogenic centers are present in the compound, the most stable stereoisomer will be present in a larger quantity relative to other stereoisomer (s) in equilibrium with the most stable stereoisomer.

The following examples are meant to illustrate the invention. They are not meant to limit the invention in any way.

EXAMPLES

Example 1—Preparation of the C.1-C.15 Fragment

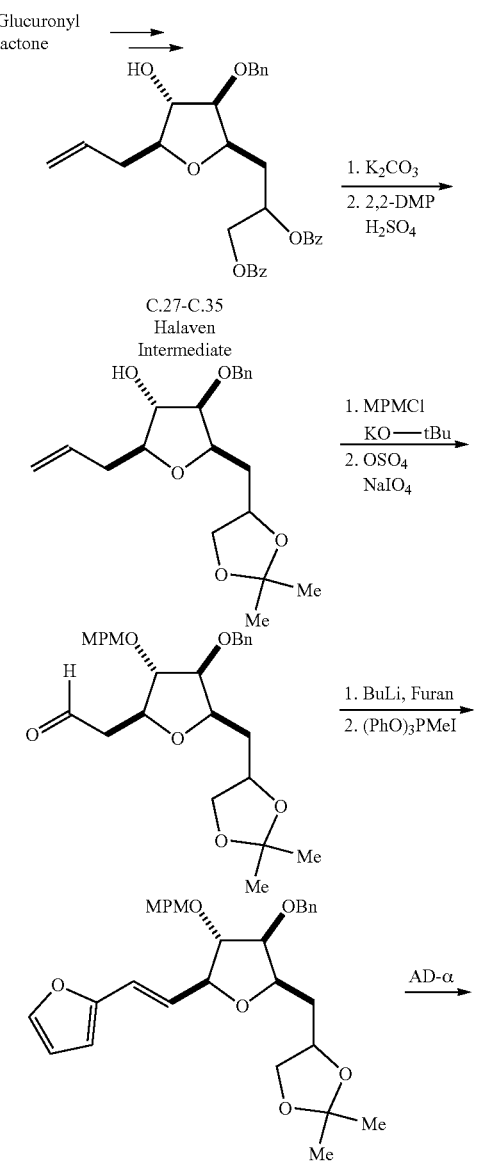

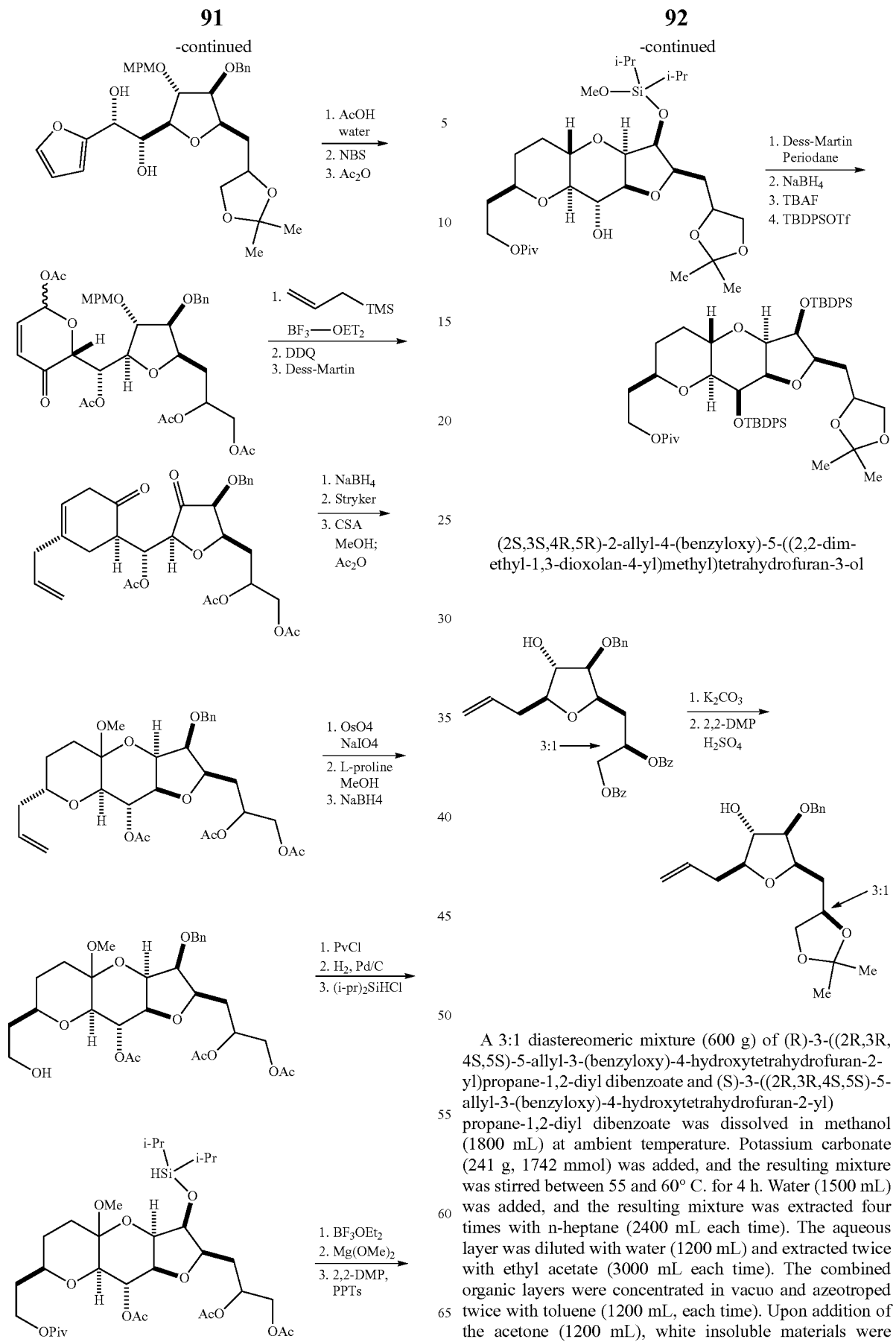

(2S,3S,4R,5R)-2-allyl-4-(benzyloxy)-5-((2,2-dimethyl-1,3-dioxolan-4-yl)methyl)tetrahydrofuran-3-ol A 3:1 diastereomeric mixture (600 g) of (R)-3-((2R,3R,4S,5S)-5-allyl-3-(benzyloxy)-4-hydroxytetrahydrofuran-2-yl)propane-1,2-diyl dibenzoate and (S)-3-((2R,3R,4S,5S)-5-allyl-3-(benzyloxy)-4-hydroxytetrahydrofuran-2-yl) propane-1,2-diyl dibenzoate was dissolved in methanol (1800 mL) at ambient temperature. Potassium carbonate (241 g, 1742 mmol) was added, and the resulting mixture was stirred between 55 and 60° C. for 4 h. Water (1500 mL) was added, and the resulting mixture was extracted four times with n-heptane (2400 mL each time). The aqueous layer was diluted with water (1200 mL) and extracted twice with ethyl acetate (3000 mL each time). The combined organic layers were concentrated in vacuo and azeotroped twice with toluene (1200 mL, each time). Upon addition of the acetone (1200 mL), white insoluble materials were generated. The mixture was filtered through 200 g of silica gel pad, which was then rinsed with acetone (1200 mL). The combined filtrate was concentrated in vacuo to give 216 g of brown oil, which was dissolved in acetone (864 mL) at ambient temperature. 2,2-Dimethoxypropane (103 mL, 841 mmol) and sulfuric acid (1.9 mL, 35 mmol) were added. The resulting mixture was stirred for 4h and then treated with saturated aqueous $NaHCO_3$ (8%) (216 mL) and water (540 mL). The resulting mixture was extracted twice with MTBE (864 mL each time). The combined organic layers were washed twice with 30% aqueous NaCl (430 mL each time) and then three times with water (450 mL each time). The resulting organic layer was concentrated in vacuo and azeotroped twice with toluene (864 mL) to give 219 g of the target product as a brown oil. $^1$H NMR (3:1 diastereomeric mixture, 400 MHz, $CDCl_3$) δ ppm 1.31 (s, 3H (minor)) 1.36 (s, 3H (major)) 1.40 (s, 3H) 1.93 (t, J=6.4 Hz, 2H) 1.96-2.09 (m, 1H) 2.32-2.41 (m, 1H) 2.42-2.52 (m, 1H) 3.53-3.62 (m, 1H) 3.66 (td, J=6.7, 4.7 Hz, 1H) 3.79 (dd, J=4.7, 2.1 Hz, 1H (major)) 3.81 (dd, J=4.7, 2.1 Hz, 1H (minor)) 3.97-4.04 (m, 1H) 4.06-4.12 (m, 1H) 4.12-4.17 (m, 1H) 4.24 (dt, J=13.1, 6.5 Hz, 1H) 4.51 (d, J=12.0 Hz, 1H (minor)) 4.54 (d, J=12.0 Hz, 1H (major)) 4.65 (d, J=11.7 Hz, 1H (major)) 4.66 (d, J=12.0 Hz, 1H (minor)) 5.05-5.18 (m, 2H) 5.77-5.93 (m, 1H) 7.28-7.41 (m, 5H).

4-(((2R,3S,4S,5S)-5-allyl-3-(benzyloxy)-4-((4-methoxybenzyl)oxy)tetrahydrofuran-2-yl)methyl)-2,2-dimethyl-1,3-dioxolane

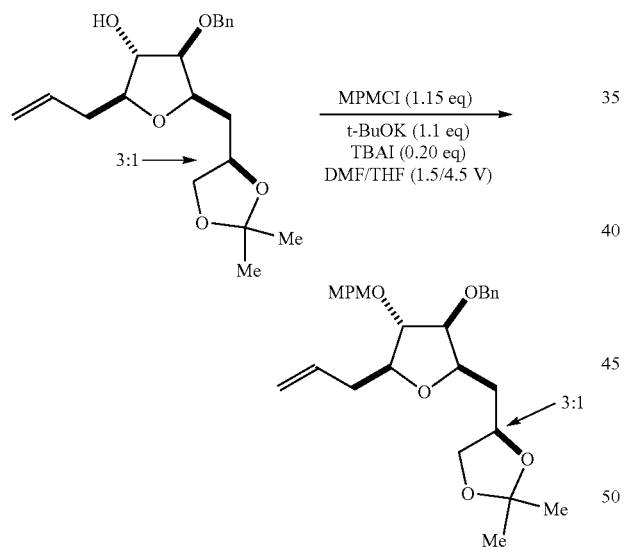

A 3:1 diastereomeric mixture of (2S,3S,4R,5R)-2-allyl-4-(benzyloxy)-5-(((R)-2,2-dimethyl-1,3-dioxolan-4-yl) methyl)tetrahydrofuran-3-ol and (2S,3S,4R,5R)-2-ally-4-(benzyloxy)-5-(((S)-2,2-dimethyl-1,3-dioxolan-4-yl) methyl)tetrahydrofuran-3-ol (219 g, 629 mmol) was azeotroped with anhydrous THF (329 mL). The resulting oil was added into a reactor with DMF (329 mL). TBAI (46.4 g, 126 mmol) was added, and the resulting mixture was cooled to a temperature ranging from 0 to 5° C. 1.0 M tert-Butyl alcohol, potassium derivative (691 mL, 691 mmol) was added at such rate to maintain the internal temperature below 10° C. Upon addition, the reaction was allowed to stir for 15 minutes. alpha-Chloro-4-methoxytoluene (98 mL, 720 mmol) was then added at such rate to maintain internal temperature below 15° C. Upon addition, the reaction was stirred between 0-5° C. After complete consumption of the starting material, the reaction was quenched with MeONa (25%) in MeOH solution (21.6 mL, 94.3 mmol) diluted in anhydrous methanol (288 mL) at such a rate that internal temperature remained below 10° C. The mixture was then allowed to warm to 20-25° C. and then concentrated in vacuo to remove volatiles. The remaining solution was partitioned between water (1095 mL) and MTBE (1643 mL). The organic layer was washed twice with 30% aqueous NaCl (876 mL), dried over $MgSO_4$, filtered and concentrated in vacuo. The resulting residue was diluted with MTBE (219 mL), and remaining solid was filtered off. The filtrate was concentrated in vacuo to give 295 g of the target product as a reddish brown oil. $^1$H NMR (3:1 diastereomeric mixture, 400 MHz, $CDCl_3$) δ ppm 1.31 (s, 3H (minor)) 1.35 (s, 3H (major)) 1.37-1.42 (m, 3H) 1.87-2.03 (m, 2H) 2.26-2.52 (m, 2H) 3.57 (t, J=7.9 Hz, 1H) 3.72 (dd, J=7.3, 3.5 Hz, 1H (major)) 3.74 (d, J=3.2 Hz, 1H (minor)) 3.78-3.86 (m, 5H) 3.98-4.14 (m, 2H) 4.15-4.30 (m, 1H) 4.33-4.41 (m, 2H) 4.42-4.46 (m, 1H) 4.57 (d, J=12.0 Hz, 1H) 5.00-5.10 (m, 2H) 5.73-5.91 (m, 1H) 6.85-6.91 (m, 2H) 7.19-7.24 (m, 2H) 7.27-7.39 (m, 5H)

2-((2S,3S,4S,5R)-4-(benzyloxy)-6-((2,2-dimethyl-1,3-dioxolan-4-yl)methyl)-3-((4-methoxybenzyl)oxy) tetrahydrofuran-2-yl)acetaldehyde

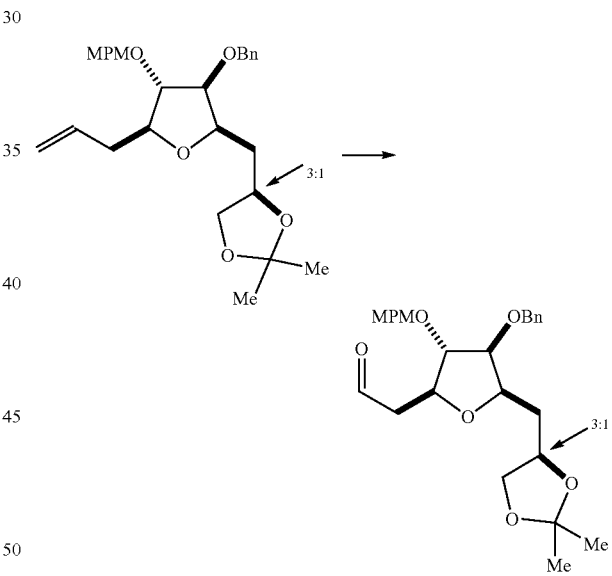

3:1 diastereomeric mixture of 2-((2S,3S,4S,5R)-4-(benzyloxy)-5-(((R)-2,2-dimethyl-1,3-dioxolan-4-yl) methyl)-3-((4-methoxybenzyl)oxy)tetrahydrofuran-2-yl)acetaldehyde and 2-((2S,3S,4S,5R)-4-(benzyloxy)-5-(((S)-2,2-dimethyl-1,3-dioxolan-4-yl)methyl)-3-((4-methoxybenzyl)oxy)tetrahydrofuran-2-yl)acetaldehyde (100 g, 213 mmol) was dissolved in 1,4-dioxane (600 mL) and water (200 mL). 2,6-Lutidine (49.7 mL, 427 mmol) and a solution of osmic acid (2.5 wt %, 25 mL, 2.458 mmol) in t-BuOH were added. The resulting mixture was cooled to a temperature below 20° C. and sodium metaperiodate (137 g, 640 mmol) was added. After being stirred for 5 h at ambient temperature, the reaction mixture was treated with water (1250 mL). The resulting mixture was extracted twice with toluene (1000 mL each time). The combined organic layers were washed sequentially with a solution of sodium sulfite (40.3 g, 320 mmol) in water (200 mL), 1.0 M hydrochloric acid in water (500 mL, 500 mmol, saturated aqueous NaHCO₃ (8%) (200 mL), and 30% aqueous NaCl (200 mL). The organic layer was concentrated in vacuo, and the residue was filtered through a silica-gel pad (150 mL), which was rinsed with n-heptane/ethyl acetate (1/1=1000 mL). Concentration in vacuo provided 102 g of the target product as dark brown oil. ¹H NMR (3:1 diastereomeric mixture, 400 MHz, CDCl₃) δ ppm 1.31 (s, 1H (minor)) 1.35 (s, 3H (major)) 1.39 (s, 3H) 1.87-2.14 (m, 2H) 2.66 (dd, J=5.8, 1.8 Hz, 1H) 2.70-2.78 (m, 1H) 3.55 (dd, J=8.2, 7.3 Hz, 1H) 3.76 (dd, J=2.9, 0.8 Hz, 1H (major)) 3.77 (dd, J=2.7, 0.6 Hz, 1H (minor)) 3.79-3.84 (m, 4H) 4.00 (dd, J=7.8, 6.0 Hz, 1H (major)) 4.06 (dd, J=8.2, 5.8 Hz, 1H (minor)) 4.12 (dt, J=8.9, 3.8 Hz, 1H) 4.17-4.24 (m, 1H) 4.28 (ddd, J=7.3, 5.6, 2.9 Hz, 1H) 4.36-4.50 (m, 3H) 4.54 (d, J=12.2 Hz, 1H) 4.55 (d, J=11.9 Hz, 1H) 6.85-6.91 (m, 2H) 7.15-7.39 (m, 7H) 9.73 (t, J=2.0 Hz, 1H)

2-((2S,3S,4S,5R)-4-(benzyloxy)-6-(((R)-2,2-dimethyl-1,3-dioxolan-4-yl)methyl)-3-((4-methoxybenzyl)oxy)tetrahydrofuran-2-yl)-1-(furan-2-yl)ethan-1-ol

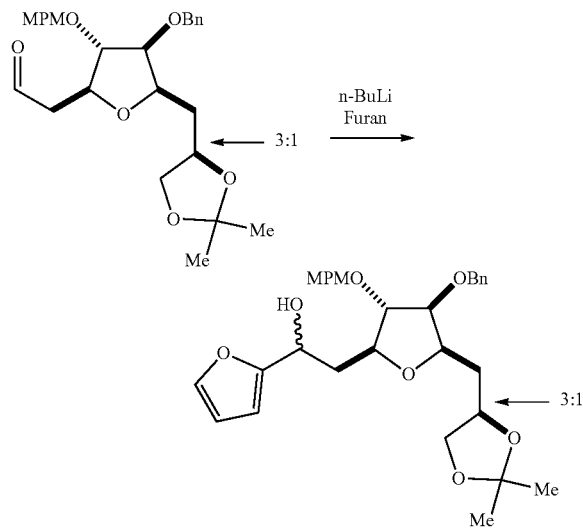

Furan (22.40 mL, 308.0 mmol) and THF (800 ml) were added into a reactor and cooled down to 0° C. n-BuLi (1.6 M, 110 mL, 276 mmol) was added while keeping the internal temperature below 15° C. After being stirred for 1 h at a temperature between 10 and 20° C., the resulting solution was cooled to a temperature below −20° C. A solution of a 3:1 diastereomeric mixture of 2-((2S,3S,4S,5R)-4-(benzyloxy)-5-(((R)-2,2-dimethyl-1,3-dioxolan-4-yl-methyl)-3-((4-methoxybenzyloxy)tetrahydrofuran-2-ylacetaldehyde and 2-((2S,3S,4S,5R)-4-(benzyloxy)-5-(((S)-2,2-dimethyl-1,3-dioxolan-4-yl)methyl)-3-((4-methoxybenzyloxy)tetrahydrofuran-2-yl)acetaldehyde (102 g, 212 mmol) in THF (300 mL) was added while keeping the internal temperature below −10° C. The resulting reaction mixture was stirred at a temperature between −5 and −15° C. for 1 h. Saturated aqueous NH₄Cl (27 wt %) (500 mL) and water (200 mL) were added, and the mixture was allowed to warm to ambient temperature. The layers were separated, and the organic layer was washed twice with 30% aqueous NaCl (400 mL) and concentrated in vacuo. The residue was filtered through a silica gel pad (300 mL), rinsing with n-heptane/ethyl acetate (3/2, 1300 mL). Concentration of the filtrate afforded 94 g of the target product as a brown oil.

4-(((2R,3S,4S,5S)-3-(benzyloxy)-5-((E)-2-(furan-2-yl)vinyl)-4-((4-methoxybenzyl)oxy)tetrahydrofuran-2-yl)methyl)-2,2-dimethyl-1,3-dioxolane

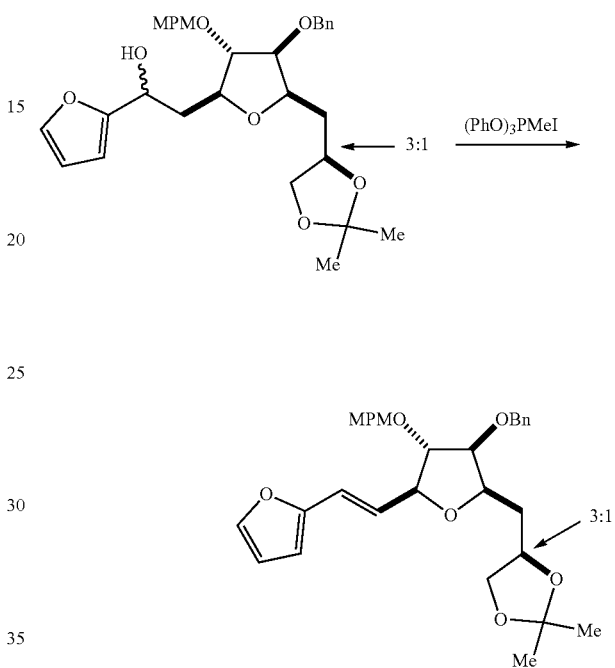

2-((2S,3S,4S,5R)-4-(benzyloxy)-5-(((R)-2,2-dimethyl-1,3-dioxolan-4-yl)methyl)-2-((4-methoxybenzyloxy)tetrahydrofuran-2-yl)-1-(furan-2-yl)ethan-1-ol (94 g) was dissolved in dimethylacetamide (893 mL). Methyltriphenoxyphosphonium iodide (99 g, 218 mmol) was added while keeping the internal temperature below 25° C. The resulting reaction was kept stirring between 20-25° C. in dark for 2.5 h. The reaction mixture was diluted with MTBE (1410 mL) and cooled down below 10° C. A solution of KOH (88 g, 1571 mmol) in water (1128 mL) was added while keeping the internal temperature below 30° C. The aqueous layer was separated out and extracted twice with MTBE (940 mL). The combined organic layers were washed three times with 30% aqueous NaCl (1128 mL) and concentrated in vacuo. The residue was filtered through a silica gel pad (200 mL), which was then rinsed with n-heptane/ethyl acetate (2/1, 1500 mL). Concentration of the filtrate gave 87.9 g of the target product as brown oil. ¹H NMR (3:1 diastereomeric mixture, 400 MHz, CDCl₃) δ ppm 1.31 (s, 3H (minor)) 1.35 (s, 3H (major)) 1.40 (s, 3H) 1.87-2.20 (m, 2H) 3.58 (t, J=7.3 Hz, 1H) 3.78-3.81 (m, 3H) 3.88 (d, J=3.4 Hz, 1H (major)) 3.89 (d, J=3.7 Hz, 1H (minor)) 4.03 (dd, J=7.8, 6.0 Hz, 1H (minor)) 4.09 (dd, J=8.2, 6.1 Hz, 1H (major)) 4.17 (dt, J=9.5, 3.7 Hz, 1H) 4.22-4.31 (m, 1H) 4.36 (dd, J=7.3, 3.4 Hz, 1H) 4.42-4.51 (m, 3H) 4.59 (d, J=12.5 Hz, 1H (major)) 4.60 (d, J=11.9 Hz, 1H (minor)) 6.15-6.26 (m, 2H) 6.37 (dd, J=3.2, 2.0 Hz, 1H) 6.39-6.49 (m, 1H) 6.84-6.89 (m, 2H) 7.19-7.24 (m, 2H) 7.26-7.38 (m, 5H)

(2R)-1-((2S,3R,4S,5R)-4-(benzyl)oxy)-6-((2,2-dimethyl-1,3-dioxolan-4-yl)methyl)-3-((4-methoxybenzyl)oxy)tetrahydrofuran-2-yl)-2-(furan-2-yl)ethane-1,2-diol 3-((2R,3S,4R,5S)-3-(benzyloxy)-5-((2R)-2-(furan-2-yl)-1,2-dihydroxyethyl)-4-((4-methoxybenzyl)oxy)tetrahydrofuran-2-yl)propane-1,2-diol

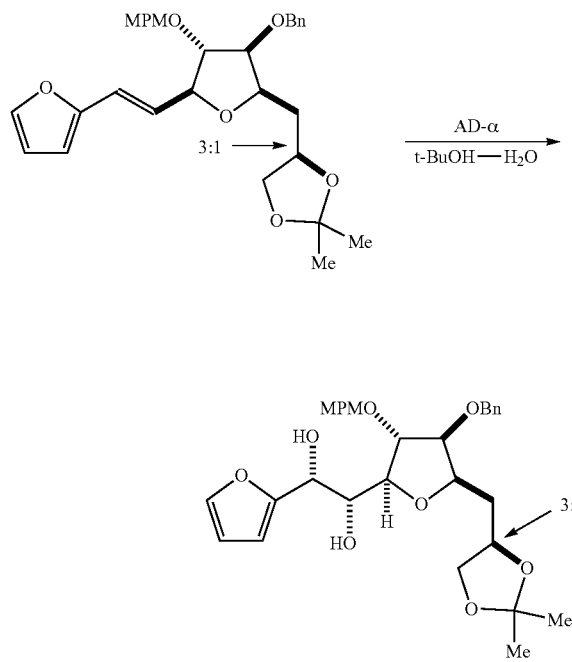

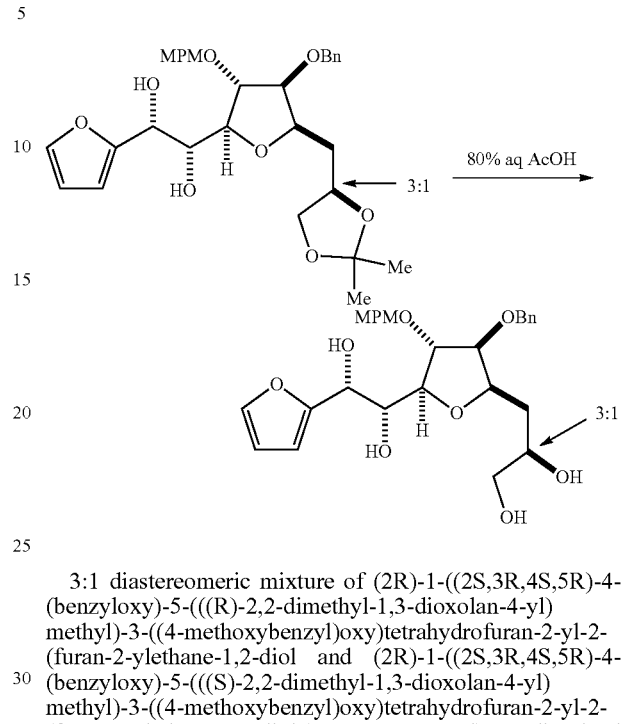

To a reactor were added (DHQ)₂PHAL (1.267 g, 1.627 mmol, potassium osmium(VI) oxide (0.216 g, 0.651 mmol, potassium carbonate (67.5 g, 488 mmol, and potassium ferricyanide(III) hydrate (161 g, 488 mmol. Water (847 mL) and 2-methylpropan-2-ol (424 mL) were added. The resulting mixture was cooled below 7° C. Methane sulfonamide (18.57 g, 195 mmol) followed by a solution of a 3:1 diastereomeric mixture of (R)-4-(((2R,3S,4S,5S)-3-(benzyloxy)-5-((E)-2-(furan-2-yl)vinyl)-4-((4-methoxybenzyloxy)tetrahydrofuran-2-yl)methyl)-2,2-dimethyl-1,3-dioxolane and (S)-4-(((2R,3S,4S,5S)-3-(benzyloxy)-5-((E)-2-(furan-2-yl)vinyl)-4-((4-methoxybenzyl)oxy)tetrahydrofuran-2-yl)methyl)-2,2-dimethyl-1,3-dioxolane (84.7 g, 162.693 mmol) in tert-butanol (424 mL) was added. The resulting mixture was stirred for 3 days between 13-18° C. Sodium sulfite (103 g, 813 mmol) and water (339 mL) were added, and the resulting mixture was stirred for 30-60 min while warming to ambient temperature. The mixture was extracted twice with ethyl acetate (2100 mL). The combined organic layers were washed with 2M aqueous KOH (296 mL) and 30% aqueous NaCl (424 mL). Concentration in vacuo followed by silica gel plug purification using a 25-66% gradient of ethyl acetate in n-heptane as eluent provided 71.6 g of the target product as a brown oil. ¹H NMR (3:1 diastereomeric mixture, 400 MHz, CDC) δ ppm 1.33-1.38 (m, 3H) 1.39-1.42 (m, 3H) 1.85-2.09 (m, 2H) 3.57 (t, J=7.8 Hz, 1H) 3.78 (d, J=3.1 Hz, 1H) 3.81 (s, 3H) 3.83-3.87 (m, 1H) 3.89 (br. s., 1H) 4.04-4.12 (m, 3H) 4.16-4.24 (m, 1H) 4.34-4.49 (m, 3H) 4.62 (d, J=11.6 Hz, 1H (major)) 4.63 (d, J=11.6 Hz, 1H (minor)) 4.73 (d, J=7.0 Hz, 1H (major)) 4.76 (d, J=6.1 Hz, 1H (minor)) 6.34-6.37 (m, 2H) 6.86-6.91 (m, 2H) 7.16-7.24 (m, 2H) 7.27-7.44 (m, 6H).

3:1 diastereomeric mixture of (2R)-1-((2S,3R,4S,5R)-4-(benzyloxy)-5-(((R)-2,2-dimethyl-1,3-dioxolan-4-yl)methyl)-3-((4-methoxybenzyl)oxy)tetrahydrofuran-2-yl-2-(furan-2-ylethane-1,2-diol and (2R)-1-((2S,3R,4S,5R)-4-(benzyloxy)-5-(((S)-2,2-dimethyl-1,3-dioxolan-4-yl)methyl)-3-((4-methoxybenzyl)oxy)tetrahydrofuran-2-yl-2-(furan-2-ylethane-1,2-diol (71.6 g, 129 mmol) was dissolved in acetic acid (501 mL). Water (125 mL) was added, and the resulting mixture was stirred at ambient temperature overnight. The reaction mixture was concentrated in vacuo and azeotroped with toluene (500 mL). The residue was filtered through silica-gel pad (200 mL), which was then rinsed with n-heptane/ethyl acetate (1/1, 1 L) and ethyl acetate (3.5 L). Concentration of the filtrate gave 69.4 g of the target product as brown oil.

3-((2R,3S,4R,5R)-5-((1S)-acetoxy((2R)-acetoxy-3-oxo-3,6-dihydro-2H-pyran-2-yl)ethyl)-3-(benzyloxy)-4-((4-methoxybenzyl)oxy)tetrahydrofuran-2-yl)propane-1,2-diyl diacetate

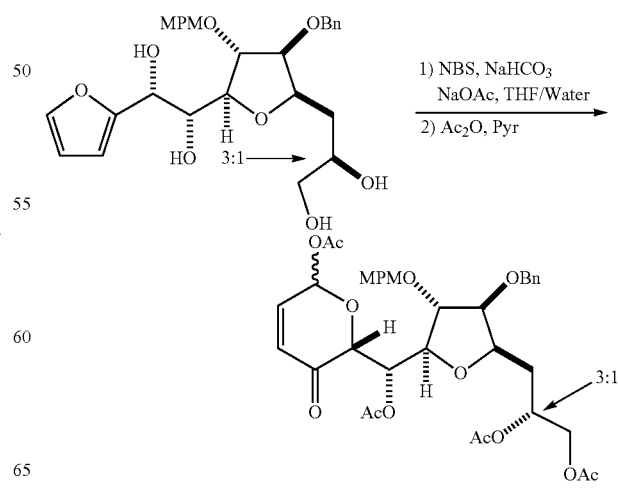

A 3:1 diastereomeric mixture of (R)-3-((2R,3S,4R,5S)-3-(benzyloxy)-5-((1R,2R)-2-(furan-2-yl)-1,2-dihydroxyethyl)-4-((4-methoxybenzyl)oxy)tetrahydrofuran-2-yl)propane-1,2-diol and (S)-3-((2R,3S,4R,5S)-3-(benzyloxy)-5-((1R,2R)-2-(furan-2-yl)-1,2-dihydroxyethyl)-4-((4-methoxybenzyl)oxy)tetrahydrofuran-2-yl)propane-1,2-diol (69.4 g) was dissolved in THF (989 mL) and water (247 mL) and cooled down below 5° C. Sodium bicarbonate (21.53 g, 256.3 mmol) and sodium acetate (10.51 g, 128.1 mmol) were added. NBS (23.94 g, 134.5 mmol) was added while keeping the internal temperature below 5° C. After being stirred for 1 h at a temperature between 0 and 5° C., the reaction mixture was treated with a solution of potassium iodide (10.63 g, 64.06 mmol) in water (165 mL) and diluted with EtOAc (2000 mL). The organic layer was washed with a solution of sodium thiosulfate (16.21 g, 102.5 mmol) in water (198 mL) followed by 30% aqueous NaCl (132 mL). Solvents were removed in vacuo. The resulting residue (71 g) was dissolved in dichloromethane (613 mL) and cooled down to 0° C. Pyridine (198 mL, 2444 mol), acetic anhydride (121 mL, 1285 mol) and 4-dimethylaminopyridine (1.57 g, 12.8 mmol) were added. After being stirred overnight at a temperature between 0 and 15° C., the reaction mixture was treated with saturated aqueous NH$_4$Cl (27 wt %)(545 mL) and water (136 mL). The layers were separated, and the aqueous layer was extracted with dichloromethane (341 mL). The combined organic layers were washed twice with 0.5 M aqueous hydrochloric acid (409 mL) followed by 30% aqueous NaCl (477 mL). Concentration followed by filtration through a silica gel pad (60 mL), which was then rinsed with heptane/ethyl acetate (1/1, 1500 mL), provided 92 g of the target product as a brown oil.

3-((2R,3S,4R,5R)-5-(1S)-acetoxy((2R)-6-allyl-3-oxo-3,6-dihydro-2H-pyran-2-yl)methyl)-3-(benzyloxy)-4-((4-methoxybenzyl)oxy)tetrahydrofuran-2-yl)propane-1,2-diyl diacetate

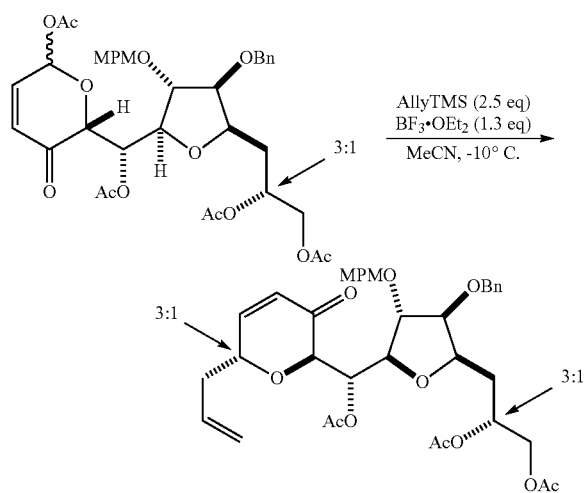

3-((2R,3S,4R,5R)-5-((1S)-Acetoxy((2R)-6-acetoxy-3-oxo-3,6-dihydro-2H-pyran-2-yl)methyl)-3-(benzyloxy)-4-((4-methoxybenzyl)oxy)tetrahydrofuran-2-ylpropane-1,2-diyl diacetate (92 g, 129 mmol) was dissolved in acetonitrile (902 mL) and cooled to −15° C. Allyltrimethylsilane (51.3 mL, 323 mmol) followed by BF$_3$·OEt$_2$ (21.26 mL, 167.7 mmol) was added while keeping internal temperature below −10° C. The resulting solution was stirred at a temperature between −10 and 0° C. until the reaction was complete. Saturated aqueous NaHCO$_3$ (8%) (902 mL) and MTBE (721 mL) were then added, and the resulting mixture was allowed to warm to ambient temperature. The layers were separated, and the aqueous layer was extracted with MTBE (721 mL). The combined organic layers were washed twice with 30% aqueous NaCl (721 mL) and concentrated in vacuo. The residue was diluted with MTBE (1500 mL) and washed sequentially with 1M HCl (250 mL), saturated aqueous NaHCO$_3$ (8%) (250 mL), and 30% aqueous NaCl (250 mL). Concentration followed by filtration through a silica gel pad (100 mL), which was then rinsed with n-heptane/ethyl acetate (2/3, 1200 mL), provided 54.2 g of the target product as a brown oil.

3-((2R,3R,4R,5R)-5-(1S)-acetoxy((2R)-6-allyl-3-oxo-3,6-dihydro-2H-pyran-2-yl)methyl)-3-(benzyloxy)-4-hydroxytetrahydrofuran-2-yl)propane-1,2-diyl diacetate

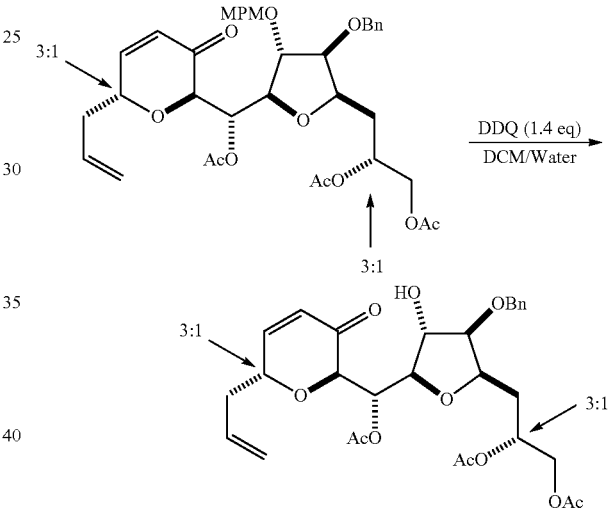

3-((2R,3S,4R,5R)-5-((1S)-acetoxy((2R)-8-allyl-3-oxo-3,6-dihydro-2H-pyran-2-yl)methyl)-3-(benzyloxy)-4-((4-methoxybenzyloxy)tetrahydrofuran-2-yl)propane-1,2-diyl diacetate (54.2 g) was dissolved in dichloromethane (542 mL) and treated with water (136 mL) and DDQ (25.3 g, 111 mmol). After being stirred for 2 h at ambient temperature, the reaction mixture was diluted with dichloromethane (700 mL) and water (700 mL). Saturated aqueous NaHCO$_3$ (8%) (870 mL) and sodium thiosulfate (35.2 g, 223 mmol) were added, and the resulting mixture was stirred at ambient temperature for 10 min. The layers were separated, and the aqueous layer was extracted with dichloromethane (271 mL). The combined organic layers were washed with saturated aqueous NaHCO$_3$ (8%) (325 mL) and 30% aqueous NaCl (217 mL). Concentration in vacuo and purification by silica gel column chromatography using a 20-60% gradient of ethyl acetate in n-heptane as eluent afforded 31.2 g of the target product as a brown oil. 1H NMR (a 9:3:3:1 mixture of 4 diastereomers, 400 MHz, CDCl$_3$) δ ppm 1.84-1.98 (m, 2H) 2.04 (d, J=12.9 Hz, 9H) 2.43 (d, J=8.2 Hz, 2H) 3.89 (dt, J=7.6, 2.1 Hz, 1H) 3.98-4.06 (m, 2H) 4.07-4.18 (m, 2H) 4.34 (dd, J=11.9, 3.3 Hz, 1H) 4.43 (d, J=5.1 Hz, 1H) 4.55 (d, J=11.7 Hz, 1H) 4.60-4.65 (m, 1H) 4.66-4.73 (m, 1H) 5.12-

5.23 (m, 3H) 5.51 (dd, J=6.6, 5.1 Hz, 1H (major)) 5.55 (dd, J=5.9, 4.7 Hz, 1H (minor)) 5.75-5.88 (m, 1H) 6.12 (dd, J=10.6, 2.3 Hz, 1H) 6.90 (dd, J=10.4, 1.4 Hz, 1H (minor)) 6.95 (dd, J=10.6, 2.3 Hz, 1H (major)) 7.27-7.40 (m, 5H)

3-((2R,3S,5S)-5-((1R)-acetoxy((2R)-6-allyl-3-oxo-3,6-dihydro-2H-pyran-2-yl)methyl)-3-(benzyloxy)-4-oxotetrahydrofuran-2-yl)propane-1,2-diyl diacetate

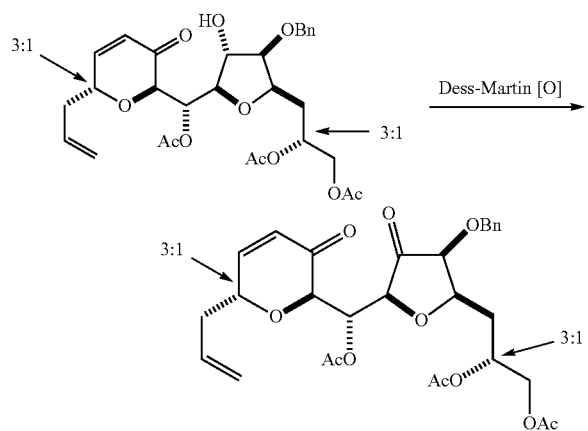

To 3-((2R,3R,4R,5R)-5-((1S)-acetoxy((2R)-6-ally-3-oxo-3,6-dihydro-2H-pyran-2-yl)methyl)-3-(benzyloxy)-4-hydroxytetrahydrofuran-2-yl)propane-1,2-diyl diacetate (27.4 g, 48.9 mmol) was added dichloromethane (219 mL) at ambient temperature. Sodium bicarbonate (12.32 g, 146.6 mmol, Dess-Martin periodinane (30.1 g, 70.872 mmol) and water (0.176 mL, 9.78 mmol) were added. The resulting mixture was stirred at ambient temperature until all starting material was consumed. It was then diluted with water (301 mL) and MTBE (301 mL). Sodium bicarbonate (12.32 g, 146.6 mmol) and sodium thiosulfate (19.32 g, 122.2 mmol) were added, and the resulting mixture was stirred at ambient temperature over 10 min. The layers were separated, and the aqueous layer was extracted with MTBE (219 mL). The combined organic layers were washed with saturated aqueous NaHCO$_3$ (8%) (137 mL) and 30% aqueous NaCl (137 mL). Concentration in vacuo followed by azeotroping with toluene provided 33.1 g of the target product as a dark brown oil.

3-((2R,3S,5S)-5-(1R)-acetoxy((2R)-6-allyl-3-oxo-3,6-dihydro-2H-pyran-2-yl)methyl)-3-(benzyloxy)-4-hydroxytetrahydrofuran-2-yl)propane-1,2-diyl diacetate

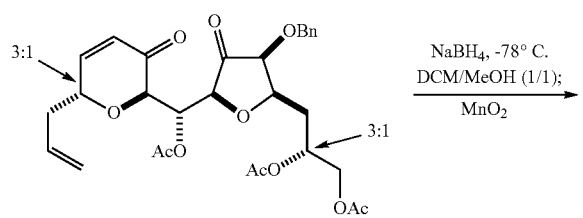

3-((2R,3S,5S)-5-((1R)-acetoxy((2R)-6-allyl-3-oxo-3,6-dihydro-2H-pyran-2-yl)methyl)-3-(benzyloxy)-4-oxotetrahydrofuran-2-yl)propane-1,2-diyl diacetate was dissolved in dichloromethane (406 mL) and MeOH (406 mL) and cooled to a temperature below −75° C. Sodium borohydride (2.75 g, 72.3 mmol) was added portionwise while keeping the internal temperature below −75° C. After 1 h, acetone (95 mL, 1290 mmol) was added while keeping the internal temperature below −75° C. Saturated aqueous NH$_4$Cl (27 wt %) (216 mL), water (108 mL) and MTBE (325 mL) were added. The resulting mixture was allowed to warm up to ambient temperature. The layers were separated and the aqueous layer was extracted with MTBE (271 mL). The combined organic layers were washed twice with 30% aqueous NaCl (189 mL) and dried over MgSO$_4$. Filtration followed by concentration in vacuo provided 30.8 g of brown thick oil, which was dissolved in dichloromethane (271 mL). To the resulting solution was added manganese dioxide (42.1 g, 484 mmol). The resulting slurry was vigorously stirred at ambient temperature overnight. 40 g of Celite® was then added, and the resulting slurry was stirred at ambient temperature for 20 min. Filtration through a Celite® pad, concentration in vacuo, and purification by silica gel column chromatography using n-heptane/ethyl acetate (½) as eluent gave 23.8 g of the target product as a foam solid.

3-((2R,3S,5S)-5-((1R)-acetoxy((2R)-6-allyl-3-oxotetrahydro-2H-pyran-2-yl)methyl)-3-(benzyloxy)-4-hydroxytetrahydrofuran-2-yl)propane-1,2-diyl diacetate

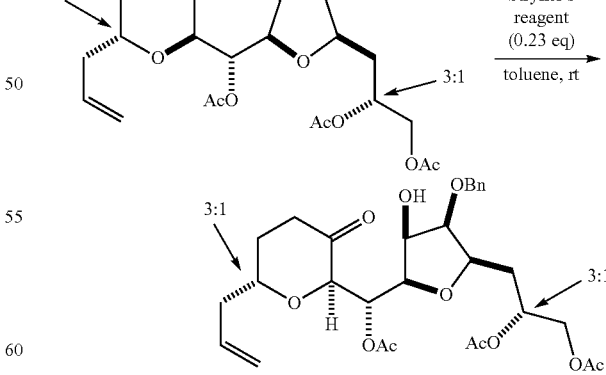

3-((2R,3S,5S)-5-((1R)-acetyloxy((2R)-6-allyl-3-oxo-3,6-dihydro-2H-pyran-2-yl)methyl)-3-(benzyloxy)-4-hydroxytetrahydrofuran-2-yl)propane-1,2-diyl diacetate (20 g, 35.7 mmol) was dissolved in deoxygenated toluene (460 mL) at ambient temperature. The resulting solution was purged with nitrogen for 1 h and deoxygenated (purged with nitrogen for 40 min) water (1.22 mL, 67.8 mmol) was added. Hydrido(triphenylphosphine)copper(I) hexamer (16.0 g, 8.16 mmol) was added in 3 portions. The resulting red slurry was stirred over 4 h. Upon completion, the reaction was exposed to air. Copper-containing decomposition products precipitated out. The resulting brown slurry was filtered through a Celite pad, which was then rinsed with toluene until no product was observed in eluent. Concentration in vacuo followed by purification by column chromatography using a 20-66% gradient of ethyl acetate in n-heptane as eluent gave 18.07 g of the target product as a brown oil.

3-((2R,3S,3aS,8aR,9S,9aR)-9-acetoxy-7-allyl-3-(benzyloxy)-4a-methoxydecahydrofuro[3,2-b]pyrano[2,3-e]pyran-2-yl)propane-1,2-diyl diacetate

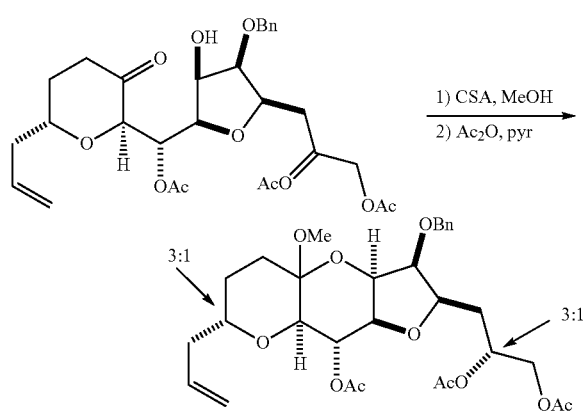

3-((2R,3S,5S)-5-(((1R)-acetoxy((2R)-6-ally-3-oxotetrahydro-2H-pyran-2-yl)methyl)-3-(benzyloxy)-4-oxotetrahydrofuran-2-yl)propane-1,2-diyl diacetate (23.4 g, 41.6 mmol) was dissolved in methanol (281 mL). ((1S,4R)-7,7-dimethyl-2-oxobicyclo[2.2.1]heptan-1-yl)methanesulfonic acid (1.1 g, 5.0 mmol) was added, and the resulting solution was stirred at 60° C. until all starting material was consumed. The mixture was cooled to ambient temperature and treated with TEA (0.870 mL, 6.24 mmol). Solvents were removed, and the residue was dissolved in ethyl acetate (488 mL). The resulting solution was washed with 30% aqueous NaCl (70.2 mL), dried over MgSO$_4$, filtered, and concentrated in vacuo. The residue was dissolved in dichloromethane (140 mL) and pyridine (46.8 mL) at ambient temperature. Acetic anhydride (23.59 mL, 249.6 mmol) and 4-dimethylaminopyridine (0.508 g, 4.16 mmol) were added, and the resulting solution was stirred at ambient temperature for 1 h. The reaction mixture was treated with saturated aqueous NH$_4$Cl (27 wt %) (140 mL), water (46.8 mL) and MTBE (281 mL). The organic layer was separated and washed sequentially with 1M aqueous hydrochloric acid (94 mL), saturated aqueous NaHCO$_3$ (8%) (70.2 mL), and 30% aqueous NaCl (70.2 mL). Drying over MgSO$_4$, filtration, concentration and purification by silica gel column chromatography using a 25-40% gradient of ethyl acetate in n-heptane as eluent provided 12.3 g of the target product as a pale brown oil.

$^1$H NMR (9:3:3:1 mixture of 4 diastereomers, CDCl$_3$) δ ppm 1.29-1.48 (m, 1H) 1.54-1.78 (m, 3H) 1.93-2.16 (m, 11H) 2.17-2.40 (m, 2H) 3.25 (s, 3H (minor 1)) 3.29 (s, 3H (minor 2)) 3.30 (s, 3H (major)) 3.55 (d, J=11.1 Hz, 1H (major)) 3.56 (d, J=11.4 Hz, 1H (minor)) 3.62-3.75 (m, 1H) 3.98-4.26 (m, 4H) 4.29-4.38 (m, 1H) 4.39-4.45 (m, 1H) 4.50 (d, J=11.7 Hz, 1H (minor 2)) 4.52 (d, J=12.0 Hz, 1H (major)) 4.57 (d, J=12.0 Hz, 1H (minor 3)) 4.59 (d, J=12.3 Hz, 1H (minor 1)) 4.73-4.83 (m, 1H) 4.96-5.09 (m, 2H) 5.18-5.27 (m, 1H) 5.26 (dd, J=11.3, 6.0 Hz, 1H) 5.37 (dd, J=11.4, 5.9 Hz, 1H (major)) 5.72 (dd, J=17.1, 10.1 Hz, 1H (minor)) 7.27-7.40 (m, 5H)

3-((2R,3S,3aS,7R,8aR,9S,9aR)-9-acetoxy-3-(benzyloxy)-7-(2-hydroxyethyl)-4a-methoxydecahydrofuro[3,2-b]pyrano[2,3-e]pyran-2-yl)propane-1,2-diyl diacetate

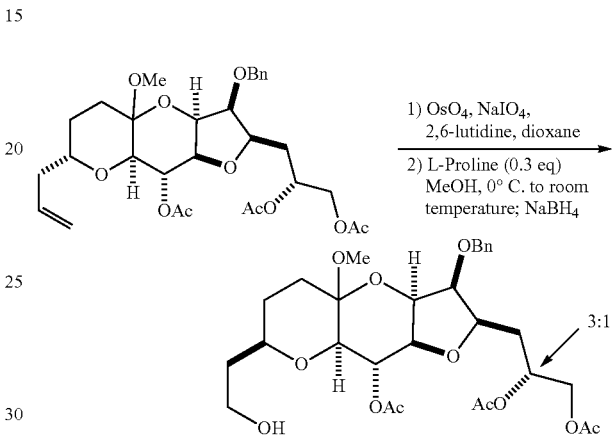

3-((2R,3S,3aS,8aR,9S,9aR)-9-acetoxy-7-ally-3-(benzyloxy)-4a-methoxydecahydrofuro[3,2-b]pyrano[2,3-e]pyran-2-yl)propane-1,2-diyl diacetate (13.5 g, 23.4 mmol) was dissolved in 1,4-dioxane (176 mL) and water (58.1 mL). 2,6-Lutidine (8.18 mL, 70.2 mmol), 4.0% osmic acid in water (3.27 mL, 0.515 mmol), and sodium metaperiodate (25.04 g, 117.1 mmol) were added. The resulting solution was stirred at ambient temperature until all starting material was consumed. Upon completion, water (203 mL) and toluene (203 mL) were added. The aqueous layer was separated and extracted with toluene (135 mL). The combined organic layers were washed sequentially with 1M hydrochloric acid (67.5 mL, 67.5 mmol), saturated aqueous NaHCO$_3$ (8%) (54.0 mL), 10% aqueous Na$_2$S$_2$O$_3$ (40.5 mL), and 30% aqueous NaCl (81 mL). The resulting solution was dried over MgSO$_4$ and concentrated in vacuo. The residue (15.6 g) was dissolved in methanol (201 mL) at ambient temperature. The resulting solution was cooled to a temperature below 10° C., and L-proline (0.801 g, 6.96 mmol) was added in one portion. The resulting solution was stirred overnight while warming to ambient temperature. After being stirred for additional 6 h at ambient temperature, the reaction mixture was diluted with MTBE (335 mL), and saturated aqueous NaHCO$_3$ (8%) (201 mL) and water (108 mL) were added. The layers were separated, and the aqueous layer was extracted twice with MTBE (201 mL each time). The combined organic layers were washed twice with 30% aqueous NaCl (107 mL), dried over MgSO$_4$, and concentrated in vacuo. The residue (21 g) was dissolved in methanol (201 mL) and cooled to 0° C. Sodium borohydride (1.14 g, 30.1 mmol) was added in 5 portions. Once the reaction was complete, saturated aqueous NH$_4$Cl (27 wt %) (134 mL) and water (67.1 mL, 3723.506 mmol) were added. The mixture was extracted twice with ethyl acetate (470 mL). The combined organic layer was washed with 30% aqueous NaCl (107 mL), dried over MgSO₄, filtered, and concentrated in vacuo. The residue was filtered through a silica gel pad (200 mL), which was then rinsed with n-heptane/ethyl acetate (1/1, 400 mL) and ethyl acetate (1200 mL). The combined filtrate was concentrated in vacuo to give 10.75 g of the target product.

3-((2R,3S,3aS,7R,8aR,9S,9aR)-9-acetoxy-3-(benzyloxy)-4a-methoxy-7-(2-(pivaloyloxy)ethyl)decahydrofuro[3,2-b]pyrano[2,3-e]pyran-2-yl)propane-1,2-diyl diacetate

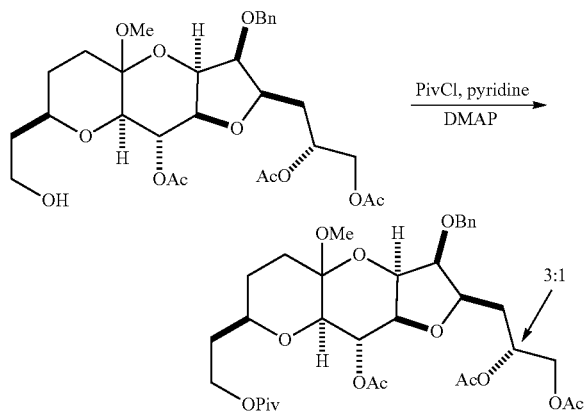

3-((2R,3S,3aS,7R,8aR,9S,9aR)-9-acetoxy-3-(benzyloxy)-7-(2-hydroxyethyl)-4a-methoxydecahydrofuro[3,2-b]pyrano[2,3-e]pyran-2-yl)propane-1,2-diyl diacetate (10.6 g, 18.3 mmol) was dissolved in dichloromethane (106 mL) at 17-22° C. Pyridine (10.60 mL, 131 mmol), pivaloyl chloride (6.74 mL, 54.8 mmol), and 4-dimethylaminopyridine (0.446 g, 3.65 mmol) were added. After 2 h at ambient temperature, saturated aqueous NaHCO₃ (8%) (106 mL), water (31.8 mL), and MTBE (159 mL) were added. After 10 min of being stirred at ambient temperature, the layers were separated, and the organic layer was washed with saturated aqueous NaHCO₃ (8%) (53.0 mL) and 30% aqueous NaCl (53.0 mL). Drying over MgSO₄, concentration in vacuo, and purification by silica-gel column chromatography using a 33-50% gradient of ethyl acetate in n-heptane as eluent provided 12.1 g of the target product as a pale brown oil.

¹H NMR (major isomer only, 400 MHz, CDCl₃) δ ppm 1.14-1.20 (m, 9H) 1.43-1.88 (m, 6H) 1.93-2.14 (m, 1H) 2.02 (s, 3H) 2.03 (s, 3H) 2.05 (s, 3H) 2.16-2.28 (m, 1H) 3.26 (s, 3H) 3.32-3.42 (m, 1H) 3.76 (s, 1H) 4.01-4.20 (m, 6H) 4.24 (t, J=4.0 Hz, 1H) 4.36 (dd, J=12.0, 2.9 Hz, 1H) 4.58 (d, J=12.3 Hz, 1H) 4.80 (dd, J=12.0, 3.8 Hz, 1H) 5.02 (s, 1H) 5.13-5.29 (m, 2H) 7.30-7.39 (m, 5H)

3-((2R,3S,3aS,7R,8aR,9S,9aR)-9-acetoxy-3-hydroxy-4a-methoxy-7-(2-(pivaloyloxy)ethyl)decahydrofuro[3,2-b]pyrano[2,3-e]pyran-2-yl)propane-1,2-diyl diacetate

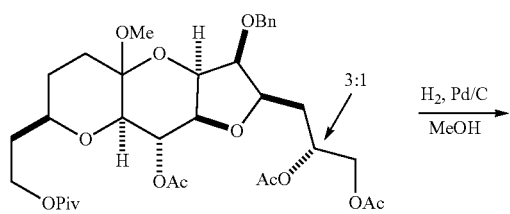

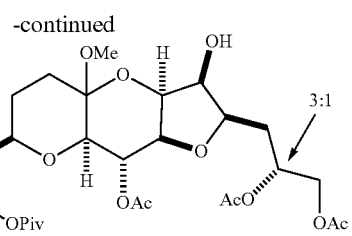

3-((2R,3S,3aS,7R,8aR,9S,9aR)-9-acetoxy-3-(benzyloxy)-4a-methoxy-7-(2-(pivaloyloxy)ethyl)decahydrofuro[3,2-b]pyrano[2,3-e]pyran-2-yl)propane-1,2-diyl diacetate (12.08 g, 18.17 mmol) was dissolved in methanol (121 mL) and EtOAc (60.4 mL). 10% Palladium on carbon (4.8 g) was added, and the resulting mixture was treated with hydrogen using a hydrogen balloon at ambient temperature until all starting material was consumed. The resulting mixture was purged with nitrogen and filtered through a Celite® pad (20 g), which was then rinsed with EtOAc until no target product remained in the pad. The filtrate was concentrated in vacuo and azeotroped with toluene (72.5 mL). The residue was filtered through a silica-gel pad (200 mL), which was then rinsed with n-heptane/ethyl acetate (50% to 100%). Concentration of the combined filtrate provided 9.5 g of the target product.

3-((2R,3S,3aR,7R,8aR,9S,9aR)-9-acetoxy-3-((diisopropylsilyl)oxy)-4a-methoxy-7-(2-(pivaloyloxy)ethyl)decahydrofuro[3,2-b]pyrano[2,3-e]pyran-2-yl)propane-1,2-diyl diacetate

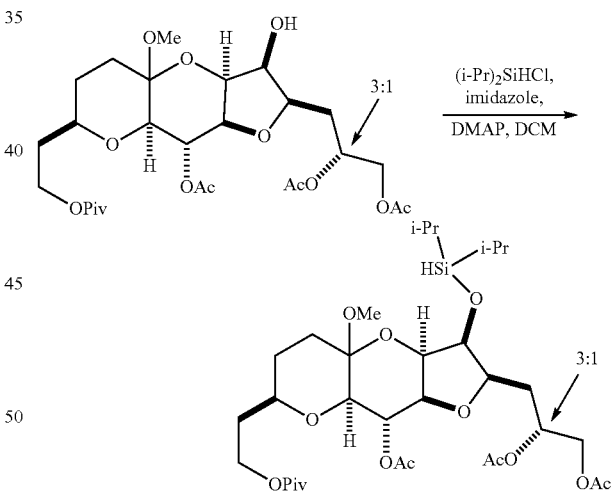

3-((2R,3S,3aS,7R,8aR,9S,9aR)-9-acetoxy-3-hydroxy-4a-methoxy-7-(2-(pivaloyloxy)ethyl)decahydrofuro[3,2-b]pyrano[2,3-e]pyran-2-yl)propane-1,2-diyl diacetate (9.5 g, 16.5 mmol) was dissolved in dichloromethane (95 mL, 1480 mmol) at ambient temperature. Imidazole (3.49 g, 51.3 mmol), diisopropylchlorosilane (5.64 mL, 33.1 mmol), and 4-dimethylaminopyridine (0.202 g, 1.65 mmol) were added. After being stirred for 2 h at ambient temperature, the reaction was quenched with saturated aqueous NH₄Cl (27 wt %) (95 mL). The resulting mixture was extracted with MTBE (143 mL), and the organic layer was washed with 30% aqueous NaCl (47.5 mL) and dried over MgSO₄. Filtration, concentration in vacuo, and purification by silica gel column chromatography using 180 g silica gel pretreated with n-heptane/EtOAc/TEA (500/50/1 mL) provided 9.5 g of the target product as a colorless oil. $^1$H NMR (3:1 diastereomeric mixture, 400 MHz, CDCl$_3$) d ppm 0.99-1.10 (m, 14H) 1.18 (s, 9H) 1.44-2.00 (m, 7H) 2.01-2.07 (m, 9H) 2.08-2.19 (m, 1H) 3.26 (s, 3H) 3.33-3.43 (m, 1H) 3.72 (t, J=3.2 Hz, 1H (minor)) 3.76 (t, J=3.8 Hz, 1H (major)) 3.98-4.19 (m, 5H) 4.28 (s, 1H) 4.35 (dd, J=12.2, 2.8 Hz, 1H) 4.47 (dd, J=6.9, 4.5 Hz, 1H) 4.96 (t, J=2.9 Hz, 1H (minor)) 5.01 (t, J=3.4 Hz, 1H (major)) 5.12-5.32 (m, 1H)

3-((2R,3S,3aR,7R,8aS,9R,9aR)-9-acetoxy-3-((fluorodiisopropylsilyl)oxy)-7-(2-(pivaloyloxy)ethyl)decahydrofuro[3,2-b]pyrano[2,3-e]pyran-2-yl)propan-1,2-diyl diacetate

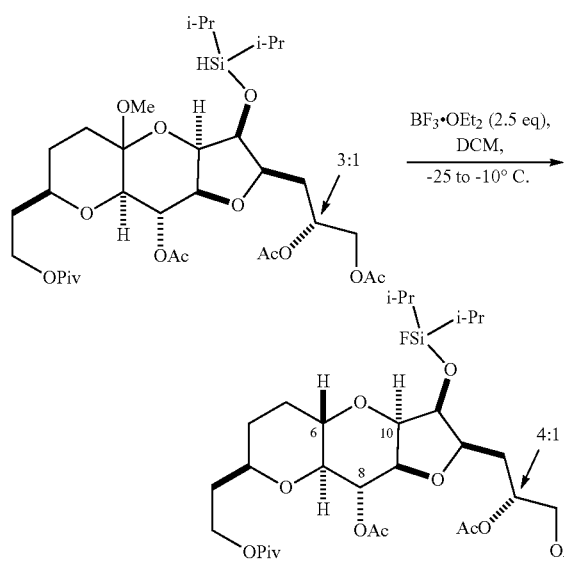

3-((2R,3S,3aR,7R,8aR,9S,9aR)-9-acetoxy-3-((diisopropysilyl)oxy)-4a-methoxy-7-(2-(pivaloyloxy)ethyl)decahydrofuro[3,2-b]pyrano[2,3-e]pyran-2-yl)propane-1,2-diyl diacetate (9.50 g, 13.8 mmol) was dissolved in dichloromethane (143 mL, 2215 mmol) and cooled below −25° C. BF$_3$·OEt$_2$ (2.55 mL, 20.7 mmol) was added, and the resulting pale yellow solution was stirred for 5 h while warming to −10° C. Saturated aqueous NaHCO$_3$ (8%) (95 mL) and dichloromethane (47.5 mL) were added. The layers were separated, and the aqueous layer was extracted with dichloromethane (28.5 mL). The combined organic layers were washed with 30% aqueous NaCl (47.5 mL) and dried over MgSO$_4$. Concentration in vacuo and purification by silica gel column chromatography using a 20-100% gradient of ethyl acetate in n-heptane as eluent provided 5.24 g of the target product.

$^1$H NMR (4:1 diastereomeric mixture, 400 MHz, CDC) d ppm 1.12-1.16 (m, 14H) 1.18 (s, 9H) 1.23-1.47 (m, 2H) 1.64-1.77 (m, 3H) 1.78-1.88 (m, 1H) 1.91-2.03 (m, 2H) 2.04 (s, 3H) 2.05 (s, 3H) 2.09 (s, 3H) 2.92 (dd, J=10.3, 9.4 Hz, 1H) 3.29-3.40 (m, 1H) 3.84-3.97 (m, 2H) 3.98-4.19 (m, 4H) 4.29 (dd, J=12.0, 3.2 Hz, 1H) 4.38-4.49 (m, 2H) 5.13-5.25 (m, 1H) 5.32 (dd, J=10.5, 7.9 Hz, 1H).

2-((2R,3S,3aR,4aS,7R,8aR,9R,9aS)-2-(2,3-dihydroxypropyl)-3-((diisopropyl(methoxy)silyl)oxy)-9-hydroxydecahydrofuro[3,2-b]pyrano[2,3-e]pyran-7-yl)ethyl pivalate

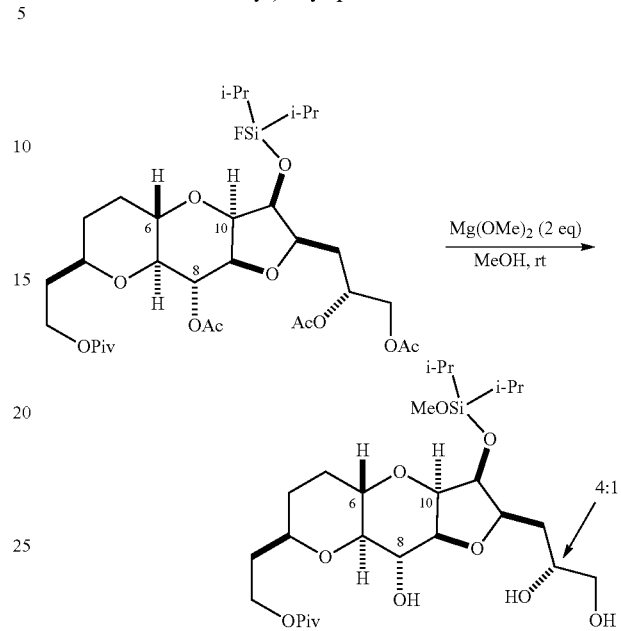

3-((2R,3S,3aR,4aS,7R,8aS,9R,9aR)-9-acetoxy-3-((fluorodiisopropylsilyl)oxy)-7-(2-(pivaloyloxy)ethyl)decahydrofuro[3,2-b]pyrano[2,3-e]pyran-2-yl)propane-1,2-diyl diacetate (297 mg, 0.439 mmol) was dissolved in methanol (4.46 mL) at ambient temperature. 0.5 M Magnesium methoxide in MeOH (1.573 mL, 0.878 mmol) was added and the resulting solution was stirred overnight. Additionally the magnesium methoxide solution (0.5 M, 1.57 mL, 0.878 mmol) was added, and the resulting solution was stirred at ambient temperature for 10 h before quenching by saturated aqueous NH$_4$Cl (27 wt %) (5.0 mL). EtOAc (10 mL) and water (2.0 mL) were added, and the resulting white mixture was stirred at ambient temperature for 20 min. The layers were separated, and the aqueous layer was extracted twice with EtOAc (16 mL). The combined organic layers were washed twice with 30% aqueous NaCl (4.0 mL) and dried over MgSO$_4$. Filtration and concentration in vacuo provided 0.211 g of the target product as an off-white foam solid.

2-((2R,3S,3aR,4aS,7R,8aR,9R,9aS)-3-((diisopropyl(methoxy)silyl)oxy)-2-((2,2-dimethyl-1,3-dioxolan-4-yl)methyl)-9-hydroxydecahydrofuro[3,2-b]pyrano[2,3-e]pyran-7-yl)ethyl pivalate

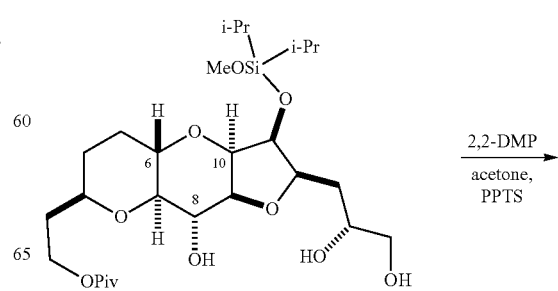

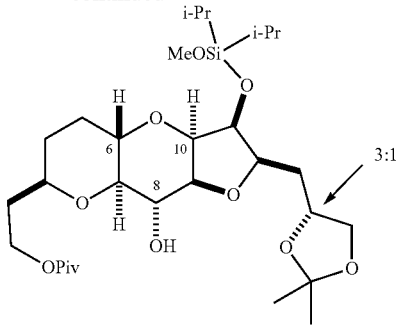

2-((2R,3S,3aR,4aS,7R,8aR,9R,9aS)-2-(2,3-dihydroxypropyl)-3-((diisopropyl(methoxy)silyl)oxy)-9-hydroxy-decahydrofuro[3,2-b]pyrano[2,3-e]pyran-7-yl)ethyl pivalate (0.190 g, 0.338 mmol) was dissolved in acetone (2.280 mL). 2,2-Dimethoxypropane (0.570 mL, 4.641 mmol) and pyridinium p-toluenesulfonate (0.017 g, 0.068 mmol) were added. The resulting solution was stirred at ambient temperature over 1 h and treated with saturated aqueous NaHCO₃ (8%) (3.80 mL). The resulting mixture was extracted twice with MTBE (10 mL), and the combined organic layers were washed with 30% aqueous NaCl (1.900 mL, 33.299 mmol) and dried over MgSO₄. Filtration and concentration gave 0.214 g of the target product.

2-((2R,3S,3aR,4aS,7R,8aS,9aR)-3-((diisopropyl(methoxy)silyl)oxy)-2-((2,2-dimethyl-1,3-dioxolan-4-yl)methyl)-9-oxodecahydrofuro[3,2-b]pyrano[2,3-e]pyran-7-yl)ethyl pivalate

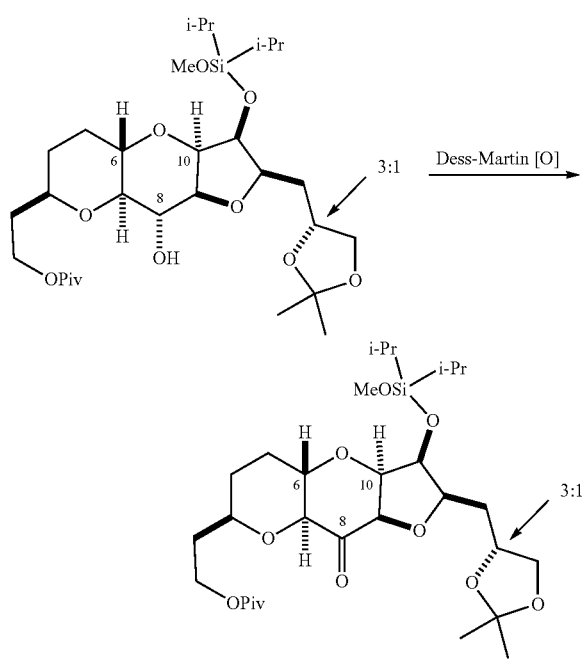

2-((2R,3S,3aR,4aS,7R,8aR,9R,9aS)-3-((Diisopropyl(methoxy)silyl)oxy)-2-((2,2-dimethyl-1,3-dioxolan-4-yl)methyl)-9-hydroxydecahydrofuro[3,2-b]pyrano[2,3-e]pyran-7-yl)ethyl pivalate (0.214 g) was dissolved in dichloromethane (4.07 mL). Sodium bicarbonate (0.113 g, 1.349 mmol) and Dess-Martin periodinane (0.286 g, 0.674 mmol) were added. After being stirred at ambient temperature overnight, the reaction mixture was diluted with MTBE (10.17 mL, 85.34 mmol) and water (4.07 mL, 225.7 mmol). A saturated aqueous NaHCO₃ (8%) (2.033 mL) and sodium thiosulfate (0.213 g, 1.349 mmol) were then added, and the resulting mixture was stirred at ambient temperature for 30 min. The layers were separated, and the aqueous layer was extracted with MTBE (6.10 mL). The combined organic layers were washed with 30% aqueous NaCl (2.033 mL) and dried over MgSO₄. Filtration followed by concentration gave 206 mg of the target product.

2-((2R,3S,3aR,4aS,7R,8aR,9S,9aS)-3-((diisopropyl(methoxy)silyl)oxy)-2-((2,2-dimethyl-1,3-dioxolan-4-yl)methy-9-hydroxydecahydrofuro[3,2-b]pyrano[2,3-e]pyran-7-yl)ethyl pivalate

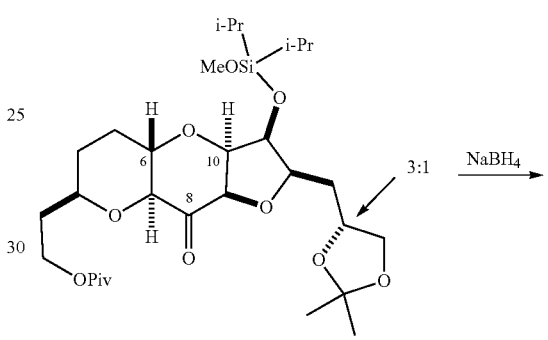

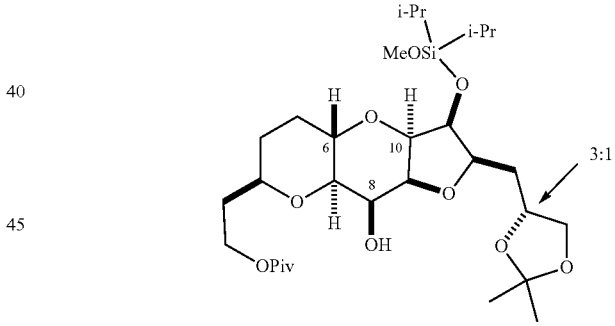

2-((2R,3S,3aR,4aS,7R,8aS,9aR)-3-((diisopropyl(methoxy)silyl)oxy)-2-((2,2-dimethyl-1,3-dioxolan-4-yl)methyl)-9-oxodecahydrofuro[3,2-b]pyrano[2,3-e]pyran-7-ylethyl pivalate (206 mg) was dissolved in methanol (4.04 mL) and cooled to 0° C. Sodium borohydride (0.019 g, 0.504 mmol) was then added.

The reaction was stirred for 30 min at 0° C. and quenched with saturated aqueous NH₄Cl (27 wt %) (4.0 mL). The resulting mixture was extracted twice with MTBE (8.0 mL). The combined organic layers were washed with 30% aqueous NaCl (2.0 mL) and dried over MgSO₄. Filtration followed by concentration in vacuo provided 216 mg of the target product.

2-((2R,3S,3aS,4aS,7R,8aR,9S,9aS)-2-((2,2-dimethyl-1,3-dioxolan-4-yl)methyl)-3,9-dihydroxydecahydrofuro[3,2-b]pyrano[2,3-e]pyran-7-yl)ethyl pivalate

2-((2R,3S,3aR,4aS,7R,8aS,9S,9aR)-3,9-bis((tert-butyldiphenylsilyl)oxy)-2-(2,3-dihydroxypropyl)decahydrofuro[3,2-b]pyrano[2,3-e]pyran-7-yl)ethyl pivalate

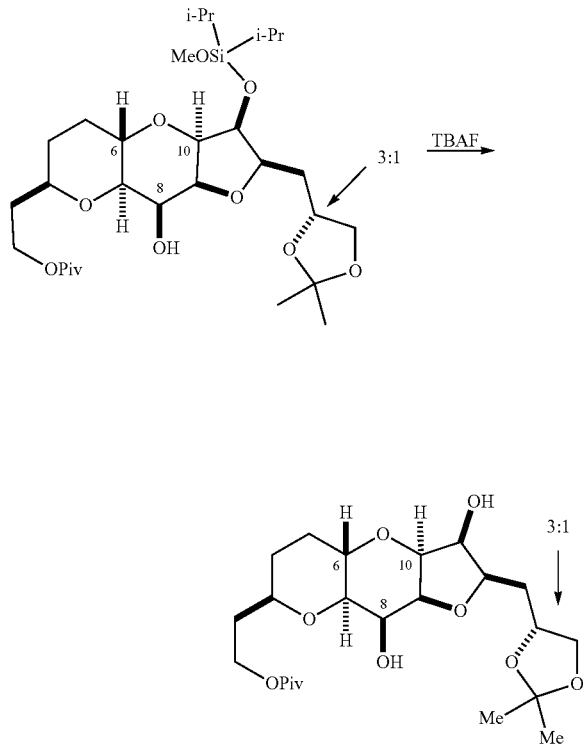

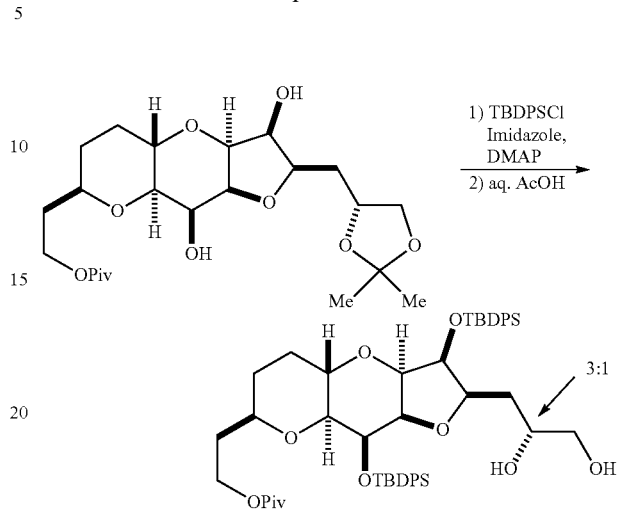

2-((2R,3S,3aS,4aS,7R,8R,9S,9aS)-2-((2,2-dimethyl-1,3-dioxolan-4-yl)methyl)-3,9-dihydroxydecahydrofuro[3,2-b]pyrano[2,3-e]pyran-7-yl)ethyl pivalate (110 mg, 0.24 mmol) was dissolved in DMF (2.200 mL) at ambient temperature. Imidazole (131 mg, 1.92 mmol, tert-butyldiphenylchlorosilane (308 µl, 1.20 mmol), and 4-dimethylaminopyridine (14.65 mg, 0.12 mmol) were added. The resulting mixture was stirred at 45° C. overnight. Additional imidazole (163 mg, 2.40 mmol, TBDPS-Cl (308 µl, 1.199 mmol), and 4-dimethylaminopyridine (29.3 mg, 0.24 mmol) were added. After being stirred at a temperature between 60 and 70° C. for 10 h, the reaction mixture was treated with MTBE (15 mL) and a saturated NH$_4$Cl solution (8 mL). The aqueous layer was separated and extracted with MTBE (10 mL). The combined organic layers were washed twice with 30% aqueous NaCl (3 mL each) and dried over MgSO$_4$. Filtration followed by purification by silica gel column chromatography provided 0.75 g of 2-((2R,3S,3aR,4aS,7R,8aS,9S,9aR)-3,9-bis((tert-butyldiphenylsilyl)oxy)-2-((2,2-dimethyl-1,3-dioxolan-4-yl)methyl)decahydrofuro[3,2-b]pyrano[2,3-e]pyran-7-yl)ethyl pivalate of 10 wt % purity along with mono silyl ether (81 mg) and the starting material (19 mg). The mono silyl ether (81 mg, 0.116 mmol) and the recovered starting material (19 mg, 0.041 mmol) were dissolved in dichloromethane (1.5 mL) and cooled to 0° C. 2,6-Lutidine (0.068 ml, 0.581 mmol) and tert-butyldiphenylsilyl trifluoromethanesulfonate (0.097 mL, 0.314 mmol) were added. After being stirred overnight at ambient temperature, the reaction mixture was treated with saturated NH$_4$Cl solution (5 mL). The resulting mixture was extracted twice with MTBE (12 mL). The combined organic layers were washed with 1M aqueous hydrochloric acid (3 mL), saturated NaHCO$_3$ (2 mL) and 30% aqueous NaCl (2 mL). Drying over MgSO$_4$ and concentration in vacuo provided 0.215 g of thick oil, which was combined into the previously isolated product. To the combined crude product were added acetic acid (8.0 mL) and water (2.0 mL) at ambient temperature. The resulting mixture was stirred at 25-30° C. overnight. Additional acetic acid (5 mL) and water (1 mL) were added, and the reaction mixture was stirred at a temperature between 35 and 40° C. for 4 h. Concentration in vacuo followed by purification by silica gel column chro-

2-((2R,3S,3aR,4aS,7R,8aR,9S,9aS)-3-(((diisopropyl(methoxy)silyl)oxy)-2-((2,2-dimethyl-1,3-dioxolan-4-yl)methyl)-9-hydroxydecahydrofuro[3,2-b]pyrano[2,3-e]pyran-7-ylethyl pivalate (216 mg) was dissolved in THF (4.0 mL) at ambient temperature and cooled below 10° C. 1.0 M TBAF in THF (0.500 mL, 0.50 mmol) was added. Once all starting material was consumed, saturated aqueous NH$_4$Cl (27 wt %) (4.0 mL) was added, and the resulting mixture was extracted twice with MTBE (10.04 mL). The combined organic layers were washed with 30% aqueous NaCl (2.0 mL) and dried over MgSO$_4$. Filtration followed by concentration and purification by silica gel column chromatography using a 33-80% gradient of ethyl acetate in n-heptane as eluent gave 117 mg of the target product as a white solid.

$^1$H NMR (3:1 diastereomeric mixture, 400 MHz, CDCl$_3$) δ ppm 1.19 (s, 9H) 1.35 (s, 3H (minor)) 1.36 (s, 3H (major)) 1.40 (s., 3H (minor)) 1.41 (s, 3H (major)) 1.70-2.01 (m, 7H) 2.13-2.21 (m, 1H) 3.00 (dd, J=9.7, 2.1 Hz, 1H (major)) 3.01 (dd, J=9.7, 2.1 Hz, 1H (minor)) 3.46-3.54 (m, 1H) 3.59 (dd, J=8.2, 7.3 Hz, 1H (major)) 3.61 (dd, J=8.1, 7.2 Hz, 1H (minor)) 4.00-4.22 (m, 8H) 4.22-4.31 (m, 1H) 4.43 (dd, J=8.9, 4.5 Hz, 1H)

Figure 7:
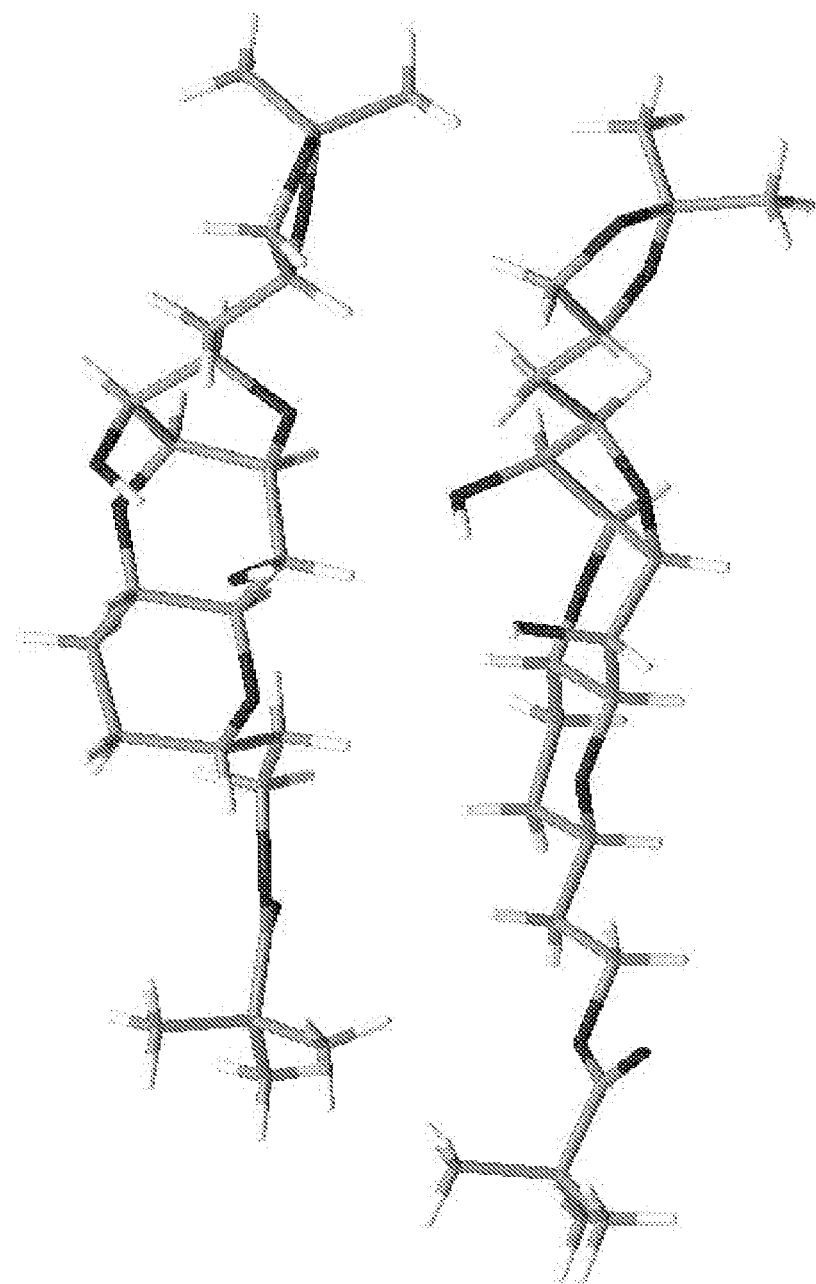
FIG. 7 is a depiction of a co-crystal of 2-((2R,3S,3aS,4aS,7R,8aR,9S,9aS)-2-((2,2-dimethyl-1,3-dioxolan-4-yl)methyl)-3,9-dihydroxydecahydrofuro[3,2-b]pyrano[2,3-e]pyran-7-yl)ethyl pivalate and its C3-epimer.

A co-crystal of the desired product and the C3-epimer was obtained, and the structure was confirmed by single crystal X-ray analysis (see FIG. 7).

matography using a 20-60% gradient of ethyl acetate in n-heptane as eluent provided 0.171 g of the target product as a film oil.

$^1$H NMR (3:1 diastereomeric mixture, 400 MHz, CDCl$_3$) δ ppm 1.05-1.12 (m, 18H) 1.18 (s, 9H) 1.28-1.68 (m, 5H) 1.82-1.93 (m, 2H) 1.95-2.10 (m, 1H) 2.63 (d, J=4.7 Hz, 1H (major)) 2.75 (d, J=5.6 Hz, 1H (minor)) 3.00 (dd, J=9.7, 4.1 Hz, 1H (major)) 3.15 (dd, J=10.3, 4.7 Hz, 1H (minor)) 3.23-3.30 (m, 1H) 3.31-3.38 (m, 1H) 3.43-3.51 (m, 1H) 3.61 (dd, J=6.7, 4.7 Hz, 1H) 3.70 (t, J=5.0 Hz, 1H) 3.79-3.84 (m, 1H) 3.87 (ddd, J=9.3, 6.2, 3.2 Hz, 1H) 3.95 (t, J=6.6 Hz, 2H) 4.06-4.14 (m, 1H) 4.23 (t, J=5.3 Hz, 1H) 4.30 (dd, J=6.3, 5.1 Hz, 1H (major)) 4.33 (dd, J=6.6, 4.2 Hz, 1H (minor)) 7.28-7.45 (m, 12H) 7.62-7.79 (m, 8H)

2-((2R,3S,3aR,4aS,7R,8aS,9S,9aR)-3,9-bis((tert-butyldiphenylsilyl)oxy)-2-(2-oxoethyl)decahydrofuro[3,2-b]pyrano[2,3-e]pyran-7-yl)ethyl pivalate

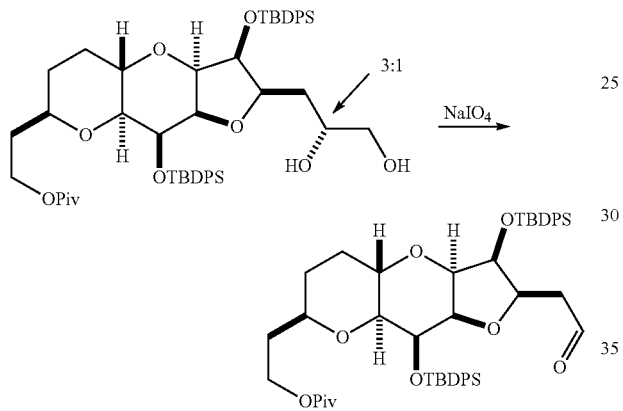

To 2-((2R,3S,3aR,4aS,7R,8aS,9S,9aR)-3,9-bis((tert-butyldiphenysilyl)oxy)-2-(2,3-dihydroxypropyl)decahydrofuro[3,2-b]pyrano[2,3-e]pyran-7-yl)ethyl pivalate (143 mg, 0.16 mmol) were added THF (2.9 mL) and water (1.4 mL) at ambient temperature. The resulting mixture was cooled to 0° C. and treated with sodium periodate (180 mg, 0.842 mmol). After being stirred at ambient temperature for 2 h, the reaction mixture was diluted with MTBE (12 mL). The mixture was washed with saturated aqueous NaHCO$_3$ (8%) (3.0 mL) and 30% aqueous NaCl (2.0 mL) and dried over MgSO$_4$. Filtration followed by concentration in vacuo provided 136 mg of the target product.

2-((2R,3S,3aR,4aS,7R,8aS,9S,9aR)-3,9-bis((tert-butyldiphenylsilyl)oxy)-2-(2-hydroxybut-3-en-1-yl)decahydrofuro[3,2-b]pyrano[2,3-e]pyran-7-yl)ethyl pivalate

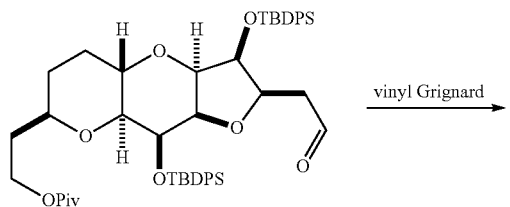

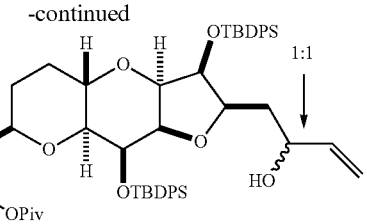

2-((2R,3S,3aR,4aS,7R,8aS,9S,9aR)-3,9-bis((tert-butyldiphenylsiyoxy)-2-(2-oxoethyl)decahydrofuro[3,2-b]pyrano[2,3-e]pyran-7-yl)ethyl pivalate (136 mg) was dissolved in THF (2.72 mL, 33.2 mmol) and cooled to −30° C. Vinyl magnesium bromide (1.0 M in THF, 0.394 mL, 0.394 mmol) was added and the resulting solution was stirred at a temperature between −30 and −35° C. for 20 min. Saturated aqueous NH$_4$Cl (27 wt %) (4.0 mL) was added, and the resulting mixture was warmed to ambient temperature. The mixture was extracted with MTBE (10 mL), and the organic layer was washed with 30% aqueous NaCl (2.0 mL) and dried over MgSO$_4$. Filtration and concentration of the filtrate provided 129 mg of the target product as a white foam solid.

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)ethyl pivalate

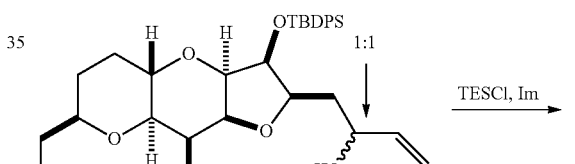

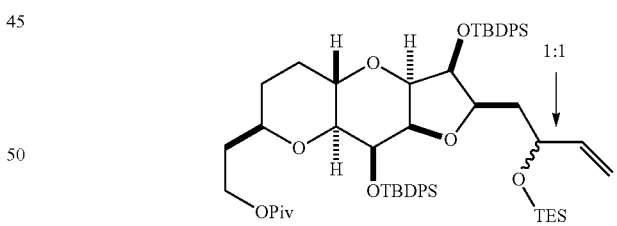

2-((2R,3S,3aR,4aS,7R,8aS,9S,9aR)-3,9-bis((tert-butyldiphenylsilyl)oxy)-2-(2-hydroxybut-3-en-1-yl)decahydrofuro[3,2-b]pyrano[2,3-e]pyran-7-yl)ethyl pivalate (129 mg) was dissolved in dichloromethane (3.0 mL) at ambient temperature. Imidazole (39.4 mg, 0.579 mmol), chlorotriethylsilane (0.049 mL, 0.289 mmol), and 4-dimethylaminopyridine (0.884 mg, 7.24 μmol) were added. After being stirred at ambient temperature for 2 h, the reaction was quenched with saturated aqueous NH$_4$Cl (27 wt %, 5.0 mL). The resulting mixture was extracted with MTBE (15 mL). The organic layer was washed with 30% aqueous NaCl (3.0 mL), dried over MgSO$_4$, filtered, and concentrated in vacuo to give 0.155 g of the desired product as an oil.

115

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)ethanol

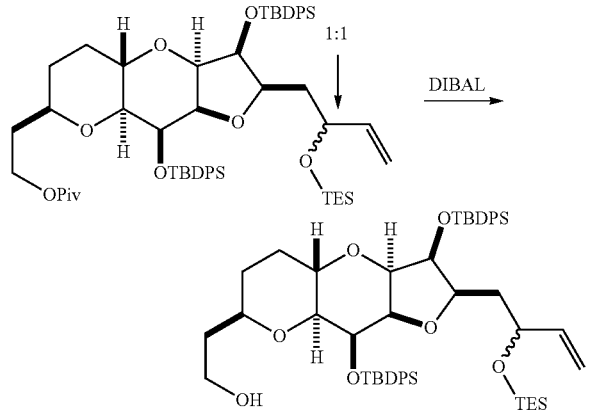

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)ethyl pivalate (155 mg, 0.145 mmol) was dissolved in dichloromethane (2.91 mL) and cooled to −78° C. DIBAL in toluene (1.0 M, 0.724 mL, 0.724 mmol) was added, and the resulting solution was stirred for 1 h. Methanol (0.1 mL, 2.5 mmol) and a solution of Rochelle's salt (613 mg, 2.173 mmol) in water (2.9 mL) were added, and the resulting mixture was allowed to warm to ambient temperature. The layers were separated, and the aqueous layer was extracted with dichloromethane (2.91 mL). The combined organic layers were washed with 30% aqueous NaCl (1.457 mL) and dried over MgSO$_4$. Filtration, concentration and purification by silica gel column chromatography using a 20-33% gradient of ethyl acetate in n-heptane as eluent provided 107 mg of the target product as a white foam. $^1$H NMR (1:1 diastereomeric mixture, 400 MHz, CDCl$_3$) δ ppm 0.48-0.57 (m, 3H) 0.58-0.67 (m, 3H) 0.83-0.93 (m, 4.5H) 0.94-1.02 (m, 4.5H) 1.06-1.18 (m, 18H) 1.28-1.72 (m, 6.5H) 1.85-1.94 (m, 1H) 1.95-2.04 (m, 0.5H) 2.12 (dd, J=10.3, 4.4 Hz, 1H) 2.98 (dd, J=9.7, 3.2 Hz, 0.5H) 3.11 (dd, J=9.7, 6.2 Hz, 0.5H) 3.30 (t, J=5.1 Hz, 0.5H) 3.33-3.40 (m, 0.5H) 3.41-3.57 (m, 2.5H) 3.58-3.70 (m, 2H) 3.84-3.90 (m, 0.5H) 3.92-4.02 (m, 0.5H) 4.03-4.25 (m, 2.5H) 4.32 (dd, J=5.9, 3.2 Hz, 0.5H) 4.34-4.41 (m, 0.5H) 4.93-5.16 (m, 2H) 5.59-5.80 (m, 1H) 7.24-7.46 (m, 12H) 7.57-7.83 (m, 8H).

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetaldehyde

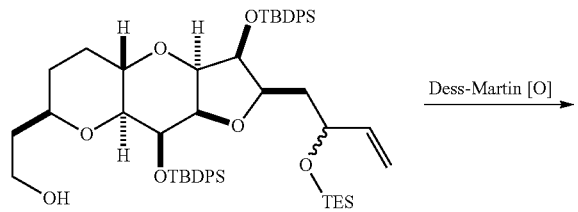

116

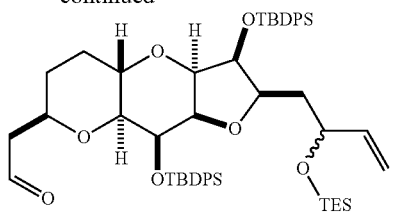

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)ethanol (80 mg, 0.087 mmol) was dissolved in dichloromethane (1.60 mL, 24.9 mmol) at ambient temperature. Sodium bicarbonate (36.5 mg, 0.434 mmol) and Dess-Martin periodinane (110 mg, 0.26 mmol) were added. After being stirred for 3 h, the reaction mixture was treated with MTBE (10 mL), saturated aqueous NaHCO$_3$ (8%) (2.0 mL), water (1.0 mL), and sodium thiosulfate (137 mg, 0.868 mmol). The resulting mixture was stirred at ambient temperature over 30 min. The layers were separated, and the organic layer was washed with 30% aqueous NaCl (2.0 mL) and dried over MgSO$_4$. Filtration, concentration, and filtration through silica gel plug with n-Heptane/EtOAc (2/1, 20 mL) provided 76 mg of the target product as a colorless film.

$^1$H NMR (1:1 diastereomeric mixture, 400 MHz, CDCl$_3$) δ ppm 0.45-0.56 (m, 3H) 0.56-0.65 (m, 3H) 0.79-1.00 (m, 9H) 1.06-1.17 (m, 18H) 1.27-1.40 (m, 4.5H) 1.59-1.67 (m, 1H) 1.77 (m, 0.5H) 1.85-1.99 (m, 1H) 2.04-2.09 (m, 1H) 2.14 (br. s., 0.5H) 2.16-2.20 (m, 0.5H) 2.23 (dd, J=4.5, 1.9 Hz, 0.5 H) 2.30 (dd, J=7.9, 2.1 Hz, 0.5H) 2.97 (dd, J=9.7, 3.2 Hz, 0.5H) 3.03 (m, J=9.8, 5.7 Hz, 0.5H) 3.47 (dd, J=6.3, 4.5 Hz, 0.5H) 3.54-3.76 (m, 2.5H) 3.92 (dd, J=7.0, 5.6 Hz, 0.5H) 3.98-4.29 (m, 3.5H) 4.37 (dd, J=6.2, 3.2 Hz, 1H) 4.94 (dt, J=10.3, 1.4 Hz, 0.5H) 4.99-5.07 (m, 1H) 5.09-5.18 (m, 0.5H) 5.58-5.78 (m, 1H) 7.27-7.44 (m, 12H) 7.63-7.82 (m, 8H) 9.43 (t, J=2.1 Hz, 0.5H) 9.51 (t, J=1.9 Hz, 0.5H)

Example 2: Preparation of the Substrate for C.15-C.16 Macrocyclization (E)-3-((2R,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-6-methylenetetrahydro-2H-pyran-2-yl)ethyl)-4-methylenetetrahydrofuran-2-yl)acrylaldehyde

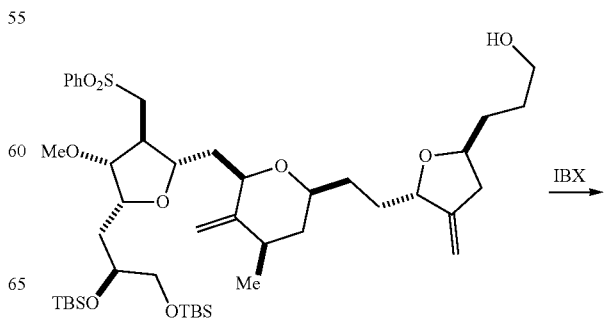

117

-continued

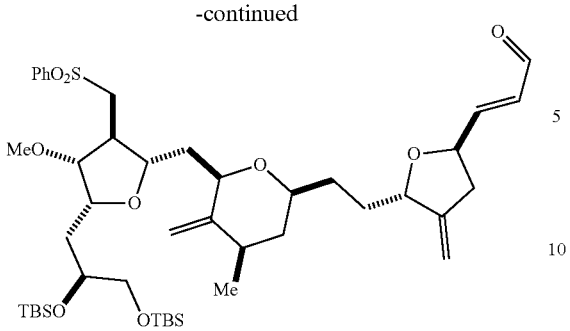

118

-continued

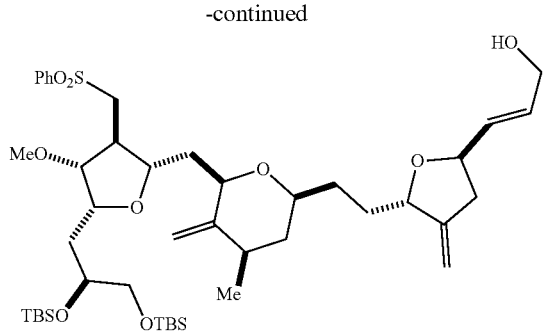

To a stirred solution of 3-((2S,5S)-5-(2-((2S,4R,6R)-8-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-ylethyl)-4-methylenetetrahydrofuran-2-ylpropan-1-ol (2.5 g, 2.9 mmol) in DMSO/Toluene (20/40 mL) was added IBX (4.11 g, 14.7 mmol, benzoic acid (1.79 g, 14.7 mmol, and sodium bicarbonate (0.42 g, 5.0 mmol) at ambient temperature. After degassing, the reaction mixture was stirred for 6 h at 75° C. (reaction flask was wrapped with aluminum-foil to protect from light). Additional IBX (2 g after 5 h, 3 g after 10 h) was added, and the mixture was stirred for additional 6 h at 77° C. 150 mL MTBE was added, and the resulting mixture was washed twice with saturated NaHCO$_3$ solution. The organic layer was dried over MgSO$_4$, filtered, and purified by silica gel column chromatography to give 1.5 g of the target product. $^1$H NMR (400 MHz, CDCl$_3$) δ ppm −0.03-0.02 (m, 12H) 0.79-0.82 (m, 18H) 1.01 (d, J=6.6 Hz, 3H) 1.38-1.341 (m, 1H) 1.42-1.54 (m, 3H) 1.58-1.85 (m, 4H) 1.90-1.95 (m, 1H) 1.97-2.16 (m, 3H) 2.35-2.45 (m, 2H) 2.46-2.49 (m, 2H) 2.76-2.81 (m, 1H) 2.91-3.00 (m, 2H) 3.34 (s, 3H) 3.35-3.42 (m, 2H) 3.46-3.62 (m, 2H) 3.56-3.62 (m, 1H) 3.65-3.68 (m, 2H) 3.70-3.77 (m, 2H) 4.07-4.28 (m, 1H) 4.66-4.70 (m, 2H) 4.78 (br s, 1H) 4.84-4.90 (m, 1H) 6.17 (ddd, J=15.6, 7.8, 1.6 Hz, 1H) 6.70 (dd, J=15.6, 4.6 Hz, 1H) 7.50-7.55 (m, 2H) 7.60-7.64 (m, 1H) 7.87 (d, J=9.9 Hz, 2H) 9.49 (d, J=7.8 Hz, 1H)

(E)-3-((2R,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-6-methylenetetrahydro-2H-pyran-2-yl)ethyl)-4-methylenetetrahydrofuran-2-yl)prop-2-en-1-ol (E)-3-((2R,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)acrylaldehyde (3.4 g) was dissolved in THF (70 mL) and cooled to −70° C. DIBAL in toluene (1.0 M, 5.42 mL) was added at this temperature, and the resulting solution was slowly warmed to −50° C. over a period of 2 h. At this time, the reaction was quenched with methanol, followed by the addition of aqueous ammonium chloride and MTBE. The resulting mixture was stirred for 2 h at room temperature. Extractive workup of this mixture furnished a crude product, which was purified by flash silica gel chromatography with hexanes/ethyl acetate (3:1 to 1:1) as eluent to afford 2.4 g of the desired product as an oil. $^1$H NMR (400 MHz, CDCl$_3$) δ ppm −0.03-0.05 (m, 12H) 0.80-0.86 (m, 18H) 0.94-1.03 (m, 4H) 1.31-1.41 (m, 2H) 1.42-1.53 (m, 3H) 1.61-1.88 (m, 3H) 1.92-1.98 (m, 2H) 2.10-2.17 (m, 2H) 2.20-2.33 (m, 1H) 2.46-2.49 (m, 1H) 2.50-2.66 (m, 1H) 2.92-3.01 (m, 2H) 3.38 (s, 3H) 3.39-3.43 (m, 2H) 3.47-3.59 (m, 1H) 3.61-3.63 (m, 1H) 3.64-3.78 (m, 3H) 4.07-4.08 (m, 1H) 4.02-4.05 (m, 1H) 4.36-4.41 (m, 1H) 4.60-4.63 (br s, 1H) 4.71 (br s, 1H) 4.85-4.89 (m, 1H) 5.62-5.68 (m, 1H) 5.79-5.81 (m, 1H) 7.52-7.56 (m, 2H) 7.60-7.64 (m, 1H) 7.87-7.89 (m, 1H).

(S)-5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)methyl)-2,2,3,3,8,8,9,9-octamethyl-4,7-dioxa-3,8-disiladecane

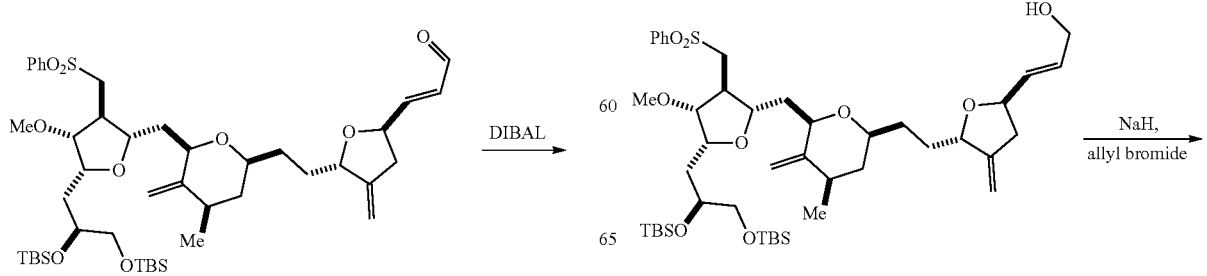

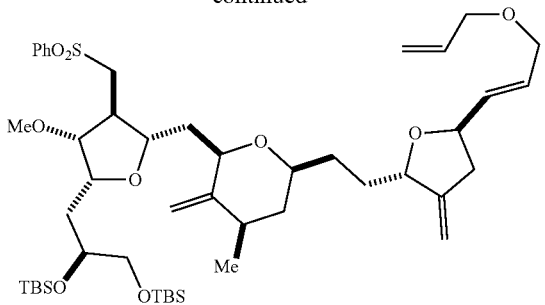

To a solution of (E)-3-((2R,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)prop-2-en-1-ol (0.42 g, 0.50 mmol) in dry THF (5 mL) at 5° C. was added sodium hydride (60% in oil, 30 mg, 0.74 mmol)), and the resulting slurry was aged at ambient temperature for 20 min. Allyl bromide (0.060 mL, 0.69 mmol) and TBAI (0.018 mg, 0.049 mmol) were added. The resulting mixture was stirred for 16 h at ambient temperature. The reaction was quenched by addition of saturated aqueous NH$_4$Cl. Extraction with ethyl acetate, concentration in vacuo, and purification by silica gel column chromatography gave 0.28 g of the target product as an oil.

$^1$H NMR (400 MHz, CDCl$_3$) δ ppm 0.037 (s, 3H) 0.044 (s, 3H) 0.09 (s, 3H) 0.10 (s, 3H) 0.87-0.89 (m, 18H) 1.06 (d, J=6.6 Hz, 3H) 1.22-1.32 (m, 1H) 1.37-1.48 (m, 2H) 1.52-1.62 (m, 2H) 1.71-1.78 (m, 1H) 1.79-1.93 (m, 2H) 1.96-2.07 (m, 1H) 2.13-2.26 (m, 2H) 2.31-2.42 (m, 1H) 2.52-2.60 (m, 1H) 2.63-2.74 (m, 1H) 2.96-3.08 (m, 2H) 3.35-3.41 (m, 1H) 3.43 (s, 3H) 3.48 (m, J=5.5 Hz, 1H) 3.54-3.62 (m, 2H) 3.64-3.71 (m, 1H) 3.76-3.87 (m, 3H) 3.94-4.00 (m, 4H) 4.26-4.34 (m, 1H) 4.43 (q, J=6.6 Hz, 1H) 4.63-4.72 (m, 1H) 4.77 (d, J=1.6 Hz, 1H) 4.85 (s, 1H) 4.89-4.96 (m, 1H) 5.17 (dq, J=10.5, 1.3 Hz, 1H) 5.27 (dq, J=17.2, 1.6 Hz, 1H) 5.65-5.82 (m, 2H) 5.84-5.98 (m, 1H) 7.61 (d, J=7.8 Hz, 2H) 7.65-7.73 (m, 1H) 7.90-8.01 (m, 2H).

(1S)-1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-1-(phenylsulfonyl)propan-2-ol

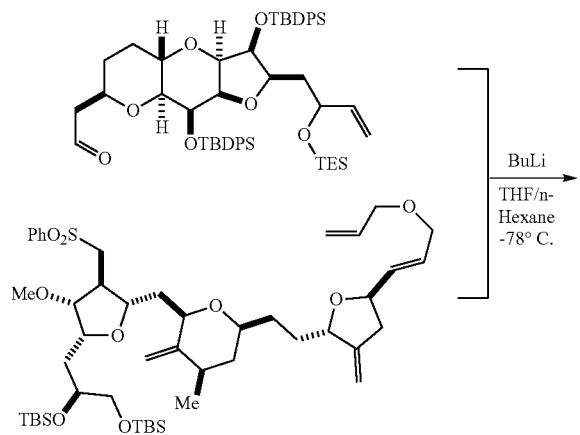

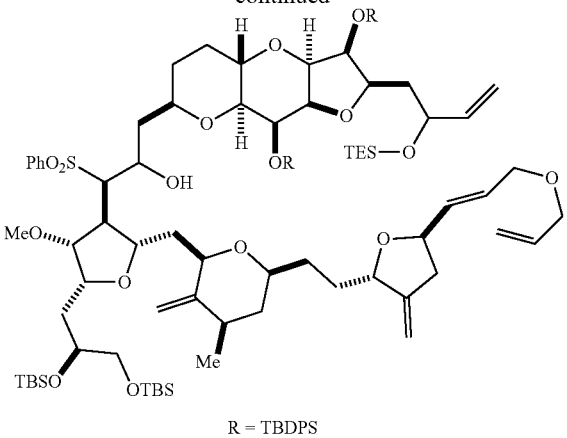

2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetaldehyde (76 mg, 0.083 mmol) was dissolved in THF (0.760 mL, 9.275 mmol) and cooled to 0° C. n-Butyl lithium (1.6 M, 0.108 mL, 0.174 mmol) was added, and the resulting solution was stirred at 0° C. for 30 min and then cooled to −78° C. A solution of (S)-5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)methyl)-2,2,3,3,8,8,9,9-octamethyl-4,7-dioxa-3,8-disiladecane (147 mg, 0.165 mmol) in n-hexane (1.52 mL) was added, and the reaction mixture was stirred at −78° C. for 1 h. Saturated aqueous NH$_4$Cl (27 wt %) (3.0 mL), water (1.0 mL), and MTBE (8.0 mL) were added, and the resulting mixture was warmed up to ambient temperature. The organic layer was separated, washed with 30% aqueous NaCl (2.0 mL), and dried over MgSO$_4$. Filtration, concentration in vacuo, and purification by silica gel column chromatography using a 20-50% gradient of ethyl acetate in n-heptane as eluent provided 152 mg of the target product.

(1S)-1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-1-(phenylsulfonyl)propan-2-one

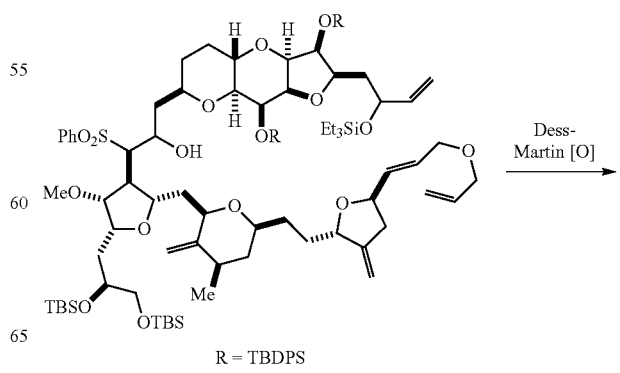

121

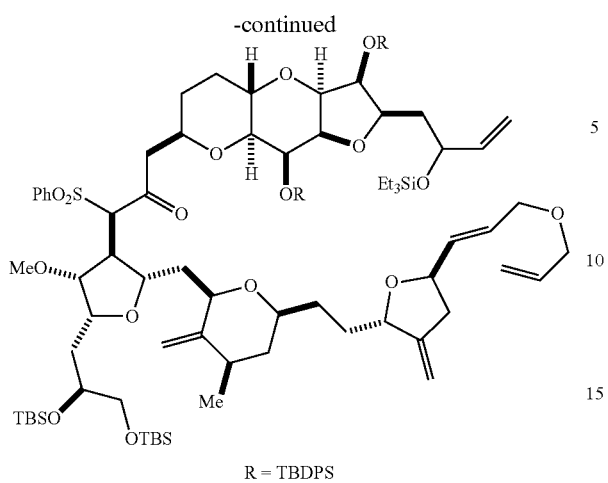

R = TBDPS (1S)-1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-1-(phenylsulfonyl)propan-2-ol (152 mg, 0.084 mmol) was dissolved in dichloromethane (3.04 mL) at ambient temperature. Sodium bicarbonate (35.3 mg, 0.42 mmol) and Dess-Martin periodinane (89 mg, 0.21 mmol) were added, and the resulting mixture was stirred at ambient temperature overnight. MTBE (7.600 mL), water (1.52 mL), saturated aqueous $NaHCO_3$ (8%) (3.04 mL), and sodium thiosulfate (133 mg, 0.84 mmol) were added. After stirring at ambient temperature for 1 h, the layers were separated. The organic layer was washed with 30% aqueous NaCl (3.0 mL) and dried over $MgSO_4$. Filtration, concentration, and purification by silica gel column chromatography using a 12-25% gradient of ethyl acetate in n-heptane as eluent provided 77 mg of the target product.

1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)propan-2-one

122

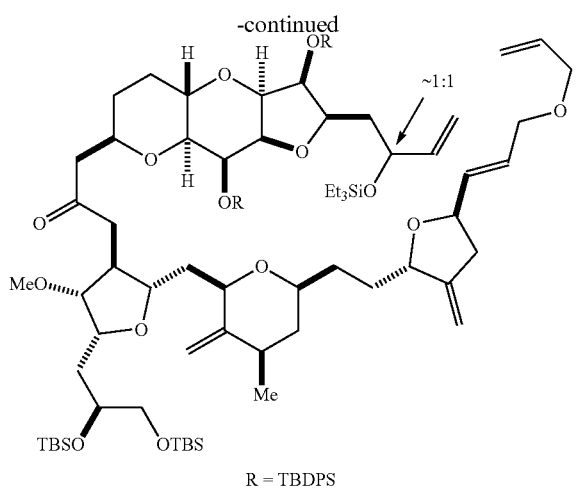

R = TBDPS (1S)-1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-1-(phenylsulfonyl)propan-2-one (77 mg) was dissolved in THF (1.2 mL) and MeOH (0.77 mL). The resulting solution was cooled to −78° C. and treated with 0.1 M samarium diiodide (1.28 mL, 0.128 mmol) for 1 h. The reaction was quenched with a mixture of Rochelle's salt (385 mg, 1.36 mmol), potassium carbonate (385 mg, 2.79 mmol), and water (3.85 mL). MTBE (5.0 mL) was added, and the resulting mixture was warmed to ambient temperature. The layers were separated, and the aqueous layer was extracted with MTBE (5.0 mL). The combined organic layers were washed with 30% aqueous NaCl (2.0 mL) and dried over $MgSO_4$. Filtration, concentration, and purification by silica gel column chromatography using a 25-33% gradient of ethyl acetate in n-heptane as eluent provided 46 mg of the target product. $^1$H NMR (1:1 diastereomeric mixture, 400 MHz, $CDCl_3$) δ ppm −0.01-0.13 (m, 12H) 0.46-0.65 (m, 6H) 0.84-0.99 (m, 27H) 1.02-1.16 (m, 21H) 1.22-1.36 (m, 1H) 1.45-1.82 (m, 10H) 1.87-2.29 (m, 9H) 2.32-2.45 (m, 2H) 2.65-2.77 (m, 1H) 2.98 (dd, J=9.5, 3.1 Hz, 0.5H) 3.04 (dd, J=9.7, 5.3 Hz, 0.5H) 3.20 (t, J=4.0 Hz, 1H) 3.30 (s, 1.5H) 3.34 (m, 1.5H) 3.39-3.90 (m, 12H) 3.92-4.03 (m, 4H) 4.06-4.24 (m, 3H) 4.31-4.39 (m, 1H) 4.39-4.51 (m, 2H) 4.73-4.86 (m, 3H) 4.91-5.06 (m, 3H) 5.16 (d, J=1.2 Hz, 1H) 5.22-5.30 (m, 1H) 5.58-5.82 (m, 3H) 5.84-5.97 (m, 1H) 7.26-7.43 (m, 12H) 7.62-7.80 (m, 8H)

Example 3: Preparation of a Compound of Formula (ID) through C.15-C.16 Macrocyclization

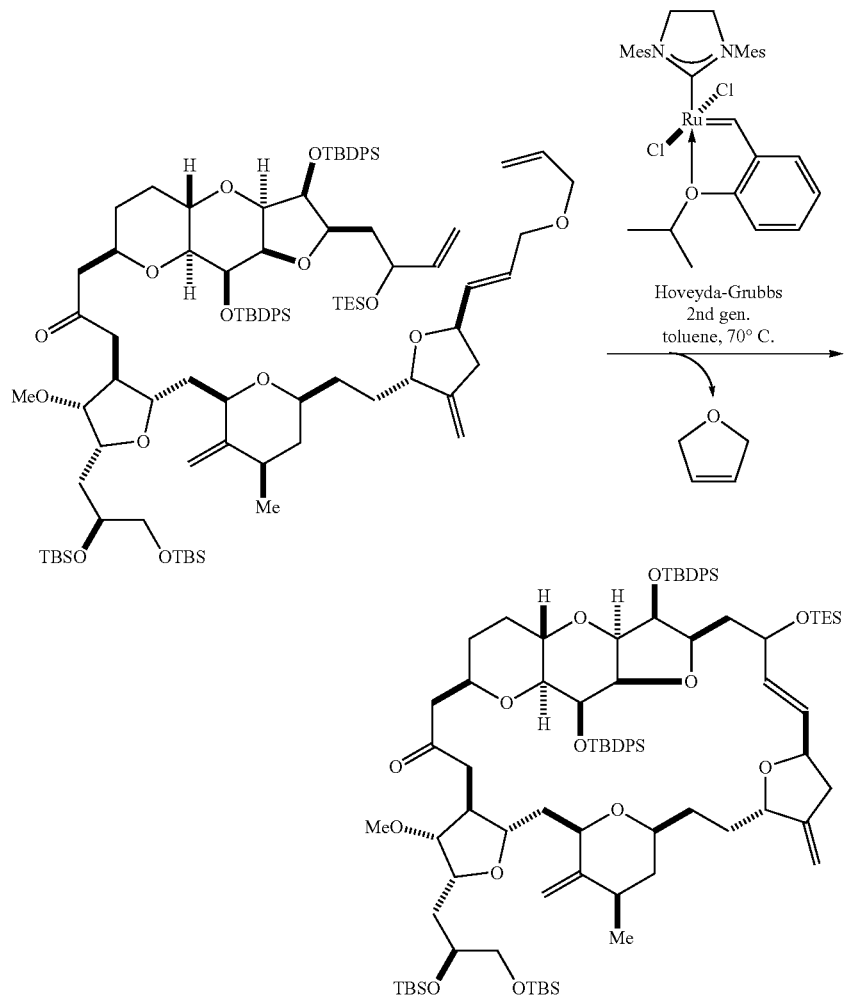

1-((2S,3S,4R,5R)-2-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-5-((S)-2,3-bis((tert-butyldimethylsilyl)oxy)propyl)-4-methoxytetrahydrofuran-3-yl)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)propan-2-one (32 mg, 0.019 mmol) was dissolved in toluene (7.0 mL). Hoveyda-Grubbs 2$^{nd}$ generation catalyst (1.448 mg, 2.304 μmol) was added, and the resulting solution was heated to 70° C. After being stirred at 70° C. overnight, the reaction mixture was cooled to ambient temperature and concentrated in vacuo. Silica gel column chromatography of the residue using a 10-50% gradient of ethyl acetate in n-heptane as eluent afforded 9.3 mg of the target product. MS m/z 1591.1 [M+Na]$^+$. $^1$H NMR (1.5:1 diastereomeric mixture, 400 MHz, CDCl$_3$) δ ppm 0.01-0.10 (m, 12H) 0.58 (td, J=7.8, 5.7 Hz, 6H) 0.81-0.97 (m, 30H) 1.00-1.12 (m, 18H) 1.17-2.80 (m, 24H) 2.88 (t, J=9.1 Hz, 1H (major)) 2.97 (t, J=9.4 Hz, 1H (minor)) 3.29-3.35 (m, 1H) 3.37 (s, 3H (major)) 3.42 (s, 3H (minor)) 3.42-3.85 (m, 10H), 3.96-4.15 (m, 3H) 4.34 (m, 2H) 4.40- 4.48 (m, 1H) 4.54-4.70 (m, 1H) 4.78-4.82 (m, 1H) 4.85 (br. s., 1H) 4.90-4.92 (m, 1H) 4.96-5.01 (m, 1H) 5.51 (dd, J=15.2, 7.0 Hz, 1H (minor)) 5.81 (ddd, J=15.4, 7.6, 1.3 Hz, 1H (major)) 6.32 (dd, J=15.2, 3.5 Hz, 1H (major)) 6.59 (dd, J=15.4, 8.9 Hz, 1H (minor)) 7.28-7.45 (m, 12H) 7.52-7.78 (m, 8H)

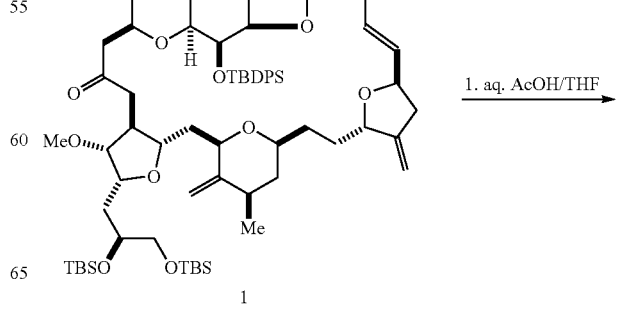

1. aq. AcOH/THF

1

-continued

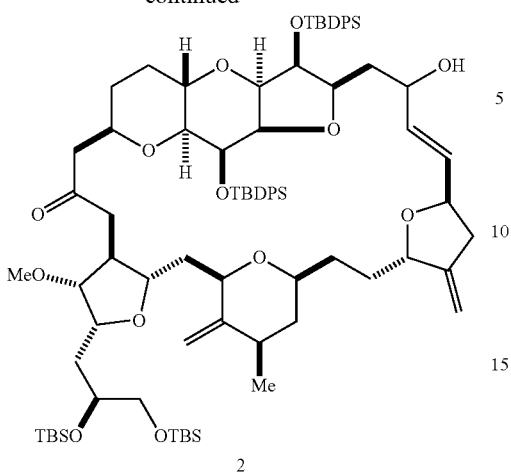

2

Compound 1 (4.6 mg, 2.9 μmol) was dissolved in THF (1.1 mL) at ambient temperature. To the solution was added acetic acid (0.5 mL) and water (0.3 mL). After being stirred for 3 h at ambient temperature, the resulting mixture was concentrated in vacuo. The residue was purified by silica gel column chromatography using a 10-33% gradient of ethyl acetate in n-heptane as eluent to give 4.0 mg of compound 2. $^1$H NMR (major isomer, 400 MHz, CDCl$_3$) δ ppm −0.02-0.09 (m, 12H) 0.88 (s, 9H) 0.89 (s, 9H) 1.03 (s, 9H) 1.05 (d, J=6.4 Hz, 3H) 1.07 (s, 9H) 1.25-2.81 (m, 24H) 2.95 (t, J=9.1 Hz, 1H) 3.33 (d, J=3.5 Hz, 1H) 3.40 (s, 3H) 3.44-3.53 (m, 2H) 3.53-3.61 (m, 2H) 3.66-3.85 (m, 8H) 4.08 (dd, J=8.6, 3.7 Hz, 1H) 4.29-4.40 (m, 2H) 4.42-4.48 (m, 1H) 4.60-4.69 (m, 2H) 4.79 (s, 1H) 4.86 (br. s., 1H) 4.90 (s, 1H) 4.99 (br. s., 1H) 5.79 (ddd, J=15.7, 7.9, 1.6 Hz, 1H) 6.54 (dd, J=15.4, 3.7 Hz, 1H) 7.28-7.45 (m, 12H) 7.52-7.76 (m, 8H)

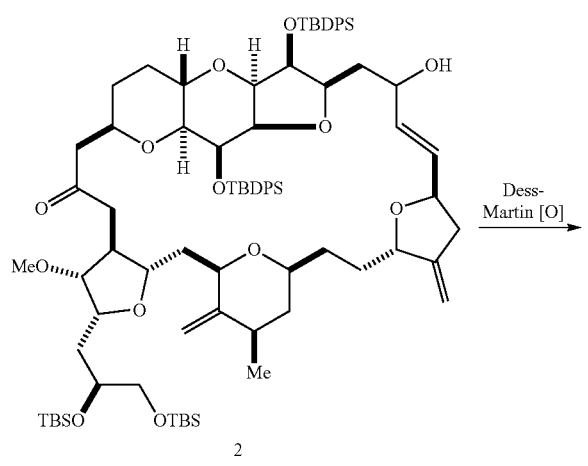

2

-continued

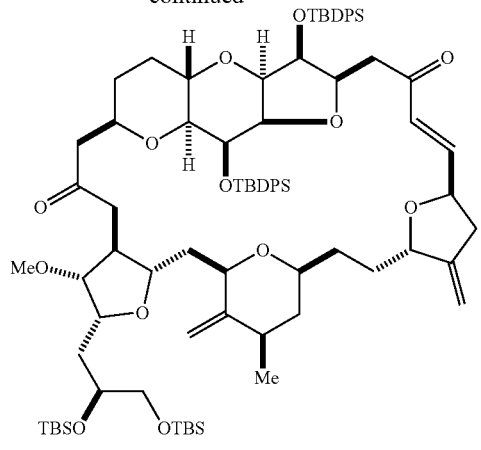

3

Compound 2 (4.0 mg, 2.751 μmol) was dissolved in dichloromethane (1.0 mL) at ambient temperature. Sodium bicarbonate (1.4 mg, 0.017 mmol) and Dess-Martin periodinane (3.5 mg, 8.3 μmol) were added, and the resulting mixture was stirred at ambient temperature overnight. MTBE (3.0 mL), water (1.0 mL), saturated aqueous NaHCO$_3$ (8%) (1.0 mL), and sodium thiosulfate (2.174 mg, 0.014 mmol) were added. The resulting mixture was stirred at ambient temperature over 30 min. The organic layer was separated, washed with 30% aqueous NaCl (0.5 mL) and dried over MgSO$_4$. Filtration followed by concentration in vacuo provided 3.3 mg of compound 3.

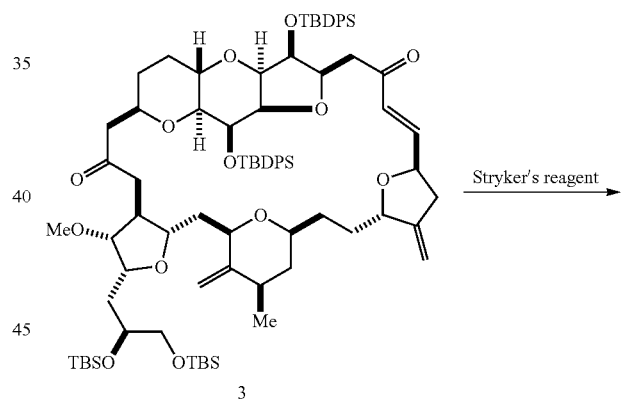

3

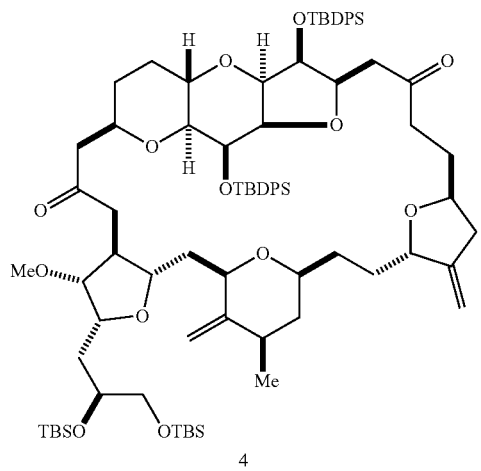

4

Compound 3 (3.3 mg, 2.3 µmol) was dissolved in deoxygenated toluene (0.5 mL) at ambient temperature. Deoxygenated (purged with nitrogen for 40 min) water (2 µL, 0.11 mmol) followed by Stryker's reagent (4.5 mg, 2.3 µmol) was added. After 1 h, additional Stryker's reagent (2 mg) was added. After being stirred for additional 1 h, the reaction mixture was treated with air. A precipitate formed. Concentration followed by purification by column chromatography using a 10-20% gradient of ethyl acetate in n-heptane as eluent afforded 2.5 mg of compound 4.

$^1$H NMR (400 MHz, CDCl$_3$) δ ppm 0.03-0.10 (m, 12H) 0.88 (s, 9H) 0.90 (s, 9H) 1.00 (s, 9H) 1.05 (d, J=6.4 Hz, 3H) 1.08 (s, 9H) 1.20-2.20 (m, 21H) 2.25-2.35 (m, 1H) 2.46-2.81 (m, 6H) 2.90-2.99 (m, 1H) 3.05 (t, J=11.7 Hz, 1H) 3.09 (t, J=9.1 Hz, 1H) 3.32 (d, J=2.3 Hz, 1H) 3.42 (s, 3H) 3.48 (dd, J=4.5, 3.7 Hz, 1H) 3.51 (dd, J=10.5, 5.0 Hz, 1H) 3.58 (dd, J=10.4, 5.7 Hz, 1H) 3.69-3.92 (m, 7H) 4.05 (dd, J=8.8, 3.2 Hz, 1H) 4.11-4.20 (m, 1H) 4.35 (m, 1H) 4.37-4.44 (m, 1H) 4.78 (s, 1H) 4.86 (d, J=1.5 Hz, 1H) 4.90 (s, 1H) 4.98 (d, J=1.8 Hz, 1H) 7.27-7.46 (m, 12H) 7.58-7.69 (m, 8H)

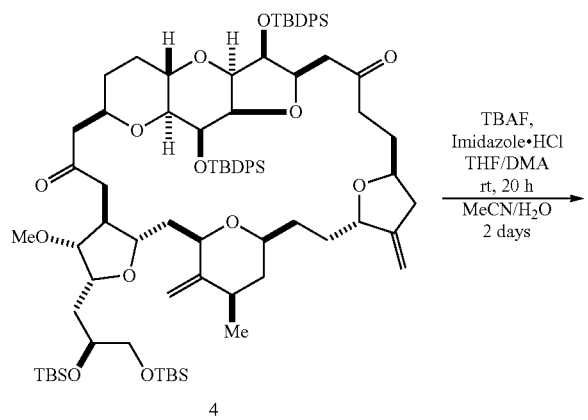

4

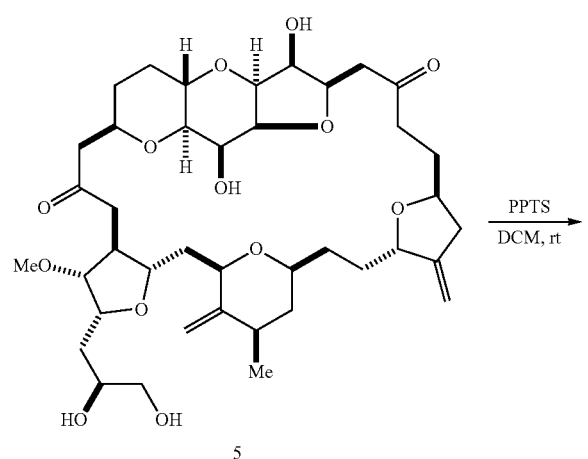

5

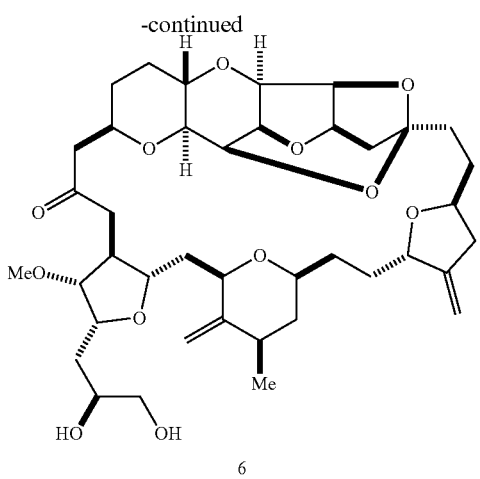

6

To compound 4 (2.5 mg, 1.719 µmol) in a vial was added THF (230 µl) and N,N-dimethylacetamide (88 µl) at ambient temperature. A mixture of TBAF (34 µl, 0.034 mmol) and imidazole hydrochloride (1.8 mg, 0.017 mmol) was added, and the resulting mixture was stirred over 20 h at ambient temperature. A mixture of acetonitrile (60 µL) and water (20 µL) was added, and the resulting mixture was stirred at ambient temperature for 2 days. 30% aqueous NaCl (0.13 mL) and toluene (0.7 mL) were added. The layers were separated, and the aqueous layer was extracted twice with a mixture of THF (1.4 mL) and toluene (1.4 mL). The combined organic layer was concentrated under a stream of nitrogen. The residue was dissolved in dichloromethane (0.2 mL) at ambient temperature, and PPTS (0.80 mg, 3.2 µmol) was added. After 1 h and after 4 h, additional PPTS (0.4 mg and 3 mg, respectively) was added. Once all starting material was consumed, the reaction mixture was purified by silica gel column chromatography using heptane/ethyl acetate (1/1), ethyl acetate, and MTBE/MeCN (1/1) as eluent to give 1.6 mg of compound 6. The structure was confirmed by comparison of the $^1$H NMR spectrum with the reported spectrum.

$^1$H NMR (500 MHz, methanol-d$_4$) δ ppm 1.01-1.10 (m, 2H) 1.14 (d, J=6.6 Hz, 3H) 1.30-1.64 (m, 7H) 1.70-2.54 (m, 17H) 2.67-2.81 (m, 2H) 2.87-2.94 (m, 1H) 2.96-2.98 (m, 1H) 3.38-3.41 (m, 1H) 3.45 (s, 3H) 3.50 (dd, J=11.4, 6.2 Hz, 1H) 3.54 (dd, J=11.0, 4.4 Hz, 1H) 3.69-3.80 (m, 2H) 3.84-3.94 (m, 3H) 4.01 (t, J=10.6 Hz, 1H) 4.10-4.18 (m, 2H) 4.21 (dd, J=6.4, 4.6 Hz, 1H) 4.27-4.39 (m, 2H) 4.51 (d, J=10.6 Hz, 1H) 4.64 (t, J=4.4 Hz, 1H) 4.74 (t, J=4.6 Hz, 1H) 4.86 (br. s., 1H) 4.92 (s, 1H) 5.06 (s, 1H) 5.17 (d, J=1.8 Hz, 1H)

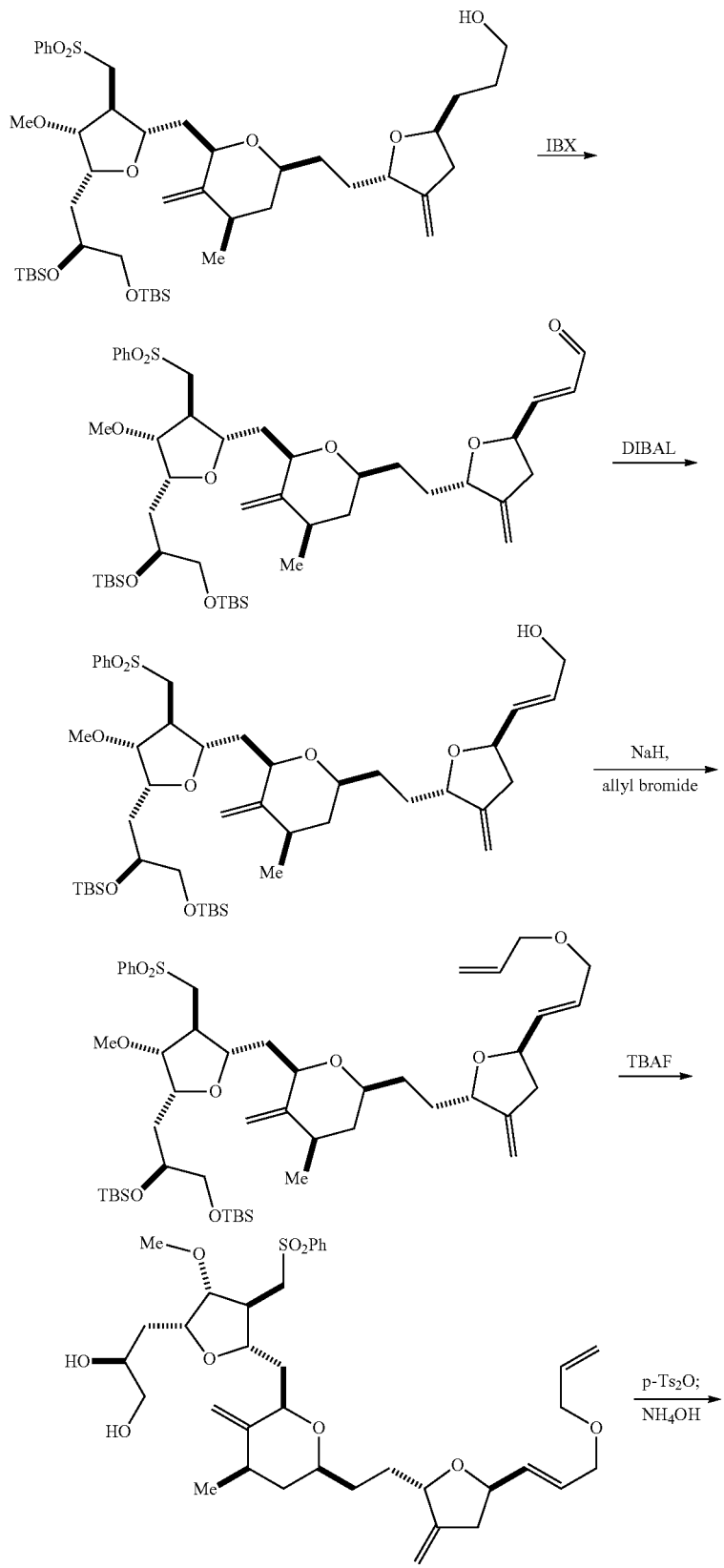

131

-continued

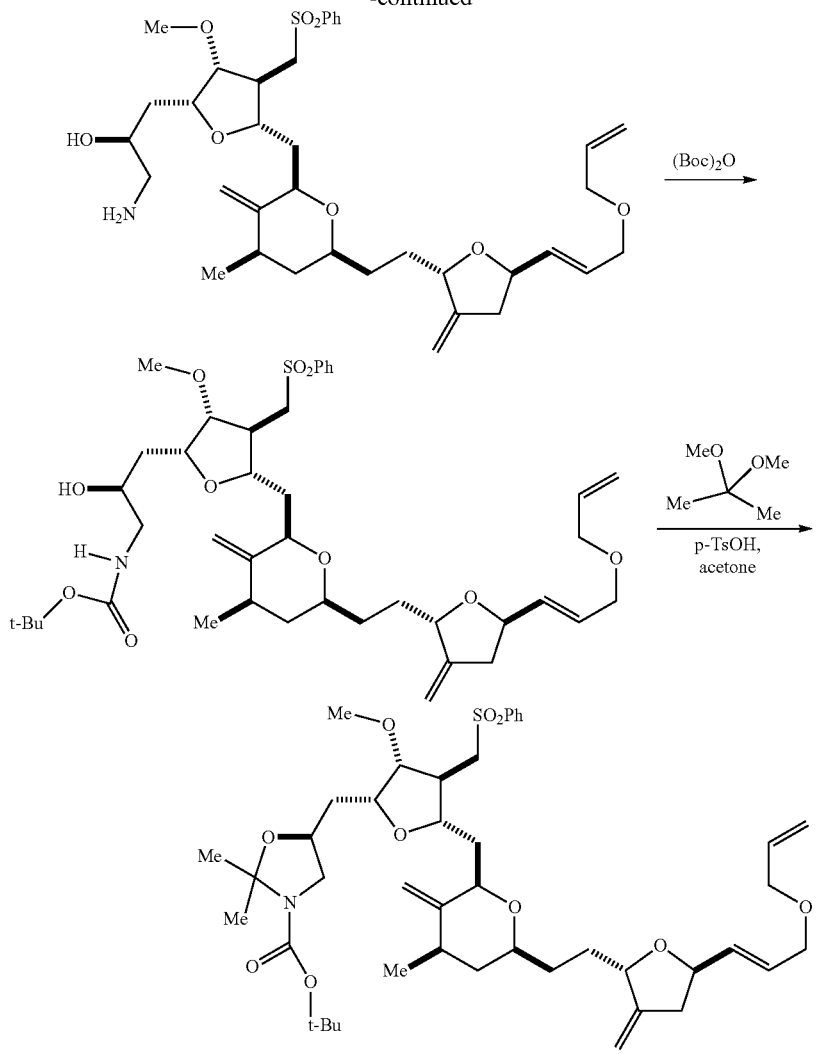

(S)-3-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)propane-1,2-diol

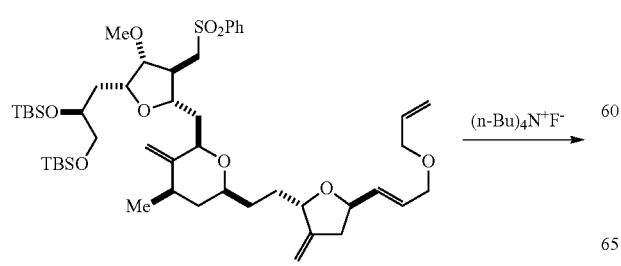

132

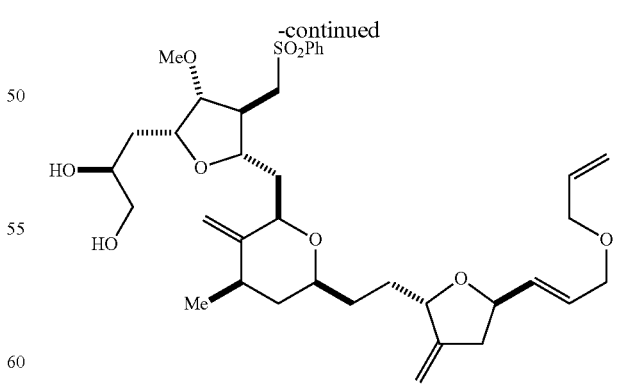

To a stirred solution of (S)-5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)methyl)-2,2, 3,3,8,8,9,9-octamethyl-4,7-dioxa-3,8-disiladecane (3.8 g, 4.27 mmol) in THF (50 mL) at 5° C. was added 1M THF solution of TBAF (12.8 mL, 12.8 mmol). The reaction was warmed to room temperature. After aging for 16 h at this temperature, the reaction was quenched by addition of aqueous ammonium chloride (10 mL). After dilution with ethyl acetate (30 mL), the phases were separated. The aqueous layer was back-extracted with ethyl acetate (2×50 mL), and the organic layers were combined. The combined organic layers were dried over MgSO$_4$. Removal of the solvent under reduced pressure and flash silica gel chromatography of the residue with heptanes-ethyl acetate (2:1 to 1:2) as eluent afforded 2.3 g (81%) of desired product as an oil.

$^1$H NMR (400 MHz, CDCl$_3$) δ ppm 1.34-1.41 (m, 2H) 1.47-1.54 (m, 4H) 1.67-1.77 (m, 3H) 1.86-1.96 (m, 3H) 2.10-2.17 (m, 2H) 2.28-2.33 (m, 1H) 2.51-2.55 (m, 1H) 2.56-2.66 (m, 1H) 2.99-3.08 (m, 2H) 3.29-3.34 (m, 2H) 3.38 (s, 3H) 3.39-3.59 (m, 4H) 3.73-3.78 (m, 1H) 3.84-3.90 (m, 3H) 3.90-3.92 (m, 4H) 4.20-4.28 (m, 1H), 4.37-4.39 (m, 1H) 4.63-4.64 (m, 1H) 4.73 (br s, 1H), 4.78 (brs, 1H) 4.86 (m, 1H) 5.10-5.13 (m, 1H) 5.19-5.23 (m, 1H) 5.66-5.73 (m, 1H) 5.81-5.88 (m, 1H) 7.53-7.57 (m, 2H) 7.62-7.67 (m, 1H) 7.86-7.90 (m, 2H).

(S)-1-((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)-3-aminopropan-2-ol

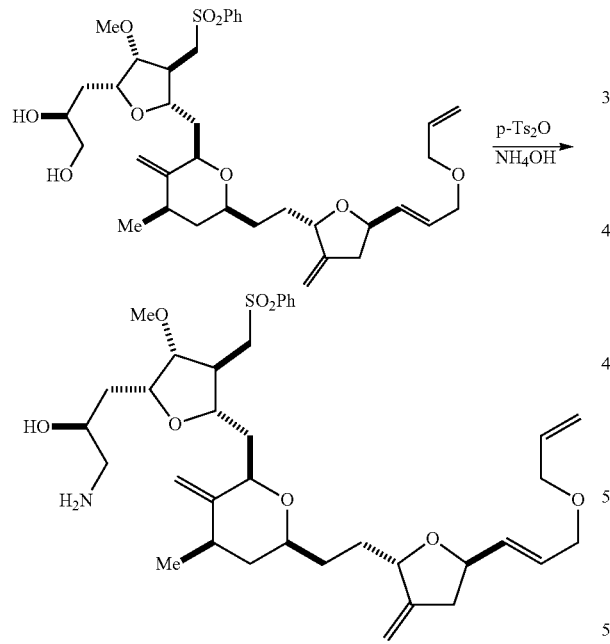

To a stirred solution of (S)-3-((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-3-methyl-ene-tetrahydro-2H-pyran-2-yl)methyl)-3-methoxy-4-((phenylsulfonyl)methyl)tetrahydrofuran-2-yl)propane-1,2-diol (1.05 g, 1.59 mmol) in methylene chloride (30 mL) was added 2,4,6-collidine (0.84 mL, 6.35 mmol) and pyridine (7 μl, 0.08 mmol). The resulting mixture was cooled to −10° C., and Ts$_2$O (1.1 g, 1.75 mmol) was added in two portions. The reaction was stirred for 3 h at a temperature between −10 and −5° C. and at 0° C. for 2 h. The reaction then was warmed to room temperature, and isopropanol (75 mL) and ammonium hydroxide (85 mL) were added. After aging 16 h at room temperature, additional ammonium hydroxide (20 ml) was added, and stirring was continued for 6 h at a temperature between 26 and 30° C. After removal of organic solvents under reduced pressure, the residue was extracted with methylene chloride (3×40 mL). The combined organic layers were washed with brine and dried over MgSO$_4$. Removal of the solvent and silica gel chromatography of the residue with hexanes/ethyl acetate (2:1 to pure ethyl acetate) as eluent afforded the desired product as a foam. Since the product was contaminated with small amount of 2,4,6-collidine, it was further purified by precipitation of product from cyclohexane or n-heptane (740 mg, 70.6%). $^1$H NMR (400 MHz, CDCl$_3$) δ ppm 0.95-1.11 (m, 3H) 1.22-1.37 (m, 2H) 1.46-1.50 (m, 2H) 1.78-1.84 (m, 3H) 2.04-2.19 (m, 3H) 2.26-2.37 (m, 2H) 2.50-2.59 (m, 2H) 2.63-2.90 (m, 2H) 2.92-3.04 (m, 2H) 3.12-3.22 (m, 1H) 3.26 (s, 3H) 3.36-3.39 (m, 2H) 3.44-3.49 (m, 1H) 3.54-3.56 (m, 1H) 3.60-3.68 (m, 1H) 3.78-3.94 (m, 4H), 4.03-4.06 (m, 1H) 4.07-4.19 (m, 1H) 4.36-4.38 (m, 1H), 4.58-4.86 (m, 4H) 5.08-5.16 (m, 2H) 5.63-5.68 (m, 2H) 5.66-5.83 (m, 1H) 7.48-7.62 (m, 3H) 7.84-7.89 (m, 2H).

tert-butyl ((S)-3-((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)-2-hydroxypropyl)carbamate

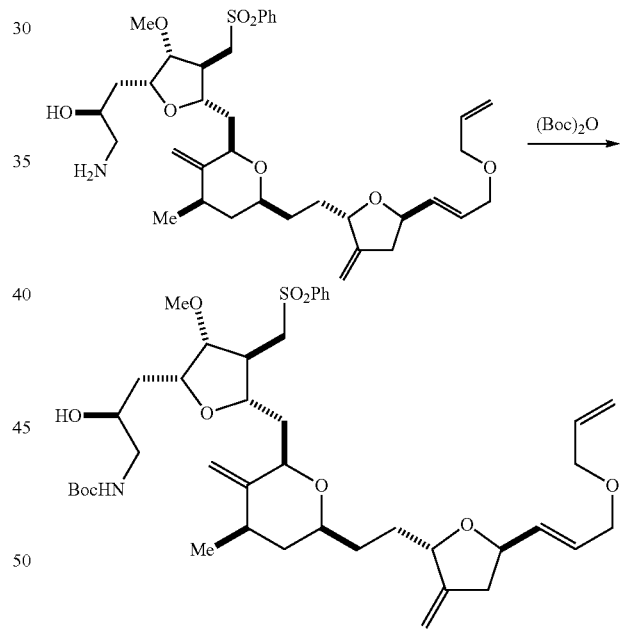

To a stirred solution of (S)-1-((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-3-methyl-ene-tetrahydro-2H-pyran-2-yl)methyl)-3-methoxy-4-((phenylsulfonyl)methyl)tetrahydrofuran-2-yl)-3-aminopropan-2-ol (0.7 g, 1.06 mmol) and triethylamine (0.22 mL, 1.6 mmol) in methylene chloride (20 mL) was added di-tert-butyl dicarbonate (290 mg, 1.34 mmol) at room temperature. The mixture was aged for 14 h at room temperature under nitrogen with a vent for CO$_2$ release. After quenching with aq. sat ammonium chloride (15 ml), phases were separated. The aqueous layer was extracted with methylene chloride (15 mL), and the combined organic layers were washed with brine and concentrated to dryness. The resulting crude product was purified by silica gel column chromatography using hexanes-ethyl acetate (3:1 to 1:1) to give the product as an oil (0.6 g, 74%). $^1$H NMR (400 MHz, CDCl$_3$) δ ppm 1.15-1.25 (m, 7H) 1.30-1.42 (m, 2H) 1.37 (br s, 9H) 1.43-1.56 (m, 3H) 1.67-1.72 (m, 2H) 1.81-1.93 (m, 2H) 2.09-2.19 (m, 2H) 2.27-2.33 (m, 1H) 2.40-2.50 (m, 1H) 2.51-2.59 (m, 1H) 2.61-2.65 (m, 1H) 3.00-3.10 (m, 2H) 3.20-3.30 (m, 1H) 3.33-3.39 (m, 1H) 3.36 (s, 3H) 3.51-3.53 (m, 1H) 3.65-3.74 (m, 1H) 3.79-3.86 (m, 1H) 3.90-3.91 (m, 3H) 4.24-4.34 (m, 1H) 4.36-4.38 (m, 1H) 4.62 (d, J=1.9 Hz 1H) 4.72 (br s, 1H) 4.77 (brs, 1H) 4.85 (d, J=1.9 Hz, 1H) 4.93 (brs, 1H) 5.12 (dd, J=10.5, 1.5 Hz, 1H), 5.18-5.23 (m, 1H) 5.65-5.72 (m, 2H) 5.80-5.87 (m, 1H) 7.52-7.56 (m, 2H) 7.61-7.65 (m, 1H) 7.845-7.89 (m, 2H).

(S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)methyl)-2,2-dimethyloxazolidine-3-carboxylate

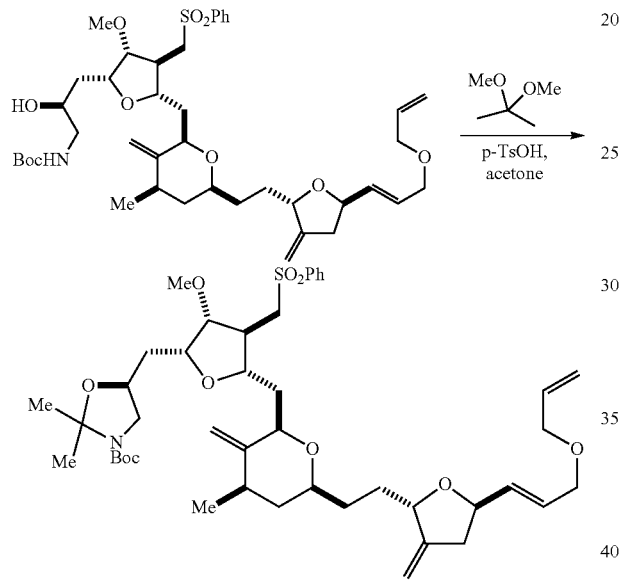

To a stirred solution of tert-butyl ((S)-3-((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylene-tetrahydro-2H-pyran-2-yl)methyl)-3-methoxy-4-((phenylsulfonyl)methyl)tetrahydrofuran-2-yl)-2-hydroxypropyl)carbamate (0.50 g, 0.66 mmol) in acetone (10 mL) was added 2,2-dimethoxypropane (1.0 mL, 8.16 mmol) and p-toluenesulfonic acid monohydrate (15 mg, 0.08 mmol). The reaction mixture was stirred for 1.5 h at room temperature. After adding sodium bicarbonate (200 mg), the reaction was stirred for additional 10 min. After dilution with ethyl acetate (40 mL) and saturated aqueous NaHCO$_3$ (20 mL), the resulting mixture was phase separated. The organic layer was back-extracted with ethyl acetate (25 mL). The combined organic layers were washed with brine and concentrated to dryness. The resulting crude product was further purified by silica gel column chromatography using a gradient from 4:1 to 2:1 of heptanes/ethyl acetate as eluent to give 400 mg of the desired product as an oil (76%). $^1$H NMR (400 MHz, CDCl$_3$) δ ppm 1.15-1.29 (m, 4H) 1.3-1.5 (m, 4H), 1.40 (br s 9H) 1.49 (s, 6H) 1.66-1.69 (m, 1H) 1.78-1.83 (m, 1H) 1.89-1.98 (m, 1H) 2.03-2.12 (m, 3H) 2.27-2.32 (m, 1H) 2.51-2.59 (m, 1H) 2.61-2.64 (m, 1H) 2.97-3.08 (m, 3H) 3.20-3.33 (m, 1H) 3.37 (s, 3H) 3.46-3.53 (m, 1H) 3.61-3.67 (m, 3H) 3.80-3.91 (m, 4H) 4.07-4.11 (m, 1H) 4.20-4.25 (m, 1H) 4.34-4.37 (m, 1H) 4.65 (d, d=2.0 Hz, 1H) 4.71 (brs, 1H) 4.78 (brs, 1H) 4.84 (d J=2.0 Hz, 1H) 5.10-5.23 (m, 2H) 5.61-5.72 (m, 2H) 5.80-5.87 (m, 1H) 7.53-7.57 (m, 2H) 7.61-7.65 (m, 1H) 7.89-7.90 (m, 2H).

1-((5S)-5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-((1S)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-hydroxy-1-(phenylsulfonyl)propyl)-3-methoxytetrahydrofuran-2-yl)methyl)-2,2-dimethyloxazolidin-3-yl)-2,2-dimethylpropan-1-one

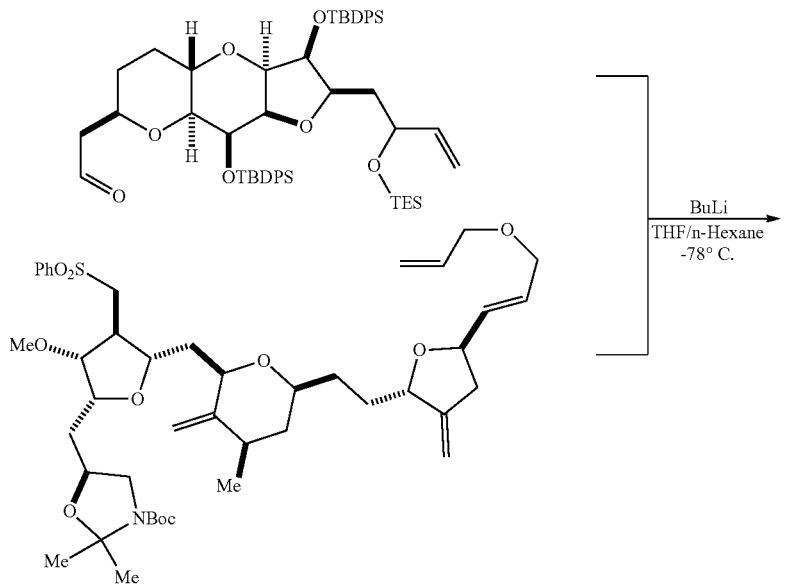

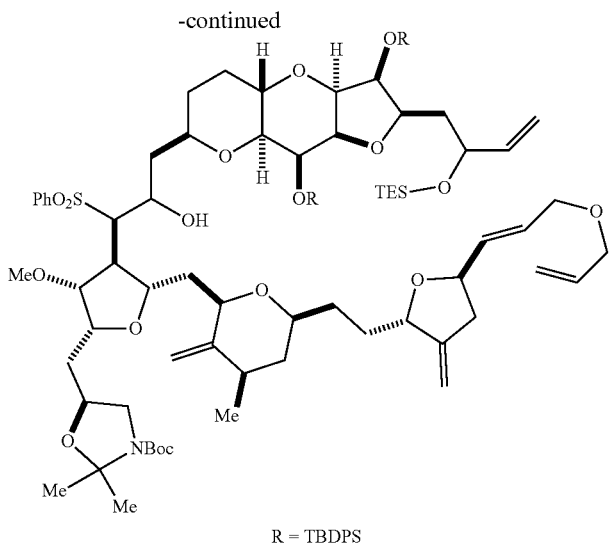

R = TBDPS 2-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)acetaldehyde (100 mg, 0.109 mmol) was dissolved in THF (1.0 mL) and cooled to 0° C. n-Butyl lithium (1.6 M, 0.109 mL, 0.174 mmol) was added, and the resulting solution was stirred at 0° C. for 30 min and then cooled to −78° C. A solution of 1-((S)-5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-3-methoxy-4-((phenylsulfonyl)methyl)tetrahydrofuran-2-yl)methyl)-2,2-dimethyloxazolidin-3-yl)-2,2-dimethylpropan-1-one (0.128 g, 0.163 mmol) in n-heptane (2.0 mL), and the reaction mixture was stirred at −78° C. for 1 h. Saturated aqueous NH$_4$Cl (27 wt %) (4.0 mL), water (1.3 mL), and MTBE (10.5 mL) were added, and the resulting mixture was warmed to ambient temperature. The organic layer was separated, washed with 30% aqueous NaCl (2.6 mL), and dried over MgSO$_4$. Filtration, concentration in vacuo, and purification by silica gel column chromatography using a 20-66% gradient of ethyl acetate in n-heptane as eluent provided 142 mg of the target product.

(5S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-((1S)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-oxo-1-(phenylsulfonyl)propyl)-3-methoxytetrahydrofuran-2-yl)methyl)-2,2-dimethyloxazolidine-3-carboxylate

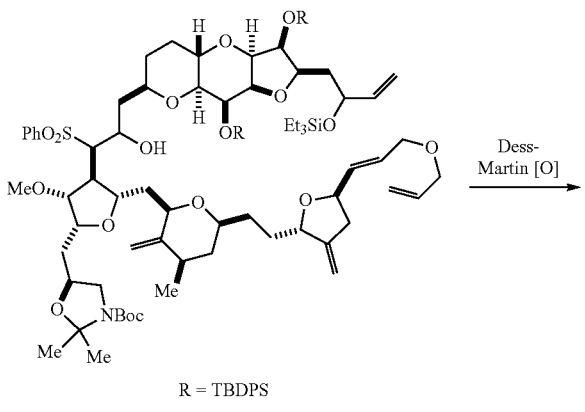

R = TBDPS

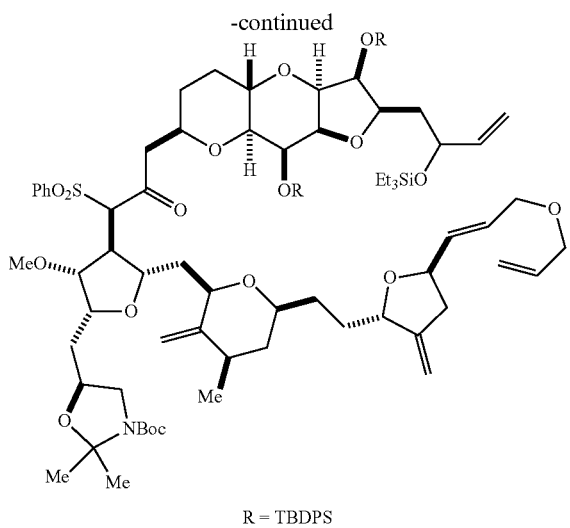

R = TBDPS (5S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-((1S)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-hydroxy-1-(phenylsulfonyl)propyl)-3-methoxytetrahydrofuran-2-yl)methyl)-2,2-dimethyloxazolidine-3-carboxylate (0.142 g, 0.083 mmol) was dissolved in dichloromethane (5.0 mL) at ambient temperature. Sodium bicarbonate (35 mg, 0.41 mmol) and Dess-Martin periodinane (105 mg, 0.248 mmol) were added, and the resulting mixture was stirred at ambient temperature overnight. MTBE (14.2 mL), water (7.1 mL), and sodium thiosulfate (131 mg, 0.83 mmol) were added. After stirring at ambient temperature for 1 h, the layers were separated. The organic layer was washed with saturated aqueous NaHCO₃ (8%) (2.84 mL), 30% aqueous NaCl (2.8 mL) and dried over MgSO₄. Filtration, concentration, and filtration through silica gel plug, which was then rinsed with 33% ethyl acetate in n-heptane, provided 120 mg of the target product as a colorless film.

(5S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-(3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-oxopropyl)-3-methoxytetrahydrofuran-2-yl)methyl)-2,2-dimethyloxazolidine-3-carboxylate

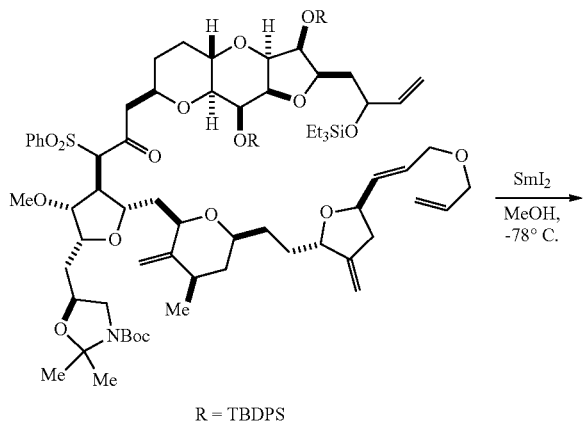

R = TBDPS

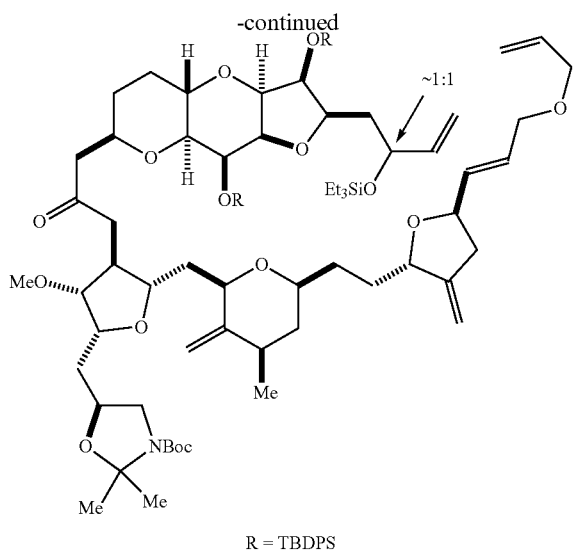

R = TBDPS (5S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-((1S)-3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-oxo-1-(phenylsulfonyl)propyl)-3-methoxytetrahydrofuran-2-yl)methyl)-2,2-dimethyloxazolidine-3-carboxylate (0.120 g, 0.07 mmol) was dissolved in THF (1.9 mL) and MeOH (1.2 mL). The resulting solution was cooled to −78° C. and treated with 0.1 M samarium diiodide (2.1 mL, 0.21 mmol) for 30 min. Additional 0.1 M samarium diiodide (2.1 mL, 0.21 mmol) was added, and the resulting mixture was stirred for 30 min at −78° C. The reaction was quenched with saturated Rochelle's salt solution (8 mL). Water (4 mL) and MTBE (7.2 mL) were added, and the resulting mixture was warmed to ambient temperature. The layers were separated, and the aqueous layer was extracted with MTBE (7.2 mL). The combined organic layers were washed with 30% aqueous NaCl (2.4 mL) and dried over MgSO₄. Filtration, concentration, and purification by silica gel column chromatography using a 20-50% gradient of ethyl acetate in n-heptane as eluent provided 74 mg of the target product as a white foam. ¹H NMR (1:1 diastereomeric mixture, 400 MHz, CDCl₃) δ ppm 0.45-0.65 (m, 6H) 0.82-1.00 (m, 9H) 1.03 (d, J=7.0 Hz, 1.5H) 1.04 (d, J=7.0 Hz, 1.5H) 1.06-1.17 (m, 18H) 1.27-1.82 (m, 14H) 1.47 (br. s., 12H) 1.85-2.47 (m, 10H) 2.67-2.77 (m, 1H) 2.95-3.07 (m, 1H) 3.08-3.18 (m, 1H) 3.23 (br. s., 1H) 3.29 (s, 1.5H) 3.31 (s, 1.5H) 3.36-3.82 (m, 10H) 3.87 (t, J=6.3 Hz, 0.5H) 3.96 (d, J=5.5 Hz, 4H) 3.99-4.25 (m, 5H) 4.33 (dd, J=6.3, 3.1 Hz, 1H) 4.41 (br. s., 1H) 4.44-4.52 (m, 1H) 4.73-4.82 (m, 2H) 4.83 (s, 1H) 4.91-5.15 (m, 2H) 4.97 (d, J=2.0 Hz, 1H) 5.16 (br. s., 0.5H) 5.18 (s, 0.5H) 5.24 (d, J=1.6 Hz, 0.5H) 5.28 (d, J=1.6 Hz, 0.5H) 5.61-5.81 (m, 3H) 5.84-5.97 (m, 1H) 7.27-7.43 (m, 12H) 7.62-7.81 (m, 8H)

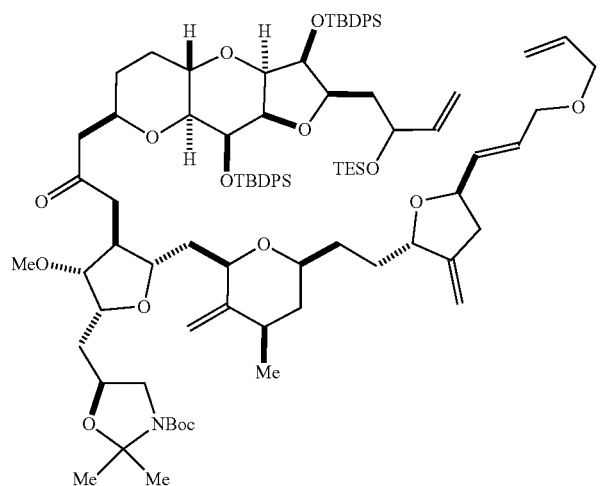
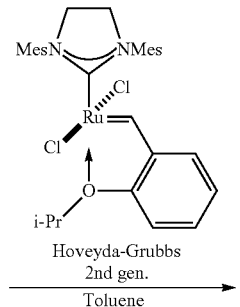

Hoveyda-Grubbs
2nd gen.
⟶
Toluene

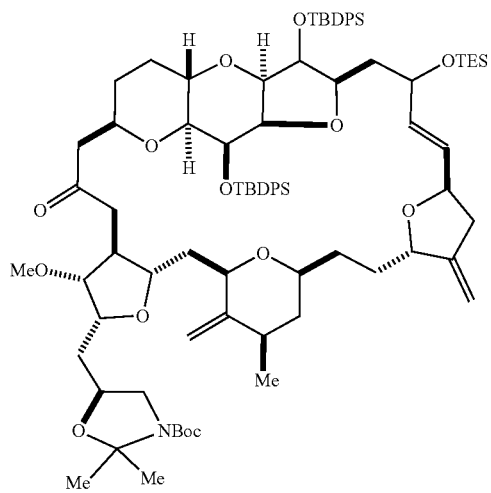

To a solution of Hoveyda-Grubbs 2nd Generation Catalyst (11.8 mg, 0.019 mmol) in toluene (50 mL) at 70° C. was added a solution of (5S)-tert-butyl 5-(((2R,3R,4S,5S)-5-(((2R,4R,6S)-6-(2-((2S,5R)-5-((E)-3-(allyloxy)prop-1-en-1-yl)-3-methylenetetrahydrofuran-2-yl)ethyl)-4-methyl-3-methylenetetrahydro-2H-pyran-2-yl)methyl)-4-(3-((2R,3S,3aR,4aS,7R,8aS,9S,9aR)-3,9-bis((tert-butyldiphenylsilyl)oxy)-2-(2-((triethylsilyl)oxy)but-3-en-1-yl)decahydrofuro[3,2-b]pyrano[2,3-e]pyran-7-yl)-2-oxopropyl)-3-methoxytetrahydrofuran-2-yl)methyl)-2,2-dimethyloxazolidine-3-carboxylate (74 mg, 0.047 mmol) in toluene (10 mL) over 4 h. After stirring at 80° C. for 10 h, the reaction mixture was cooled to ambient temperature and concentrated in vacuo. Silica gel column chromatography of the residue using a 10-33% gradient of ethyl acetate in n-heptane as eluent afforded 35 mg of the target product. $^1$H NMR (1.4; 1 diastereomeric mixture, 400 MHz, CDCl$_3$) δ ppm 0.45-0.66 (m, 6H) 0.83-0.96 (m, 9H) 0.99-1.16 (m, 21H) 1.27-3.03 (m, 31H) 1.47 (br. s., 9H) 3.10-3.20 (m, 1H) 3.28-3.91 (m, 12H) 3.35 (s, 3H (major)) 3.40 (s, 3H (minor)) 3.99-4.09 (m, 1H) 4.11-4.17 (m, 1H) 4.29-4.38 (m, 1H) 4.41-4.49 (m, 1H) 4.56-4.70 (m, 1H) 4.77-4.82 (m, 1H) 4.85 (br. s., 1H) 4.89-4.93 (m, 1H) 4.97-5.01 (m, 1H) 5.51 (dd, J=15.4, 7.6 Hz, 1H (minor)) 5.81 (ddd, J=15.4, 7.8, 1.4 Hz, 1H (major)) 6.33 (d, J=15.6 Hz, 1H (major)) 6.58 (dd, J=15.4, 9.2 Hz, 1H (minor)) 7.27-7.45 (m, 12H) 7.58-7.79 (m, 8H)

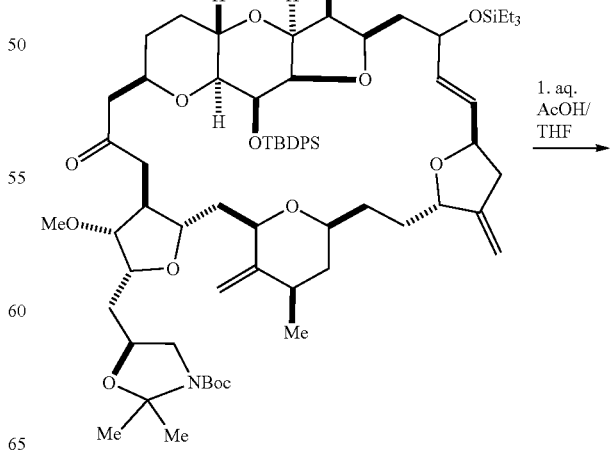

1. aq. AcOH/ THF
⟶

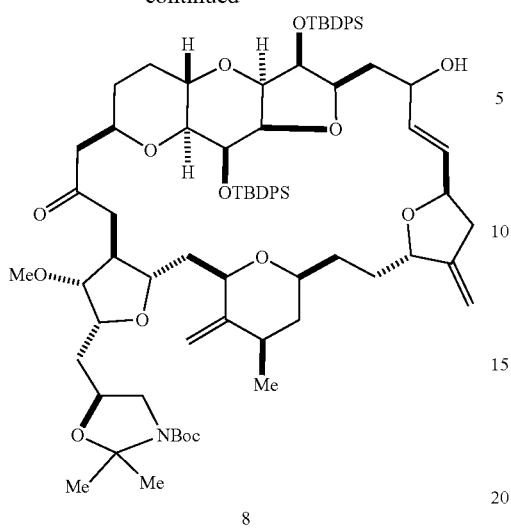

8

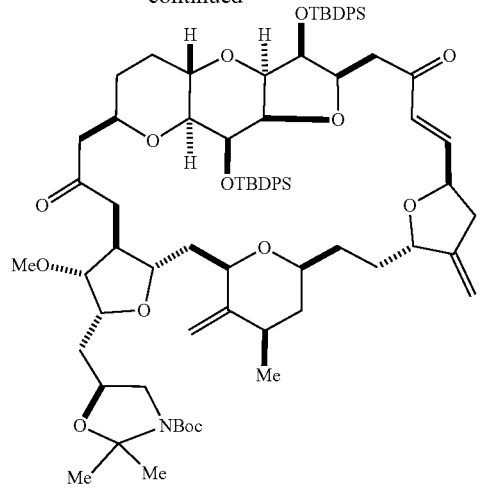

9

Compound 7 (35 mg, 24 μmol) was dissolved in THF (3.9 mL) at ambient temperature. To the solution was added acetic acid (1.8 mL) and water (1.1 mL). After being stirred for 3.5 h at ambient temperature, the resulting mixture was concentrated in vacuo. The residue was purified by silica gel column chromatography using a 20-50% gradient of ethyl acetate in n-heptane as eluent to give 32 mg of compound 8.

Compound 8 (32 mg, 23 μmol) was dissolved in dichloromethane (1.9 mL) at ambient temperature. Sodium bicarbonate (11.8 mg, 0.141 mmol) and Dess-Martin periodinane (30 mg, 0.070 mmol) were added, and the resulting mixture was stirred at ambient temperature for 5 h. MTBE (10 mL), water (5 mL), saturated aqueous NaHCO$_3$ (8%) (2.0 mL), and sodium thiosulfate (56 mg, 0.35 mmol) were added. The resulting mixture was stirred at ambient temperature over 30 min. The organic layer was separated, washed with 30% aqueous NaCl (2 mL) and dried over MgSO$_4$. Filtration followed by concentration in vacuo and purification by silica gel column chromatography using a 20-50% gradient of ethyl acetate in n-heptane as eluent provided 17 mg of compound 9 as a colorless film. $^1$H NMR (400 MHz, CDCl$_3$) δ ppm 0.98 (s, 9H) 1.04-1.10 (m, 12H) 1.26 (br. s., 3H) 1.29-1.84 (m, 8H) 1.47 (br. s., 9H) 1.55 (s, 3H) 1.90-1.98 (m, 2H) 2.03-2.11 (m, 3H) 2.13-2.24 (m, 2H) 2.46-2.56 (m, 3H) 2.61 (dd, J=16.0, 7.4 Hz, 2H) 2.74-2.83 (dd, J=16.2, 5.7 Hz, 2H) 3.06-3.21 (m, 2H) 3.25-3.33 (m, 1H) 3.37 (d, J=3.9 Hz, 1H) 3.38 (s, 3H) 3.44-3.52 (m, 1H) 3.63-3.93 (m, 8H) 4.06 (dd, J=8.4, 3.7 Hz, 1H) 4.12-4.21 (m, 1H) 4.35 (t, J=6.4 Hz, 1H) 4.46-4.54 (m, 1H) 4.70 (q, J=6.8 Hz, 1H) 4.79 (s, 1H) 4.87-4.95 (m, 2H) 5.03 (d, J=2.0 Hz, 1H) 6.58 (dd, J=16.0, 7.8 Hz, 1H) 6.79 (dd, J=16.0, 5.5 Hz, 1H) 7.28-7.44 (m, 12H) 7.56-7.70 (m, 8H)

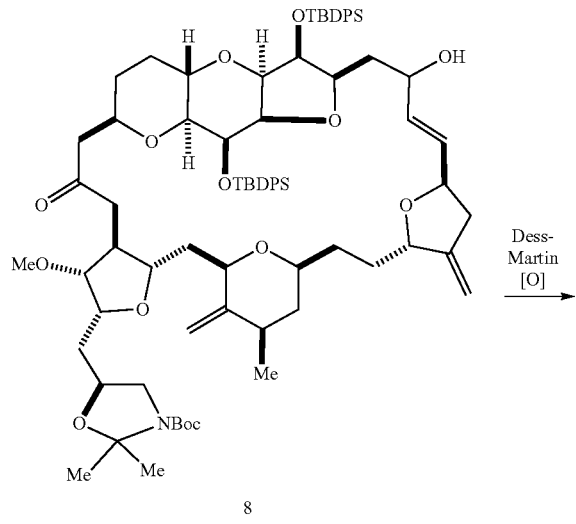

8

Dess-Martin [O]

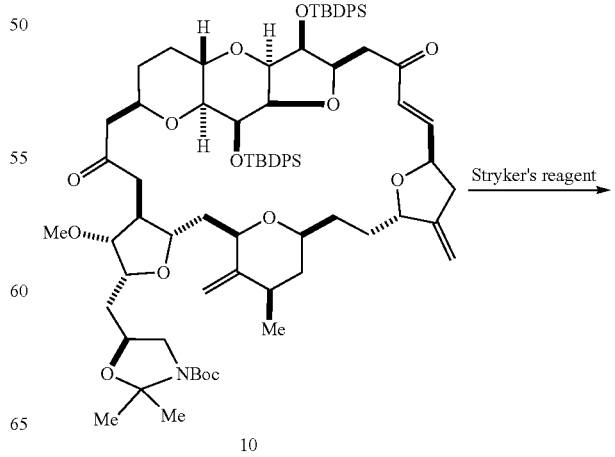

10

Stryker's reagent

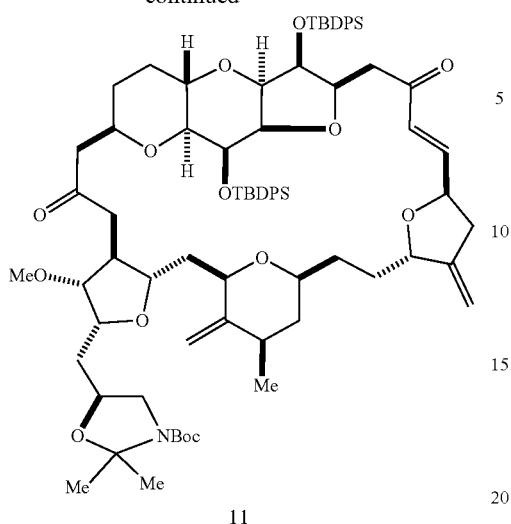

11

Compound 10 (17 mg, 0.012 mmol) was dissolved in deoxygenated toluene (2.6 mL) at ambient temperature. Deoxygenated (purged with nitrogen for 40 min) water (10 µL, 0.57 mmol) followed by Stryker's reagent (24.5 mg, 12 µmol) was added. After 1 h, additional Stryker's reagent (20 mg) was added. After being stirred for additional 1 h, the reaction mixture was treated with air. A precipitate formed. Purification by column chromatography using a 10-50% gradient of ethyl acetate in n-heptane as eluent afforded 14.7 mg of compound 11 as a colorless film. $^1$H NMR (400 MHz, CDCl$_3$) δ ppm 1.00 (s, 9H) 1.06 (d, J=6.3 Hz, 3H) 1.08 (s, 9H) 1.23-1.33 (m, 6H) 1.47 (brs, 12H), 1.50-2.00 (m, 11H) 2.06-2.23 (m, 4H) 2.26-2.34 (m, 1H) 2.46-2.54 (m, 1H) 2.54-2.82 (m, 5H) 2.89-3.00 (m, 1H) 3.03-3.12 (m, 2H) 3.13-3.20 (m, 1H) 3.36 (d, J=3.1 Hz, 1H) 3.41 (s, 3H) 3.47-3.51 (m, 1H) 3.63-3.85 (m, 7H) 3.92 (ddd, J=10.9, 7.4, 3.5 Hz, 1H) 4.05 (dd, J=8.8, 3.3 Hz, 1H) 4.11-4.22 (m, 2H) 4.31-4.42 (m, 2H) 4.79 (s, 1H) 4.85 (s, 1H) 4.90 (s, 1H) 4.98 (d, J=1.6 Hz, 1H) 7.26-7.48 (m, 12H) 7.57-7.71 (m, 8H)

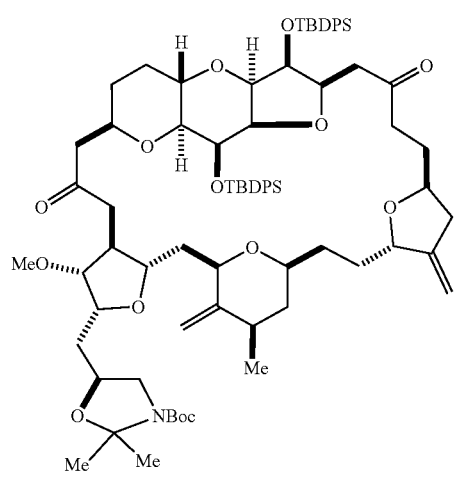

11 p-TsOH →

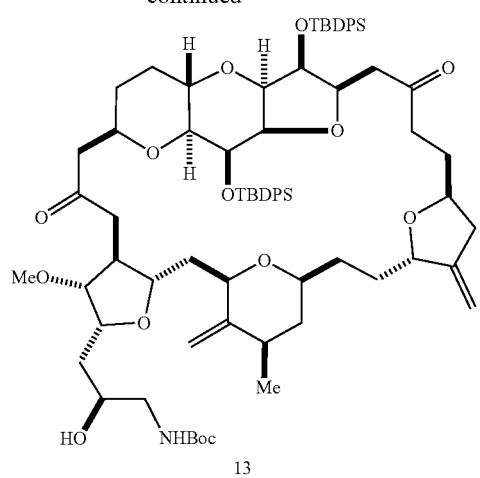

13

To a solution of compound 11 (14.7 mg, 10.8 µmol) in methanol (1 mL) was added p-toluenesulfonic acid monohydrate (2.05 mg, 10.8 µmol) at ambient temperature. The resulting solution was stirred for 3 h and treated with saturated aqueous NaHCO$_3$ (8%) (3 mL). The resulting mixture was extracted twice with MTBE (12 mL). The combined organic layers were washed with 30% aqueous NaCl (2 ml) and dried over MgSO$_4$. Filtration followed by concentration in vacuo provided 14.7 mg of compound 13 as colorless

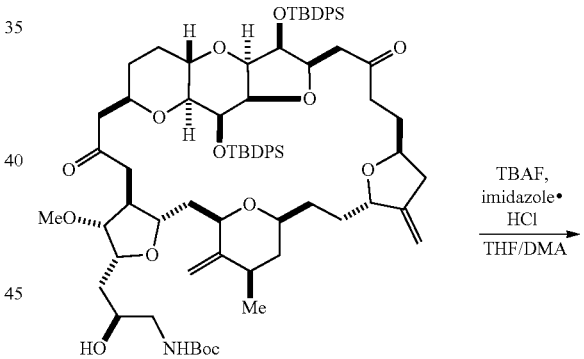

13

TBAF, imidazole·HCl
THF/DMA →

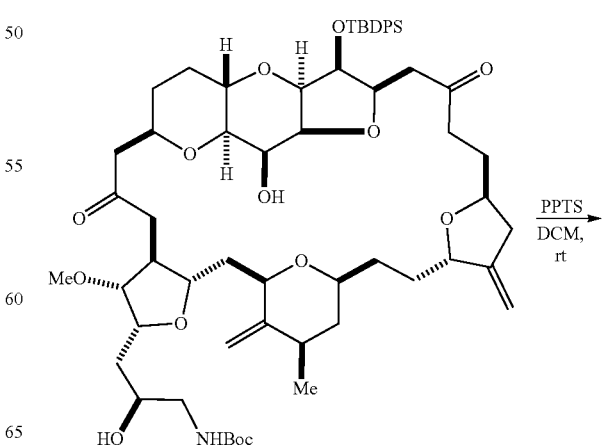

PPTS
DCM, rt →

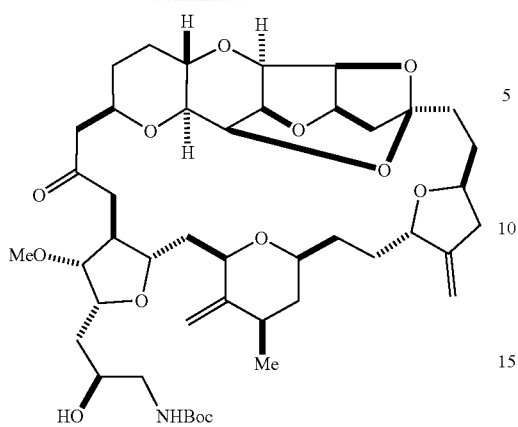

14

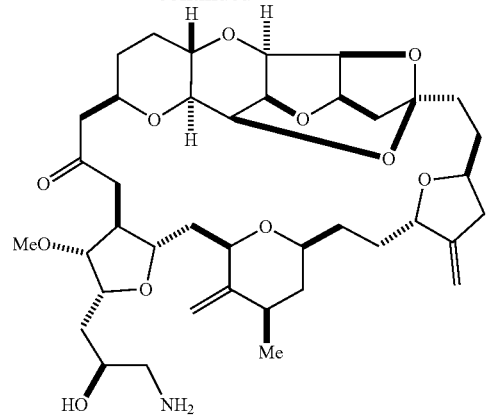

15

Compound 13 (14.7 mg, 10.7 μmol) was dissolved in THF (1.3 mL) and N,N-dimethylacetamide (0.5 mL) at ambient temperature. 1.0 M TBAF in THF (0.22 mL, 0.022 mmol) and imidazole hydrochloride (11.3 mg, 0.108 mmol) were added, and the resulting mixture was stirred for 20 h at ambient temperature. 30% aqueous NaCl (2 mL) and toluene (3 mL) were added. The layers were separated, and the aqueous layer was extracted twice with a mixture of THF (3 mL) and toluene (3 mL). The combined organic layer was concentrated in vacuo. The residue was dissolved in dichloromethane (1.5 mL) at ambient temperature, and pyridinium p-toluenesulfonate (27 mg, 0.107 mmol) was added. After 3 h, the reaction mixture was purified by silica gel column chromatography using ethyl acetate as eluent to give 6.5 mg of compound 14 as a white foam. $^{1}$H NMR (400 MHz, CDCl$_3$) δ ppm 1.10 (d, J=6.6 Hz, 3H) 1.28-1.79 (m, 11H) 1.44 (s, 9H) 1.89-2.51 (m, 15H) 2.71 (dd, J=16.0, 10.2 Hz, 1H) 2.85 (dd, J=6.6, 2.0 Hz, 1H) 2.89 (dd, J=7.4, 2.3 Hz, 1H) 3.08-3.17 (m, 1H) 3.26 (d, J=3.1 Hz, 1H) 3.42 (s, 3H) 3.55 (br. s., 1H) 3.58-3.66 (m, 2H) 3.81 (dt, J=9.4, 3.3 Hz, 1H) 3.87-3.99 (m, 3H) 4.03 (dd, J=6.3, 4.3 Hz, 1H) 4.09-4.16 (m, 1H) 4.19 (dd, J=6.4, 4.5 Hz, 1H) 4.29 (dd, J=10.6, 4.3 Hz, 1H) 4.31-4.38 (m, 2H) 4.60 (t, J=4.5 Hz, 1H) 4.69 (t, J=4.7 Hz, 1H) 4.81 (d, J=1.2 Hz, 1H) 4.89 (s, 1H) 4.93 (br. s, 1H) 4.98-5.05 (m, 1H) 5.07 (d, J=2.0 Hz, 1H)

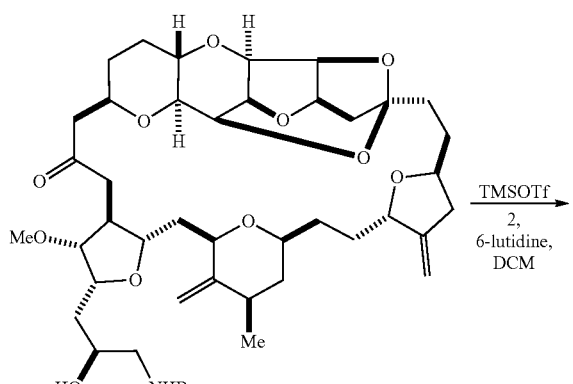

14
→ TMSOTf, 2,6-lutidine, DCM

To a solution of compound 14 (3.2 mg, 3.9 μmol) in dichloromethane (0.5 mL) at 0° C. were added 2,6-lutidine (4.9 μL, 0.042 mmol) and trimethylsilyl trifluoromethanesulfonate (5.9 μL, 0.033 mmol) was added, and the resulting solution was warmed to ambient temperature. After 1 h and 3 h, additional 2,6-lutidine (5 μl) and trimethylsilyl trifluoromethanesulfonate (6 μl) were added each time. After additional 1.5 h stirring, the reaction was quenched with water (3 mL). The resulting mixture was extracted twice with dichloromethane (5 mL each time). The combined organic layers were dried over MgSO$_4$, filtered, and concentrated in vacuo. The residue was dissolved in methanol (0.5 mL), and potassium carbonate (1 mg, 7 μmol) was added at ambient temperature. The resulting mixture was stirred overnight and then concentrated in vacuo. The residue was purified by silica gel column chromatography using ethyl acetate, DCM/methanol (9/1), and DCM/methanol/NH$_4$OH (9/1/0.1) as eluent to give 1.6 mg compound 15. The structure was confirmed by comparison of the $^{1}$H NMR spectrum with the reported spectrum.

$^{1}$H NMR (400 MHz, CD$_3$OD) δ ppm 0.97-1.07 (m, 1H) 1.11 (d, J=6.3 Hz, 3H) 1.30-1.62 (m, 6H) 1.67-2.26 (m, 13H) 2.27-2.42 (m, 3H) 2.42-2.51 (m, 2H) 2.62-2.78 (m, 2H) 2.83-2.96 (m, 3H) 3.04 (dd, J=12.7, 3.3 Hz, 1H) 3.37 (d, J=3.1 Hz, 1H) 3.43 (s, 3H) 3.74 (d, J=11.7 Hz, 1H) 3.82-4.02 (m, 5H) 4.08-4.14 (m, 2H) 4.18 (dd, J=4.7, 6.6 Hz, 1H) 4.26-4.35 (m, 2H) 4.48 (d, J=10.9 Hz, 1H) 4.62 (t, J=4.3 Hz, 1H) 4.71 (t, J=4.3 Hz, 1H) 4.82-4.84 (m, 1H) 4.86-4.87 (m, 1H) 5.02 (br. s, 1H) 5.14 (d, J=1.6 Hz, 1H)

Example 4: Preparation of a Compound of Formula (ID) through C.3-C.4 Macrocyclization
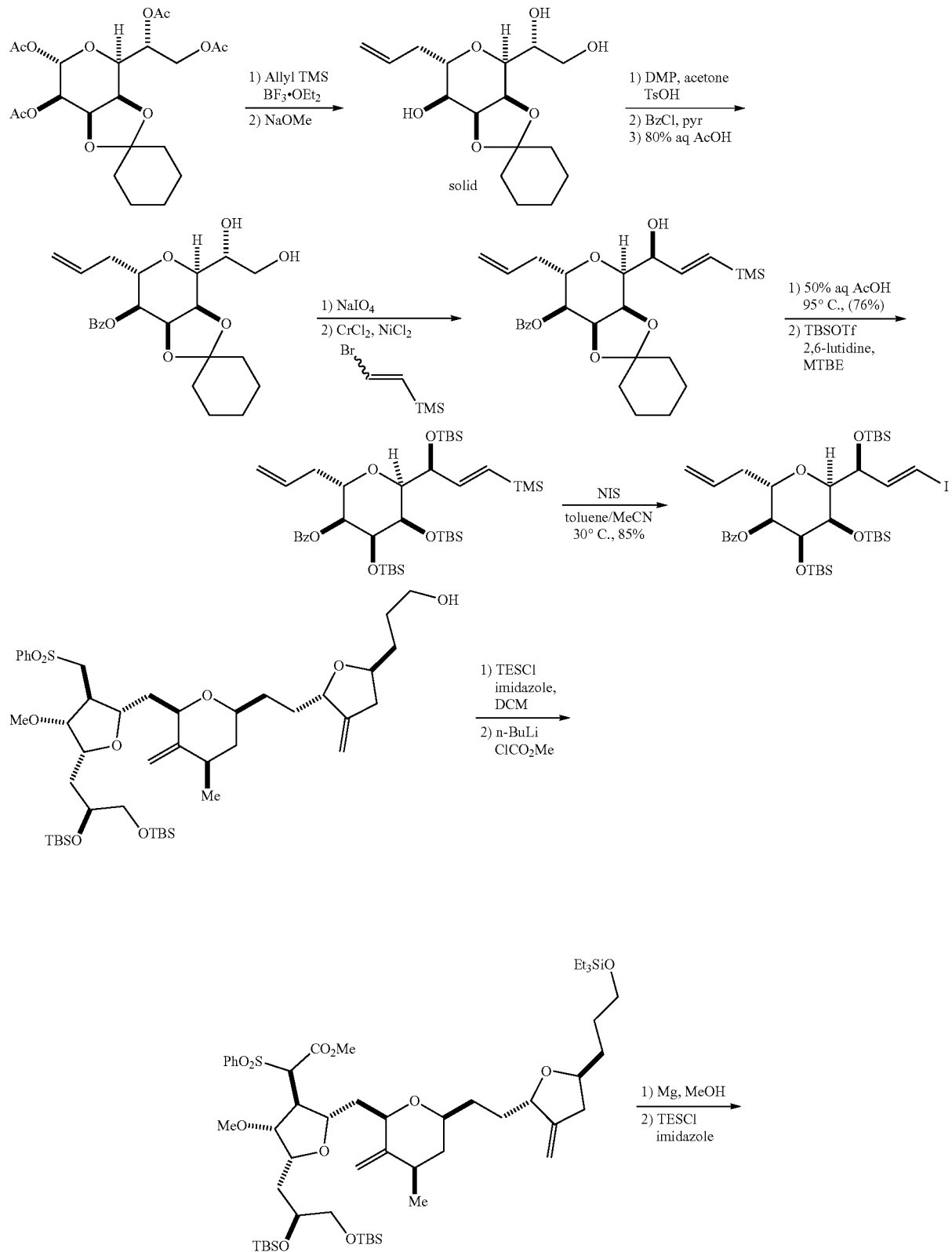

151
152
-continued
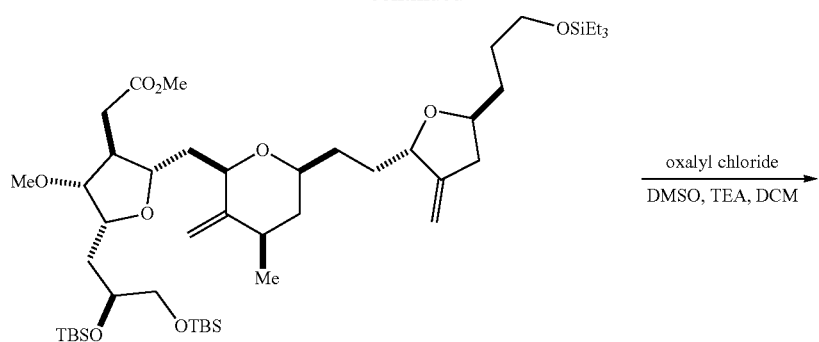
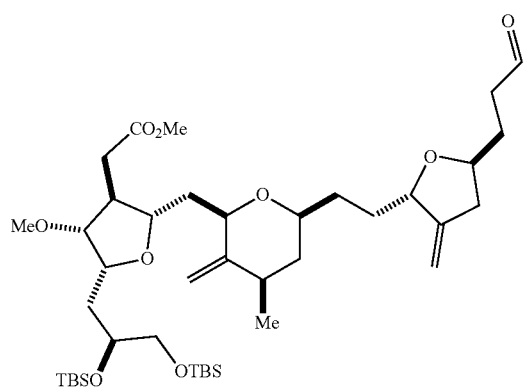
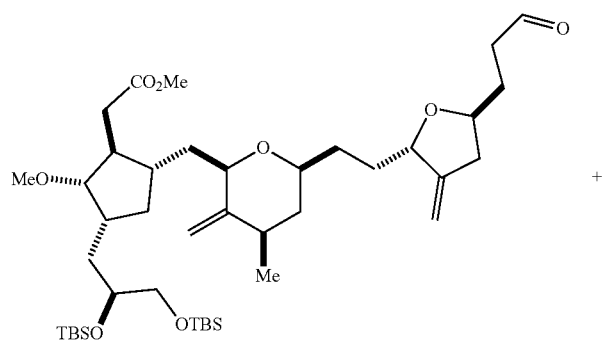
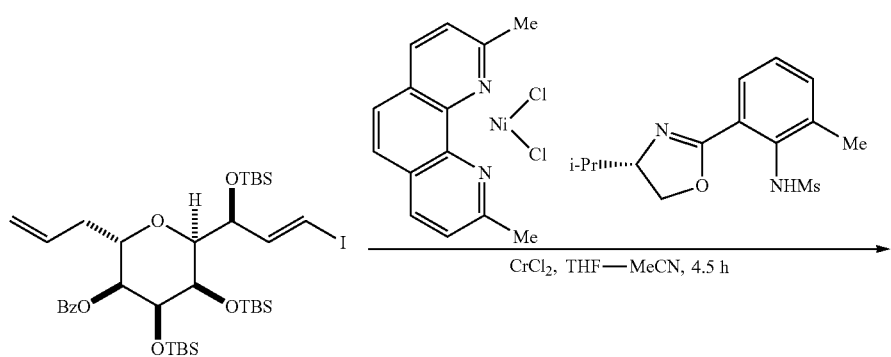

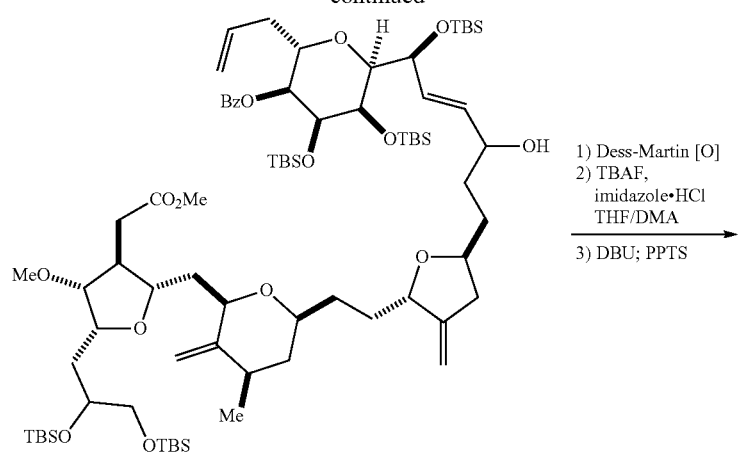
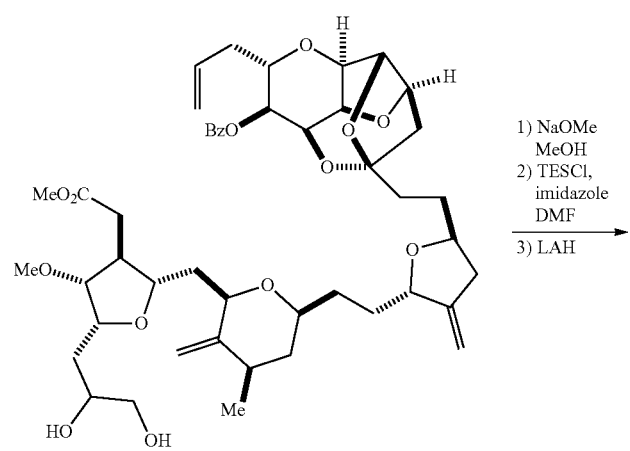
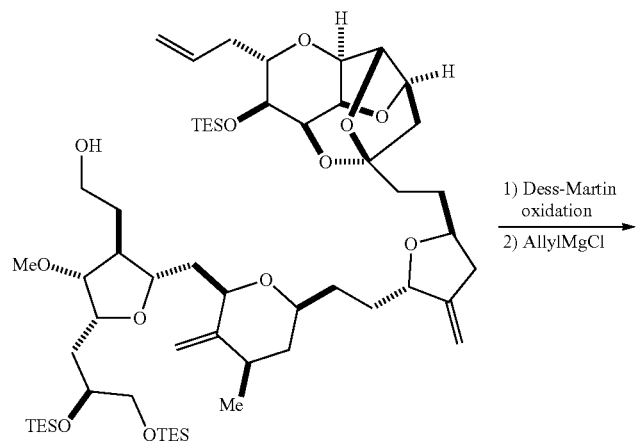

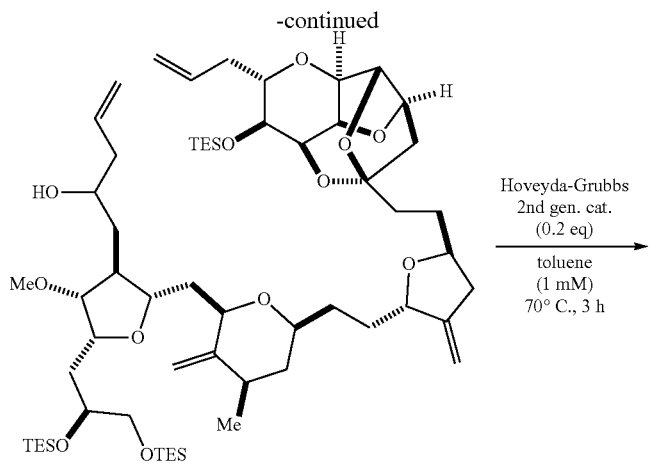

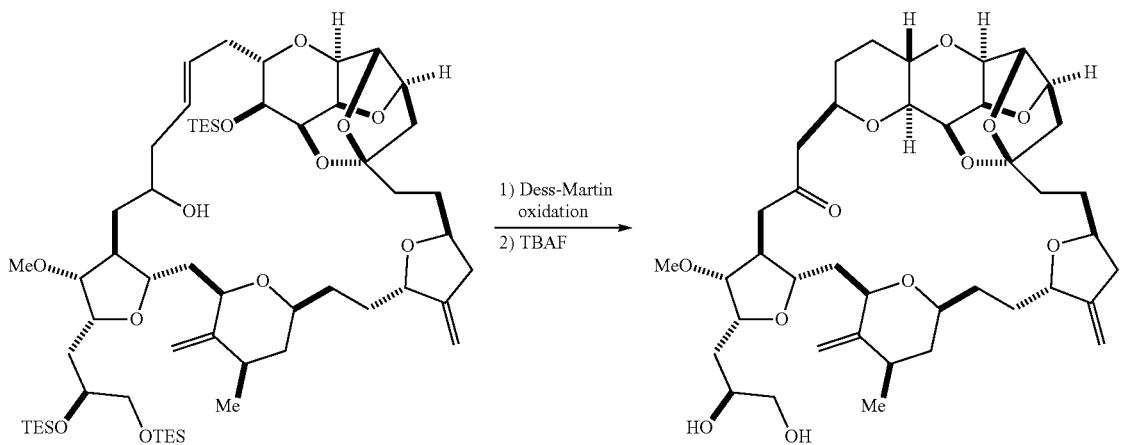

(R)-1-((3aR,4S,6S,7S,7aR)-7-acetoxy-6-allyltetra-hydro-3aH-spiro[[1,3]dioxolo[4,5-c]pyran-2,1'-cy-clohexan]-4-yl)ethane-1,2-diyl diacetate

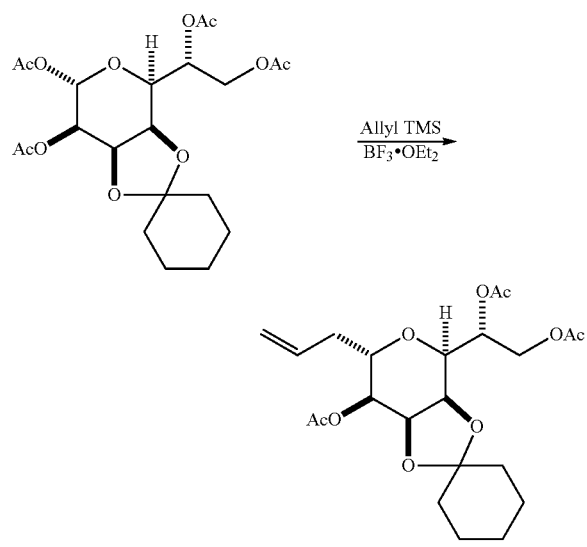

To a solution of (3aR,4S,6S,7R,7aR)-4-((R)-1,2-diacetoxyethyl)tetrahydro-3aH-spiro[[1,3]dioxolo[4,5-c]pyran-2,1'-cyclohexane]-6,7-diyl diacetate (10 g, 21.812 mmol) in acetonitrile (70.0 mL) was added allyltrimethylsilane (10.40 mL, 65.44 mmol). The resulting solution was cooled to 0° C., and $BF_3 \cdot OEt_2$ (5.53 mL, 43.6 mmol) was added, while the internal temperature was maintained below 10° C. After being stirred for 6 h at a temperature between 0 and 10° C., the reaction mixture was treated with saturated aqueous $NaHCO_3$ (8%) (100 mL). The resulting mixture was extracted with toluene (200 mL). The combined organic layers were washed twice with water (200 mL) and concentrated in vacuo to give 11 g of the target product as a white solid.

$^1$H NMR (400 MHz, $CDCl_3$) δ ppm 1.23-1.85 (m, 10H) 2.07 (s, 3H) 2.10 (s, 3H) 2.14 (s, 3H) 2.21-2.33 (m, 2H) 3.74 (dd, J=7.6, 1.8 Hz, 1H) 4.11 (ddd, J=9.7, 6.6, 5.1 Hz, 1H) 4.25 (dd, J=12.6, 4.4 Hz, 1H) 4.32 (dd, J=7.9, 1.8 Hz, 1H) 4.46 (dd, J=12.6, 2.6 Hz, 1H) 4.59 (dd, J=7.9, 2.6 Hz, 1H) 4.92 (dd, J=9.7, 2.6 Hz, 1H) 5.07 (t, J=1.2 Hz, 1H) 5.09-5.16 (m, 1H) 5.22 (ddd, J=7.5, 4.8, 2.6 Hz, 1H) 5.69-5.90 (m, 1H).

157

(R)-1-((3aR,4S,6S,7S,7aS)-6-allyl-7-hydroxytetra-hydro-3aH-spiro[[1,3]dioxolo[4,5-c]pyran-2,1'-cyclohexan]-4-yl)ethane-1,2-diol

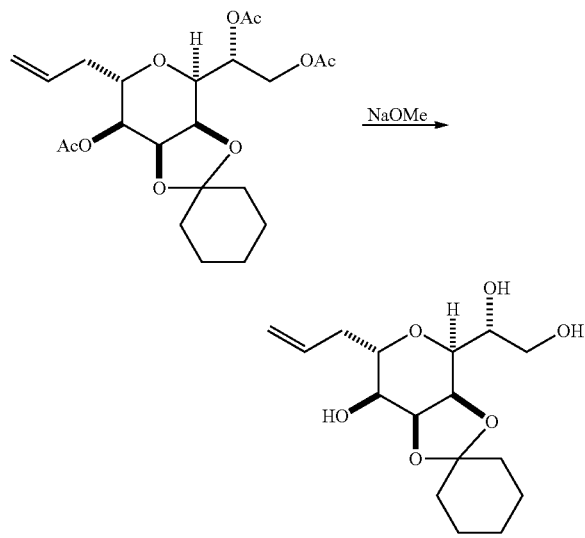

To a solution of (R)-1-((3aR,4S,6S,7S,7aR)-7-acetoxy-6-allyltetrahydro-3aH-spiro[[1,3]dioxolo[4,5-c]pyran-2,1'-cyclohexan]-4-yl)ethane-1,2-diyl diacetate (11.0 g, 21.7 mmol) in methanol (12 mL) and MTBE (57 mL) was added sodium methoxide solution in MeOH (25 wt %, 7.45 mL, 32.6 mmol) at ambient temperature. After 2.5 h, the reaction mixture was cooled to 10-15° C. Acetic acid (2.0 mL, 35 mmol) was added while keeping the internal temperature below 20° C. The resulting mixture was concentrated in vacuo. Saturated aqueous NaHCO₃ (8%) (38.3 mL) was added and the resulting mixture was extracted four times with EtOAc (191 mL). The combined organic layers were washed with 30% aqueous NaCl (19 mL) and dried over MgSO₄. Filtration, concentration in vacuo, and purification by silica gel column chromatography using a 50-100% gradient of ethyl acetate in n-heptane as eluent provided 6.75 g of the target product as a yellow solid.

$^1$H NMR (400 MHz, CDCl₃) δ ppm 1.33-1.80 (m, 10H) 2.29-2.39 (m, 1H) 2.47-2.56 (m, 1H) 3.58-3.67 (m, 2H) 3.73 (dd, J=11.7, 4.1 Hz, 1H) 3.78 (dd, J=12.0, 3.8 Hz, 1H) 3.83-3.95 (m, 2H) 4.43 (dd, J=8.1, 1.6 Hz, 1H) 4.54 (dd, J=7.9, 3.5 Hz, 1H) 5.03-5.30 (m, 2H) 5.78-5.99 (m, 1H).

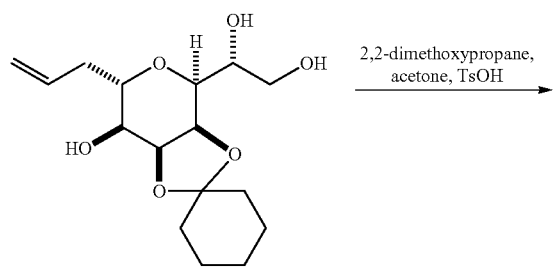

158

-continued

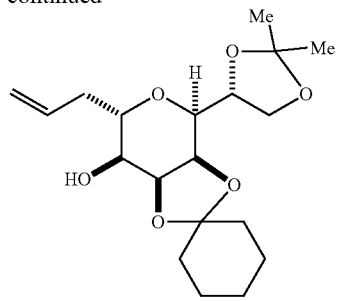

(R)-1-((3aR,4S,6S,7S,7aS)-6-allyl-7-hydroxytetrahydro-3aH-spiro[[1,3]dioxolo[4,5-c]pyran-2,1'-cyclohexan]-4-yl)ethane-1,2-diol (1.0 g, 3.18 mmol) was dissolved in acetone (5.0 mL, 68.1 mmol) at ambient temperature. 2,2-Dimethoxypropane (1.369 mL, 11.13 mmol) and p-toluenesulfonic acid monohydrate (0.061 g, 0.318 mmol) were added, and the resulting mixture was stirred for 30 min. Saturated aqueous NaHCO₃ (10 mL) were added, and the resulting mixture was extracted three times with EtOAc (12 mL each time). The combined organic layers were washed with brine (5 mL) and dried over MgSO₄. Filtration followed by concentration in vacuo gave 1.09 g of the target product as a white solid.

(3aR,4S,6S,7S,7aR)-6-allyl-4-((R)-1,2-dihydroxyethyl)tetrahydro-3aH-spiro[[1,3]dioxolo[4,5-c]pyran-2,1'-cyclohexan]-7-yl benzoate

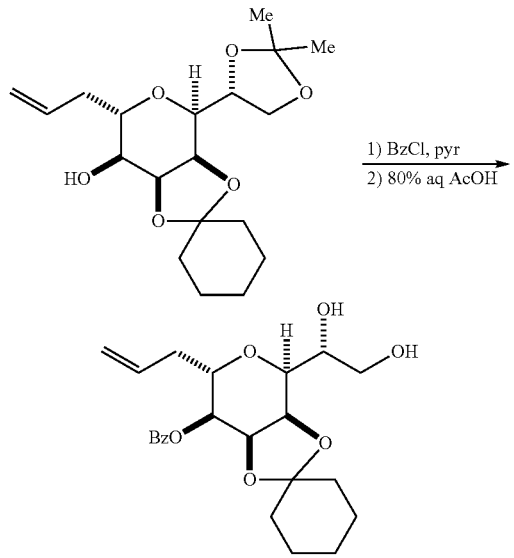

To a solution of (3aR,4S,6S,7S,7aS)-6-allyl-4-((R)-2,2-dimethyl-1,3-dioxolan-4-yl)tetrahydro-3aH-spiro[[1,3]dioxolo[4,5-c]pyran-2,1'-cyclohexan]-7-o (1.09 g, 3.075 mmol) in pyridine (5.45 mL) at ambient temperature were added benzoyl chloride (0.714 mL, 6.151 mmol) and 4-dimethylaminopyridine (0.019 g, 0.154 mmol). After complete consumption of the starting material, saturated aqueous NH₄Cl (27 wt %) (15 mL), MTBE (40 mL), and water (5.0 mL) were added. The layers were separated, and the organic layer was washed sequentially with 1M aqueous hydrochloric acid (10 mL, 10.00 mmol), saturated aqueous NaHCO₃

(8%) (5.0 mL), and 30% aqueous NaCl (5.0 mL). The resulting organic layer was dried over MgSO$_4$, filtered and concentrated in vacuo. The residue (1.1 g) was dissolved in acetic acid (16 mL) and water (4 mL). The resulting mixture was stirred at ambient temperature overnight and then at a temperature between 35 and 40° C. for 24 h. The mixture was then concentrated in vacuo and azeotroped twice with toluene. The residue was purified by silica gel plug purification to give 1.1 g of the target product as a pale yellow solid (3aS,4R,6S,7S,7aR)-6-allyl-4-formyltetrahydro-3aH-spiro[[1,3]dioxolo[4,5-c]pyran-2,1'-cyclohexan]-7-yl benzoate

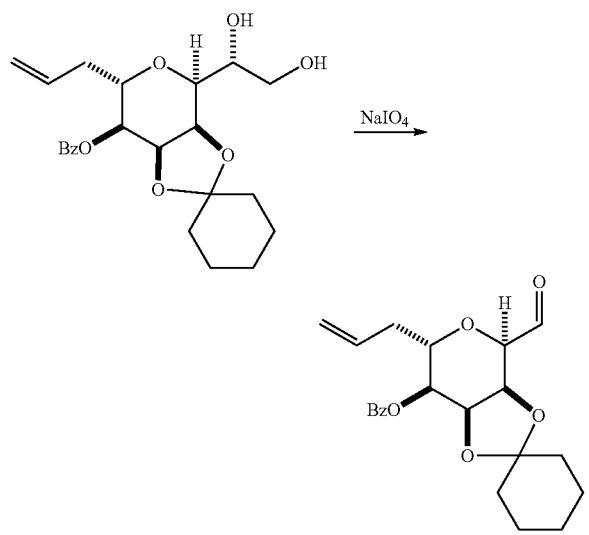

(3aR,4S,6S,7S,7aR)-6-allyl-4-((R)-1,2-dihydroxyethyl)tetrahydro-3aH-spiro[[1,3]dioxolo[4,5-c]pyran-2,1'-cyclohexan]-7-yl benzoate (1.1 g, 2.629 mmol) was dissolved in ethyl acetate (11.00 mL) and water (11.00 mL) and cooled to 0° C. Sodium periodate (0.843 g, 3.943 mmol) was added, and the resulting mixture was stirred for 2.5 h at ambient temperature. Additional sodium periodate (0.2 g) was then added. After additional stirring for 2.5 h, the layers were separated. The aqueous layer was extracted twice with EtOAc (11.00 mL), and the combined organic layers were washed with 30% aqueous NaCl (5.50 mL) and dried over MgSO$_4$. Filtration followed by concentration in vacuo provided 0.98 g of as a foam solid.

(3aR,4S,6S,7S,7aR)-6-allyl-4-((S,E)-1-hydroxy-3-(trimethylsilyl)allyl)tetrahydro-3aH-spiro[[1,3]dioxolo[4,5-c]pyran-2,1'-cyclohexan]-7-yl benzoate

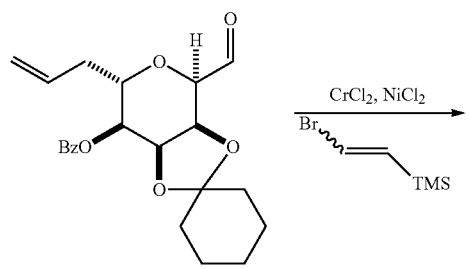

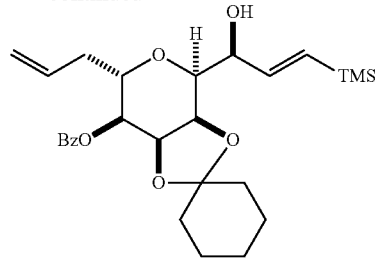

To a solution of (3aS,4R,6S,7S,7aR)-6-allyl-4-formyltetrahydro-3aH-spiro[[1,3]dioxolo[4,5-c]pyran-2,1'-cyclohexan]-7-yl benzoate (0.98 g) in acetonitrile (7 mL) was added (2-bromovinyl)trimethylsilane (1.941 mL, 12.68 mmol). The resulting solution was degassed for 0.5 h. To another reactor were added chromium(II) chloride (3.12 g, 25.36 mmol), nickel(II) chloride (0.033 g, 0.254 mmol), DMSO (6.86 mL), and MeCN (6.86 mL), and the resulting mixture was cooled to 0-5° C. The aldehyde and vinyl bromide solution was added to the chromium and nickel mixture. The reaction mixture was stirred overnight at a temperature between 5 and 15° C. and then treated with methanol (20.42 mL), water (20.58 mL), and MTBE (24.50 mL). The layers were separated, and the aqueous layer was extracted twice with MTBE (34.3 mL). The combined organic layers were washed twice with 30% aqueous NaCl (19.60 mL) and dried over MgSO$_4$. Filtration followed by concentration in vacuo provided 0.521 g of the target product as white foam solid.

$^1$H NMR (400 MHz, CDCl$_3$) δ ppm 0.07 (s, 9H) 1.21-1.87 (m, 10H) 2.24-2.33 (m, 1H) 2.34-2.43 (m, 1H) 2.59-2.68 (m, 1H) 3.49 (dd, J=6.6, 2.0 Hz, 1H) 4.28-4.37 (m, 2H) 4.54 (dd, J=8.0, 1.8 Hz, 1H) 4.72 (dd, J=7.8, 2.7 Hz, 1H) 5.02-5.09 (m, 2H) 5.13 (dd, J=9.8, 2.7 Hz, 1H) 5.77-5.93 (m, 1H) 6.07 (dd, J=18.7, 1.6 Hz, 1H) 6.23 (dd, J=19.1, 4.3 Hz, 1H) 7.43-7.48 (m, 2H) 7.57 (d, J=7.4 Hz, 1H) 8.07 (dd, J=8.4, 1.4 Hz, 2H)

(2S,3R,4R,5S,6S)-2-allyl-4,5-dihydroxy-6-((S,E)-1-hydroxy-3-(trimethylsilyl)allyl)tetrahydro-2H-pyran-3-yl benzoate

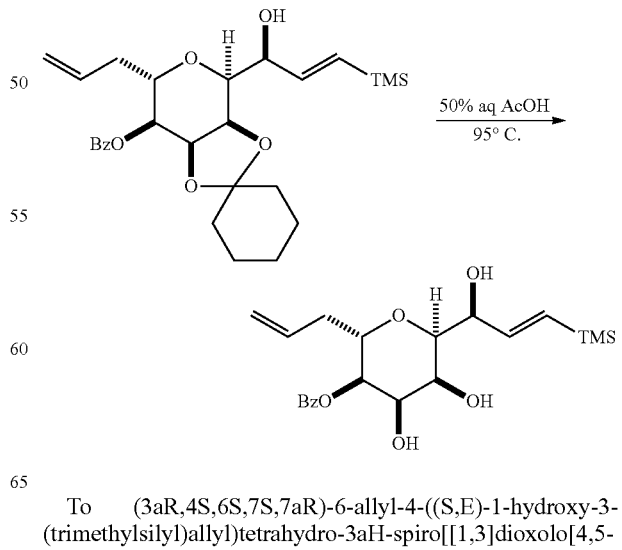

To (3aR,4S,6S,7S,7aR)-6-allyl-4-((S,E)-1-hydroxy-3-(trimethylsilyl)allyl)tetrahydro-3aH-spiro[[1,3]dioxolo[4,5- c]pyran-2,1'-cyclohexan]-7-yl benzoate (0.521 g, 1.071 mmol) were added acetic acid (7.8 mL) and water (7.8 mL). The reaction mixture was heated to 90-97° C. for 100 min and concentrated in vacuo. The residue was azeotroped with toluene and purified by silica gel plug to give 0.33 g of the target product as a white foam solid.

(2S,3S,4S,5R,6S)-2-allyl-4,5-bis((tert-butyldimethylsilyl)oxy)-6-((S,E)-1-((tert-butyldimethylsilyl)oxy)-3-(trimethylsilyl)allyl)tetrahydro-2H-pyran-3-yl benzoate

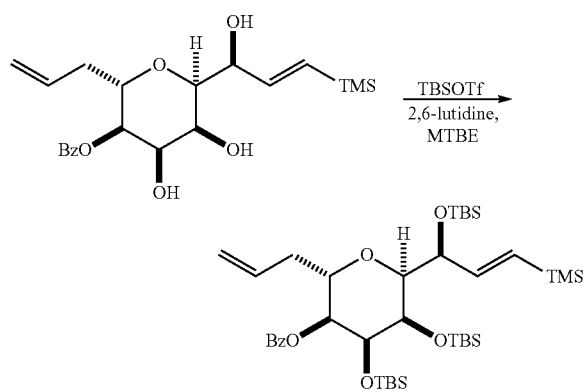

(2S,3R,4R,5S,6S)-2-allyl-4,5-dihydroxy-6-((S,E)-1-hydroxy-3-(trimethylsilyl)allyl)tetrahydro-2H-pyran-3-yl benzoate (0.33 g) was dissolved in MTBE (4.95 mL) and cooled to 0° C. 2,6-Dimethylpyridine (0.95 mL, 8.1 mmol) and tert-butyldimethylsilyl trifluoromethanesulfonate (0.84 mL, 3.7 mmol) were added. The resulting mixture was stirred at ambient temperature overnight. Saturated aqueous NH$_4$Cl (27 wt %) (4.95 mL), MTBE (9.90 mL), and water (3.30 mL) were added. The organic layer was separated and dried over MgSO$_4$. Filtration, concentration, and purification by silica gel column chromatography using a 0-10% gradient of ethyl acetate in n-heptane as eluent afforded 0.619 g of the target product as an oil.

(2S,3S,4S,5R,6S)-2-allyl-4,5-bis((tert-butyldimethylsilyl)oxy)-6-((S,E)-1-((tert-butyldimethylsilyl)oxy)-3-iodoallyl)tetrahydro-2H-pyran-3-yl benzoate

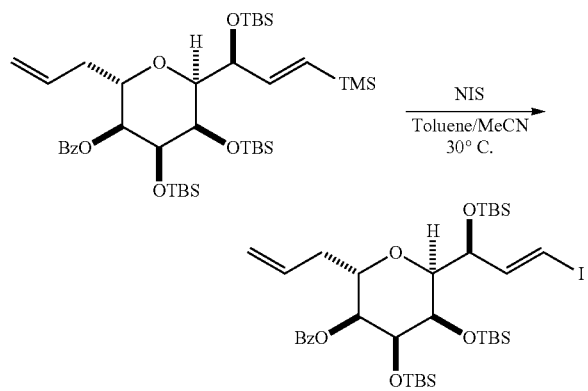

(2S,3S,4S,5R,6S)-2-allyl-4,5-bis((tert-butyldimethylsilyl)oxy)-6-((S,E)-1-((tert-butyldimethylsilyl)oxy)-3-(trimethylsilyl)allyl)tetrahydro-2H-pyran-3-yl benzoate (0.510 g, 0.681 mmol) was dissolved in toluene (2.295 mL) and MeCN (4.59 mL) at ambient temperature. To the solution were added tert-butyldimethylsilyl chloride (7.69 mg, 0.051 mmol) and NIS (0.919 g, 4.08 mmol). The reaction mixture was stirred at 28-31° C. for 20 h and cooled to ambient temperature. Toluene (24.29 mL), sodium thiosulfate (1.076 g, 6.806 mmol) and saturated aqueous NaHCO$_3$ (8%) (5.10 mL) were added, and the resulting mixture was stirred over 2 h at ambient temperature. The layers were separated, and the organic layer was washed twice with 30% aqueous NaCl (7.29 mL) and dried over MgSO$_4$. Filtration followed by concentration and purification by silica gel column chromatography using a 0-10% gradient of ethyl acetate in n-heptane as eluent provided 467 mg of the target product as a pale yellow oil.

$^1$H NMR (400 MHz, CDCl$_3$) δ ppm −0.04-0.27 (m, 18H) 0.89 (br. s., 9H) 0.90 (br. s., 9H) 0.96 (s, 9H) 2.22-2.53 (m, 2H) 3.24-3.69 (m, 1H) 3.76-4.50 (m, 4H) 4.95-5.35 (m, 3H) 5.71-5.90 (m, 1H) 6.36 (d, J=14.9 Hz, 1H) 6.50-6.73 (m, 1H) 7.33-7.46 (m, 1H) 7.48-7.60 (m, 2H) 7.96-8.15 (m, 2H).

(S)-5-(((2R,3R,4S,5S)-3-methoxy-5-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)-4-((phenylsulfonyl)methyl)tetrahydrofuran-2-yl)methyl)-2,2,3,3,8,8,9,9-octamethyl-4,7-dioxa-3,8-disiladecane

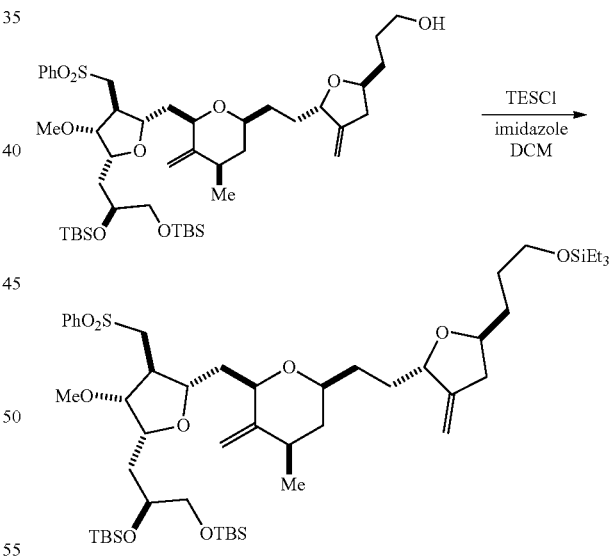

3-((2S,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propan-1-ol (1.00 g, 1.175 mmol) was dissolved in dichloromethane (7.00 mL) at ambient temperature. Imidazole (0.240 g, 3.52 mmol) and chlorotriethylsilane (0.300 mL, 1.76 mmol) were added, and the resulting mixture was stirred at ambient temperature for 1 h., at which time a saturated aqueous NH$_4$Cl (27 wt %) (12.00 mL, 64.205 mmol) was added, and the resulting mixture was extracted with MTBE (15.00 mL, 125.924 mmol). The combined organic layers were washed with 30% aqueous NaCl (10.00 mL, 52.578 mmol) and dried over MgSO₄. Concentration and azeotroping with toluene provided 1.177 g of the target product as an oil.

Methyl (R)-2-((2S,3S,4R,5R)-5-((S)-2,3-bis((tert-butyldimethylsilyl)oxy)propyl)-4-methoxy-2-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)tetrahydrofuran-3-yl)-2-(phenylsulfonyl)acetate

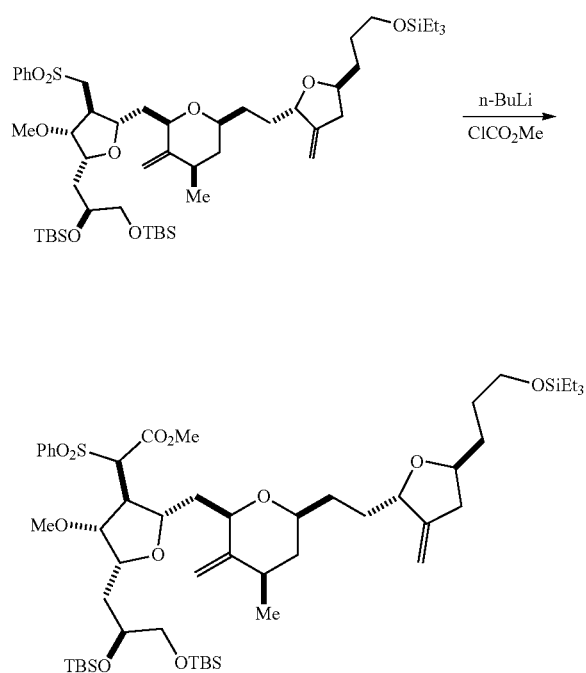

(S)-5-(((2R,3R,4S,5S)-3-methoxy-5-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)-4-((phenylsulfonyl)methyl)tetrahydrofuran-2-yl)methyl)-2,2,3,3,8,8,9,9-octamethyl-4,7-dioxa-3,8-disiladecane (1.177 g, 1.17 mmol) was dissolved in THF (11.3 mL) and cooled to 0° C. n-BuLi (1.6 M, 0.95 mL, 1.5 mmol) was added. The resulting solution was stirred for 20 min at 0° C. and cooled to −78° C. Methyl chloroformate (0.14 mL, 1.8 mmol) was added, and the resulting solution was stirred for 1.5 h with warming to −40° C. Saturated aqueous NH₄Cl (27 wt %) (10 mL), water (5 mL) and MTBE (11 mL) were added, and the resulting mixture was warmed to ambient temperature. The layers were separated, and the organic layer was washed with saturated aqueous NaCl (4 mL) and dried over MgSO₄. Filtration followed by concentration in vacuo provided 1.267 g of the target product as colorless oil.

methyl 2-((2S,3S,4R,5R)-5-((S)-2,3-bis((tert-butyldimethylsilyl)oxy)propyl)-4-methoxy-2-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)tetrahydrofuran-3-yl)acetate

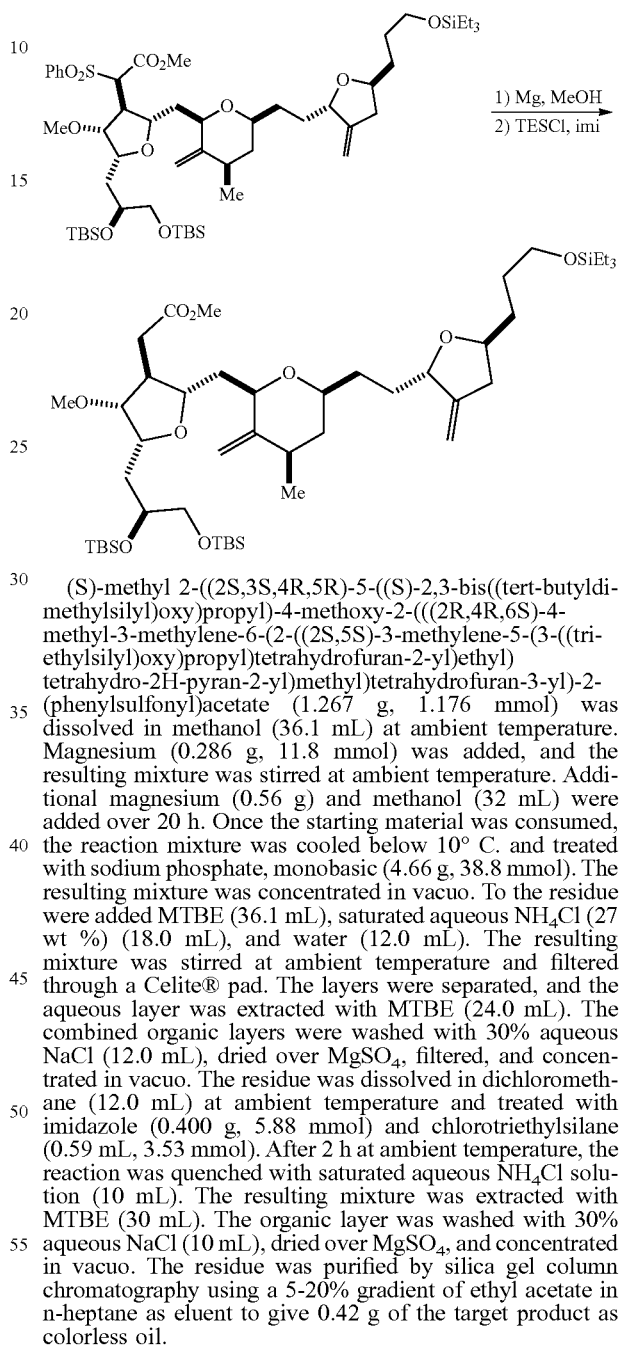

(S)-methyl 2-((2S,3S,4R,5R)-5-((S)-2,3-bis((tert-butyldimethylsilyl)oxy)propyl)-4-methoxy-2-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)tetrahydrofuran-3-yl)-2-(phenylsulfonyl)acetate (1.267 g, 1.176 mmol) was dissolved in methanol (36.1 mL) at ambient temperature. Magnesium (0.286 g, 11.8 mmol) was added, and the resulting mixture was stirred at ambient temperature. Additional magnesium (0.56 g) and methanol (32 mL) were added over 20 h. Once the starting material was consumed, the reaction mixture was cooled below 10° C. and treated with sodium phosphate, monobasic (4.66 g, 38.8 mmol). The resulting mixture was concentrated in vacuo. To the residue were added MTBE (36.1 mL), saturated aqueous NH₄Cl (27 wt %) (18.0 mL), and water (12.0 mL). The resulting mixture was stirred at ambient temperature and filtered through a Celite® pad. The layers were separated, and the aqueous layer was extracted with MTBE (24.0 mL). The combined organic layers were washed with 30% aqueous NaCl (12.0 mL), dried over MgSO₄, filtered, and concentrated in vacuo. The residue was dissolved in dichloromethane (12.0 mL) at ambient temperature and treated with imidazole (0.400 g, 5.88 mmol) and chlorotriethylsilane (0.59 mL, 3.53 mmol). After 2 h at ambient temperature, the reaction was quenched with saturated aqueous NH₄Cl solution (10 mL). The resulting mixture was extracted with MTBE (30 mL). The organic layer was washed with 30% aqueous NaCl (10 mL), dried over MgSO₄, and concentrated in vacuo. The residue was purified by silica gel column chromatography using a 5-20% gradient of ethyl acetate in n-heptane as eluent to give 0.42 g of the target product as colorless oil.

$^1$H NMR (400 MHz, CDCl₃) δ ppm 0.03 (s, 3H) 0.04 (s, 3H) 0.06 (s, 3H) 0.07 (s, 3H) 0.55-0.62 (m, 6H) 0.87-0.88 (m, 9H) 0.88 (s, 9H) 0.92-0.97 (m, 9H) 1.07 (d, J=6.6 Hz, 3H) 1.43-1.70 (m, 8H) 1.79 (s, 2H) 1.92-2.02 (m, 2H) 2.09-2.19 (m, 1H) 2.20-2.45 (m, 6H) 2.59-2.69 (m, 1H) 3.29 (s, 3H) 3.41 (d, J=3.9 Hz, 1H) 3.46-3.65 (m, 5H) 3.67-3.73 (m, 1H) 3.69 (s, 3H) 3.74-3.81 (m, 2H) 3.83-3.91 (m, 1H) 3.95-4.06 (m, 1H) 4.34-4.43 (m, 1H) 4.79 (d, J=1.6 Hz, 1H) 4.82 (d, J=2.0 Hz, 1H) 4.87 (s, 1H) 4.96 (d, J=2.0 Hz, 1H).

methyl 2-((2S,3S,4R,5R)-5-((S)-2,3-bis((tert-butyldimethylsilyl)oxy)propyl)-4-methoxy-2-(((2R,4R,6S)-4-methyl-3-methylene-6-(2-((2S,5S)-3-methylene-5-(3-oxopropyl)tetrahydrofuran-2-yl)ethyl)tetrahydro-2H-pyran-2-yl)methyl)tetrahydrofuran-3-yl)acetate

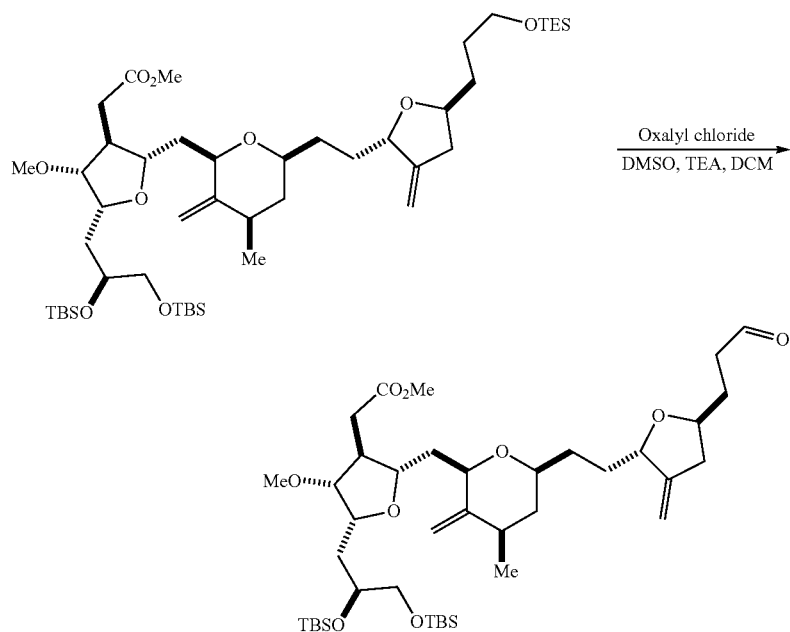

A solution of oxalyl chloride (0.2 M, 0.10 mL, 0.20 mmol) in dichloromethane was diluted with dichloromethane (1.0 mL) and cooled to −78° C. A solution of DMSO (0.030 mL, 0.419 mmol) in dichloromethane (0.300 mL, 4.66 mmol) followed by a solution of methyl 2-((2S,3S,4R,5R)-5-((S)-2,3-bis((tert-butyldimethylsilyl)oxy)propyl)-4-methoxy-2-(((2R,4R,6S)-4-methyl-3-methylene-6-(2-((2S,5S)-3-methylene-5-(3-((triethylsilyl)oxy)propyl)tetrahydrofuran-2-yl)ethyl)tetrahydro-2H-pyran-2-yl)methyl)tetrahydrofuran-3-yl)acetate (0.10 g, 0.113 mmol) in dichloromethane (0.500 mL) was added. The resulting solution was stirred for 30 min at −50° C., cooled to −78° C. and treated with triethylamine (0.095 mL, 0.679 mmol). The mixture was warmed to ambient temperature over 1 h, diluted with MTBE (15 mL), and washed with saturated aqueous NH₄Cl solution (5 mL) and 30% aqueous NaCl (3 mL). The organic layer was dried over MgSO₄, filtered, and concentrated in vacuo. The residue was filtered through a silica gel plug with MTBE. Concentration of the filtrate in vacuo provided 89 mg of the target product as an oil.

$^1$H NMR (400 MHz, CDCl₃) δ ppm 0.04 (s, 3H) 0.04 (s, 3H) 0.06 (s, 3H) 0.07 (s, 3H) 0.88 (s, 9H) 0.89 (s, 9H) 1.08 (d, J=6.3 Hz, 3H) 1.42-1.69 (m, 5H) 1.74-1.85 (m, 4H) 1.93-2.03 (m, 2H) 2.10-2.19 (m, 1H) 2.22-2.32 (m, 3H) 2.34-2.46 (m, 2H) 2.47-2.62 (m, 2H) 2.63-2.73 (m, 1H) 3.29 (s, 3H) 3.42 (d, J=3.5 Hz, 1H) 3.50 (d, J=5.1 Hz, 2H) 3.56 (d, J=5.9 Hz, 1H) 3.67-3.73 (m, 1H) 3.70 (s, 3H) 3.78 (d, J=5.5 Hz, 2H) 3.84-3.91 (m, 1H) 4.04 (quin, J=6.4 Hz, 1H) 4.34 (d, J=6.6 Hz, 1H) 4.79-4.81 (m, 1H) 4.84 (d, J=2.3 Hz, 1H) 4.88 (s, 1H) 4.98 (d, J=2.3 Hz, 1H) 9.79 (t, J=1.4 Hz, 1H)

(2S,3S,4S,5R,6S)-2-allyl-6-((1S,E)-6-((2S,5S)-5-(2-((2S,4R,6R)-6-(((2S,3S,4R,5R)-5-((S)-2,3-bis((tert-butyldimethylsilyl)oxy)propyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-hydroxyhex-2-en-1-yl)-4,5-bis((tert-butyldimethylsilyl)oxy)tetrahydro-2H-pyran-3-yl benzoate

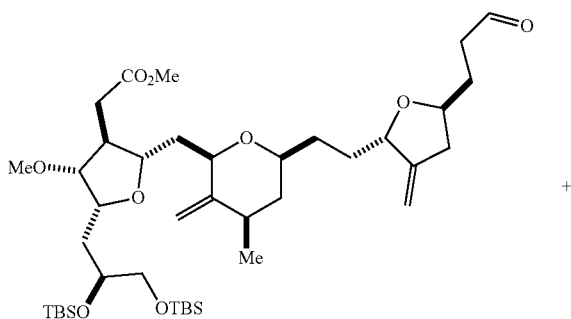

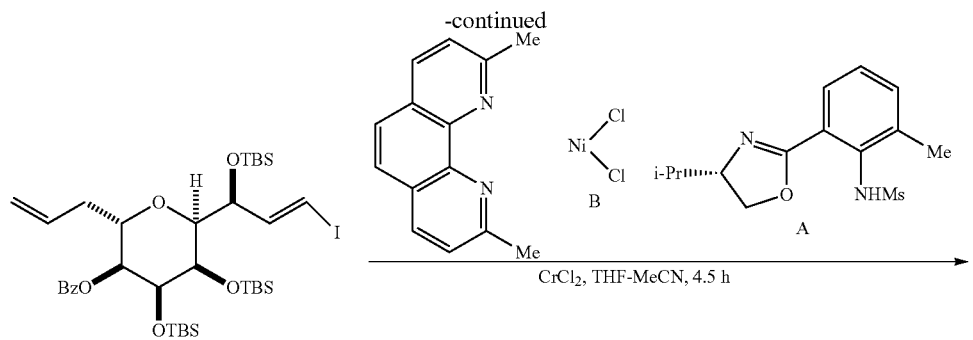

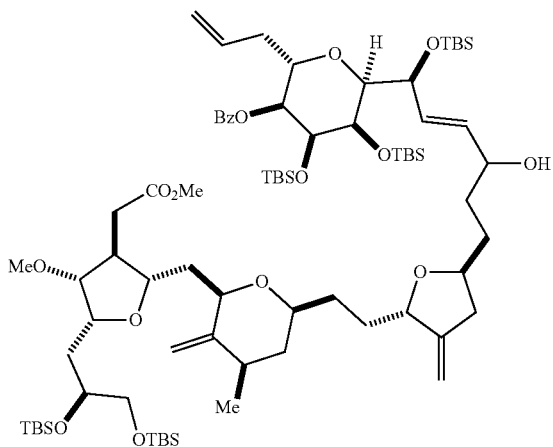

(S)—N-(2-(4-isopropyl-4,5-dihydrooxazol-2-yl)-6-methylphenyl)methanesulfonamide (688 mg, 2.32 mmol) was dissolved in acetonitrile (4 mL) and purged with nitrogen for 30 min. Chromous chloride (285 mg, 2.32 mmol) and triethylamine (320 μL, 2.32 mmol) were added, and the resulting dark green mixture was stirred at 35° C. for 1 h. In another reactor, methyl 2-((2S,3S,4R,5R)-5-((S)-2,3-bis (((tert-butyldimethylsilyl)oxy)propyl)-4-methoxy-2-(((2R, 4R,6S)-4-methyl-3-methylene-6-(2-((2S,5S)-3-methylene-5-(3-oxopropyl)tetrahydrofuran-2-yl)ethyl)tetrahydro-2H-pyran-2-yl)methyl)tetrahydrofuran-3-yl)acetate (89 mg, 0.116 mmol) and (2S,3S,4S,5R,6S)-2-allyl-4,5-bis((tert-butyldimethylsilyl)oxy)-6-((S,E)-1-((tert-butyldimethylsilyl)oxy)-3-iodoallyl)tetrahydro-2H-pyran-3-yl benzoate (107 mg, 0.133 mmol) were dissolved in THF (870 μL) and acetonitrile (680 μL) and purged with nitrogen for 10 min. Nickel(II) chloride complex with 2,9-dimethyl-1,10-phenanthroline (7.84 mg, 0.023 mmol) followed by the sulfonamide complex solution prepared above was added. The resulting mixture was stirred vigorously for 5 h at 15-23° C. and diluted with n-heptane (6.5 mL). The resulting mixture was filtered through a Celite® pad, which was then rinsed with n-heptane (10 mL) and acetonitrile (10 mL). The layers were separated, and the bottom acetonitrile layer was extracted twice with n-heptane (7 mL each). The combined n-heptane layers were washed twice with acetonitrile (5 mL each) and concentrated in vacuo. The residue was purified by silica gel column chromatography using a 10-33% gradient of ethyl acetate in n-heptane as eluent to give 99 mg of the target product as white foam solid.

(2S,3S,4S,5R,6S)-2-allyl-6-((S,E)-6-((2S,5S)-5-(2-((2S,4R,6R)-6-(((2S,3S,4R,5R)-5-((S)-2,3- bis((tert-butyldimethylsilyl)oxy)propyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-oxohex-2-en-1-yl)-4,5-bis ((tert-butyldimethylsilyl)oxy)tetrahydro-2H-pyran-3-yl benzoate

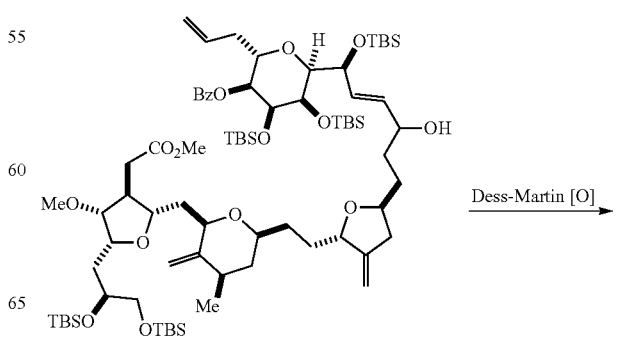

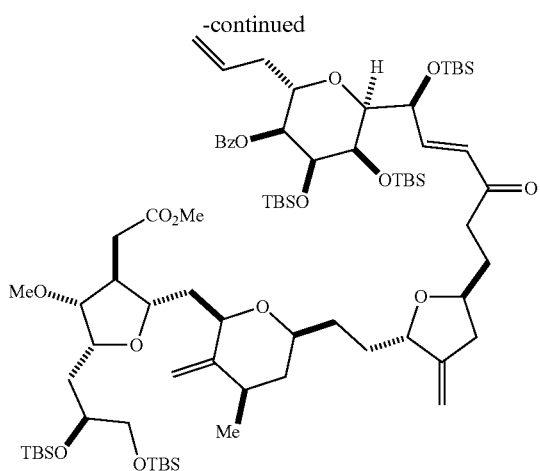

To a solution of (2S,3S,4S,5R,6S)-2-allyl-6-((1 S,E)-6-((2S,5S)-5-(2-((2S,4R,6R)-6-(((2S,3S,4R,5R)- 5-((S)-2,3-bis((tert-butyldimethylsilyl)oxy)propyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-hydroxyhex-2-en-1-yl)-4,5-bis((tert-butyldimethylsilyl)oxy)tetrahydro-2H-pyran-3-yl benzoate (0.284 g, 0.197 mmol) in dichloromethane (5.7 mL) at ambient temperature were added sodium bicarbonate (83 mg, 0.98 mmol) and Dess-Martin periodinane (250 mg, 0.59 mmol). After being stirred over 2 h at ambient temperature, the reaction mixture was diluted with MTBE (8.5 mL). Water (2.8 mL), sodium thiosulfate (0.155 mg, 0.983 mmol), and saturated aqueous NaHCO$_3$ (8%) (2.84 mL) were added, and the resulting mixture was stirred for 30 min. The layers were separated, and the organic layer was washed twice with 30% aqueous NaCl (1.4 mL each time) and dried over MgSO$_4$. Filtration and concentration in vacuo provided 270 mg of the target product as white foam.

$^1$H NMR (400 MHz, CDCl$_3$) δ ppm −0.13-0.23 (m, 30H) 0.87 (s, 9H) 0.88 (br. s, 18H) 0.90-0.91 (m, 9H) 0.96 (s, 9H) 1.07 (d, J=6.3 Hz, 3H) 1.41-1.70 (m, 6H) 1.72-1.86 (m, 4H) 1.93-2.03 (m, 2H) 2.09-2.19 (m, 1H) 2.20-2.56 (m, 7H) 2.57-2.80 (m, 3H) 3.29 (s, 3H) 3.41 (d, J=3.5 Hz, 2H) 3.43-3.55 (m, 4H) 3.56 (m, J=5.5 Hz, 1H) 3.65-3.73 (m, 1H) 3.69 (s, 3H) 3.74-3.82 (m, 2H) 3.84-3.90 (m, 1H) 3.92-4.15 (m, 4H) 4.30-4.41 (m, 1H) 4.59-4.70 (m, 1H) 4.79 (d, J=1.2 Hz, 1H) 4.81-4.85 (m, 1H) 4.87 (s, 1H) 4.95-5.00 (m, 1H) 5.05-5.29 (m, 2H) 5.62-5.83 (m, 1H) 6.27 (d, J=15.2 Hz, 1H) 6.65-6.85 (m, 1H) 7.34-7.48 (m, 2H) 7.50-7.60 (m, 1H) 7.92-8.14 (m, 2H)

(2S,3aR,4aR,5R,6S,7S,8aR,8bS)-7-allyl-2-(2-((2S,5S)-5-(2-((2S,4R,6R)-6-(((2S,3S,4R,5R)- 5-((S)-2,3-dihydroxypropyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)ethyl)octahydro-2H-2,5-epoxyfuro[2',3':4,5]furo[3,2-b]pyran-6-yl benzoate

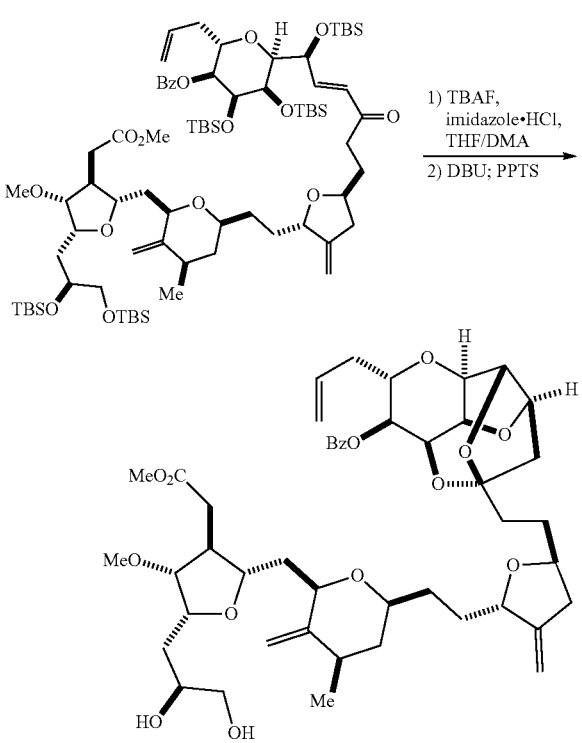

(2S,3S,4S,5R,6S)-2-allyl-6-((S,E)-6-((2S,5S)-5-(2-((2S,4R,6R)-6-(((2S,3S,4R,5R)-5-((S)-2,3- bis((tert-butyldimethylsilyl)oxy)propyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-oxohex-2-en-1-yl)-4,5-bis((tert-butyldimethylsilyl)oxy)tetrahydro-2H-pyran-3-yl benzoate (0.270 g, 0.187 mmol) was dissolved in N,N-dimethylacetamide (4.3 mL), and THF (10.8 mL) at ambient temperature. A mixture of tetrabutylammonium fluoride (1.0 M, 1.9 mL, 1.9 mmol) and imidazole hydrochloride (0.098 g, 0.936 mmol) was added, and the resulting solution was stirred at ambient temperature for 20 h. Water (5.4 mL) and toluene (11 mL) were added and the layers were separated. The aqueous layer was extracted twice with a mixture of toluene (11 mL) and THF (11 mL). The combined organic layers were washed with 30% aqueous NaCl (5.4 mL), dried over MgSO$_4$, filtered, and concentrated in vacuo. The residue was azeotroped with a mixture of acetonitrile (3.2 mL) and water (1.1 mL) three times to give 0.26 g of brown oil. The crude product was dissolved in dichloromethane (5.0 mL) and treated with DBU (0.050 mL, 0.332 mmol) for 1 h at ambient temperature. Pyridinium p-toluenesufonate (496 mg, 1.98 mmol) was added, and the resulting mixture was stirred for 3 h at ambient temperature. The reaction mixture was purified by silica-gel column chromatography using a 0-100% gradient of acetonitrile in ethyl acetate as eluent to afford 44 mg of the target product.

$^1$H NMR (400 MHz, CDCl$_3$) δ ppm 1.08 (d, J=6.6 Hz, 3H) 1.43-2.49 (m, 23H) 2.68 (ddd, J=15.7, 6.5, 1.6 Hz, 1H) 3.32 (s, 3H) 3.46-3.57 (m, 3H) 3.61-3.66 (m, 1H) 3.69 (s, 3H) 3.76 (dd, J=9.0, 3.9 Hz, 1H) 3.83 (dt, J=7.7, 5.3 Hz, 1H) 3.90-4.01 (m, 2H) 4.03 (d, J=7.0 Hz, 1H) 4.21 (dd, J=6.6, 4.3 Hz, 1H) 4.30 (dd, J=6.4, 4.5 Hz, 1H) 4.35-4.40 (m, 1H) 4.64 (dd, J=4.1, 2.1 Hz, 1H) 4.66-4.69 (m, 1H) 4.70-4.80 (m, 3H) 4.81 (d, J=1.6 Hz, 1H) 4.85 (d, J=1.6 Hz, 1H) 4.86 (s, 1H) 4.97 (d, J=2.0 Hz, 1H) 5.00-5.04 (m, 1H) 5.06 (d, J=1.6 Hz, 1H) 5.80-5.99 (m, 1H) 7.41-7.46 (m, 2H) 7.54-7.59 (m, 1H) 8.04 (dd, J=8.4, 1.4 Hz, 2H).

methyl 2-((2S,3S,4R,5R)-2-(((2R,4R,6S)-6-(2-((2S,5S)-5-(2-((3aR,4aR,5R,6S,7S,8aR,8bS)-7-allyl-6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)acetate removed with a stream of nitrogen. The residue was azeotroped with toluene and dissolved in DMF (1.5 mL) at ambient temperature. To the resulting solution were added imidazole (58.4 mg, 0.857 mmol), chlorotriethylsilane (0.096 mL, 0.572 mmol), and 4-dimethylaminopyridine (7.0 mg, 0.057 mmol). The resulting mixture was stirred at ambient temperature for 2 days and then treated with saturated aqueous NaHCO$_3$ (8%) (3.0 mL). The resulting mixture was extracted twice with MTBE (12 mL). The combined organic layers were washed with 30% aqueous NaCl (4.0 mL) and dried over MgSO$_4$. Filtration followed by concentration and purification by silica gel column chromatography using a 10-33% gradient of ethyl acetate in n-heptane as eluent provided 110 mg of the target product.

2-((2S,3S,4R,5R)-2-(((2R,4R,6S)-6-(2-((2S,5S)-5-(2-((2S,3aR,4aR,5R,6S,7S,8aR,8bS)-7-allyl-6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)ethan-1-ol

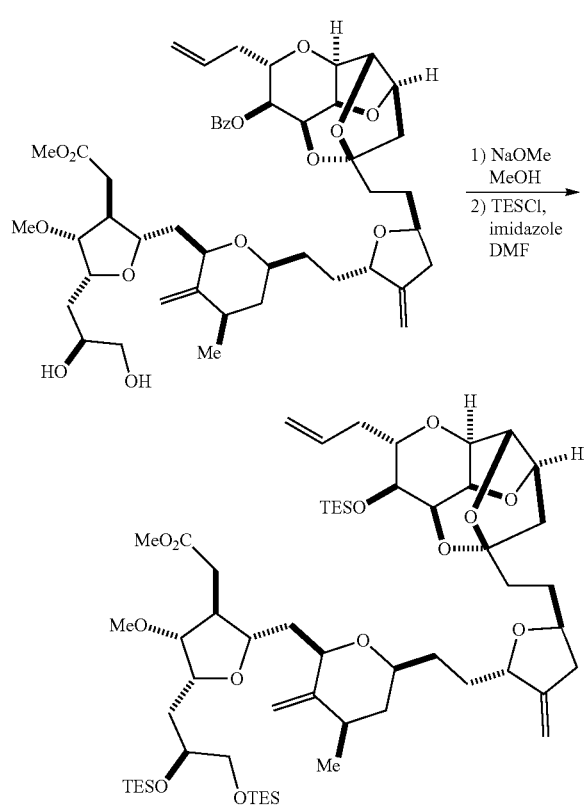

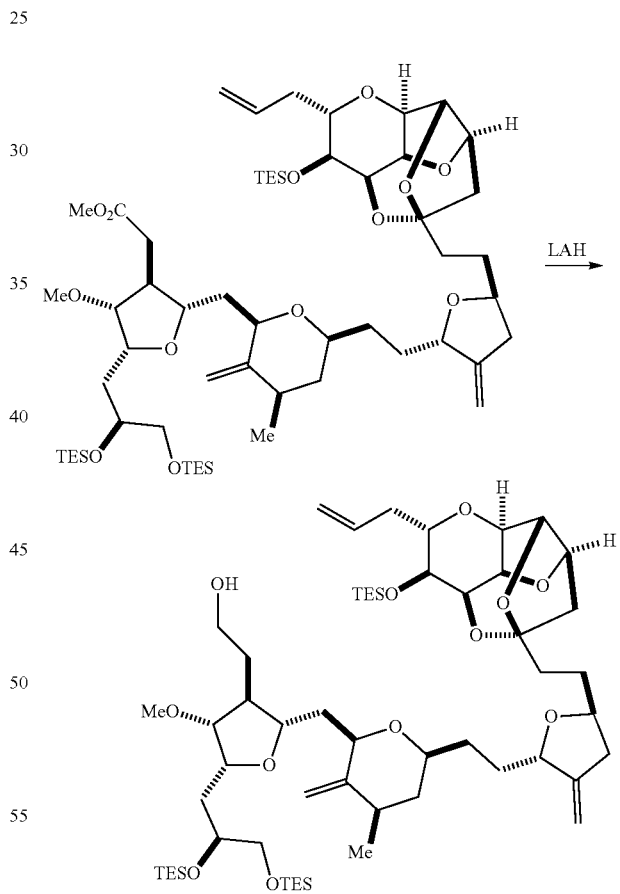

(3aR,4aR,5R,6S,7S,8aR,8bS)-7-allyl-2-(2-((2S,5S)-5-(2-((2S,4R,6R)-6-(((2S,3S,4R,5R)-5-((S)-2,3-dihydroxypropyl)-4-methoxy-3-(2-methoxy-2-oxoethyl)tetrahydrofuran-2-yl)methyl)-4-methyl-5-methylenetetrahydro-2H-pyran-2-yl)ethyl)-4-methylenetetrahydrofuran-2-yl)ethyl)octahydro-2H-2,5-epoxyfuro[2',3':4,5]furo[3,2-b]pyran-6-yl benzoate (48.7 mg, 0.057 mmol) was dissolved in THF (1.5 mL) and cooled to 0° C. A solution of sodium methoxide in methanol (25 wt %, 17 µL, 0.074 mmol) was added, and the resulting solution was stirred at ambient temperature for 1 h. Acetic acid (6.54 µL, 0.114 mmol) was added, and solvents were methyl 2-((2S,3S,4R,5R)-2-(((2R,4R,6S)-6-(2-((2S,5S)-5-(2-((3aR,4aR,5R,6S,7S,8aR,8bS)-7-allyl-6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)acetate (110 mg) was dissolved in THF (3.0 mL) and cooled to 0° C. A solution of lithium aluminum hydride in THF (1.0 M, 0.11 mL, 0.11 mmol) was added, and the resulting solution was stirred for 30 min. Saturated aqueous NH₄Cl (27 wt %) (3.0 mL) and water (1 mL) were added, and the resulting mixture was extracted twice with MTBE (6 mL each time). The combined organic layers were washed with 30% aqueous NaCl (4.0 mL) and dried over MgSO₄. Filtration followed by concentration and purification by silica gel column chromatography using a 25-50% gradient of ethyl acetate in n-heptane as eluent provided 26. 6 mg of the target product.

¹H NMR (400 MHz, CDCl₃) δ ppm 0.56-0.65 (m, 18H) 0.91-0.99 (m, 27H) 1.07 (d, J=6.2 Hz, 3H) 1.46-1.83 (m, 12H) 1.89-2.17 (m, 8H) 2.20-2.31 (m, 2H) 2.51-2.59 (m, 1H) 2.60-2.69 (m, 1H) 3.22 (dd, J=9.4, 2.3 Hz, 1H) 3.30 (s, 3H) 3.45 (dd, J=4.3, 3.1 Hz, 1H) 3.50-3.62 (m, 3H) 3.68-3.78 (m, 3H) 3.78-3.84 (m, 1H) 3.84-3.90 (m, 1H) 3.90-3.96 (m, 1H) 3.97-4.05 (m, 2H) 4.18 (dd, J=6.6, 4.7 Hz, 1H) 4.29 (dd, J=4.1, 2.1 Hz, 1H) 4.30-4.36 (m, 1H) 4.37-4.43 (m, 1H) 4.58 (t, J=4.5 Hz, 1H) 4.66 (t, J=4.7 Hz, 1H) 4.79-4.80 (m, 1H) 4.83 (d, J=2.0 Hz, 1H) 4.88 (s, 1H) 4.96 (d, J=2.0 Hz, 1H) 5.07 (d, J=10.2 Hz, 1H) 5.14 (d, J=1.2 Hz, 1H) 5.91 (dddd, J=17.3, 10.1, 7.7, 5.9 Hz, 1H)

2-((2S,3S,4R,5R)-2-(((2R,4R,6S)-6-(2-((2S,5S)-5-(2-((3aR,4aR,5R,6S,7S,8aR,8bS)-7-allyl- 6-((triethylsilyl)oxy)octahydro-2H-2,5-epoxyfuro[2',3': 4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)acetaldehyde To a solution of 2-((2S,3S,4R,5R)-2-(((2R,4R,6S)-6-(2-((2S,5S)-5-(2-((3aR,4aR,5R,6S,7S,8aR,8bS)-7-allyl-6-((triethylsilyl)oxy)octahydro-2H-2,5-epoxyfuro[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)ethanol (13.3 mg, 0.013 mmol) in dichloromethane (1.0 mL) at ambient temperature were added sodium bicarbonate (10.5 mg, 0.125 mmol) and Dess-Martin periodinane (26.5 mg, 0.063 mmol). After being stirred for 40 min, the reaction mixture was treated with MTBE (6.0 mL), water (3.0 mL) and sodium thiosulfate (15.82 mg, 0.10 mmol). After 10 min of being stirred, the layers were separated, and the organic layer was washed twice with 30% aqueous NaCl (2.0 mL) and dried over MgSO₄. Concentration in vacuo provided 12 mg of the target product.

1-((2S,3S,4R,5R)-2-(((2R,4R,6S)-6-(2-((2S,5S)-5-(2-((3aR,4aR,5R,6S,7S,8aR,8bS)-7-allyl- 6-((triethylsilyl)oxy)octahydro-2H-2,5-epoxyfuro[2',3': 4,5] furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)pent-4-en-2-ol

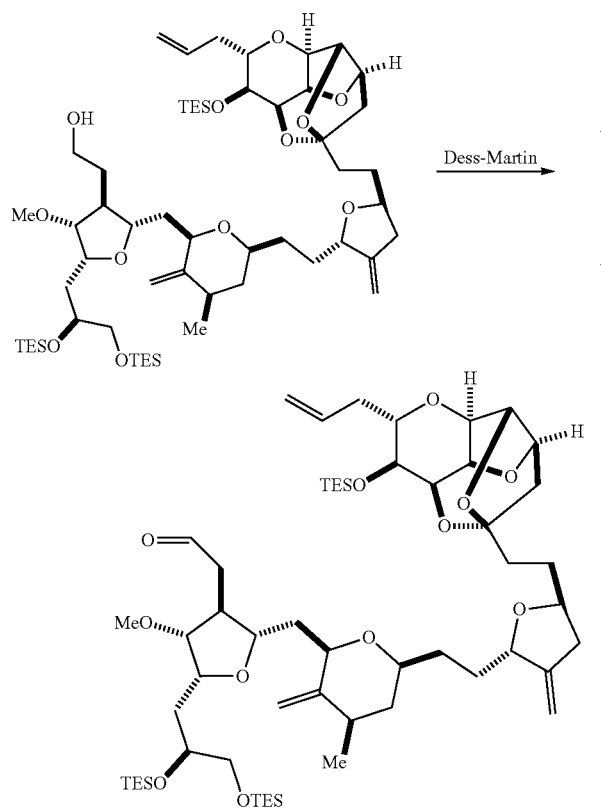

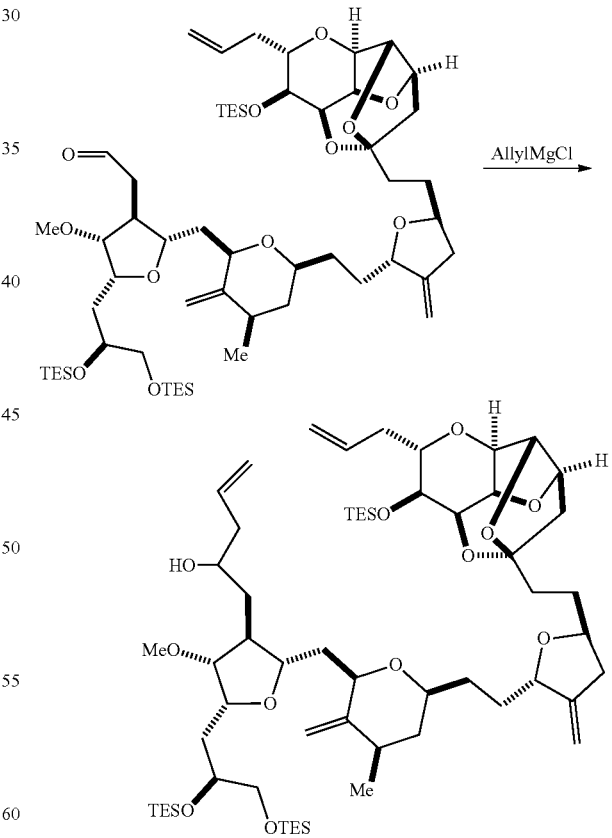

2-((2S,3S,4R,5R)-2-(((2R,4R,6S)-6-(2-((2S,5S)-5-(2-((3aR,4aR,5R,6S,7S,8aR,8bS)-7-allyl- 6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3- bis((triethylsilyl)oxy)propyl)-4-methoxytetrahydrofuran-3-yl)acetaldehyde (12 mg, 0.011 mmol) was dissolved in THF (1.0 mL) and cooled to 0° C. A solution of allylmagnesium chloride in THF (2.0 M, 0.017 mL, 0.034 mmol) was added. The resulting solution was stirred for 20 min and then treated with saturated aqueous NH₄Cl (27 wt %) (3.0 mL). The resulting mixture was extracted with MTBE (10 mL). The organic layer was washed twice with 30% aqueous NaCl (2.0 mL), dried over MgSO₄, filtered, and concentrated in vacuo. The residue was purified by silica gel column chromatography using a 20-33% gradient of ethyl acetate in n-heptane as eluent provided 11.7 mg of the target product.

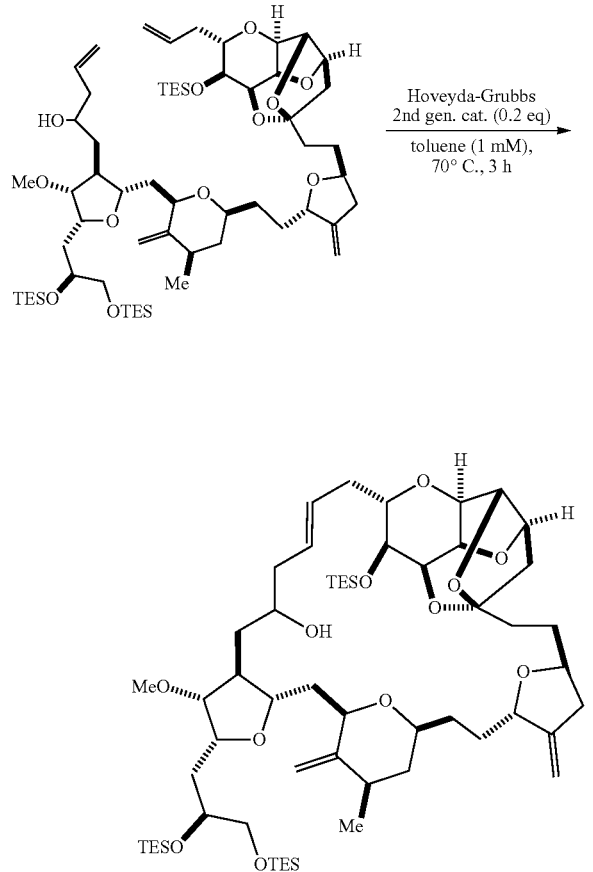

1-((2S,3S,4R,5R)-2-(((2R,4R,6S)-6-(2-((2S,5S)-5-(2-((3aR,4aR,5R,6S,7S,8aR,8bS)-7-allyl- 6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl)pent-4-en-2-ol (11.7 mg, 10.60 μmol) was dissolved in toluene (10 mL) and heated to 50° C. Hoveyda-Grubbs 2nd Generation Catalyst (1.333 mg, 2.12 μmol) was added, and the resulting solution was stirred for 3 h at a temperature between 68-73° C. The reaction mixture was cooled to ambient temperature and purified by silica gel column chromatography using a 20-33% gradient of ethyl acetate in n-heptane as eluent to provide 7.7 mg of the target product.
¹H NMR (400 MHz, CDCl₃) δ ppm 0.56-0.68 (m, 18H) 0.85-1.02 (m, 27H) 1.08 (d, J=6.2 Hz, 3H) 1.28-2.35 (m, 23H) 2.39-2.84 (m, 3H) 3.17 (ddd, J=9.5, 5.6, 2.1 Hz, 1H) 3.31 (s, 3H) 3.41-3.64 (m, 4H) 3.65-4.07 (m, 6H) 4.17 (d, J=6.6 Hz, 1H) 4.28 (dd, J=4.1, 2.1 Hz, 1H) 4.31-4.41 (m, 3H) 4.56-4.69 (m, 2H) 4.79 (s, 1H) 4.83 (br. s., 1H) 4.92 (s, 1H) 4.96 (d, J=2.3 Hz, 1H) 5.45-5.61 (m, 1H) 5.62-5.76 (m, 1H)

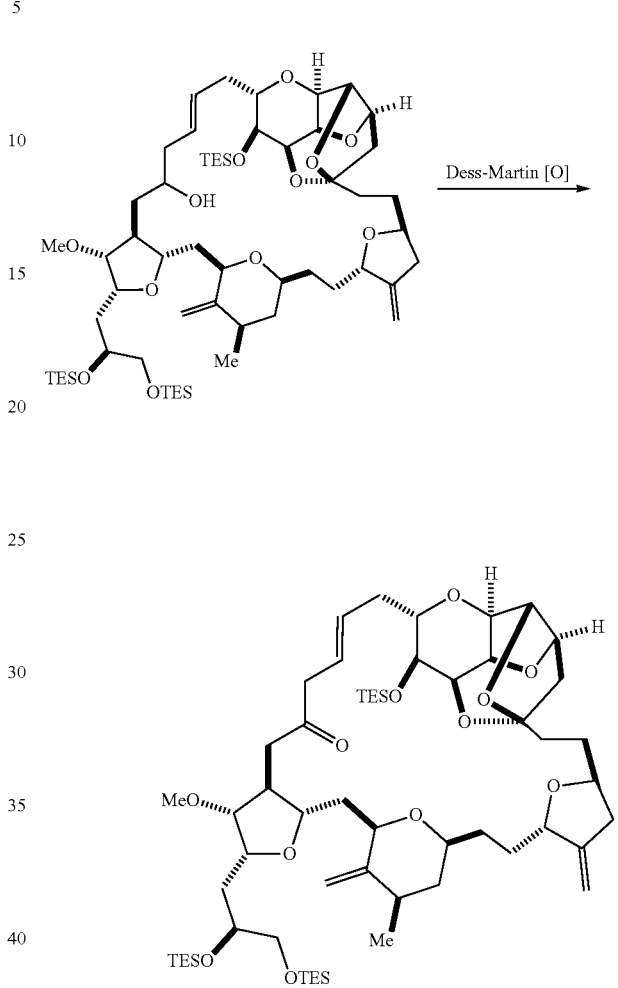

The starting material (7.7 mg, 7.158 μmol) was dissolved in dichloromethane (0.70 mL) and treated with sodium bicarbonate (6.01 mg, 0.072 mmol) and Dess-Martin periodinane (12.14 mg, 0.029 mmol). After being stirred at ambient temperature for 1 h, the reaction mixture was diluted with MTBE (5.0 mL) and water (3.0 mL). Sodium thiosulfate (11.32 mg, 0.072 mmol) was added and the resulting mixture was stirred at for 20 min. The layers were separated and the organic layer was washed with 30% aqueous NaCl (1.0 mL) and dried over MgSO₄. Filtration followed by concentration and purification by silica gel column chromatography using n-heptane/ethyl acetate (2/1) as eluent afforded 6.8 mg of the target product as a film.
¹H NMR (400 MHz, CDCl₃) δ ppm 0.55-0.65 (m, 18H) 0.91-1.02 (m, 27H) 1.08 (d, J=6.6 Hz, 3H) 1.40-2.33 (m, 20H) 2.49-2.67 (m, 4H) 3.03 (dd, J=15.6, 7.8 Hz, 1H) 3.08-3.14 (m, 1H) 3.16 (dd, J=9.4, 2.0 Hz, 1H) 3.30 (d, J=3.1 Hz, 1H) 3.35 (s, 3H) 3.44-3.57 (m, 3H) 3.73-3.87 (m, 3H) 3.87-3.94 (m, 1H) 3.97-4.00 (m, 1H) 4.18 (dd, J=6.6, 4.3 Hz, 1H) 4.29 (dd, J=4.1, 2.1 Hz, 1H) 4.32-4.44 (m, 3H) 4.59-4.66 (m, 2H) 4.79 (s, 1H) 4.83 (s, 1H) 4.91 (s, 1H) 4.98 (s, 1H) 5.57 (dt, J=15.2, 7.0 Hz, 1H) 5.69 (dt, J=14.8, 6.2 Hz, 1H)

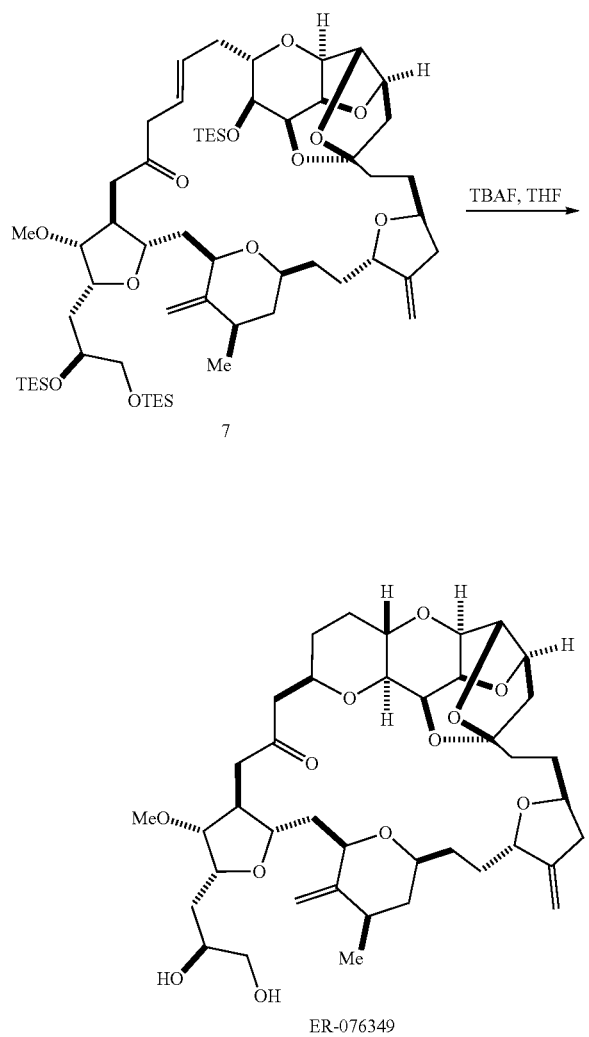

ER-076349

To a solution of compound 7 (3.4 mg, 3.167 μmol) in THF (0.5 mL) at ambient temperature was added TBAF (1.0 M, 0.025 mL, 0.025 mmol). The resulting solution was stirred for 25 h at ambient temperature and then purified by silica gel column chromatography using a 0-100% gradient of acetonitrile in ethyl acetate as eluent to provide 1.6 mg of the target product. The structure was confirmed by comparison of the $^1$H NMR spectrum to that of an authentic sample.

$^1$H NMR (400 MHz, CDCl$_3$) δ ppm 1.10 (d, J=6.6 Hz, 1H) 1.19-1.83 (m, 8H) 1.92-2.36 (m, 12H) 2.39-2.58 (m, 3H) 2.72 (dd, J=16.0, 9.8 Hz, 1H) 2.82-2.92 (m, 2H) 2.94-3.02 (m, 1H) 3.29 (d, J=3.1 Hz, 1H) 3.44 (s, 3H) 3.51-3.69 (m, 4H) 3.86 (dt, J=9.0, 3.1 Hz, 1H) 3.89-3.99 (m, 3H) 4.03 (dd, J=6.3, 4.3 Hz, 1H) 4.08-4.16 (m, 1H) 4.19 (dd, J=6.6, 4.7 Hz, 1H) 4.26-4.41 (m, 3H) 4.61 (t, J=4.7 Hz, 1H) 4.69 (t, J=4.3 Hz, 1H) 4.82 (d, J=1.6 Hz, 1H) 4.89 (br. s., 1H) 4.93 (br. s, 1H) 5.07 (d, J=2.0 Hz, 1H)

Example 5: Preparation of a Compound of Formula (ID) through C.2-C.3 Macrocyclization Methyl 2-((2S,3S,4R,5R)-5-((S)-2,3-bis((triethylsilyl)oxy)propyl)-2-(((2R,4R,6S)-6-(2-((2S,5S)-5-(2-((2S,3aR,4aR,5R,6S,7S,8aR,8bS)-7-(3-hydroxypropyl)-6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-4-methoxytetrahydrofuran-3-yl)acetate

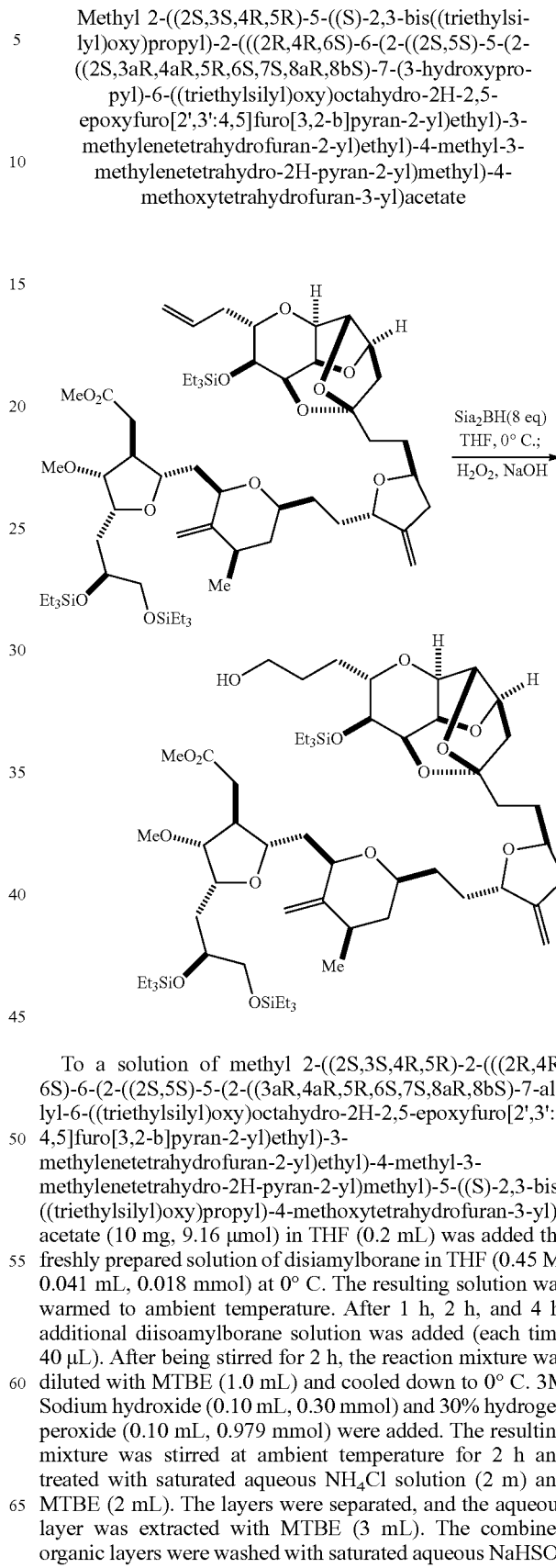

To a solution of methyl 2-((2S,3S,4R,5R)-2-(((2R,4R,6S)-6-(2-((2S,5S)-5-(2-((3aR,4aR,5R,6S,7S,8aR,8bS)-7-allyl-6-((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-5-((S)-2,3-bis((triethylsilyl)oxy)propyl)-4-methoxytetrahydrofuran-3-yl) acetate (10 mg, 9.16 μmol) in THF (0.2 mL) was added the freshly prepared solution of disiamylborane in THF (0.45 M, 0.041 mL, 0.018 mmol) at 0° C. The resulting solution was warmed to ambient temperature. After 1 h, 2 h, and 4 h, additional diisoamylborane solution was added (each time 40 μL). After being stirred for 2 h, the reaction mixture was diluted with MTBE (1.0 mL) and cooled down to 0° C. 3M Sodium hydroxide (0.10 mL, 0.30 mmol) and 30% hydrogen peroxide (0.10 mL, 0.979 mmol) were added. The resulting mixture was stirred at ambient temperature for 2 h and treated with saturated aqueous NH$_4$Cl solution (2 m) and MTBE (2 mL). The layers were separated, and the aqueous layer was extracted with MTBE (3 mL). The combined organic layers were washed with saturated aqueous NaHSO$_3$ (1 mL) and 30% aqueous NaCl (1 mL) and dried over MgSO₄. Filtration followed by concentration in vacuo and purification by silica gel column chromatography using a 20-33% gradient of ethyl acetate in n-heptane as eluent provided 3.6 mg of the target product.

¹H NMR (400 MHz, CDCl₃) δ ppm 0.53-0.66 (m, 18H) 0.91-0.99 (m, 27H) 1.08 (d, J=6.6 Hz, 3H) 1.17-1.24 (m, 1H) 1.36 (m, 2H) 1.65-1.85 (m, 9H) 1.88-2.03 (m, 6H) 2.14 (d, J=12.9 Hz, 2H) 2.21-2.32 (m, 3H) 2.35 (m, 1H) 2.40 (m, 1H) 2.59-2.69 (m, 1H) 3.19 (dd, J=9.6, 2.1 Hz, 1H) 3.29 (s, 3H) 3.43 (d, J=3.5 Hz, 1H) 3.49 (dd, J=10.2, 5.1 Hz, 2H) 3.56 (dd, J=10.9, 6.6 Hz, 1H) 3.62-3.69 (m, 2H) 3.69-3.72 (m, 4H) 3.78 (dd, J=9.0, 4.7 Hz, 1H) 3.80-3.90 (m, 3H) 3.97-4.06 (m, 2H) 4.18 (dd, J=6.8, 4.5 Hz, 1H) 4.24-4.31 (m, 2H) 4.34-4.41 (m, 1H) 4.57 (t, J=4.7 Hz, 1H) 4.68 (t, J=4.7 Hz, 1H) 4.80 (s, 1H) 4.82 (s, 1H) 4.87 (s, 1H) 4.96 (d, J=2.0 Hz, 1H).

dimethyl (3-((2S,3S,4R,5R)-5-((S)-2,3-bis((triethylsilyl)oxy)propyl)-2-(((2R,4R,6S)-6-(2-((2S,5S)-5-(2-((2S,3aR,4aR,5R,6S,7S,8aR,8bS)-7-(3-hydroxypropyl)-6-((triethylsilyl)oxy)octahydro-2H-2,5-epoxyfuro[2',3': 4,5]furo[3,2-b]pyran-2-yl)ethyl)-3-methylenetetrahydrofuran-2-yl)ethyl-4-methyl-3-methylenetetrahydro-2H-pyran-2-yl)methyl)-4-methoxytetrahydrofuran-3-yl)-2-oxopropyl) phosphonate propyl)-2-(((2R,4R,6S)-6-(2-((2S,5S)-5-(2-((3aR,4aR,5R,6S,7S,8aR,8bS)-7-(3-hydroxypropyl)-6-((triethylsilyl)oxy) octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-4-methoxytetrahydrofuran-3-yl)acetate (3.6 mg, 3.244 µmol) in THF (0.50 mL) was then added. The reaction mixture was stirred for 1.5 h at −78° C. and treated with saturated aqueous NH₄Cl solution (2 mL). The resulting mixture was diluted with ethyl acetate (2 mL) and warmed to ambient temperature. The layers were separated, and the aqueous layer was extracted with ethyl acetate (5 mL). The combined organic layers were dried over MgSO₄, filtered, concentrated, and purified by silica gel column chromatography using Heptane/EtOAc (1/1), EtOAc, EtOAc/MeCN (1/1), and DCM/MeOH (10/1) as eluents to provide 1 mg of the target product.

MS m/z 1202.2 [M+H]⁺, 1203.2, 1204.2. ¹H NMR (400 MHz, CDCl₃) δ ppm 0.55-0.66 (m, 18H) 0.92-0.99 (m, 27H) 1.07 (d, J=6.6 Hz, 3H) 1.15-2.18 (m, 22H) 2.20-2.30 (m, 1H) 2.64-2.70 (m, 1H) 3.07 (d, J=9.8 Hz, 1H) 3.13 (d, J=9.8 Hz, 1H) 3.16-3.24 (m, 1H) 3.33 (dd, J=10.2, 3.5 Hz, 1H) 3.33 (s, 3H) 3.48-3.59 (m, 4H) 3.63-3.72 (m, 2H) 3.73-3.88 (m, 4H) 3.77-3.79 (m, 3H) 3.81 (s, 3H) 3.99-4.06 (m, 2H) 4.16-4.21 (m, 1H) 4.26-4.31 (m, 2H) 4.34-4.40 (m, 1H) 4.57 (t, J=4.3 Hz, 1H) 4.68 (t, J=4.7 Hz, 1H) 4.79 (s, 1H) 4.84 (br. s, 1H) 4.86 (s, 1H) 4.97 (br. s, 1H)

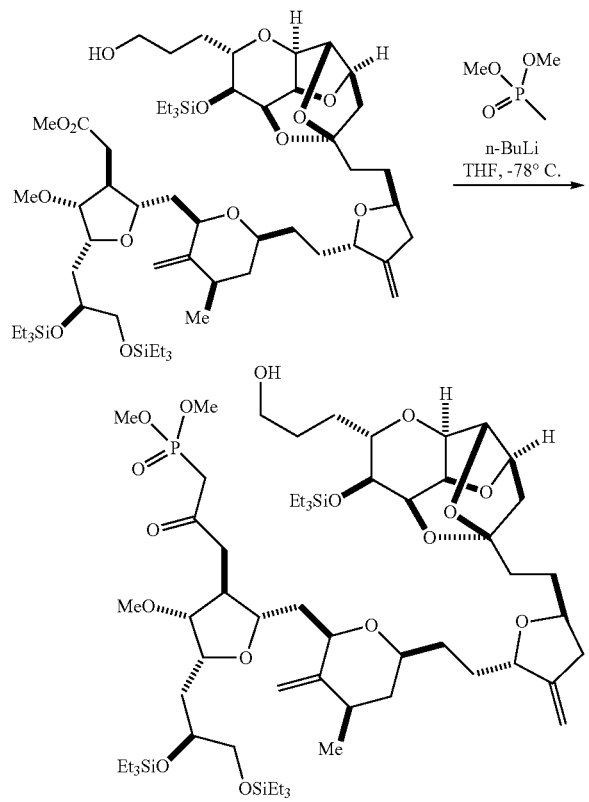

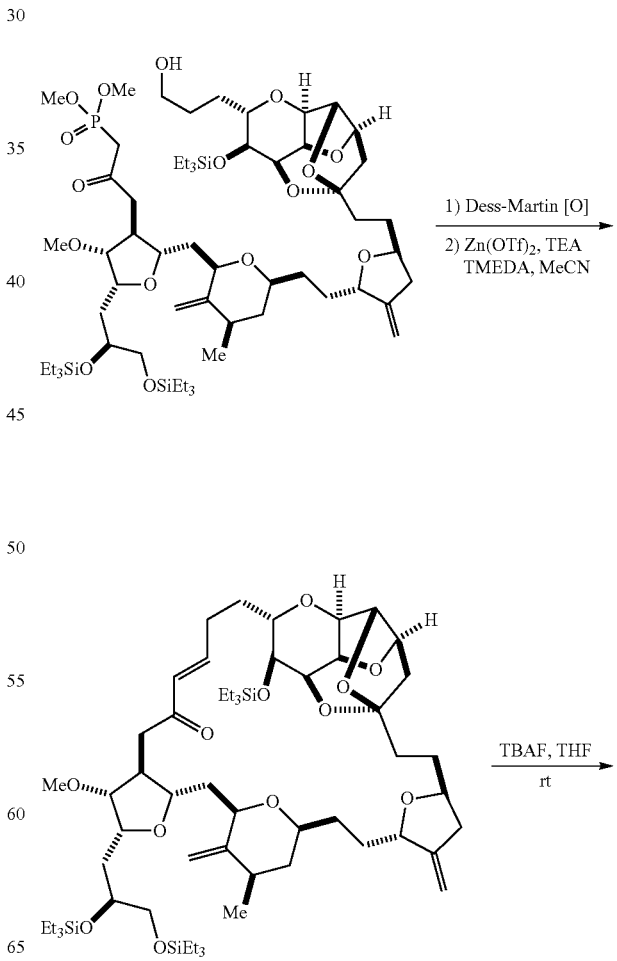

To a solution of dimethyl methylphosphonate (11 µL, 0.097 mmol) in THF (0.50 mL) was added n-BuLi (1.6 M, 0.061 mL, 0.097 mmol) at −78° C., and the resulting solution was stirred for 40 min at −78° C. A solution of methyl 2-((2S,3S,4R,5R)-5-((S)-2,3-bis((triethylsilyl)oxy)

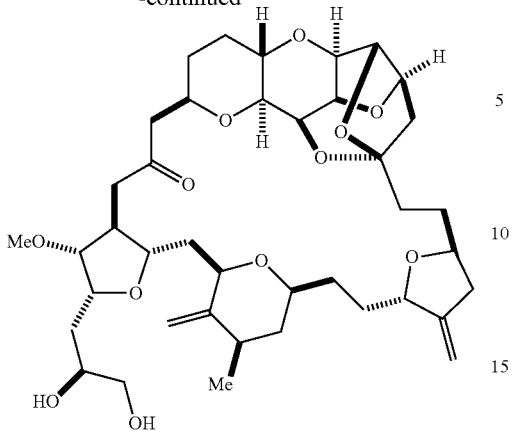

Dimethyl(3-((2S,3S,4R,5R)-5-((S)-2,3-bis((triethylsilyl)oxy)propyl)-2-(((2R,4R,6S)-6-(2-((2S,5S)-5-(2-((3aR,4aR,5R,6S,7S,8aR,8bS)-7-(3-hydroxypropyl)-6-(((triethylsilyl)oxy)octahydro-2H-2,5-epoxyfuro[2',3':4,5]furo[3,2-b]pyran-2-yl)ethyl)-3-methylenetetrahydrofuran-2-yl)ethyl)-4-methyl-3-methylenetetrahydro-2H-pyran-2-yl)methyl)-4-methoxytetrahydrofuran-3-yl)-2-oxopropyl)phosphonate (1 mg, 0.832 μmol) was dissolved in dichloromethane and treated with sodium bicarbonate (1.4 mg, 0.017 mmol) and Dess-Martin periodinane (3.5 mg, 8.3 μmol) at ambient temperature. After 2 h, the reaction mixture was diluted with MTBE (1 mL) and water (0.5 mL). Sodium thiosulfate (3 mg) was added, and the resulting mixture was stirred for 20 min at ambient temperature. The layers were separated, and the aqueous layer was extracted with EtOAc (2 mL). The combined organic layers were dried over MgSO$_4$ and concentrated in vacuo. The residue was diluted with toluene and filtered through a silica gel plug, which was then rinsed with EtOAc. The filtrate was concentrated in vacuo, and the resulting residue was dissolved in THF (1.0 mL). A slurry mixture of zinc trifluoromethanesulfonate (2.4 mg, 0.0067 mmol), TEA (3 μL, 0.020 mmol), and TMEDA (0.5 μL, 0.0033 mmol) in THF (2 mL) was added. The resulting reaction mixture was stirred at ambient temperature for 1 day and treated with MTBE (6 mL) and 30% aqueous NaCl (2 mL). The organic layer was separated and washed with 30% aqueous NaCl (1.5 mL). Drying, filtration, and concentration in vacuo gave the target product. MS m/z 1073.6 [M+H]$^+$. The crude macrocyclic product was dissolved in THF (0.5 mL) at ambient temperature and treated with 1.0 M TBAF in THF (0.020 mL, 0.02 mmol). After stirring at ambient temperature overnight, formation of the target product was confirmed by LCMS analysis with an authentic sample (retention time and MS data). MS m/z 731.6 [M+H]$^+$, 753.6 [M+Na]$^+$.

Example 6: Preparation of a Compound of Formula (VIIB)

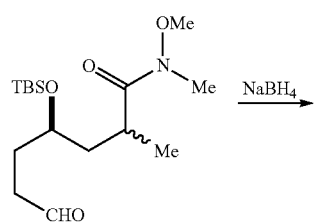

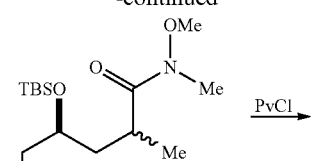

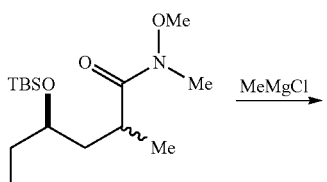

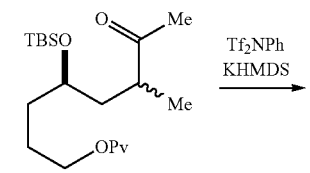

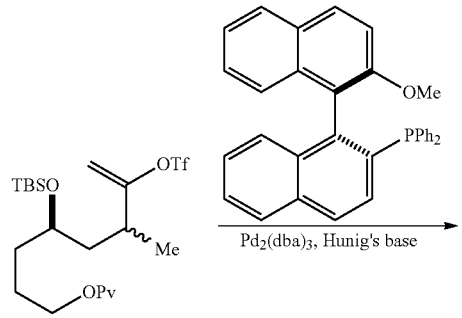

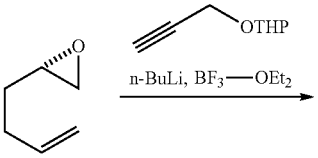

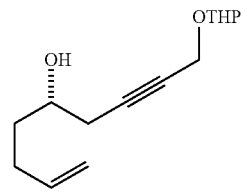

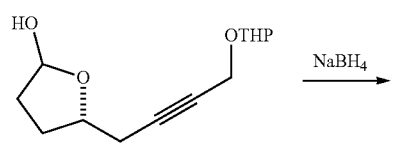

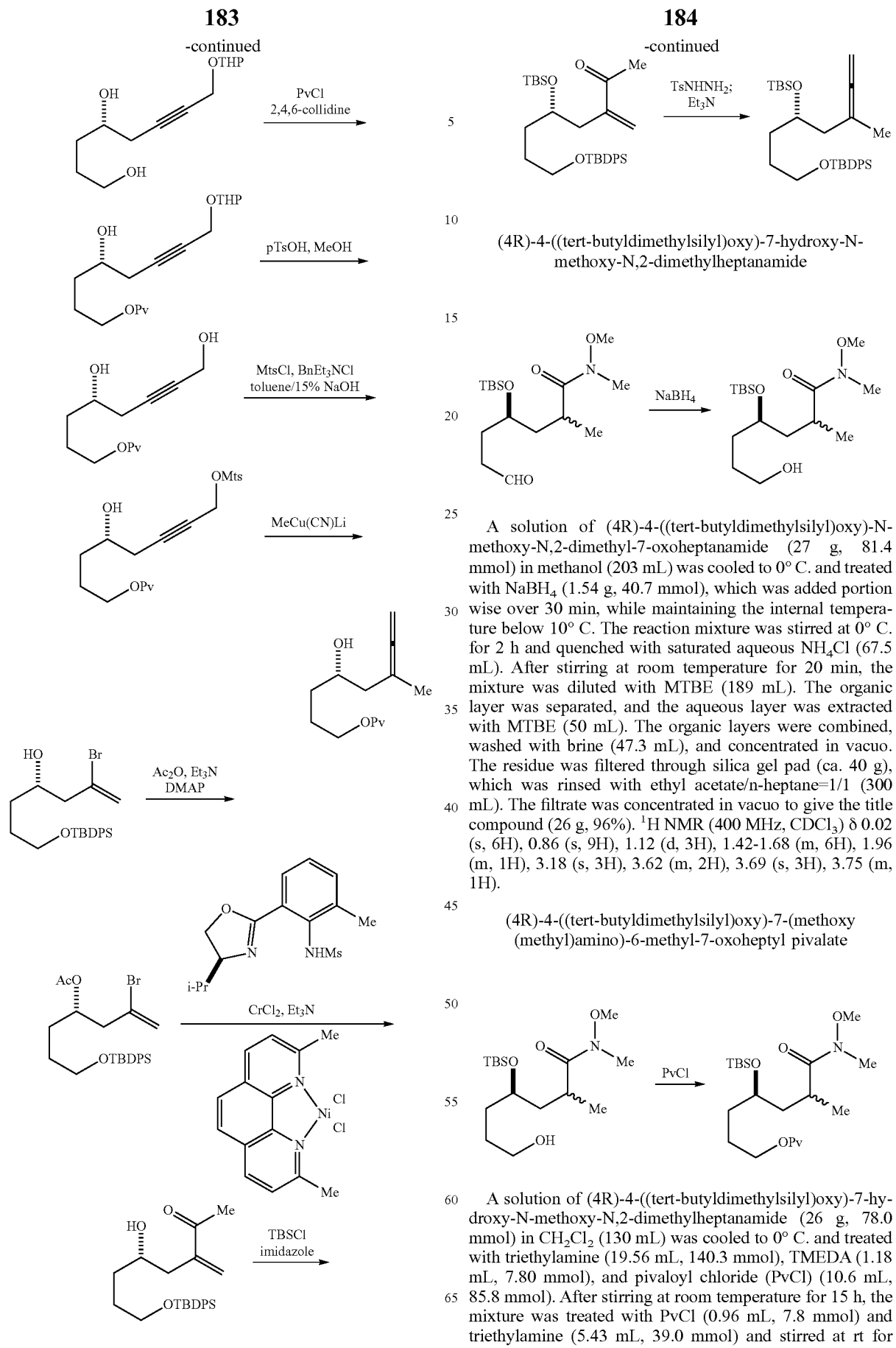

(4R)-4-((tert-butyldimethylsilyl)oxy)-7-hydroxy-N-methoxy-N,2-dimethylheptanamide A solution of (4R)-4-((tert-butyldimethylsilyl)oxy)-N-methoxy-N,2-dimethyl-7-oxoheptanamide (27 g, 81.4 mmol) in methanol (203 mL) was cooled to 0° C. and treated with NaBH₄ (1.54 g, 40.7 mmol), which was added portion wise over 30 min, while maintaining the internal temperature below 10° C. The reaction mixture was stirred at 0° C. for 2 h and quenched with saturated aqueous NH₄Cl (67.5 mL). After stirring at room temperature for 20 min, the mixture was diluted with MTBE (189 mL). The organic layer was separated, and the aqueous layer was extracted with MTBE (50 mL). The organic layers were combined, washed with brine (47.3 mL), and concentrated in vacuo. The residue was filtered through silica gel pad (ca. 40 g), which was rinsed with ethyl acetate/n-heptane=1/1 (300 mL). The filtrate was concentrated in vacuo to give the title compound (26 g, 96%). ¹H NMR (400 MHz, CDCl₃) δ 0.02 (s, 6H), 0.86 (s, 9H), 1.12 (d, 3H), 1.42-1.68 (m, 6H), 1.96 (m, 1H), 3.18 (s, 3H), 3.62 (m, 2H), 3.69 (s, 3H), 3.75 (m, 1H).

(4R)-4-((tert-butyldimethylsilyl)oxy)-7-(methoxy(methyl)amino)-6-methyl-7-oxoheptyl pivalate A solution of (4R)-4-((tert-butyldimethylsilyl)oxy)-7-hydroxy-N-methoxy-N,2-dimethylheptanamide (26 g, 78.0 mmol) in CH₂Cl₂ (130 mL) was cooled to 0° C. and treated with triethylamine (19.56 mL, 140.3 mmol), TMEDA (1.18 mL, 7.80 mmol), and pivaloyl chloride (PvCl) (10.6 mL, 85.8 mmol). After stirring at room temperature for 15 h, the mixture was treated with PvCl (0.96 mL, 7.8 mmol) and triethylamine (5.43 mL, 39.0 mmol) and stirred at rt for another 5 h. The reaction was quenched with water (260 mL). The organic layer was separated, and the aqueous layer was extracted with MTBE (260 mL). The organic layers were combined, washed with brine, and dried over MgSO$_4$ to give the title compound (32.07 g, 99%). $^1$H NMR (400 MHz, CDCl$_3$) δ 0.02 (s, 6H), 0.86 (s, 9H), 1.12 (d, 3H), 1.18 (s, 9H), 1.40-1.55 (m, 4H), 1.68 (m, 2H), 1.92 (m, 1H), 3.17 (s, 3H), 3.69 (m, 4H), 4.03 (t, 2H).

(4R)-4-((tert-butyldimethylsilyl)oxy)-6-methyl-7-oxooctyl pivalate

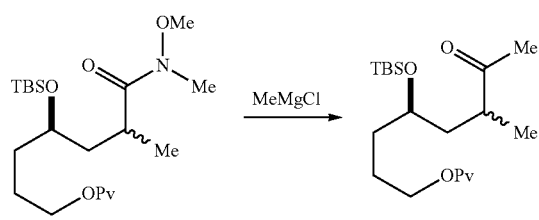

A solution of (4R)-4-((tert-butyldimethylsilyl)oxy)-7-(methoxy(methyl)amino)-6-methyl-7-oxoheptyl pivalate (32.07 g, 76.79 mmol) in THF (96 mL) was cooled to −20° C. and treated with 3 M MeMgCl in THF (30.7 mL, 92.1 mmol) over 10 min, while maintaining the internal temperature below −10° C. The mixture was warmed up to 0° C. over 2 h and stirred at 0° C. for 13 h. Additional 3 M MeMgCl in THF (5.12 mL, 15.4 mmol) was added and stirring was continued at 0° C. for another 5 h. The reaction was quenched with saturated aqueous NH$_4$Cl (80 mL) and extracted twice with MTBE (96 mL). The organic layers were combined, dried over MgSO$_4$ and concentrated in vacuo to give the title compound (28.64 g, 100%). $^1$H NMR (400 MHz, CDCl$_3$) δ 0.02 (s, 6H), 0.86 (s, 9H), 1.10 (d, 3H), 1.19 (s, 9H), 1.34 (m, 1H), 1.50 (m, 2H), 1.64 (m, 2H), 1.88 (m, 1H), 2.13 (s, 3H), 2.68 (m, 1H), 3.68 (m, 1H), 4.03 (t, 2H).

(4R)-4-((tert-butyldimethylsilyl)oxy)-6-methyl-7-(((trifluoromethyl)sulfonyl)oxy)oct-7-en-1-yl pivalate

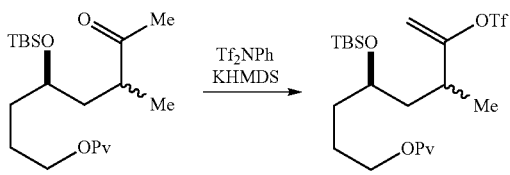

A mixture of (4R)-4-((tert-butyldimethylsilyl)oxy)-6-methyl-7-oxooctyl pivalate (15.0 g, 40.3 mmol) and 1,1,1-trifluoro-N-phenyl-N-(trifluoromethyl)sulfonyl methanesulfonamide (21.6 g, 60.4 mmol) in THF (150 mL) was cooled to −20° C. and treated with 0.5 M KHMDS in toluene (105 mL, 52.3 mmol) over 20 min, while maintaining the internal temperature below −20° C. The mixture was stirred at −20° C. for 1 h. Additional 0.5 M KHMDS in toluene (8.05 mL, 4.03 mmol) was added, and stirring was continued at −20° C. for another 1 h. The reaction was quenched with saturated aqueous NH$_4$Cl (105 mL) and extracted twice with n-heptane (105 mL). The organic layers were combined, washed with brine, and concentrated in vacuo. The residue was treated with n-heptane (80 mL) and aged in a freezer (−20° C.) overnight. The precipitate was filtered and rinsed with n-heptane. The filtrate was concentrated in vacuo and purified by column chromatography (ethyl acetate/n-heptane=1/20 to 1/10) to give the title compound (14.25 g, 70%). $^1$H NMR (400 MHz, CDCl$_3$) δ 0.02 (d, 6H), 0.86 (s, 9H), 1.15 (d, 3H), 1.18 (s, 9H), 1.40-1.55 (m, 4H), 1.6-1.71 (m, 2H), 2.54 (m, 1H), 3.74 (m, 1H), 4.03 (t, 2H), 4.90 (d, 1H), 5.09 (d, 1H).

(R)-4-((tert-butyldimethylsilyl)oxy)-6-methylocta-6,7-dien-1-yl pivalate

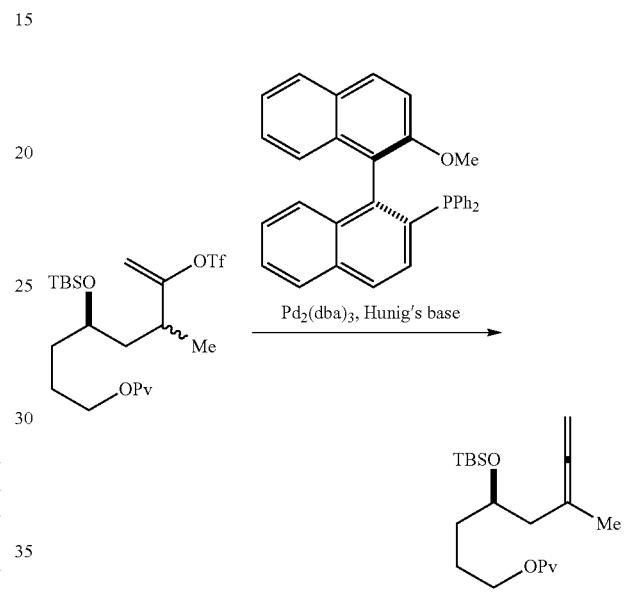

A mixture of Pd$_2$(dba)$_3$ (7.3 mg, 7.9 μmol) and (S)-(−)-(diphenylphosphino)-2'-methoxy-1,1'-binaphthyl (0.015 g, 0.032 mmol) was purged with nitrogen and treated with n-heptane (2.0 mL). The mixture was stirred at 50° C. for 4.5 h. After cooling to room temperature (rt), the mixture was filtered through Celite® pad to remove catalyst, and the Celite® pad was rinsed with n-heptane. After concentration, the residue was purified by column chromatography (ethyl acetate/n-heptane=1/20 to 1/10) to give the title compound (130 mg, 93%). $^1$H NMR (400 MHz, CDCl$_3$) δ 0.02 (s, 6H), 0.84 (s, 9H), 1.18 (s, 9H), 1.40-1.75 (m, 4H), 1.68 (t, 3H), 2.02-2.17 (m, 2H), 3.80 (m, 1H), 4.03 (t, 2H), 4.55 (m, 2H).

(5S)-9-((tetrahydro-2H-pyran-2-yl)oxy)non-1-en-7-yn-5-ol

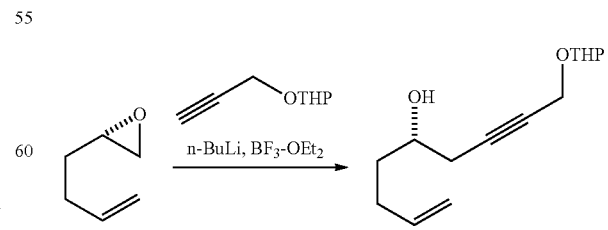

A solution of tetrahydro-2-(2-propynyloxy)-2H-pyran (27 g, 192.6 mmol) in THF (270 mL) was cooled to −78° C. and treated with 2 M n-BuLi in cyclohexane (99 mL, 198.4 mmol) over 30 min, while maintaining the internal temperature below −65° C. After stirring for 40 min at −78° C., to the mixture was added BF$_3$.OEt$_2$ (25.1 mL, 198.4 mmol) over 5 min, the resulting mixture was stirred at −78° C. for 15 min. A solution of (S)-2-(but-3-en-1-yl)oxirane (20.79 g, 211.9 mmol) in THF (54.0 mL) was added over 30 min, while maintaining the internal temperature below −65° C., and stirring was continued at −78° C. for 1 h. The reaction was quenched with saturated aqueous NH$_4$Cl (270 mL) and warmed to rt. The organic layer was separated and the aqueous layer was extracted with MTBE (270 mL). The organic layers were combined, washed with saturated aqueous NaHCO$_3$ (81 mL) and brine (80 mL), and dried over MgSO$_4$ to give the title compound (40.1 g, 87%). $^1$H NMR (400 MHz, CDCl$_3$) δ 1.45-1.88 (m, 7H), 2.00-2.30 (m, 3H), 2.34-2.50 (m, 2H), 3.51 (m, 1H), 3.70-3.88 (m, 2H), 4.25 (m, 2H), 4.80 (m, 1H), 5.00 (m, 2H), 5.81 (m, 1H).

(4S)-4-hydroxy-8-((tetrahydro-2H-pyran-2-yl)oxy) oct-6-ynal

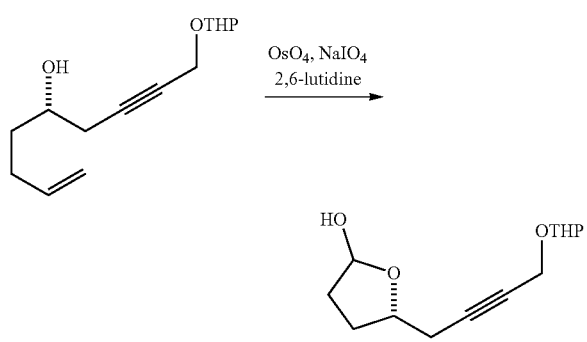

A mixture of (5S)-9-((tetrahydro-2H-pyran-2-yl)oxy)non-1-en-7-yn-5-ol (38 g, 159.4 mmol), 1,4-dioxane (798 mL), and water (266 mL) was treated with sodium periodate (136 g, 637.8 mmol) and 2,6-lutidine (37.1 mL, 319.0 mmol). The mixture was cooled with an ice-bath and treated with OsO$_4$ (0.020 g, 0.08 mmol); the ice-bath was removed, and the mixture was stirred at room temperature (rt) for 20 min. Additional OsO$_4$ (0.020 g, 0.08 mmol) was added, and stirring was continued at rt for another 6 h. The mixture was diluted with water (1824 mL) and CH$_2$Cl$_2$ (836 mL). The organic layer was separated, and the aqueous layer was extracted with CH$_2$Cl$_2$ (836 mL). The organic layers were combined, dried over MgSO$_4$, and concentrated in vacuo to give the title compound (55 g, 144%).

(4S)-8-((tetrahydro-2H-pyran-2-yl)oxy)oct-6-yne-1, 4-diol

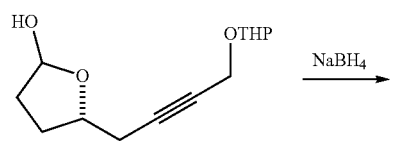

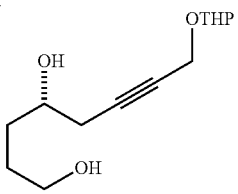

A solution of (4S)-4-hydroxy-8-((tetrahydro-2H-pyran-2-yl)oxy)oct-6-ynal (55 g, 160 mmol) in methanol (308 mL) was cooled to 0° C. and treated with sodium borohydride (1.818 g, 48.066 mmol), which was added portion wise. After stirring at 0° C. for 1 h, additional sodium borohydride (0.606 g, 16.0 mmol) was added in two portions with a 0.5 h interval, and stirring was continued at 0° C. for another 0.5 h. The reaction was quenched with saturated aqueous NH$_4$Cl (308 mL) and stirred at room temperature (rt) for 0.5 h. The mixture was extracted sequentially with MTBE (308 mL×2) and ethyl acetate (308 mL×2). The organic layers were combined and washed with brine (116 mL). After concentration, the residue was loaded on silica gel pad and eluted with MTBE (ca. 600 mL). The filtrate was concentrated in vacuo to give the title compound (33.66 g, 87%). $^1$H NMR (400 MHz, CDCl$_3$) δ 1.48-1.86 (m, 10H), 2.34-2.50 (m, 2H), 3.51 (m, 1H), 3.60-3.72 (m, 2H), 3.72-3.88 (m, 2H), 4.25 (m, 2H), 4.80 (m, 1H).

(4S)-4-hydroxy-8-((tetrahydro-2H-pyran-2-yl)oxy) oct-6-yn-1-yl pivalate

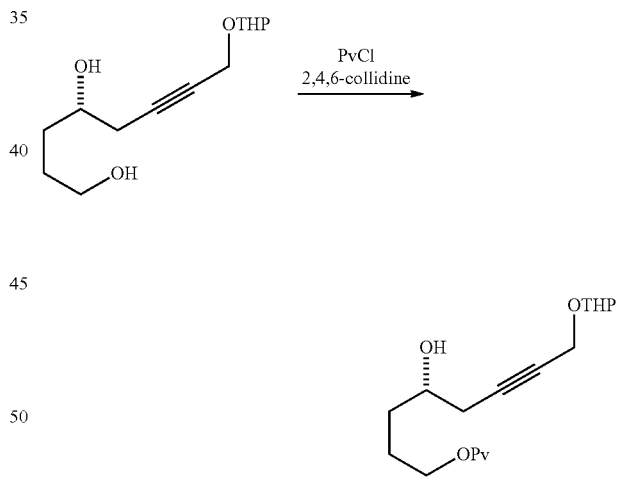

A solution of (4S)-8-((tetrahydro-2H-pyran-2-yl)oxy)oct-6-yne-1,4-diol (15.0 g, 61.9 mmol) in CH$_2$Cl$_2$ (120 mL) was treated with 2,4,6-collidine (34.4 mL, 260 mmol) and cooled to 0° C. After addition of pivaloyl chloride (8.38 mL, 68.094 mmol) and DMAP (0.378 g, 3.095 mmol), the mixture was stirred at 0° C. for 4.5 h. The reaction was quenched with water (105 mL) and extracted twice with MTBE (105 mL). The organic layers were combined, washed with 1 N HCl (105 mL) and brine (45.0 mL), and concentrated in vacuo to give the title compound (22 g, 109%). $^1$H NMR (400 MHz, CDCl$_3$) δ 1.21 (s, 9H), 1.48-1.86 (m, 10H), 2.30-2.50 (m, 2H), 3.52 (m, 1H), 3.72-3.86 (m, 2H), 4.06 (m, 2H), 4.16-4.32 (m, 2H), 4.79 (m, 1H).

(S)-4,8-dihydroxyoct-6-yn-1-yl pivalate

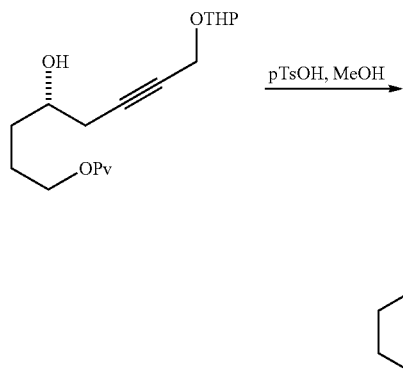

A solution of (4S)-4-hydroxy-8-((tetrahydro-2H-pyran-2-yl)oxy)oct-6-yn-1-yl pivalate (22 g, 67.4 mmol) in methanol (110 mL) was treated with p-TsOH (0.641 g, 3.37 mmol). After being stirred at rt for 5.5 h, the mixture was treated with saturated aqueous NaHCO$_3$ (56.6 mL) and concentrated in vacuo. The residue was sequentially extracted with MTBE (154 mL) and ethyl acetate (154 mL×2). The organic layers were combined and washed with brine. After concentration, the residue was purified by silica gel column chromatography (ethyl acetate/n-heptane=1/10 to 3/2) to give the title compound (7.2 g, 37% for 5 steps). $^1$H NMR (400 MHz, CDCl$_3$) δ 1.19 (s, 9H), 1.55-1.63 (m, 2H), 1.63-1.83 (m, 2H), 2.35 (m, 1H), 2.47 (m, 1H), 3.77 (m, 1H), 4.08 (t, 2H), 4.25 (m, 2H).

(S)-4-hydroxy-8-((mesitylsulfonyl)oxy)oct-6-yn-1-yl pivalate

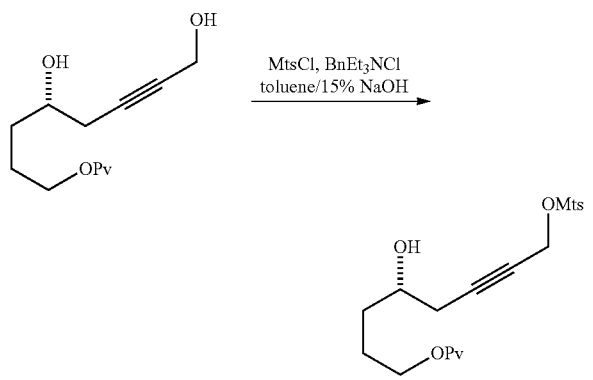

A 0° C., a mixture of (S)-4,8-dihydroxyoct-6-yn-1-yl pivalate (6.67 g, 27.527 mmol), benzyltriethylammonium chloride (0.313 g, 1.38 mmol), toluene (66.7 mL), and 15% aqueous NaOH (66.7 mL, 250 mmol) was treated with 2-mesitylenesulfonyl chloride (MtsCl) (3.61 g, 16.5 mmol) in toluene (40.0 mL) over 20 min, while maintaining the internal temperature below 5° C. The mixture was stirred at 0° C. for another 1 h. The organic layer was separated, and the aqueous layer was extracted with MTBE (74.1 mL). The organic layers were combined and dried over MgSO$_4$. After concentration, the residue was purified by silica gel column chromatography (ethyl acetate/n-heptane=1/10 to 5/3) to give the title compound (2.49 g, 21%). $^1$H NMR (400 MHz, CDCl$_3$) δ 1.19 (s, 9H), 1.45-1.55 (m, 2H), 1.55-1.83 (m, 4H), 2.30 (s, 3H), 2.62 (s, 6H), 3.65 (m, 1H), 4.08 (t, 2H), 4.69 (m, 2H), 6.99 (s, 2H).

(S)-4-hydroxy-6-methylocta-6,7-dien-1-yl pivalate

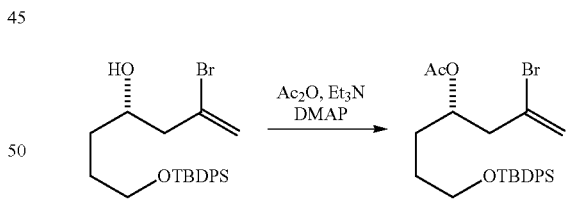

A suspension of copper(I) cyanide (0.788 g, 8.80 mmol) in THF (21.4 mL) was cooled to −78° C. and treated with 1.6 M MeLi in diethyl ether (5.50 mL, 8.80 mmol) over 20 min, while maintaining the internal temperature below −60° C. The mixture was stirred −78° C. for 20 min and warmed to 0° C. over 40 min. The mixture was cooled to −78° C., stirred for another 10 min, and treated with a solution of (S)-4-hydroxy-8-((mesitylsulfonyl)oxy)oct-6-yn-1-yl pivalate (2.49 g, 5.87 mmol) in THF (10.7 mL) over 20 min, while maintaining the internal temperature below −65° C. After stirring at −78° C. for 1 h, the reaction was quenched with a mixture of saturated aqueous NH$_4$Cl (37.4 mL) and 28% aqueous NH$_4$OH (4.98 mL), and warmed to room temperature (rt). The organic layer was separated, and the aqueous layer was extracted twice with MTBE (24.90 mL). The organic layers were combined and washed with brine. After concentration, the residue was purified by silica gel column chromatography (ethyl acetate/n-heptane=1/10 to 1/3) to give the title compound (1.136 g, 81%). $^1$H NMR (400 MHz, CDCl$_3$) δ 1.28 (s, 9H), 1.48-1.56 (m, 2H), 1.65-1.75 (m, 3H), 1.75-1.85 (m, 2H), 2.00-2.13 (m, 2H), 3.78 (m, 1H), 4.08 (m, 2H), 4.68 (m, 2H).

(S)-2-bromo-7-((tert-butyldiphenylsilyl)oxy)hept-1-en-4-yl acetate

A solution of (S)-2-bromo-7-(tert-butyldiphenylsilyl)oxy)hept-1-en-4-ol (6.0 g, 13.408 mmol) in CH$_2$Cl$_2$ (48.0 mL) was treated with triethylamine (3.74 mL, 26.8 mmol), acetic anhydride (1.52 mL, 16.1 mmol), and DMAP (0.164 g, 1.34 mmol). After stirring at room temperature (rt) for 20 h, the reaction was quenched with water (30.0 mL) and diluted with MTBE (30.0 mL). The organic layer was separated and washed with brine. After concentration, the residue was purified by silica gel column chromatography (ethyl acetate/n-heptane=1/20 to 1/8) to give the title compound (5.254 g, 80%). $^1$H NMR (400 MHz, CDCl$_3$) δ 1.05 (s, 9H), 1.52-1.70 (m, 3H), 1.76 (m, 1H), 2.02 (s, 3H), 2.60 (dd, 1H), 2.73 (dd, 1H), 3.68 (m, 2H), 5.19 (m, 1H), 5.49 (s, 1H), 5.63 (s, 1H), 7.39 (m, 6H), 7.65 (m, 4H).

(S)-8-((tert-butyldiphenylsilyl)oxy)-5-hydroxy-3-methyleneoctan-2-one

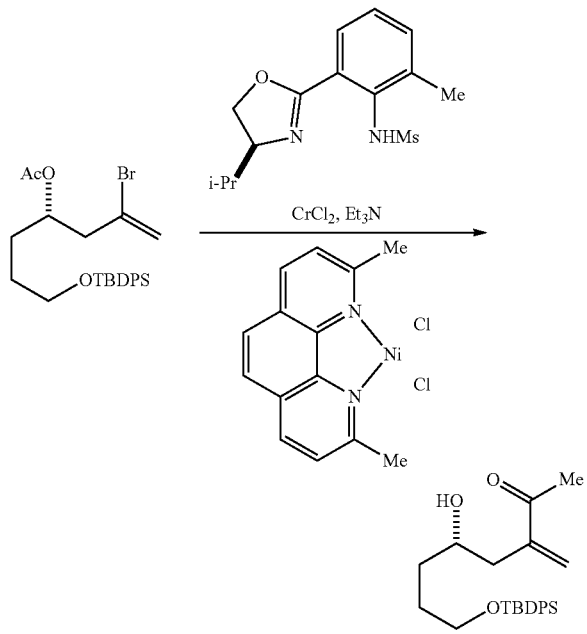

A solution of (S)—N-(2-(4-isopropyl-4,5-dihydrooxazol-2-yl)-6-methylphenyl)methanesulfonamide (2.44 g, 8.23 mmol) in a degassed THF (26.0 mL) was treated with chromium(II) chloride (1.01 g, 8.23 mmol), purged with nitrogen for 5 min, and heated to 30° C. After addition of triethylamine (1.15 mL, 8.23 mmol), the mixture was stirred at 30-35° C. for 1 h. The mixture was cooled to 0° C., treated with nickel(II) chloride 2,9-dimethyl-1,10-phenanthroline complex (0.090 g, 0.27 mmol), purged with nitrogen for 5 min, and then treated with a solution of (S)-2-bromo-7-((tert-butyldiphenylsilyl)oxy)hept-1-en-4-yl acetate (1.3 g, 2.7 mmol) in THF (10 mL) (8 mL+2 mL rinse). The mixture was stirred at 0° C. for 10 min and at rt for 2 h. The reaction mixture was treated with Florisil® (5.8 g) and stirred at rt for 30 min. The mixture was diluted with n-heptane (19.5 mL), filtered through florisil pad and rinsed with MTBE (19.5 mL). The filtrate was washed with water (13 mL) and brine (6.50 mL). After concentration, the residue was purified by column chromatography (ethyl acetate/n-heptane=1/10 to 1/2) to give the title compound (613 mg, 56%). $^1$H NMR (400 MHz, CDCl$_3$) δ 1.01 (s, 9H), 1.42-1.70 (m, 4H), 2.32 (dd, 1H), 2.36 (s, 3H), 2.55 (m, 1H), 3.69 (m, 3H), 5.90 (s, 1H), 6.11 (s, 1H), 7.39 (m, 6H), 7.65 (m, 4H).

(S)-5-((tert-butyldimethylsilyl)oxy)-8-((tert-butyldiphenylsilyl)oxy)-3-methyleneoctan-2-one

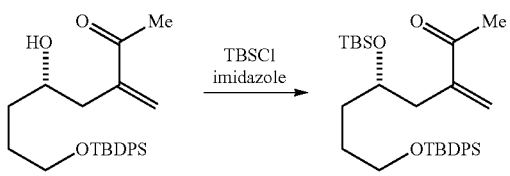

A solution of (S)-8-((tert-butyldiphenylsilyl)oxy)-5-hydroxy-3-methyleneoctan-2-one (0.643 g, 1.57 mmol) in DMF (5.14 mL) was treated with TBSCl (0.283 g, 1.88 mmol) and imidazole (0.213 g, 3.13 mmol). The mixture was stirred at rt for 4.5 h. The reaction was quenched with water (12.86 mL) and extracted twice with MTBE (19.29 mL). The organic layers were combined, and washed with water (12.9 mL) and brine (6.43 mL). After concentration, the residue was purified by column chromatography (ethyl acetate/n-heptane=1/10 to 1/8) to give the title compound (456 mg, 56%). $^1$H NMR (400 MHz, CDCl$_3$) δ 0.00 (s, 6H), 0.88 (s, 9H), 1.03 (s, 9H), 1.42-1.70 (m, 4H), 2.31 (s, 3H), 2.32 (dd, 1H), 2.44 (dd, 1H), 3.63 (t, 2H), 3.79 (m, 1H), 5.81 (s, 1H), 6.04 (s, 1H), 7.39 (m, 6H), 7.66 (m, 4H).

(S)-2,2,3,3,11,11-hexamethyl-5-(2-methylbuta-2,3-dien-1-yl)-10,10-diphenyl-4,9-dioxa-3,10-disiladodecane

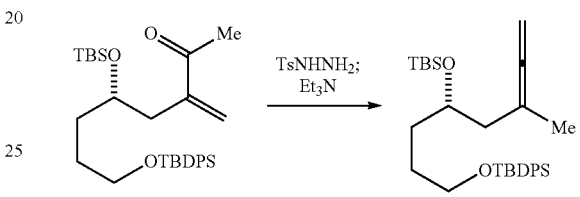

A solution of (S)-5-(tert-butyldimethylsilyl)oxy)-8-((tert-butyldiphenylsilyl)oxy)-3-methyleneoctan-2-one (0.20 g, 0.381 mmol) in ethanol (2.0 mL) was treated with p-toluenesulfonyl hydrazide (0.078 g, 0.42 mmol) and stirred at rt for 59 h. The resulting mixture was treated with ethanol (2.000 mL), triethylamine (0.11 mL, 0.76 mmol), and molecular sieves 4 Å (500 mg). After being stirred at 85° C. (bath) for 1 d, the mixture was filtered through Celite® pad to remove molecular sieves and rinsed with MTBE (20.0 mL). The filtrate was washed with water (5 mL) and brine (5 mL) and concentrated in vacuo. The residue was purified by silica gel column chromatography (ethyl acetate/n-heptane=1/20 to 1/10) to give the title compound (68 mg, 35%). $^1$H NMR (400 MHz, CDCl$_3$) δ 0.01 (s, 3H), 0.02 (s, 3H), 0.87 (s, 9H), 1.04 (s, 9H), 1.42-1.66 (m, 4H), 1.68 (t, 3H), 2.00-2.20 (m, 2H), 3.63 (t, 2H), 3.79 (m, 1H), 4.52 (m, 2H), 7.39 (m, 6H), 7.66 (m, 4H).

Example 7: Preparation of a Compound of Formula (VIIC)

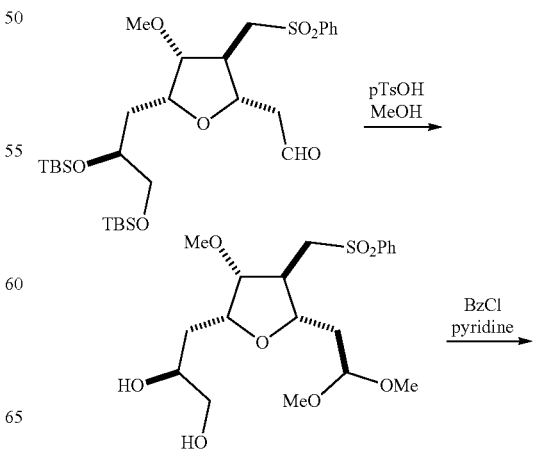

193
-continued
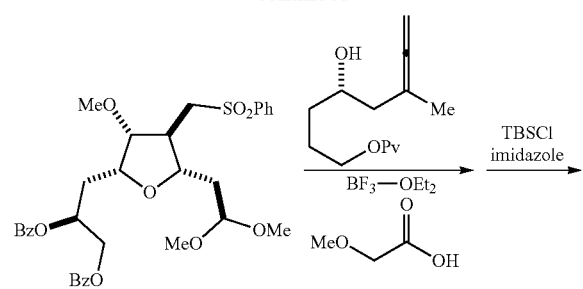
TBSCl
imidazole
→
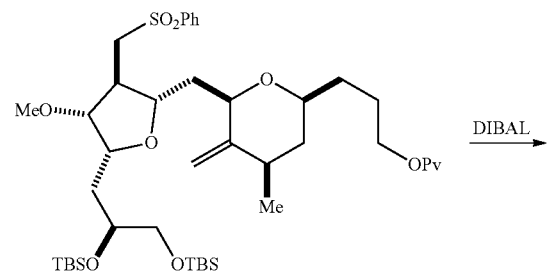
DIBAL
→
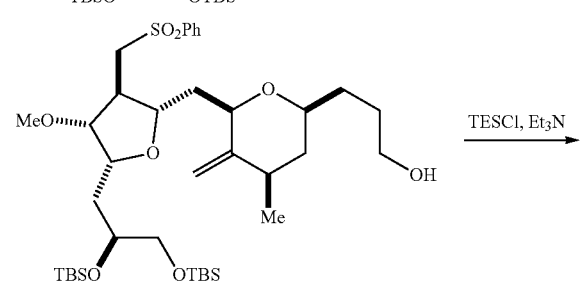
TESCl, Et₃N
→
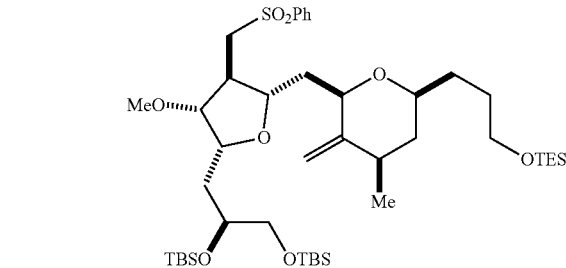
pTsOH
MeOH
→
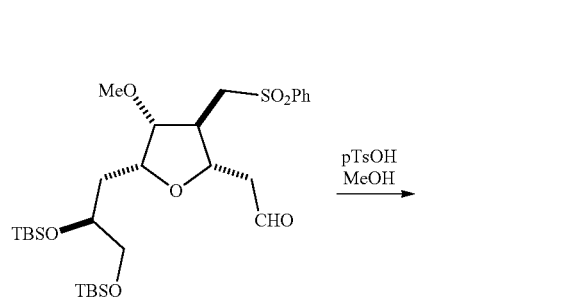
BzCl
pyridine
→
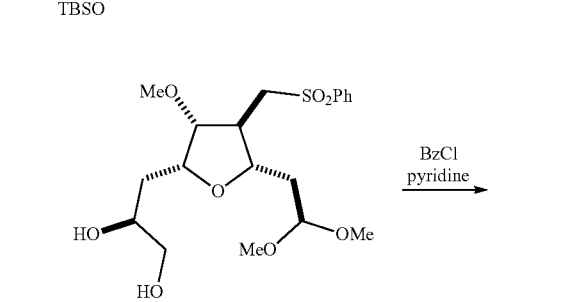
194
-continued
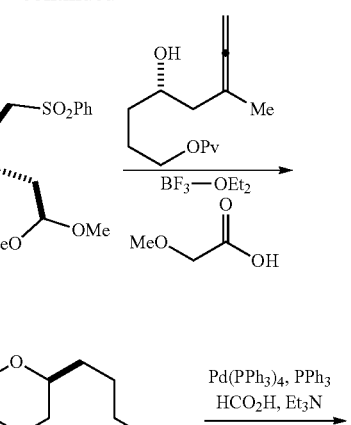
TBSCl
imidazole
→
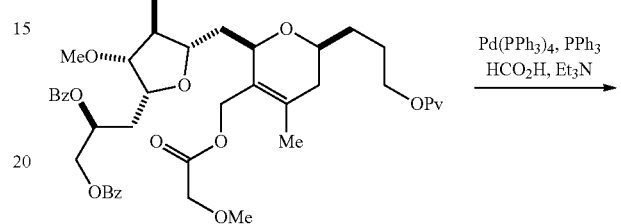
Pd(PPh₃)₄, PPh₃
HCO₂H, Et₃N
→
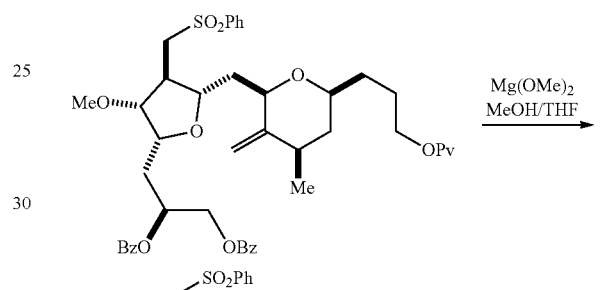
Mg(OMe)₂
MeOH/THF
→
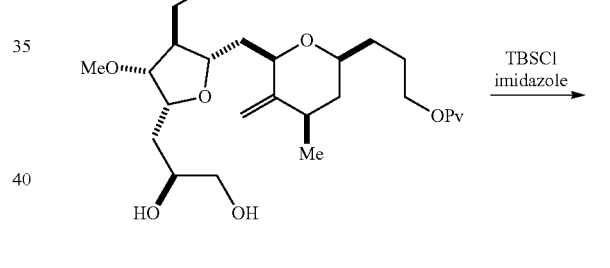
TBSCl
imidazole
→
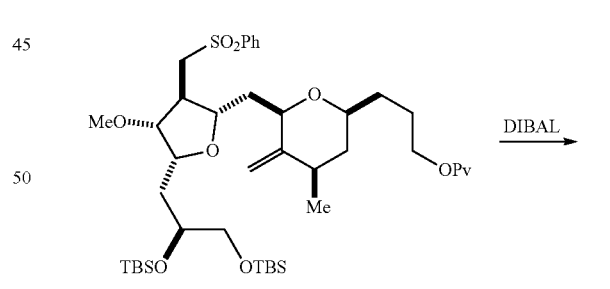
DIBAL
→
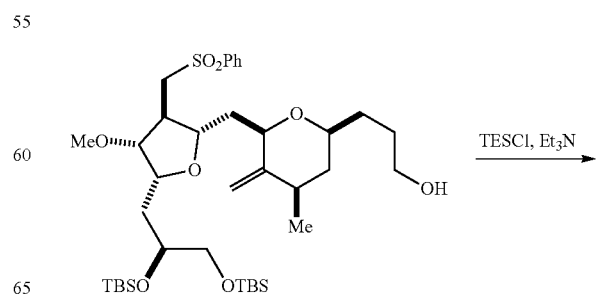
TESCl, Et₃N
→

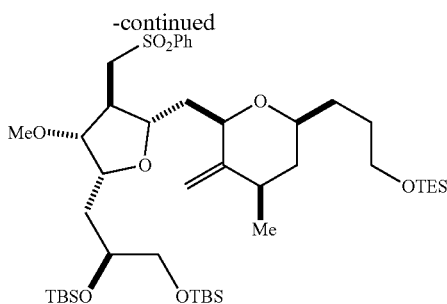

(S)-3-((2R,3R,4S,5S)-5-(2,2-dimethoxyethyl)-3-methoxy-4-((phenylsulfonyl)methyl) tetrahydrofuran-2-yl)propane-1,2-diol

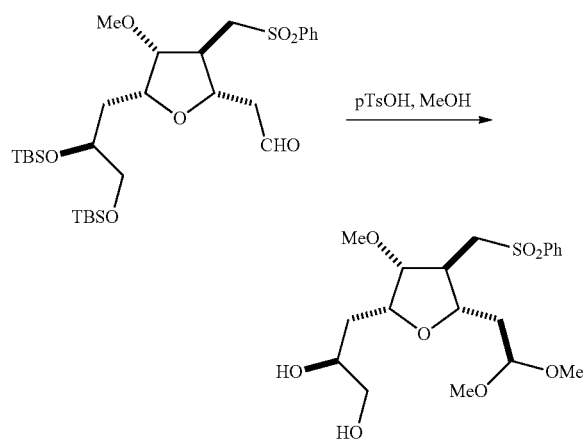

A solution of 2-((2S,3S,4R,5R)-5-((S)-2,3-bis((tert-butyldimethylsilyl)oxy)propyl)-4-methoxy-3-((phenylsulfonyl)methyl) tetrahydrofuran-2-yl)acetaldehyde (20.0 g, 33.28 mmol) in methanol (100 mL) was treated with CSA (0.773 g, 3.33 mmol) and stirred at rt for 3 d. The reaction was quenched with saturated aqueous NaHCO$_3$ (50 mL) and extracted with MTBE (100 mL) and ethyl acetate (100 mL×3). The organic layers were combined, dried over MgSO$_4$, and concentrated in vacuo to give the title compound (19.79 g). $^1$H NMR (400 MHz, CDCl$_3$) δ 1.80 (m, 1H), 1.85-2.00 (m, 3H), 2.56 (m, 1H), 3.12 (m, 2H), 3.28 (s, 3H), 3.31 (s, 3H), 3.42 (s, 3H), 3.55 (m, 1H), 3.62-3.71 (m, 2H), 3.90-3.98 (m, 3H), 4.43 (m, 1H), 7.60 (m, 2H), 7.69 (m, 1H), 7.98 (m, 2H).

(S)-3-((2R,3R,4S,5S)-5-(2,2-dimethoxyethyl)-3-methoxy-4-((phenylsulfonyl)methyl) tetrahydrofuran-2-yl)propane-1,2-diyl dibenzoate

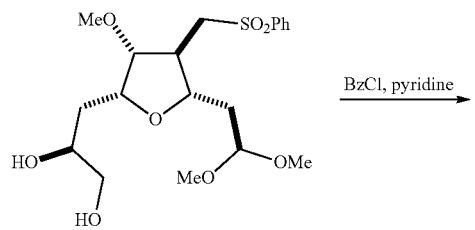

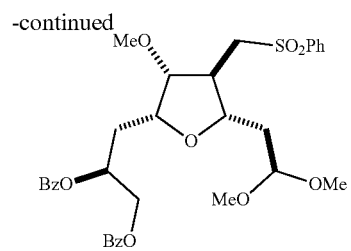

A solution of (S)-3-((2R,3R,4S,5S)-5-(2,2-dimethoxyethyl)-3-methoxy-4-((phenylsulfonyl)methyl) tetrahydrofuran-2-yl)propane-1,2-diol (19.79 g, 47.29 mmol) in pyridine (99 mL, 1223.429 mmol) was cooled to 0° C. and treated with benzoyl chloride (12.08 mL, 104.0 mmol). The mixture was stirred at rt for 20 h. Additional reagents were added and stirring was continued for 3 d. The reaction was quenched with water (400 mL) and extracted with MTBE (200 mL×3). The organic layers were combined, washed with 1 N HCl (100 mL) and then with saturated aqueous NaHCO$_3$ (50 mL), dried over MgSO$_4$, and concentrated in vacuo.

The residue was dissolved in CH$_2$Cl$_2$ (297 mL) and treated with triethylamine (26.4 mL, 189.2 mmol), benzoyl chloride (10.98 mL, 94.58 mmol), and DMAP (0.289 g, 2.364 mmol). The mixture was stirred at rt for 24 h. More triethylamine (23.2 mL, 166.3 mmol), benzoyl chloride (7.74 mL, 66.6 mmol), and DMAP (0.578 g, 4.72 mmol) were added and stirring was continued at rt for 7 d. The reaction was quenched with water (300 mL). The organic layer was separated, and the aqueous layer was extracted with CH$_2$Cl$_2$ (150 mL). The organic layers were combined and concentrated in vacuo. The residue was purified by silica gel column chromatography (ethyl acetate/n-heptane=1/10 to 1/1) to give the title compound (17.82 g, 85% for two steps). $^1$H NMR (400 MHz, CDCl$_3$) δ 1.89 (m, 2H), 2.25 (m, 2H), 2.55 (m, 1H), 3.09 (m, 2H), 3.22 (s, 3H), 3.24 (s, 3H), 3.42 (s, 3H), 3.59 (m, 1H), 3.89 (m, 1H), 3.92 (m, 1H), 4.39 (m, 1H), 4.57 (d, 2H), 5.63 (m, 1H), 7.44 (m, 4H), 7.56 (m, 4H), 7.68 (m, 1H), 7.92 (d, 2H), 8.04 (m, 4H).

(S)-3-((2R,3R,4S,5S)-3-methoxy-5-(((2R, 6S)-4-methyl-3-(2-methoxyacetoxy)methyl-6-(3-(pivaloyloxy)propyl)-3,6-dihydro-2H-pyran-2-yl)methyl)-4-((phenyl sulfonyl)methyl)tetrahydrofuran-2-yl)propane-1,2-diyl dibenzoate

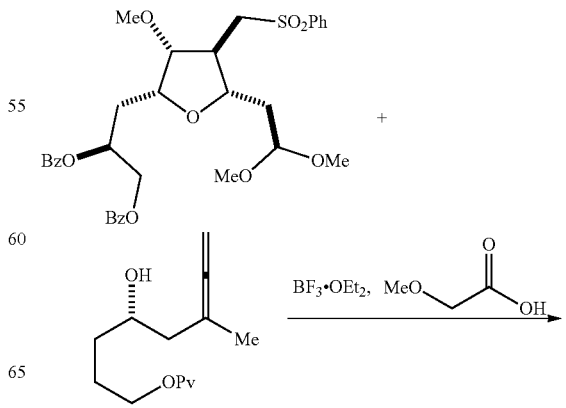

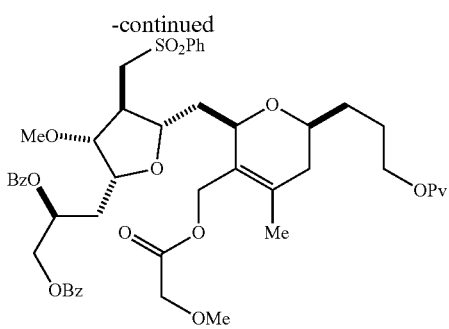

A mixture of (S)-4-hydroxy-6-methylocta-6,7-dien-1-yl pivalate (1.14 g, 4.73 mmol) and (S)-3-((2R,3R,4S,5S)-5-(2,2-dimethoxyethyl)-3-methoxy-4-((phenylsulfonyl) methyl) tetrahydrofuran-2-yl)propane-1,2-diyl dibenzoate (3.41 g, 5.44 mmol) was dissolved in CH$_2$Cl$_2$ (47.7 mL) and cooled to −40° C. The mixture was sequentially treated with methoxyacetic acid (5.44 mL, 70.9 mmol) and BF$_3$-OEt$_2$ (1.80 mL, 14.2 mmol). The mixture was warmed to −30° C. over 1 h and stirred at −30° C. for 0.5 h. The reaction was quenched with saturated aqueous NaHCO$_3$ (119 mL) and extracted twice with ethyl acetate (100 mL). The organic layers were combined, dried over MgSO$_4$, and concentrated in vacuo. The residue was purified by silica gel column chromatography (ethyl acetate/n-heptane=1/10 to 2/3) to give the title compound (3.61 g, 86%). $^1$H NMR (400 MHz, CDCl$_3$) δ 1.14 (m, 1H), 1.24 (s, 9H), 1.40-1.55 (m, 3H), 1.65 (m, 1H), 1.72 (s, 3H), 1.81 (m, 1H), 1.95 (m, 2H), 2.25 (m, 2H), 2.71 (m, 1H), 3.02 (dd, 1H), 3.11 (dd, 1H), 3.38 (m, 1H), 3.42 (s, 6H), 3.63 (m, 1H), 3.70 (m, 1H), 3.90-4.00 (m, 3H), 4.02 (d, 2H), 4.15 (m, 1H), 4.54 (d, 2H), 4.59 (d, 1H), 4.72 (d, 1H), 5.59 (m, 1H), 7.42 (m, 4H), 7.56 (m, 4H), 7.65 (m, 1H), 7.90 (d, 2H), 8.01 (m, 4H).

(S)-3-((2R,3R,4S,5S)-3-methoxy-5-(((2R,4R,6S)-4-methyl-3-methylene-6-(3-(pivaloyloxy)propyl)tetra-hydro-2H-pyran-2-yl)methyl)-4-((phenylsulfonyl) methyl) tetrahydrofuran-2-yl)propane-1,2-diyl dibenzoate

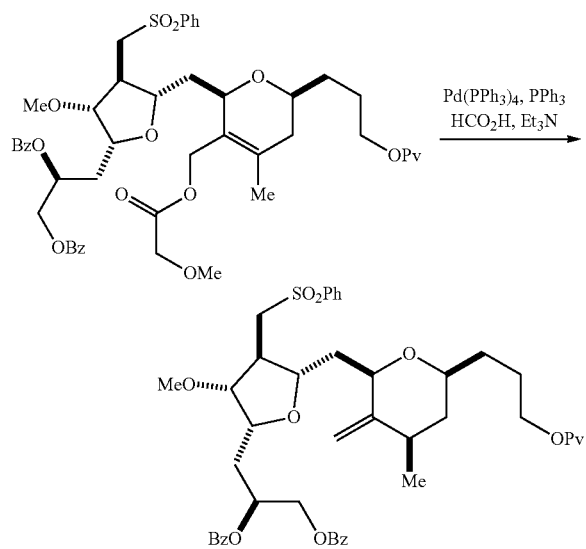

A mixture of Pd(Ph$_3$P)$_4$ (0.467 g, 0.404 mmol) and triphenylphosphine (0.424 g, 1.62 mmol) in a degassed THF (36.1 mL) was heated to 60° C. and stirred for 5 min. The mixture was treated with a mixture of (S)-3-((2R,3R,4S,5S)-3-methoxy-5-(((2R,6S)-4-methyl-3-(2-methoxyacetoxy) methyl-6-(3-(pivaloyloxy)propyl)-3,6-dihydro-2H-pyran-2-yl)methyl)-4-((phenyl sulfonyl)methyl)tetrahydrofuran-2-yl)propane-1,2-diyl dibenzoate (3.61 g, 4.04 mmol), formic acid (0.775 mL, 20.2 mmol), and triethylamine (2.82 mL, 20.2 mmol) in a degassed THF (36.1 mL). The mixture was stirred at 60° C. for 52 h. After cooling to rt, the mixture was diluted with MTBE (36.1 mL) and washed with water (18.1 mL) and then with brine. After concentration, the residue was purified by silica gel column chromatography (ethyl acetate/n-heptane=1/10 to 1/2) to give the title compound (2.8 g, 74% for 2 steps from allene). $^1$H NMR (400 MHz, CDCl$_3$) δ 1.00 (m, 1H), 1.05 (d, 3H), 1.14 (s, 9H), 1.38 (m, 3H), 1.61 (m, 1H), 1.72 (m, 1H), 1.91 (m, 1H), 2.1-2.32 (m, 4H), 2.62 (m, 1H), 3.02 (dd, 1H), 3.06 (dd, 1H), 3.36 (m, 1H), 3.42 (s, 3H), 3.66 (m, 1H), 3.72 (m, 1H), 3.81 (m, 1H), 3.84-3.96 (m, 3H), 4.56 (d, 2H), 4.77 (s, 1H), 4.83 (s, 1H), 5.59 (m, 1H), 7.40 (m, 4H), 7.52 (m, 4H), 7.62 (m, 1H), 7.90 (m, 2H), 8.01 (m, 4H).

3-((2S,4R,6R)-6-(((2S,3S,4R,5R)-5-((S)-2,3-dihydroxypropyl)-4-methoxy-3-((phenylsulfonyl)methyl) tetrahydrofuran-2-yl)methyl)-4-methyl-5-methyl-enetetrahydro-2H-pyran-2-yl)propyl pivalate

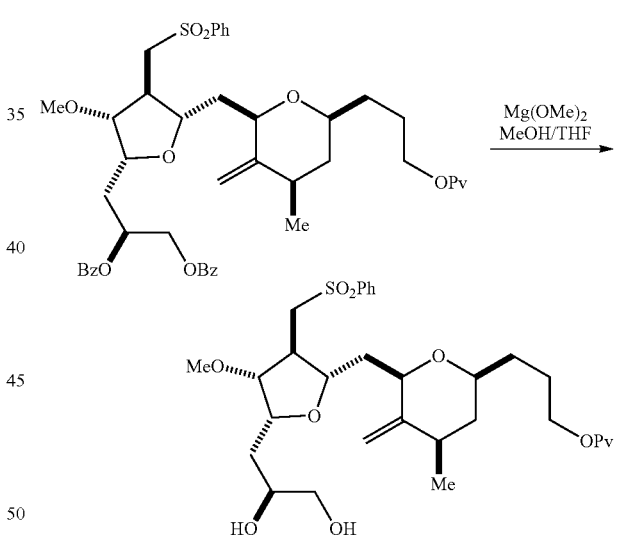

A solution of (S)-3-((2R,3R,4S,5S)-3-methoxy-5-(((2R,4R,6S)-4-methyl-3-methylene-6-(3-(pivaloyloxy) propyl) tetrahydro-2H-pyran-2-yl)methyl)-4-((phenylsulfonyl) methyl)tetrahydrofuran-2-yl)propane-1,2-diyl dibenzoate (2.8 g, 3.5 mmol) in a mixture of THF (2.80 mL) and methanol (56.0 mL) was treated with 6-10% Mg(OMe)$_2$ in methanol (18.5 g, 13.9 mmol). After stirring at rt for 22 h, the reaction was quenched with saturated aqueous NH$_4$Cl (22.4 mL) and extracted with MTBE (56.0 mL) and ethyl acetate (42.0 mL×2). The organic layers were combined and dried over MgSO$_4$. After concentration, the residue was azeotroped with methanol and toluene to give a crude product, which was used for the next step without further purification. $^1$H NMR (400 MHz, CDCl$_3$) δ 1.02 (m, 1H), 1.05 (d, 3H), 1.30 (s, 9H), 1.38 (m, 3H), 1.61 (m, 1H), 1.72

(m, 1H), 1.85 (m, 1H), 1.90-2.03 (m, 2H), 2.05-2.27 (m, 2H), 2.67 (m, 1H), 3.05 (bd, 1H), 3.23 (dd, 1H), 3.42 (s, 3H), 3.45 (m, 1H), 3.60 (m, 1H), 3.70 (m, 1H), 3.75 (m, 1H), 3.80-4.01 (m, 5H), 4.10 (m, 1H), 4.80 (s, 1H), 4.88 (s, 1H), 7.60 (m, 2H), 7.62 (m, 1H), 7.95 (m, 2H).

3-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)propyl pivalate

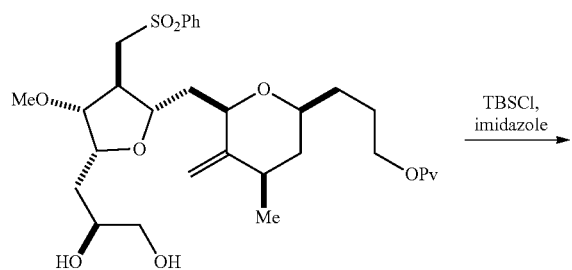

3-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)propan-1-ol

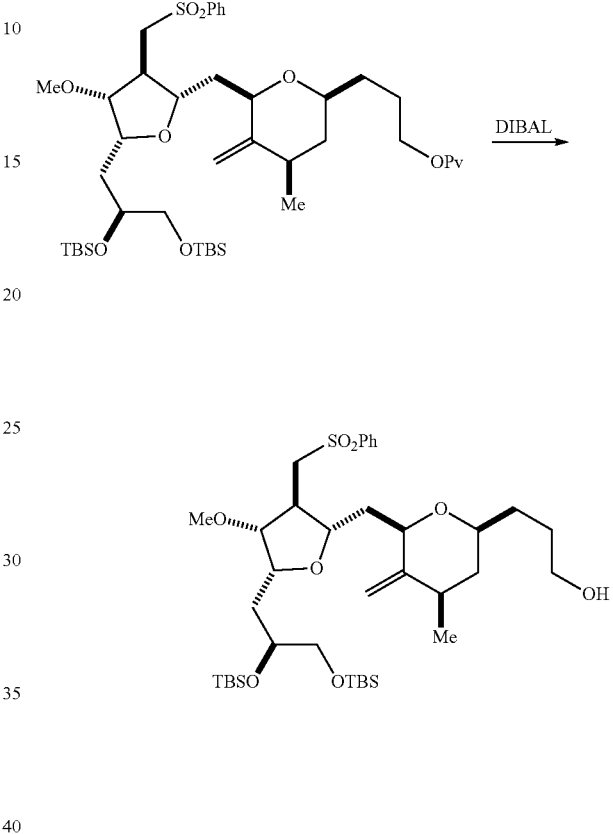

A solution of 3-((2S,4R,6R)-6-(((2S,3S,4R,5R)-5-((S)-2,3-dihydroxypropyl)-4-methoxy-3-((phenylsulfonyl)methyl)tetrahydrofuran-2-yl)methyl)-4-methyl-5-methylenetetrahydro-2H-pyran-2-yl)propyl pivalate (2.07 g, 3.469 mmol) in DMF (16.56 mL, 213.871 mmol) was treated with imidazole (0.945 g, 13.9 mmol) and TBSCl (1.20 g, 7.98 mmol). The mixture was stirred at rt for 1 h. Additional imidazole (0.945 g, 13.9 mmol) and TBSCl (1.20 g, 7.98 mmol) were added, and stirring was continued at rt for another 18 h. The reaction was quenched with water (41.4 mL) and extracted with MTBE (41.4 mL×2). The organic layers were combined and dried over MgSO$_4$. After concentration, the residue was purified by silica gel column chromatography (1/10 to 1/5) to give the title compound (3.115 g, 109%). $^1$H NMR (400 MHz, CDCl$_3$) δ 0.03 (s, 6H), 0.09 (s, 6H), 0.91 (s, 18H), 1.02 (m, 1H), 1.05 (d, 3H), 1.15 (s, 9H), 1.40 (m, 3H), 1.61 (m, 1H), 1.72 (m, 1H), 1.82 (m, 1H), 1.90 (m, 1H), 1.99 (m, 1H), 2.15-2.27 (m, 2H), 2.58 (m, 1H), 3.02 (m, 2H), 3.39 (m, 1H), 3.40 (s, 3H), 3.45 (m, 1H), 3.55 (m, 1H), 3.65 (m, 2H), 3.75-3.85 (m, 3H), 3.85-4.0 (m, 2H), 4.79 (s, 1H), 4.88 (s, 1H), 7.60 (m, 2H), 7.62 (m, 1H), 7.92 (m, 2H).

A solution of 3-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)propyl pivalate (3.11 g, 3.77 mmol) in CH$_2$Cl$_2$ (31.1 mL) was cooled to −78° C. and treated with 1M DIBAL in toluene (8.29 mL, 8.29 mmol). The mixture was stirred at −78° C. for 1 h. Additional 1M DIBAL in toluene (1.507 mL, 1.507 mmol) was added, and stirring was continued for another 1.5 h. After quenching the reaction with methanol (1.53 mL, 37.7 mmol), the mixture was treated with 1 N HCl (37.7 mL) and stirred at rt for 1 h. The mixture was extracted with MTBE (31.1 mL×2). The organic layers were combined, washed with saturated aqueous NaHCO$_3$ (15.6 mL), dried over MgSO$_4$, and concentrated in vacuo to give the title compound (2.9 g, 104%). $^1$H NMR (400 MHz, CDCl$_3$) δ 0.03 (s, 6H), 0.09 (s, 6H), 0.88 (s, 18H), 1.08 (m, 1H), 1.08 (d, 3H), 1.48 (m, 3H), 1.63 (m, 1H), 1.72 (m, 1H), 1.82 (m, 1H), 1.88-2.02 (m, 2H), 2.12-2.27 (m, 2H), 2.58 (m, 1H), 3.03 (dd, 1H), 3.10 (dd, 1H), 3.40 (s, 3H), 3.42-3.50 (m, 2H), 3.55 (m, 3H), 3.68 (m, 2H), 3.80 (m, 3H), 4.79 (s, 1H), 4.88 (s, 1H), 7.60 (m, 2H), 7.62 (m, 1H), 7.97 (m, 2H).

201

(S)-5-(((2R,3R,4S,5S)-3-methoxy-5-(((2R,4R,6S)-4-methyl-3-methylene-6-(3-((triethylsilyl)oxy)propyl)tetrahydro-2H-pyran-2-yl)methyl)-4-((phenylsulfonyl)methyl)tetrahydrofuran-2-yl)methyl)-2,2,3,3,8,8,9,9-octamethyl-4,7-dioxa-3,8-disiladecane

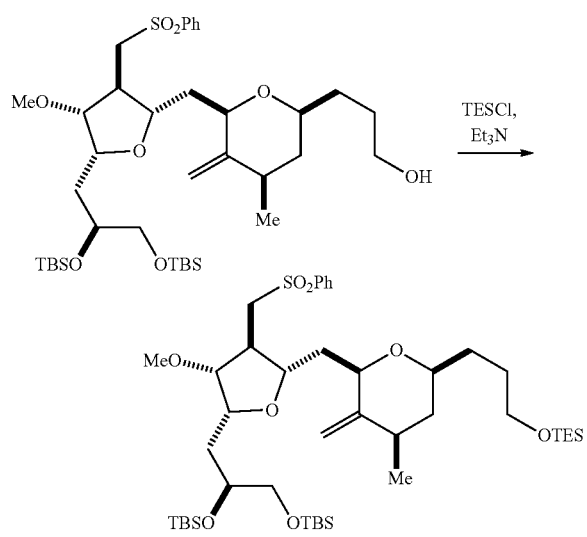

A solution of 3-((2S,4R,6R)-6-(((2S,3S,4R,5R)-5-((S)-2,3-bis((tert-butyldimethylsilyl)oxy) propyl)-4-methoxy-3-((phenylsulfonyl)methyl)tetrahydrofuran-2-yl)methyl)-4-methyl-5-methylenetetrahydro-2H-pyran-2-yl)propan-1-ol (2.9 g, 3.9 mmol) in CH$_2$Cl$_2$ (29.0 mL) was treated with triethylamine (1.09 mL, 7.83 mmol) and chlorotriethylsilane (0.799 mL, 4.70 mmol). After stirring at rt for 17 h, the reaction was quenched with water (29.0 mL) and extracted twice with MTBE (29.0 mL). The organic layers were combined and washed with brine. After concentration, the residue was purified by silica gel column chromatography (ethyl acetate/n-heptane=1/20 to 1/5) to give the title compound (2.95 g, 88%). $^1$H NMR (400 MHz, CDCl$_3$) δ 0.03 (s, 6H), 0.04 (s, 6H), 0.56 (q, 6H), 0.82-1.00 (m, 27H), 1.02 (m, 1H), 1.06 (d, 3H), 1.30-1.52 (m, 4H), 1.74 (m, 1H), 1.78-1.90 (m, 2H), 2.00 (m, 1H), 2.15-2.23 (m, 2H), 2.56 (m, 1H), 2.96-3.10 (m, 2H), 3.35 (m, 1H), 3.43 (s, 3H), 3.43-3.62 (m, 5H), 3.68 (m, 1H), 3.79 (m, 2H), 3.83 (m, 1H), 4.78 (s, 1H), 4.85 (s, 1H), 7.60 (m, 2H), 7.62 (m, 1H), 7.96 (m, 2H).

Example 7: Preparation of a Compound of Formula (VD)

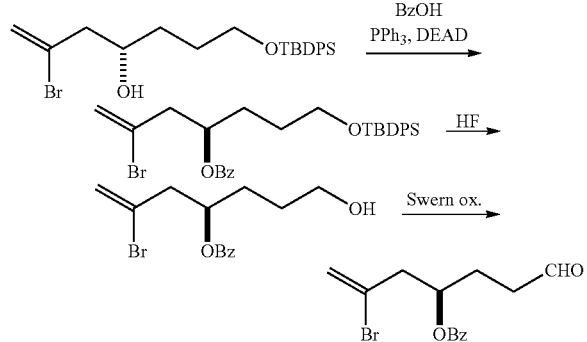

202

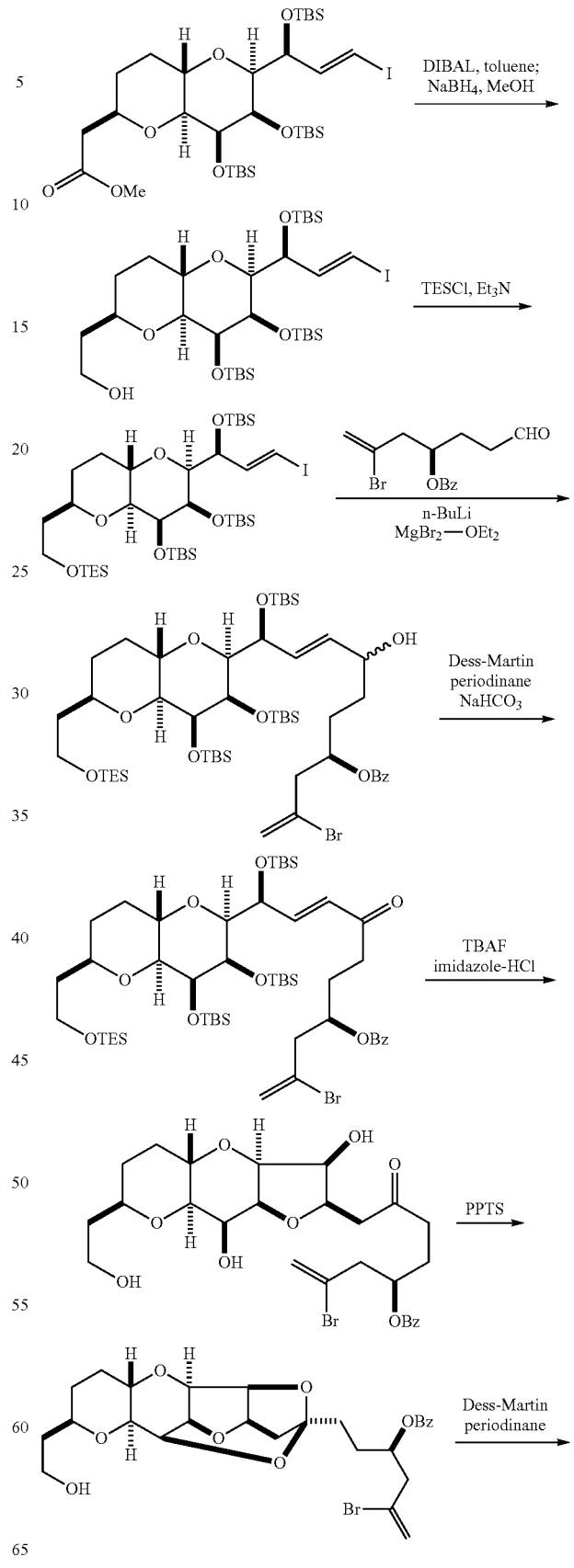

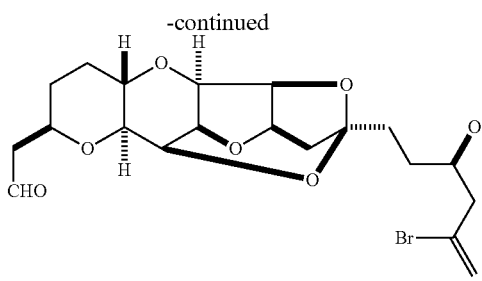

(R)-2-bromo-7-((tert-butyldiphenylsilyl)oxy)hept-1-en-4-yl benzoate

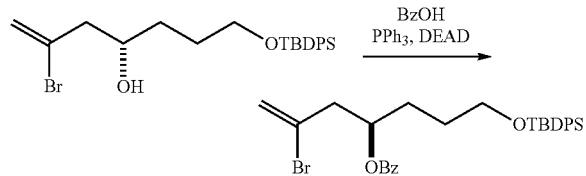

A solution of (S)-2-bromo-7-((tert-butyldiphenylsilyl)oxy)hept-1-en-4-ol (25.0 g, 55.9 mmol) in toluene (200 mL) was treated with benzoic acid (8.19 g, 67.0 mmol) and triphenylphosphine (17.58 g, 67.0 mmol). After cooling to 0° C., the mixture was treated with DEAD (24.32 mL, 61.46 mmol) over 20 min, while maintaining the internal temperature below 6° C. and stirred at 0° C. for 2 h. The mixture was treated with n-heptane (83 mL) and stirred at 0° C. for 30 min. The precipitate was filtered and washed with n-heptane (83 mL). The filtrate was concentrate in vacuo to give the title compound (46.6 g).

(R)-2-bromo-7-hydroxyhept-1-en-4-yl benzoate

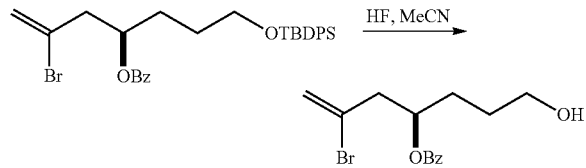

A solution of (R)-2-bromo-7-((tert-butyldiphenylsilyl)oxy)hept-1-en-4-yl benzoate (30.8 g, 55.8 mmol) in acetonitrile (200 mL) was treated with 48% HF in water (10.1 mL, 279 mmol) and stirred at rt for 13 h. The reaction was quenched with saturated aqueous NaHCO$_3$ (308 mL) and diluted with MTBE (154 mL). The organic layer was separated, and the aqueous layer was extracted with MTBE (154 mL). The organic layers were combined and washed with brine. After concentration, the residue was purified by silica gel column chromatography (ethyl acetate/n-heptane=1/10 to 1/2) to give the title compound (14.67 g, 84%). $^1$H NMR (400 MHz, CDCl$_3$) δ 1.29 (m, 1H), 1.75-1.90 (m, 2H), 2.73 (dd, 1H), 2.90 (dd, 1H), 3.69 (t, 2H), 5.46 (m, 1H), 5.48 (s, 1H), 5.69 (s, 1H), 7.41 (m, 2H), 7.58 (m, 1H), 8.02 (m, 2H).

(R)-2-bromo-7-oxohept-1-en-4-yl benzoate

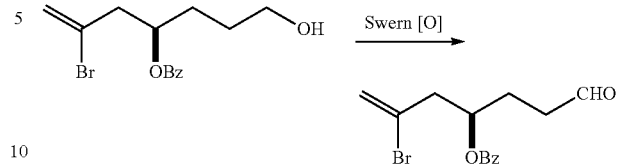

A solution of 2 M oxalyl chloride in CH$_2$Cl$_2$ (6.96 mL, 13.9 mmol) in CH$_2$Cl$_2$ (21.80 mL) was cooled to −78° C. and treated with DMSO (1.976 mL, 27.843 mmol), while maintaining the internal temperature below −60° C. After stirring at −78° C. for 10 min, a solution of (R)-2-bromo-7-hydroxyhept-1-en-4-yl benzoate (2.18 g, 6.961 mmol) in CH$_2$Cl$_2$ (10.90 mL) was added, and stirring was continued at −78° C. for 30 min. Triethylamine (9.70 mL, 69.6 mmol) was added, while maintaining the internal temperature below −60° C. Then, the mixture was stirred at −78° C. for 10 min and 0° C. for 30 min. The mixture was treated with water (21.80 mL) and extracted twice with MTBE (32.7 mL). The organic layers were combined, and washed with water (21.80 mL) and brine. After concentration, the residue was purified by silica gel column chromatography (ethyl acetate/n-heptane=1/10 to 1/3) to give the title compound (1.477 g, 68%). $^1$H NMR (400 MHz, CDCl$_3$) δ 2.04 (m, 1H), 2.14 (m, 1H), 2.60 (m, 2H), 2.73 (dd, 1H), 2.92 (dd, 1H), 5.45 (m, 1H), 5.50 (s, 1H), 5.70 (s, 1H), 7.43 (m, 2H), 7.58 (m, 1H), 8.02 (m, 2H), 9.79 (s, 1H).

2-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)ethanol

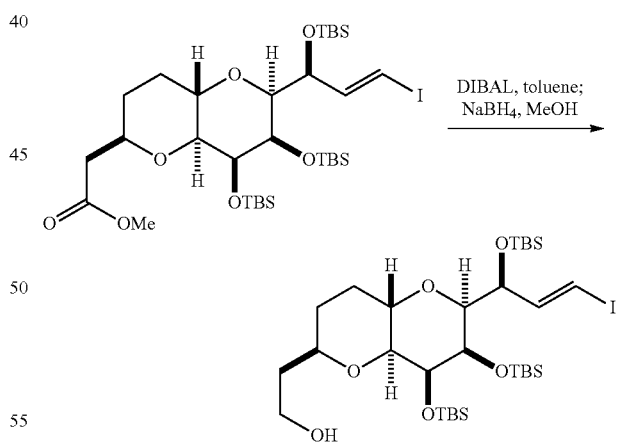

Methyl 2-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)acetate (90.0 g, 31.5 mmol, a solution in toluene, ca. 27%) was diluted with toluene (316 mL) and cooled to −78° C. The mixture was treated with 1M DIBAL in toluene (37.8 mL, 37.8 mmol) and stirred at −78° C. for 1 h. After removing the cold bath, the reaction was quenched with methanol (7.65 mL, 189 mmol) and treated with 1 N HCl (243 mL, 243 mmol) and MTBE (170 mL). After stirring at rt for 30 min, the organic layer was separated, and the aqueous layer was extracted with MTBE (170 mL). The organic layers were combined, washed sequentially with 1 N HCl (122 mL), water (122 mL), saturated aqueous NaHCO$_3$ (122 mL), and brine (120 mL).

After concentration, the residue was dissolved in methanol (194 mL), cooled to 0° C., and treated with sodium borohydride (0.596 g, 15.8 mmol). The reaction mixture was stirred at 0° C. for 1 h and quenched with 1 N HCl (63.0 mL, 63.0 mmol). After dilution with MTBE (365 mL), the organic layer was separated and washed sequentially with 1 N HCl (63.0 mL) and saturated aqueous NaHCO$_3$ (122 mL) (with brine). The organic layer was dried over MgSO$_4$ and concentrated in vacuo to give the title compound (23.44 g, 100%).

(((2S,3R,4S,4aS,6R,8aS)-2-((S,E)-1-((tert-butyldimethylsilyl)oxy)-3-iodoallyl)-6-(2-((triethylsilyl)oxy)ethyl)octahydropyrano[3,2-b]pyran-3,4-diyl)bis(oxy))bis(tert-butyldimethylsilane)

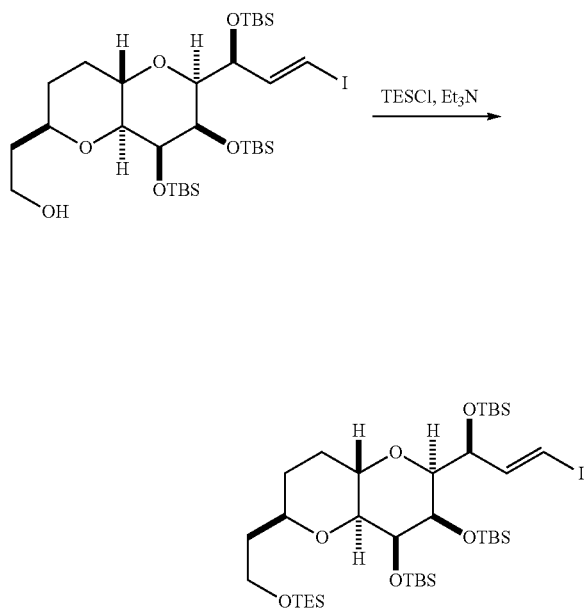

A solution of 2-((2R,4aS,6S,7R,8S,8aS)-7,8-bis((tert-butyldimethylsilyl)oxy)-6-((S,E)-1-((tert-butyldimethylsilyl)oxy)-3-iodoallyl) octahydropyrano[3,2-b]pyran-2-yl) ethanol (23.44 g, 31.548 mmol) in CH$_2$Cl$_2$ (211 mL) was treated with chlorotriethylsilane (6.44 mL, 37.9 mmol) and triethylamine (8.79 mL, 63.1 mmol), and stirred at rt for 3 h. Additional chlorotriethylsilane (1.06 mL, 6.31 mmol) and triethylamine (1.32 mL, 9.46 mmol) were added, and stirring was continued at rt for another 8 h. The reaction was quenched with water (117 mL). The organic layer was separated, and the aqueous layer was extracted with MTBE (117 mL). The organic layers were combined, and dried over MgSO$_4$. After concentration, the residue was purified by silica gel column chromatography (ethyl acetate/n-heptane=1/20 to 1/10) to give the title compound (23.7 g, 95%).
$^1$H NMR (400 MHz, CDCl$_3$) δ 0.02 (s, 3H), 0.03 (s, 3H), 0.10 (s, 3H), 0.11 (s, 3H), 0.12 (s, 3H), 0.14 (s, 3H), 0.59 (q, 6H), 0.86 (s, 9H), 0.9-1.0 (m, 27H), 1.25-1.35 (m, 2H), 1.60-1.72 (m, 3H), 1.92 (m, 1H), 2.84 (d, 1H), 3.45 (m, 2H), 3.58 (m, 1H), 3.73 (m, 1H), 3.83 (dd, 1H), 3.89 (dd, 1H), 4.09 (m, 1H), 4.91 (m, 1H), 6.29 (d, 1H), 6.85 (dd, 1H).

(4R,10S,E)-10-((2S,3R,4S,4aS,6R,8aS)-3,4-bis((tert-butyldimethylsilyl)oxy)-6-(2-((triethylsilyl)oxy)ethyl)octahydropyrano[3,2-b]pyran-2-yl)-2-bromo-10-((tert-butyldimethylsilyl)oxy)-7-hydroxydeca-1,8-dien-4-yl benzoate

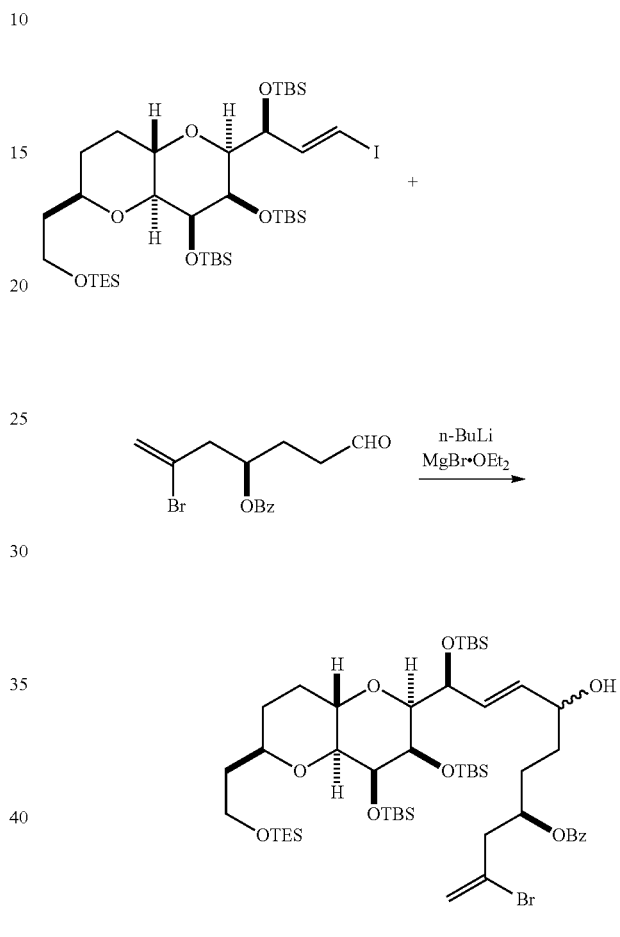

A solution of (((2S,3R,4S,4aS,6R,8aS)-2-((S,E)-1-((tert-butyldimethylsilyl)oxy)-3-iodoallyl)-6-(2-((triethylsilyl)oxy)ethyl)octahydropyrano[3,2-b]pyran-3,4-diyl)bis(oxy))bis(tert-butyldimethylsilane) (4.48 g, 5.22 mmol) in THF (32.5 mL) was cooled to −78° C. and treated with 1.6 M n-BuLi in n-hexane (3.26 mL, 5.22 mmol), while maintaining the internal temperature below −65° C. After stirring at −78° C. for 20 min, the mixture was treated with a solution of magnesium bromide diethyl etherate (1.35 g, 5.22 mmol) in THF (16.25 mL), while maintaining the internal temperature below −65° C., and stirred at −78° C. for 30 min. A solution of (R)-2-bromo-7-oxohept-1-en-4-yl benzoate (1.477 g, 4.747 mmol) and magnesium bromide diethyl etherate (1.35 g, 5.22 mmol) in THF (18.3 mL) was added, and the resulting mixture was stirred at −78° C. for 10 min, slowly warmed to −25° C. over 4 h and stirred at −25° C. for 1 h. The reaction was quenched with saturated aqueous NH$_4$Cl (29.5 mL) and extracted twice with MTBE (29.5 mL). The organic layers were combined and washed with brine. After concentration, the residue was purified by silica gel column chromatography (ethyl acetate/n-heptane=1/10 to 1/5) to give the title compound (3.35 g, 68%).

207

(4R,10S,E)-10-((2S,3R,4S,4aS,6R,8aS)-3,4-bis((tert-butyldimethylsilyl)oxy)-6-(2-((triethylsilyl)oxy)ethyl)octahydropyrano[3,2-b]pyran-2-yl)-2-bromo-10-((tert-butyldimethylsilyl)oxy)-7-oxodeca-1,8-dien-4-yl benzoate

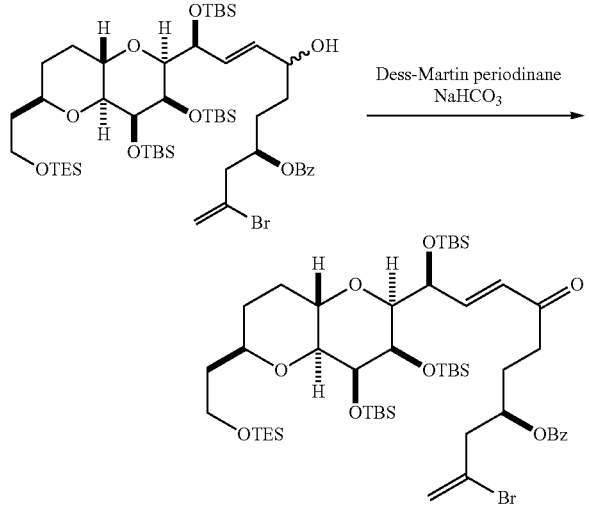

A solution of (4R,10S,E)-10-((2S,3R,4S,4aS,6R,8aS)-3,4-bis((tert-butyldimethylsilyl)oxy)-6-(2-((triethylsilyl)oxy)ethyl)octahydropyrano[3,2-b]pyran-2-yl)-2-bromo-10-((tert-butyldimethylsilyl)oxy)-7-hydroxydeca-1,8-dien-4-yl benzoate (3.35 g, 3.213 mmol) in CH$_2$Cl$_2$ (33.5 mL) was treated with sodium bicarbonate (0.540 g, 6.43 mmol) and Dess-Martin periodinane (1.64 g, 3.86 mmol). The mixture was stirred at rt for 1 h. The reaction was quenched with saturated aqueous NaHCO$_3$ (25.1 mL) and 20% Na$_2$SO$_3$ (25.1 mL) and extracted twice with MTBE (26.8 mL). The organic layers were combined and washed with brine (16.75 mL). After concentration, the residue was purified by silica gel column chromatography (ethyl acetate/n-heptane=1/20 to 1/8) to give the title compound (2.26 g, 68%). $^1$H NMR (400 MHz, CDCl$_3$) δ 0.07 (s, 3H), 0.02 (s, 3H), 0.11 (s, 6H), 0.12 (s, 3H), 0.13 (s, 3H), 0.60 (q, 6H), 0.82 (s, 9H), 0.88 (t, 9H), 0.92 (s, 9H), 0.94 (s, 9H), 1.05-1.25 (m, 3H), 1.48-1.60 (m, 3H), 1.70 (m, 1H), 2.00-2.20 (m, 2H), 2.69 (m, 2H), 2.72 (dd, 1H), 2.82 (d, 2H), 2.91 (dd, 1H), 3.29 (m, 1H), 3.42 (m, 1H), 3.63 (m, 1H), 3.72 (m, 1H), 3.91 (m, 2H), 4.10 (bs, 1H), 5.11 (m, 1H), 5.43 (m, 1H), 5.49 (d, 1H), 5.68 (s, 1H), 6.29 (d, 1H), 7.08 (dd, 1H), 7.41 (m, 2H), 7.52 (m, 1H), 8.01 (m, 2H).

(R)-2-bromo-8-((2R,3S,3aS,4aS,7R,8aR,9S,9aS)-3,9-dihydroxy-7-(2-hydroxyethyl)decahydrofuro[3,2-b]pyrano[2,3-e]pyran-2-yl)-7-oxooct-1-en-4-yl benzoate

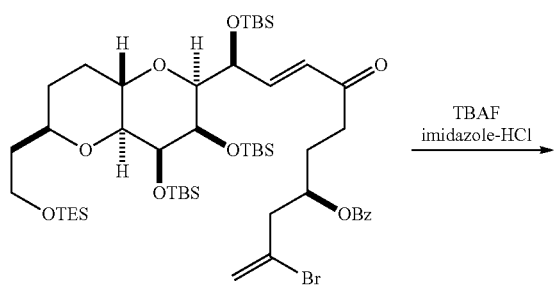

208

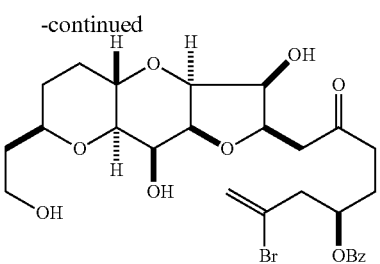

A mixture of imidazole hydrochloride (0.704 g, 6.73 mmol) and 1 M TBAF in THF (14.12 mL, 14.1 mmol) in THF (45.2 mL) was treated with a solution of (4R,10S,E)-10-((2S,3R,4S,4aS,6R,8aS)-3,4-bis((tert-butyldimethylsilyl)oxy)-6-(2-((triethylsilyl)oxy)ethyl) octahydropyrano[3,2-b]pyran-2-yl)-2-bromo-10-((tert-butyldimethylsilyl)oxy)-7-oxodeca-1,8-dien-4-yl benzoate (2.26 g, 2.17 mmol) in THF (31.6 mL). The mixture was stirred at rt for 7 d. The mixture was treated with toluene (56.5 mL) and water (56.5 mL). The organic layer was separated, and the aqueous layer was extracted twice with a mixture of toluene (38.4 mL) and THF (38.4 mL). The organic layers were combined, concentrated in vacuo and then azeotroped three times with acetonitrile (18.1 mL) to give the title compound (1.4 g).

(R)-5-bromo-1-((2S,3aR,4aR,5S,5aS,7R,9aS,10aR,10bS)-7-(2-hydroxyethyl) dodecahydro-2,5-epoxyfuro[2',3':4,5]furo[3,2-b]pyrano[2,3-e]pyran-2-yl)hex-5-en-3-yl benzoate

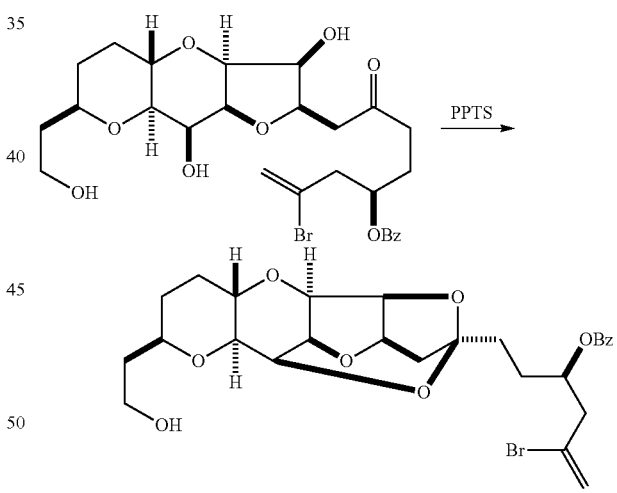

A solution of (R)-2-bromo-8-((2R,3S,3aS,4aS,7R,8aR,9S,9aS)-3,9-dihydroxy-7-(2-hydroxyethyl)decahydrofuro[3,2-b]pyrano[2,3-e]pyran-2-yl)-7-oxooct-1-en-4-yl benzoate (1.27 g, 2.17 mmol) in CH$_2$Cl$_2$ (68.4 mL) was treated with PPTS (3.00 g, 11.9 mmol) and stirred at rt for 23 h. After concentration, the residual solid (PPTS) was treated with ethyl acetate (50.7 mL), stirred at rt for 10 min, filtered, and rinsed with ethyl acetate. The filtrate was concentrated, treated again with ethyl acetate (10.14 mL), and stirred at rt for 2 h. The precipitate was filtered, washed with ethyl acetate (3 mL), and dried under N$_2$ purge to give the title compound (1$^{st}$ crop, 495 mg, contaminated with 14% PPTS).

The filtrate was treated with ethyl acetate (ca. 3 mL) at 40° C. and stirred at ambient temperature for 2 h. The precipitate was filtered, washed with ethyl acetate (1 mL), and dried under N$_2$ purge to give the title compound (2$^{nd}$ crop, 175 mg, total 47% (1$^{st}$ and 2$^{nd}$ crops combined) for 2 steps). $^1$H NMR (400 MHz, CDCl$_3$) δ 1.30-1.50 (m, 2H), 1.65-2.16 (m, 10H), 2.79 (m, 1H), 2.86-2.94 (m, 2H), 3.61 (m, 1H), 3.70-3.84 (m, 2H), 4.05 (dd, 1H), 4.19 (dd, 1H), 4.27 (m, 1H), 4.42 (m, 1H), 4.60 (dd, 1H), 4.68 (dd, 1H), 5.40 (m, 1H), 5.47 (s, 1H), 5.68 (s, 1H), 7.41 (m, 2H), 7.57 (m, 1H), 8.03 (m, 2H).

(R)-5-bromo-1-((2S,3aR,4aR,5S,5aS,7R,9aS,10aR,10bS)-7-(2-oxoethyl)decahydro-2,5-epoxyfuro[2',3':4,5]furo[3,2-b]pyrano[2,3-e]pyran-2-(3H)-yl)hex-5-en-3-yl benzoate

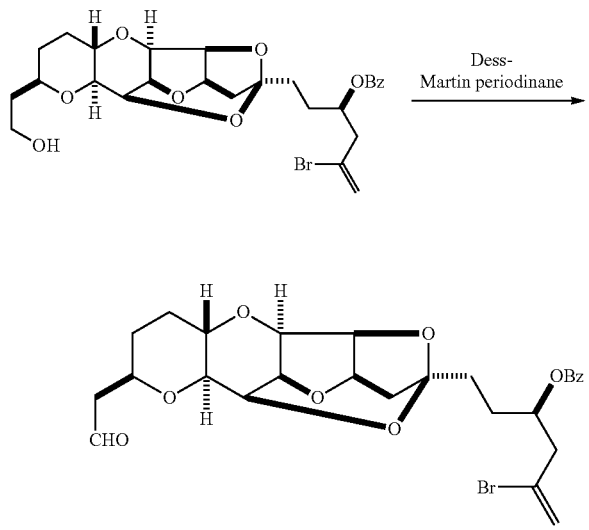

A mixture of (R)-5-bromo-1-((2S,3aR,4aR,5S,5aS,7R,9aS,10aR,10bS)-7-(2-hydroxyethyl)dodecahydro-2,5-epoxyfuro[2',3':4,5]furo[3,2-b]pyrano[2,3-e]pyran-2-yl)hex-5-en-3-yl benzoate (0.49 g, 0.87 mmol) and sodium bicarbonate (0.182 g, 2.17 mmol) in CH$_2$Cl$_2$ (4.9 mL) was treated with Dess-Martin periodinane (0.551 g, 1.30 mmol), and stirred at rt for 2 h. The reaction was quenched with 20% Na$_2$SO$_3$ (2.5 mL) and saturated aqueous NaHCO$_3$ (2.5 mL). The mixture was extracted three times with MTBE (4.9 mL) and ethyl acetate (4.9 mL). The combined organic layers were dried over MgSCO$_4$ and concentrated in vacuo.

The residue was dissolved in ethyl acetate (ca. 3 mL) with heating and slowly cooled to rt over 20 h. The precipitate was filtered, washed with ethyl acetate (1 mL), and dried under N$_2$ purge for 2 h to give the title compound (216 mg, 44%) along with 200 mg from the filtrate. $^1$H NMR (400 MHz, CDCl$_3$) δ 1.40 (m, 2H), 1.77 (m, 1H), 1.86 (m, 1H), 1.92-2.16 (m, 6H), 2.48 (m, 1H), 2.73 (m, 1H), 2.78 (m, 1H), 2.87-2.95 (m, 2H), 3.89 (m, 1H), 4.08 (dd, 1H), 4.20 (dd, 1H), 4.28 (m, 1H), 4.43 (m, 1H), 4.51 (dd, 1H), 4.69 (dd, 1H), 5.46 (m, 1H), 5.48 (s, 1H), 5.68 (s, 1H), 7.43 (m, 2H), 7.55 (m, 1H), 8.03 (m, 2H), 9.79 (s, 1H).

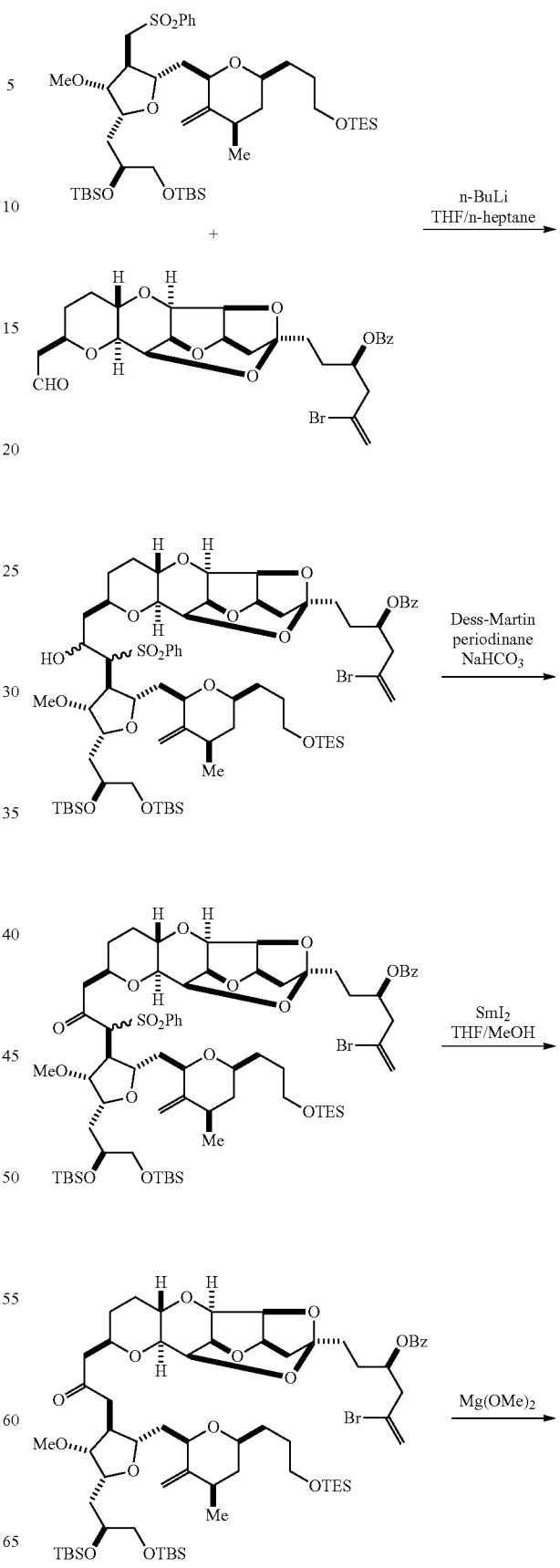

211
-continued

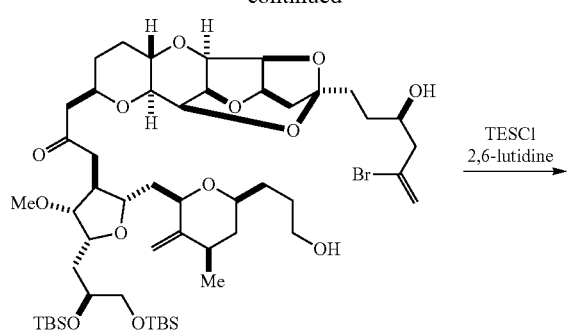

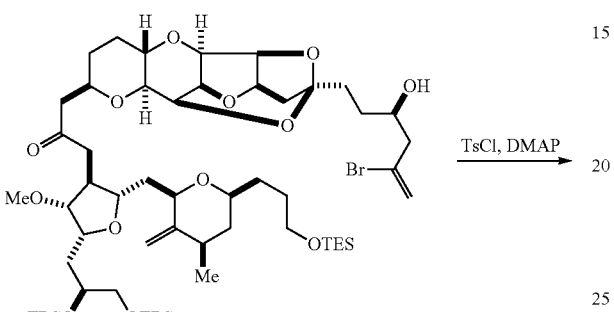

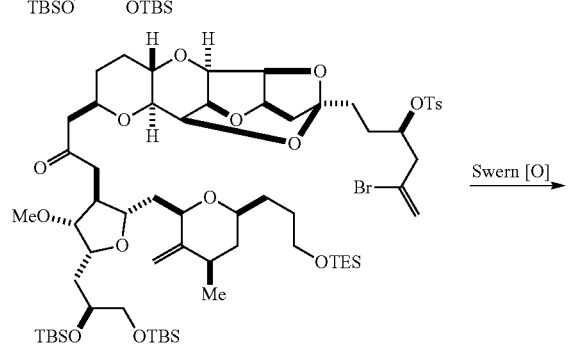

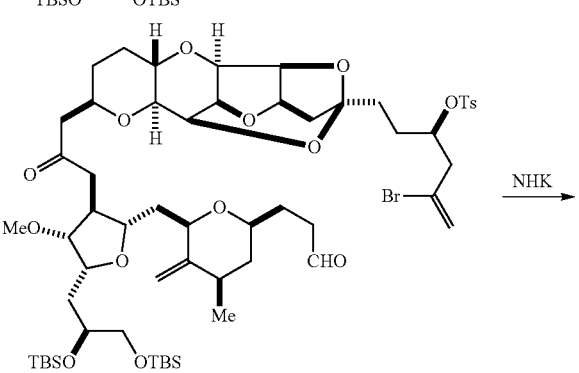

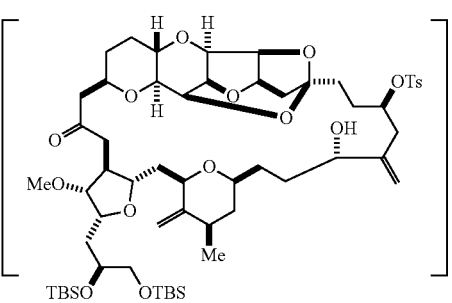

212
-continued

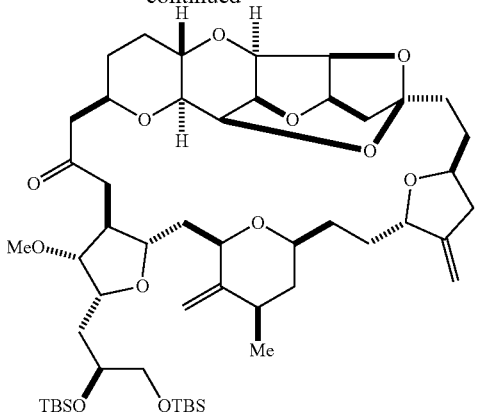

(3R)-1-((2S,3aR,4aR,5S,5aS,7R,9aS,10aR,10bS)-7-(3-((2S,3S,4R,5R)-5-((S)-2,3-bis((tert- butyldimethylsilyl)oxy)propyl)-4-methoxy-2-(((2R,4R,6S)-4-methyl-3-methylene-6-(3-((triethylsilyl)oxy)propyl) tetrahydro-2H-pyran-2-yl)methyl) tetrahydrofuran-3-yl)-2-hydroxy-3-(phenylsulfonyl)propyl) dodecahydro-2,5-epoxyfuro[2',3':4,5]furo[3,2-b]pyrano[2,3-e]pyran-2-yl-5-bromohex-5-en-3-yl benzoate

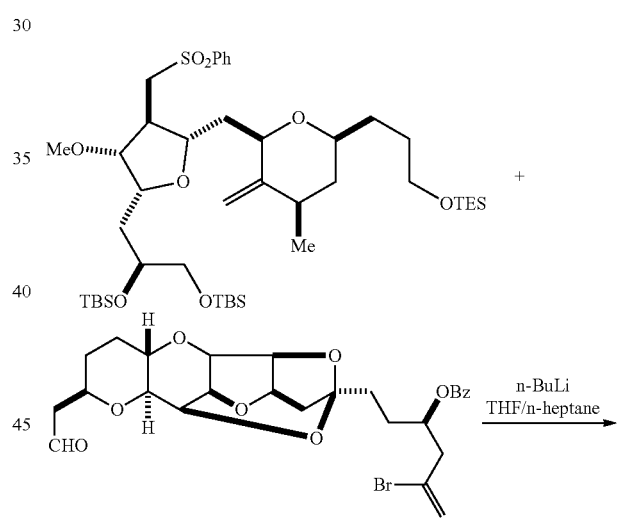

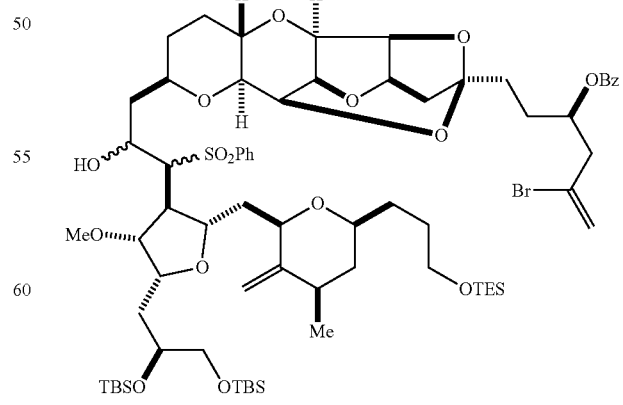

A solution of (S)-5-(((2R,3R,4S,5S)-3-methoxy-5-(((2R,4R,6S)-4-methyl-3-methylene-6-(3-((triethylsilyl)oxy)propyl)tetrahydro-2H-pyran-2-yl)methyl)-4-((phenylsulfonyl)methyl)tetrahydrofuran-2-yl)methyl)-2,2,3,3,8,8,9,9-octamethyl-4,7-dioxa-3,8-disiladecane (0.478 g, 0.559 mmol) in THF (4.2 mL) was cooled to −5° C. The mixture was treated with 1.6 M n-BuLi in n-hexane (0.349 mL, 0.559 mmol) and stirred at −5° C. for 30 min. After cooling to −78° C., the mixture was treated with a solution of (R)-5-bromo-1-((2S,3aR,4aR,5S,5aS,7R,9aS,10aR,10bS)-7-(2-oxoethyl)dodecahydro-2,5-epoxyfuro[2',3':4,5]furo[3,2-b]pyrano[2,3-e]pyran-2-yl)hex-5-en-3-yl benzoate (0.21 g, 0.373 mmol) in a mixture of n-heptane (1.1 mL) and THF (3.2 mL), while maintaining the internal temperature below −65° C. After stirring at −78° C. for 4 h, the reaction was quenched with saturated aqueous NH₄Cl (5 mL) and extracted three times with MTBE (10 mL). The organic layers were combined, dried over MgSO₄ and concentrated in vacuo to give the title compound (690 mg, 130%).

(R)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)-4-methoxy-2-(((2R,4R,6S)-4-methyl-3-methylene-6-(3-((triethylsilyl)oxy)propyl)tetrahydro-2H-pyran-2-yl)methyl) tetrahydrofuran-3-yl)-2-oxo-3-(phenylsulfonyl)propyl)dodecahydro-2,5-epoxyfuro[2',3':4,5]furo[3,2-b]pyrano[2,3-e]pyran-2-yl-5-bromohex-5-en-3-yl benzoate

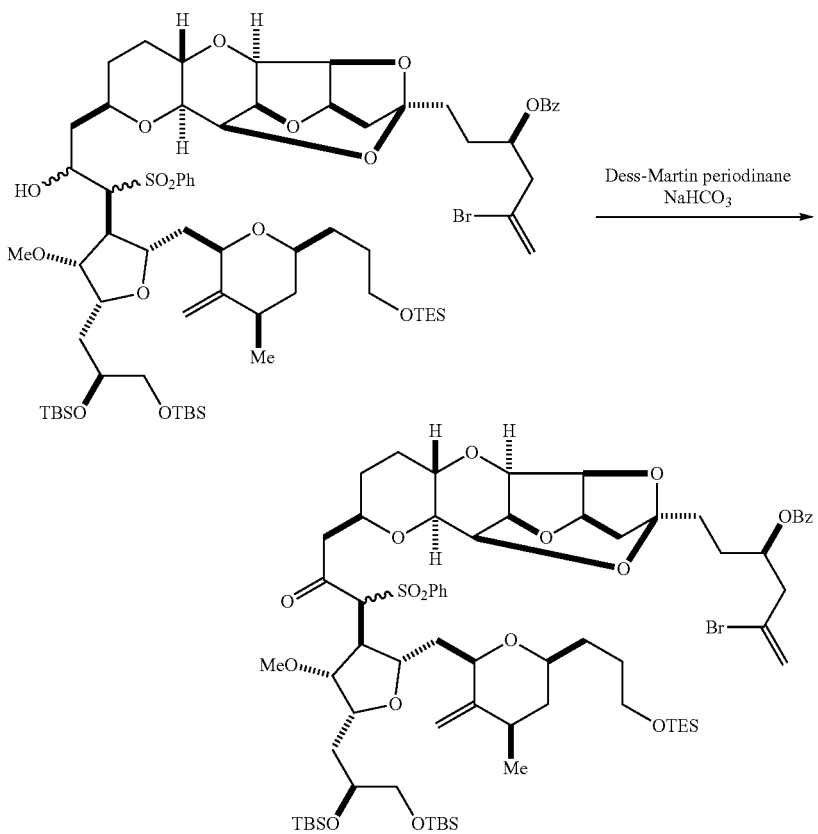

A solution of (3R)-1-((2S,3aR,4aR,5S,5aS,7R,9aS,10aR,10bS)-7-(3-((2S,3S,4R,5R)-5-((S)-2,3-bis((tert- butyldimethylsilyl)oxy)propyl)-4-methoxy-2-(((2R,4R,6S)-4-methyl-3-methylene-6-(3-((triethylsilyl)oxy)propyl)tetrahydro-2H-pyran-2-yl)methyl)tetrahydrofuran-3-yl)-2-hydroxy-3-(phenylsulfonyl)propyl)dodecahydro-2,5-epoxyfuro[2',3':4,5]furo[3,2-b]pyrano[2,3-e]pyran-2-yl)-5-bromohex-5-en-3-yl benzoate (0.69 g, 0.49 mmol) in CH₂Cl₂ (6.9 mL) was treated with sodium bicarbonate (0.061 g, 0.73 mmol) and Dess-Martin periodinane (0.248 g, 0.584 mmol). The reaction mixture was stirred at rt for 1 h, quenched with saturated aqueous NaHCO₃ (6.9 mL) and 20% Na₂SO₃ (6.9 mL), and extracted twice with MTBE (10.35 mL, 86.888 mmol). The organic layers were combined and washed with brine. After concentration, the residue was purified by silica gel column chromatography (ethyl acetate/n-heptane=1/10 to 1/2) to give the title compound (366 mg, 69% for 2 steps).

215

(R)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)- 4-methoxy-2-(((2R,4R,6S)-4-methyl-3-methylene-6-(3-((triethylsilyl)oxy)propyl)tetrahydro-2H-pyran-2-yl)methyl) tetrahydrofuran-3-yl)-2-oxopropyl)dodecahydro-2,5-epoxyfuro[2',3':4,5]furo[3,2-b]pyrano[2,3-e]pyran-2-yl-5-bromohex-5-en-3-yl benzoate

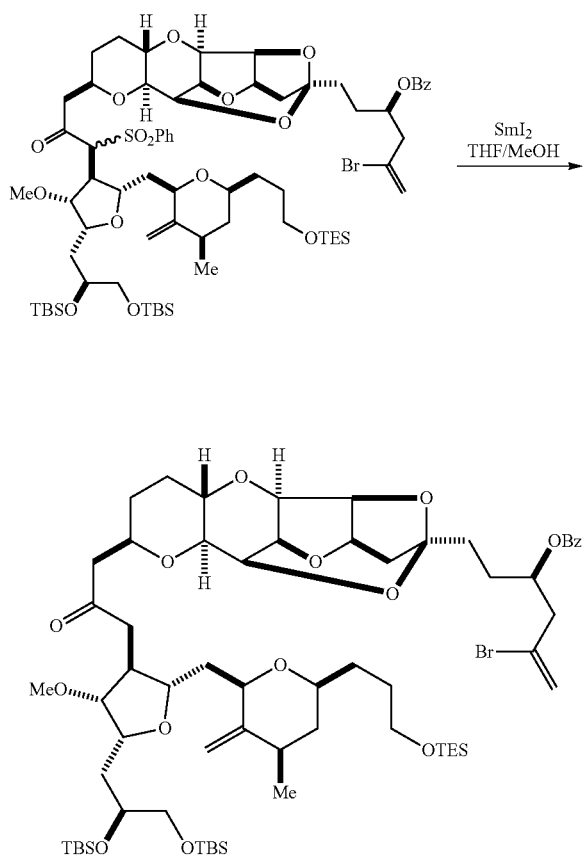

A solution of (R)-1-((2S,3aR,4aR,5S,5aS,7R,9aS,10aR,10bS)-7-(3-((2S,3S,4R,5R)-5-((S)-2,3-bis((tert- butyldimethylsilyl)oxy)propyl)-4-methoxy-2-(((2R,4R,6S)-4-methyl-3-methylene-6-(3-((triethylsilyl)oxy)propyl)tetrahydro-2H-pyran-2-yl)methyl)tetrahydrofuran-3-yl)-2-oxo-3-(phenylsulfonyl)propyl)dodecahydro-2,5-epoxyfuro[2',3':4,5]furo[3,2-b]pyrano[2,3-e]pyran-2-yl)-5-bromohex-5-en-3-yl benzoate (0.366 g, 0.258 mmol) in a mixture of THF (2.9 mL) and methanol (1.8 mL) was cooled to −78° C. and treated with 0.1 M SmI$_2$ in THF (5.55 mL, 0.555 mmol). After stirring at −78° C. for 1 h, the cold bath was removed, and the mixture was treated with a mixture of potassium sodium tartrate (1.83 g, 6.48 mmol) and potassium carbonate (1.7 g, 13 mmol) in water (18.3 mL). The mixture was vigorously stirred at rt for 10 min and extracted twice with MTBE (7.32 mL). The organic layers were combined and washed with brine. After concentration, the residue was purified by silica gel column chromatography (ethyl acetate/n-heptane=1/10 to 1/2) to give the title compound (289 mg, 88%). $^1$H NMR (400 MHz, CDCl$_3$) δ 0.15 (s, 9H), 0.30 (s, 3H), 0.58 (q, 6H), 0.88 (s, 9H), 0.89 (s, 9H), 0.95 (t, 9H), 0.98-1.05 (m, 2H), 1.06 (d, 3H), 1.20-1.72 (m, 7H), 1.72- 1.84 (m, 3H), 1.84-2.16 (m, 9H), 2.25 (m, 1H), 2.42 (m, 2H), 2.55 (dd, 1H), 2.72-2.86 (m, 2H), 2.92 (m, 2H), 3.34 (dd, 1H), 3.52 (s, 3H), 3.44-3.68 (m, 6H), 3.75 (m, 2H), 3.85 (m, 2H), 4.04 (m, 1H), 4.19 (dd, 1H), 4.24 (m, 1H), 4.39 (m, 1H), 4.59 (m, 1H), 4.67 (m, 1H), 4.78 (s, 1H), 4.84 (m, 1H), 5.45 (m, 1H), 5.48 (s, 1H), 5.68 (s, 1H), 7.41 (m, 2H), 7.58 (m, 1H), 8.02 (m, 2H).

1-((2S,3S,4R,5R)-5-((S)-2,3-bis((tert-butyldimethylsilyl)oxy)propyl)-2-(((2R,4R,6S)-6-(3-hydroxypropyl)-4-methyl-3-methylenetetrahydro-2H-pyran-2-yl)methyl)-4-methoxytetrahydrofuran-3-yl)-3-((2S,3aR,4aR,5S,5aS,7R,9aS,10aR,10bS)-2-((R)-5-bromo-3-hydroxyhex-5-en-1-yl)dodecahydro-2,5-epoxyfuro[2',3':4,5]furo[3,2-b]pyrano[2,3-e]pyran-7-yl)propan-2-one

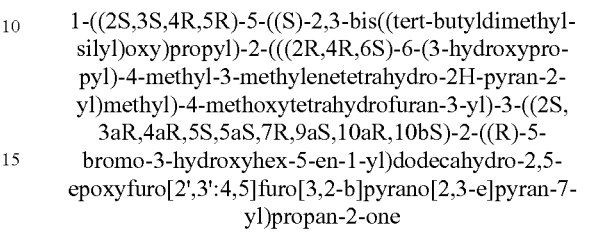

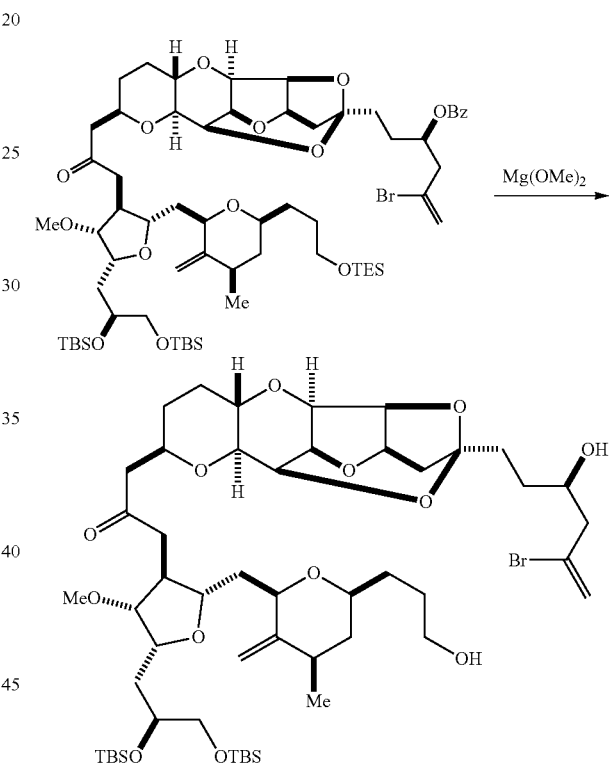

A solution of (R)-1-((2S,3aR,4aR,5S,5aS,7R,9aS,10aR,10bS)-7-(3-((2S,3S,4R,5R)-5-((S)-2,3-bis((tert- butyldimethylsilyl)oxy) propyl)-4-methoxy-2-(((2R,4R,6S)-4-methyl-3-methylene-6-(3-((triethylsilyl)oxy)propyl)tetrahydro-2H-pyran-2-yl)methyl)tetrahydrofuran-3-yl)-2-oxopropyl)dodecahydro-2,5-epoxyfuro[2',3':4,5]furo[3,2-b]pyrano[2,3-e]pyran-2-yl)-5-bromohex-5-en-3-yl benzoate (0.285 g, 0.223 mmol) in a mixture of methanol (5.7 mL) and THF (0.29 mL) was treated with 6-10% Mg(OMe)$_2$ in methanol (1.29 g, 0.893 mmol) and stirred at rt for 5 d. Potassium carbonate (0.093 g, 0.67 mmol) was added, and stirring was continued at rt for another 1 d. The reaction was quenched with saturated aqueous NH$_4$Cl (4.28 mL) and brine (4.28 mL) and extracted three times with MTBE (11.40 mL). The organic layers were combined, dried over MgSO$_4$, and concentrated in vacuo to give the title compound (280 mg, 119%).

217

1-((2S,3S,4R,5R)-5-((S)-2,3-bis((tert-butyldimethyl-silyl)oxy)propyl)-4-methoxy-2-(((2R,4R,6S)-4-methyl-3-methylene-6-(3-((triethylsilyl)oxy)propyl) tetrahydro-2H-pyran-2-yl) methyl)tetrahydrofuran-3-yl)-3-((2S,3aR,4aR,5S,5aS,7R,9aS,10aR,10bS)-2-((R)-5-bromo-3-hydroxyhex-5-en-1-yl)dodecahydro-2,5-epoxyfuro [2',3':4,5]furo[3,2-b]pyrano [2,3-e] pyran-7-yl)propan-2-one

218

(R)-1-((2S,3aR,4aR,5S,5aS,7R,9aS,10aR,10bS)-7-(3-((2S,3S,4R,5R)-5-((S)-2,3-bis ((tert-butyldimeth-ylsilyl)oxy)propyl)- 4-methoxy-2-(((2R,4R,6S)-4-methyl-3-methylene-6-(3-((triethylsilyl)oxy)propyl) tetrahydro-2H-pyran-2-yl)methyl) tetrahydrofuran-3-yl)-2-oxopropyl)decahydro-2,5-epoxyfuro[2',3':4,5]furo[3,2-b]pyrano[2,3-e]pyran-2-(3H)-yl)-5-bromohex-5-en-3-yl 4-methylbenzenesulfonate

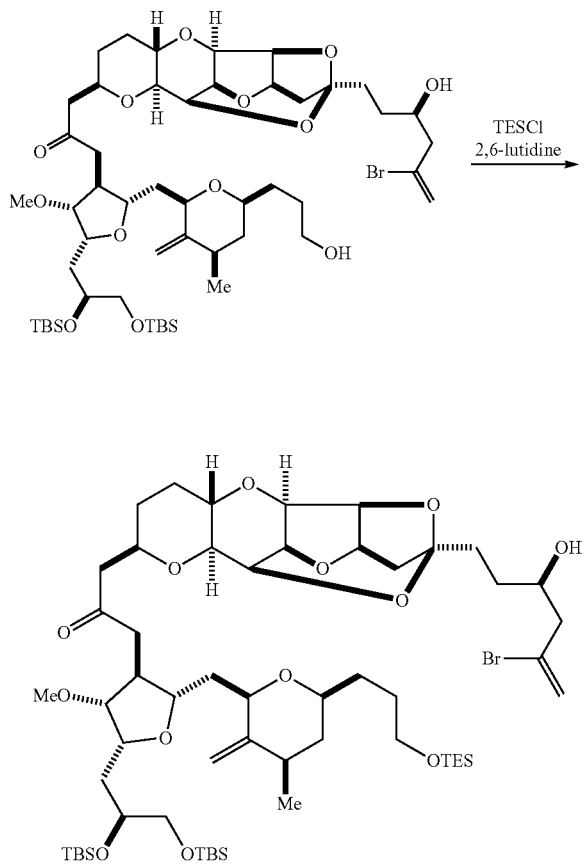

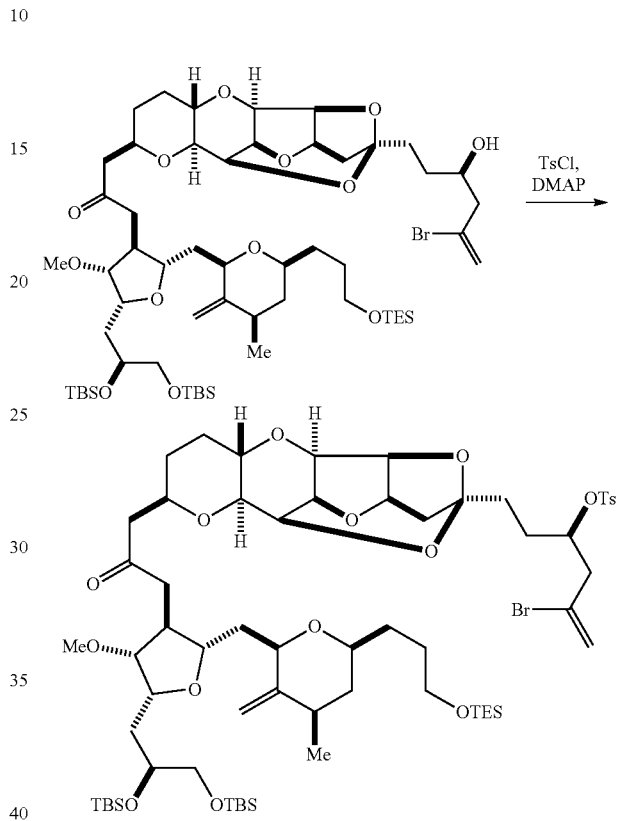

A solution of 1-((2S,3S,4R,5R)-5-((S)-2,3-bis((tert-butyldimethylsilyl)oxy)propyl)-2-(((2R,4R,6S)-6-(3-hydroxypropyl)-4-methyl-3-methylenetetrahydro-2H-pyran-2-yl)methyl)-4-methoxy tetrahydrofuran-3-yl)-3-((2S,3aR, 4aR,5S,5aS,7R,9aS,10aR,10bS)-2-((R)-5-bromo-3-hydroxyhex-5-en-1-yl)dodecahydro-2,5-epoxyfuro[2',3':4, 5]furo[3,2-b]pyrano[2,3-e]pyran-7-yl)propan-2-one (0.28 g, 0.265 mmol) in $CH_2Cl_2$ (5.6 mL) was cooled to −78° C. and treated with 2,6-lutidine (0.123 mL, 1.06 mmol) and chlorotriethylsilane (0.054 mL, 0.32 mmol). The reaction mixture was stirred at −78° C. for 2 h. The reaction was quenched with methanol (0.107 mL, 2.65 mmol) and stirred at −78° C. for 10 min. After removing the cold bath, the mixture was treated with water (5.6 mL) and warmed to rt. The mixture was extracted twice with MTBE (11.20 mL). The organic layers were combined, washed with 0.1 N HCl (6.09 mL, 0.609 mmol) and saturated aqueous $NaHCO_3$ (2.80 mL), dried over $MgSO_4$, and concentrated in vacuo to give the title compound (327 mg, 105%).

1-((2S,3S,4R,5R)-5-((S)-2,3-bis((tert-butyldimethylsilyl) oxy)propyl)-4-methoxy-2-(((2R,4R,6S)-4-methyl-3-methylene-6-(3-((triethylsilyl)oxy)propyl)tetrahydro-2H-pyran-2-yl) methyl)tetrahydrofuran-3-yl)-3-((2S,3aR,4aR,5S,5aS, 7R,9aS,10aR,10bS)-2-((R)-5-bromo-3-hydroxyhex-5-en-1-yl)dodecahydro-2,5-epoxyfuro[2',3':4,5]furo[3,2-b]pyrano [2,3-e]pyran-7-yl)propan-2-one (0.327 g, 0.279 mmol) was dissolved in $CH_2Cl_2$ (4.9 mL) and treated with DMAP (0.102 g, 0.837 mmol) and p-TsCl (0.064 g, 0.34 mmol). The mixture was stirred at rt for 16 h. Additional DMAP (0.020 g, 0.17 mmol) and p-TsCl (0.016 g, 0.084 mmol) were added, and stirring was continued at rt for another 24 h. The reaction mixture was diluted with MTBE (20 mL) and sequentially washed with 0.1 N HCl (8.4 mL×2), saturated aqueous $NaHCO_3$ (3.3 mL), and brine (3.3 mL). After concentration, the residue was purified by column chromatography (ethyl acetate/n-heptane=1/10 to 2/3) to give the title compound (215 mg, 72% for 3 steps). $^1$H NMR (400 MHz, $CDCl_3$) δ 0.03 (2s, 9H), 0.60 (s, 3H), 0.59 (q, 6H), 0.85 (s, 9H), 0.87 (s, 9H), 0.94 (t, 9H), 0.96-1.10 (m, 2H), 1.06 (d, 3H), 1.28-1.60 (m, 5H), 1.60-1.84 (m, 6H), 1.84-2.16 (m, 8H), 2.24 (m, 1H), 2.42 (m, 2H), 2.51 (dd, 1H), 2.64 (dd, 1H), 2.72 (dd, 1H), 2.82 (dd, 1H), 2.90 (d, 1H), 3.26 (m, 1H), 3.52 (s, 3H), 3.44-3.68 (m, 6H), 3.75 (m, 2H), 3.84 (m, 2H), 4.04 (m, 1H), 4.19 (m, 1H), 4.35 (m, 1H), 4.58

(m, 1H), 4.66 (m, 1H), 4.67 (m, 1H), 4.78 (s, 1H), 4.85 (m, 1H), 4.84 (s, 1H), 5.35 (m, 1H), 5.58 (s, 1H), 7.35 (d, 2H), 7.80 (d, 2H)

(R)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)- 4-methoxy-2-(((2R,4R,6S)-4-methyl-3-methylene-6-(3-oxopropyl)tetrahydro-2H-pyran-2-yl)methyl)tetrahydrofuran-3-yl)-2-oxopropyl)dodecahydro-2,5-epoxyfuro[2',3':4,5]furo[3,2-b]pyrano[2,3-e]pyran-2-yl-5-bromohex-5-en-3-yl 4-methylbenzenesulfonate

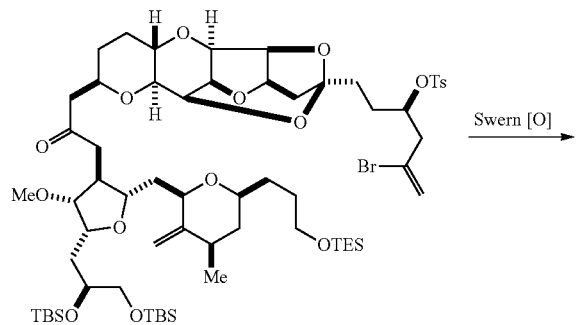

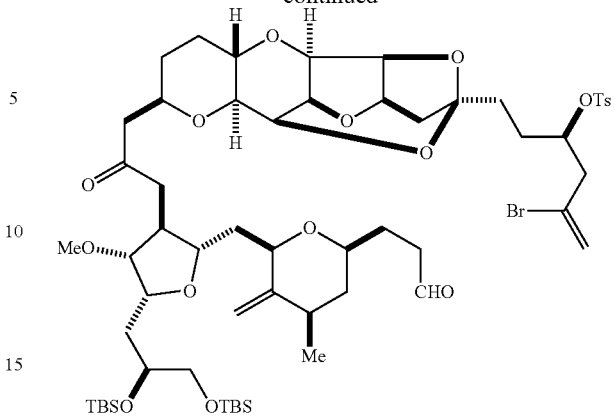

A solution of 2 M oxalic chloride in CH$_2$Cl$_2$ (0.810 mL, 1.62 mmol) in CH$_2$Cl$_2$ (4.30 mL) was cooled to −78° C. and treated with DMSO (0.230 mL, 3.24 mmol). After stirring for 10 min at −78° C., a solution of (R)-1-((2S,3aR,4aR,5S, 5aS,7R,9aS,10aR,10bS)-7-(3-((2S,3S,4R,5R)-5-((S)-2,3-bis ((tert-butyldimethylsilyl)oxy)propyl)-4-methoxy-2-(((2R, 4R,6S)-4-methyl-3-methylene-6-(3-((triethylsilyl)oxy) propyl)tetrahydro-2H-pyran-2-yl)methyl) tetrahydrofuran-3-yl)-2-oxopropyl)dodecahydro-2,5-epoxyfuro[2',3':4,5] furo[3,2-b]pyrano [2,3-e]pyran-2-yl)-5-bromohex-5-en-3-yl 4-methylbenzenesulfonate (0.215 g, 0.162 mmol) in CH$_2$Cl$_2$ (2.2 mL) was added. The mixture was stirred at −78° C. for 10 min and at −40° C. for 1 h. After cooling back to −78° C., the mixture was treated with triethylamine (1.13 mL, 8.10 mmol) and stirred at −78° C. for 10 min and at 0° C. for 20 min. The resulting mixture was treated with water (4.3 mL) and diluted with MTBE (21.5 mL). The organic layer was separated and washed with brine. After concentration, the residue was purified by silica gel column chromatography (ethyl acetate/n-heptane=1/10 to 1/1) to give the title compound (166 mg, 85%).

BisTBS Ether

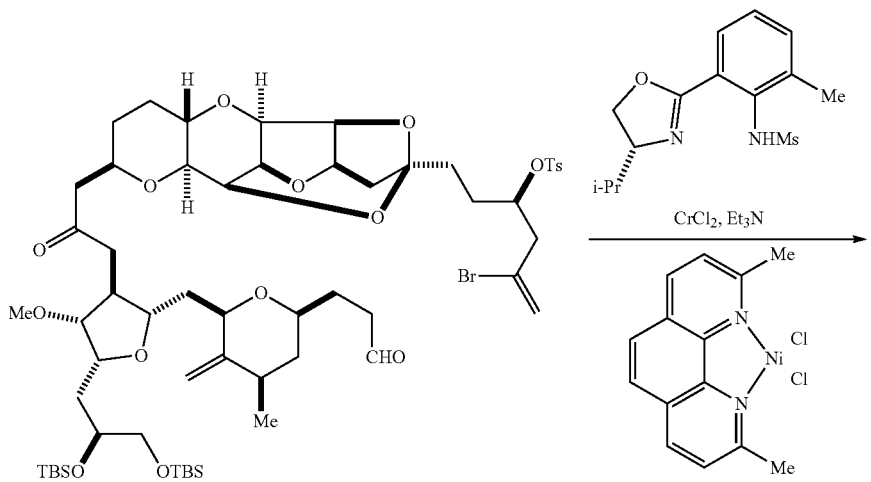

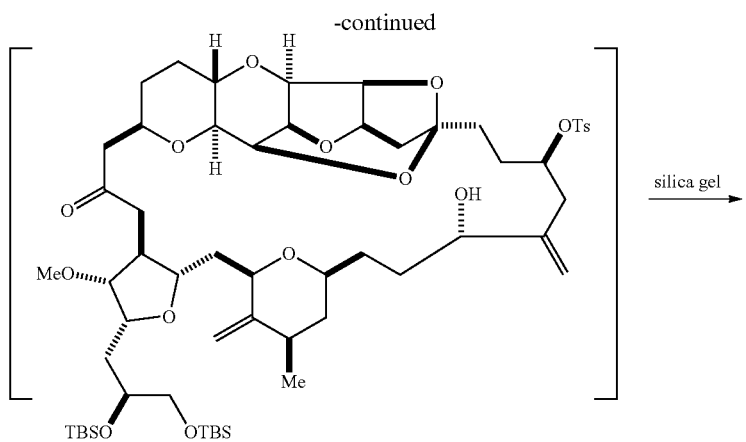

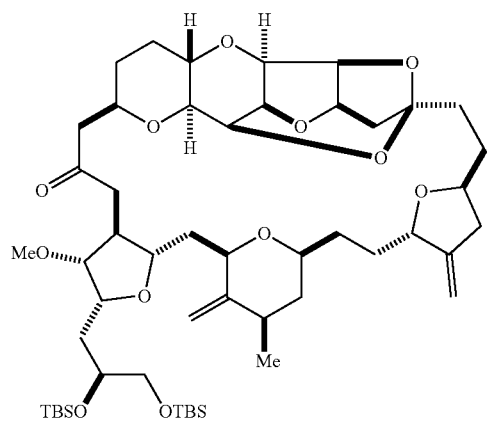

Chromous chloride (0.520 g, 4.23 mmol) was added to a 3-necked flask, which was purged with $N_2$ for 5 min, and to the flask was added a solution of (R)—N-(2-(4-isopropyl-4,5-dihydrooxazol-2-yl)-6-methylphenyl)methanesulfonamide (1.25 g, 4.23 mmol) in a degassed THF (7.5 mL). The mixture was heated to 30° C., treated with triethylamine (0.590 mL, 4.23 mmol), and stirred at 33° C. for 1 h. After cooling to 0° C., the mixture was treated with nickel(II) chloride 2,9-dimethyl-1,10-phenanthroline complex (0.023 g, 0.069 mmol) and purged with $N_2$ for 5 min. After removing the ice-bath, a solution of (R)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)-4-methoxy-2-(((2R,4R,6S)-4-methyl-3-methylene-6-(3-oxopropyl)tetrahydro-2H-pyran-2-yl)methyl)tetrahydrofuran-3-yl)-2-oxopropyl)dodecahydro-2,5-epoxyfuro[2',3':4,5]furo[3,2-b]pyrano[2,3-e]pyran-2-yl)-5-bromohex-5-en-3-yl 4-methylbenzenesulfonate (0.083 g, 0.069 mmol) in a degassed THF (4.98 mL) was added over 2 h by syringe pump. The mixture was stirred at rt for another 2 h. After cooling to 0° C., the reaction was quenched with ethylenediamine (0.926 mL, 13.7 mmol), while maintaining the internal temperature below 10° C., and stirred at rt for 10 min. The mixture was treated with water (9.96 mL) and extracted twice with MTBE (9.96 mL). The organic layers were combined, dried over $MgSO_4$, and concentrated in vacuo.

The residue was dissolved in isopropanol (IPA) (4.98 mL), treated with silica gel (166 mg), and stirred at rt for 23 h. The precipitate was filtered and washed with IPA (3 mL) and heptane (3 mL). The filtrate was aged in a freezer for 2 d. The resulting precipitate was filtered and washed with IPA (5 mL). The filtrate was concentrated and purified by silica gel column chromatography (ethyl acetate/n-heptane=1/10 to 3/2) to give the title compound (33 mg, 50%), the structure of which was confirmed by comparison of its $^1H$ NMR spectrum with that of an authentic sample. $^1H$ NMR (400 MHz, $C_6D_6$) δ 0.05 (s, 6H), 0.14 (s, 3H), 0.16 (s, 3H), 0.77 (d, 3H), 0.94 (s, 9H), 0.99 (s, 9H), 1.05-1.30 (m, 2H), 1.30-1.46 (m, 3H), 1.20-1.72 (m, 2H), 1.50-1.70 (m, 3H), 1.84-2.00 (m, 4H), 2.05-2.20 (m, 3H), 2.28-2.40 (m, 4H), 2.50 (m, 2H), 2.60 (m, 2H), 2.70 (m, 2H), 2.86 (m, 1H), 3.50 (m, 1H), 3.52-3.72 (m, 4H), 3.58 (s, 3H), 3.74-3.84 (m, 2H), 3.95 (m, 1H), 4.00-4.22 (m, 7H), 4.04 (m, 1H), 4.38 (m, 1H), 4.56 (bm, 1H), 4.57 (s, 1H), 4.74 (s, 1H), 4.98 (m, 2H).

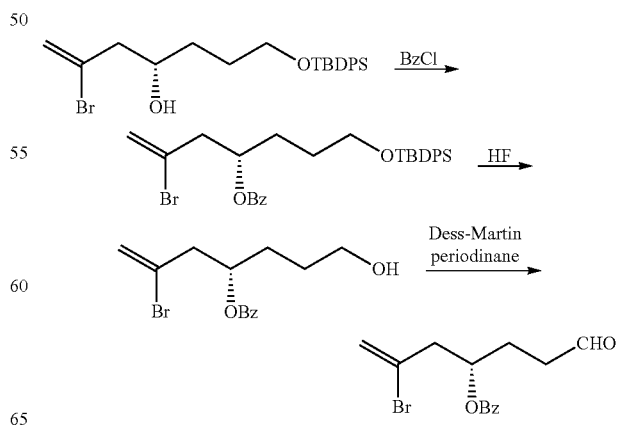

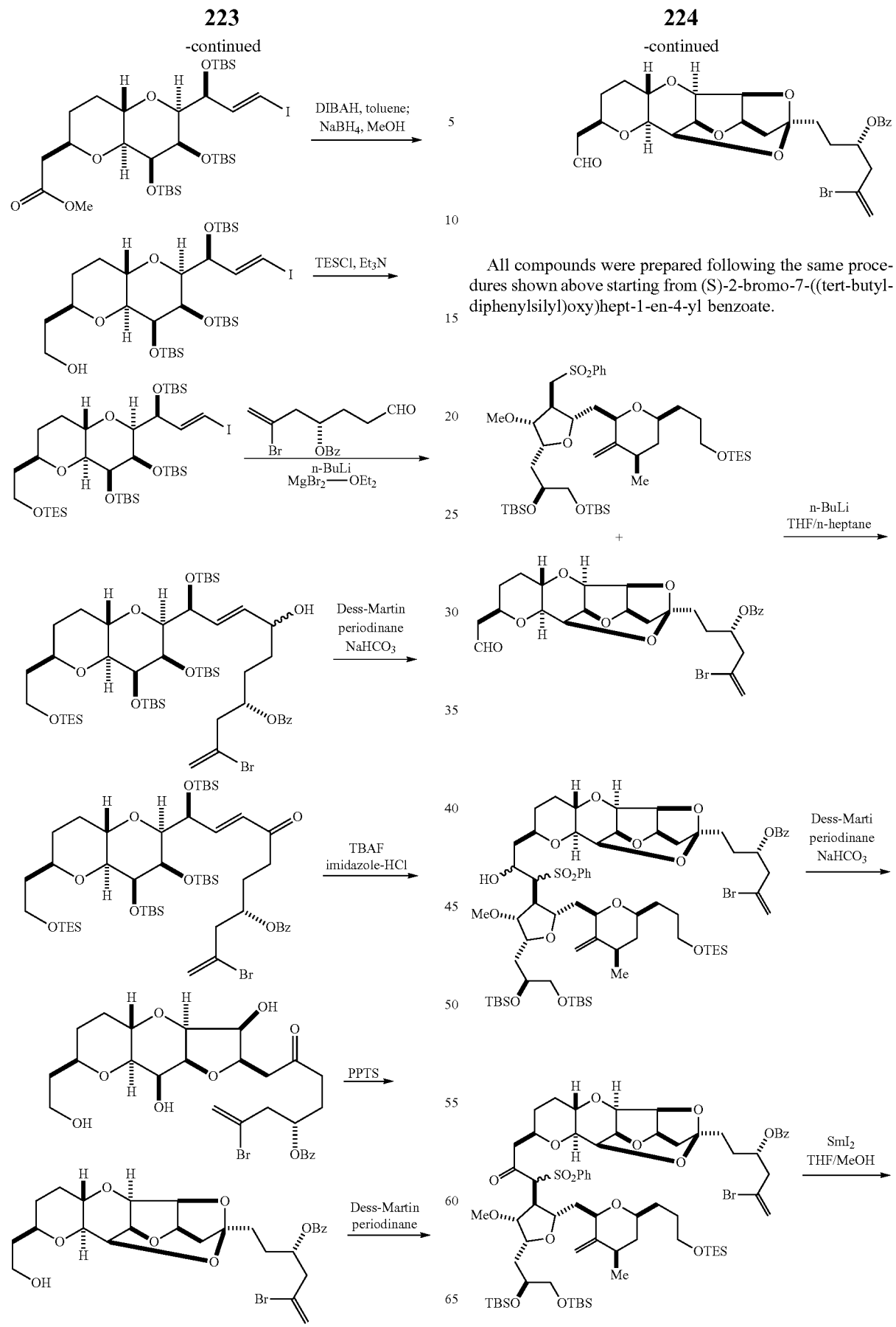
All compounds were prepared following the same procedures shown above starting from (S)-2-bromo-7-((tert-butyldiphenylsilyl)oxy)hept-1-en-4-yl benzoate.

225
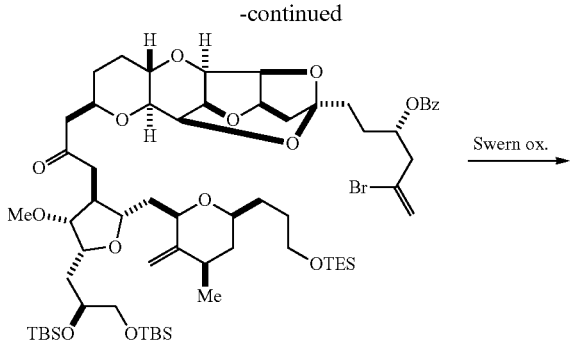
Swern ox.
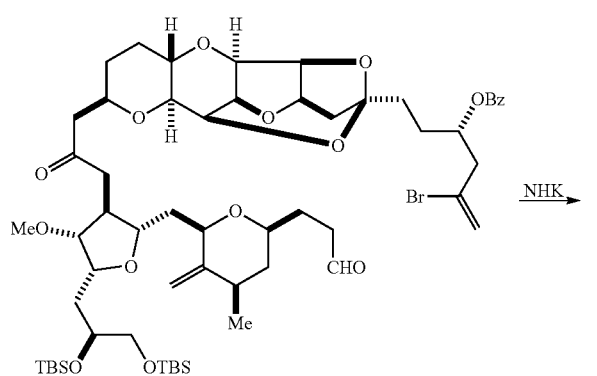
NHK
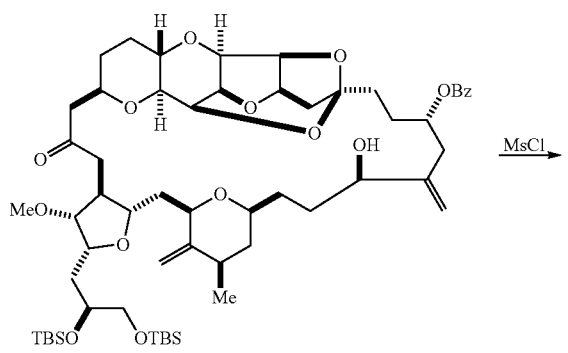
MsCl
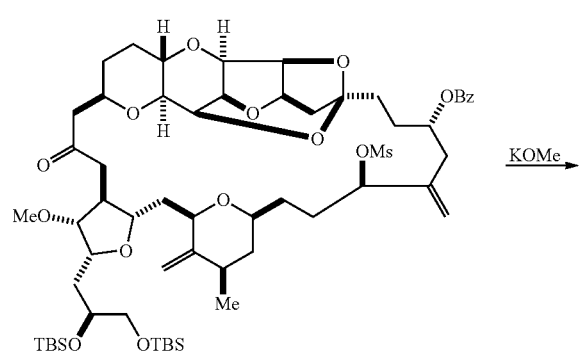
KOMe
226
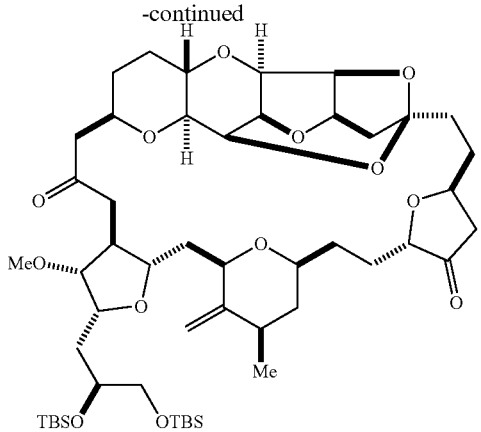
(S)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)- 4-methoxy-2-(((2R,4R,6S)-4-methyl-3-methylene-6-(3-oxopropyl)tetrahydro-2H-pyran-2-yl)methyl)tetrahydrofuran-3-yl)-2-oxopropyl)dodecahydro-2,5-epoxyfuro[2',3':4,5]furo[3,2-b]pyrano[2,3-e]pyran-2-yl)-5-bromohex-5-en-3-yl benzoate
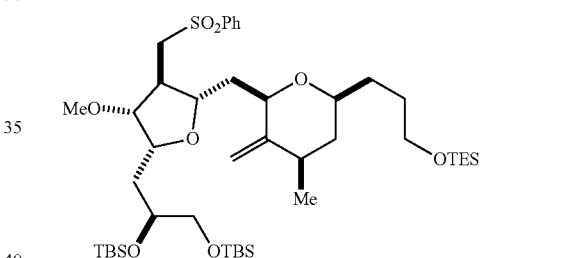
+
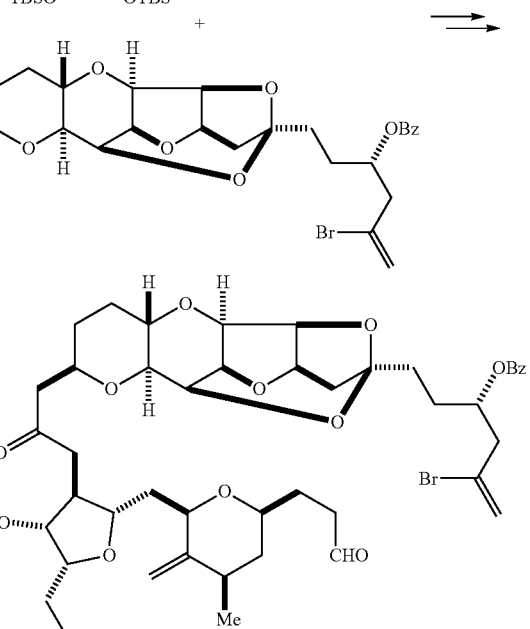
⇒
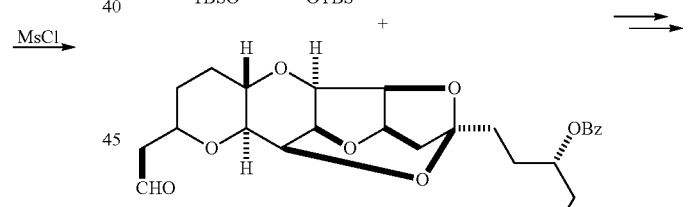

The compound was prepared following the same procedures shown above for (3R)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)-4-methoxy-2-(((2R,4R,6S)-4-methyl-3-methylene-6-(3-((triethylsilyl)oxy)propyl)tetrahydro-2H-pyran-2-yl)methyl) tetrahydrofuran-3-yl)-2-hydroxy-3-(phenylsulfonyl)propyl)dodecahydro-2,5-epoxyfuro[2',3':4,5]furo[3,2-b]pyrano[2,3-e]pyran-2-yl)-5-bromohex-5-en-3-yl benzoate with the exception that (S)-5-bromo-1-((2S,3aR,4aR,5S,5aS,7R,9aS,10aR,10bS)-7-(2-oxoethyl)decahydro-2,5-epoxyfuro[2',3':4,5]furo[3,2-b]pyrano[2,3-e]pyran-2(3H)-yl)hex-5-en-3-yl benzoate was used as a starting material.

tetrahydrofuran-3-yl)-2-oxopropyl)dodecahydro-2,5-epoxyfuro[2',3':4,5]furo[3,2-b]pyrano[2,3-e]pyran-2-yl)-5-bromohex-5-en-3-yl benzoate (compound 8; 0.136 g, 0.117 mmol) in a degassed THF (6.80 mL) was added over 1.5 h by syringe pump. The mixture was stirred at rt for another 2 h. The reaction was cooled to 0° C., quenched with ethylenediamine (1.045 mL, 15.47 mmol), while maintaining the internal temperature below 10° C., and stirred at rt for 10 min. The mixture was treated with water (16.3 mL) and extracted with n-heptane (8.2 mL) and then twice with MTBE (16.3 mL). The organic layers were combined, dried over MgSCO$_4$, and concentrated in vacuo. The residue was treated with n-heptane (20 mL) and stirred at rt for 20 min.

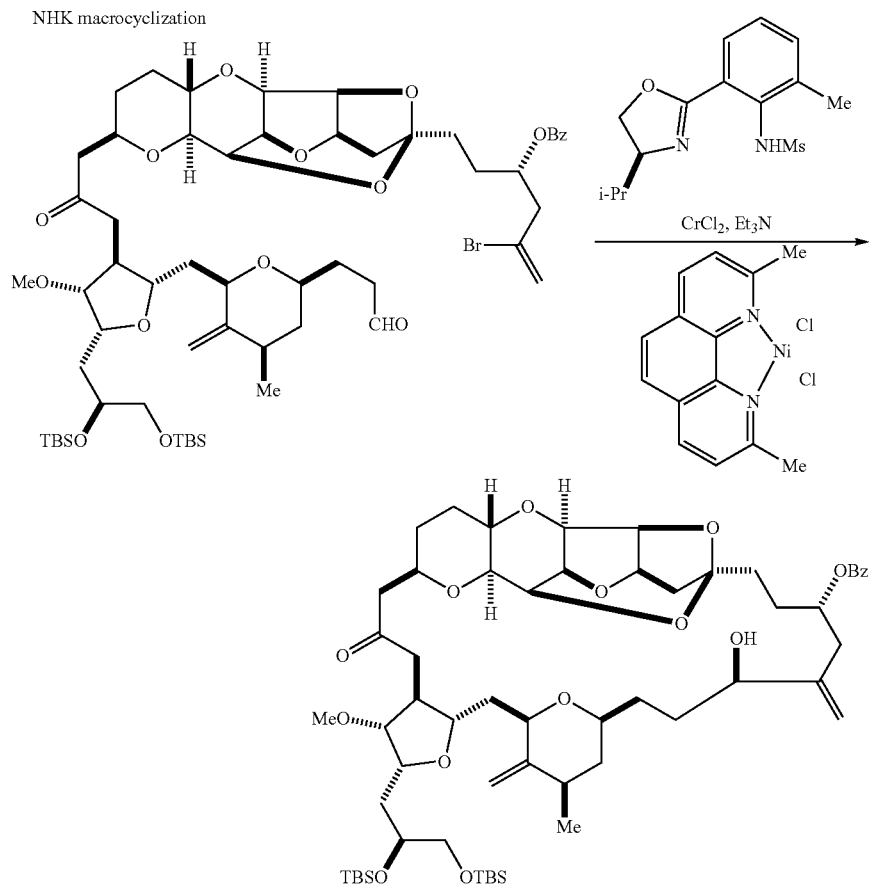

16

Chromous chloride (0.636 g, 5.18 mmol) was added to a 3-necked flask, which was purged with N$_2$ for 5 min, and to the flask was added a solution of (S)—N-(2-(4-isopropyl-4,5-dihydrooxazol-2-yl)-6-methylphenyl)methanesulfonamide (1.535 g, 5.18 mmol) in a degassed THF (6.80 mL). The resulting mixture was heated to 30° C., charged with triethylamine (0.722 mL, 5.18 mmol), and stirred at 33° C. for 1 h. After cooling to 0° C., the mixture was treated with nickel(II) chloride 2,9-dimethyl-1,10-phenanthroline complex (0.040 g, 0.12 mmol) and purged with N$_2$ for 5 min. After removing the ice-bath, a solution of (S)-1-((2S,3aR,4aR,5S,5aS,7R,9aS,10aR,10bS)-7-(3-((2S,3S,4R,5R)-5-((S)-2,3-bis((tert-butyldimethylsilyl)oxy)propyl)-4-methoxy-2-(((2R,4R,6S)-4-methyl-3-methylene-6-(3-oxopropyl)tetrahydro-2H-pyran-2-yl)methyl)

The precipitated ligand was filtered off and rinsed with heptane (20 mL) and IPA (10 mL). The filtrate was aged in a freezer (−20° C.) for 20 h. The precipitate was filtered and rinsed with IPA. The filtrate was concentrated and purified by silica gel column chromatography (ethyl acetate/n-heptane=1/10 to 1/1) to give compound 16 (88 mg, 69%). $^1$H NMR (400 MHz, CDCl$_3$) δ 0.02 (s, 9H), 0.6 (s, 3H), 0.86 (s, 18H), 1.10 (m, 4H), 1.42 (m, 3H), 1.64-2.00 (m, 8H), 2.06-2.30 (m, 8H), 2.45 (m, 2H), 2.64 (m, 2H), 2.94 (m, 2H), 3.11 (m, 1H), 3.19 (m, 1H), 3.36 (s, 3H), 3.48 (m, 1H), 3.56 (m, 1H), 3.64-3.90 (m, 5H), 3.80-4.30 (m, 4H), 4.41 (m, 1H), 4.59 (m, 1H), 4.68 (m, 1H), 4.79 (m, 1H), 4.92 (s, 1H), 5.06 (s, 1H), 5.28 (s, 1H), 5.40 (m, 1H), 7.41 (m, 2H), 7.58 (m, 1H), 8.02 (m, 2H).

Mesylation of NHK Product

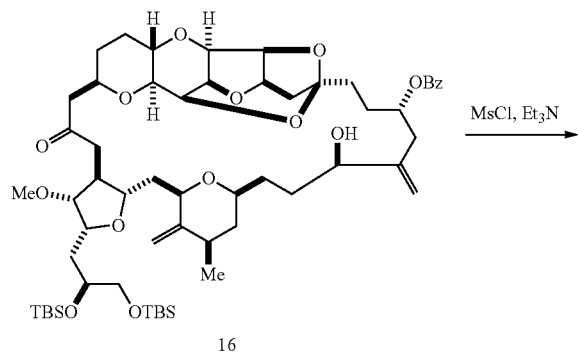

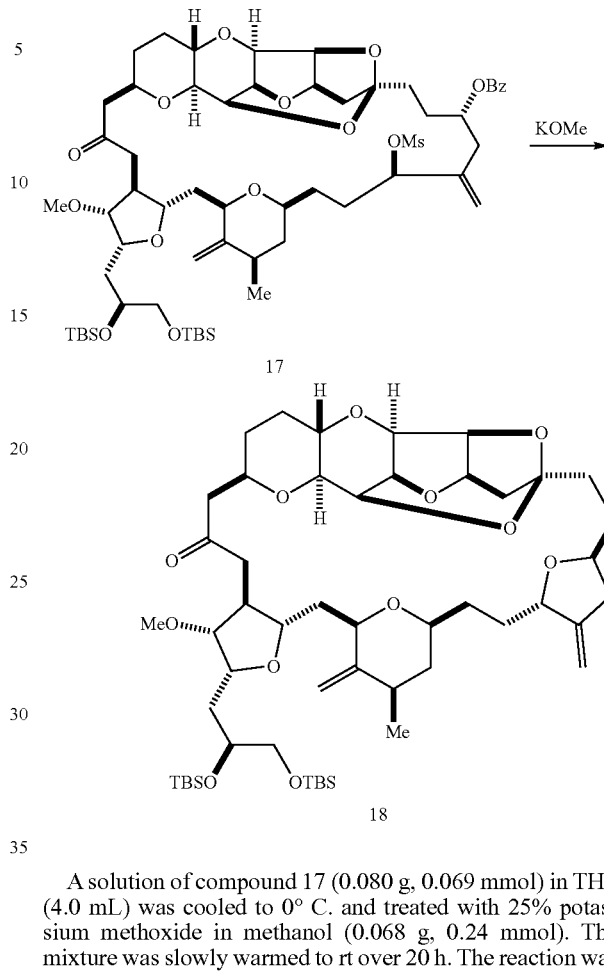

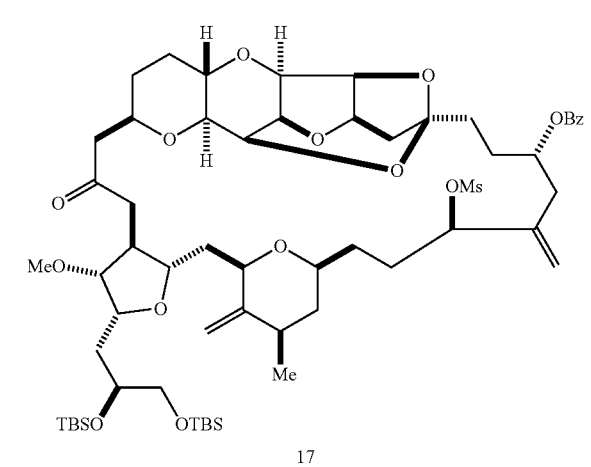

A solution of Compound 16 (0.084 g, 0.078 mmol) in THF (2.94 mL) was cooled to 0° C. and treated with triethylamine (0.043 mL, 0.31 mmol) and methanesulfonyl chloride (0.018 mL, 0.23 mmol). After stirring at 0° C. for 30 min, the reaction was quenched with water (3.36 mL) and extracted three times with MTBE (5.04 mL). The organic layers were combined, dried over MgSO$_4$, and concentrated to give compound 17 (88 mg).

Cyclization with KOMe

A solution of compound 17 (0.080 g, 0.069 mmol) in THF (4.0 mL) was cooled to 0° C. and treated with 25% potassium methoxide in methanol (0.068 g, 0.24 mmol). The mixture was slowly warmed to rt over 20 h. The reaction was quenched with saturated aqueous NH$_4$Cl (2.4 mL) and extracted three times with MTBE (6.4 mL). The organic layers were combined and dried over MgSO$_4$. After concentration, the residue was purified by silica gel column chromatography (ethyl acetate/n-heptane=1/10 to 2/1) to give compound 18 (45 mg, 68% for 2 steps). $^1$H NMR (400 MHz, C$_6$D$_6$) δ 0.05 (s, 6H), 0.14 (s, 3H), 0.16 (s, 3H), 0.77 (d, 3H), 0.94 (s, 9H), 0.99 (s, 9H), 1.05-1.30 (m, 2H), 1.30-1.46 (m, 3H), 1.20-1.72 (m, 2H), 1.50-1.70 (m, 3H), 1.84-2.00 (m, 4H), 2.05-2.20 (m, 3H), 2.28-2.40 (m, 4H), 2.50 (m, 2H), 2.60 (m, 2H), 2.70 (m, 2H), 2.86 (m, 1H), 3.50 (m, 1H), 3.52-3.72 (m, 4H), 3.58 (s, 3H), 3.74-3.84 (m, 2H), 3.95 (m, 1H), 4.00-4.22 (m, 7H), 4.04 (m, 1H), 4.38 (m, 1H), 4.56 (bm, 1H), 4.57 (s, 1H), 4.74 (s, 1H), 4.98 (m, 2H).

Example 8: Preparation of a Compound of Formula (ID) through C.26-C.27 Macrocyclization

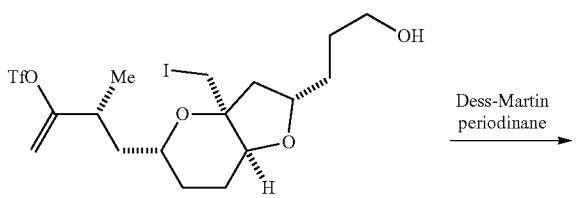

231 232

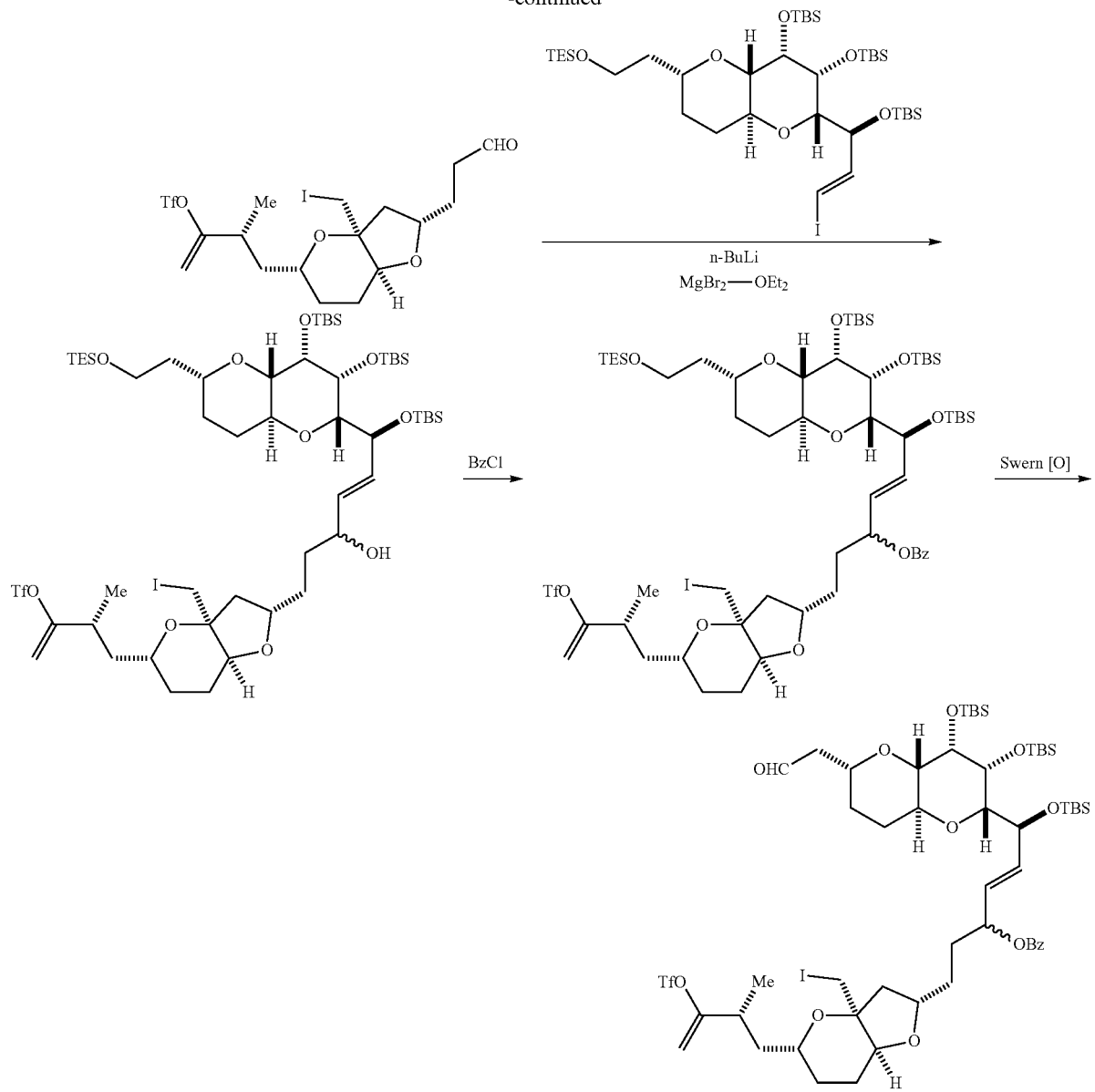

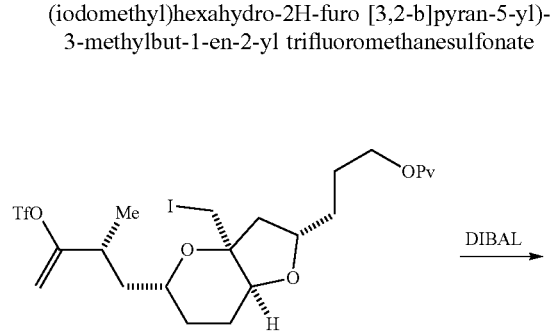

(R)-4-((2S,3aS,5R,7aS)-2-(3-hydroxypropyl)-3a-(iodomethyl)hexahydro-2H-furo [3,2-b]pyran-5-yl)-3-methylbut-1-en-2-yl trifluoromethanesulfonate

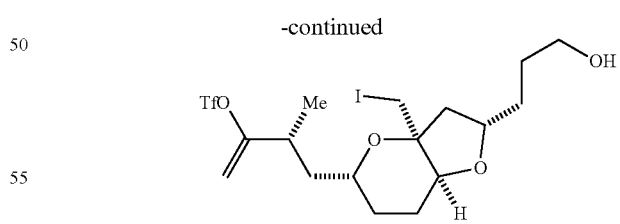

-continued

A solution of 3-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)propyl pivalate (6.80 g, 10.9 mmol) in CH$_2$Cl$_2$ (68.0 mL) was cooled to −78° C. and treated with 1 M DIBAL in toluene (23.88 mL, 23.88 mmol) over 20 min, while maintaining the internal temperature below −70° C. The reaction mixture was stirred at −78° C. for 30 min. The reaction was quenched with methanol (4.39 mL), while maintaining the internal temperature below −60° C. After removing the cold bath, the mixture was treated with 1 N HCl (109 mL) and MTBE (102 mL) and stirred at ambient temperature for 20 min. The organic layer was separated, and the aqueous layer was extracted with MTBE (102 mL). The organic layers were combined, dried over MgSO₄, and concentrated to give the title compound (8.8 g, contaminated with toluene). ¹H NMR (400 MHz, CDCl₃) δ 1.14 (d, 3H), 1.22 (m, 1H), 1.45-1.70 (m, 8H), 1.72-1.90 (m, 2H), 2.42 (m, 1H), 2.83 (m, 1H), 3.40 (d, 1H), 3.46 (d, 1H), 3.55 (m, 1H), 3.65 (m, 2H), 3.79 (m, 1H), 4.22 (m, 1H), 5.03 (d, 1H), 5.10 (d, 1H).

(R)-4-((2S,3aS,5R,7aS)-3a-(iodomethyl)-2-(3-oxo-propyl)hexahydro-2H-furo[3,2-b]pyran-5-yl)-3-methylbut-1-en-2-yl trifluoromethanesulfonate

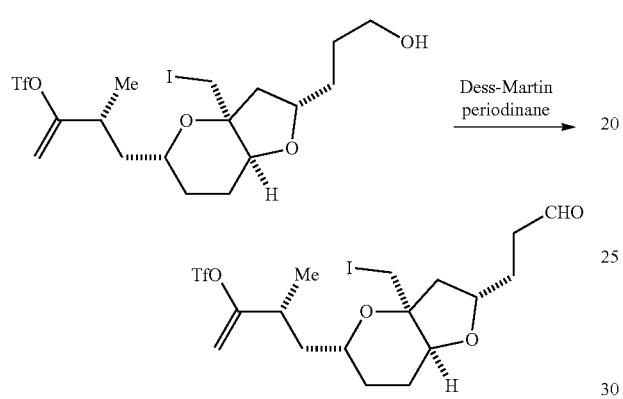

A solution of (R)-4-((2S,3aS,5R,7aS)-2-(3-hydroxypropyl)-3a-(iodomethyl)hexahydro-2H-furo[3,2-b]pyran-5-yl)-3-methylbut-1-en-2-yl trifluoromethanesulfonate (2.64 g, 4.87 mmol) in CH₂Cl₂ (26.4 mL) was treated with Dess-Martin periodinane (3.10 g, 7.30 mmol) and stirred at rt for 1 h. The reaction was quenched with saturated aqueous NaHCO₃ (20 mL) and 20% Na₂SO₃ (20 mL) and extracted three times with MTBE (20 mL). The organic layers were combined and washed with brine. After concentration, the residue was purified by silica gel column chromatography (ethyl acetate/n-heptane1=/10 to 1/3) to give the title compound (970 mg, 56% for 2 steps). ¹H NMR (400 MHz, CDCl₃) δ 1.14 (d, 3H), 1.15-1.30 (m, 2H), 1.45-1.70 (m, 5H), 1.72-1.90 (m, 2H), 2.32 (dd, 1H), 2.52 (m, 2H), 2.83 (m, 1H), 3.37 (d, 1H), 3.43 (d, 1H), 3.52 (m, 1H), 3.72 (m, 1H), 4.19 (m, 1H), 5.01 (d, 1H), 5.09 (d, 1H), 9.76 (s, 1H).

(3R)-4-((2S,3aS,5R,7aS)-2-((6S,E)-6-((2S,3R,4S, 4aS,6R,8aS)-3,4-bis((tert-butyldimethylsilyl)oxy)-6-(2-((triethylsilyl)oxy)ethyl)octahydropyrano[3,2-b] pyran-2-yl)-6-((tert-butyldimethylsilyl)oxy)-3-hydroxyhex-4-en-1-yl)-3a-(iodomethyl) hexahydro-2H-furo[3,2-b]pyran-5-yl)-3-methylbut-1-en-2-yl trifluoromethanesulfonate

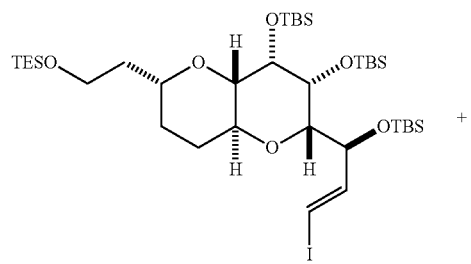

+

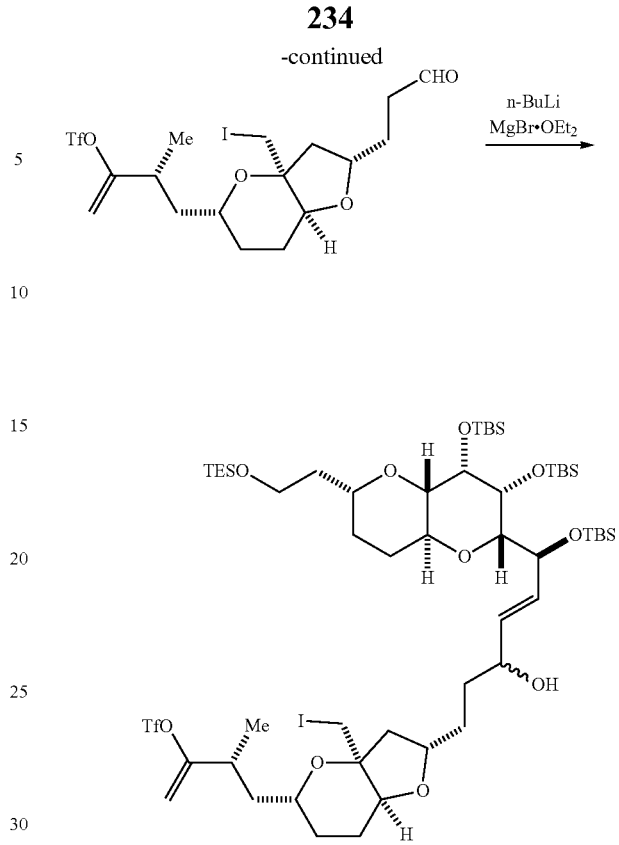

A solution of (((2S,3R,4S,4aS,6R,8aS)-2-((S,E)-1-((tert-butyldimethylsilyl)oxy)-3-iodoallyl)-6-(2-((triethylsilyl) oxy)ethyl)octahydropyrano[3,2-b]pyran-3,4-diyl)bis(oxy)) bis(tert-butyldimethylsilane) (1.295 g, 1.51 mmol) in THF (10.20 mL) was cooled to −78° C. and treated with 1.6 M n-BuLi in hexane (0.944 mL, 1.51 mmol), while maintaining the internal temperature below −60° C. After stirring at −78° C. for 15 min, the mixture was treated with a solution of magnesium bromide diethyl etherate (0.390 g, 1.51 mmol) in a mixture of THF (6 mL) and toluene (1 mL), while maintaining the internal temperature below −60° C., and stirred at −78° C. for 30 min. A solution of (R)-4-((2S,3aS, 5R,7aS)-3a-(iodomethyl)-2-(3-oxopropyl)hexahydro-2H-furo[3,2-b]pyran-5-yl)-3-methylbut-1-en-2-yl trifluoromethanesulfonate (0.68 g, 1.258 mmol) in THF (6.80 mL) was added, and the resulting mixture was stirred at −78° C. for 3 h and slowly warmed to rt over 14 h. The reaction was quenched with saturated aqueous NH₄Cl (6.80 mL) and extracted twice with MTBE (0.150 mL). The organic layers were combined and washed with brine. After concentration, the residue was purified by silica gel column chromatography (ethyl acetate/n-heptane=1/10 to 1/3) to give the title compound (455 mg, 28%).

235

(6S,E)-6-((2S,3R,4S,4aS,6R,8aS)-3,4-bis((tert-butyldimethylsilyl)oxy)-6-(2-((triethylsilyl)oxy)ethyl)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

236

(6S,E)-6-((2S,3R,4S,4aS,6R,8aS)-3,4-bis((tert-butyldimethylsilyl)oxy)-6-(2-oxoethyl)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

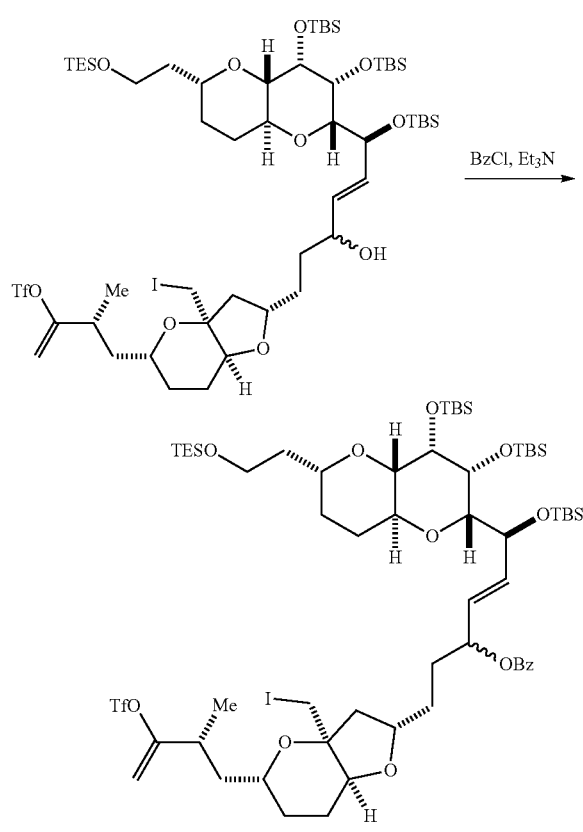

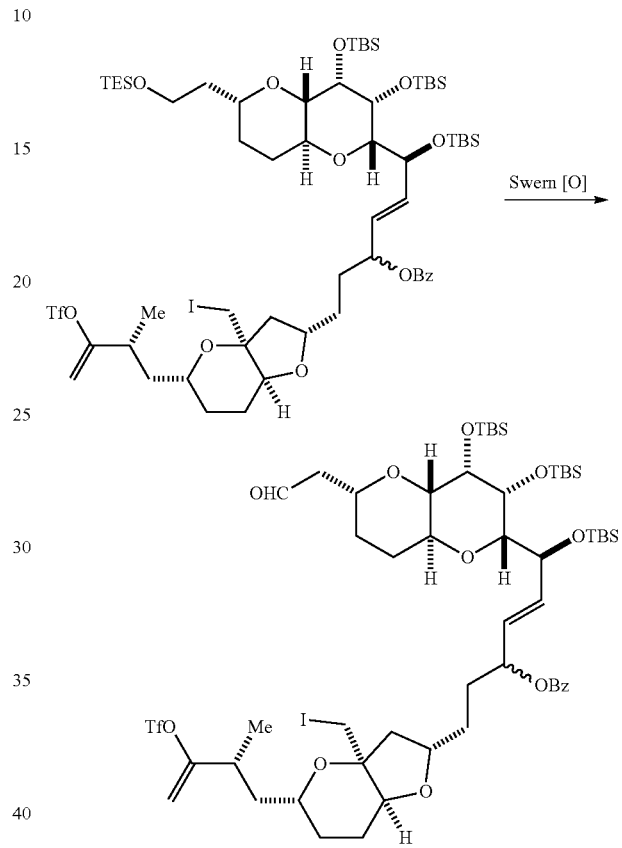

A solution of (3R)-4-((2S,3aS,5R,7aS)-2-((6S,E)-6-((2S,3R,4S,4aS,6R,8aS)-3,4-bis((tert-butyldimethylsilyl)oxy)-6-(2-((triethylsilyl)oxy)ethyl) octahydropyrano[3,2-b]pyran-2-yl)-6-((tert-butyldimethylsilyl)oxy)-3-hydroxyhex-4-en-1-yl)-3a-(iodomethyl)hexahydro-2H-furo[3,2-b]pyran-5-yl)-3-methylbut-1-en-2-yl trifluoromethanesulfonate (0.455 g, 0.358 mmol) in CH$_2$Cl$_2$ (4.55 mL) was treated with benzoyl chloride (0.083 mL, 0.72 mmol), triethylamine (0.15 mL, 1.1 mmol) and DMAP (4.4 mg, 0.036 mmol). The mixture was stirred at ambient temperature for 40 h. The reaction was quenched with water (4.6 mL) and extracted twice with MTBE (9.1 mL). The organic layers were combined and washed with brine. After concentration, the residue was purified by silica gel column chromatography (ethyl acetate/n-heptane=1/10 to 1/5) to give the title compound (316 mg, 64%). $^1$H NMR (400 MHz, CDCl$_3$) δ −0.08-0.12 (multiples, 18H), 0.55 (m, 6H), 0.81 (2s, 9H), 0.85-1.00 (m, 27H), 1.05-1.30 (m, 2H), 1.12 (d, 3H), 1.40-1.90 (m, 16H), 2.29 (m, 1H), 2.80 (m, 2H), 3.30-3.45 (m, 3H), 3.53 (m, 2H), 3.65 (m, 1H), 3.72 (m, 1H), 3.83 (m, 2H), 4.08 (m, 1H), 4.19 (m, 1H), 4.98 (m, 1H), 5.02 (m, 1H), 5.07 (m, 1H), 5.60 (m, 1H), 5.77 (m, 1H), 6.05 (m, 1H), 7.40 (m, 2H), 7.52 (m, 1H), 8.02 (m, 2H).

A solution of oxalyl chloride (0.141 mL, 1.61 mmol) in CH$_2$Cl$_2$ (6.32 mL) was cooled to −78° C. and treated with DMSO (0.228 mL, 3.22 mmol). After stirring for 10 min at −78° C., the mixture was treated with a solution of (6S,E)-6-((2S,3R,4S,4aS,6R,8aS)-3,4-bis((tert-butyldimethylsilyl)oxy)-6-(2-((triethylsilyl)oxy)ethyl)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate (0.316 g, 0.230 mmol) in CH$_2$Cl$_2$ (3.8 mL) The mixture was stirred at −78° C. for 20 min and at −40° C. for 1 h. After cooling to −78° C., the mixture was treated with triethylamine (1.12 mL, 8.04 mmol) and stirred at −78° C. for 10 min and at 0° C. for 20 min. The reaction mixture was treated with water (6.3 mL) and diluted with MTBE (6.32 mL). The organic layer was separated and washed with brine. After concentration, the residue was purified by silica gel column chromatography (ethyl acetate/n-heptane=1/10 to 1/2) to give the title compound (284 mg).

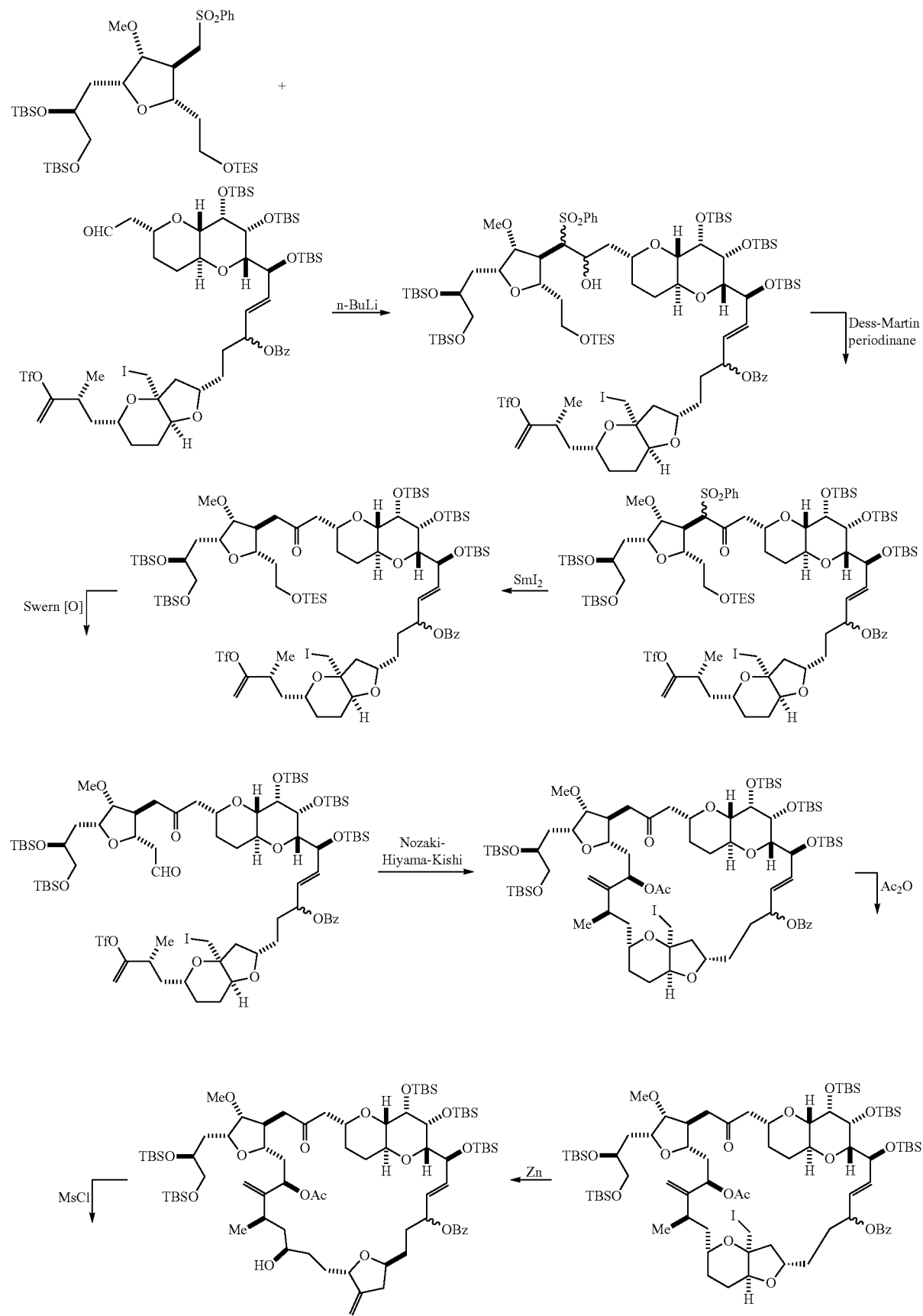

239

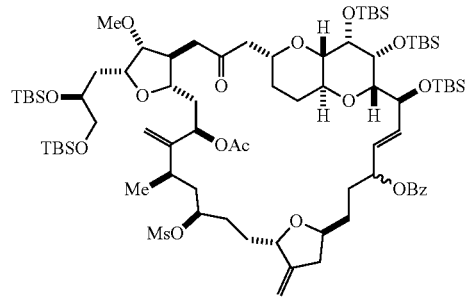

(6S,E)-6-((2S,3R,4S,4aS,6R,8aS)-6-(3-((2S,4R,5R)-5-((S)-2,3-bis((tert-butyldimethylsilyl)oxy)propyl)-4-methoxy-2-(2-((triethylsilyl)oxy)ethyl) tetrahydrofuran-3-yl)-2-hydroxy-3-(phenylsulfonyl)propyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

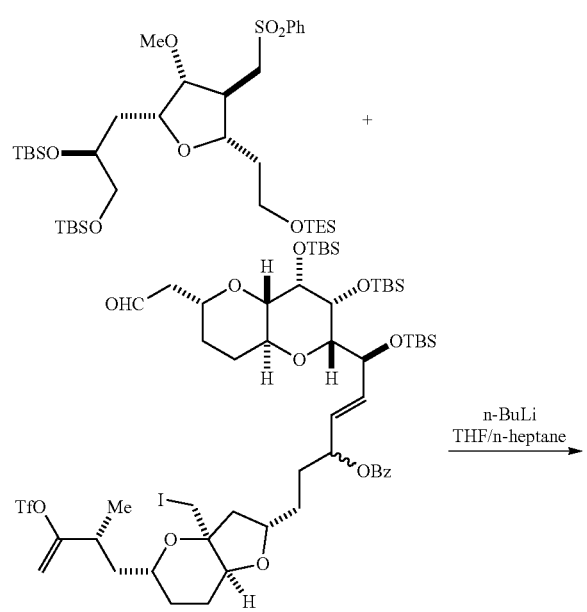

240

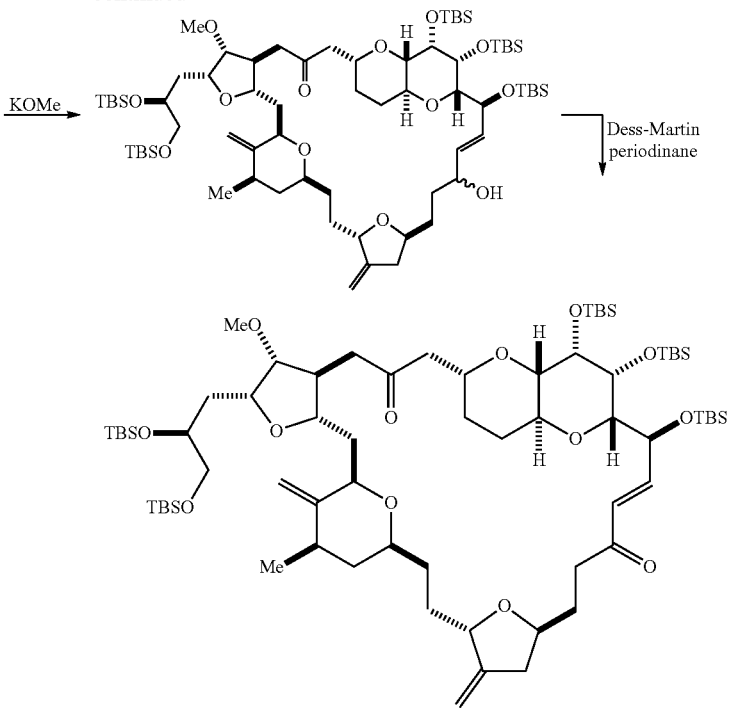

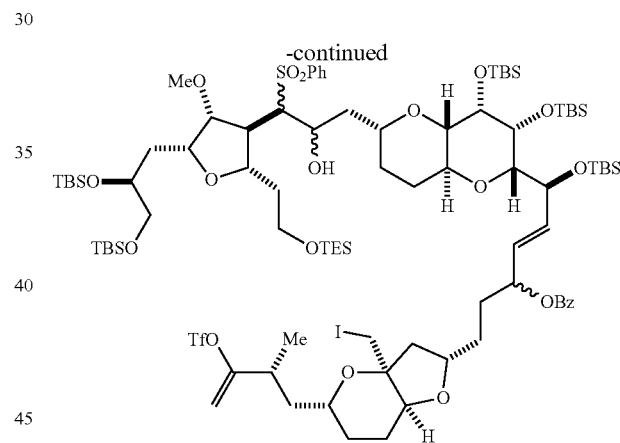

A solution of (S)-5-(((2R,3R,4S,5S)-3-methoxy-4-((phenylsulfonyl)methyl)-5-(2-((triethylsilyl)oxy)ethyl)tetrahydrofuran-2-yl)methyl)-2,2,3,3,8,8,9,9-octamethyl-4,7-dioxa-3,8-disiladecane (0.214 g, 0.298 mmol) in THF (3 mL) was cooled to −5° C. The mixture was treated with 1.6 M n-BuLi in hexane (0.186 mL, 0.298 mmol) and stirred at −5° C. for 20 min. After cooling to −78° C., the mixture was treated with a solution of (6S,E)-6-((2S,3R,4S,4aS,6R,8aS)-3,4-bis((tert-butyldimethylsilyl)oxy)-6-(2-oxoethyl)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate (0.150 g, 0.119 mmol) in n-heptane (4.2 mL). The mixture was stirred at −78° C. for 4 h. The reaction was quenched with saturated aqueous NH$_4$Cl (7.5 mL) and extracted twice with MTBE (15 mL). The organic layers were combined and washed with brine. After concentration, the residue was purified by silica gel column chromatography (ethyl acetate/n-heptane=1/20 to 1/2) to give the title compound (177 mg, 75%).

(6S,E)-6-((2S,3R,4S,4aS,6R,8aS)-6-(3-((2S,3S,4R,5R)-5-((S)-2,3-bis((tert-butyldimethylsilyl)oxy)propyl)-4-methoxy-2-(2-((triethylsilyl)oxy)ethyl) tetrahydrofuran-3-yl)-2-oxo-3-(phenylsulfonyl)propyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

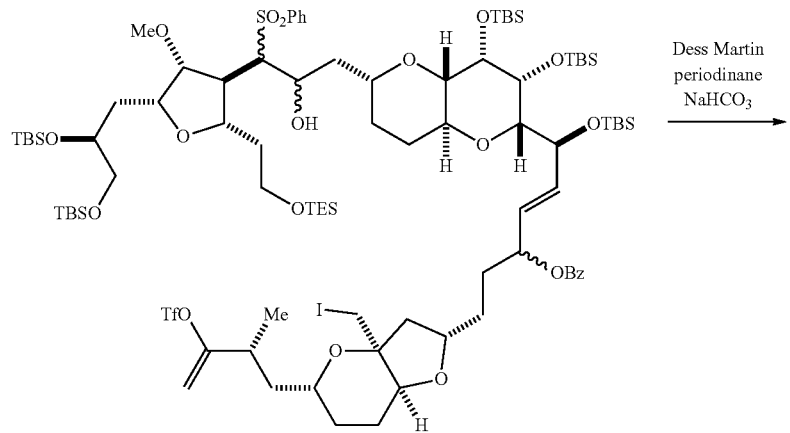

A solution of (6S,E)-6-((2S,3R,4S,4aS,6R,8aS)-6-(3-((2S,4R,5R)-5-((S)-2,3-bis((tert-butyldimethylsilyl)oxy)propyl)-4-methoxy-2-(2-((triethylsilyl)oxy)ethyl)tetrahydrofuran-3-yl)-2-hydroxy-3-(phenylsulfonyl)propyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate (0.177 g, 0.09 mmol) in CH$_2$Cl$_2$ (3.54 mL) was treated with sodium bicarbonate (0.011 g, 0.13 mmol) and Dess-Martin periodinane (0.057 g, 0.13 mmol) and stirred at rt for 1 h. Additional Dess-Martin periodinane (0.019 g, 0.045 mmol) was added, and stirring was continued at rt for another 1 h. The reaction was quenched with saturated aqueous NaHCO$_3$ (3.5 mL) and 20% Na$_2$SO$_3$ (3.5 mL) and extracted twice with MTBE (3.5 mL). The organic layers were combined and washed with brine. After concentration, the residue was purified by silica gel column chromatography (ethyl acetate/n-heptane=1/10 to 1/3) to give the title compound (170 mg, 96%).

243

(6S,E)-6-((2S,3R,4S,4aS,6R,8aS)-6-(3-((2S,3S,4R,5R)-5-((S)-2,3-bis((tert-butyldimethylsilyl)oxy)propyl)-4-methoxy-2-(2-((triethylsilyl)oxy)ethyl)tetrahydrofuran-3-yl)-2-oxopropyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

244

(6S,E)-6-((2S,3R,4S,4aS,6R,8aS)-6-(3-((2S,3S,4R,5R)-5-((S)-2,3-bis((tert-butyldimethylsilyl)oxy)propyl)-4-methoxy-2-(2-oxoethyl)tetrahydrofuran-3-yl)-2-oxopropyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate

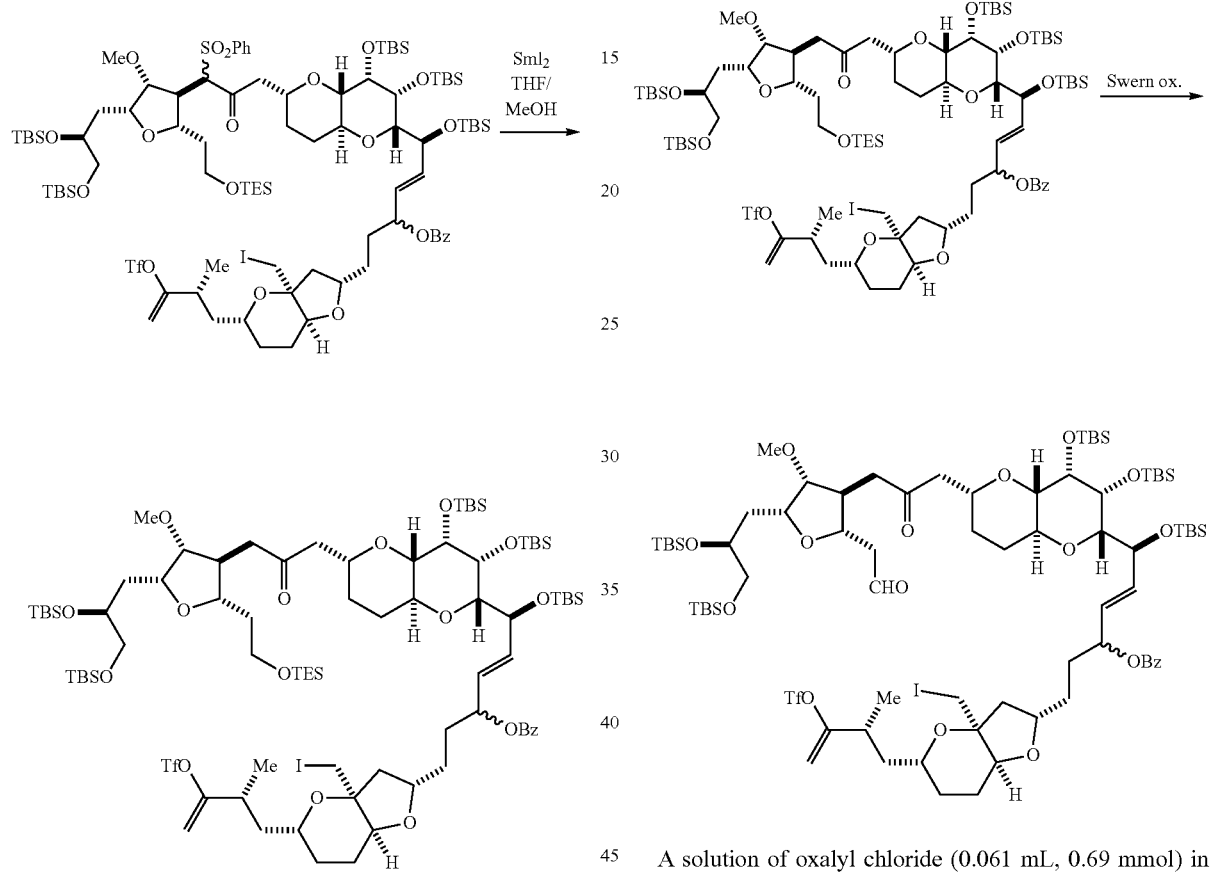

A solution of (6S,E)-6-((2S,3R,4S,4aS,6R,8aS)-6-(3-((2S,3S,4R,5R)-5-((S)-2,3-bis((tert-butyldimethylsilyl)oxy)propyl)-4-methoxy-2-(2-((triethylsilyl)oxy)ethyl)tetrahydrofuran-3-yl)-2-oxo-3-(phenylsulfonyl)propyl)-3,4-bis((tert-butyldimethylsilyl)oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl)hexahydro-2H-furo[3,2-b]pyran-2-yl)hex-4-en-3-yl benzoate (0.17 g, 0.086 mmol) in a mixture of THF (1.4 mL) and methanol (0.85 mL) was cooled to −78° C. and treated with 0.1 M SmI$_2$ in THF (1.29 mL, 0.129 mmol). After stirring at −78° C. for 1 h, additional 0.1 M SmI$_2$ in THF (0.86 mL, 0.086 mmol) was added, and stirring was continued at −78° C. for another 2 h. The reaction was quenched with a mixture of Rochelle's Salt (510 mg, 1.807 mmol), potassium carbonate (509 mg, 3.69 mmol), and water (5.1 mL) and extracted twice with MTBE (8.5 mL). The organic layers were combined and dried over MgSCO$_4$ to give the title compound (127 mg, 80%).

A solution of oxalyl chloride (0.061 mL, 0.69 mmol) in CH$_2$Cl$_2$ (2.54 mL) was cooled to −78° C. and treated with DMSO (0.098 mL, 1.4 mmol). After stirring at −78° C. for 10 min, a solution of (6S,E)-6-((2S,3R,4S,4aS,6R,8aS)-6-(3-((2S,3S,4R,5R)-5-((S)-2,3-bis((tert-butyldimethylsilyl)oxy)propyl)-4-methoxy-2-(2-((triethylsilyl)oxy)ethyl)tetrahydrofuran-3-yl)-2-oxopropyl)-3,4-bis((tert-butyldimethylsilyl) oxy)octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-(((trifluoromethyl)sulfonyl)oxy)but-3-en-1-yl) hexahydro-2H-furo[3,2-b]pyran-2-yl)hex-4-en-3-yl benzoate (0.127 g, 0.069 mmol) in CH$_2$Cl$_2$ (2.5 mL) was added. The resulting solution was stirred at −78° C. for 10 min and at −40° C. for 1 h. After cooling to −78° C., the mixture was treated with triethylamine (0.5 mL, 3.6 mmol) and stirred at −78° C. for 10 min and at 0° C. for 20 min. The mixture was treated with water (5 mL) and extracted twice with MTBE (10 mL). The organic layers were combined and washed with brine. After concentration, the residue was purified by silica gel column chromatography (ethyl acetate/n-heptane=1/10 to 1/5) to give the title compound (86 mg, 72%).

NHK Macrocyclization

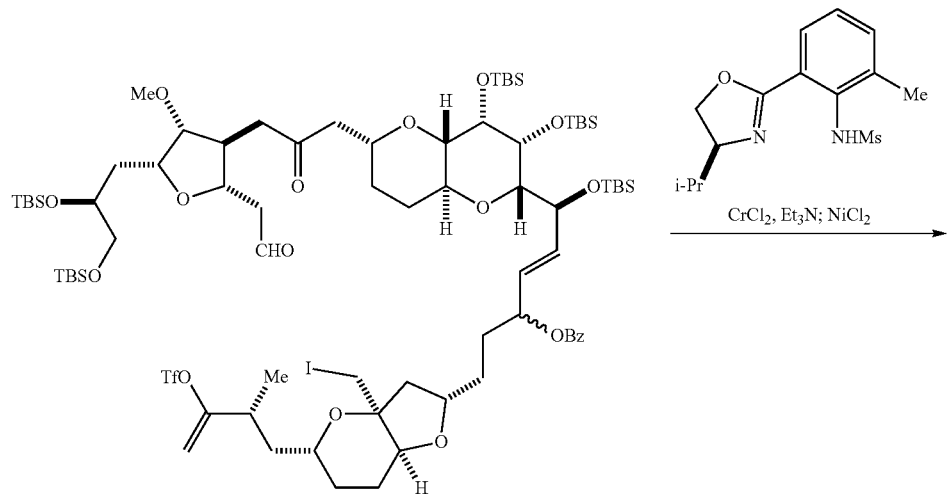

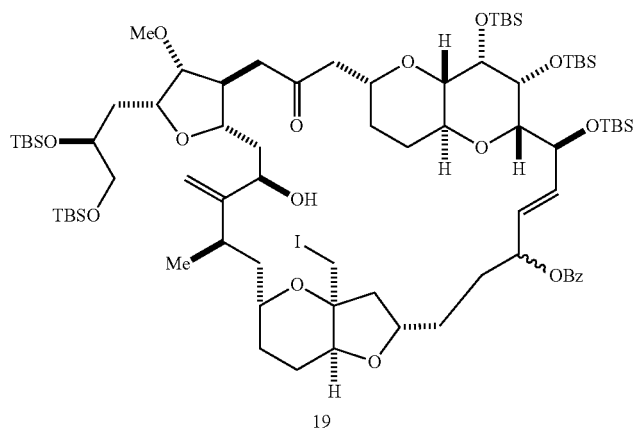

19

(S)—N-(2-(4-isopropyl-4,5-dihydrooxazol-2-yl)-6-methylphenyl) methanesulfonamide (0.829 g, 2.797 mmol) was dissolved in a degassed acetonitrile (7.12 mL) and treated with chromous chloride (0.346 g, 2.82 mmol). After purging with nitrogen gas for 5 min, the mixture was heated to 30° C. and treated with Et$_3$N (0.39 mL, 2.8 mmol). The mixture was stirred at 34° C. for 1 h. After cooling to 0° C., the mixture was treated with nickel chloride (6.7 mg, 0.052 mmol) and purged with nitrogen gas for 5 min. After removing the ice-bath, the mixture was treated with a solution of (6S,E)-6-((2S,3R,4S,4aS,6R,8aS)-6-(3-((2S,3S,4R,5R)-5-((S)-2,3-bis((tert-butyldimethylsilyl)oxy) propyl)-4-methoxy-2-(2-oxoethyl)tetrahydrofuran-3-yl)-2-oxopropyl)-3,4-bis((tert-butyldimethylsilyl)oxy) octahydropyrano[3,2-b]pyran-2-yl)-6-((tert-butyldimethylsilyl)oxy)-1-((2S,3aS,5R,7aS)-3a-(iodomethyl)-5-((R)-2-methyl-3-((((trifluoromethyl) sulfonyl)oxy) but-3-en-1-yl)hexahydro-2H-furo[3,2-b] pyran-2-yl)hex-4-en-3-yl benzoate (0.089 g, 0.052 mmol) in a mixture of THF (3.1 mL) and acetonitrile (1.4 mL) over 40 min via syringe pump. The mixture was stirred at 20° C. for another 2 h. The mixture was diluted with n-heptane (8.90 mL), filtered to remove insoluble residue, and washed with n-heptane (8.90 mL). The heptane layer was separated, and the acetonitrile layer was extracted with n-heptane (8.9 mL). The heptane layers were combined and washed twice with acetonitrile (8.90 mL). After concentration, the residue was purified by silica gel column chromatography (ethyl acetate/n-heptane=1/10 to 1/2) to give the compound 19 (18 mg and 11 mg of two products epimeric at C.14, total 36%). Mass [M+NH$_4$]=1587.0 and 1586.9, respectively for two products (calc. 1586.8).

Acetylation

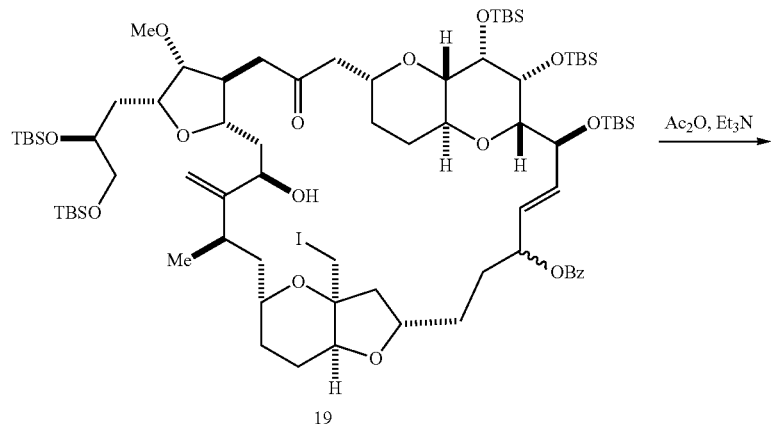

A solution of compound 19 (0.029 g, 0.018 mmol) in CH$_2$Cl$_2$ (3 mL) was treated with acetic anhydride (0.012 mL, 0.13 mmol), triethylamine (0.026 mL, 0.19 mmol) and DMAP (0.226 mg, 1.85 µmol). After stirring for 1 h at rt, additional triethylamine (0.026 mL, 0.19 mmol), acetic anhydride (0.012 mL, 0.13 mmol), and DMAP (0.226 mg, 1.85 µmol) were added, and stirring was continued at rt for another 3 h. The reaction was quenched with water and extracted twice with MTBE. The organic layers were combined and dried over MgSO$_4$. After concentration, the residue was filtered through silica gel pad, and the filtrate was concentrated in vacuo to give compound 20 (30 mg).

Vasella Fragmentation

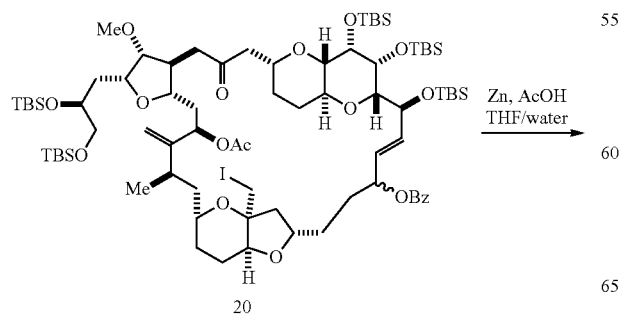

-continued

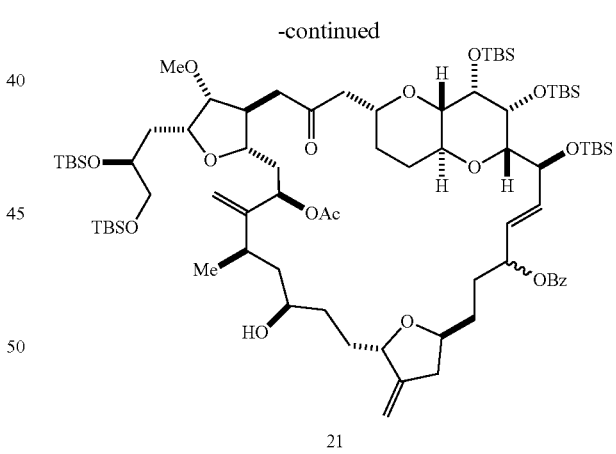

A solution of compound 20 (0.030 g, 0.019 mmol) in THF (1.2 mL) was treated with water (0.3 mL), zinc dust (0.036 g, 0.56 mmol), and acetic acid (0.021 mL, 0.37 mmol). The mixture was stirred at rt for 2 h. Additional zinc dust (0.036 g, 0.56 mmol) and acetic acid (0.021 mL, 0.37 mmol) were added, and stirring was continued at rt for 15 h. The mixture was diluted with MTBE (30 mL) and filtered through a Celite® pad to remove insoluble solid. The filtrate was washed twice with saturated aqueous NaHCO$_3$ (5 mL), dried over MgSO$_4$, and concentrated in vacuo to give compound 21 (27 mg).

Mesylation

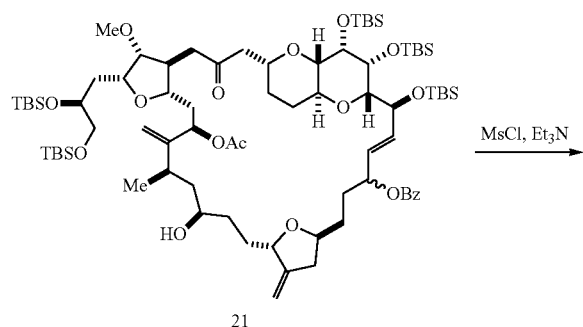

21

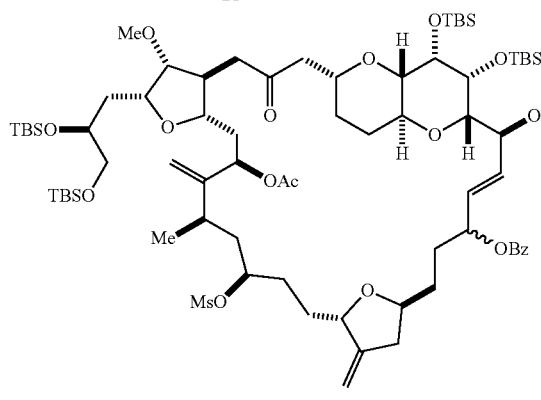

22

Cyclization with KOMe

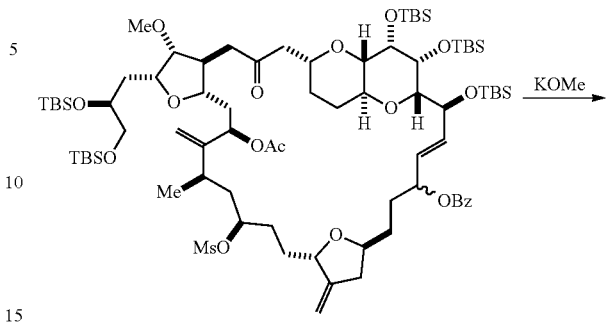

23

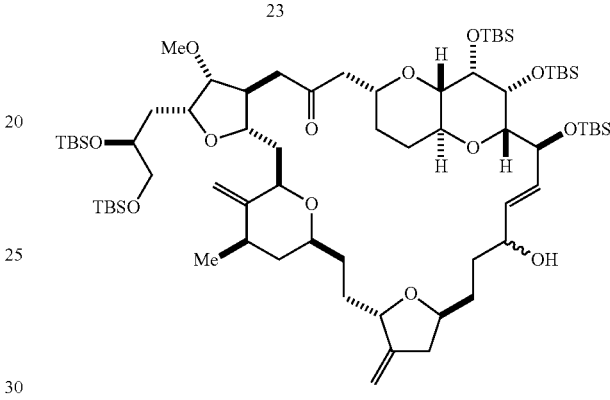

24

A solution of compound 21 (0.027 g, 0.018 mmol) in THF (2 mL) was cooled to 0° C. and treated with MsCl (5.7 µL, 0.073 mmol) and triethylamine (0.020 mL, 0.15 mmol). The mixture was stirred at 0° C. for 1 h. The reaction was quenched with water (4 mL) and extracted twice with MTBE (8 mL). The organic layers were combined, dried over MgSO$_4$, and concentrated in vacuo to give compound 22 (27 mg).

A solution of compound 23 (0.027 g, 0.017 mmol) in THF (3 mL) was cooled to 0° C. and treated with 25% potassium methoxide in methanol (0.025 mL, 0.086 mmol). The mixture was stirred at 0° C. for 3 h and slowly warmed to 15° C. over 14 h. The reaction was quenched with saturated aqueous NH$_4$Cl (2.70 mL) and extracted with MTBE (8.10 mL). The organic layer was separated, dried over MgSO$_4$, and concentrated in vacuo to give compound 24 (23 mg).

Oxidation to a Conjugate Ketone

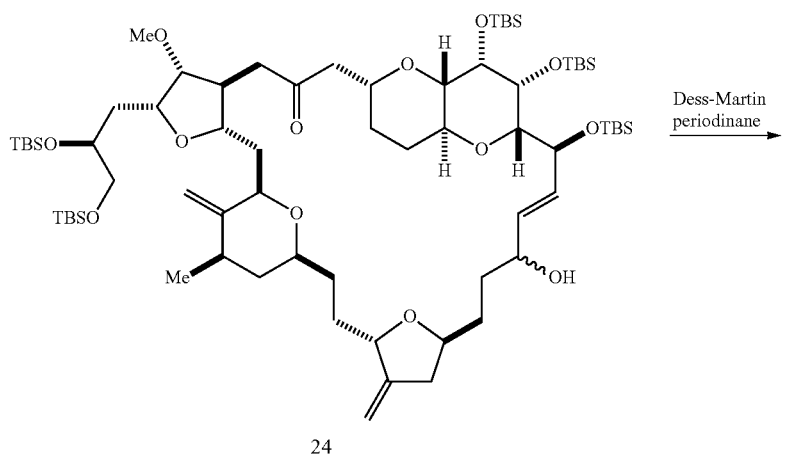

24

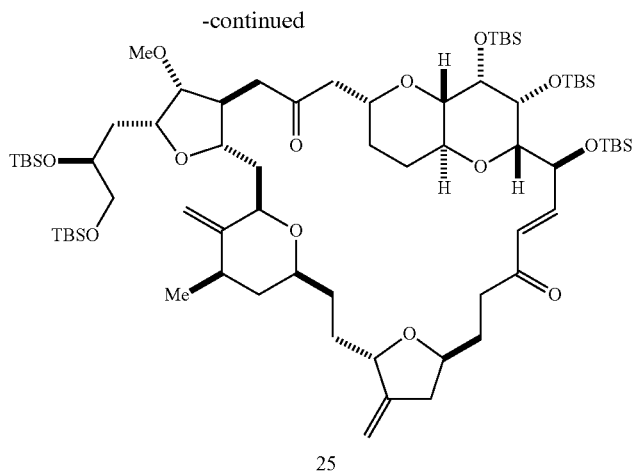

25

A solution of compound 24 (0.023 g, 0.017 mmol) in CH$_2$Cl$_2$ (2 mL) was treated with Dess-Martin periodinane (0.015 g, 0.035 mmol) and stirred at rt for 30 min. The reaction was quenched with saturated aqeuous NaHCO$_3$ (2 mL) and 20% Na$_2$SO$_3$ (2 mL) and extracted with MTBE (2 mL). The organic layer was dried over MgSO$_4$. After concentration, the residue was purified by silica gel column chromatography (ethyl acetate/n-heptane=1/10 to 1/5) to give compound 25 (1 mg). The structure was confirmed by comparison of the $^1$H NMR spectrum with that of an authentic sample. $^1$H NMR (400 MHz, C$_6$D$_6$) δ −0.08 (s, 3H), 0.02 (s, 12H), 0.03 (s, 3H), 0.04 (s, 3H), 0.11 (s, 3H), 0.13 (s, 3H), 0.18 (s, 3H), 0.85 (s, 27H), 0.92 (s, 9H), 0.95 (s, 9H), 1.01 (m, 1H), 1.05 (d, 3H), 1.20-1.45 (m, 4H), 1.53 (m, 3H), 1.60-1.85 (m, 7H), 1.92 (m, 2H), 2.03 (m, 1H), 2.25 (m, 2H), 2.48 (m, 2H), 2.60-2.78 (m, 4H), 2.84 (dd, 1H), 2.93 (dd, 1H), 3.29 (s, 3H), 3.39 (m, 2H), 3.48 (m, 1H), 3.53 (m, 2H), 3.66 (m, 1H), 3.77 (m, 1H), 3.70-3.80 (m, 4H), 4.01 (d, 1H), 4.05 (s, 2H), 4.22 (m, 1H), 4.75 (s, 1H), 4.82 (s, 1H), 4.88 (s, 1H), 4.98 (s, 1H), 4.99 (m, 1H), 6.33 (d, 1H), 7.25 (dd, 1H).

Example 9: Preparation of a Compound of Formula (ID) Through a C.0-C.1 Macrocyclization

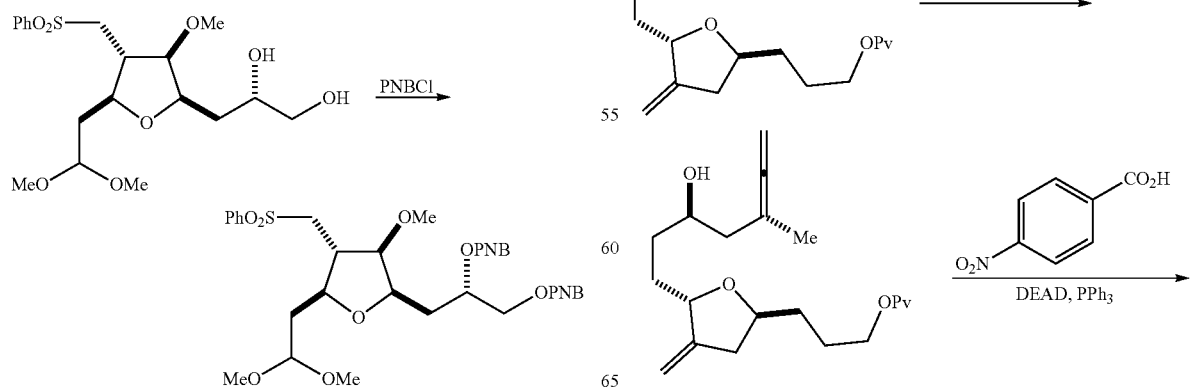

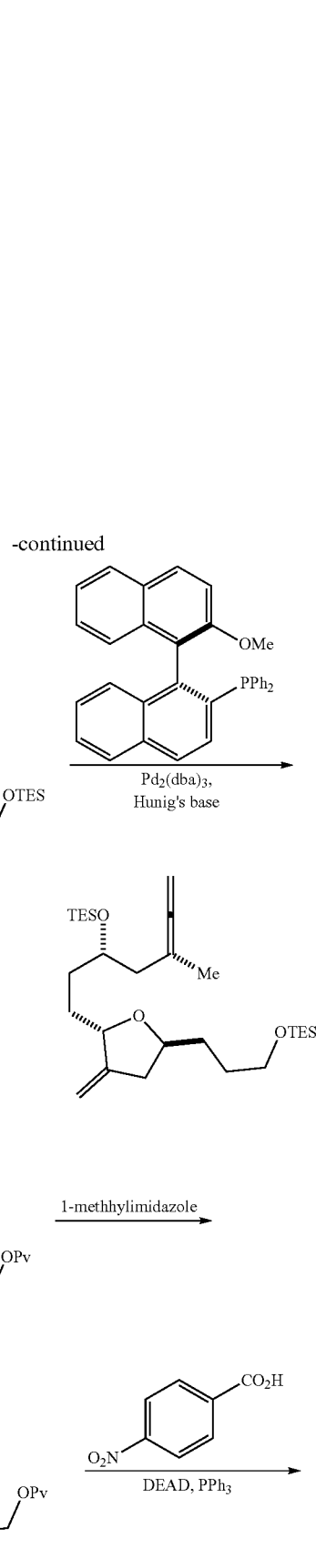

253
-continued
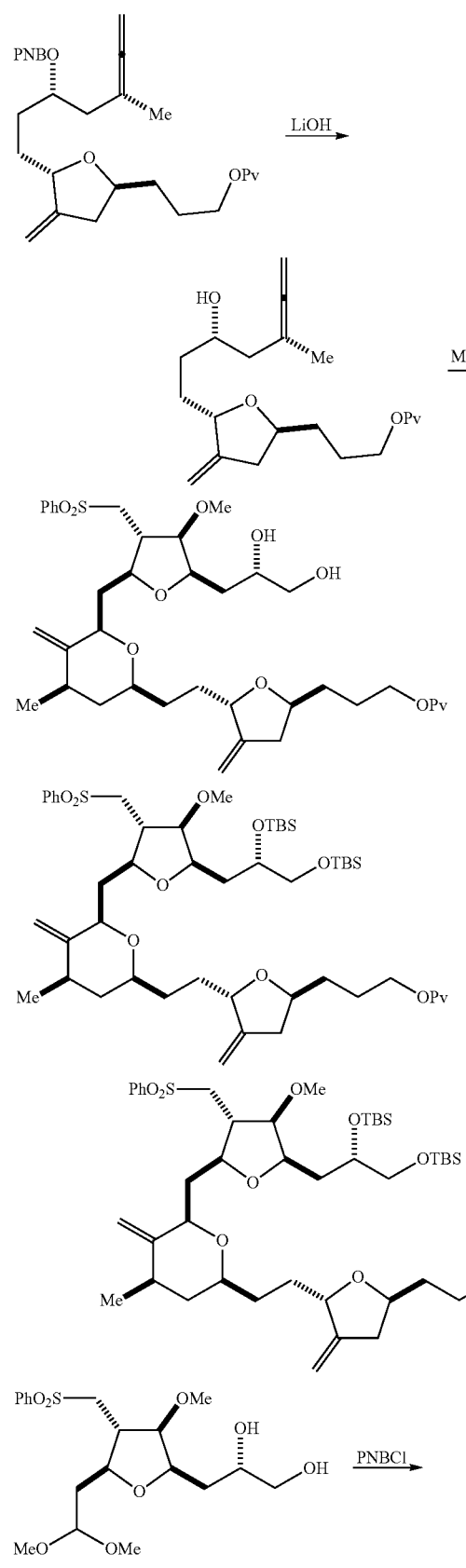
254
-continued
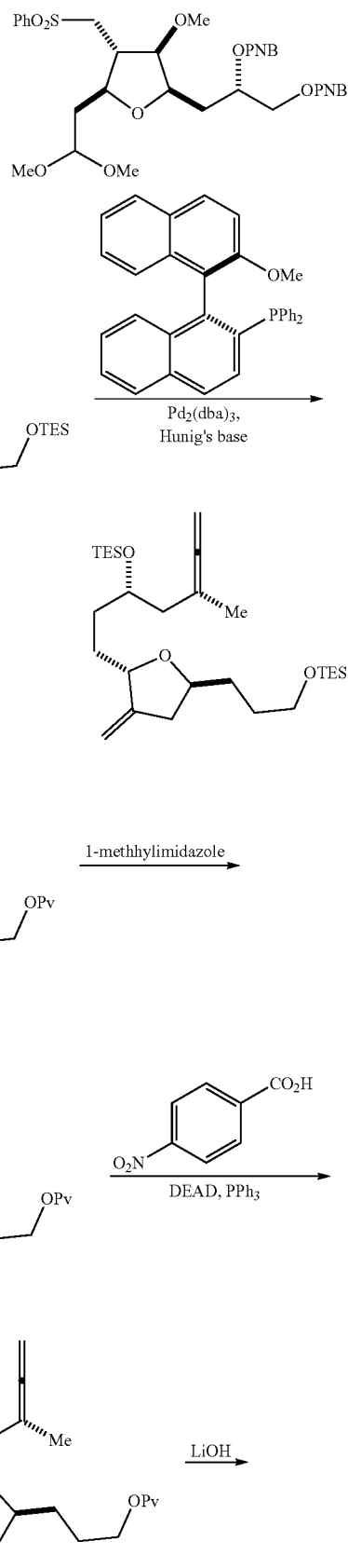

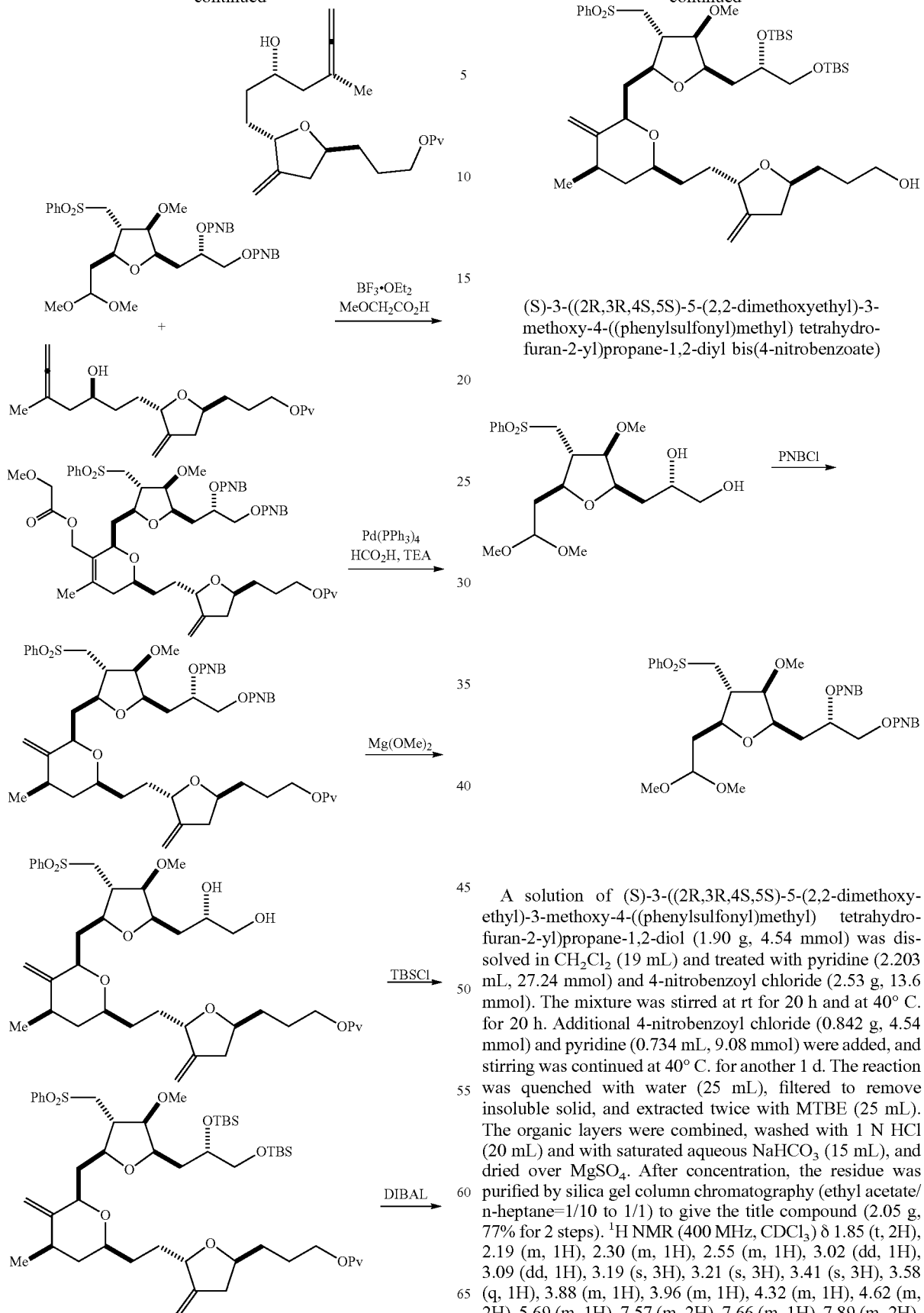

(S)-3-((2R,3R,4S,5S)-5-(2,2-dimethoxyethyl)-3-methoxy-4-((phenylsulfonyl)methyl) tetrahydrofuran-2-yl)propane-1,2-diyl bis(4-nitrobenzoate)

A solution of (S)-3-((2R,3R,4S,5S)-5-(2,2-dimethoxyethyl)-3-methoxy-4-((phenylsulfonyl)methyl) tetrahydrofuran-2-yl)propane-1,2-diol (1.90 g, 4.54 mmol) was dissolved in CH$_2$Cl$_2$ (19 mL) and treated with pyridine (2.203 mL, 27.24 mmol) and 4-nitrobenzoyl chloride (2.53 g, 13.6 mmol). The mixture was stirred at rt for 20 h and at 40° C. for 20 h. Additional 4-nitrobenzoyl chloride (0.842 g, 4.54 mmol) and pyridine (0.734 mL, 9.08 mmol) were added, and stirring was continued at 40° C. for another 1 d. The reaction was quenched with water (25 mL), filtered to remove insoluble solid, and extracted twice with MTBE (25 mL). The organic layers were combined, washed with 1 N HCl (20 mL) and with saturated aqueous NaHCO$_3$ (15 mL), and dried over MgSO$_4$. After concentration, the residue was purified by silica gel column chromatography (ethyl acetate/n-heptane=1/10 to 1/1) to give the title compound (2.05 g, 77% for 2 steps). $^1$H NMR (400 MHz, CDCl$_3$) δ 1.85 (t, 2H), 2.19 (m, 1H), 2.30 (m, 1H), 2.55 (m, 1H), 3.02 (dd, 1H), 3.09 (dd, 1H), 3.19 (s, 3H), 3.21 (s, 3H), 3.41 (s, 3H), 3.58 (q, 1H), 3.88 (m, 1H), 3.96 (m, 1H), 4.32 (m, 1H), 4.62 (m, 2H), 5.69 (m, 1H), 7.57 (m, 2H), 7.66 (m, 1H), 7.89 (m, 2H), 8.13 (d, 2H), 8.18 (d, 2H), 8.25 (m, 4H).

257

Triethyl(((S)-5-methyl-1-((2S,5S)-3-methylene-5-(3-((triethylsilyl)oxy)propyl) tetrahydrofuran-2-yl)hepta-5,6-dien-3-yl)oxy)silane

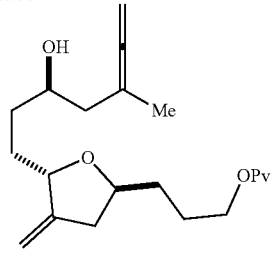

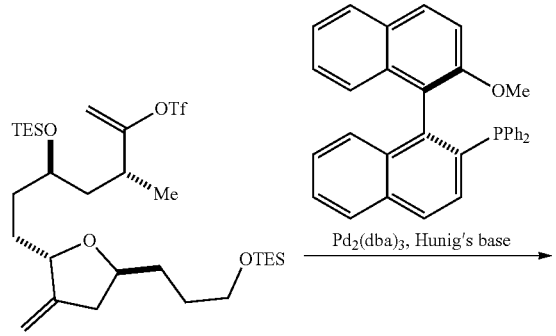

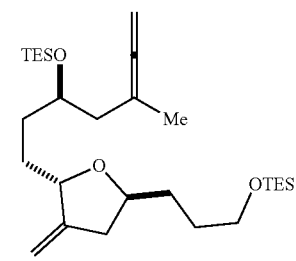

A mixture of Pd₂(dba)₃ (5.7 mg, 6.2 µmol) and (S)-(–)-(diphenylphosphino)-2'-methoxy-1,1'-binaphthyl (0.012 g, 0.025 mmol) was purged with nitrogen for 5 min, treated with n-heptane (1 mL), and stirred at rt for 10 min. After addition of Hünig's base (0.11 mL, 0.62 mmol) and a solution of (3R,5R)-3-methyl-7-((2S,5S)-3-methylene-5-((triethylsilyl)oxy)propyl)tetrahydrofuran-2-yl)-5-((triethylsilyl)oxy)hept-1-en-2-yl trifluoromethanesulfonate (0.20 g, 0.31 mmol) in n-heptane (2 mL), the mixture was stirred at rt for 20 h, at 35° C. for 2 d, and at 50° C. for 1 d. The mixture was cooled to rt, filtered through a Celite® pad to remove the catalyst, and the pad was rinsed with n-heptane. The colorless filtrate was concentrated in vacuo to give the title compound (a 1:1 mixture of SM and the allene).

3-((2S,5S)-5-((R)-3-hydroxy-5-methylhepta-5,6-dien-1-yl)-4-methylenetetrahydrofuran-2-yl)propyl pivalate

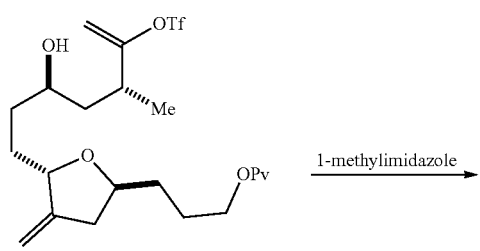

258

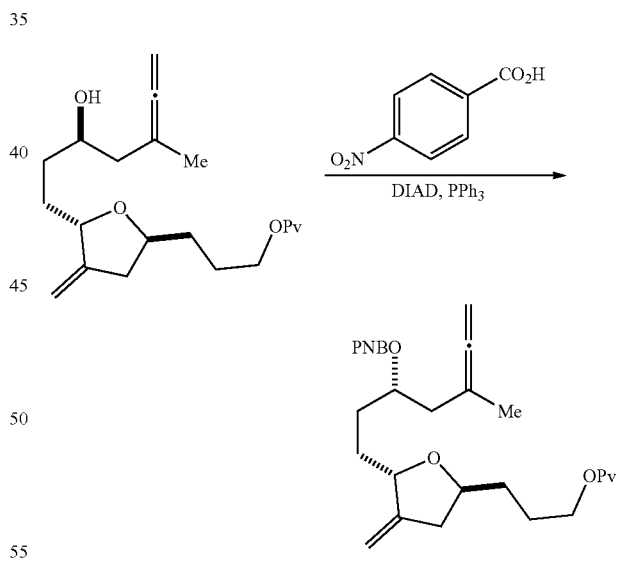

3-((2S,5S)-5-((3R,5R)-3-hydroxy-5-methyl-6-(((trifluoromethyl)sulfonyl)oxy)hept-6-en-1-yl)-4-methylenetetrahydrofuran-2-yl)propyl pivalate (90.0 g, 180 mmol) was dissolved in 1,2-dichloroethane (900 mL) and treated with 1-methylimidazole (25.8 mL, 323.632 mmol). The mixture was stirred at 85° C. for 5 h. After cooling to rt, the mixture was diluted with MTBE (1.8 L), sequentially washed with 1.0 M HCl in water (500 mL), water (200 mL), saturated aqueous sodium bicarbonate (150 mL), and brine (150 mL), and dried over Na₂SO₄. After concentration, the residue was purified by column chromatography (ethyl acetate/n-heptane=3/7) to give a mixture of the allene and acetylene. The mixture was further purified by prep. HPLC to give the title compound (20 g, 31%). ¹H NMR (400 MHz, CDCl₃) δ 1.10 (s, 9H), 1.40-1.80 (m, 8H), 1.72 (s, 3H), 2.10 (m, 2H), 2.27 (dd, 1H), 2.46 (bs, 1H), 2.70 (dd, 1H), 3.80 (m, 1H), 4.08 (m, 3H), 4.39 (bm, 1H), 4.66 (m, 2H), 4.87 (s, 1H), 5.00 (s, 1H).

(S)-5-methyl-1-((2S,5S)-3-methylene-5-(3-(pivaloyloxy)propyl)tetrahydrofuran-2-yl)hepta-5,6-dien-3-yl 4-nitrobenzoate

3-((2S,5S)-5-((R)-3-hydroxy-5-methylhepta-5,6-dien-1-yl)-4-methylenetetrahydrofuran-2-yl)propyl pivalate (6.94 g, 19.8 mmol) was dissolved in toluene (35.4 mL) and treated with 4-nitrobenzoic acid (4.30 g, 25.7 mmol) and triphenylphosphine (6.75 g, 25.7 mmol). After cooling to 0° C., the mixture was charged with DIAD (4.62 mL, 23.7 mmol) and stirred at 0° C. for 2.5 h. The mixture was diluted with MTBE (156 mL) and washed with saturated aqueous NaHCO₃ (39.0 mL). After concentration, the residue was purified by silica gel column chromatography (ethyl acetate/n-heptane=1/9) to give the title compound (9.9 g, 100%). ¹H NMR (400 MHz, CDCl₃) δ 1.19 (s, 9H), 1.49 (m, 1H), 1.53-1.80 (m, 5H), 1.73 (s, 3H), 1.88 (m, 2H), 2.28 (m, 2H), 2.41 (m, 1H), 2.68 (m, 1H), 4.02 (m, 1H), 4.08 (m, 2H), 4.40 (m, 1H), 4.45 (m, 1H), 4.52 (m, 1H), 4.81 (s, 1H), 4.99 (s, 1H), 5.34 (m, 1H), 8.20 (m, 2H), 8.30 (m, 2H).

3-((2S,5S)-5-((S)-3-hydroxy-5-methylhepta-5,6-dien-1-yl)-4-methylenetetrahydrofuran-2-yl)propyl pivalate

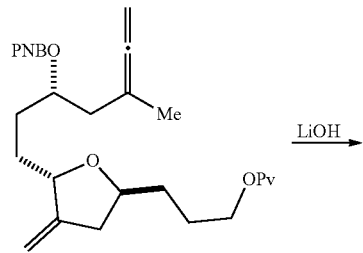

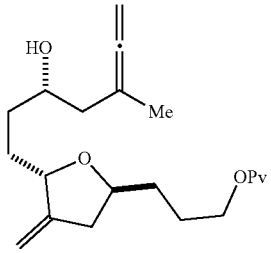

(S)-5-methyl-1-((2S,5S)-3-methylene-5-(3-(pivaloyloxy)propyl)tetrahydrofuran-2-yl)hepta-5,6-dien-3-yl 4-nitrobenzoate (9.90 g, 19.8 mmol) was dissolved in a mixture of THF (100 mL) and water (50 mL) and treated with lithium hydroxide monohydrate (2.50 g, 59.4 mmol). The mixture was stirred at rt for 16 h. The reaction mixture was diluted with brine (118 mL) and extracted with MTBE (470 mL). The organic layer was concentrated and purified by silica gel column chromatography (ethyl acetate/n-heptane=15/85) to give the title compound (5.55 g, 80%). ¹H NMR (400 MHz, CDCl₃) δ 1.20 (s, 9H), 1.40-1.80 (m, 9H), 1.65 (s, 3H), 2.10 (m, 2H), 2.25 (dd, 1H), 2.68 (dd, 1H), 3.79 (m, 1H), 4.05 (m, 2H), 4.40 (m, 1H), 4.62 (m, 2H), 4.85 (s, 1H), 5.00 (s, 1H).

(S)-3-((2R,3R,4S,5S)-3-methoxy-5-(((2R,6S)-3-(2-methoxyacetoxy)methyl-4-methyl-6-(2-((2S,5S)-3-methylene-5-(3-(pivaloyloxy)propyl)tetrahydrofuran-2-yl)ethyl)-3,6-dihydro-2H-pyran-2-yl)methyl)-4-((phenylsulfonyl)methyl) tetrahydrofuran-2-yl)propane-1,2-diyl bis(4-nitrobenzoate)

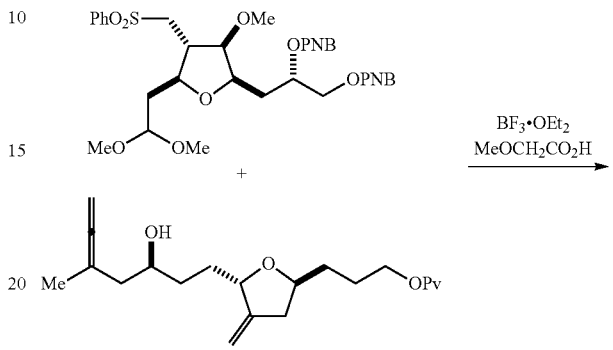

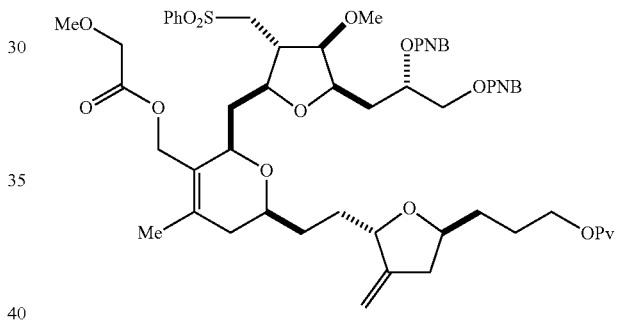

A mixture of 3-((2S,5S)-5-((S)-3-hydroxy-5-methylhepta-5,6-dien-1-yl)-4-methylenetetrahydrofuran-2-yl)propyl pivalate (0.200 g, 0.571 mmol) and (S)-3-((2R,3R,4S, 5S)-5-(2,2-dimethoxyethyl)-3-methoxy-4-((phenylsulfonyl)methyl)tetrahydrofuran-2-yl)propane-1,2-diyl bis(4-nitrobenzoate) (0.573 g, 0.799 mmol) was dissolved in CH₂Cl₂ (8.0 mL) and cooled to −30° C. The mixture was sequentially treated with methoxyacetic acid (0.657 mL, 8.56 mmol) and then BF₃-OEt₂ (0.217 ML, 1.71 mmol) and stirred between −30° C. and −20° C. for 7 h. The reaction was quenched with saturated aqueous NaHCO₃ (14.4 mL) and extracted twice with MTBE (10 mL). The organic layers were combined and washed with brine. After concentration, the residue was purified by silica gel column chromatography (ethyl acetate/n-heptane=1/10 to 2/3) to give the title compound (518 mg, 83%). ¹H NMR (400 MHz, CDCl₃) δ 1.18 (s, 9H), 1.40-1.74 (m, 8H), 1.70 (s, 3H), 1.76-1.96 (m, 4H), 2.16-2.34 (m, 3H), 2.60-2.70 (m, 2H), 3.00 (dd, 1H), 3.16 (dd, 1H), 3.34 (m, 1H), 3.42 (s, 3H), 3.45 (s, 3H), 3.61 (m, 1H), 3.82 (m, 1H), 3.94-3.46 (m, 7H), 4.26 (m, 1H), 4.52 (d, 1H), 4.58-4.69 (m, 3H), 4.73 (s, 1H), 4.92 (s, 1H), 5.66 (m, 1H), 7.58 (m, 2H), 7.62 (m, 1H), 7.90 (m, 2H), 8.1-8.3 (m, 8H).

(S)-3-((2R,3R,4S,5S)-3-methoxy-5-(((2R,4R,6S)-4-methyl-3-methylene-6-(2-((2S,5S)-3-methylene-5-(3-(pivaloyloxy)propyl)tetrahydrofuran-2-yl)ethyl)tetrahydro-2H-pyran-2-yl)methyl)-4-((phenylsulfonyl)methyl)tetrahydrofuran-2-yl) propane-1,2-diyl bis(4-nitrobenzoate)

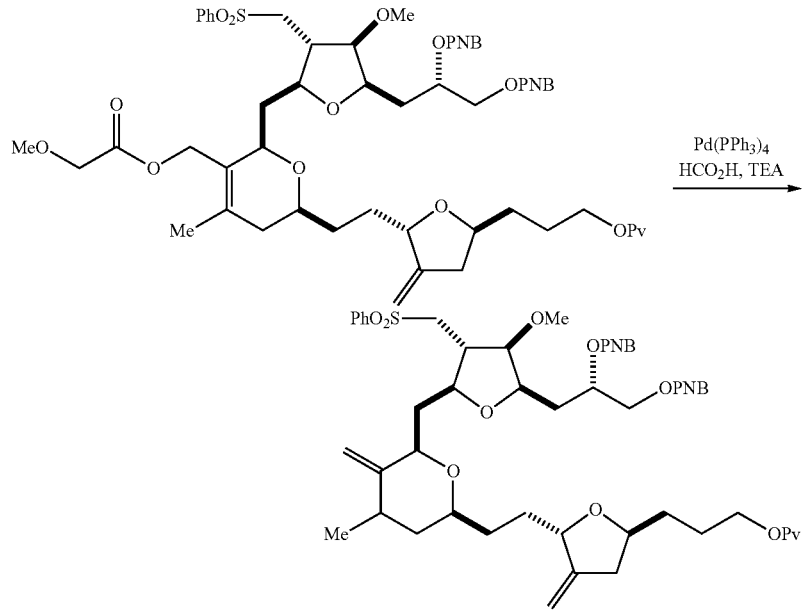

A mixture of Pd(Ph₃P)₄ (0.024 g, 0.021 mmol) and triphenylphosphine (0.022 g, 0.084 mmol) in THF (2.3 mL) (in a vial with a cap) was heated to 60° C. and stirred for 5 min. The mixture was treated with a mixture of (S)-3-((2R,3R,4S,5S)-3-methoxy-5-(((2R,6S)-3-(2-methoxyacetoxy)methyl-4-methyl-6-(2-((2S,5S)-3-methylene-5-(3-(pivaloyloxy)propyl)tetrahydrofuran-2-yl)ethyl)-3,6-dihydro-2H-pyran-2-yl)methyl)-4-((phenylsulfonyl)methyl)tetrahydrofuran-2-yl)propane-1,2-diyl bis(4-nitrobenzoate) (0.230 g, 0.21 mmol), formic acid (0.040 mL, 1.1 mmol) and triethylamine (0.147 mL, 1.05 mmol) in THF (3.4 mL). The mixture was stirred at 60° C. (bath) for 46 h. After cooling to rt, the mixture was treated with water (10.5 mL) and extracted twice with MTBE (10.5 mL). The organic layers were combined and washed with brine (10 mL). After concentration, the residue was purified by silica gel column chromatography (ethyl acetate/n-heptane=1/10 to 1/2) to give the title compound (148 mg, 70%). ¹H NMR (400 MHz, CDCl₃) δ 1.06 (d, 3H), 1.18 (s, 9H), 1.24-1.68 (m, 8H), 1.68-1.80 (m, 2H), 1.86 (m, 1H), 2.04-2.28 (m, 4H), 2.56 (m, 1H), 2.58-2.68 (m, 2H), 3.05 (m, 2H), 3.36 (m, 1H), 3.46 (s, 3H), 3.58 (dd, 1H), 3.73 (m, 1H), 3.85 (m, 1H), 3.95 (m, 1H), 4.01 (m, 1H), 4.06 (m, 2H), 4.23 (m, 1H), 4.60-4.72 (m, 3H), 4.78 (s, 2H), 4.92 (s, 1H), 5.72 (m, 1H), 7.62 (m, 2H), 7.70 (m, 1H), 7.97 (m, 2H), 8.1-8.3 (m, 8H).

3-((2S,5S)-5-(2-((2S,4R,6R)-6-(((2S,3S,4R,5R)-5-((S)-2,3-dihydroxypropyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propyl pivalate

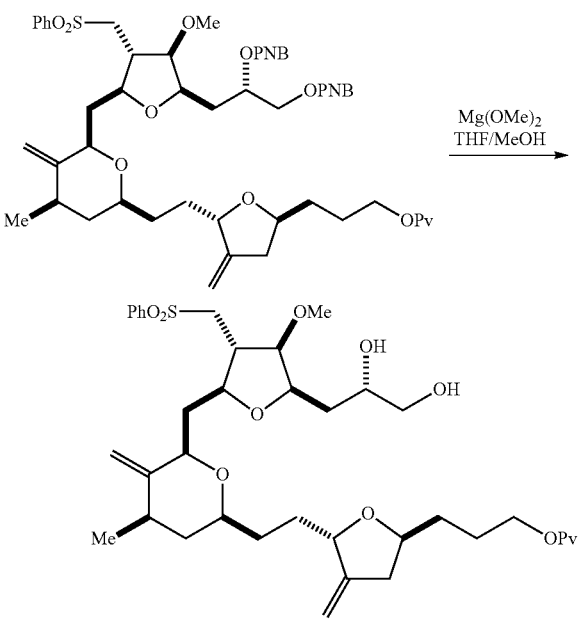

A solution of (S)-3-((2R,3R,4S,5S)-3-methoxy-5-(((2R,4R,6S)-4-methyl-3-methylene-6-(2-((2S,5S)-3-methylene-5-(3-(pivaloyloxy)propyl)tetrahydrofuran-2-yl)ethyl)tetrahydro-2H-pyran-2-yl)methyl)-4-((phenylsulfonyl)methyl)tetrahydrofuran-2-yl)propane-1,2-diyl bis(4-nitrobenzoate) (1.90 g, 1.89 mmol) in a mixture of THF (1.9 mL) and methanol (38 mL) was treated with 6-10% Mg(OMe)$_2$ in methanol (2.07 mL, 1.13 mmol). The mixture was stirred at rt for 2 h. The reaction was quenched with saturated aqueous NH$_4$Cl (19 mL), concentrated to remove methanol, and extracted three times with ethyl acetate (19 mL). The organic layers were combined and dried over MgSO$_4$. After concentration, the residue was purified by column chromatography (ethyl acetate/n-heptane=1/10 to 2/1) to give the title compound (934 mg, 70%). $^1$H NMR (400 MHz, CDCl$_3$) δ 1.08 (d, 3H), 1.20 (s, 9H), 1.34-1.84 (m, 11H), 1.90-2.06 (m, 2H), 2.14-2.26 (m, 3H), 2.58-2.68 (m, 2H), 3.04-3.16 (m, 2H), 3.41 (m, 1H), 3.46 (s, 3H), 3.56 (dd, 1H), 3.60 (m, 1H), 3.66 (dd, 1H), 3.83 (m, 1H), 3.92 (s, 2H), 3.92-4.00 (m, 2H), 4.07 (m, 2H), 4.26 (bm, 1H), 4.68 (d, 1H), 4.80 (d, 1H), 4.85 (s, 1H), 4.92 (s, 1H), 7.62 (m, 2H), 7.70 (m, 1H), 7.99 (m, 2H).

3-((2S,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl) tetrahydrofuran-2-yl)methyl)-4-methyl-5-methylenetetrahydro-2H-pyran-2-yl) ethyl)-4-methylenetetrahydrofuran-2-yl)propyl pivalate

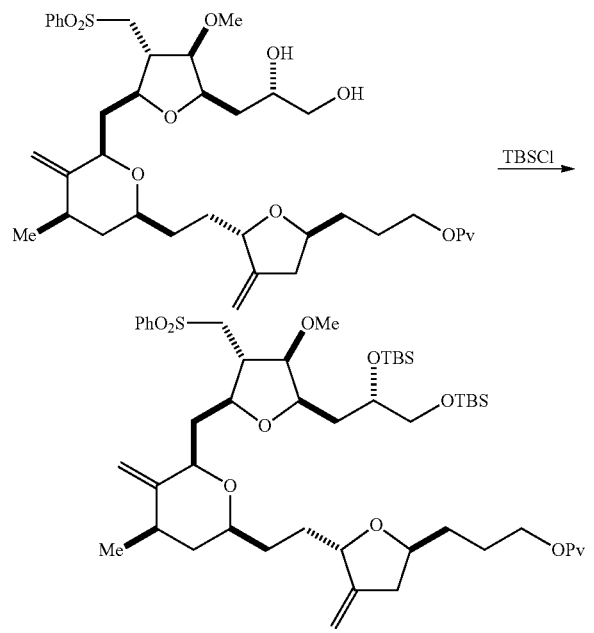

A solution of 3-((2S,5S)-5-(2-((2S,4R,6R)-6-(((2S,3S,4R,5R)-5-((S)-2,3-dihydroxypropyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propyl pivalate (0.040 g, 0.057 mmol) in DMF (1 mL) was treated with imidazole (0.019 g, 0.28 mmol) and TBSCl (0.026 g, 0.17 mmol) and stirred at rt for 3 h. Additional TBSCl (0.026 g, 0.17 mmol) and imidazole (0.019 g, 0.28 mmol) were added, and stirring was continued at rt for 3 d. The reaction was quenched with water (4 mL) and diluted with MTBE (5 mL). The organic layer was separated, washed twice with water (4 mL), and dried over MgSO$_4$ to give the title compound (40 mg).

3-((2S,5S)-5-(2-((2S,4R,6R)-6-(((2S,3S,4R,5R)-5-((S)-2,3-bis((tert-butyldimethylsilyl) oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propan-1-ol

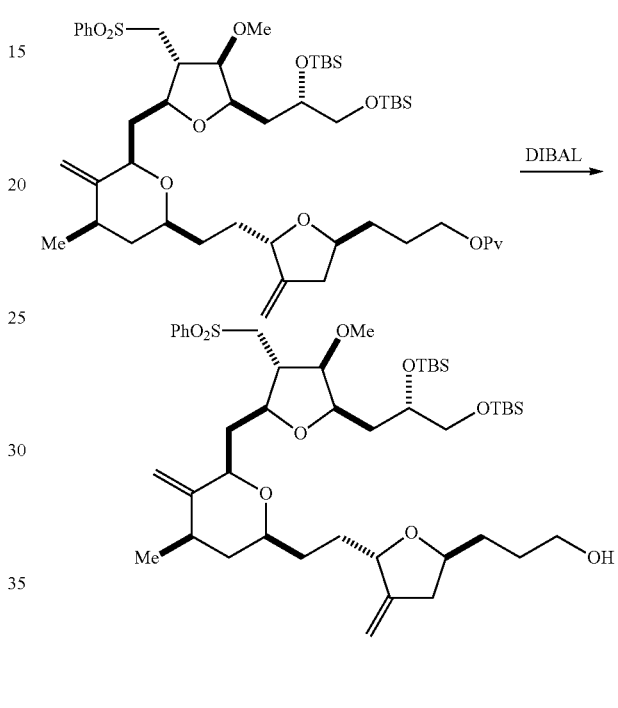

A solution of 3-((2S,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl) tetrahydrofuran-2-yl)methyl)-4-methyl-5-methylenetetrahydro-2H-pyran-2-yl)ethyl)-4-methylenetetrahydrofuran-2-yl)propyl pivalate (0.040 g, 0.043 mmol) in toluene (1.5 mL) was cooled to −78° C. and treated with 1.5 M DIBAL in toluene (0.114 mL, 0.171 mmol). The mixture was stirred at −78° C. for 30 min. Additional 1.5 M DIBAL in toluene (0.057 mL, 0.086 mmol) was added and stirring was continued at −78° C. for another 1 h. The reaction was quenched with 1 N HCl (1 mL) and MTBE (10 mL) and stirred at rt for 1 h. The organic layer was separated and sequentially washed with water (5 mL), saturated aqueous NaHCO$_3$ (5 mL), and brine (3 mL). After concentration, the residue was purified by silica gel column chromatography (ethyl acetate/n-heptane=1/10 to 2/3) to give the title compound (13 mg, 60% for 3 steps). $^1$H NMR (400 MHz, CDCl$_3$) δ 0.02 (s, 6H), 0.04 (s, 6H), 0.88 (s, 18H), 1.02 (d, 3H), 1.34-1.48 (m, 2H), 1.48-1.70 (m, 6H), 1.76 (m, 1H), 1.80-1.94 (m, 3H), 2.02 (m, 1H), 2.14-2.28 (m, 3H), 2.56 (m, 1H), 2.64 (m, 1H), 3.20 (m, 2H), 3.40 (m, 1H), 3.43 (s, 3H), 3.48 (dd, 1H), 3.65-3.72 (m, 5H), 3.76-3.86 (m, 3H), 3.98 (m, 1H), 4.30 (m, 1H), 4.68 (s, 1H), 4.78 (s, 1H), 4.86 (s, 1H), 4.92 (s, 1H), 7.60 (m, 2H), 7.70 (m, 1H), 8.21 (m, 2H).

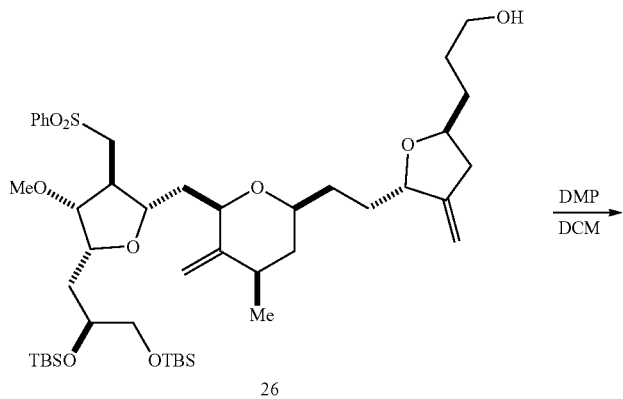
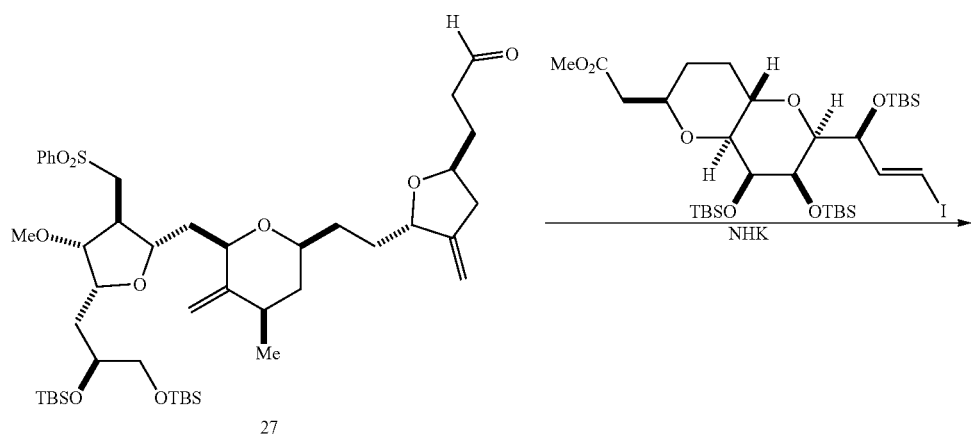
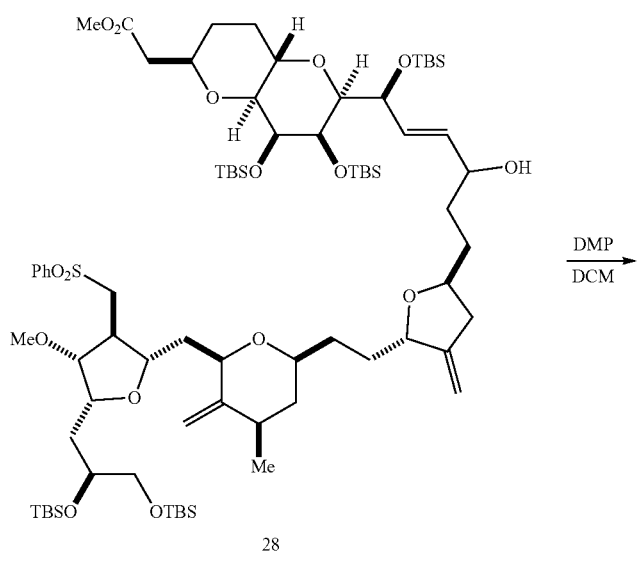

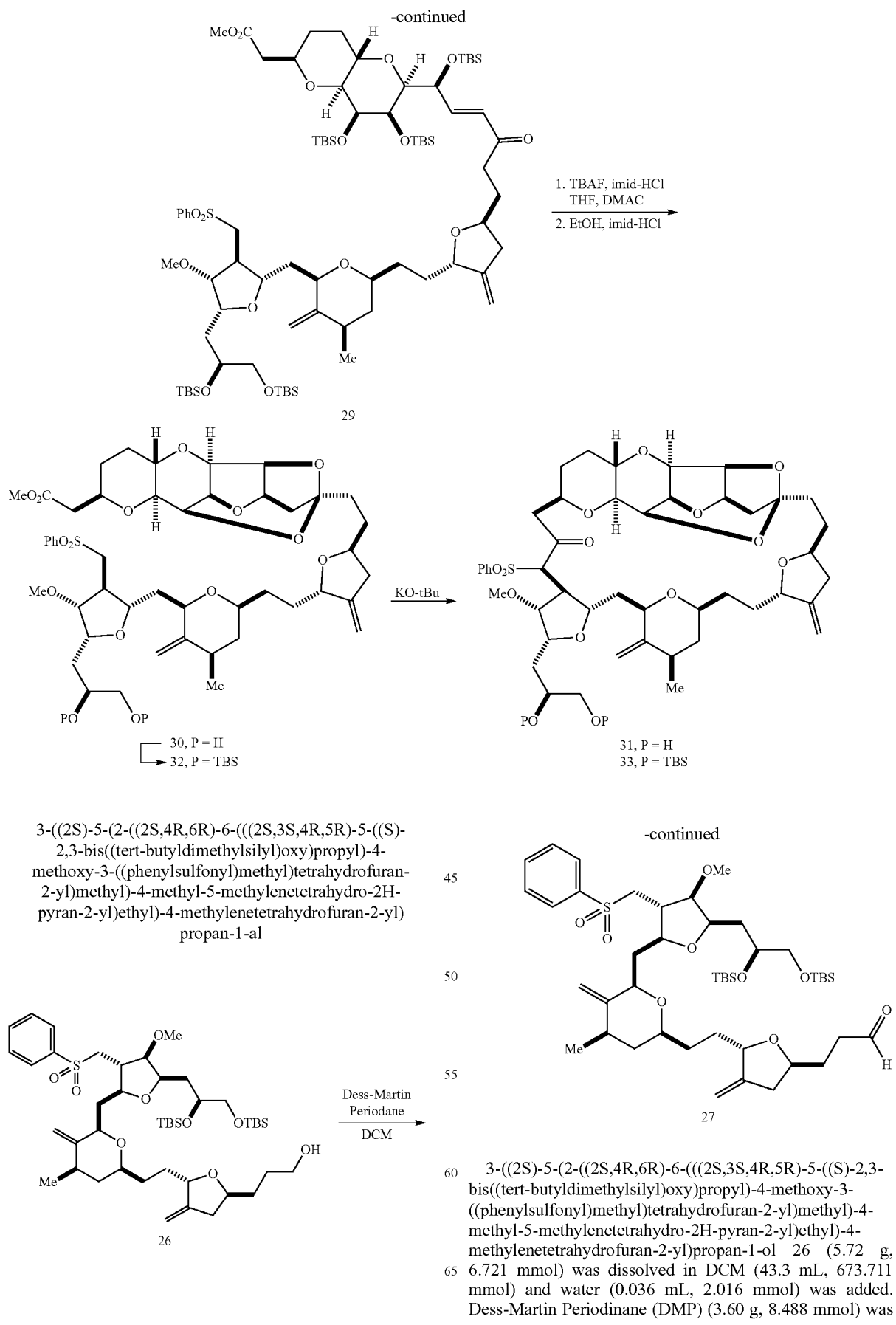

3-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propan-1-al 3-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propan-1-ol 26 (5.72 g, 6.721 mmol) was dissolved in DCM (43.3 mL, 673.711 mmol) and water (0.036 mL, 2.016 mmol) was added. Dess-Martin Periodinane (DMP) (3.60 g, 8.488 mmol) was added in portions over 4 minutes, while maintaining the temperature below 25° C., and the reaction was monitored by TLC (MTBE and silica gel). Additional DMP (2.550 g, 5.012 mmol) was added, and the reaction was stirred until compound 26 was consumed. Saturated aqueous sodium bicarbonate (50 mL) was added followed by 10% aqueous sodium thiosulfate (50 mL). The mixture was partitioned and the aqueous layer extracted twice with dichloromethane (DCM). The combined DCM extracts were washed with water, and the solution was dried over sodium sulfate and concentrated to provide 27 (5.63 g, 99% yield) as an orange oil that was used as is in the next step.

Methyl 2-((2R,4aS,6S,7R,8S,8aS)-6-((1S,E)-6-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-hydroxyhex-2-en-1-yl)-7,8-bis((tert-butyldimethylsilyl)oxy)octahydropyrano[3,2-b]pyran-2-yl)acetate

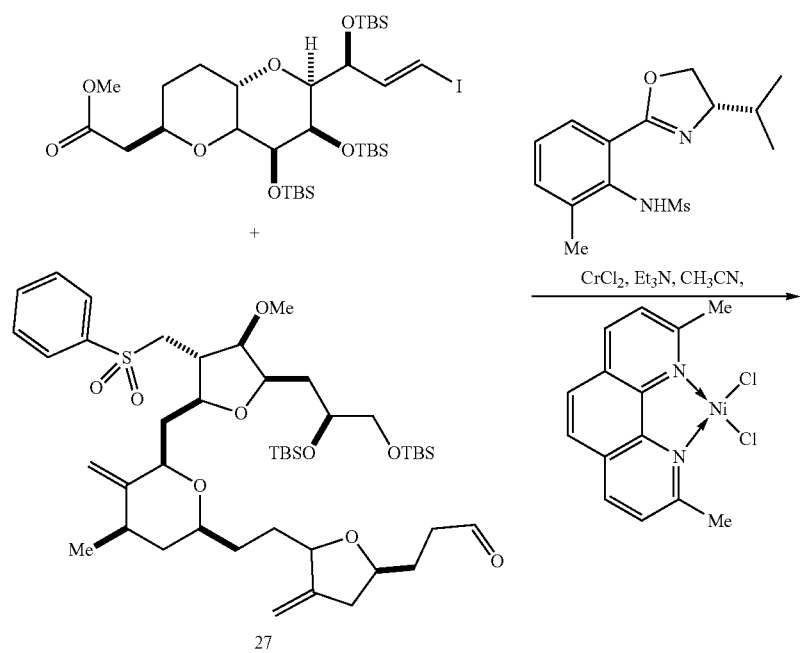

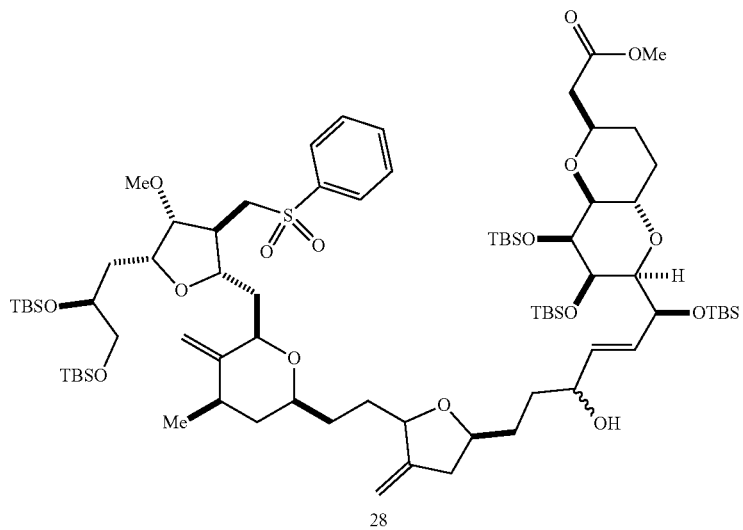

(S)—N-(2-(4-isopropyl-4,5-dihydrooxazol-2-yl)-6-methylphenyl)methanesulfonamide (3.84 g, 12.94 mmol) was added to a three-neck flask fitted with 3-way stopcock, septum, and solid addition pistol. Chromium(II) chloride (1.59 g, 12.94 mmol) was added to the solid addition pistol, and the apparatus was purged with nitrogen (3× vacuum/N$_2$-back-flush through the 3-way stopcock). Tetrahydrofuran (17.58 mL) was added. CrCl$_2$ was added in portions to the vigorously stirred solution. The resulting suspension was warmed to 30° C., and TEA (1.85 mL, 12.94 mmol) was added. The solution was stirred for 60 minutes before cooling to 0° C. [(2,9-dimethyl-1,10-phenanthroline)dichloronickel(II)] complex (0.224 g, 0.663 mmol) in tetrahydrofuran (2.5 mL) was added followed by a mixture of 3-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)propanal 27 (2.198 g, 2.588 mmol) and methyl 2-((2R,4aS,6S,7R,8S,8aS)-7,8-bis((tert-butyldimethylsilyl)oxy)-6-((S,E)-1-((tert-butyldimethylsilyl)oxy)-3-iodoallyl)octahydropyrano[3,2-b]pyran-2-yl)acetate (2.394 g, 3.106 mmol) in THF (4.4 mL) was added. The reaction was warmed to RT and monitored by TLC and HPLC. Upon completion, the reaction was cooled to 5-10° C. and ethylenediamine (2.184 mL, 25.88 mmol) was added. The mixture was stirred for 1 hour, and then n-heptane (25 mL) and water (25 mL) were added. The layers were separated and the aqueous layer was extracted twice with n-heptane (25 mL). The combined organic layers were combined and washed with aqueous hydrogen chloride (1.0N, 25 mL), water (25 mL), saturated aqueous sodium bicarbonate (25 mL), and saturated aqueous sodium chloride (25 mL). The solution was dried with sodium sulfate, filtered, and partially concentrated in vacuo. The precipitate of (S)—N-(2-(4-isopropyl-4,5-dihydrooxazol-2-yl)-6-methylphenyl)methanesulfonamide was filtered, and the cake was washed with heptane (20 mL). The filtrate and wash were concentrated to dryness, and the crude product was purified on Biotage® Snap KP-SiI 100 g cartridge conditioned with heptane (4CV). The crude product was loaded with heptane and eluted with heptane/ethyl acetate (9:1, 4:1,7:3, and 1:1 heptane/ethyl acetate, 5 CV each). The fractions containing product were pooled to provide 28 (2.773 g, 72%) as a pale yellow oil upon removal of volatiles in vacuo.

Methyl 2-((2R,4aS,6S,7R,8S,8aS)-6-((1S,E)-6-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-oxohex-2-en-1-yl)-7,8-bis((tert-butyldimethylsilyl)oxy)octahydropyrano[3,2-b]pyran-2-yl)acetate

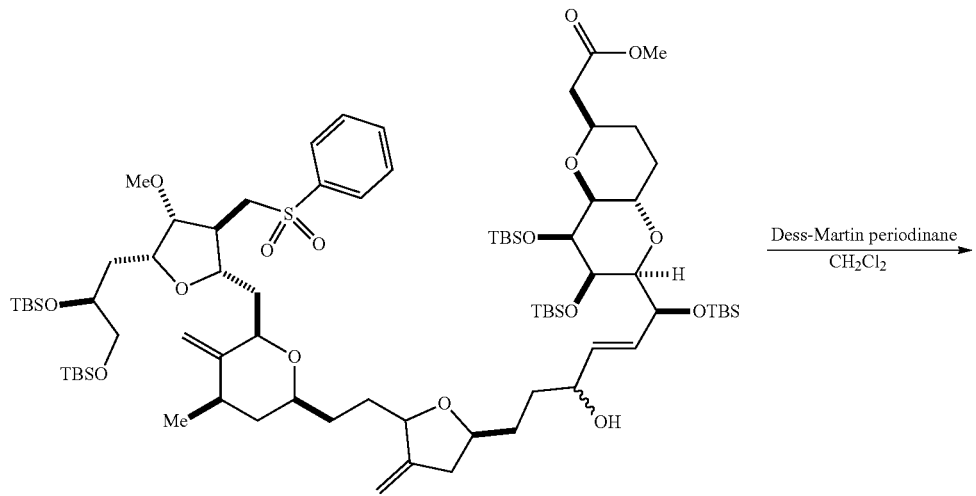

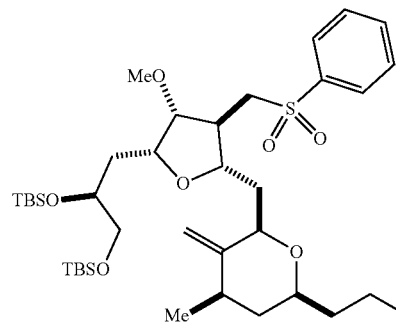
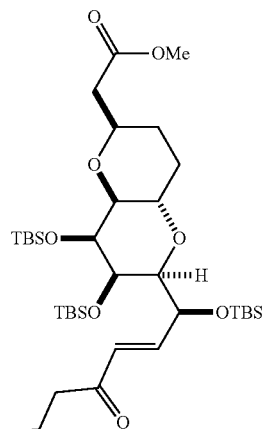

29

Methyl 2-((2R,4aS,6S,7R,8S,8aS)-6-(((1S,E)-6-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-hydroxyhex-2-en-1-yl)-7,8-bis((tert-butyldimethylsilyl)oxy)octahydropyrano[3,2-b]pyran-2-yl)acetate 28 (2.773 g, 0.1.856 mmol) was dissolved in DCM (13.4 mL), and water (1.67 μL, 0.093 mmol) was added. Dess-Martin periodinane (0.944 g, 2.227 mmol) was added in portions, while maintaining the temperature below 22° C. When the reaction was deemed complete, 25 mL saturated aqueous sodium bicarbonate was added followed by 10% aqueous sodium thiosulfate (25 mL). The mixture was stirred for 20 minutes, and the layers partitioned. The aqueous layer was extracted with dichloromethane (DCM) (2×40 mL). The combined organic layers were concentrated in vacuo to provide 29 (2.688 g, 1.8 mmol, 97% yield). $^1$H NMR (400 MHz, CDCl$_3$) δ: 7.92 (dd, 2H), 7.68 (t, 1H), 7.60 (t, 2H), 7.55-7.63 (m, 2H), 7.08 (dd, 1H), 6.29 (d, 1H), 5.08-5.14 (m, 1H), 4.85-4.89 (m, 1H), 4.83 (s, 1H), 4.76 (s, 1H), 4.62 (d, 1H), 4.17-4.24 (m, 1H), 4.07 (s, 1H), 3.87-4.02 (m, 1H), 3.83 (s, 4H), 3.65-3.66 (m, 3H), 3.65 (s, 3H), 3.62-3.69 (m, 2H), 3.52-3.61 (m, 2H), 3.47 (dd, 1H), 3.41-3.42 (m, 3H), 3.41 (s, 3H), 3.25-3.43 (m, 6H), 2.95-3.06 (m, 1H), 2.90 (dd, 1H), 2.44-2.73 (m, 4H), 2.30-2.37 (m, 1H), 2.12-2.24 (m, 2H), 1.95-2.02 (m, 1H), 1.63-1.92 (m, 6H), 1.13-1.58 (m, 5H), 1.02-1.08 (m, 3H), 1.05 (d, 3H), 0.98-1.10 (m, 3H), 0.93-0.95 (m, 2H), 0.94 (s, 9H), 0.92 (s, 9H), 0.87 (s, 18H), 0.89-0.85 (m, 2H), 0.85 (s, 9H), 0.12 (s, 3H), 0.11 (s, 3H), 0.08 (s, 3H), 0.08 (s, 3H), 0.03 (s, 3H).

Methyl 2-((2S,3aR,4aR,5S,5aS,7R,9aS,10aR,10bS)-2-(2-((2S,5S)-5-(2-((2S,4R,6R)-6-(((2S,3S,4R,5R)-5-((S)-2,3-dihydroxypropyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)ethyl)dodecahydro-2,5-epoxyfuro[2',3':4,5]furo[3,2-b]pyrano[2,3-e]pyran-Z-yl)acetate

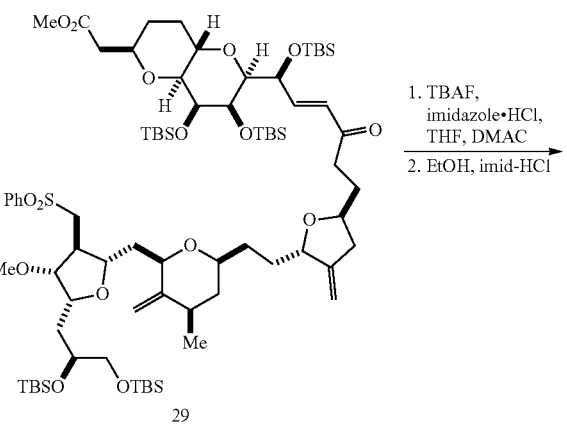

29

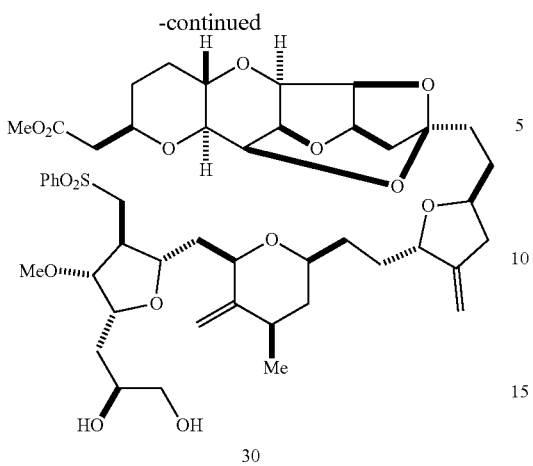

30

Methyl 2-((2R,4aS,6S,7R,8S,8aS)-6-((1S,E)-6-((2S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)-1-((tert-butyldimethylsilyl)oxy)-4-oxohex-2-en-1-yl)-7,8-bis((tert-butyldimethylsilyl)oxy)octahydropyrano[3,2-b]pyran-2-yl)acetate 29 (4.26 g, 2.854 mmol) was dissolved in THF (63.9 mL, 779.855 mmol) and N,N-dimethylacetamide (21.30 mL, 227.375 mmol). Imidazole hydrochloride (0.880 g, 8.421 mmol) was added followed by TBAF in THF (18.55 mL, 18.554 mmol). The reaction was monitored by TLC (silica gel; 1:1 MTBE/heptane and 9:1 EtOAc/MeOH) and stirred for 10 d. When the reaction was deemed complete, the reaction mixture was concentrated in vacuo at RT, and the residue was dissolved in ethanol (90 mL). 1H-imidazole hydrochloride (2.510 g, 24.007 mmol) and water (42.6 mL, 2364.659 mmol) were added, and the reaction was monitored by TLC for the formation of compound 30. After 24 h, an additional portion of imidazole hydrochloride (2.5 g) was added, and the solution was stirred for 72 h. Aqueous saturated sodium bicarbonate was added followed by toluene, and the mixture was concentrated in vacuo to remove EtOH. The residue was diluted with 30 volumes of 2:1 (v/v) THF/toluene, and the phases separated. The aqueous layer was extracted with 10 volumes of 1:1 (v/v) THF/toluene. The combined organic layers were washed with water (2×10 volumes), dried with sodium sulfate, and concentrated in vacuo. The residue was purified on Biotage® with 300 g HP-SiI cartridge using 2:1 toluene/acetonitrile (1 L), 1:1 toluene/acetonitrile (2 L), and 9:1 acetonitrile/MeOH. Fractions containing compound 30 were pooled and concentrated in vacuo to provide 1.8 g product. $^1$H NMR (400 MHz, CDCl$_3$) δ 7.93 (d, 2H), 7.68 (t, 1H), 7.60 (t, 2H), 4.89 (d, 1H), 4.82 (s, 1H), 4.77 (s, 1H), 4.68-4.65 (m, 2H), 4.60-4.57 (m, 1H), 4.42-4.40 (m, 1H), 4.29-4.22 (m, 2H), 4.18 (dd, 1H), 4.05 (dd, 1H), 3.98-3.88 (m, 4H), 3.80 (td, 2H), 3.64 (s, 3H), 3.70-3.49 (m, 1H), 3.42 (s, 3H), 3.38-3.28 (m, 2H), 3.15-3.00 (m, 2H), 2.91 (dd, 1H), 2.65-2.54 (m, 3H), 2.38 (d, 1H), 2.34 (d, 1H), 2.24-2.12 (m, 6H), 2.11-1.84 (m, 5H), 1.84-1.57 (m, 6H), 1.56-1.45 (m, 2H), 1.44-1.26 (m, 4H), 1.09-0.97 (m, 4H).

Methyl 2-((2S,3aR,4aR,5S,5aS,7R,9aS,10aR,10bS)-2-(2-((2S,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)ethyl)dodecahydro-2,5-epoxyfuro[2',3':4,5]furo[3,2-b]pyrano[2,3-e]pyran-7-yl)acetate

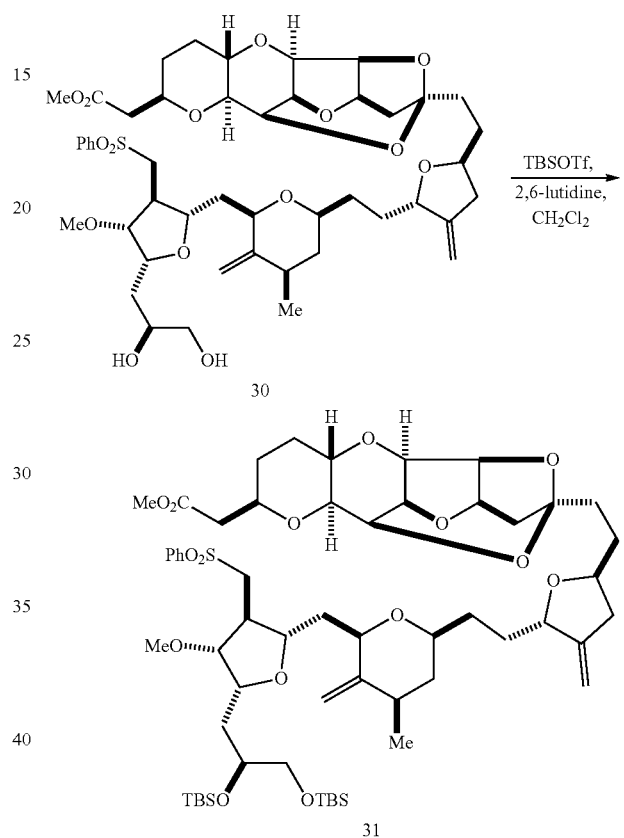

Methyl 2-((2S,3aR,4aR,5S,5aS,7R,9aS,10aR,10bS)-2-(2-((2S,5S)-5-(2-((2S,4R,6R)-6-(((2S,3S,4R,5R)-5-((S)-2,3-dihydroxypropyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)ethyl)dodecahydro-2,5-epoxyfuro[2',3':4,5]furo[3,2-b]pyrano[2,3-e]pyran-7-yl)acetate 30 (0.734 g, 0.813 mmol) was dissolved in dichloromethane (DCM) (7.34 mL, 114.076 mmol). 2,6-Lutidine (0.568 mL, 4.877 mmol) was added the solution, which was then cooled to 0° C. tert-Butyldimethylsilyl trifluoromethanesulfonate (0.467 mL, 2.032 mmol) was added, and the reaction was stirred and monitored for completion by TLC. Upon completion of the reaction, aqueous saturated sodium bicarbonate was added, and the mixture was stirred for 15 minutes. The layers were separated, and the aqueous layer was extracted with DCM. The combined organic layers were washed sequentially with water, 0.1 N HCl, water, and aqueous saturated sodium bicarbonate. The combined organic layers were concentrated in vacuo to provide a yellow oil. The product was purified by suction silica gel column chromatography (14 g SiO$_2$, 230-400 m). The crude reaction mixture was loaded with DCM/heptane, and the column was eluted with heptane/MTBE (1:1 (v/v), 150 mL) followed by MTBE (2×150 mL). The fractions containing the product were pooled and concentrated in vacuo to provide 31 (848 mg) of white foam. $^1$H NMR (400 MHz, C6D$_6$) δ=7.96-7.90 (m, 2H), 7.08-7.02 (m, 3H), 4.88-4.84 (m, 1H), 4.82-4.78 (m, 1H), 4.76-4.71 (m, 1H), 4.66-4.62 (m, 1H), 4.52-4.42 (m, 1H), 4.39-4.29 (m, 2H), 4.15-4.04 (m, 4H), 4.03-3.84 (m, 5H), 3.81-3.60 (m, 6H), 3.45 (s, 3H), 3.27 (s, 3H), 3.16-3.08 (m, 1H), 2.94 (s, 2H), 2.58-2.48 (m, 3H), 2.48-2.34 (m, 2H), 2.30-1.87 (m, 12H), 1.00 (s, 9H), 0.94 (s, 9H), 0.96-0.90 (m, 2H), 0.93 (d, J=2.0 Hz, 1H), 0.93 (d, J=1.6 Hz, 1H), 0.89-0.81 (m, 8H), 0.19 (s, 2H), 0.17 (s, 3H), 0.06 (s, 3H), 0.06 (s, 3H)

Bis-TBS Ether Phenylsulfone 32

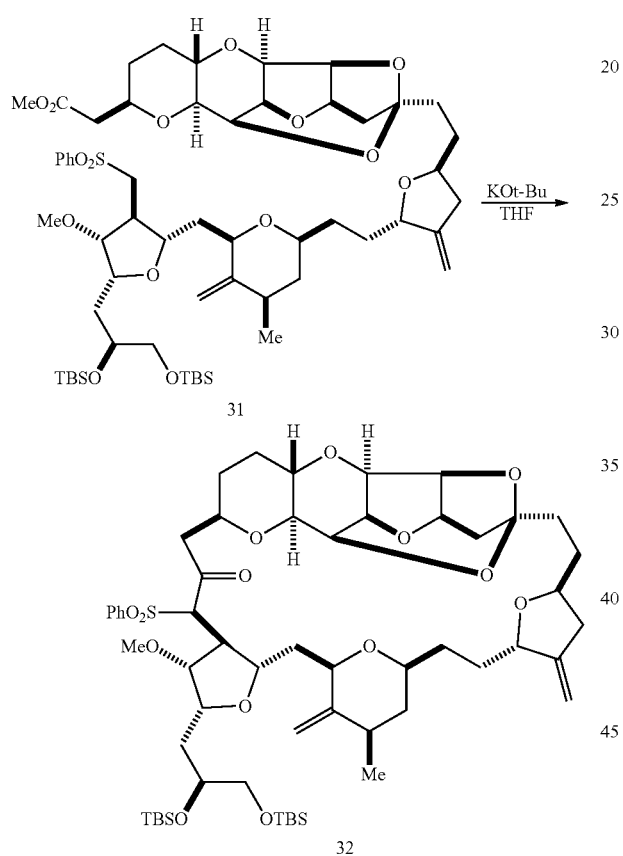

Treat methyl 2-((2S,3aR,4aR,5S,5aS,7R,9aS,10aR,10bS)-2-(2-((2S,5S)-5-(2-((2S,4R,6R)-6-(((2S,3S,4R,5R)-5-((S)-2,3-bis((tert-butyldimethylsilyl)oxy)propyl)-4-methoxy-3-((phenylsulfonyl)methyl)tetrahydrofuran-2-yl)methyl)-4-methyl-5-methylenetetrahydro-2H-pyran-2-yl)ethyl)-4-methylenetetrahydrofuran-2-yl)ethyl)dodecahydro-2,5-epoxyfuro[2',3':4,5]furo[3,2-b]pyrano[2,3-e]pyran-7-yl) acetate 31 in a solvent (e.g., THF, 2-methyltetrahydrofuran, MTBE, DME, toluene, chlorobenzene, tert-butanol, isopropanol, or another solvent) (30-100 volumes) with a base (e.g., potassium t-butoxide, KHMSA, potassium pentoxide, or a similar base) (1-5 equiv.). The resulting mixture is stirred at at a temperature between −20° C. and reflux and is monitored for consumption of starting material. The reaction can be quenched by addition of 0.1 N HCl (10 volumes). The mixture can be extracted with MTBE or other suitable organic solvent. The organic layers can be combined and washed sequentially with water, saturated aqueous sodium bicarbonate, and water. The resulting organic solution can be dried over Na$_2$SO$_4$, filtered, and concentrated in vacuo to provide 32. The product can be purified by chromatography if necessary.

Bis TBS-Ether 18

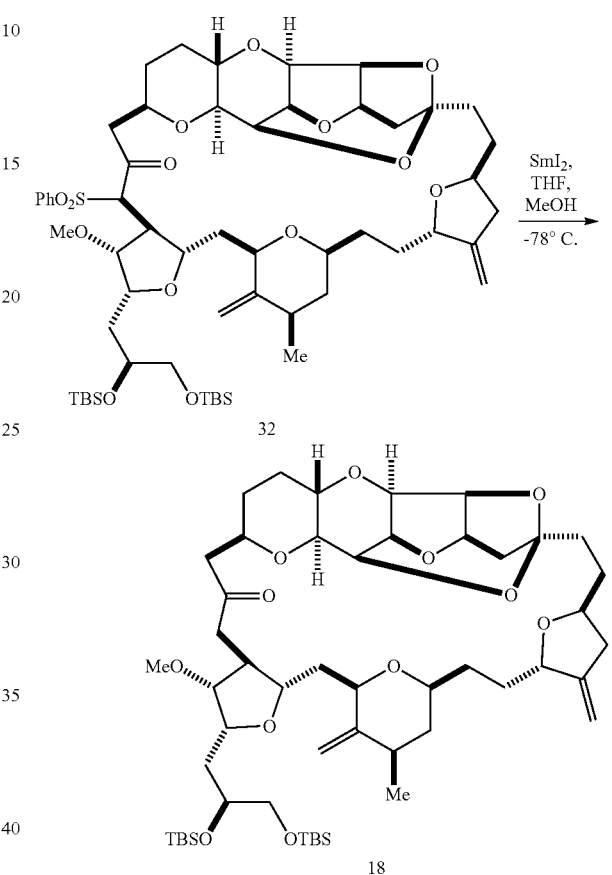

Compound 32 was dissolved in THF (0.35 mL) and MeOH (0.25 mL), and the solution was cooled to −78° C. Samarium (II) iodide (1.0 M in THF, 0.12 mL, 2.5 eq) was added, and the reaction was monitored by TLC. The reaction progressed to approximately 50% completion. Additional samarium (II) iodide was added (1.0M in THF, 0.6 mL, 12.5 eq) in portions over 1 h. The reaction conversion remained at 50%. The reaction mixture was worked up by the addition of Rochelle salt/potassium carbonate/water (1:1:10 ratio; 20 mL) and extracted with EtOAc (3×20 mL). The combined extracts were sequentially washed with saturated sodium bicarbonate, water, and brine before drying with sodium sulfate. After filtering, the filtrate is concentrated in vacuo to provide a residue of 18 and 32. $^1$H NMR analysis against an authentic sample of 18 confirmed the structural assignment.

Other Embodiments

Various modifications and variations of the described device and methods of use of the invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention that are obvious to those skilled in the art are intended to be within the scope of the invention.

Other embodiments are in the claims.

The invention claimed is:
1. A method of preparing an intermediate in the synthesis of eribulin, said method comprising:
   (1) performing a Prins reaction by contacting a compound of formula (VIIA) with a compound of formula (VIIB) and R₃OH,
   wherein R₃ is an optionally substituted acyl;
   wherein the compound of formula (VIIA) has the following structure:

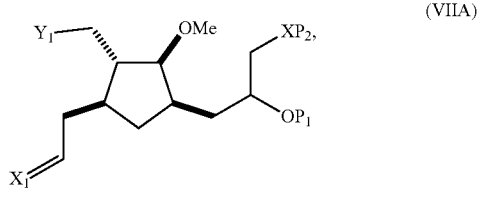

(VIIA)

wherein
Y₁ is SO₂R₁ or COOR₁, and R₁ is optionally substituted alkyl, optionally substituted aryl, or optionally substituted arylalkyl;
X₁ is O, or X₁, together with the carbon to which it is attached, forms a cyclic acetal; and
X is O, and
    each of P₁ and P₂ is independently H or a hydroxyl protecting group,
    or
    P₁ and P₂, together with the atoms to which each is attached, combine to form a cyclic protected diol;
    or
X is N, and
    P₁ is H or a hydroxyl protecting group, and X and P₂ combine to form optionally masked amino;
    or
    P₁ and P₂, together with the atoms to which each is attached, combine to form an aminal or 1,3-oxazolidin-2-one-5-yl;
wherein the compound of formula (VIIB) has the following structure:

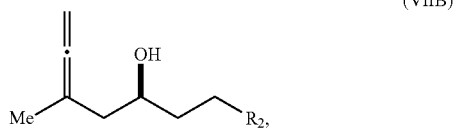

(VIIB)

wherein
R₂ is —CH₂—OP₃, —CH=CH₂,

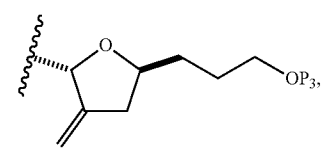

-continued

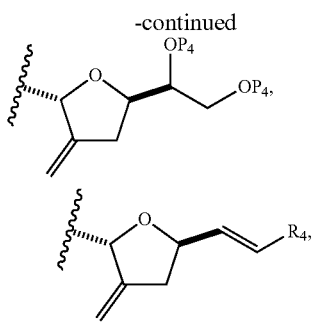

wherein P₃ is H or a hydroxyl protecting group; each P₄ is independently a hydroxyl protecting group, or both P₄ groups, together with the atoms to which each is attached, combine to form a cyclic protected diol; and R₄ is H or —CH₂X₂CH₂CH=CH₂, wherein X₂ is O, —CH₂—, or NP₅, wherein P₅ is sulfonyl;
and wherein said intermediate is a compound of formula (VIIC):

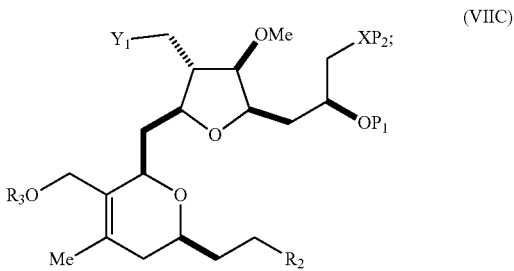

(VIIC)

or
(2) (A) cleaving the double bond in a compound of formula (VIIIA) to afford a compound of formula (VIIIB), the compound of formula (VIIIA) having the structure:

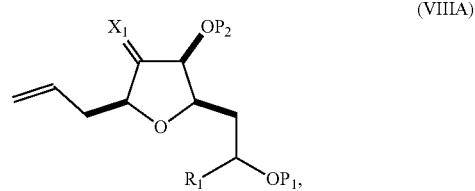

(VIIIA)

wherein
X₁ is oxo, or X₁, together with the carbon atom to which it is attached, forms a ketal or —(CH(OP₃))—, wherein P₃ is H or a hydroxyl protecting group;
R₁ is H or —CH₂OP₄;
each of P₁, P₂, and P₄ is independently a hydroxyl protecting group, or
P₁ and P₄, together with the atoms to which each is attached, combine to form a cyclic protected diol; and the compound of formula (VIIIB) having the structure:

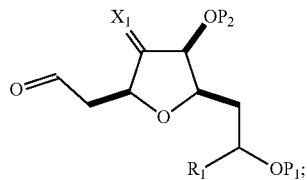

(VIIIB)

(B) reacting the compound of formula (VIIIB) with a compound of formula (VIIIB-a) to afford a compound of formula (VIIIC):

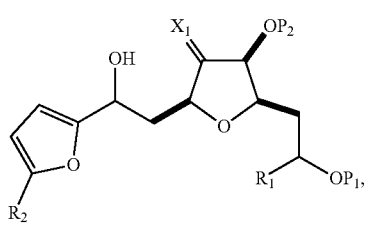

(VIIIC)

wherein $R_2$ is H or —$CH_2CH_2OP_5$, and $P_5$ is a hydroxyl protecting group;

and the compound of formula (VIIIB-a) has the following structure:

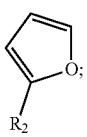

(VIIIB-a)

(C) reacting the compound of formula (VIIIC) with a dehydrating agent to afford a compound of formula (VIIID):

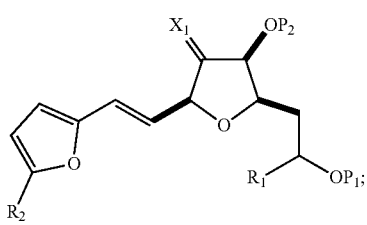

(VIIID)

(D) reacting the compound of formula (VIIID) with a dihydroxylating agent to afford a compound of formula (VIIIE):

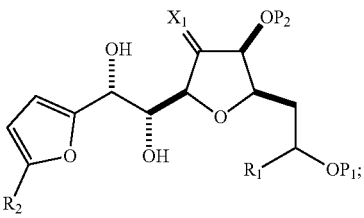

(VIIIE)

(E) preparing a compound of formula (VIIIF) through a reaction sequence comprising reacting the compound of formula (VIIIE) with N-bromosuccinimide to afford a first intermediate, reacting said first intermediate with an acylating agent to afford a second intermediate, and (a), when $R_2$ is —$CH_2CH_2OP_5$, contacting said second intermediate with a reducing agent, or (b), when $R_2$ is H, allylating said second intermediate compound of formula (VIIIF):

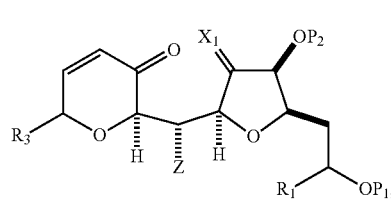

(VIIIF)

wherein Z is an ester or —$OP_7$, wherein $P_7$ is H or a hydroxyl protecting group, and $R_3$ is —$CH_2CH_2OP_5$ or —$CH_2CH{=}CH_2$;

(F) reacting the compound of formula (VIIIF) with a 1,4-reducing agent to afford a compound of formula (VIIIG):

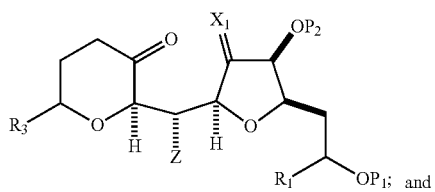

(VIIIG)

and (G) forming a compound of formula (VIIIH) through a reaction sequence comprising reacting the compound of formula (VIIIG) with a Brønsted acid and Y—H, wherein Y is optionally substituted $C_{1-6}$ alkyl, the compound of formula (VIIIH) having the following structure:

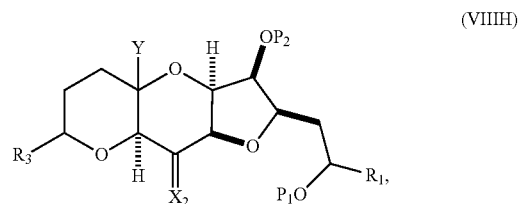

(VIIIH)

wherein Y is optionally substituted $C_{1-6}$ alkyl ether; $R_2$ is —$CH_2CH_2OP_5$; $X_2$ is oxo, or $X_2$, together with the carbon to which it is attached, forms a ketal or —$(CH(OP_6))$—, wherein $P_6$ is a hydroxyl protecting group.

2. The method of claim 1, comprising performing a Prins reaction by contacting the compound of formula (VIIA) with a compounds of formula (VIIB) and $R_3OH$.

3. The method of claim 2, wherein said performing a Prins reaction comprises reacting the compound of formula (VIIA) with a Lewis acid.

4. The method of claim 1, comprising:

(A) cleaving the double bond in the compound of formula (VIIIA) to afford the compound of formula (VIIIB);

(B) reacting the compound of formula (VIIIB) with the compound of formula (VIIIB-a) to afford the compound of formula (VIIIC);

(C) reacting the compound of (VIIIC) with a dehydrating agent to afford the compound of formula (VIIID);

(D) reacting the compound of formula (VIIID) with a dehydroxylating agent to afford the compound of formula (VIIIE);

(E) preparing the compound of formula (VIIIF) through a reaction sequence comprising reacting the compound of formula (VIIIE) with N-bromosuccinimide to afford the first intermediate, reacting said first intermediate with an acylating agent to afford the second intermediate, and (a), when $R_2$ is —$CH_2CH_2OP_5$, contacting said second intermediate with a reducing agent, or (b), when $R_2$ is H, allylating said second intermediate compound of formula (VIIIF);

(F) reacting the compound of formula (VIIIF) with a 1,4-reducing agent to afford a compound of formula (VIIIG); and (G) forming the compound of formula (VIIIH) through the reaction sequence comprising reacting the compound of formula (VIIIG) with a Brønsted acid and Y—H.

5. The method of claim 4, further comprising:

(H) replacing $P_2$ in the compound of formula (VIIIH) with —$Si(R_4)_2H$ to afford a compound of formula (VIIIJ):

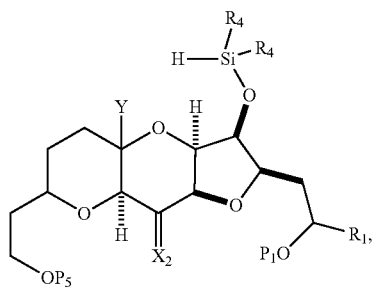

(VIIIJ)

wherein each $R_4$ is independently optionally substituted alkyl, optionally substituted aryl, or optionally substituted arylalkyl;

(I) reacting the compound of formula (VIIIJ) with a Lewis acid to afford a compound of formula (VIIIK):

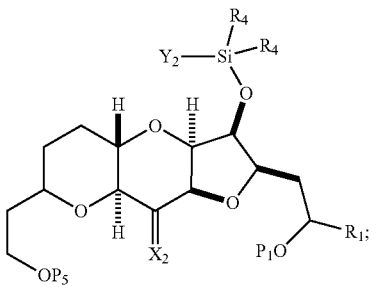

(VIIIK)

wherein $Y_2$ is fluoro, chloro, or bromo; and (J) reacting the compound of formula (VIIIK) with a hydroxyl protecting group removing agent and then reacting with a hydroxyl protecting agent to afford a compound of formula (VIIIL):

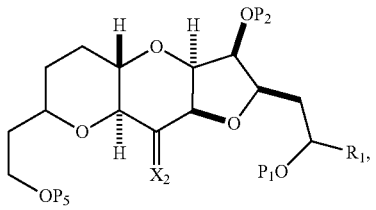

(VIIIL)

wherein $P_2$ is a hydroxyl protecting group.

* * * * *